(12) United States Patent
Deng et al.

(10) Patent No.: US 11,053,235 B2
(45) Date of Patent: Jul. 6, 2021

(54) SUBSTITUTED 1,4-DIHYDROPYRIMIDINES FOR THE TREATMENT OF HBV INFECTION OR HBV-INDUCED DISEASES

(71) Applicant: Janssen Sciences Ireland Unlimited Company, County Cork (IE)

(72) Inventors: Gang Deng, Shanghai (CN); Yimin Jiang, Londonberry, NH (US); Qian Liu, Shanghai (CN); Chao Liang, Shanghai (CN); Zhao-Kui Wan, Shanghai (CN); Wing Shun Cheung, Shanghai (CN); Zhanling Cheng, Shanghai (CN); Yanping Xu, Noblesville, IN (US)

(73) Assignee: Janssen Sciences Ireland Unlimited Company, County Cork (IE)

( * ) Notice: Subject to any disclaimer, the term of this patent is extended or adjusted under 35 U.S.C. 154(b) by 0 days.

(21) Appl. No.: 16/537,395

(22) Filed: Aug. 9, 2019

(65) Prior Publication Data

US 2020/0048242 A1 Feb. 13, 2020

Related U.S. Application Data

(60) Provisional application No. 62/716,823, filed on Aug. 9, 2018.

(51) Int. Cl.

| *A61K 31/505* | (2006.01) |
|---|---|
| *C07D 239/20* | (2006.01) |
| *C07D 417/14* | (2006.01) |
| *A61K 45/06* | (2006.01) |
| *A61K 38/17* | (2006.01) |
| *A61K 31/675* | (2006.01) |
| *C07K 16/28* | (2006.01) |
| *A61K 31/7068* | (2006.01) |

(52) U.S. Cl.
CPC .......... *C07D 417/14* (2013.01); *A61K 31/675* (2013.01); *A61K 31/7068* (2013.01); *A61K 38/1793* (2013.01); *A61K 45/06* (2013.01); *C07K 16/2818* (2013.01)

(58) Field of Classification Search
CPC ............................. A61K 31/505; C07D 239/20
USPC .......................................... 514/256; 544/242
See application file for complete search history.

(56) References Cited

U.S. PATENT DOCUMENTS 6,696,451 B1 2/2004 Stoltefuss

FOREIGN PATENT DOCUMENTS

| CN | 103626752 | | 3/2014 | | |
|---|---|---|---|---|---|
| CN | 103626752 A | * | 3/2014 | .......... | A61K 31/506 |
| CN | 103664897 A | | 3/2014 | | |
| CN | 103664899 A | | 3/2014 | | |
| CN | 103664925 A | | 3/2014 | | |
| WO | 199954326 A1 | | 10/1999 | | |
| WO | 200145712 | | 6/2001 | | |
| WO | 200168641 A1 | | 9/2001 | | |
| WO | 2008154817 A1 | | 12/2008 | | |
| WO | 2009016225 | | 2/2009 | | |
| WO | 2010/069147 A1 | | 6/2010 | | |
| WO | 2013006394 A1 | | 1/2013 | | |
| WO | 2013019967 A1 | | 2/2013 | | |
| WO | 2013/096744 A1 | | 6/2013 | | |
| WO | 2013102655 A1 | | 7/2013 | | |
| WO | 2014/029193 A1 | | 2/2014 | | |
| WO | 2014037480 A1 | | 3/2014 | | |
| WO | 2014106019 A2 | | 7/2014 | | |
| WO | 2014184328 A1 | | 11/2014 | | |
| WO | 2015074546 | | 5/2015 | | |
| WO | 2015078392 | | 6/2015 | | |
| WO | 2015132276 A1 | | 9/2015 | | |
| WO | 2015144093 A1 | | 10/2015 | | |
| WO | 2016016316 | | 2/2016 | | |
| WO | 2016146508 | | 9/2016 | | |
| WO | 2016146598 A1 | | 9/2016 | | |
| WO | WO-2017011552 A1 | * | 1/2017 | .......... | A61K 31/506 |
| WO | 2017/064156 A1 | | 4/2017 | | |
| WO | 2017064156 A1 | | 4/2017 | | |
| WO | 2017076791 A1 | | 5/2017 | | |
| WO | 2017108630 A1 | | 6/2017 | | |
| WO | 2017140750 A1 | | 8/2017 | | |
| WO | 2018036941 A1 | | 3/2018 | | |
| WO | 2018050571 A1 | | 3/2018 | | |
| WO | 2008070707 | | 6/2018 | | |
| WO | WO-2019001420 A1 | * | 1/2019 | ............ | A61K 45/06 |
| WO | 2019214610 A1 | | 11/2019 | | |
| WO | WO-2019214610 A1 | * | 11/2019 | .......... | C07D 401/14 |
| WO | WO 20/001448 | * | 1/2020 | | |
| WO | 2020125729 A1 | | 6/2020 | | |
| WO | 2020125730 A1 | | 6/2020 | | |

OTHER PUBLICATIONS

English-Language Machine Translation of CN-103626752-A (2014) (Year: 2014).*
Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Ren, et al, "Discovery of hepatitis B virus capsid assembly inhibitors leading to a heteroaryldihydropyrimidine based clinical candidate (GLS4)", Bioorganic & Medicinal Chemistry, vol. 25; pp. 1042-1056 (2017).

(Continued)

*Primary Examiner* — Douglas M Willis

(57) ABSTRACT

The application describes dihydropyrimidine derivatives which are useful in the treatment or prevention of HBV infection or of HBV-induced diseases, more particularly of HBV chronic infection or of diseases induced by HBV chronic infection, as well as pharmaceutical or medical applications thereof.

17 Claims, No Drawings

Specification includes a Sequence Listing.

(56) References Cited

OTHER PUBLICATIONS

Qui, et al, "Discovery and Pre-Clinical Characterization of Third-Generation 4-H Heteroaryldihydropyrimidine (HAP) Analogues as Hepatitis B Virus (HBV) Capsid Inhibitors", Journal of Medicinal Chemistry, vol. 60 (8); pp. 3352-3371 (2017).
Bourne, et al., "Small-Molecule Effectors of Hepatitis B Virus Capsid Assembly Give Insight into Virus Life Cycle", Journal of Virology, vol. 82(20): pp. 10262-10270 (Oct. 2008).
Tu, et al., "Exploring the binding mechanism of Heteroaryldihydropyrimidines and Hepatitis B Virus capsid combined 3D-QSAR and molecular dynamics", Antiviral Research, vol. 137: pp. 151-164 (2017).
International Written Opinion dated Mar. 27, 2019 for PCT Application No. PCT/CN2018/092875, filed on Jun. 26, 2018.
International Search Report and Written Opinion dated Mar. 29, 2019 for PCT Application No. PCT/CN2018/092875, filed on Jun. 26, 2018.
International Search Report and Written Opinion dated Sep. 29, 2019 for PCT Application No. PCT/CN2019/092857 filed on Jun. 25, 2019.
Shlenev, et al., "2-Halobenzoyl Chlorides in the Synthesis of (1,3,4) Thiadiazolo (3,2,-a) quinazolin-5-one Derivatives", Russian Journal of Organic Chemistry, (2017), pp. 1870-1877, vol. 53(12).

\* cited by examiner

SUBSTITUTED 1,4-DIHYDROPYRIMIDINES FOR THE TREATMENT OF HBV INFECTION OR HBV-INDUCED DISEASES

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant worldwide medical problem, due to suboptimal treatment options and sustained rates of new infections in most parts of the developing world.

Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress.

Capsid structures also respond to environmental cues to allow un-coating after viral entry.

Consistently, the appropriate timing of capsid assembly and dis-assembly, the appropriate capsid stability and the function of core protein have been found to be critical for viral infectivity.

Background references on dihydropyrimidine derivatives in the treatment of HBV infection include WO 2014/029193, CN103664899, CN103664925, and CN103664897.

There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

SUMMARY

Provided, in one aspect, is a compound of formula (I)

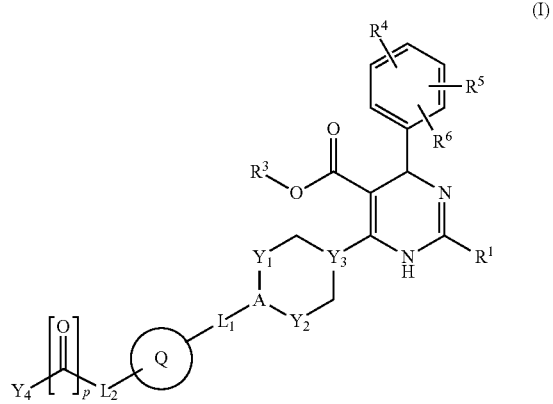

including the deuterated isomers, stereoisomers and the tautomeric forms thereof,
wherein
  Y represents bond or $CR^7R^8$;
wherein
  $Y_2$ represents a bond or $CR^7R^8$, wherein $R^7$ and $R^8$ are independently selected from hydrogen and C1-C4 alkyl, and A represents CH or N; or $Y_2$ is $CR^9$ and A is C thus forming a C=C bond, wherein $R^9$ is hydrogen or $C_1$-$C_4$ alkyl;
wherein $Y_3$ represents CH;
or Y1 and Y2 represent a bond, and a further —$CH_2$— is present directly connecting A and Y3 to form a bridged 5-membered cyclic hydrocarbon;
wherein $Y_4$ represents OH, $OR^{14}$ or $R^{14}$ wherein $R^{14}$ is $C_1$-$C_4$ alkyl;
wherein Q represents a bond or a 5- to 6-membered aromatic ring,
wherein said 5- to 6-membered aromatic ring optionally comprises 1-3 heteroatoms,
wherein said 5- to 6-membered aromatic ring is optionally substituted with one or more substituents each independently selected from the group consisting of
  $C_1$-$C_4$ alkyl,
  halogen,
  $OR^{13}$ wherein $R^{13}$ is H or $C_1$-$C_4$ alkyl,
  $NR^{10}R^{11}$ where $R^{10}$ and $R^{11}$ are independently selected from H and $C_1$-$C_4$ alkyl, or $R^{10}$ and $R^{11}$ form a C4, C5 or C6 membered ring,
  $C_1$-$C_4$ alkyl substituted with one or more halogen,
  $C_1$-$C_4$ alkyl substituted with $OR^{12}$ wherein each $R^{12}$ is H or $C_1$-$C_4$ alkyl;
wherein if Q represents a bond, $Y_4$ is selected from the group consisting of phenyl,
  pyrazolyl,
  isoxazolyl,
  thiadiazolyl,
  phenyl substituted with $C_1$-$C_4$ alkyl,
  pyrazolyl substituted with $C_1$-$C_4$ alkyl,
  isoxazolyl substituted with $C_1$-$C_4$ alkyl, and
  thiadiazolyl substituted with $C_1$-$C_4$ alkyl;
wherein $L_1$ is selected from the group consisting of
  a bond,
  $C_1$-$C_4$ alkyl, and C$_1$-C$_4$ alkyl substituted with one or more substituents each independently selected from the group consisting of
C$_1$-C$_4$ alkyl,
halogen,
oxo,
OR$^7$ wherein R$^7$ independently is hydrogen or C$_1$-C$_4$ alkyl, and
C$_1$-C$_4$ alkyl substituted with one or more halogen;
wherein L$_2$ is selected from the group consisting of
a bond,
C$_1$-C$_4$ alkyl, and
a 3-7 membered saturated ring optionally containing one or more hetereoatom(s), the heteroatom being a nitrogen
wherein each of said C$_1$-C$_4$ alkyl and said 3-7 membered saturated ring are optionally substituted with one or more substituents each independently selected from the group consisting of
C$_1$-C$_4$ alkyl,
halogen,
OR$^{15}$ wherein R$^{15}$ independently is hydrogen or C$_1$-C$_4$ alkyl, and
C$_1$-C$_4$ alkyl substituted with one or more halogen;
wherein p is an integer selected from 0 and 1, more particularly 1;
wherein R$_1$ is selected from the group consisting of thiazolyl, pyridyl, thiazolyl substituted with one or more halogen and pyridyl substituted with one or more halogen;
wherein R$^3$ is C$_1$-C$_3$ alkyl; and
wherein R$^4$, R$^5$ and R$^6$ each independently are selected from the group consisting of hydrogen, C$_1$-C$_3$ alkyl and halogen;
or a pharmaceutically acceptable salt or a solvate thereof.

In another aspect, provided herein is a pharmaceutical composition comprising at least one compound of Formula I, or a pharmaceutically acceptable salt thereof, together with a pharmaceutically acceptable carrier.

In another aspect, provided herein is a pharmaceutical composition comprising at least one disclosed compound, together with a pharmaceutically acceptable carrier. In another aspect, provided herein is a method of treating an HBV infection in an individual in need thereof, comprising administering to the individual a therapeutically effective amount of a compound of Formula I or a pharmaceutically acceptable salt thereof.

In yet a further aspect, provided herein is a product comprising a first compound and a second compound as a combined preparation for simultaneous, separate or sequential use in the prevention or treatment of an HBV infection or of an HBV-induced disease in mammal in need thereof, wherein said first compound is different from said second compound, wherein said first compound is the compound of any one of claims 1-8 or the pharmaceutical composition of claim 9, and wherein said second compound is an HBV inhibitor which is chosen from among:
cytokines having HBV replication inhibition activity,
antibodies having immune checkpoint modulation activity,
substituted pyrimidines having HBV capsid assembly inhibition activity or having TLR agonist activity,
antiretroviral nucleoside analogues, and
the combinations thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula I, or a pharmaceutically acceptable salt thereof.

In an embodiment, any of the methods provided herein can further comprise administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and any combination thereof.

In a still further aspect, a process is provided for producing the compound of formula I, wherein p is 1, and A is CH, the processing comprising:
reacting an activated acyl compound of formula III-1,

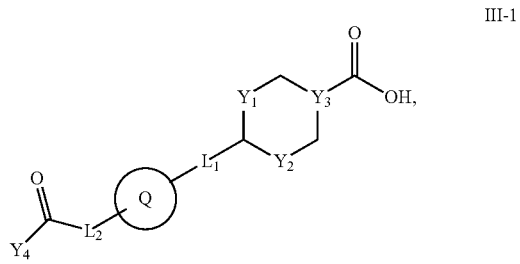

III-1 with R$^3$-malonate into an intermediate of formula IV-1,

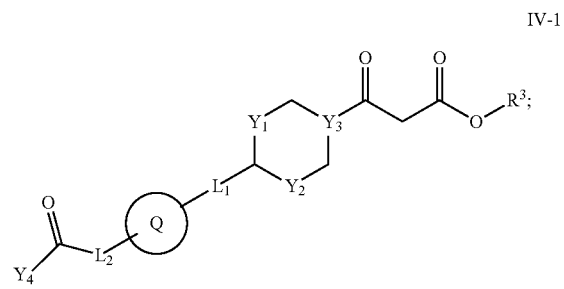

IV-1 subjecting the compound of formula IV-1 with compounds of general formula V and VI, i.e.,

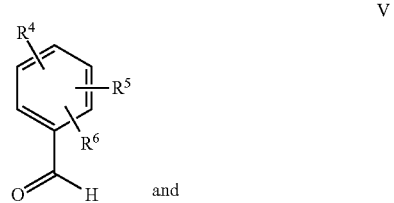

V

VI to a multiple component reaction in the presence of a base in order to provide an intermediate of formula VII

VII

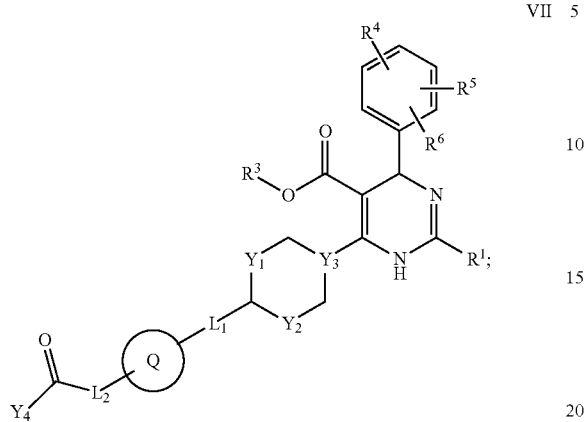

subjecting the intermediate of formula VII to ester hydrolysis in order to provide a compound of formula I.

Alternatively, another process is provided for producing the compound of formula I, wherein p is 1, and A is N, and wherein the compound produced is a compound satisfying formula II, the processing comprising:

reacting an activated acyl compound of formula III-2,

III-2

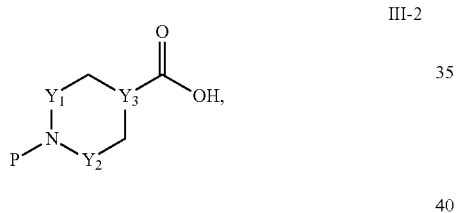

P is protecting group with $R^3$-malonate into an intermediate of formula IV-2,

IV-2

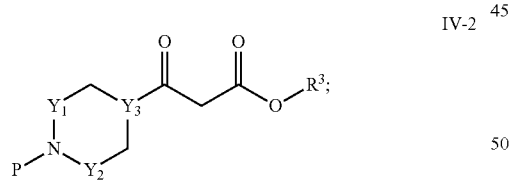

P is protecting group subjecting the compound of formula IV-2 with compounds of general formula V and VI, i.e.,

V

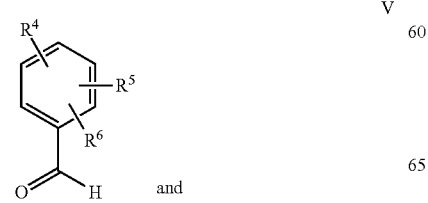

and

VI

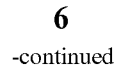

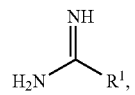

to a multiple component reaction in the presence of a base in order to provide an intermediate of formula VIII,

VIII

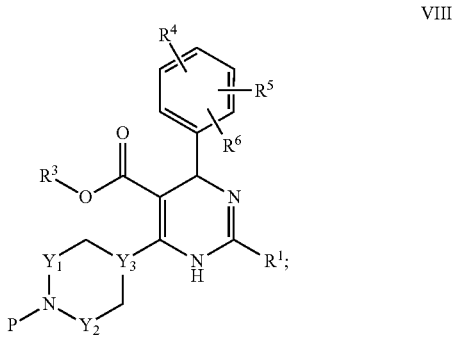

P is protecting group subjecting the compound of formula VIII with the deprotection reaction to provide an intermediate of formula IX,

IX

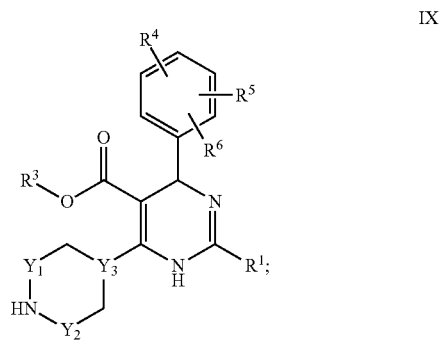

subjecting the compound of formula IX with a coupling reaction to provide an intermediate of formula XI,

XI

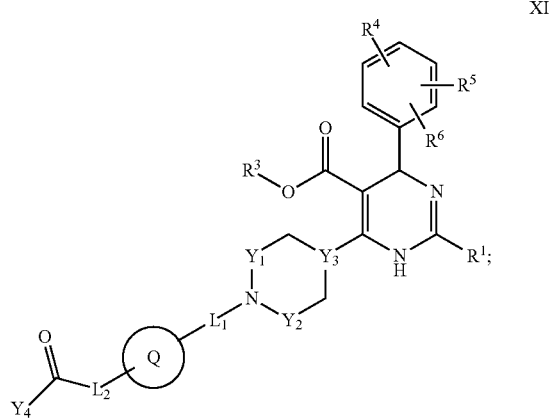

subjecting the intermediate of formula XI to ester hydrolysis in order to provide a compound of formula II (here formula II equals formula I).

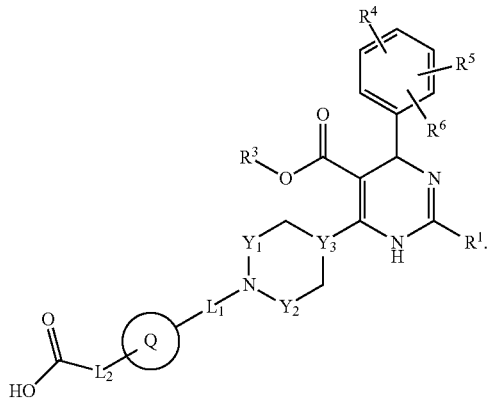

DETAILED DESCRIPTION

The application provides compounds of formula (I),

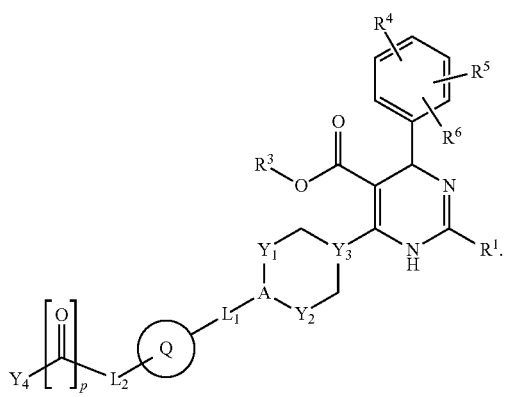

including the deuterated isomers, stereoisomers and the tautomeric forms thereof,
wherein
$Y_1$ represents a bond or $CR^7R^8$;
wherein
$Y_2$ represents a bond or $CR^7R^8$, wherein $R^7$ and $R^8$ are independently selected from hydrogen and $C_1$-$C_4$ alkyl, and A represents CH or N; or $Y_2$ is $CR^9$ and A is C thus forming a C=C bond, wherein $R^9$ is hydrogen or $C_1$-$C_4$ alkyl;
wherein $Y_3$ represents CH;
or Y1 and Y2 represent a bond, and a further —CH2-is present directly connecting A and Y3 to form a bridged 5-membered cyclic hydrocarbon;
wherein $Y_4$ represents OH, $OR^{14}$ or $R^{14}$ wherein $R^{14}$ is $C_1$-$C_4$ alkyl;
wherein Q represents a bond or a 5- to 6-membered aromatic ring,
wherein said 5- to 6-membered aromatic ring optionally comprises 1-3 heteroatoms,
wherein said 5- to 6-membered aromatic ring is optionally substituted with one or more substituents each independently selected from the group consisting of
$C_1$-$C_4$ alkyl,
halogen,
$OR^{13}$ wherein $R^{13}$ is H or $C_1$-$C_4$ alkyl,
$NR^{10}R^{11}$ where $R^{10}$ and $R^{11}$ are independently selected from H and C1-C4 alkyl, or $R^{10}$ and $R^{11}$ form a C4, C5 or C6 membered ring,
$C_1$-$C_4$ alkyl substituted with one or more halogen,
$C_1$-$C_4$ alkyl substituted with $OR^{12}$ wherein each $R^{12}$ is H or $C_1$-$C_4$ alkyl;
wherein if Q represents a bond, $Y_4$ is selected from the group consisting of
phenyl,
pyrazolyl,
isoxazolyl,
thiadiazolyl,
phenyl substituted with $C_1$-$C_4$ alkyl,
pyrazolyl substituted with $C_1$-$C_4$ alkyl,
isoxazolyl substituted with $C_1$-$C_4$ alkyl, and
thiadiazolyl substituted with $C_1$-$C_4$ alkyl;
wherein $L_1$ is selected from the group consisting of a bond,
$C_1$-$C_4$ alkyl, and
$C_1$-$C_4$ alkyl substituted with one or more substituents each independently selected from the group consisting of
$C_1$-$C_4$ alkyl,
halogen,
oxo,
$OR^7$ wherein $R^7$ independently is hydrogen or $C_1$-$C_4$ alkyl, and
C1-C4 alkyl substituted with one or more halogen;
wherein $L_2$ is selected from the group consisting of
a bond,
$C_1$-$C_4$ alkyl, and
a 3-7 membered saturated ring optionally containing one or more hetereoatom(s), the heteroatom being a nitrogen
wherein each of said $C_1$-$C_4$ alkyl and said 3-7 membered saturated ring are optionally substituted with one or more substituents each independently selected from the group consisting of
$C_1$-$C_4$ alkyl,
halogen,
$OR^{15}$ wherein $R^{15}$ independently is hydrogen or $C_1$-$C_4$ alkyl, and
$C_1$-$C_4$ alkyl substituted with one or more halogen;
wherein p is an integer selected from 0 and 1, more particularly 1;
wherein $R_1$ is selected from the group consisting of thiazolyl, pyridyl, thiazolyl substituted with one or more halogen and pyridyl substituted with one or more halogen;
wherein $R^3$ is $C_1$-$C_3$ alkyl; and
wherein $R^4$, $R^5$ and $R^6$ each independently are selected from the group consisting of hydrogen, $C_1$-$C_3$ alkyl and halogen;
or a pharmaceutically acceptable salt or a solvate thereof.

Provided herein are compounds, e.g., the compounds of formula (I), or pharmaceutically acceptable salts thereof, that are useful in the treatment and prevention of HBV infection in subject.

Without being bound to any particular mechanism of action, these compounds are believed to modulate or disrupt HBV assembly and other HBV core protein functions necessary for HBV replication or the generation of infectious particles and/or may disrupt HBV capsid assembly leading to empty capsids with greatly reduced infectivity or replication capacity. In other words, the compounds provided herein may act as capsid assembly modulators.

The compounds provided herein have potent antiviral activity, exhibit favorable metabolic properties, tissue distribution, safety and pharmaceutical profiles, and are suitable for use in humans. Disclosed compounds may modulate (e.g., accelerate, delay, inhibit, disrupt or reduce) normal viral capsid assembly or disassembly, bind capsid or alter metabolism of cellular polyproteins and precursors. The modulation may occur when the capsid protein is mature, or during viral infectivity. Disclosed compounds can be used in methods of modulating the activity or properties of HBV cccDNA, or the generation or release of HBV RNA particles from within an infected cell.

In one embodiment, the compounds described herein are suitable for monotherapy and are effective against natural or native HBV strains and against HBV strains resistant to currently known drugs. In another embodiment, the compounds described herein are suitable for use in combination therapy.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or 10%, including 5%, ±1%, and 0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_3$ alkyl means an alkyl having one to three carbon atoms, $C_1$-$C_4$ alkyl means an alkyl having one to four carbon) and includes straight and branched chains. Examples include methyl, ethyl, propyl, isopropyl, butyl, isobutyl, tert-butyl. Embodiments of alkyl include, but are not limited to, $C_1$-$C_{10}$ alkyl, such as $C_1$-$C_6$ alkyl, such as $C_1$-$C_4$ alkyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "3-7 membered saturated ring" refers to a mono cyclic non-aromatic saturated radical, wherein each of the atoms forming the ring (i.e., skeletal atoms) is a carbon atom, unless such ring contains one or more heteroatoms if so further defined. 3-7 Membered saturated rings include groups having 3 to 7 ring atoms. Monocyclic 3-7 membered saturated rings include, but are not limited to, cyclopropyl, cyclobutyl, cyclopentyl, cyclohexyl, cycloheptyl.

As used herein, 3-7 membered saturated ring optionally comprising one or more heteroatoms refers to a heteroalicyclic group containing one or more, more in particular, one, two or three, even more in particular, one or two, and most particular, one ring heteroatoms each selected from O, S, and N. In one embodiment, each heterocyclyl group has from 3 to 7 atoms in its ring system, with the proviso that the ring of said group does not contain two adjacent O or S atoms. The heterocyclic system may be attached to the remainder of the molecule, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, tetrahydrofuran, thiophane, piperidine, piperazine, morpholine, thiomorpholine.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . . " (e.g., "$R^4$ is selected from A, B and C") is understood to be equivalent to the terminology "selected from the group consisting of . . . " (e.g., "$R^4$ is selected from the group consisting of A, B and C").

In an embodiment of the compound of formula (I), $Y^4$ is OH, methoxyl or ethoxyl.

In an embodiment of the compound of formula (I), $R^3$ is methyl or ethyl.

In an embodiment of the compound of formula (I), $R^4$, $R^5$ and $R^6$ each independently are chosen from among $CH_3$, F, Cl and Br, more particularly from F and Cl.

In an embodiment of the compound of formula (I), Q is selected from the group consisting of oxazolyl, isoxazolyl, oxadiazolyl, pyrimidinyl, pyrazinyl, pyridazinyl, pyridyl, pyrazolyl, imidazoyl, thiazolyl, thiadiazolyl, and phenyl.

In an embodiment of the compound of formula (I), $Y_1$, $Y_2$, and $Y_3$ are CH.

In an embodiment of the compound of formula (I), $L_2$ is methylene, ethylene, isobutylene, or cyclobutylene.

All combinations of the foregoing embodiments are expressly included.

In embodiment, the compound of formula (I) is selected from the compounds satisfying the following formulae:

Compound I-1-C

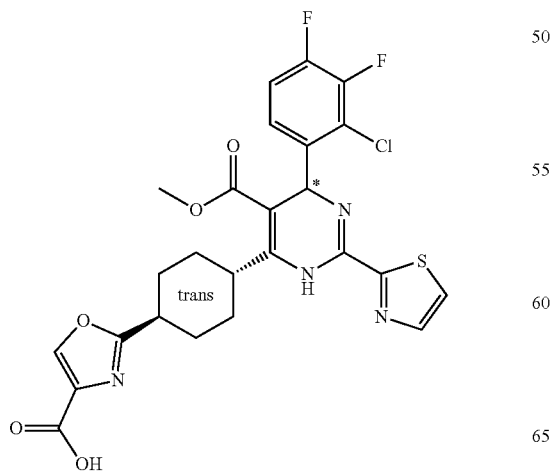

Compound I-2-D

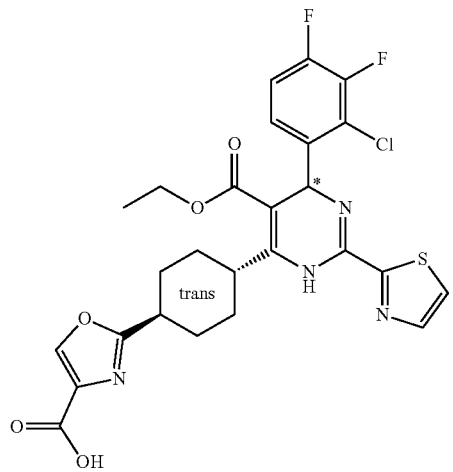

Compound I-4-B

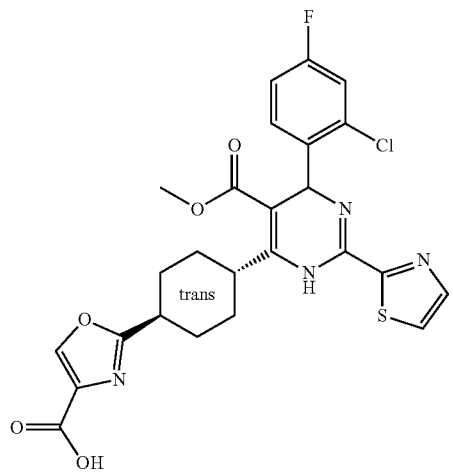

Compound I-6-B

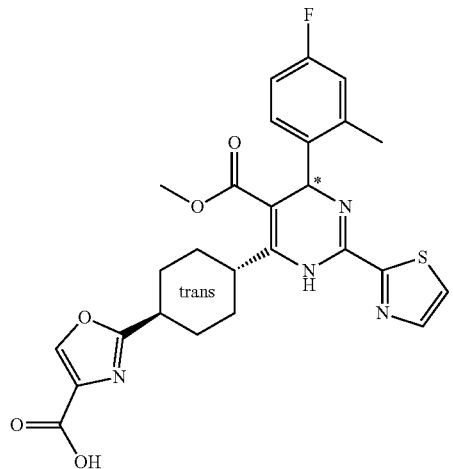

Compound I-9-B
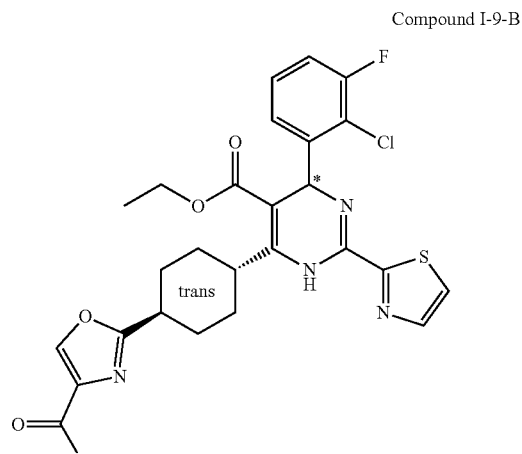
Compound I-13-C
Compound I-13-D
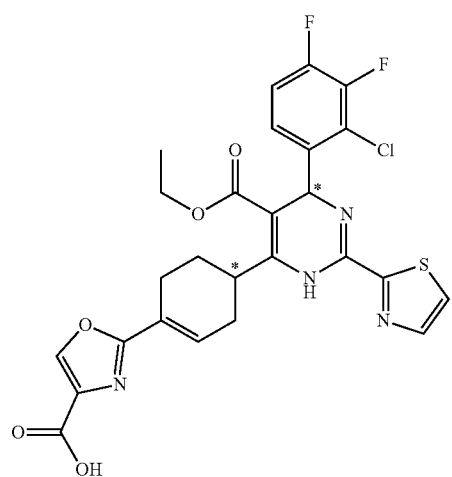
Compound I-14-B
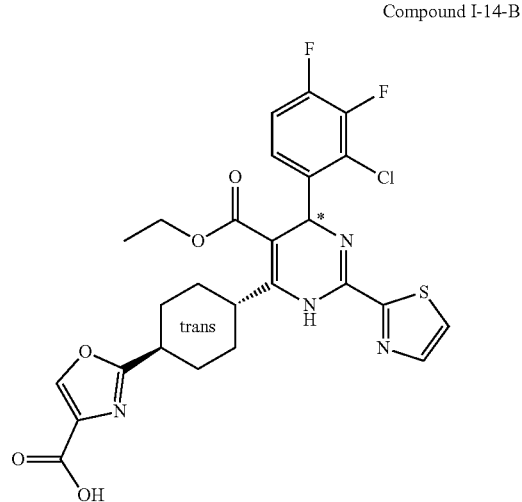
Compound I-16-B
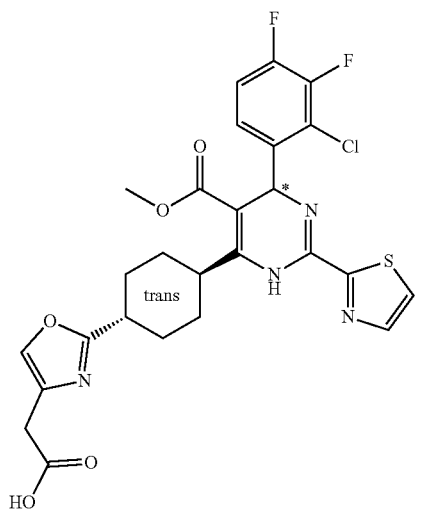
Compound I-17-A
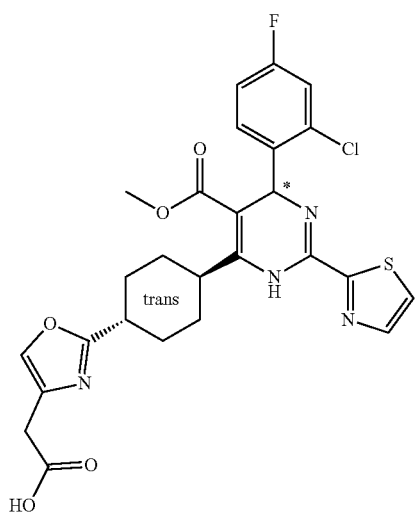
Compound I-18-A
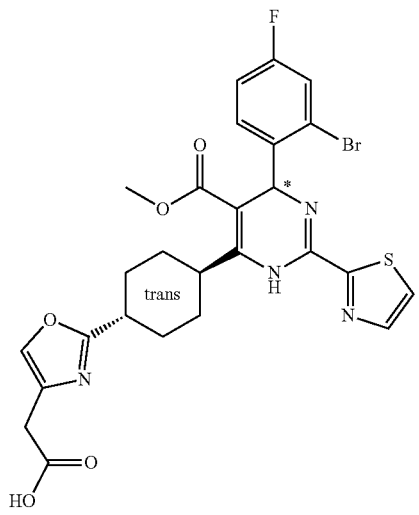

Compound I-19-B
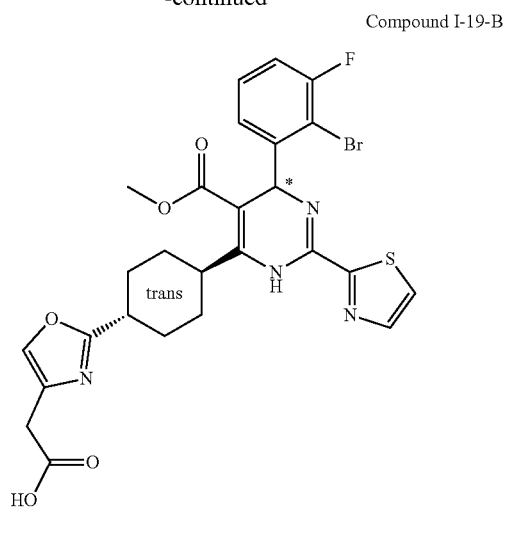
Compound I-20-B
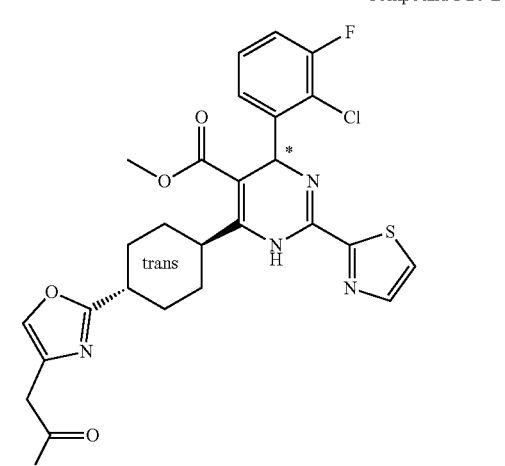
Compound I-23-B
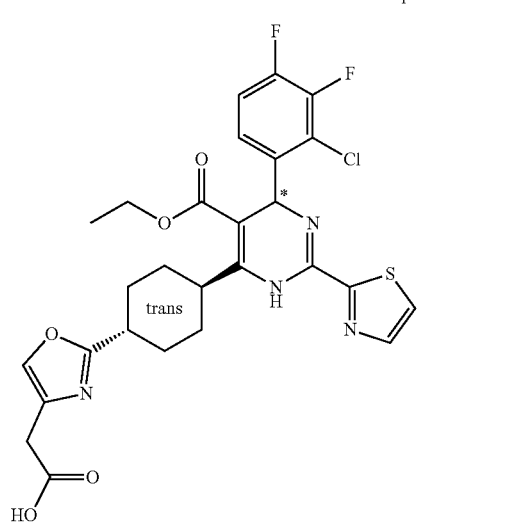
Compound I-24
Compound I-24-A
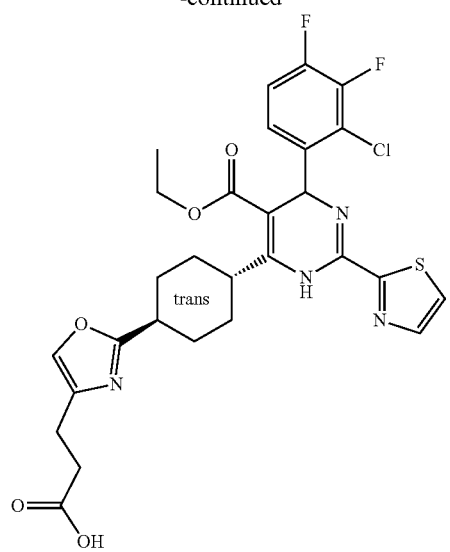
Compound I-25-B
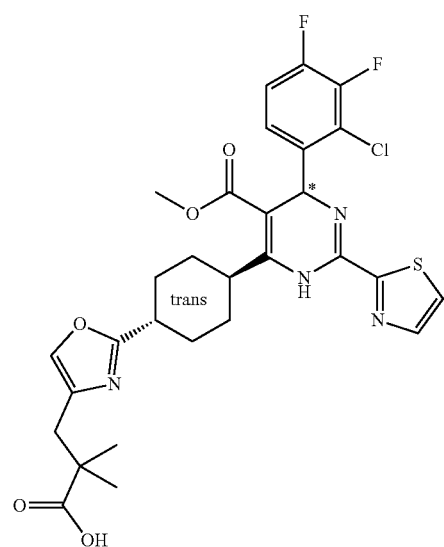
Compound I-28-B
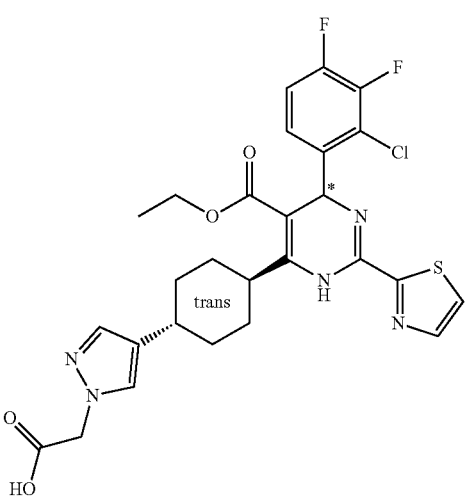

Compound I-32-B
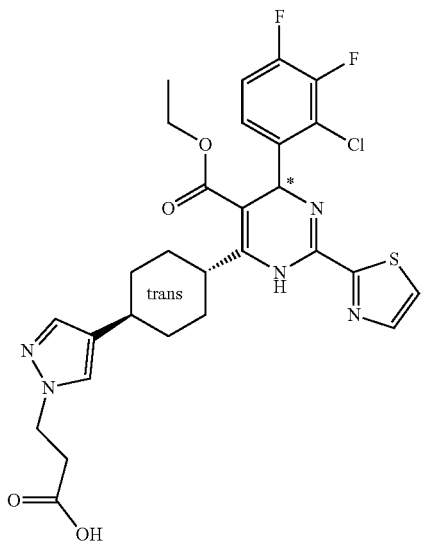
Compound I-33-C
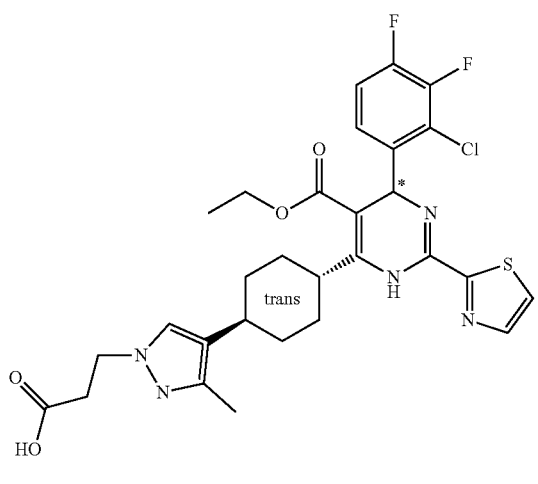
Compound I-38-B
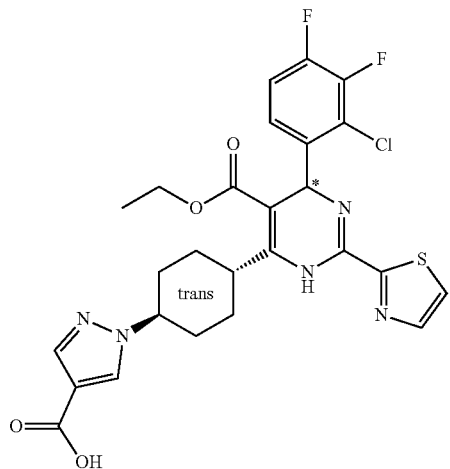
Compound II-1-B
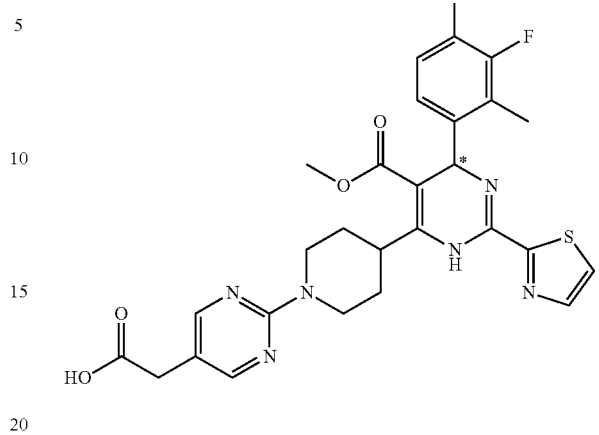
Compound II-2-B
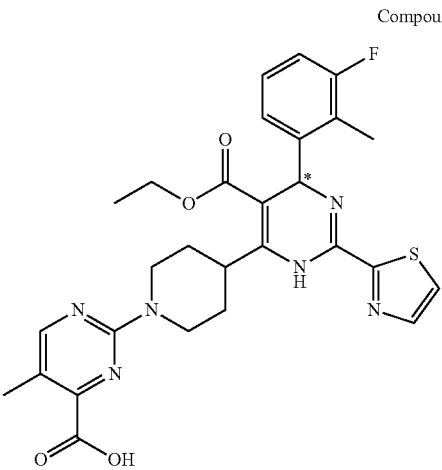
Compound II-3-B
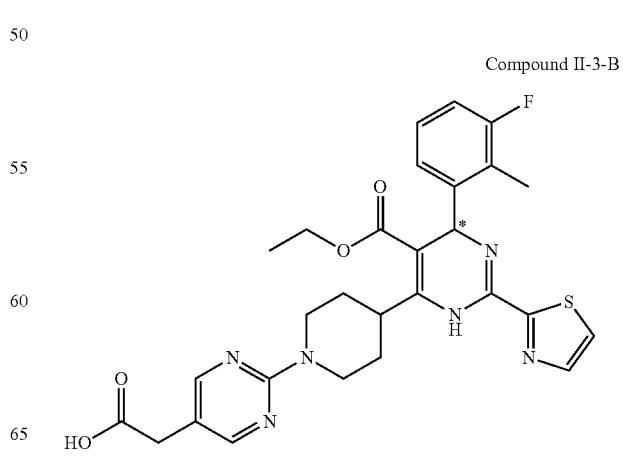

Compound II-5-B
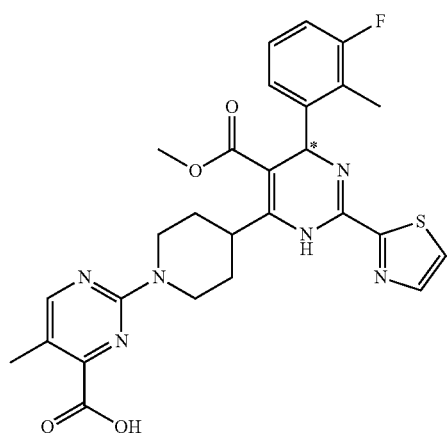
Compound II-6-B
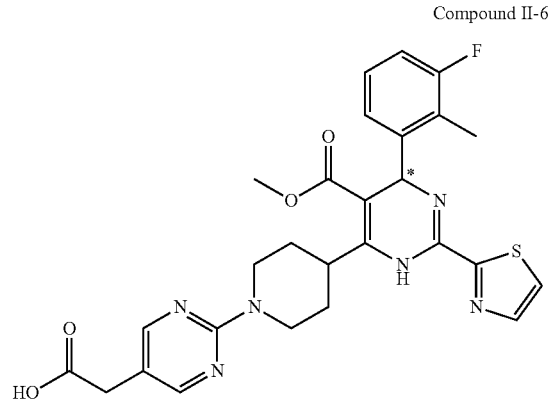
Compound II-8-B
Compound II-9-B
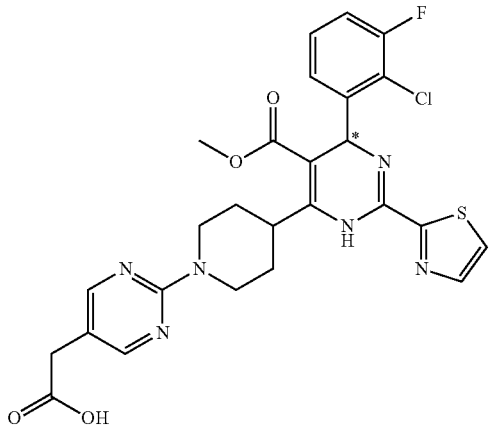
Compound II-10-B
Compound II-14-A
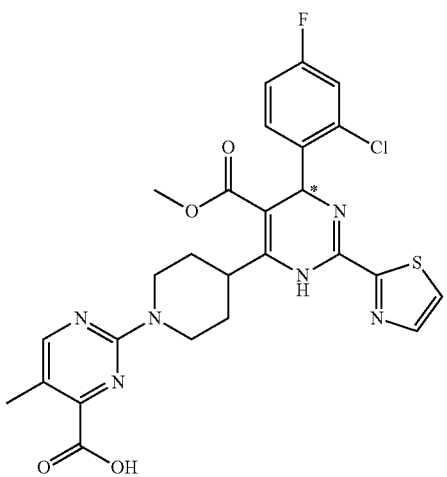

Compound II-15-A
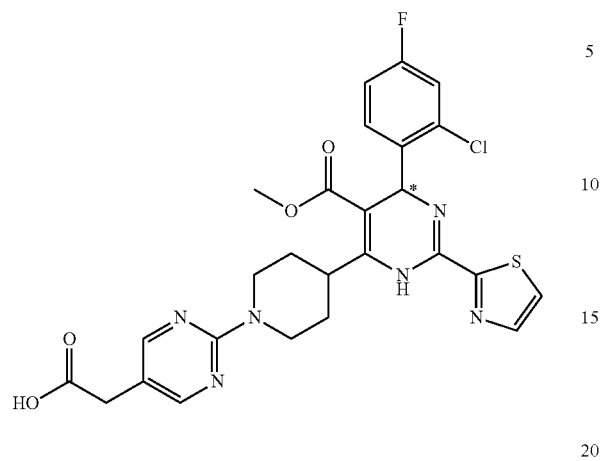
Compound II-19-A
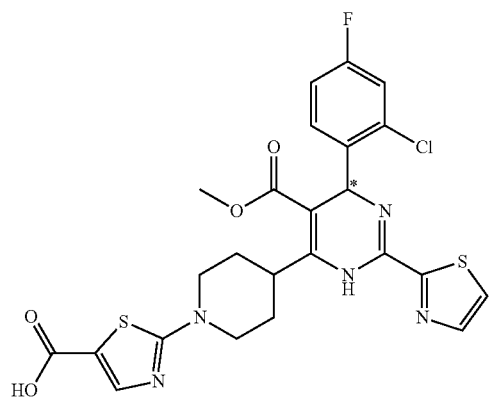
Compound II-16-B
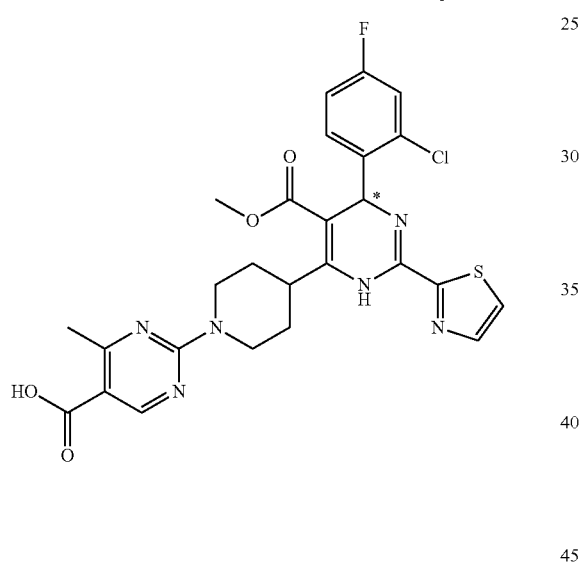
Compound II-20-B
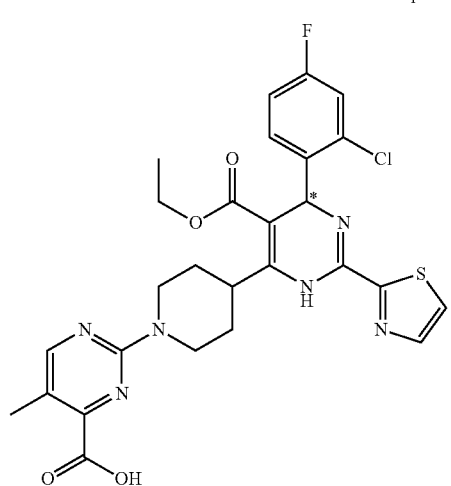
Compound II-18-B
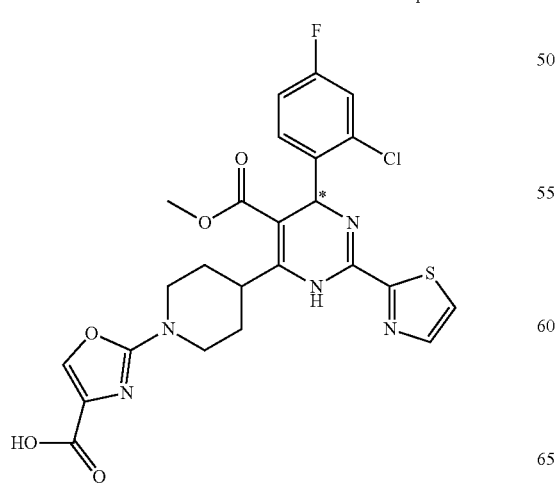
Compound II-22-B
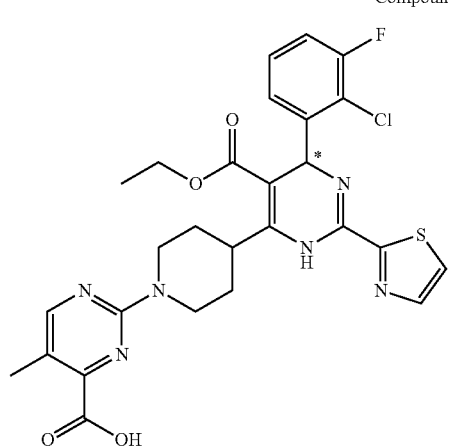

Compound II-24-B
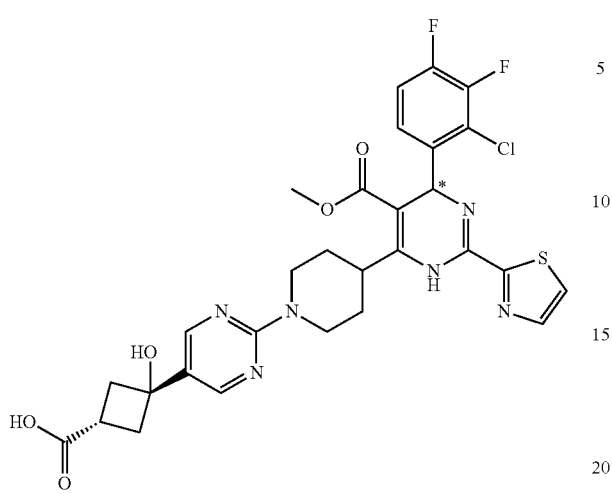
Compound II-29-B
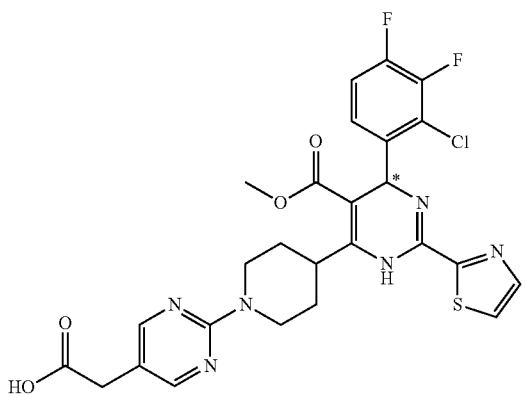
Compound II-27-B
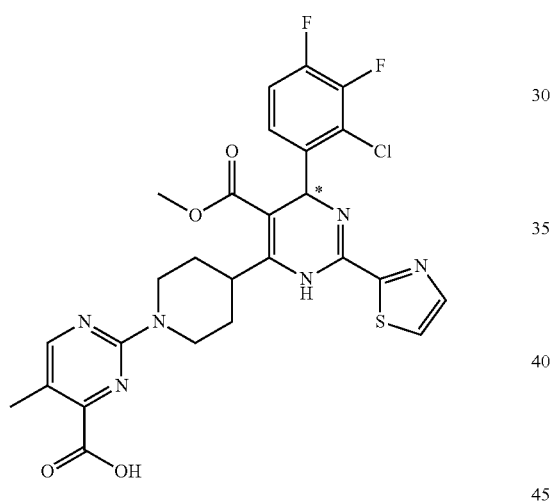
Compound II-30-B
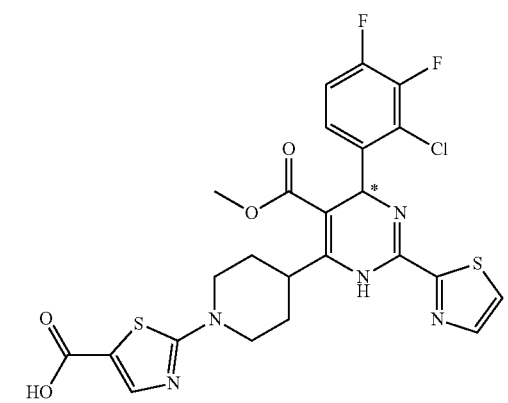
Compound II-28-B
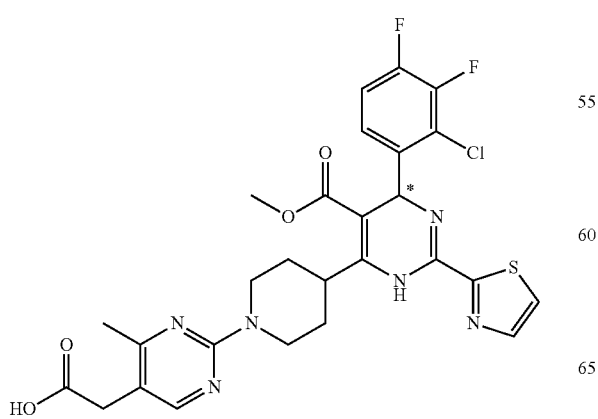
Compound II-41-B
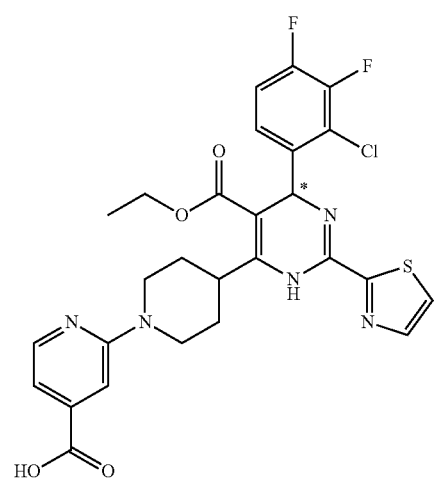

Compound II-50-B
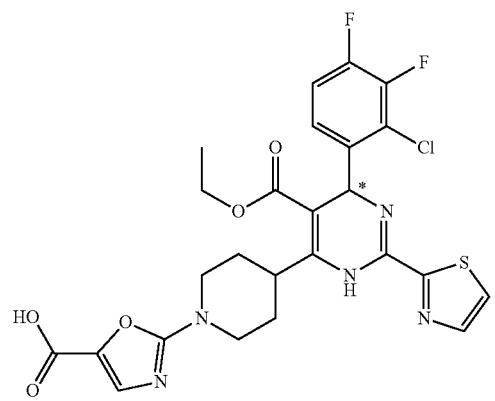
Compound II-55-B
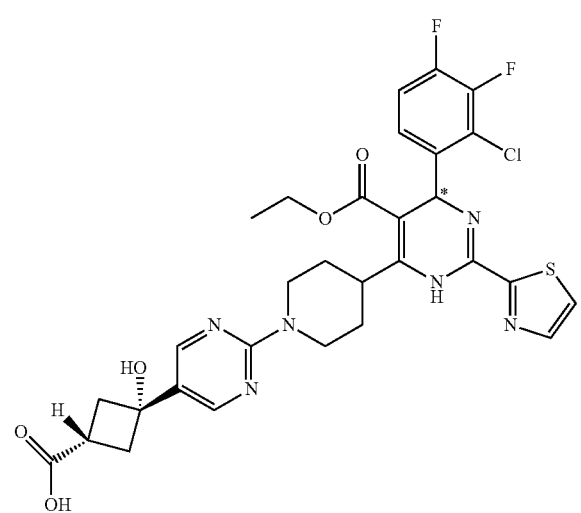
Compound II-58-B
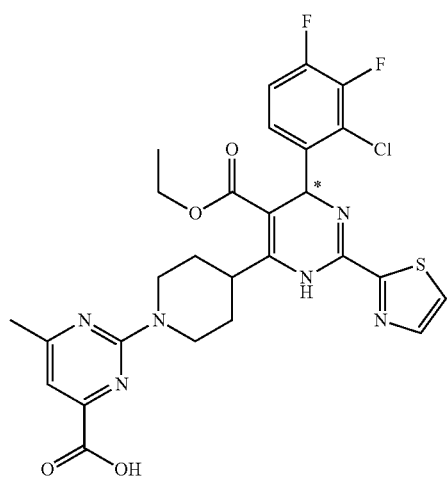
Compound II-59-B
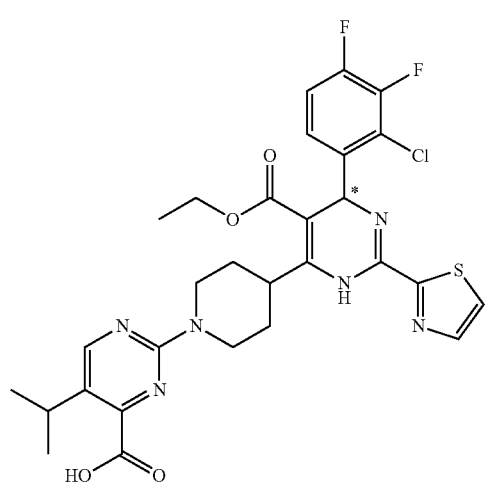
Compound II-60-B
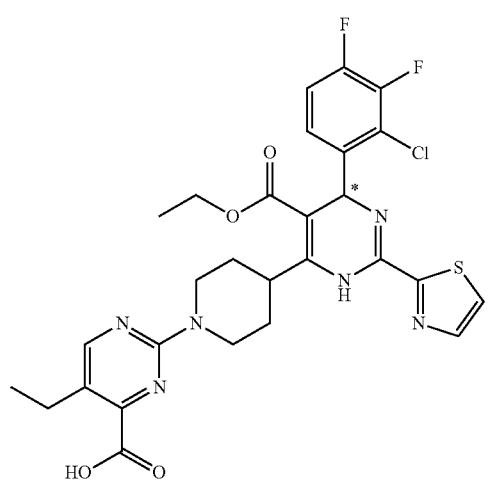
Compound II-61-B
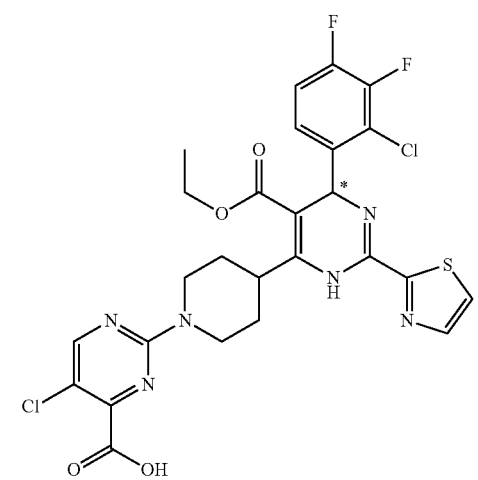

Compound II-63-B
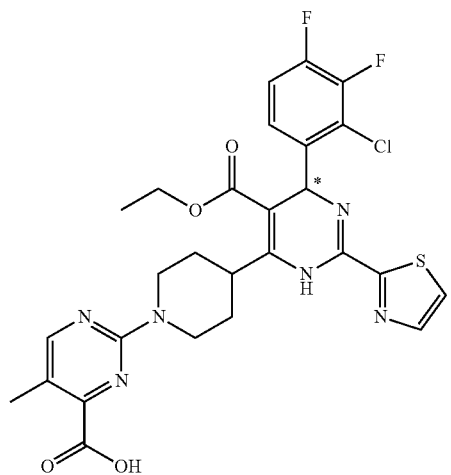
Compound II-67-B
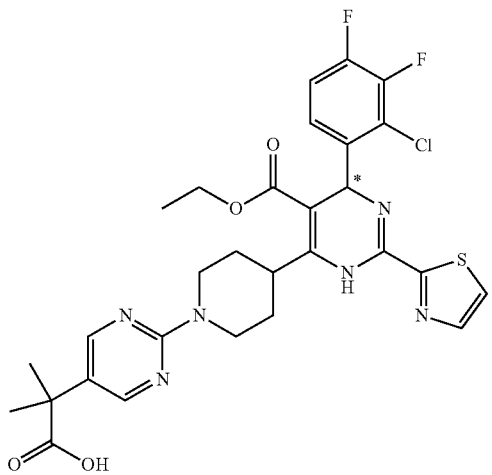
Compound II-65-B
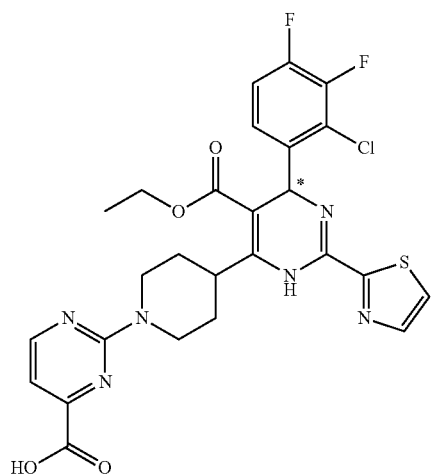
Compound II-68-B
Compound II-66-B
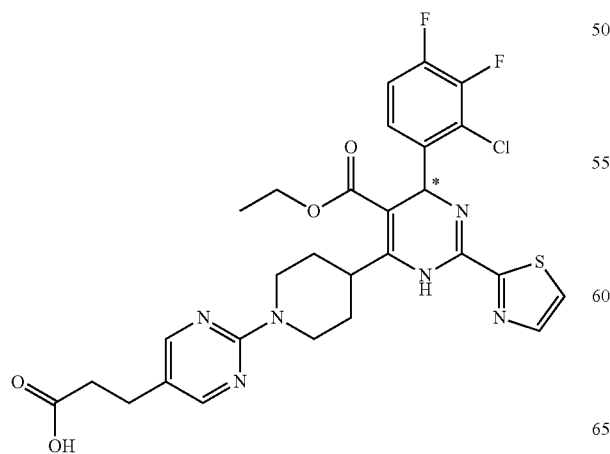
Compound II-69-B
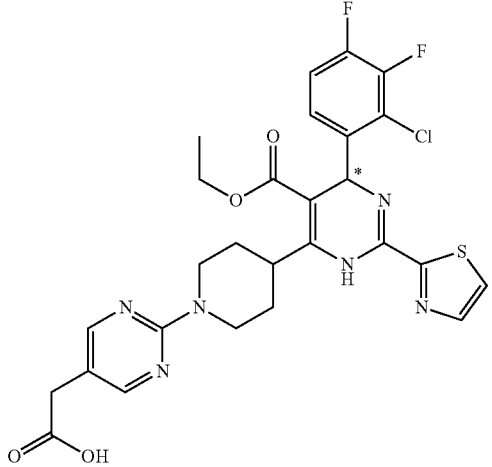

Compound II-70-B
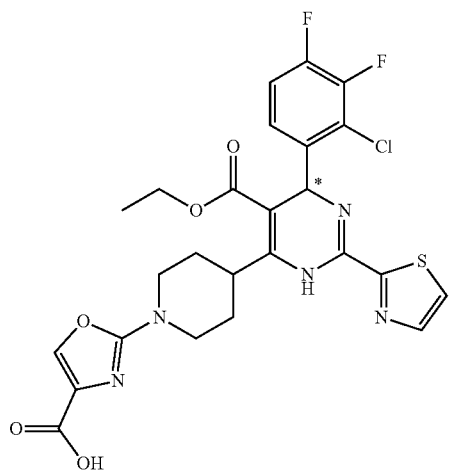
Compound II-74-B
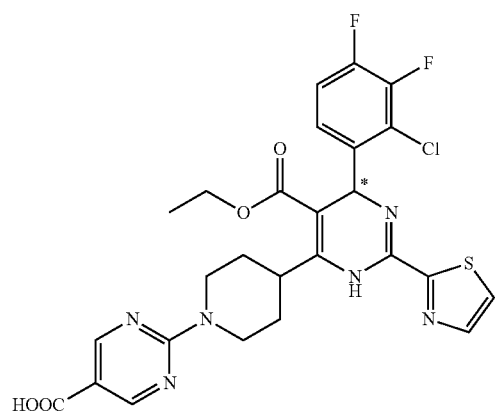
Compound II-78-B
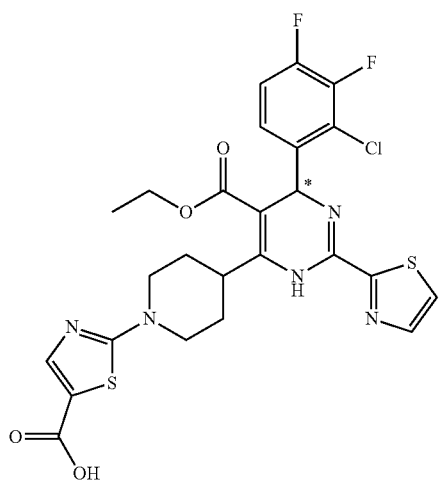
Compound II-80-B
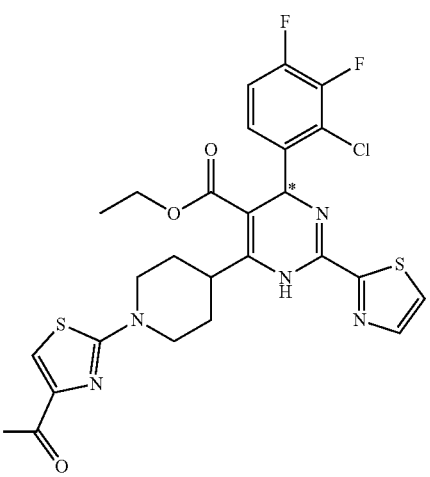
Compound II-82-B
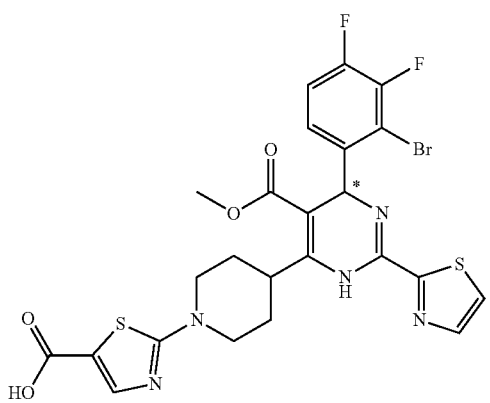
Compound II-84-B
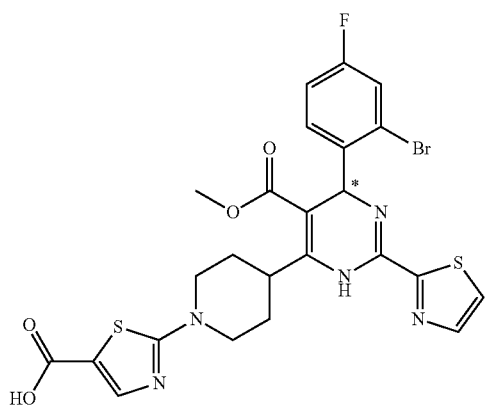

Compound II-86-B

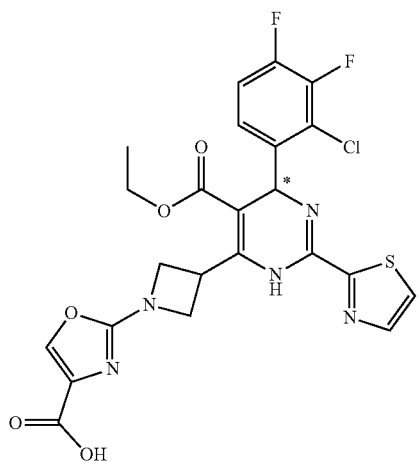

Compound II-17-B

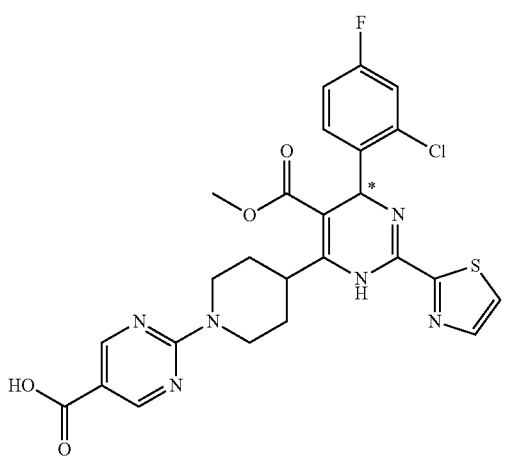

The disclosed compounds may possess one or more stereocenters, and each stereocenter may exist independently in either the R or S configuration. The stereochemical configuration may be assigned at indicated centers as (*) when the absolute stereochemistry is undetermined at the stereocenter although the compound itself has been isolated as a single stereoisomer and is enatiomerically/diastereomerically pure. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

When the absolute R or S stereochemistry of a compound cannot be determined, it can be identified by the retention time after chromatography under particular chromatographic conditions as determined by chromatography column, eluent etc.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$ $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and techniques known to a person skilled in the art. General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein. General synthesis schemes are given in the Examples below.

Accordingly, a process is provided for producing the compound of formula (I), wherein said process comprises reacting an activated acyl compound of formula III-1,

III-1

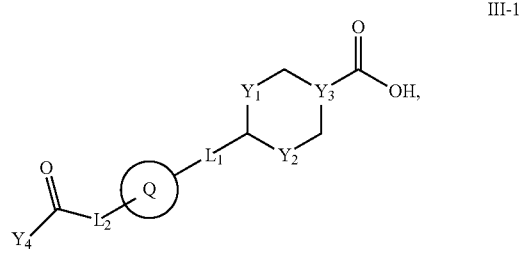

with R3-malonate into an intermediate of formula IV-1,

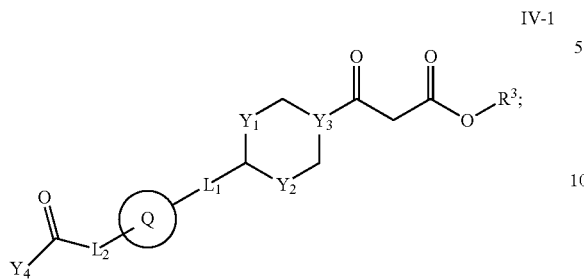

IV-1 subjecting the compound of formula IV-1 with compounds of general formula V and VI, i.e.,

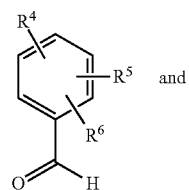

V

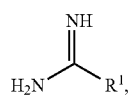

VI to a multiple component reaction in the presence of a base in order to provide an intermediate of formula VII

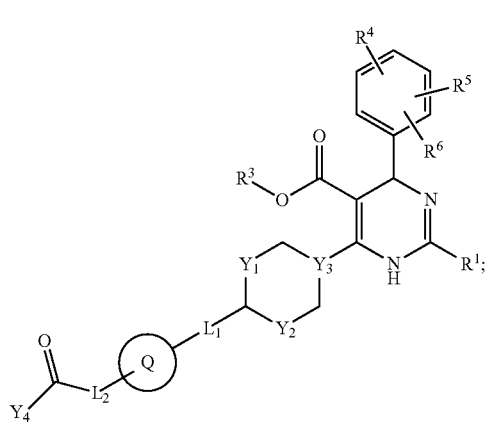

VII subjecting the intermediate of formula VII to ester hydrolysis in order to provide a compound of formula I.

In an other embodiment a process is provided for producing the compound of formula (I), wherein p is 1, and A is N, and wherein the compound produced is a compound satisfying formula II, the processing comprising:

reacting an activated acyl compound of formula III-2,

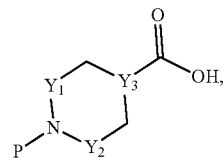

III-2

P is protecting group with $R^3$-malonate into an intermediate of formula IV-2,

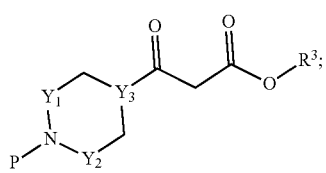

IV-2

P is protecting group subjecting the compound of formula IV-2 with compounds of general formula V and VI, i.e.,

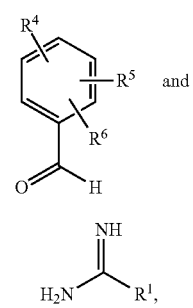

V

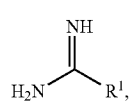

VI to a multiple component reaction in the presence of a base in order to provide an intermediate of formula VIII,

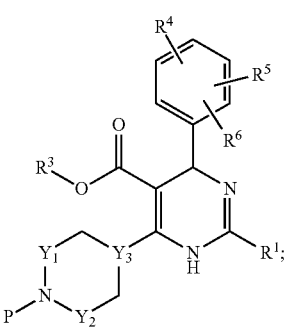

VIII

P is protecting group subjecting the compound of formula VIII with the deprotection reaction to provide an intermediate of formula IX,

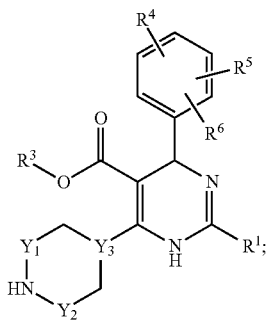

subjecting the compound of formula IX with a coupling reaction to provide an intermediate of formula XI,

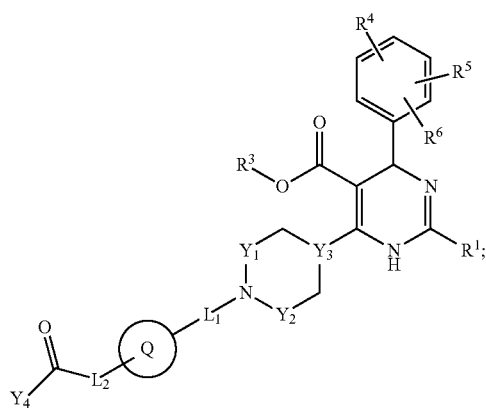

subjecting the intermediate of formula XI to ester hydrolysis in order to provide a compound of formula II:

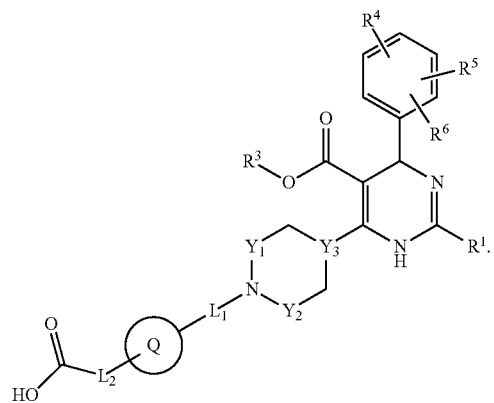

Methods

Provided herein is a method of treating an HBV infection in an individual in need thereof, comprising administering to the individual a therapeutically effective amount of a disclosed compound.

Also provided herein is a method of eradicating an HBV infection in an individual in need thereof, comprising administering to the individual a therapeutically effective amount of a disclosed compound.

Provided herein is a method of reducing viral load associated with an HBV infection in an individual in need thereof, comprising administering to the individual a therapeutically effective amount of a disclosed compound.

Further, provided herein is a method of reducing reoccurrence of an HBV infection in an individual in need thereof, comprising administering to the individual a therapeutically effective amount of a disclosed compound.

Provided herein is a method of inhibiting or reducing the formation or presence of HBV DNA-containing particles or HBV RNA-containing particles in an individual in need thereof, comprising administering to the individual a therapeutically effective amount of a disclosed compound.

In certain aspects, the methods and/or compositions described herein are effective for inhibiting or reducing the formation or presence of HBV-associated particles in vitro or in vivo (e.g., in a cell, in a tissue, in an organ (e.g., in the liver), in an organism or the like). HBV-associated particles may contain HBV DNA (i.e., linear and/or covalently closed circular DNA (cccDNA)) and/or HBV RNA (i.e., pre-genomic RNA and/or sub-genomic RNA). Accordingly, HBV-associated particles include HBV DNA-containing particles or HBV RNA-containing particles.

As used herein, "HPV-associated particles" refer to both infectious HBV virions (i.e., Dane particles) and non-infectious HBV subviral particles (i.e., HBV filaments and/or HBV spheres). HBV virions comprise an outer envelope including surface proteins, a nucleocapsid comprising core proteins, at least one polymerase protein, and an HBV genome. HBV filaments and HBV spheres comprise HBV surface proteins, but lack core proteins, polymerase and an HBV genome. HBV filaments and HBV spheres are also known collectively as surface antigen (HBsAg) particles. HBV spheres comprise middle and small HBV surface proteins. HBV filaments also include middle, small and large HBV surface proteins.

HBV subviral particles can include the nonparticulate or secretory HBeAg, which serves as a marker for active replication of HBV.

Provided herein is a method of reducing an adverse physiological impact of an HBV infection in an individual in need thereof, comprising administering to the individual a therapeutically effective amount of a disclosed compound.

Also provided herein is a method of reducing, slowing, or inhibiting an HBV infection in an individual in need thereof, comprising administering to the individual a therapeutically effective amount of a disclosed compound.

Provided herein is a method of inducing reversal of hepatic injury from an HBV infection in an individual in need thereof, comprising administering to the individual a therapeutically effective amount of a disclosed compound.

Provided herein is a method of reducing the physiological impact of long-term antiviral therapy for HBV infection in an individual in need thereof, comprising administering to the individual a therapeutically effective amount of a disclosed compound.

Provided herein is a method of prophylactically treating an HBV infection in an individual in need thereof, wherein the individual is afflicted with a latent HBV infection, comprising administering to the individual a therapeutically effective amount of a disclosed compound.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the disclosed method reduces viral load in an individual suffering from an HBV infection to a greater extent or at a faster rate compared to the extent that other therapeutic classes of HBV drugs reduce viral load in the individual.

In one embodiment, the administering of a disclosed compound, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a disclosed compound, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the disclosed method reduces viral load in an individual suffering from an HBV infection, thus allowing lower doses or varying regimens of combination therapies to be used.

In one embodiment, the disclosed method causes a lower incidence of viral mutation or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the disclosed method increases the seroconversion rate from HBV infected to non-HBV infected or from detectable HBV viral load to non-detectable HBV viral load beyond that of current treatment regimens. As used herein, "seroconversion" refers to the period of time during which HBV antibodies develop and become detectable.

In one embodiment, the disclosed method increases or normalizes or restores normal health, elicits full recovery of normal health, restores life expectancy, or resolves the viral infection in the individual in need thereof.

In one embodiment, the disclosed method eliminates or decreases the number of HBV RNA particles that are released from HBV infected cells thus enhancing, prolonging, or increasing the therapeutic benefit of the disclosed compounds.

In one embodiment, the disclosed method eradicates HBV from an individual infected with HBV, thereby obviating the need for long term or life-long treatment, or shortening the duration of treatment, or allowing for reduction in dosing of other antiviral agents.

In another embodiment, the disclosed method further comprises monitoring or detecting the HBV viral load of the subject, and wherein the method is carried out for a period of time including until such time that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In an embodiment of any of the methods provided herein, the method can further comprise monitoring the HBV viral load of the subject, wherein the method is carried out for a period of time such that the HBV virus is undetectable.

Combination Therapies

The disclosed compounds may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors:

viral maturation inhibitors;

literature-described capsid assembly modulators, such as, but not limited to, BAY 41-4109;

reverse transcriptase inhibitors;

immunomodulatory agents such as TLR-agonists; and agents of distinct or unknown mechanisms, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member of the family of highly homologous species-specific proteins that inhibit viral replication and cellular proliferation and modulate immune response. Human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula I can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]-amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of Recombivax HB, Engerix-B, Elovac B, Genevac-B, or Shanvac B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine. The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with a antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered.

For any combination therapy described herein, synergistic effect may be calculated, for example, using suitable methods such as the Sigmoid-$E_{max}$ equation (Holford & Schemer, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Administration/Dosage/Formulations

In another aspect, provided herein is a pharmaceutical composition comprising at least one disclosed compound, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 2,500 mg. In some embodiments, a dose of a disclosed compound used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a disclosed compound, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES
Example 1
General Scheme 1
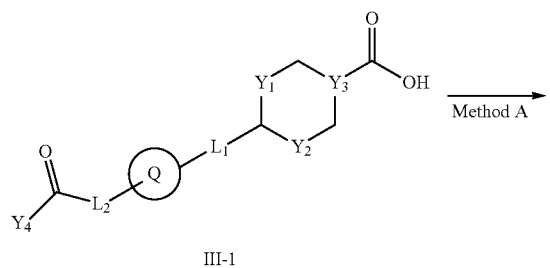
III-1
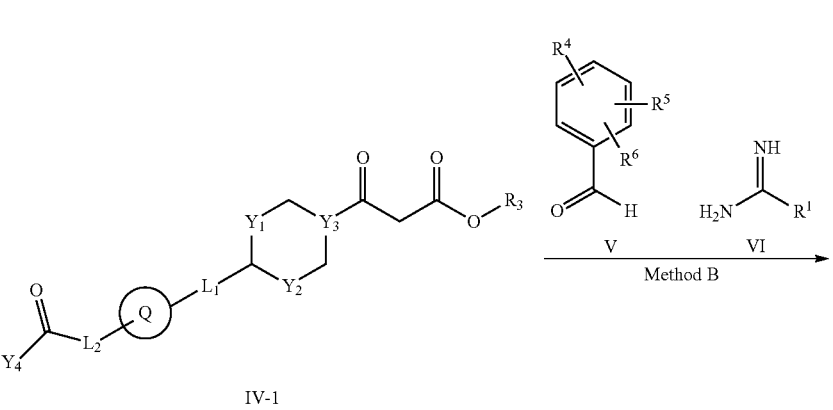
IV-1
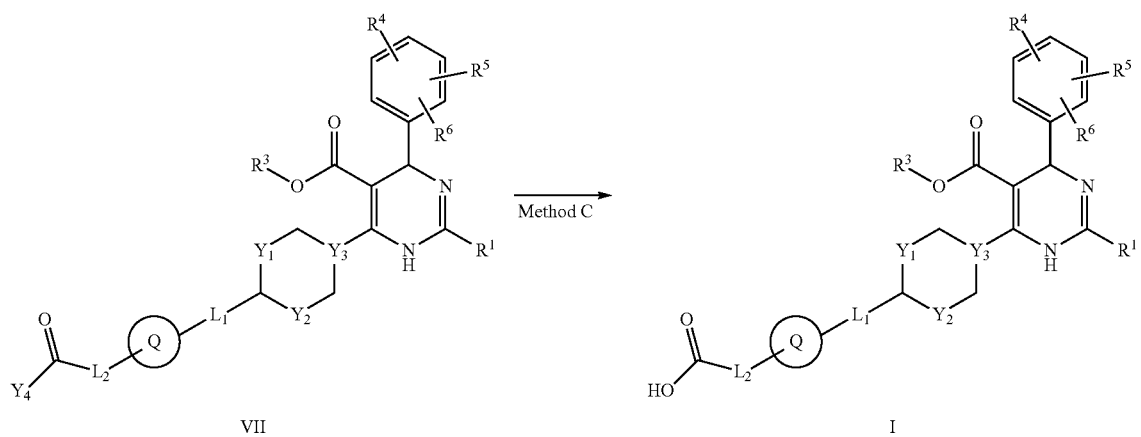
VII                                    I

General Scheme 2

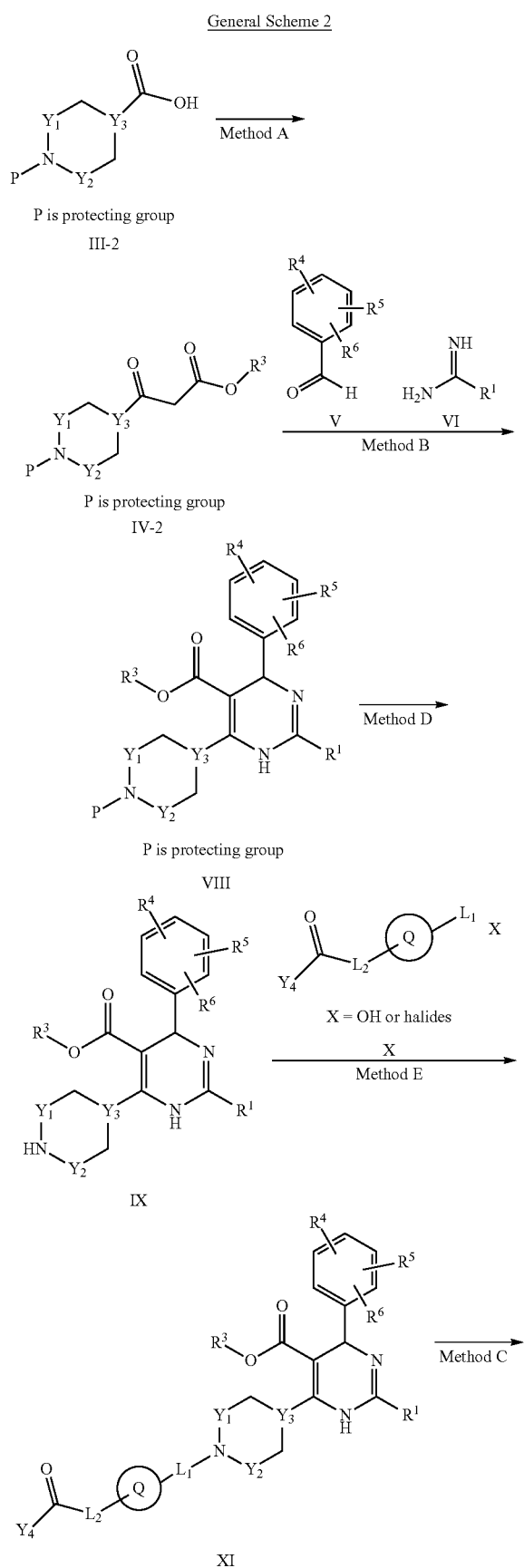

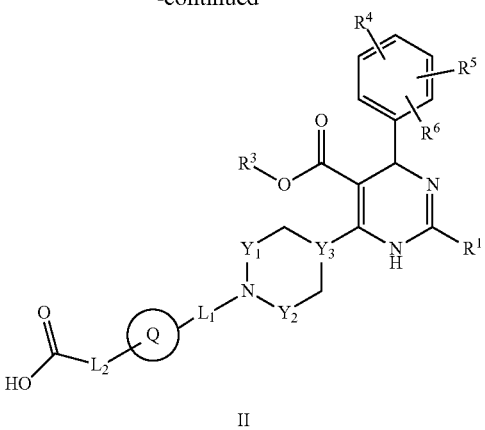

The general synthesis of final compound of general formula I is described in general scheme 1. Compound of general formula IV-1 can be synthesized with Method A. As described in Method A, an acid of general formula III-1 is activated, e.g. into an acyl imidazole, and coupled with methyl (or ethyl) potassium malonate under basic condition to generate an intermediate which in turn undergoes decarboxylation to yield the ketoester of general formula IV-1. The compound of general formula VII can be synthesized through a chemical methodology of multiple component reaction (Method B) with compounds of general formula IV-1, V and VI in the presence of base (but not limited to sodium acetate NaOAc) in solvent of choice (but not limited to ethanol). The final product of general formula I can be synthesized through an ester hydrolysis reaction (Method C).

The general synthesis of final compound of general formula II is described in general scheme 2. Compound of general formula IV-2 can be synthesized with Method A. As described in Method A, an acid of general formula III-2 is converted by reacting with N,N-carbonyldiimidazole CDI to an activated ester which then couples with methyl (or ethyl) potassium malonate under basic condition to generate an intermediate which in turn undergoes decarboxylation to yield the ketoester of general formula IV-2. The compound of general formula VIII can be synthesized through a chemical methodology of multiple component reaction (Method B) with compounds of general formula IV-2, V and VI in the presence of base (but not limited to sodium acetate NaOAc) in solvent of choice (but not limited to ethanol). The free amine of general formula IX can be synthesized by a deprotection reaction (Method D). Compound of general formula II can be synthesized from general formula IX and general formula X, through $S_NAr$ reaction (Method E), and then followed by an ester hydrolysis reaction (Method C). Some of final compounds of general formula II were synthesized through forming the ketoester intermediates and then multiple component reaction procedure.

Method A

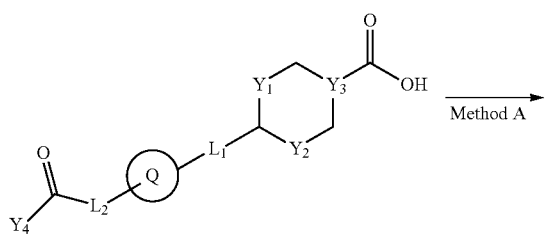

III-1

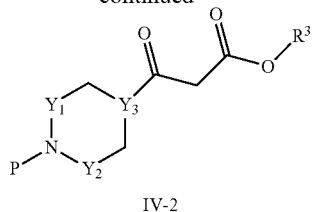

IV-2

To a solution of the acid of general formula III-1 or III-2 (1 equivalent) in acetonitrile was added N,N'-carbonyldiimidazole (1.1-2 equivalents) at room temperature. The mixture was stirred at room temperature under nitrogen atmosphere for 2 hours (mixture A). To a suspension of methyl potassium malonate (2-2.1 equivalents, $R^3$ is methyl) or ethyl potassium malonate (2-2.1 equivalents, $R^3$ is ethyl) in acetonitrile was added magnesium chloride (2.1-2.5 equivalents) and triethylamine (3-3.2 equivalents) at room temperature. After stirred under nitrogen atmosphere for 2 hours, the resulting mixture was added mixture A and stirring continued at 80-100° C. in a range of three hours to overnight. It was then cooled down to room temperature and concentrated to give a residue, which was purified by silica gel column chromatography to afford the ketoester of general formula IV-1 or IV-2.

Method B

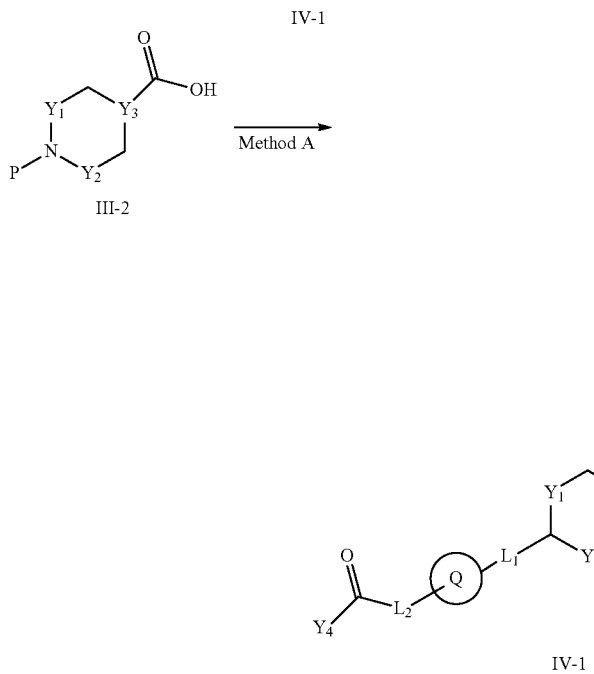

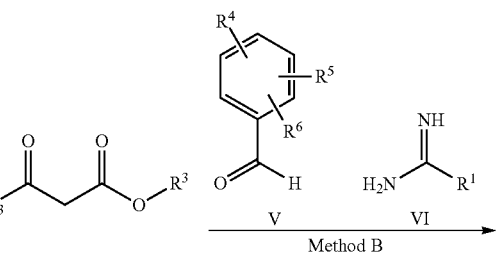

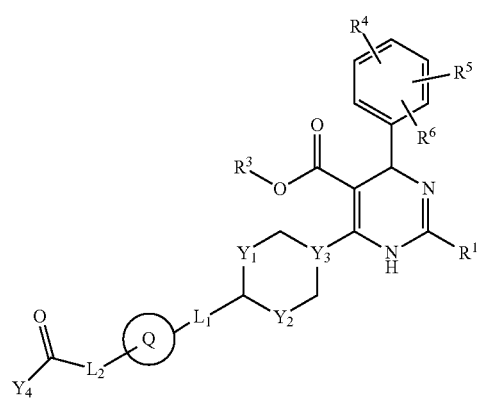

VII

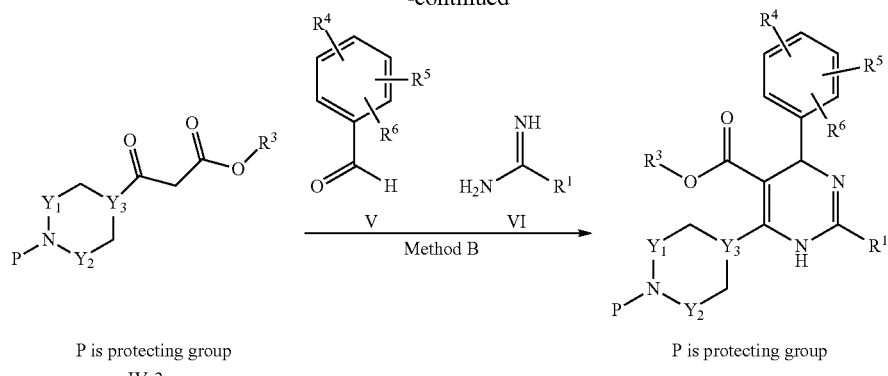

P is protecting group
IV-2

P is protecting group
VIII

To a solution of the ketoester of general formula IV-1 or IV-2 (1 equivalent) in ethanol was added the aldehyde of general formula V (1 equivalent), the carboxamidine hydrochloride of general formula VI (1 equivalent) and sodium acetate (1-1.2 equivalents). The mixture was brought up to 70-100° C. and stirred under nitrogen atmosphere from sixteen hours to overnight. After cooled down to room temperature, it was concentrated to dryness. The residue was extracted from dichloromethane, washed with water, brine, dried over anhydrous $Na_2SO_4$ and filtered. The filtrate was concentrated under reduced pressure to give a residue, which was purified by silica gel column chromatography to afford the dihydropyrimidine product of general formula VII, or general formula VIII. When applicable, the stereoisomers of the dihydropyrimidine product of general formula VII or general formula VIII were isolated and purified using chiral chromatography.

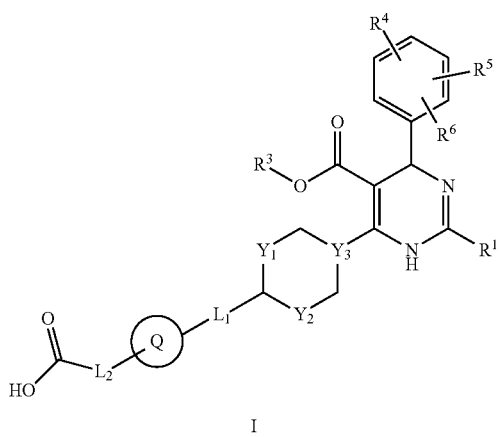

I

Method C

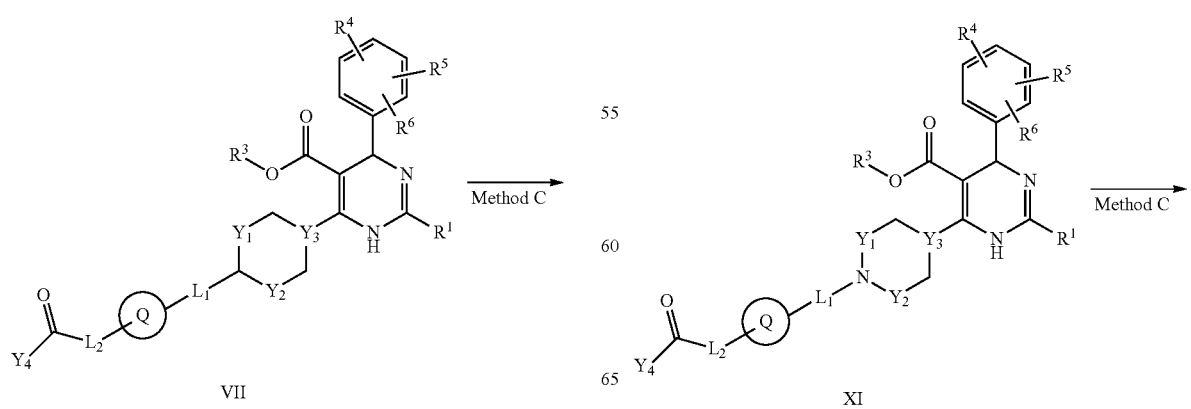

VII

XI

-continued

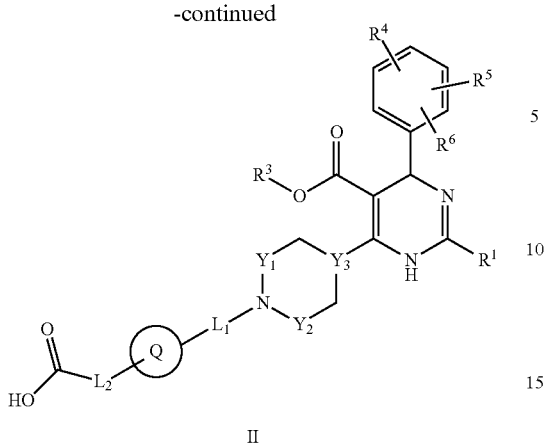

II

To a solution of the ester of general formula VII (1 equivalent), or formula XI (1 equivalent), in the solvents of tetrahydrofuran:methanol:water 2:2:1 was added lithium hydroxide hydrate (2 equivalent) at 0° C. After stirred at 0° C. for 2 hours, the mixture was added with water, and concentrated at room temperature under reduced pressure to remove volatiles. The residue was acidified with 1 M hydrochloride aqueous solution and purified by silica gel column chromatography to afford the final compound of general formula I, or II, respectively. When applicable, the stereoisomers of the dihydropyrimidine product of general formula I and II were isolated and purified using chiral chromatography.

Method D

To a solution of general formula VIII (1 equivalent) in dichloromethane was added trifluoroacetic acid (80 equivalent) at room temperature. After stirred at room temperature for 0.5 hour, the mixture was concentrated under reduced pressure to give a residue, which was dissolved in ethyl acetate and washed with saturated sodium bicarbonate aqueous solution for three times, water for three times, and brine for three times, dried over $Na_2SO_{4(s)}$ and filtered. The filtrate was concentrated under reduced pressure to give the final compound of general formula IX.

Method E

To a solution of general formula IX (1 equivalent) and general formula X (1 equivalent) in solvent (such as 1,4-dioxane, DMF) was added base (such as triethylamine, N,N-Diisopropylethylamine, or potassium carbonate, 5 equivalent) at room temperature. After stirred at 100° C. under nitrogen atmosphere for 5 hours and cooled down to room temperature, the mixture was diluted with water and extracted with ethyl acetate twice. The combined organic layers were washed with brine, dried over $Na_2SO_{4(s)}$ and filtered. The filtrate was concentrated under reduced pressure to give a residue, which was purified by C18 column to give the product of general formula XI. When applicable, the stereoisomers of the dihydropyrimidine products of general formula XI were isolated and purified using chiral chromatography.

Part I: Preparation of Acids of General Formula III-1 and III-2

Acid 1

4-(4-(methoxycarbonyl)oxazol-2-yl)cyclohexane-1-carboxylic Acid (A1)

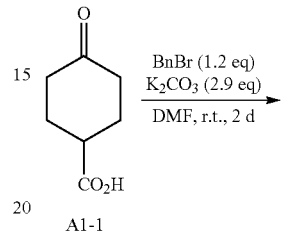

A1-1

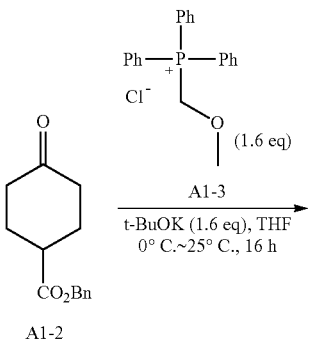

A1-2

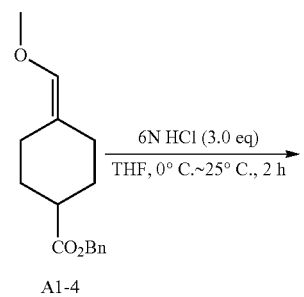

A1-4

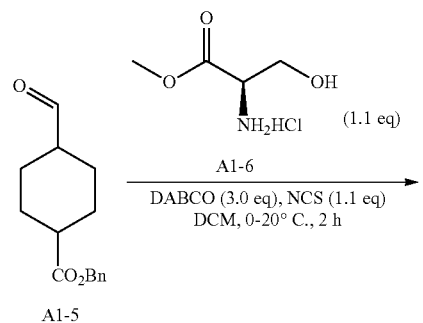

A1-5

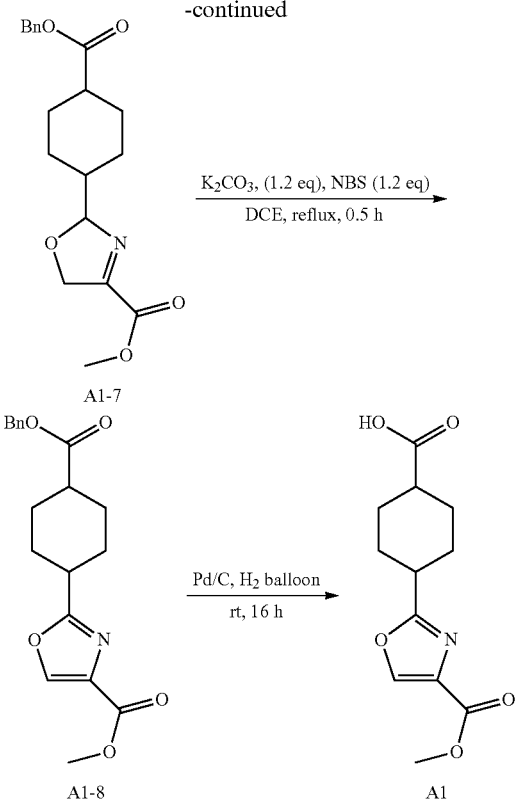

Intermediate A1-2

Benzyl 4-oxocyclohexanecarboxylate

To a solution of 4-oxocyclohexanecarboxylic acid A1-1 (20.0 g, 0.141 mol), potassium carbonate (38.9 g, 0.282 mol) in N,N-dimethylformamide (100 mL) was added (bromomethyl)benzene (28.8 g, 0.169 mol). The mixture was stirred at room temperature for 2 days. The reaction mixture was poured into water (450 mL), extracted with ethyl acetate (200 mL) for three times. The combined organic layers were washed with water (100 mL), brine (100 mL), dried over $Na_2SO_{4(s)}$, filtered and concentrated to give the crude product, which was purified by silica gel column chromatography (petroleum ether:ethyl acetate=10:1 to 5:1) to give the title compound (30.0 g, 92% yield) as yellow oil. $^1H$ NMR (300 MHz, DMSO-$d_6$) δ 7.37-7.26 (m, 5H), 5.12-5.05 (m, 2H), 2.91-2.79 (m, 1H), 2.41-2.31 (m 2H), 2.23-2.08 (m 4H), 1.87-1.72 (m 2H).

Intermediate A1-4

Benzyl 4-(methoxymethylene)cyclohexanecarboxylate

To a mixture of (methoxymethyl)triphenylphosphonium chloride A1-3 (54.8 g, 0.160 mol) in tetrahydrofuran (350 mL) was added potassium tert-butoxide (17.9 g, 0.160 mol) at 0° C. slowly to keep inner temperature below 5° C. After stirring at this temperature for 1 hour, a solution of benzyl 4-oxocyclohexanecarboxylate A1-2 (23.7 g, 0.100 mol) in tetrahydrofuran (50 mL) was added into the mixture. The mixture was warmed up to 25° C. slowly and stirred at 25° C. for 16 hours. The reaction mixture was diluted with water (500 mL). The organic phase was separated. The aqueous layer was extracted with ethyl acetate (100 mL) for three times. The combined organic layers were washed with brine (100 mL), dried over $Na_2SO_{4(s)}$ and filtered. The filtrate was concentrated to give a residue, which was purified by silica gel column chromatography (petroleum ether:ethyl acetate=200:1 to 50:1) to give the title compound (19.1 g, 72% yield) as colorless oil. $^1H$ NMR (300 MHz, CDCl$_3$) δ 7.38-7.29 (m, 5H), 5.77 (s, 1H), 5.11 (s, 2H), 3.53 (s, 3H), 2.76-2.71 (m, 1H), 2.51-2.43 (m, 1H), 2.13-2.08 (m, 1H), 2.01-1.87 (m, 3H), 1.79-1.71 (m, 1H), 1.56-1.45 (m, 2H).

Intermediate A1-5

Benzyl 4-formylcyclohexanecarboxylate

To a mixture of benzyl 4-(methoxymethylene)cyclohexane-1-carboxylate A1-4 (19.1 g, 73.5 mmol) in tetrahydrofuran (160 mL) was added 6 M hydrochloride aqueous solution (38.2 mL, 229 mmol) at 0° C. After stirred at 25° C. for 2 hours, the reaction mixture was quenched with brine (300 mL). The organic layer was separated out. The aqueous layer was extracted with ethyl acetate (200 mL) for three times. The combined organic layers were washed with brine (200 mL), dried over $Na_2SO_{4(s)}$ and filtered. The filtrate was concentrated to give the title compound (17.6 g, 98% yield) as yellow oil. $^1H$ NMR (400 MHz, CDCl$_3$) δ 9.65 (s, 0.4H), 9.63 (s, 0.6H), 7.37-7.31 (m, 5H), 5.12 (s, 1.2H), 5.11 (s, 0.8H), 2.51-2.48 (m, 0.3H), 2.35-2.22 (m, 1.5H), 2.15-2.04 (m, 2.7H), 1.99-1.93 (m, 0.5H), 1.79-1.75 (m, 1H), 1.71-1.66 (m, 1H), 1.56-1.47 (m, 1.5H), 1.34-1.26 (m, 1.5H).

Intermediate A1-7

Methyl 2-(4-((benzyloxy)carbonyl)cyclohexyl)-2,5-dihydrooxazole-4-carboxylate To a mixture of (R)-methyl 2-amino-3-hydroxypropanoate hydrochloride A1-6 (12.2 g, 78.7 mmol) in dichloromethane (350 mL) was added 1,4-diazabicyclo[2.2.2]octane (24.1 g, 215 mmol). After stirring at 25° C. under nitrogen atmosphere for 20 minutes, the mixture was added a solution of benzyl 4-formylcyclohexanecarboxylate A1-5 (17.6 g, 71.5 mmol) in dichloromethane (350 mL). The mixture was stirred at 25° C. under nitrogen atmosphere for 30 minutes. To the mixture was added N-chlorosuccinimide (10.5 g, 78.7 mmol) at 0° C. and the resulting mixture was stirred at 0° C. for 2 hours. The reaction mixture was quenched with saturate sodium metabisulfite aqueous solution (300 mL). The organic phase was separated. The aqueous layer was extracted with dichloromethane (100 mL) for three times. The combined organic layers were washed with brine (100 mL), dried over $Na_2SO_{4(s)}$ and filtered. The filtrate was concentrated to give a residue, which was purified by silica gel column chromatography (petroleum ether:ethyl acetate=20:1 to 5:1) to give the title compound (18.4 g, 74% yield) as colorless oil. $^1H$ NMR (400 MHz, CDCl$_3$) δ 7.38-7.30 (m, 5H), 5.72-5.67 (m, 1H), 5.14-5.11 (m, 2H), 4.86-4.71 (m, 2H), 3.92 (s, 3H), 2.68-2.66 (m, 0.2H), 2.35-2.31 (m, 0.8H), 2.28-2.19 (m, 0.6H), 2.16-2.06 (m, 1.6H), 1.94-1.91 (m, 0.8H), 1.84-1.69 (m, 2H), 1.62-1.40 (m, 3H), 1.26-1.17 (m, 1H).

Intermediate A1-8

Methyl 2-(4-((benzyloxy)carbonyl)cyclohexyl)oxazole-4-carboxylate

A mixture of methyl 2-(4-((benzyloxy)carbonyl)cyclohexyl)-2,5-dihydrooxazole-4-carboxylate A-7 (5.00 g, 14.5 mmol), potassium carbonate (2.30 g, 17.4 mmol) in 1,2-dichloroethane (150 mL) was stirred at 25° C. under nitrogen atmosphere for 30 minutes. N-Bromosuccinimide (3.13 g, 17.4 mmol) was added into the mixture. After refluxing for 30 minutes, the reaction mixture was cooled down to room temperature, quenched with saturate sodium sulfite aqueous solution (50 mL), saturate sodium bicarbonate aqueous solution (50 mL) and separated. The aqueous layer was extracted with ethyl acetate (50 mL) for three times. The combined organic layers were washed with brine (50 mL), dried over $Na_2SO_{4(s)}$ and filtered. The filtrate was concentrated to give a residue, which was purified by silica gel column chromatography (petroleum ether:ethyl acetate=10:1 to 3:2) to give the title compound (3.30 g, 66% yield) as white solids. LC-MS (ESI): $R_T$=1.823 min, mass calcd. for $C_{19}H_{21}NO_5$ 343.1, m/z found 344.1 [M+H]$^+$. $^1$H NMR (400 MHz, CDCl$_3$) δ 8.15 (s, 1H), 7.39-7.31 (m, 5H), 5.13 (s, 2H), 3.90 (s, 3H), 3.03-2.97 (m, 0.2H), 2.87-2.79 (m, 0.8H), 2.64-2.58 (m, 0.2H), 2.45-2.37 (m, 0.8H), 2.23-2.14 (m, 4H), 1.98-1.85 (m, 1H), 1.75-1.69 (m, 1H), 1.63-1.52 (m, 2H).

Acid 1

4-(4-(Methoxycarbonyl)oxazol-2-yl)cyclohexanecarboxylic Acid

To a mixture of methyl 2-(4-((benzyloxy)carbonyl)cyclohexyl)oxazole-4-carboxylate A1-8 (3.30 g, 9.60 mmol) in ethyl acetate (60 mL) was added 10% palladium on charcoal wt. (660 mg) under nitrogen atmosphere. The mixture was stirred at room temperature under hydrogen atmosphere (H$_2$ balloon) for 16 hours. The reaction mixture was filtered and the filtrate was concentrated to give the title compound (1.30 g, 54% yield) as red solids. $^1$H NMR (400 MHz, CDCl$_3$) δ 8.16 (s, 1H), 3.91 (s, 3H), 3.05-2.97 (m, 0.4H), 2.88-2.79 (m, 0.6H), 2.67-2.59 (m, 0.4H), 2.43-2.33 (m, 0.6H), 2.24-2.16 (m, 2H), 2.10-2.02 (m, 2H), 1.95-1.87 (m, 1H), 1.76-1.50 (m, 3H).

Acid 2

3-(4-(methoxycarbonyl)oxazol-2-yl)bicyclo[1.1.1]pentane-1-carboxylic Acid (A2)

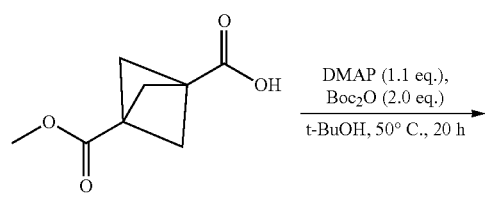

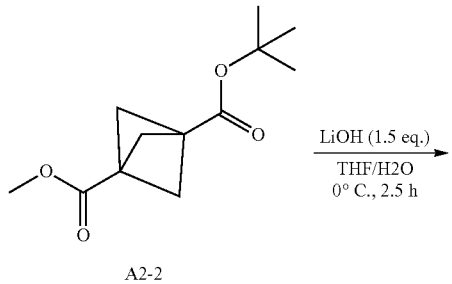

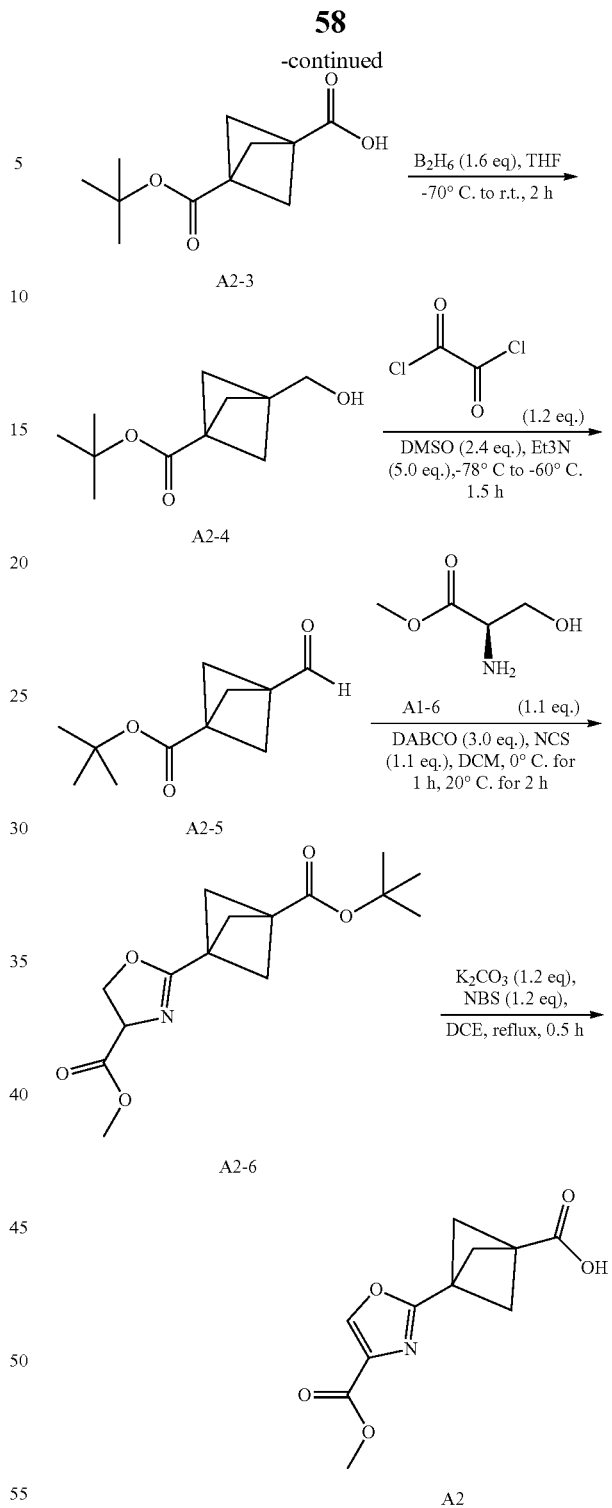

Intermediate A2-2

1-(tert-butyl) 3-methyl bicyclo[1.1.1]pentane-1,3-dicarboxylate

To a solution of 3-(methoxycarbonyl)bicyclo[1.1.1]pentane-1-carboxylic acid A2-1 (1.94 g, 11.2 mmol) and di-tert-butyl dicarbonate (4.98 g, 22.8 mmol) in tert-butanol (32 mL) was added N,N-dimethylpyridin-4-amine (1.53 g, 12.5 mmol) at room temperature. After stirred at 50° C. for 20 hours, the reaction mixture was concentrated under reduced pressure to remove the volatile and dissolved in ethyl acetate (100 mL). The resulting solution was washed with water (50 mL), 0.2 M hydrochloride aqueous solution (70 mL), saturated sodium bicarbonate aqueous solution (60 mL), water (50 mL) and brine (50 mL), dried over $Na_2SO_{4(s)}$ and filtered. The filtrate was concentrated under reduced pressure to give the title compound (2.55 g, 90% purity from $^1$H NMR, 91% yield) as white solids. $^1$H NMR (400 MHz, $CDCl_3$) δ 3.67 (s, 3H), 2.45 (s, 6H), 1.43 (s, 9H).

Intermediate A2-3

3-(tert-Butoxycarbonyl)bicyclo[1.1.1]pentane-1-carboxylic Acid

To a solution of 1-tert-butyl 3-methyl bicyclo[1.1.1]pentane-1,3-dicarboxylate A2-2 (2.55 g, 90% purity, 10.1 mmol) in tetrahydrofuran (30 mL) and water (10 mL) was added lithium hydroxide monohydrate (651 mg, 15.5 mmol) at 0° C. After stirred at 0° C. for 2.5 hours, the reaction mixture was concentrated under reduced pressure to give a residue, which was diluted with water (10 mL) and extracted with ethyl acetate (20 mL). Then the aqueous was acidified to pH 3~4 with 0.2 M hydrochloride aqueous solution and extracted with ethyl acetate (40 mL) for three times. The combined organic layers were washed with brine (40 mL), dried over $Na_2SO_{4(s)}$ and filtered. The filtrate was concentrated under reduced pressure to give the title compound (2.10 g, 90% purity from $^1$H NMR, 88% yield) as white solids. $^1$H NMR (300 MHz, DMSO-$d_6$) δ 12.53 (br s, 1H), 2.13 (s, 6H), 1.39 (s, 9H).

Intermediate A2-4 tert-Butyl 3-(hydroxymethyl)bicyclo[1.1.1]pentane-1-carboxylate

To a solution of 3-(tert-butoxycarbonyl)bicyclo[1.1.1]pentane-1-carboxylic acid A2-3 (2.10 g, 90% purity, 8.91 mmol) in tetrahydrofuran (33 ml) was added 10 M borane-dimethylsulfide complex (1.4 mL, 14.0 mmol) in tetrahydrofuran (7 ml) at −70° C. under nitrogen atmosphere. After allowed to warm to room temperature and stirred for 2 hours under nitrogen atmosphere, the reaction mixture was quenched with water (15 mL) and saturated sodium bicarbonate aqueous solution (15 mL) at 0° C. and extracted with ethyl acetate (40 mL) for three times. The combined organic layers were washed with brine (40 mL), dried over $Na_2SO_{4(s)}$ and filtered. The filtrate was concentrated under reduced pressure to give title compound (1.95 g, 90% purity from $^1$H NMR, 99% yield) as colorless oil. $^1$H NMR (300 MHz, $CDCl_3$) δ 3.61 (s, 2H), 1.93 (s, 6H), 1.43 (s, 9H).

Intermediate A2-5 tert-Butyl 3-formylbicyclo[1.1.1]pentane-1-carboxylate

To a solution of dimethylsulfoxide (1.68 g, 21.5 mmol) in dichloromethane (80 ml) was slowly added oxalyl chloride (1.38 g, 10.9 mmol) at −78° C. under nitrogen atmosphere. The reaction mixture was allowed to warm to −60° C. and stirred for 15 minutes at the same temperature. After a solution of methyl 3-(hydroxymethyl)bicyclo[1.1.1]pentane-1-carboxylate A2-4 (1.95 g, 90% purity, 8.85 mmol) in dichloromethane (15 ml) was added at −60° C., the mixture was stirred at −60° C. for 30 minutes. After triethylamine (4.52 g, 44.3 mmol) was added at −60° C., the reaction mixture was stirred at −60° C. for 30 minutes. The reaction mixture was quenched with water (20 ml) at −60° C. and warmed to room temperature. The organic layer was separated. The aqueous layer was extracted with dichloromethane (50 ml) twice. The combined organic layers were washed with 0.3 M hydrochloride aqueous solution (150 ml), water (80 mL) and brine (80 mL), dried over $Na_2SO_{4(s)}$ and filtered. The filtrate was concentrated under reduced pressure to give the title compound (1.84 g, 90% purity from $^1$H NMR, 95% yield) as white solids. $^1$H NMR (300 MHz, DMSO-$d_6$) δ 9.53 (s, 1H), 2.17 (s, 6H), 1.40 (s, 9H).

Intermediate A2-6

Methyl-2-(3-(tert-butoxycarbonyl)bicyclo[1.1.1]pentan-1-yl)-2,3-dihydrooxazole-4-carboxylate To a suspension of D-serine methyl ester hydrochloride A1-6 (1.47 g, 9.45 mmol) in dichloromethane (60 mL) was added 1,4-diazabicyclo[2.2.2]octane (2.90 g, 25.8 mmol) at room temperature. After stirred at room temperature for 30 minutes under nitrogen atmosphere, the mixture was added the solution of tert-butyl 3-formylbicyclo[1.1.1]pentane-1-carboxylate A2-5 (1.84 g, 90% purity, 8.44 mmol) in dichloromethane (40 mL) and stirring continued at room temperature for 30 minutes under nitrogen atmosphere. Then 1-chloropyrrolidine-2,5-dione (1.27 g, 9.32 mmol) was added at 0° C. and the mixture was stirred at 0° C. under nitrogen atmosphere for 2 hours. Then it was quenched with saturated sodium pyrosulfite aqueous solution (20 mL) and water (20 mL). The aqueous layer was extracted with dichloromethane (50 mL) for three times. The combined organic layers were washed with saturated sodium bicarbonate aqueous solution (50 mL) and brine (50 mL), dried over $Na_2SO_{4(s)}$ and filtered. The filtrate was concentrated under reduced pressure to give a residue, which was purified by silica gel column chromatography (dichloromethane to petroleum ether:ethyl acetate=100% to 3:1) to give the title compound (1.33 g, 90% purity from $^1$H NMR, 48% yield) as white solids. LC-MS (ESI): $R_T$=1.55 min, mass calcd. for $C_{15}H_{21}NO_5$ 295.1, m/z found 296.2 [M+H]$^+$. $^1$H NMR (400 MHz, DMSO-$d_6$) δ 5.83 (dd, J=6.4, 4.8 Hz, 1H), 4.79-4.68 (m, 2H), 3.81 (s, 3H), 1.87 (s, 6H), 1.40 (s, 9H).

Acid 2 3-(4-(Methoxycarbonyl)oxazol-2-yl)bicyclo[1.1.1]pentane-1-carboxylic Acid To a solution of methyl 2-(3-(tert-butoxycarbonyl)bicyclo[1.1.1]pentan-1-yl)-2,3-dihydrooxazole-4-carboxylate A2-6 (1.33 g, 90% purity, 4.05 mmol) in 1,2-dichloroethane (32 mL) was added 4 Å molecular sieve and potassium carbonate (672 mg, 4.86 mmol) at room temperature. After stirred at room temperature for 30 minutes, the mixture was added 1-bromopyrrolidine-2,5-dione (865 mg, 4.86 mmol), heated to reflux for 20 minutes, then cooled to 0° C. It was quenched with the addition of saturated sodium thiosulfate aqueous solution (6 mL) and saturated sodium bicarbonate aqueous solution (10 mL). The resulting mixture was filtered and the filtrate was separated. The aqueous layer was extracted with dichloromethane (30 mL) for three times, then acidified to pH 2~3 with 0.5 M hydrochloride aqueous solution. It was extracted with ethyl acetate (30 mL) for three times. The combined ethyl acetate layers were washed brine (30 mL), dried over $Na_2SO_{4(s)}$ and filtered. The filtrate was concentrated under reduced pressure to give the title compound (550 mg, 90% purity from $^1$H NMR, 51% yield) as white solids. LC-MS (ESI): $R_T$=0.29 min, mass calcd. for $C_{11}H_{11}NO_5$ 237.1, m/z found 238.2 [M+H]$^+$. $^1$H NMR (300 MHz, CDCl$_3$) δ 8.17 (s, 1H), 3.91 (s, 3H), 2.55 (s, 6H).

Acid 3

4-(4-(ethoxycarbonyl)oxazol-2-yl)cyclohex-3-enecarboxylic Acid (A3)

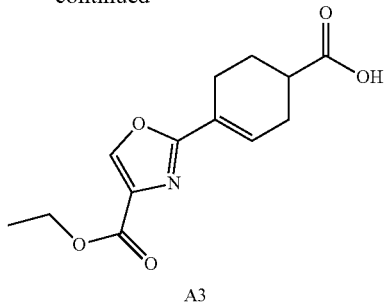

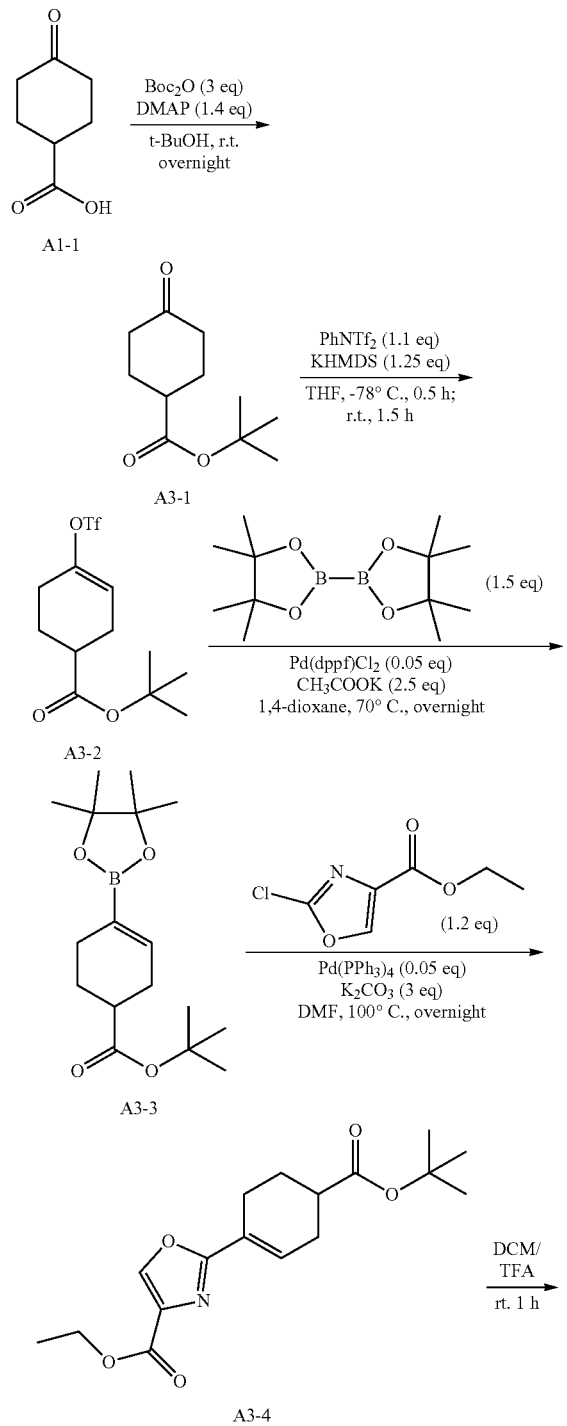

Intermediate A3-1 tert-Butyl 4-oxocyclohexanecarboxylate

To a solution of 4-oxocyclohexanecarboxylic acid A1-1 (10.2 g, 98% purity, 70.3 mmol) in tert-butanol (100 mL) was added N,N-dimethylpyridin-4-amine (12.7 g, 95% purity, 98.5 mmol) and di-tert-butyldicarbonate (46.5 g, 99% purity, 211 mmol). The reaction mixture was stirred at room temperature under nitrogen atmosphere overnight. It was then concentrated in vacuo and the obtained residue was purified by silica gel column chromatography (petroleum: ethyl acetate=10:1) to give the title compound (13.3 g, 99% purity, 94% yield) as colorless oil. $^1$H NMR (300 MHz, DMSO-d$_6$) δ 2.74-2.64 (m, 1H), 2.44-2.33 (m, 2H), 2.26-2.18 (m, 2H), 2.11-2.03 (m, 2H), 1.83-1.70 (m, 2H), 1.41 (s, 9H).

Intermediate A3-2 tert-butyl 4-(((trifluoromethyl)sulfonyl)oxy)cyclohex-3-enecarboxylate

To the solution of tert-butyl 4-oxocyclohexanecarboxylate A3-1 (2.00 g, 95% purity, 9.58 mmol) and 1,1,1-trifluoro-N-phenyl-N-((trifluoromethyl)sulfonyl) methanesulfonamide (3.84 g, 10.5 mmol) in dry tetrahydrofuran (30 mL) was added 1.0 M potassium bis(trimethylsilyl)amide in tetrahydrofuran (12 mL, 12.0 mmol) dropwise over 10 minutes at −78° C. After addition, the mixture was stirred at −78° C. for 30 minutes. Then the mixture was stirred at room temperature for 1.5 hours. The mixture was diluted with water (50 mL) and extracted with ethyl acetate (40 mL) three times. The combined organic layers was washed with brine (100 mL), dried with Na$_2$SO$_{4(s)}$ and filtered. The filtrate was concentrated and purified by silica gel chromatography (petroleum ether:ethyl acetate=100:1 to 50:1) to give the title compound (2.4 g, 95% purity from HNMR, 72% yield) as colorless oil. $^1$H NMR (400 MHz, DMSO-d$_6$) δ 5.89 (s, 1H), 2.58-2.52 (m, 1H), 2.43-2.28 (m, 4H), 2.01-1.94 (m, 1H), 1.85-1.76 (m, 1H), 1.40 (s, 9H).

Intermediate A3-3 tert-butyl 4-(4,4,5,5-tetramethyl-1,3,2-dioxaborolan-2-yl)cyclohex-3-enecarboxylate The suspension of tert-Butyl 4-(((trifluoromethyl)sulfonyl)oxy)cyclohex-3-enecarboxylate A3-2 (2.4 g, 6.90 mmol, 95% purity), bis(pinacolato)diboron (2.68 g, 10.35 mmol), [1,1'-Bis(diphenylphosphino)ferrocene]dichloropalladium (II) (258 mg, 0.345 mmol) and potassium acetate (1.73 g, 17.3 mmol) in 1,4-dioxane (25 mL) was stirred at 70° C. under nitrogen atmosphere overnight. The mixture was cooled down and diluted with water (50 mL). The resulting solution was extracted with ethyl acetate (50 mL) for three times. The combined organic layers were washed with brine (100 mL), dried over $Na_2SO_{4(s)}$ and filtered. The filtrate was concentrated and purified by silica gel chromatography (petroleum ether:ethyl acetate=100:1 to 40:1) to give the title compound (1.05 g, 95% purity from HNMR, 47% yield) as white solids. LC-MS (ESI): $R_T$=1.71 min, mass calcd. for $C_{17}H_{29}BO_4$ 308.2, m/z found 326.3 $[M+NH_4]^+$. $^1$H NMR (400 MHz, $CDCl_3$) δ 6.54 (s, 1H), 2.45-2.37 (m, 1H), 2.29-2.24 (m, 3H), 2.14-2.06 (m, 1H), 2.00-1.94 (m, 1H), 1.58-1.50 (m, 1H), 1.44 (s, 9H), 1.26 (s, 12H).

Intermediate A3-4

Ethyl 2-(4-(tert-butoxycarbonyl)cyclohex-1-en-1-yl)oxazole-4-carboxylate

The suspension of tert-butyl 4-(4,4,5,5-tetramethyl-1,3,2-dioxaborolan-2-yl) cyclohex-3-enecarboxylate A3-3 (950 mg, 95% purity, 2.93 mmol), ethyl 2-chlorooxazole-4-carboxylate (629 mg, 3.51 mmol), tetrakis(triphenylphosphine) palladium (172 mg, 0.15 mmol) and potassium carbonate (1.24 g, 8.78 mmol) in N,N-Dimethylformamide (30 mL) was stirred at 100° C. under nitrogen atmosphere overnight. After cooled down, the mixture was diluted with water (100 mL) and extracted with ethyl acetate (100 mL) twice. The combined organic layers were washed with water (100 mL), and then brine (100 mL), dried over $Na_2SO_{4(s)}$ and filtered. The filtrate was concentrated and purified by silica gel chromatography (petroleum ether:ethyl acetate=10:1) to give the title compound (630 mg, 95% purity from HNMR, 64% yield) as white solids. LC-MS (ESI): $R_T$=1.73 min, mass calcd. for $C_{17}H_{23}NO_5$ 321.2, m/z found 322.3 $[M+H]^+$. $^1$H NMR (400 MHz, $CDCl_3$) δ 8.12 (s, 1H), 6.85 (s, 1H), 3.39 (q, J=7.2 Hz, 2H), 2.76-2.72 (m, 1H), 2.54-2.48 (m, 4H), 2.15-2.09 (m, 1H), 1.81-1.72 (m, 1H), 1.46 (s, 9H), 1.38 (t, J=7.2 Hz, 3H).

Acid 3

4-(4-(ethoxycarbonyl)oxazol-2-yl)cyclohex-3-enecarboxylic Acid

To the solution of ethyl 2-(4-(tert-butoxycarbonyl)cyclohex-1-en-1-yl)oxazole-4-carboxylate A3-4 (630 mg, 95% purity, 1.86 mmol) in dichloromethane (2.5 mL) was added trifluoroacetic acid (2.5 mL). After stirred at room temperature for 1 hour, the mixture was concentrated to give the title compound (540 mg, 90% purity from HNMR, 98% yield) as light yellow solids. LC-MS (ESI): $R_T$=1.08 min, mass calcd. for $C_{13}H_{15}NO_5$ 265.1, m/z found 266.2 $[M+H]^+$. $^1$H NMR (400 MHz, DMSO-$d_6$) δ 8.77 (s, 1H), 6.78 (s, 1H), 4.28 (q, J=7.2 Hz, 2H), 2.60-2.53 (m, 2H), 2.47-2.33 (m, 3H), 2.08-2.03 (m, 1H), 1.72-1.62 (m, 1H), 1.28 (t, J=7.2 Hz, 3H).

Acid 4

4-(4-(Methoxycarbonyl)-5-methyloxazol-2-yl)cyclohexanecarboxylic Acid (A4)

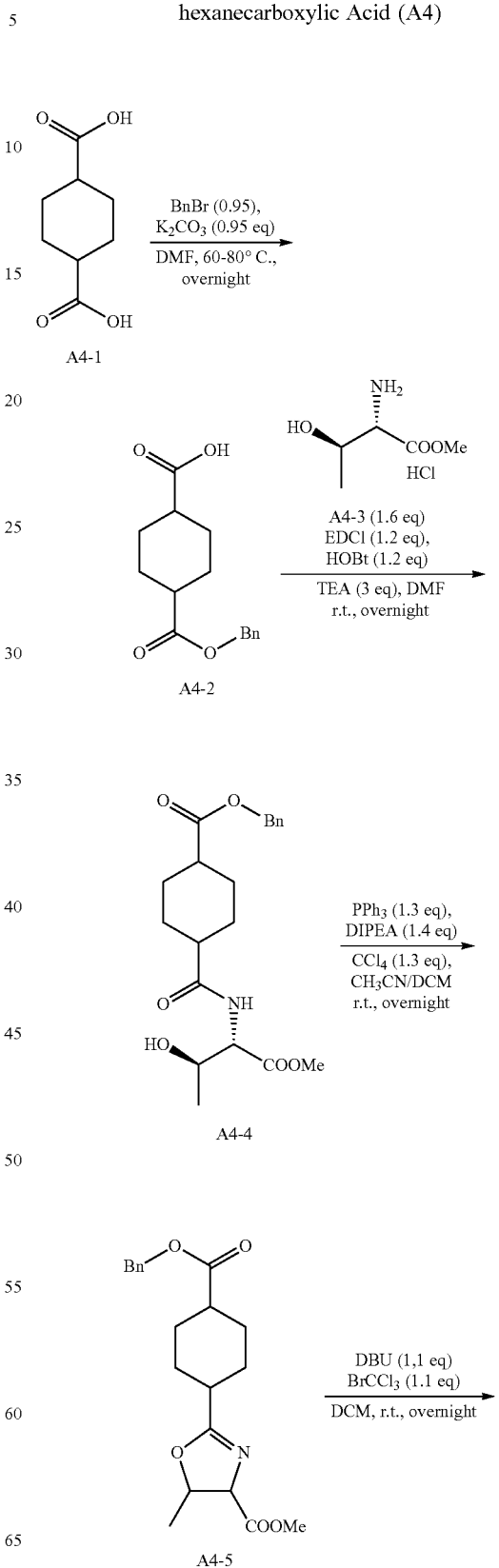

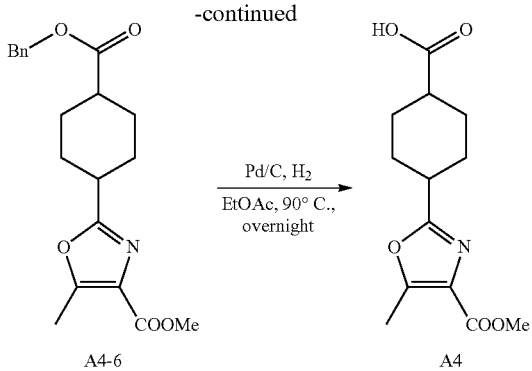

Intermediate A4-2

4-((Benzyloxy)carbonyl)cyclohexanecarboxylic Acid

To a solution of cyclohexane-1,4-dicarboxylic acid A4-1 (10.5 g, 60.0 mmol) in N,N-dimethylformamide (50 mL) was added potassium carbonate (7.96 g, 57.0 mmol) under nitrogen atmosphere. The mixture was stirred at 60° C. for 1 hour, then (bromomethyl)benzene (9.85 g, 57.0 mmol) was added. The mixture was stirred at 80° C. overnight. After cooling down to room temperature, the mixture was acidified to pH 6 with 1 M hydrochloride aqueous solution and extracted with ethyl acetate (100 mL) twice. The separated organic layers were washed with water (200 mL) twice, dried over anhydrous $Na_2SO_{4(s)}$, filtered and concentrated to give the title compound (3.4 g, 23% yield) as white solids. $^1$H NMR (300 MHz, DMSO-$d_6$) δ 12.03 (br s, 1H), 7.38-7.29 (m, 5H), 5.06 (s, 2H), 2.34-2.26 (m, 1H), 2.18-2.11 (m, 1H), 1.96-1.87 (m, 4H), 1.42-1.24 (m, 4H).

Intermediate A4-4: Benzyl 4-(((2R,3R)-3-hydroxy-1-methoxy-1-oxobutan-2-yl)carbamoyl)cyclohexanecarboxylate To a solution of 4-((benzyloxy)carbonyl)cyclohexanecarboxylic acid A4-2 (4.00 g, 14.4 mmol), (2R,3R)-methyl 2-amino-3-hydroxybutanoate hydrochloride A4-3 (4.00 g, 23.2 mmol) and 1-hydroxybenzotriazole (2.40 g, 17.4 mmol) in N,N-dimethylformamide (50 mL) was added triethylamine (4.50 g, 43.4 mmol). The resulting solution was cooled to 0° C. and then $N^1$-((ethylimino)methylene)-$N^3,N^3$-dimethylpropane-1,3-diamine hydrochloride (3.40 g, 17.4 mmol) was added. After stirring at room temperature overnight, the reaction mixture was poured into water (200 mL) and extracted with ethyl acetate (400 mL) twice. The combined organic layers were washed with water (200 mL), brine (200 mL), dried over $Na_2SO_{4(s)}$ and filtered. The filtrate was concentrated to give the title compound (4.00 g, 70% yield) as colorless oil. LC-MS (ESI): $R_T$=1.42 min, mass calcd. for $C_{20}H_{27}NO_6$ 377.2, m/z found 378.4 [M+H]$^+$. $^1$H NMR (300 MHz, CDCl$_3$) δ 7.37-7.35 (m, 5H), 6.34 (d, J=8.7 Hz, 1H), 5.13-5.08 (m, 2H), 4.61-4.56 (m, 1H), 4.38-4.32 (m, 1H), 3.76-3.73 (m, 3H), 2.37-1.98 (m, 7H), 1.53-1.42 (m, 4H), 1.21-1.16 (m, 3H).

Intermediate A4-5

Methyl 2-(4-((benzyloxy)carbonyl)cyclohexyl)-5-methyl-4,5-dihydrooxazole-4-carboxylate

To a solution of benzyl 4-(((2R,3R)-3-hydroxy-1-methoxy-1-oxobutan-2-yl)carbamoyl)cyclohexanecarboxylate A4-4 (4.00 g, 10.6 mmol) in acetonitrile (40 mL) and dichloromethane (15 mL) was added triphenylphosphine (3.60 g, 13.8 mmol) and N,N-diisopropylethylamine (1.90 g, 14.8 mmol). After carbon tetrachloride (2.10 g, 13.8 mmol) was added dropwise slowly, the reaction mixture was stirred at room temperature overnight. The reaction mixture was cooled to 0° C. and diluted in ethyl acetate (100 mL) and saturated sodium bicarbonate aqueous solution (100 mL). After stirring for 10 minutes, the organic layer was separated and washed with brine (100 mL), dried over $Na_2SO_{4(s)}$ and filtered. The filtrate was concentrated and purified by silica gel chromatography (petroleum ether:ethyl acetate=10:1 to 4:1) to give the title compound (3.80 g, 39% yield) as colorless oil. LC-MS (ESI): $R_T$=1.63 min, mass calcd. for $C_{20}H_{25}NO_5$ 359.2, m/z found 360.3 [M+H]$^+$. $^1$H NMR (300 MHz, CDCl$_3$) δ 7.38-7.29 (m, 5H), 5.12-5.10 (m, 2H), 4.87-4.71 (m, 2H), 3.75-3.71 (m, 3H), 2.57-2.51 (m, 0.5H), 2.40-2.29 (m, 1.5H), 2.13-1.92 (m, 4H), 1.76-1.66 (m, 1H), 1.52-1.46 (m, 3H), 1.27-1.23 (m, 3H).

Intermediate A4-6

Methyl 2-(4-((benzyloxy)carbonyl)cyclohexyl)-5-methyloxazole-4-carboxylate

To a solution of methyl 2-(4-((benzyloxy)carbonyl)cyclohexyl)-5-methyl-4,5-dihydrooxazole-4-carboxylate A4-5 (1.00 g, 2.80 mmol) in dichloromethane (10 mL) was added dry 1,8-diazabicyclo[5.4.0]undec-7-ene (471 mg, 3.10 mmol) dropwise at 0° C. followed by bromotrichloromethane (608 mg, 3.10 mmol). After stirring at room temperature overnight, the reaction mixture was poured in saturated ammonium chloride aqueous solution (20 mL) and extracted with dichloromethane (20 mL) twice. The combined organic layers were dried over $Na_2SO_{4(s)}$ and filtered. The filtrate was concentrated and purified by silica gel chromatography (petroleum ether:ethyl acetate=8:1 to 5:1) to give the title compound (450 mg, 45% yield) as white solids. LC-MS (ESI): $R_T$=1.70 min, mass calcd. for $C_{20}H_{23}NO_5$ 357.2, m/z found 358.3 [M+H]$^+$. $^1$H NMR (400 MHz, CDCl$_3$) δ 7.39-7.31 (m, 5H), 5.12 (s, 2H), 3.89 (s, 3H), 2.95-2.90 (m, 0.3H), 2.78-2.72 (m, 0.7H), 2.65-2.62 (m, 0.3H), 2.59 (s, 3H), 2.42-2.36 (m, 0.7H), 2.20-1.98 (m, 4H), 1.90-1.83 (m, 0.5H), 1.76-1.70 (m, 0.5H), 1.60-1.55 (m, 3H).

Acid 4

4-(4-(Methoxycarbonyl)-5-methyloxazol-2-yl)cyclohexanecarboxylic Acid

To a solution of methyl 2-(4-((benzyloxy)carbonyl)cyclohexyl)-5-methyloxazole-4-carboxylate A4-6 (1.42 g, 90% purity, 3.58 mmol) in ethyl acetate (35 mL) was added 10% palladium on charcoal wt. (420 mg). The mixture was stirred at 30° C. under hydrogen atmosphere (balloon) overnight. The reaction mixture was filtered and the filtrate was concentrated to give the title compound (1.00 g, 90% purity, 94% yield) as white solids. LC-MS (ESI): $R_T$=0.30 min, mass calcd. for $C_{13}H_{17}NO_5$ 267.1, m/z found 268.2 [M+H]$^+$. $^1$H NMR (300 MHz, CDCl$_3$) δ 3.89 (s, 3H), 2.81-2.73 (m, 1H), 2.59 (s, 3H), 2.42-2.35 (m, 1H), 2.23-2.14 (m, 4H), 1.70-1.48 (m, 4H).

Acid 5

4-((4-(Methoxycarbonyl)oxazol-2-yl)methyl)cyclohexanecarboxylic Acid (A5)

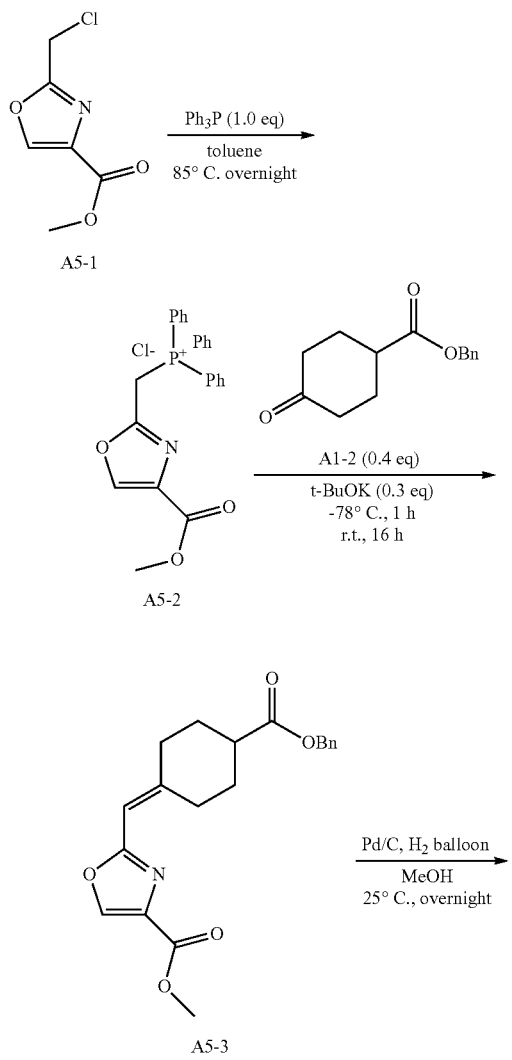

Intermediate A5-2

((4-(Methoxycarbonyl)oxazol-2-yl)methyl)triphenylphosphonium Chloride

To a solution of methyl 2-(chloromethyl)oxazole-4-carboxylate A5-1 (5.00 g, 28.2 mmol) in dry toluene (30 mL) was added triphenylphosphine (7.50 g, 28.2 mmol) at room temperature. After stirred at 85° C. under nitrogen atmosphere overnight, the reaction mixture was cooled down to room temperature and filtered to give the title compound (5.60 g, 99% purity from $^1$H NMR, 45% yield) as yellow solids. $^1$H NMR (300 MHz, CDCl$_3$) δ 8.06-8.05 (m, 1H), 7.94-7.87 (m, 6H), 7.80-7.75 (m, 3H), 7.69-7.62 (m, 6H), 6.26 (d, J=15.3 Hz, 2H), 3.81 (s, 3H).

Intermediate A5-3

Methyl 2-((4-((benzyloxy)carbonyl)cyclohexylidene)methyl)oxazole-4-carboxylate To a solution of ((4-(methoxycarbonyl)oxazol-2-yl)methyl)triphenylphosphonium chloride A5-2 (6.50 g, 99% purity, 14.7 mmol) in dry dichloromethane (45 mL) was added potassium 2-methylpropan-2-olate (1.70 g, 6.03 mmol) at −78° C. After stirring at −78° C. under nitrogen atmosphere for 1 hour, a solution of benzyl 4-oxocyclohexanecarboxylate A-2 (1.06 g, 4.50 mmol) in dichloromethane (5 mL) added slowly. After stirred at room temperature under nitrogen atmosphere for 16 hours, the mixture was diluted with dichloromethane (60 mL). The resulting solution was washed with water (100 mL), and then brine (100 mL), dried over Na$_2$SO$_{4(s)}$ and filtered. The filtrate was concentrated to give a residue, which was purified by silica gel column chromatography (petroleum ether:ethyl acetate=10:1 to 3:1) to give the title compound (1.00 g, 98% purity, 31% yield) as yellow oil. LC-MS (ESI): R$_T$=1.71 min, mass calcd. for C$_{20}$H$_{21}$NO$_5$ 355.1, m/z found 356.2 [M+H]$^+$. $^1$H NMR (300 MHz, DMSO-d$_6$) δ 8.79-8.75 (m, 1H), 7.45-7.31 (m, 5H), 6.17 (s, 1H), 5.32 (s, 1H), 5.11 (s, 1H), 3.81 (s, 1.5H), 3.61 (s, 1.5H), 3.56-3.49 (m, 1H), 2.73-2.64 (m, 1H), 2.46-2.42 (m, 1H), 2.35-2.26 (m, 2H), 2.09-1.99 (m, 2H), 1.62-1.46 (m, 2H).

Acid 5

4-((4-(Methoxycarbonyl)oxazol-2-yl)methyl)cyclohexanecarboxylic Acid

To the solution of methyl 2-((4-((benzyloxy)carbonyl)cyclohexylidene)methyl)oxazole-4-carboxylate A5-3 (1.60 g, 98% purity, 4.41 mmol) in methanol (25 mL) was added 10% palladium on charcoal wt. (353 mg). The mixture was stirred at 25° C. under hydrogen atmosphere of balloon overnight. Then the mixture was filtered off and the filtrate was concentrated to give the title compound (1.30 g, 90% purity, 99% yield) as light-yellow solids. LC-MS (ESI): R$_T$=1.14 min, mass calcd. for C$_{13}$H$_{17}$NO$_5$ 267.1, m/z found 266.1 [M−H]$^-$. $^1$H NMR (400 MHz, DMSO-d$_6$) δ 11.86 (br s, 1H), 8.75 (s, 1H), 3.79 (s, 3H), 2.72-2.67 (m, 2H), 2.48-2.43 (m, 0.6H), 2.15-2.07 (m, 0.4H), 1.93-1.81 (m, 2.5H), 1.71-1.68 (m, 1H), 1.54-1.45 (m, 2.5H), 1.30-1.17 (m, 2H), 1.11-0.98 (m, 1H).

Acid 6

4-(4-(2-ethoxy-2-oxoethyl)oxazol-2-yl)cyclohexane-1-carboxylic Acid (A6)

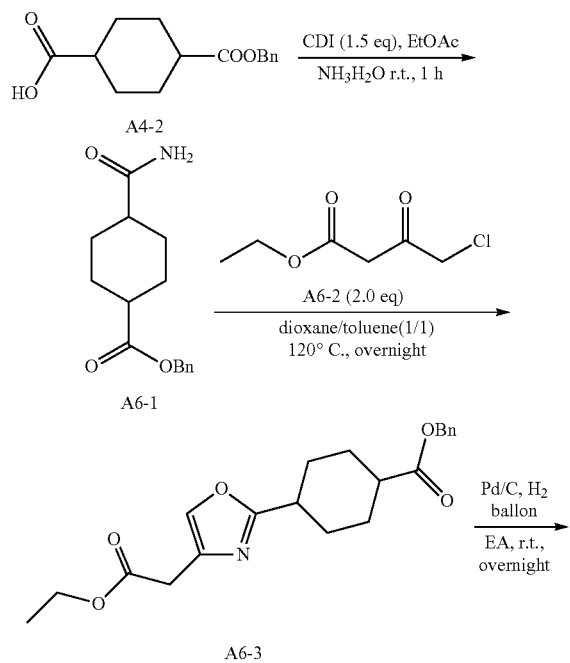

Intermediate A6-1

Benzyl 4-carbamoylcyclohexanecarboxylate

To a solution of 4-((benzyloxy)carbonyl)cyclohexanecarboxylic acid A4-2 (9.20 g, 35.1 mmol) in ethyl acetate (100 mL) was added N,N'-carbonyldiimidazole (7.39 g, 52.6 mmol) at room temperature. After stirring at room temperature for 1 hour, ammonia solution (20 mL) was added. The mixture was stirred at room temperature for 20 minutes. Then the mixture was diluted with water, acidified with 1 M hydrochloride aqueous solution (55 mL), and extracted with ethyl acetate (100 mL) twice. The separated organic layers were washed with bicarbonate aqueous solution (100 mL), dried over anhydrous $Na_2SO_{4(s)}$, filtered and concentrated to give the title compound (10.0 g, 99% yield) as yellow solids. LC-MS (ESI): $R_T$=0.61 min, mass calcd. for $C_{15}H_{19}NO_3$ 261.1, m/z found mass 262.3 $[M+H]^+$.

Intermediate A6-3

Benzyl 4-(4-(2-ethoxy-2-oxoethyl)oxazol-2-yl)cyclohexanecarboxylate

To a solution of benzyl 4-carbamoylcyclohexanecarboxylate A6-1 (6.00 g, 16.1 mmol) in toluene (50 mL) and 1,4-dioxane (50 mL) was added ethyl 4-chloro-3-oxobutanoate A6-2 (5.40 g, 32.2 mmol). The reaction mixture was heated to 120° C. and stirred at 120° C. under nitrogen atmosphere overnight. After cooling down to room temperature, the mixture was concentrated and purified by silica gel column chromatography (petroleum ether:ethyl acetate=10:1 to 7:1) to give the title compound (5.30 g, 80% yield) as light yellow oil. LC-MS (ESI): $R_T$=1.87 min, mass calcd. for $C_{21}H_{25}NO_5$ 371.2, m/z found 372.0 $[M+H]^+$. $^1$H NMR (400 MHz, $CDCl_3$) δ 7.54-7.53 (m, 1H), 7.39-7.31 (m, 5H), 5.12 (s, 2H), 4.25-4.13 (m, 2H), 3.58 (s, 0.6H), 3.57 (s, 1.4H), 2.98-2.92 (m, 0.3H), 2.78-2.72 (m, 0.7H), 2.61-2.56 (m, 0.3H), 2.43-2.35 (m, 0.7H), 2.20-1.95 (m, 4H), 1.88-1.73 (m, 1H), 1.60-1.42 (m, 3H), 1.32-1.24 (m, 3H).

Acid 6

4-(4-(2-Ethoxy-2-oxoethyl)oxazol-2-yl)cyclohexanecarboxylic Acid

To a solution of benzyl 4-(4-(2-ethoxy-2-oxoethyl)oxazol-2-yl)cyclohexanecarboxylate A6-3 (3.00 g, 1.25 mmol, 90% purity) in ethyl acetate (50 mL) was added 10% palladium on charcoal wt. (1.00 g). The mixture was stirred at room temperature under hydrogen atmosphere overnight. 10% palladium on charcoal was filtered off and the filtrate was concentrated to give the title compound (2.10 g, 98% yield) as light white solids. $^1$H NMR (400 MHz, DMSO-$d_6$) δ 12.09 (br s, 1H), 7.83-7.82 (m, 1H), 4.09 (q, J=7.2 Hz, 2H), 3.56 (d, J=1.2 Hz, 0.6H), 3.54 (d, J=0.8 Hz, 1.4H), 2.97-2.91 (m, 0.3H), 2.78-2.70 (m, 0.7H), 2.27-2.17 (m, 1H), 2.05-2.02 (m, 1H), 1.97-1.94 (m, 1H), 1.85-1.71 (m, 2H), 1.68-1.60 (m, 1H), 1.49-1.41 (m, 3H), 1.20-1.17 (m, 3H).

Acid 7

4-(4-(2-Ethoxy-2-oxoethyl)-5-methyloxazol-2-yl)cyclohexanecarboxylic Acid (A7)

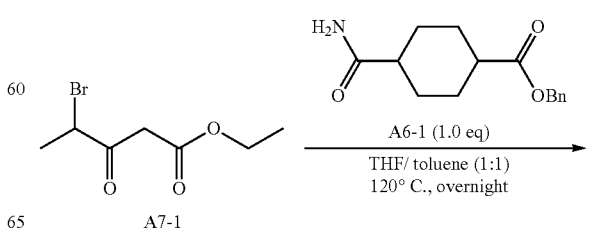

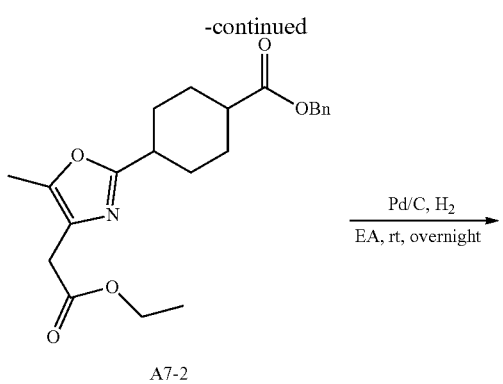

A7-2

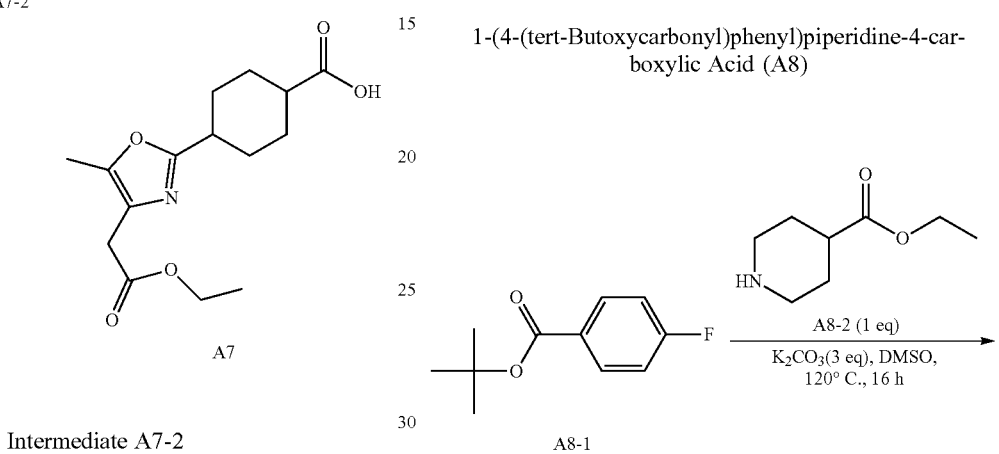

Intermediate A7-2

Benzyl 4-(4-(2-ethoxy-2-oxoethyl)-5-methyloxazol-2-yl)cyclohexanecarboxylate

To a solution of ethyl 4-bromo-3-oxopentanoate A7-1 (2.000 g, 80% purity, 6.123 mmol) in 1,4-dioxane (60 mL) and toluene (60 mL) was added benzyl 4-carbamoylcyclohexanecarboxylate A6-1 (1.710 g, 80% purity, 6.133 mmol) at room temperature under nitrogen atmosphere. After refluxed at 120° C. overnight, the reaction mixture was allowed to cool down to room temperature and concentrated under reduced pressure to afford the residue, which was purified by silica gel column chromatography (petroleum ether:ethyl acetate=10:1 to 5:1) to afford the product (360 mg, 80% purity from $^1$H NMR, 12% yield) as colorless oil. LC-MS (ESI): $R_T$=1.925 min, mass calcd. for $C_{22}H_{27}NO_5$ 385.2, m/z found 386.1 [M+H]$^+$. $^1$H NMR (400 MHz, CDCl$_3$) δ 7.37-7.32 (m, 5H), 5.12 (s, 2H), 4.16 (q, J=7.2 Hz, 2H), 3.44 (s, 2H), 2.90-2.88 (m, 0.2H), 2.71-2.67 (m, 0.7H), 2.60-2.57 (m, 0.3H), 2.40-2.35 (m, 0.8H), 2.23 (s, 2.3H), 2.18 (s, 0.7H), 2.16-2.12 (m, 3H), 2.02-1.97 (m, 1H), 1.86-1.81 (m, 0.7H), 1.72-1.69 (m, 0.3H), 1.58-1.53 (m, 3H), 1.26 (t, J=7.2 Hz, 3H).

Acid 7

4-(4-(2-Ethoxy-2-oxoethyl)-5-methyloxazol-2-yl)cyclohexanecarboxylic Acid

To a solution of benzyl 4-(4-(2-ethoxy-2-oxoethyl)-5-methyloxazol-2-yl)cyclohexanecarboxylate A7-2 (460 mg, 85% purity 1.01 mmol) in ethyl acetate (10 mL) was added 10% palladium on charcoal wt. (55 mg). The mixture was stirred at room temperature under hydrogen atmosphere overnight. Then the catalyst was filtered off and the filtrate was concentrated to give the title compound (310 mg, 80% purity from $^1$H NMR, 83% yield) as yellow oil. $^1$H NMR (400 MHz, CDCl$_3$) δ 9.56 (br s, 1H), 4.19-4.12 (m 2H), 3.47 (s, 2H), 2.90-2.86 (m, 0.2H), 2.75-2.69 (m, 0.7H), 2.61-2.59 (m, 0.3H), 2.38-2.33 (m, 0.8H), 2.24 (s, 2.3H), 2.19 (s, 0.7H), 2.16-2.12 (m, 3H), 2.02-1.96 (m, 1H), 1.88-1.84 (m, 0.5H), 1.72-1.67 (m, 0.5H), 1.60-1.53 (m, 3H), 1.26 (t, J=7.2 Hz, 3H).

Acid 8

1-(4-(tert-Butoxycarbonyl)phenyl)piperidine-4-carboxylic Acid (A8)

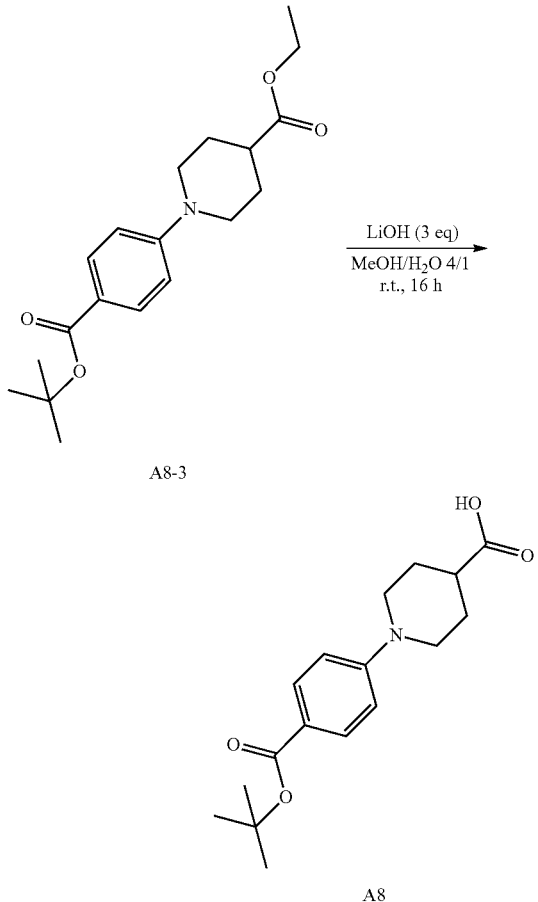

Intermediate A8-3

Ethyl 1-(4-(tert-butoxycarbonyl)phenyl)piperidine-4-carboxylate

To a mixture of tert-butyl 4-fluorobenzoate A8-1 (589 mg, 3.00 mmol) and ethyl piperidine-4-carboxylate A8-2 (472 mg, 3.00 mmol) in dimethyl sulfoxide (3 mL) was added potassium carbonate (1.24 g, 9.00 mmol) at room temperature. After stirred at 120° C. 16 hours, the mixture was poured into water (20 mL) and extracted with ethyl acetate (30 mL) for three times. The combined organic layers were washed with water (30 mL), dried over $Na_2SO_{4(s)}$ and concentrated to give a residue, which was purified by silica gel column chromatography (petroleum ether:ethyl acetate=50:1 to 10:1) to afford the title compound (480 mg, 48% yield) as white solids. $^1$H NMR (400 MHz, $CDCl_3$) δ 7.86 (d, J=8.8 Hz, 2H), 6.85 (d, J=8.8 Hz, 2H), 4.15 (q, J=7.2 Hz, 2H), 3.82-3.77 (m, 2H), 2.96-2.89 (m, 2H), 2.54-2.46 (m, 1H), 2.04-1.99 (m, 2H), 1.88-1.78 (m, 2H), 1.57 (s, 9H), 1.27 (t, J=7.2 Hz, 3H).

Acid 8

1-(4-(tert-Butoxycarbonyl)phenyl)piperidine-4-carboxylic Acid

To a solution of ethyl 1-(4-(tert-butoxycarbonyl)phenyl) piperidine-4-carboxylate A8-3 (480 mg, 1.40 mmol) in methanol (6 mL) and water (1.5 mL) was added lithium hydroxide monohydrate (176 mg, 4.20 mmol) under nitrogen atmosphere. After stirring at room temperature 16 hours, the solvent was removed and the residue was diluted with water (10 mL), acidified with 1 M hydrochloride aqueous solution to pH 4, then extracted with ethyl acetate (30 mL) for three times. The combined organic layers were dried over $Na_2SO_{4(s)}$ and concentrated to afford the title compound (400 mg, 94% yield) as white solids. $^1$H NMR (400 MHz, $CDCl_3$) δ 7.90 (d, J=8.8 Hz, 2H), 6.90 (d, J=8.8 Hz, 2H), 3.86-3.82 (m, 2H), 3.02-2.96 (m, 2H), 2.64-2.57 (m, 1H), 2.11-2.07 (m, 2H), 1.95-1.85 (m, 2H), 1.61 (s, 9H).

Acid 9

4-(4-(3-methoxy-3-oxopropyl)oxazol-2-yl)cyclohexane-1-carboxylic Acid (A9)

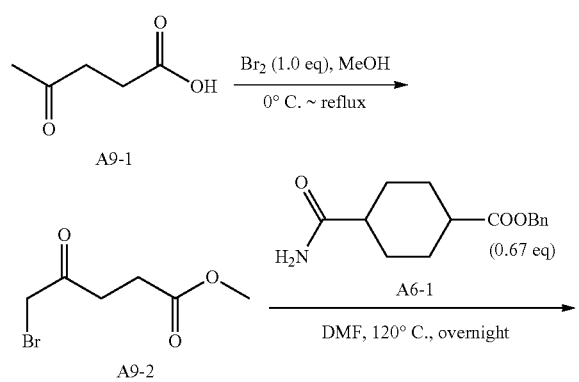

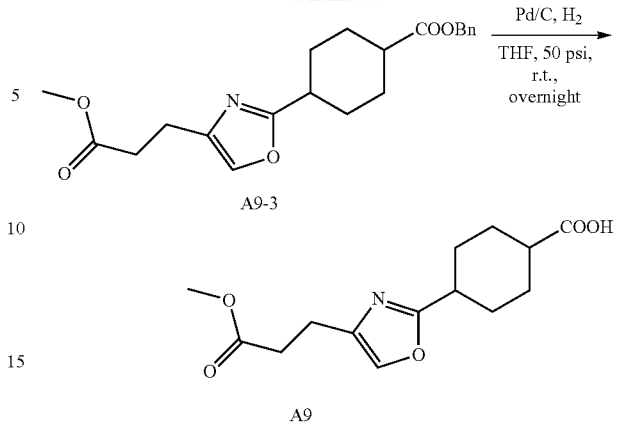

Intermediate A9-2

Methyl 5-bromo-4-oxopentanoate

To a solution of 4-oxopentanoic acid A9-1 (10.0 g, 84.4 mmol) in methanol (86 mL) was added bromine (13.6 g, 84.4 mmol) at 0° C. After stirred at room temperature for 1 hour under nitrogen atmosphere, the reaction mixture was diluted with water (20 mL) and extracted with dichloromethane (100 mL) twice. The separated organic layers were washed with saturated sodium bicarbonate aqueous solution (20 mL), dried over anhydrous $Na_2SO_{4(s)}$, filtered and concentrated to give a residue, which was purified by silica gel column chromatography (petroleum ether:ethyl acetate=5:1) to give the title compound (4.70 g, 27% yield) as yellow oil. $^1$H NMR (300 MHz, DMSO-$d_6$) δ 4.36-4.33 (m 2H), 3.57-3.52 (m 3H), 2.85-2.79 (m 2H), 2.51-2.45 (m 2H).

Intermediate A9-3

Benzyl 4-(4-(3-methoxy-3-oxopropyl)oxazol-2-yl) cyclohexanecarboxylate

To a solution of benzyl 4-carbamoylcyclohexanecarboxylate A6-1 (500 mg, 1.91 mmol) in N,N-dimethylformamide (5 mL) was added methyl 5-bromo-4-oxopentanoate A9-2 (599 mg, 2.87 mmol). After stirred at 120° C. overnight, the mixture was diluted with water (20 mL) and extracted with dichloromethane (20 mL) twice. The separated organic layers were washed with saturated sodium bicarbonate aqueous solution (20 mL), dried over anhydrous $Na_2SO_{4(s)}$, filtered and concentrated to give a residue, which was purified by silica gel column chromatography (petroleum ether:ethyl acetate=10:1 to 5:1) to give the title compound (1.20 g, 32% yield) as yellow oil. $^1$H NMR (300 MHz, DMSO-$d_6$) δ 7.64 (s, 1H), 7.35-7.29 (m, 5H), 5.06 (s, 2H), 3.55 (s, 3H), 2.73-2.66 (m, 1H), 2.67-2.62 (m, 2H), 2.57-2.52 (m, 2H), 2.42-2.33 (m, 1H), 2.01-1.95 (m, 4H), 1.52-1.36 (m, 4H).

Acid 9

4-(4-(3-Methoxy-3-oxopropyl)oxazol-2-yl)cyclohexanecarboxylic Acid

To a solution of benzyl 4-(4-(3-methoxy-3-oxopropyl) oxazol-2-yl) cyclohexanecarboxylate A9-3 (1.43 g, 3.89 mmol) in tetrahydrofuran (150 mL) was added 10% palladium on charcoal wt. (2.00 g). The reaction mixture was stirred at room temperature under hydrogen atmosphere (50 psi) overnight. The completed reaction mixture was filtered and the filtrate was concentrated to give the crude product (980 mg, 91% yield) as white solids. $^1$H NMR (300 MHz, DMSO-$d_6$) δ 12.06 (br s, 1H), 7.64 (d, J=3.0 Hz, 1H), 3.57-3.55 (m, 3H), 2.70-2.67 (m, 1H), 2.65-2.62 (m, 2H), 2.48-2.37 (m, 2H), 2.24-2.12 (m, 1H), 2.01-1.91 (m, 4H), 1.50-1.33 (m, 4H).

Acid 10

4-(4-(3-ethoxy-2,2-dimethyl-3-oxopropyl)oxazol-2-yl)cyclohexane-1-carboxylic Acid (A10)

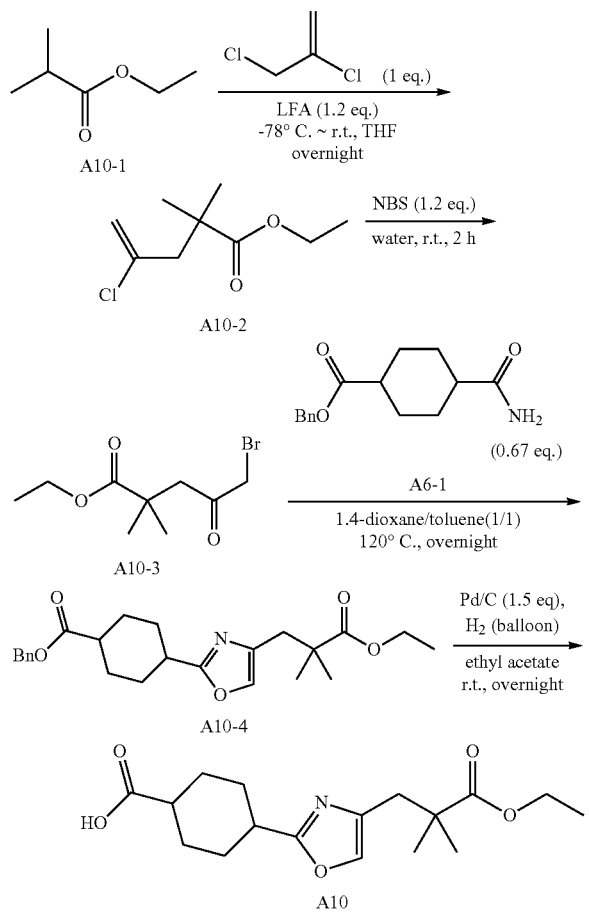

Intermediate A10-2

Ethyl 4-chloro-2,2-dimethylpent-4-enoate

To a solution of ethyl isobutyrate A10-1 (10.0 g, 86.1 mmol) in tetrahydrofuran (40 mL) was added 2 M lithium diisopropylamide in tetrahydrofuran (52 mL, 104 mmol) at −78° C. under nitrogen atmosphere. After stirred at −78° C. for 1 hour, 2,3-dichloroprop-1-ene (9.60 g, 86.5 mmol) was added at −78° C. Then the mixture was warmed up slowly to room temperature and stirred overnight. And then it was quenched with saturated ammonium chloride aqueous solution (50 mL) and extracted with ethyl acetate (50 mL) twice. The combined organic layers were washed with brine (30 mL), dried over Na$_2$SO$_{4(s)}$, filtered and concentrated to give a residue, which was purified by silica gel column chromatography (petroleum ether:ethyl acetate=10:1) to give the desired compound (13.0 g, 90% purity from $^1$H NMR, 71% yield) as colourless oil. $^1$H NMR (300 MHz, CDCl$_3$) δ 5.22 (s, 1H), 5.11 (s, 1H), 4.11 (q, J=6.9 Hz, 2H), 2.63 (s, 2H), 1.27-1.22 (m, 9H).

Intermediate A10-3

Ethyl 5-bromo-2,2-dimethyl-4-oxopentanoate

To a solution of ethyl 4-chloro-2,2-dimethylpent-4-enoate A10-2 (11.0 g, 90% purity, 51.9 mmol) in water (50 mL) was added N-bromosuccinimide (11.0 g, 61.8 mmol) under nitrogen atmosphere. After stirred at room temperature for 2 hours, the reaction mixture was diluted with water (10 mL) and extracted with ethyl acetate (40 mL) twice. The combined organic layers were washed with brine (20 mL), dried over Na$_2$SO$_{4(s)}$ and filtered. The filtrate was concentrated to give a residue, which was purified by silica gel column chromatography (petroleum ether:ethyl acetate=10:1) to give the desired compound (11.0 g, 90% purity from $^1$H NMR, 76% yield) as colourless oil. $^1$H NMR (300 MHz, CDCl$_3$) δ 4.07 (q, J=7.2 Hz, 2H), 3.85 (s, 2H), 2.89 (s, 2H), 1.22-1.45 (m, 9H).

Intermediate A10-4

Benzyl 4-(4-(3-ethoxy-2,2-dimethyl-3-oxopropyl)oxazol-2-yl)cyclohexanecarboxylate To the solution of benzyl 4-carbamoylcyclohexanecarboxylate A6-1 (7.00 g, 90% purity, 24.1 mmol) in toluene (20 mL) and 1,4-dioxane (20 mL) was added ethyl 5-bromo-2,2-dimethyl-4-oxopentanoate A10-3 (10.0 g, 90% purity, 35.8 mmol) under nitrogen atmosphere. After stirred at 120° C. overnight, the reaction mixture was cooled down to room temperature, diluted with water (20 mL) and extracted with ethyl acetate (20 mL) twice. The combined organic layers were washed with brine (20 mL), dried over Na$_2$SO$_{4(s)}$, filtered and concentrated to give a residue, which was purified by C18 column (acetonitrile:water=67% to 72%) to give the title compound (2.40 g, 90% purity from $^1$H NMR, 23% yield) as colourless oil. LC-MS (ESI): R$_T$=1.65 min, mass calcd. for C$_{24}$H$_{31}$NO$_5$ 413.2, m/z found 414.0 [M+H]$^+$. $^1$H NMR (300 MHz, CDCl$_3$) δ 7.42-7.31 (m, 5H), 7.27-7.25 (m, 1H), 5.12 (s, 2H), 4.12 (q, J=7.2 Hz, 2H), 2.79-2.66 (m, 2H), 2.48-1.63 (m, 10H), 1.30-1.21 (m, 9H).

Acid 10

4-(4-(3-Ethoxy-2,2-dimethyl-3-oxopropyl)oxazol-2-yl)cyclohexanecarboxylic Acid

To a solution of benzyl 4-(4-(3-ethoxy-2,2-dimethyl-3-oxopropyl)oxazol-2-yl)cyclohexanecarboxylate A10-4 (1.40 g, 90% purity, 3.05 mmol) in ethyl acetate (10 mL) was added 10% palladium on charcoal wt. (500 mg, 4.70 mmol) at room temperature. After stirred at room temperature under hydrogen atmosphere of balloon overnight, the reaction mixture was filtered and concentrated to give the title compound (900 mg, 90% purity from $^1$H NMR, 82% yield) as colourless oil. $^1$H NMR (300 MHz, CDCl$_3$) δ 7.25

(s, 1H), 4.12 (q, J=7.2 Hz, 2H), 2.76 (s, 2H), 2.65-1.95 (m, 6H), 1.89-1.40 (m, 4H), 1.28-1.15 (m, 9H).

Acid 11

Mixture of 4-(5-(ethoxycarbonyl)oxazol-2-yl)cyclohexanecarboxylic Acid and 4-(5-(ethoxycarbonyl)oxazol-2-yl)cyclohex-3-enecarboxylic Acid (A11)

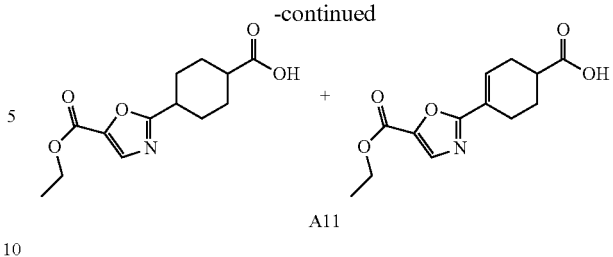

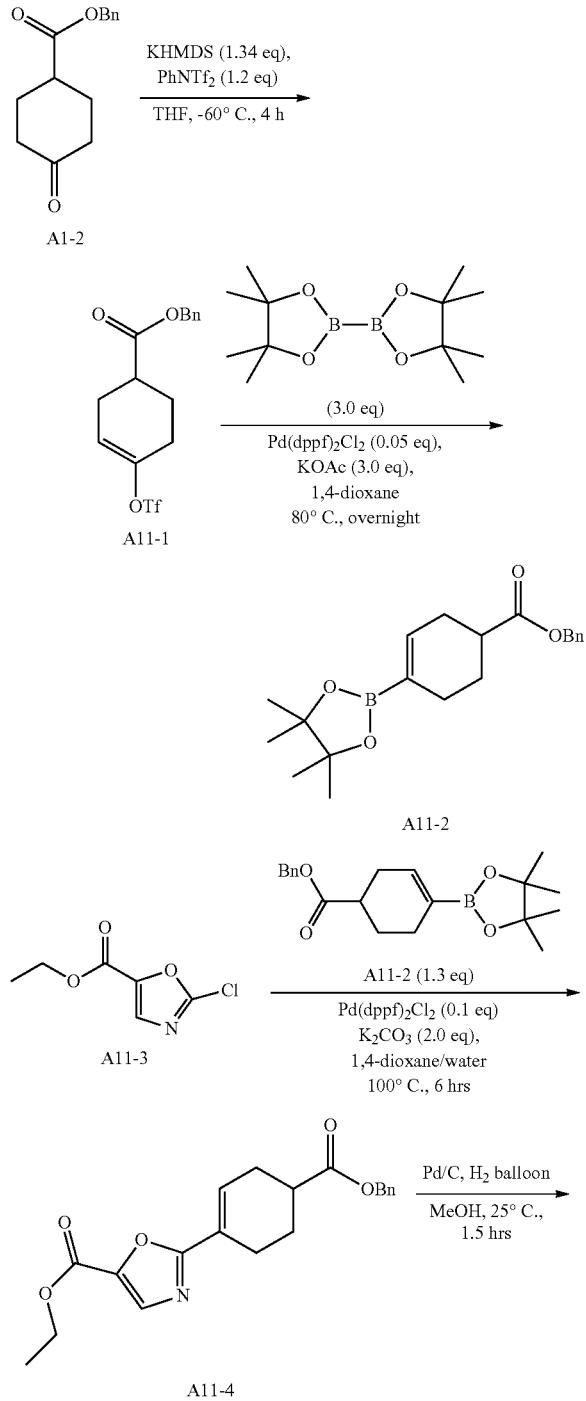

Intermediate A11-1

Benzyl 4-(((trifluoromethyl)sulfonyl)oxy)cyclohex-3-enecarboxylate

To a solution of benzyl 4-oxocyclohexanecarboxylate A1-2 (15.0 g, 98% purity, 63.3 mmol) and 1,1,1-trifluoro-N-phenyl-N-((trifluoromethyl)sulfonyl)methanesulfonamide (27.2 g, 76.1 mmol) in tetrahydrofuran (350 mL) was added 1 M potassium bis(trimethylsilyl)amide in tetrahydrofuran (85 mL, 85.0 mmol) under nitrogen atmosphere at −60° C. After stirred at −60° C. for 4 hours, the mixture was diluted with water (200 ml) and extracted with ethyl acetate (200 mL) twice. The combined organic layers were washed with brine (150 mL), dried over $Na_2SO_{4(s)}$ and filtered. The filtrate was concentrated under reduced pressure to give a residue, which was purified by silica gel column chromatography (petroleum ether:ethyl acetate=10:1 to 5:1) to give the desired compound (12.5 g, 95% purity from $^1$H NMR, 51% yield) as yellow oil. $^1$H NMR (400 MHz, $CDCl_3$) δ 7.39-7.33 (m, 5H), 7.77-7.75 (m, 1H), 5.14 (s, 2H), 2.69-2.62 (m, 1H), 2.49-2.46 (m, 2H), 2.43-2.39 (m, 2H), 2.19-2.13 (m, 1H), 2.00-1.89 (m, 1H).

Intermediate A11-2

Benzyl 4-(4,4,5,5-tetramethyl-1,3,2-dioxaborolan-2-yl)cyclohex-3-enecarboxylate

To a solution of benzyl 4-(((trifluoromethyl)sulfonyl)oxy)cyclohex-3-enecarboxylate A11-1 (8.00 g, 95% purity, 20.9 mmol), 4,4,4',4',5,5,5',5'-octamethyl-2,2'-bi(1,3,2-dioxaborolane) (15.9 g, 62.6 mmol) and potassium acetate (6.14 g, 62.6 mmol) in 1,4-dioxane (150 mL) was added 1,1'-bis(diphenylphosphino)ferrocene-palladium(II)dichloride (0.76 g, 1.04 mmol) at room temperature under nitrogen atmosphere. After stirred at 80° C. under nitrogen atmosphere overnight, the mixture was diluted with water (70 mL) and brine (70 mL). The organic layer was separated and the aqueous phase was extracted with ethyl acetate (150 mL) twice. The combined organic layers were washed with brine (100 mL), dried over $Na_2SO_{4(s)}$ and filtered. The filtrate was concentrated under reduced pressure to give a residue, which was purified by silica gel column chromatography (petroleum ether:ethyl acetate=10:1 to 5:1), then further purified by C18 column (acetonitrile:water=85% to 90%) to give the desired compound (4.60 g, 95% purity, 61% yield) as yellow oil. LC-MS (ESI): $R_T$=0.26 min, mass calcd. for $C_{20}H_{27}BO_4$ 342.2, m/z found 343.3 [M+H]$^+$. $^1$H NMR (400 MHz, $CDCl_3$) δ 7.39-7.32 (m, 5H), 6.54 (s, 1H), 5.13 (s, 2H), 2.63-2.55 (m, 1H), 2.38-2.35 (m, 2H), 2.30-2.25 (m, 1H), 2.17-2.01 (m, 2H), 1.68-1.58 (m, 1H), 1.26 (s, 12H).

Intermediate A11-4

Ethyl 2-(4-((benzyloxy)carbonyl)cyclohex-1-en-1-yl)oxazole-5-carboxylate

To a solution of ethyl 2-chlorooxazole-5-carboxylate A11-3 (3.00 g, 98% purity, 16.7 mmol) in 1,4-dioxane (100 mL) was added benzyl 4-(4,4,5,5-tetramethyl-1,3,2-dioxaborolan-2-yl)cyclohex-3-enecarboxylate A11-2 (7.85 g, 95% purity, 21.8 mmol), 1,1'-bis(diphenylphosphino)ferrocene palladium(II) dichloride (1.30 g, 98% purity, 1.74 mmol) and potassium carbonate (4.80 g, 98% purity, 34.0 mmol) in water (20 mL) at room temperature. After stirred at 100° C. for 6 hours under nitrogen atmosphere, the reaction mixture was allowed to cool down to room temperature and diluted with water (100 mL) slowly, extracted with ethyl acetate (100 mL) for three times. The combined organic layers were washed with brine (100 mL), dried over $Na_2SO_{4(s)}$ and filtered. The filtrate was concentrated under reduced pressure to give a residue, which was purified by silica gel column chromatography (petroleum ether:ethyl acetate=3:1 to 1:1) to give the title compound (5.50 g, 95% purity from $^1$H NMR, 88% yield) as white solids. LC-MS (ESI): $R_T$=1.899 min, mass calcd. for $C_{20}H_{21}NO_5$ 355.1, m/z found 356.1 [M+H]$^+$. $^1$H NMR (400 MHz, DMSO-d$_6$) δ 7.97 (s, 1H), 7.39-7.31 (m, 5H), 6.89-6.88 (m, 1H), 5.15 (s, 1H), 5.14 (s, 1H), 4.32 (q, J=7.2 Hz, 2H), 2.79-2.72 (m, 1H), 2.58-2.53 (m, 2H), 2.49-2.37 (m, 2H), 2.13-2.06 (m, 1H), 1.77-1.67 (m, 1H), 1.30 (t, J=7.2 Hz, 3H).

Acid 11

Mixture of 4-(5-(ethoxycarbonyl)oxazol-2-yl)cyclohexanecarboxylic acid and 4-(5-(ethoxycarbonyl)oxazol-2-yl)cyclohex-3-enecarboxylic Acid To a solution of ethyl 2-(4-((benzyloxy)carbonyl)cyclohex-1-en-1-yl)oxazole-5-carboxylate A11-4 (4.60 g, 95% purity, 12.3 mmol) in methanol (150 mL) was added 10% palladium on charcoal wt. (1.00 g) under nitrogen atmosphere at room temperature. After replacing the inert nitrogen atmosphere with hydrogen gas, the mixture was stirred at 25° C. under hydrogen atmosphere of balloon for 1.5 hours. The catalyst was filtered off and the filtrate was concentrated under reduced pressure to give the title product (3.60 g, 90% purity, 99% yield) as yellow oil. LC-MS (ESI): $R_T$=0.224 min and 0.293 min, mass calcd. for $C_{13}H_{17}NO_5$ and $C_{13}H_{15}NO_5$ 267.1 and 265.1, m/z found 268.1 [M+H]$^+$ and 266.0 [M+H]$^+$, respectively.

Acid 12

4-(4-(1-Ethoxy-2-methyl-1-oxopropan-2-yl)oxazol-2-yl)cyclohexanecarboxylic Acid (A12)

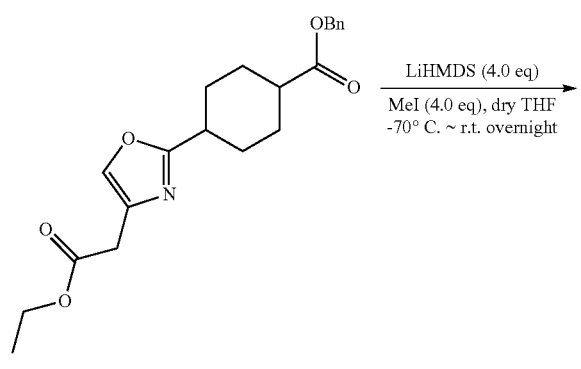

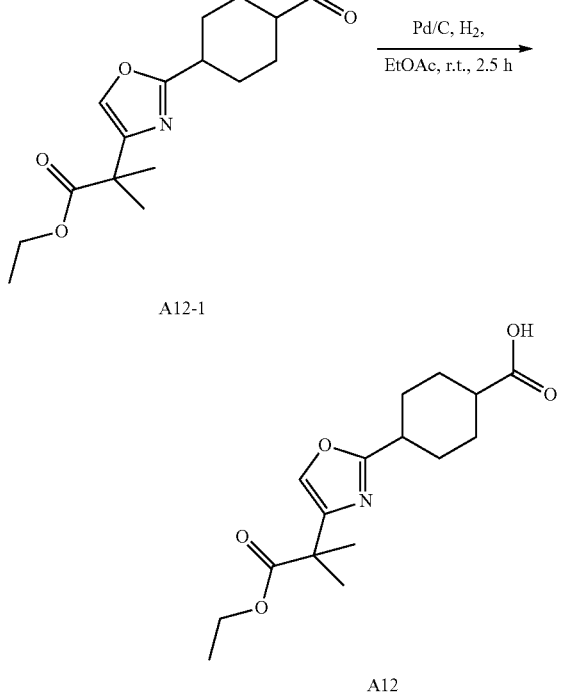

Intermediate A12-1

Benzyl 4-(4-(1-ethoxy-2-methyl-1-oxopropan-2-yl)oxazol-2-yl)cyclohexanecarboxylate To a solution of benzyl 4-(4-(2-ethoxy-2-oxoethyl)oxazol-2-yl)cyclohexanecarboxylate A6-3 (1.90 g, 90% purity, 4.60 mmol) in dry tetrahydrofuran (20 mL) was added dropwise 1.0 M lithium hexamethyldisilazide in tetrahydrofuran (18.4 mL, 18.4 mmol) at −70° C. After stirred at −70° C. for 1 hour, iodomethane (2.61 g, 18.4 mmol) was added dropwise at −70° C. and the resulting reaction mixture was allowed to warm to room temperature and stirring continued overnight. Then it was acidified with saturated ammonium chloride aqueous solution to pH 7-8 and, extracted with ethyl acetate (30 mL) twice. The combined organic layers were washed with water (30 mL) twice, brine (30 mL) twice, dried over $Na_2SO_{4(s)}$, filtered and concentrated under reduced pressure to give the title compound (1.90 g, 80% purity from HNMR, 83% yield) as a yellow oil. LC-MS (ESI): $R_T$=2.029 min, mass calcd. for $C_{23}H_{29}NO_5$ 399.2, m/z found 400.2 [M+H]$^+$. $^1$H NMR (400 MHz, CDCl$_3$) δ 7.36-7.33 (m, 6H), 5.12 (s, 2H), 4.17-4.11 (m, 2H), 2.98-2.94 (m, 0.3H), 2.80-2.74 (m, 0.7H), 2.60-2.57 (m, 0.2H), 2.43-2.35 (m, 0.8H), 2.17-1.96 (m, 4H), 1.83-1.72 (m, 1H), 1.60-1.54 (m, 3H), 1.51 (s, 6H), 1.24-1.19 (m, 3H).

Acid 12

4-(4-(1-Ethoxy-2-methyl-1-oxopropan-2-yl)oxazol-2-yl)cyclohexanecarboxylic Acid

To a solution of benzyl 4-(4-(1-ethoxy-2-methyl-1-oxopropan-2-yl)oxazol-2-yl)cyclo hexanecarboxylate A12-1 (1.90 g, 80% purity, 3.81 mmol) in ethyl acetate (20 mL)

was added 10% palladium on charcoal wt. (1 g) under nitrogen atmosphere. After stirred for 2.5 hours at room temperature under hydrogen balloon, the mixture was filtered and concentrated to get the title compound (1.50 g, crude) as white solids. LC-MS (ESI): $R_T$=1.22 min, mass calcd. for $C_{16}H_{23}NO_5$ 309.2, m/z found 308.0 [M−H]⁻.

Acid 13

4-(1-(2-ethoxy-2-oxoethyl)-1H-pyrazol-4-yl)cyclohexanecarboxylic Acid (A13)

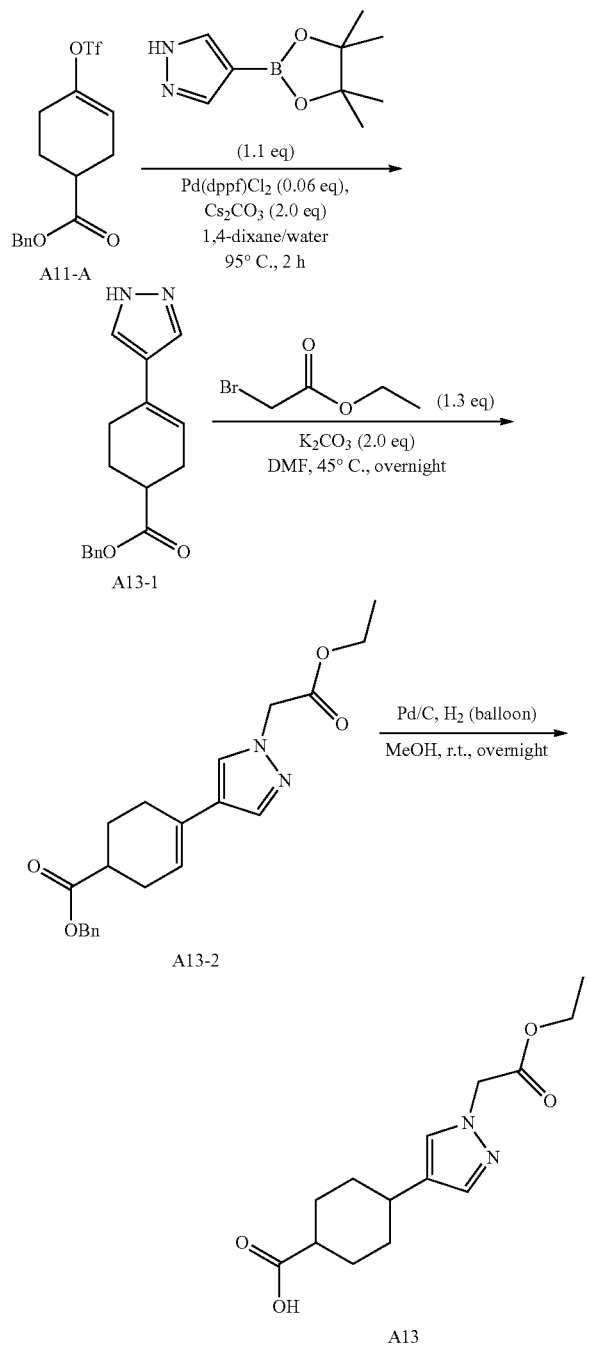

Intermediate A13-1

Benzyl 4-(1H-pyrazol-4-yl)cyclohex-3-enecarboxylate

To a suspension of benzyl 4-(((trifluoromethyl)sulfonyl)oxy)cyclohex-3-enecarboxylate A11-1 (10.0 g, 27.5 mmol) and 4-(4,4,5,5-tetramethyl-1,3,2-dioxaborolan-2-yl)-1H-pyrazole (5.90 g, 30.4 mmol) and cesium carbonate (17.9 g, 54.9 mmol) in a mixed solvent of 1,4-dioxane (100 mL) and water (33 mL) was added [1,1'-bis(diphenylphosphino)ferrocene]dichloropalladium(II) (1.20 g, 1.60 mmol) at room temperature. After stirred at 95° C. under nitrogen atmosphere for 5 hours and cooled down to room temperature, the mixture was concentrated to give a residue, which was purified by silica gel column chromatography (petroleum ether:ethyl acetate=5:1 to 1:1) and C18 column (acetonitrile:water=05% to 95%) to afford the desired product (3.70 g, 48% yield) as brown solids. LC-MS (ESI): $R_T$=1.78 min, mass calcd. for $C_{17}H_{18}N_2O_2$ 282.1, m/z found 283.1 [M+H]⁺. ¹H NMR (400 MHz, CDCl₃) δ 7.90 (s, 0.5H), 7.62 (s, 0.5H), 7.58 (s, 2H), 7.37-7.36 (m, 5H), 6.37 (s, 0.2H), 6.01 (s, 0.8H), 5.15 (s, 2H), 2.68-2.66 (m, 1H), 2.45-2.40 (m, 4H), 2.19-2.15 (m, 1H), 1.88-1.84 (m, 1H).

Intermediate A13-2

Benzyl 4-(1-(2-ethoxy-2-oxoethyl)-1H-pyrazol-4-yl)cyclohex-3-enecarboxylate

To a mixture of benzyl 4-(1H-pyrazol-4-yl)cyclohex-3-ene carboxylate A13-1 (1.40 g, 4.96 mmol) and potassium carbonate (1.40 g, 10.0 mmol) in N,N-dimethylformide (20 mL) was added ethyl 2-bromoacetate (1.08 g, 6.45 mmol) in N,N-dimethylformide (15 mL) at 0° C. Then the mixture was stirred at 45° C. overnight. After cooling down to room temperature, the mixture was poured in water (100 mL) and extracted with ethyl acetate (30 mL) for four times. The combined organic layers were concentrated to get a residue, which was purified by silica gel column chromatography (petroleum ether:ethyl acetate=10:1 to 3:1) followed by C18 column (acetonitrile:water=5% to 95%) to get the desired product (1.10 g, 61% yield) as pale green oil. LC-MS (ESI): $R_T$=1.882 min, mass calcd. for $C_{21}H_{24}N_2O_4$ 368.2, m/z found 369.1 [M+H]⁺. ¹H NMR (400 MHz, CDCl₃) δ 7.60 (s, 1H), 7.39 (s, 1H), 7.38-7.32 (m, 5H), 5.99-5.98 (m, 1H), 5.15 (s, 2H), 4.86 (s, 2H), 4.26-4.21 (m, 2H), 2.69-2.62 (m, 1H), 2.44-2.35 (m, 4H), 2.17-2.13 (m, 1H), 1.90-1.79 (m, 1H), 1.32-1.24 (m, 3H).

Acid 13

4-(1-(2-ethoxy-2-oxoethyl)-1H-pyrazol-4-yl)cyclohexanecarboxylic Acid

To a solution of benzyl 4-(1-(2-ethoxy-2-oxoethyl)-1H-pyrazol-4-yl)cyclohex-3-enecarboxylate A13-2 (1.10 g, 2.99 mmol) in methanol (20 mL) was added 10% palladium on charcoal wt. (600 mg) under nitrogen atmosphere at room temperature. Then the mixture was stirred at room temperature under hydrogen atmosphere overnight. Another batch (280 mg) combined to work-up. Then the mixture was filtered and the filtrate was concentrated to get the desired product (1.2 g, crude) as black oil. ¹H NMR (400 MHz, CDCl₃) δ 7.41 (s, 1H), 7.25 (s, 1H), 4.86 (s, 2H), 4.25-4.22

(m, 2H), 2.73-2.59 (m, 2H), 2.16-2.00 (m, 2H), 1.90-1.77 (m, 2H), 1.72-1.60 (m, 4H), 1.31-1.24 (m, 3H).

Acid 14

4-(1-(3-methoxy-3-oxopropyl)-1H-pyrazol-4-yl)cyclohexane-1-carboxylic Acid (A14)

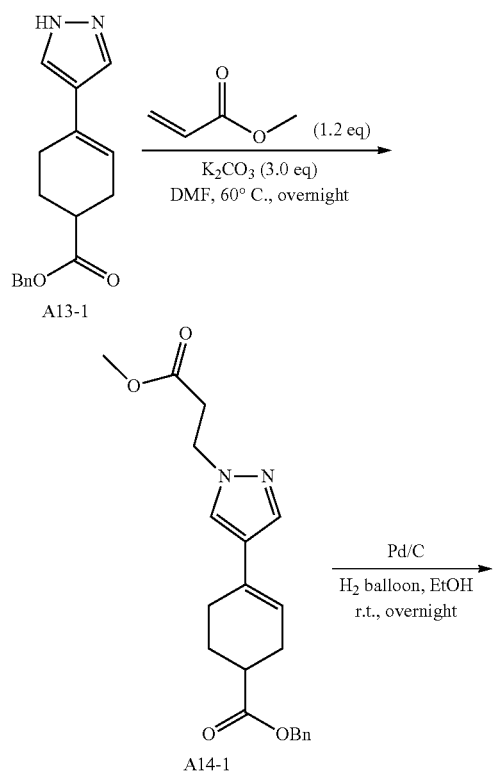

Intermediate A14-1

Benzyl 4-(1-(3-methoxy-3-oxopropyl)-1H-pyrazol-4-yl)cyclohex-3-enecarboxylate

To a solution of benzyl 4-(1H-pyrazol-4-yl)cyclohex-3-enecarboxylate A13-1 (1.40 g, 95% purity, 4.71 mmol) in N,N-dimethylformamide (15 mL) was added potassium carbonate (1.95 g, 14.1 mmol) and methyl acrylate (486 mg, 5.65 mmol) at room temperature. After stirred at 60° C. under nitrogen atmosphere overnight, it was cooled down and poured into water (50 mL), extracted with ethyl acetate (30 mL) twice. The combined organic layers were washed with brine (30 mL), dried over $Na_2SO_{4(s)}$ and filtered. The filtrate was concentrated to give a residue, which was purified by silica gel column chromatography (petroleum ether:ethyl acetate=3:1) to give the title compound (1.40 g, 65% yield) as white oil. $^1$H NMR (400 MHz, CDCl$_3$) δ 7.54 (s, 1H), 7.39-7.30 (m, 6H), 6.23-6.22 (m, 0.2H), 5.95 (br s, 0.8H), 5.15 (s, 2H), 4.39-4.36 (m, 2H), 3.68 (s, 3H), 2.91-2.87 (m, 2H), 2.68-2.61 (m, 1H), 2.43-2.30 (m, 4H), 2.18-2.12 (m, 1H), 1.89-1.79 (m, 1H).

Acid 14

4-(1-(3-methoxy-3-oxopropyl)-1H-pyrazol-4-yl)cyclohexane-1-carboxylic Acid

To a solution of benzyl 4-(1-(3-methoxy-3-oxopropyl)-1H-pyrazol-4-yl)cyclohex-3-enecarboxylate A14-1 (1.60 g, 80% purity, 3.47 mmol) in ethanol (40 mL) was added 10% palladium on charcoal wt. (500 mg) at room temperature. After stirred at room temperature under hydrogen atmosphere of balloon overnight, the reaction mixture was filtered and the filtrate was concentrated under reduced pressure to give the title compound (1.40 g, 65% purity from $^1$H NMR, 93% yield) as white oil. $^1$H NMR (400 MHz, CDCl$_3$) δ 7.61 (d, J=2.0 Hz, 0.1H), 7.52 (d, J=1.2 Hz, 0.2H), 7.45 (d, J=2.0 Hz, 0.3H), 7.36 (s, 0.7H), 7.22 (s, 0.7H), 5.65 (br s, 1H), 4.45 (t, J=6.4 Hz, 0.5H), 4.37 (t, J=6.4 Hz, 1.5H), 3.68 (d, J=2.0 Hz, 3H), 2.93-2.87 (m, 2H), 2.64 (br s, 1H), 2.47-2.30 (m, 0.4H), 2.12-2.03 (m, 2.6H), 1.86-1.79 (m, 1.3H), 1.71-1.52 (m, 2.7H), 1.36-1.26 (m, 2H).

Acid 15

4-(1-(4-Methoxy-2-methyl-4-oxobutan-2-yl)-1H-pyrazol-4-yl)cyclohexanecarboxylic Acid (A15)

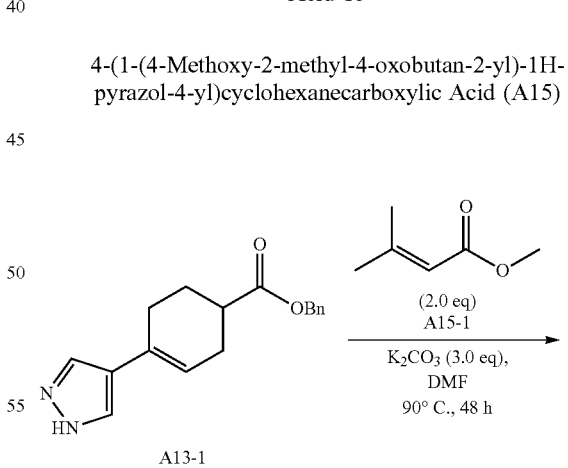

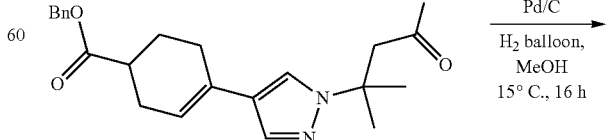

-continued

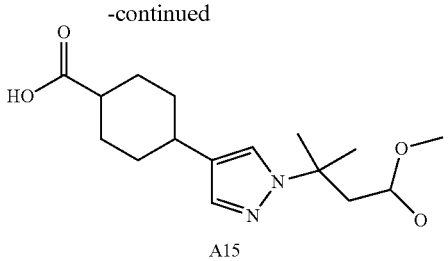

A15

Intermediate A15-2

Benzyl 4-(1-(4-methoxy-2-methyl-4-oxobutan-2-yl)-1H-pyrazol-4-yl)cyclohex-3-enecarboxylate To a solution of benzyl 4-(1H-pyrazol-4-yl)cyclohex-3-enecarboxylate A13-1 (3.00 g, 80% purity, 8.50 mmol) and methyl 3-methyl-2-butenoate A15-1 (1.95 g, 17.9 mmol) in N,N-dimethylformamide (30 mL) was added potassium carbonate (3.53 g, 25.5 mmol) at room temperature. After stirred at 90° C. for 48 hours, the reaction mixture was cooled down to room temperature and diluted with water (200 mL). It was extracted with ethyl acetate (100 mL) for three times. The combined organic layers were washed with brine (100 mL), dried over $Na_2SO_{4(s)}$ and filtered. The filtrate was concentrated to give a residue, which was purified by C18 column (acetonitrile:water=60% to 90%) to give the title compound (2.40 g, 97.8% purity, 70% yield) as yellow oil. $^1$H NMR (400 MHz, CDCl$_3$) δ 7.57 (s, 1H), 7.46 (s, 1H), 7.40-7.30 (m, 5H), 5.97-5.95 (m, 1H), 5.15 (s, 2H), 3.58 (s, 3H), 2.90 (s, 2H), 2.69-2.61 (m, 1H), 2.44-2.30 (m, 4H), 2.18-2.12 (m, 1H), 1.89-1.79 (m, 1H), 1.70 (s, 6H).

Acid 15

4-(1-(4-Methoxy-2-methyl-4-oxobutan-2-yl)-1H-pyrazol-4-yl)cyclohexanecarboxylic Acid To a mixture of benzyl 4-(1-(4-methoxy-2-methyl-4-oxobutan-2-yl)-1H-pyrazol-4-yl)cyclohex-3-enecarboxylate A15-2 (2.40 g, 97.8% purity, 5.92 mmol) in methanol (50 mL) was added 10% palladium on activated carbon wt. (500 mg) under nitrogen atmosphere. After stirred at 15° C. under hydrogen atmosphere (balloon) for 16 hours, the mixture was filtered and the filtrate was concentrated to give the title compound (1.90 g, 90% purity from $^1$H NMR, 94% yield) as white solids. $^1$H NMR (400 MHz, DMSO-d$_6$) δ 12.07 (s, 1H), 7.56 (s, 0.4H), 7.54 (s, 0.6H), 7.28 (s, 0.4H), 7.26 (s, 0.6H), 3.47 (s, 1.2H), 3.46 (s, 1.8H), 2.84 (s, 2H), 2.60-2.53 (m, 0.6H), 2.42-2.34 (m, 0.4H), 2.22-2.15 (m, 0.4H), 1.95-1.85 (m, 2.6H), 1.78-1.69 (m, 1.6H), 1.63-1.51 (m, 9H), 1.42-1.23 (m, 1.4H).

Acid 16

4-(1-(4-methoxy-4-oxobutan-2-yl)-1H-pyrazol-4-yl)cyclohexane-1-carboxylic Acid A16

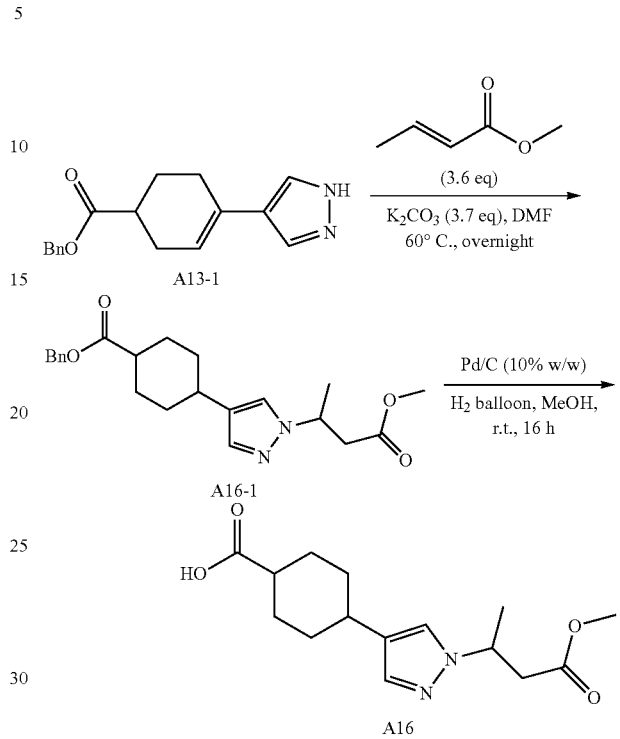

Intermediate A16-1

Benzyl 4-(1-(4-Methoxy-4-oxobutan-2-yl)-1H-pyrazol-4-yl)cyclohex-3-enecarboxylate To a solution of benzyl 4-(1H-pyrazol-4-yl)cyclohex-3-enecarboxylate A13-1 (6.40 g, 50% purity, 11.3 mmol) in N,N-dimethylformide (30 mL) was added (E)-methyl but-2-enoate (4.10 g, 40.9 mmol) and potassium carbonate (5.80 g, 42.0 mmol) at room temperature. After stirred at 60° C. under nitrogen atmosphere overnight, the reaction mixture was cooled down to room temperature and concentrated under reduced pressure to give a residue, which was diluted with water (100 mL) and extracted with ethyl acetate (80 mL) for three times. The combined organic layers were washed with water (80 mL) twice, brine (80 mL) twice, dried over $Na_2SO_{4(s)}$ and filtered. The filtrate was concentrated under reduced pressure to give a crude product, which was purified by C18 column (acetonitrile:water=65% to 70%) to give the title compound (5.00 g, 70% purity from $^1$H NMR, 81% yield) as light yellow oil. $^1$H NMR (400 MHz, CDCl$_3$) δ 7.55 (s, 1H), 7.37-7.30 (m, 6H), 5.95 (d, J=1.6 Hz, 1H), 5.15 (s, 2H), 4.77-4.70 (m, 1H), 3.64 (s, 3H), 3.02-3.00 (m, 1H), 2.76-2.72 (m, 1H), 2.69-2.60 (m, 1H), 2.44-2.33 (m, 4H), 2.18-2.14 (m, 1H), 1.89-1.80 (m, 1H), 1.58-1.53 (m, 3H).

Acid 16

4-(1-(4-methoxy-4-oxobutan-2-yl)-1H-pyrazol-4-yl)cyclohexane-1-carboxylic Acid To a solution of benzyl 4-(1-(4-methoxy-4-oxobutan-2-yl)-1H-pyrazol-4-yl)cyclohex-3-enecarboxylate A16-1

(5.00 g, 70% purity, 9.15 mmol) in methanol (100 mL) was added 10% palladium on charcoal wt. (500 mg). After stirred at room temperature for 16 hours under hydrogen atmosphere of balloon, the mixture was filtered and the filtrate was concentrated to give the title compound (4.30 g, 62% purity from $^1$H NMR, 99% yield) as colorless oil. $^1$H NMR (400 MHz, CDCl$_3$) δ 7.37 (s, 1H), 7.22 (s, 1H), 6.21 (t, J=2.4H, 1H), 4.78-4.69 (m, 2H), 3.64 (s, 3H), 3.02-2.97 (m, 1H), 2.76-2.72 (m, 1H), 2.65-2.61 (m, 1.0H), 2.11-2.03 (m, 2.4H), 1.85-1.81 (m, 1.6H), 1.71-1.67 (m, 3.2H), 1.55-1.53 (m, 3H), 1.42-1.25 (m, 0.8H).

Acid 17

4-(1-(3-methoxy-3-oxopropyl)-1H-pyrazol-4-yl)cyclohexane-1-carboxylic Acid (A17)

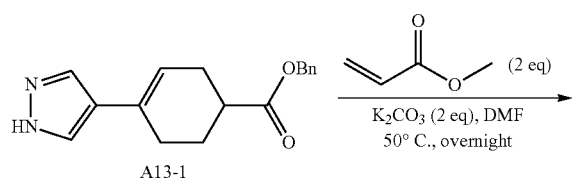

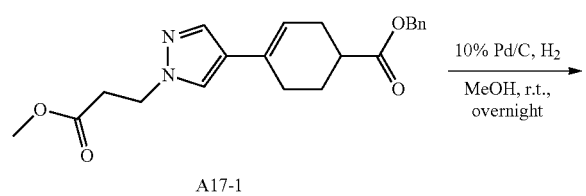

Intermediate A17-1

Benzyl 4-(1-(3-methoxy-3-oxopropyl)-1H-pyrazol-4-yl)cyclohex-3-enecarboxylate

To a solution of benzyl 4-(1H-pyrazol-4-yl)cyclohex-3-enecarboxylate A13-1 (2.2 g, 7.8 mmol) in N,N-dimethylformamide (400 mL) was added acrylic acid methyl ester (1.34 g, 15.6 mmol) and potassium carbonate (2.15 g, 15.6 mmol) at room temperature. After stirred at 50° C. under nitrogen atmosphere overnight, the mixture was cooled down to room temperature, poured into water (80 mL) and extracted with ethyl acetate (50 mL) for three times. The combined organic layers were washed with water (50 mL) for three times, brine (50 mL), dried over Na$_2$SO$_{4(s)}$ and filtered. The filtrate was concentrated under reduced pressure to give a crude product, which was purified by silica gel column chromatography (petroleum ether:ethyl acetate=4:1 to 2:1) to give the title compound (1.8 g, 63% yield) as colorless oil. LC-MS (ESI): R$_T$=2.467 min, mass calcd. for C$_{21}$H$_{24}$N$_2$O$_4$ 368.2, m/z found 369.1 [M+H]$^+$. $^1$H NMR (400 MHz, CDCl$_3$) δ 7.54 (s, 1H), 7.44-7.36 (m, 6H), 5.96-5.94 (m, 1H), 5.15 (s, 2H), 4.37 (t, J=6.8 Hz, 2H), 3.68 (s, 3H), 2.90-2.87 (m, 2H), 2.68-2.61 (m, 1H), 2.44-2.41 (m, 2H), 2.36-2.32 (m, 2H), 2.18-2.11 (m, 1H), 1.89-1.79 (m, 1H).

Acid 17

4-(1-(3-Methoxy-3-oxopropyl)-1H-pyrazol-4-yl)cyclohexane-1-carboxylic Acid

To a solution of benzyl 4-(1-(3-methoxy-3-oxopropyl)-1H-pyrazol-4-yl)cyclohex-3-enecarboxylate A17-1 (1.80 g, 4.89 mmol) in methanol (20 mL) was added 10% palladium on charcoal wt (200 mg). The reaction was stirred at room temperature under hydrogen atmosphere overnight. The completed reaction was filtered and the filtrate was concentrated under reduced pressure to give the title compound (1.0 g, 75% yield) as colorless oil. $^1$H NMR (400 MHz, DMSO-d$_6$) δ 12.04 (br s, 1H), 7.47 (s, 1H), 7.26 (s, 1H), 4.27 (t, J=6.8 Hz, 2H), 3.58 (s, 3H), 2.83 (t, J=6.8 Hz, 2H), 2.55-2.51 (m, 1H), 2.50-2.49 (m, 1H), 1.94-1.86 (m, 3H), 1.73-1.70 (m, 2H), 1.60-1.48 (m, 3H).

Acid 18

(cis)-4-(1-(3-Methoxy-3-oxopropyl)-3-methyl-1H-pyrazol-4-yl)cyclohexanecarboxylic Acid (A18)

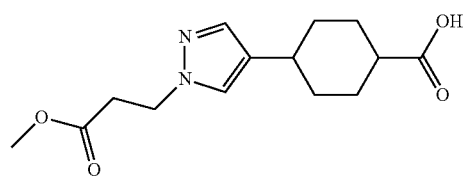

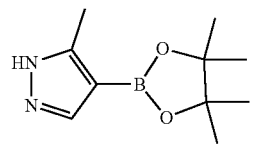

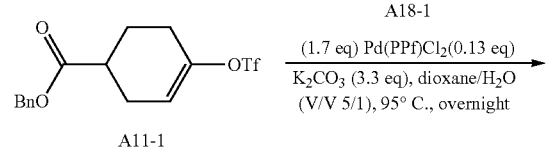

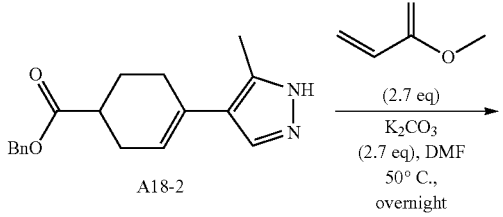

-continued
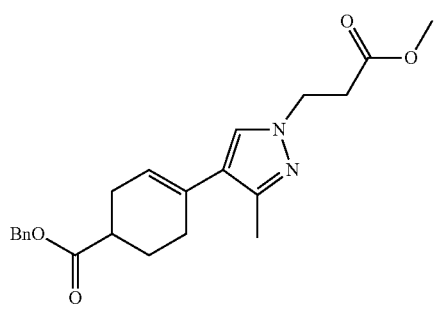
A18-3
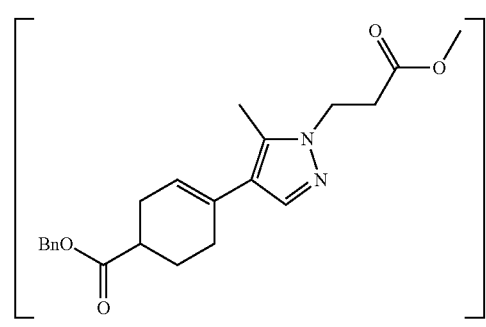
Pd/C,
H₂,
MeOH
r.t.,
overnight
→
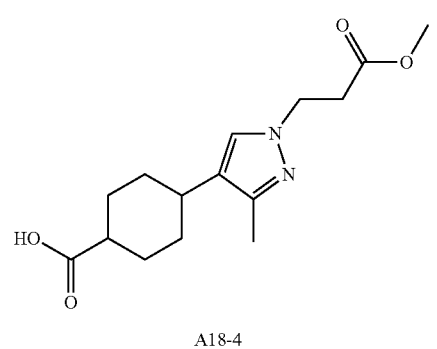
A18-4
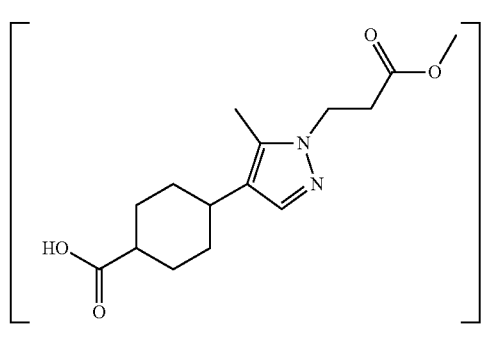
K₂CO₃
(2.2 eq),
BnBr
(1.7 eq.)
DMF,
r.t.,
overnight
→
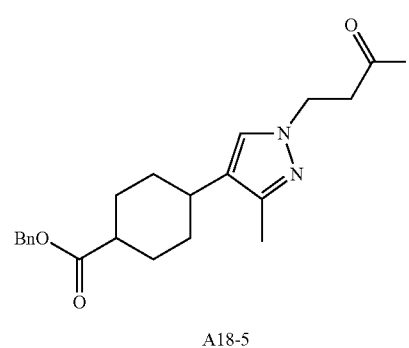
A18-5
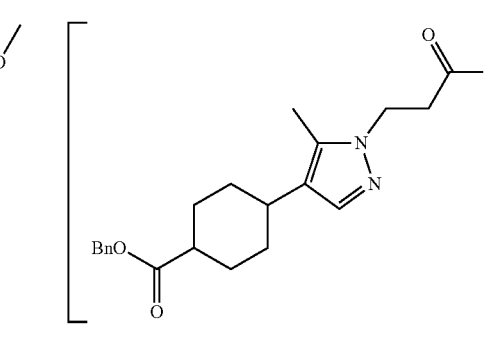
Chiral
separation
→
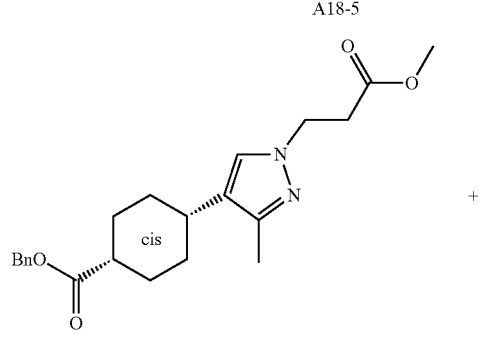
A18-5A
+
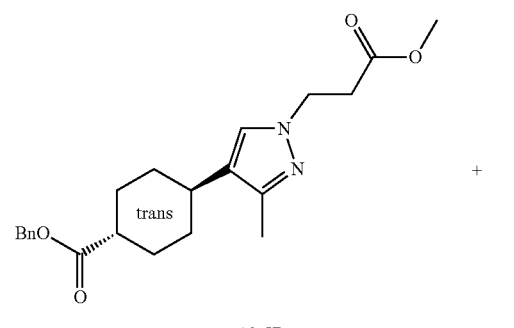
A18-5B
+
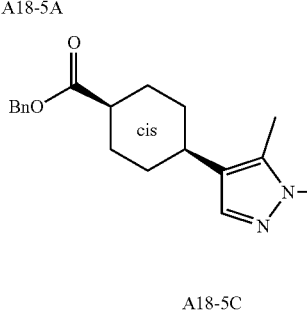
A18-5C
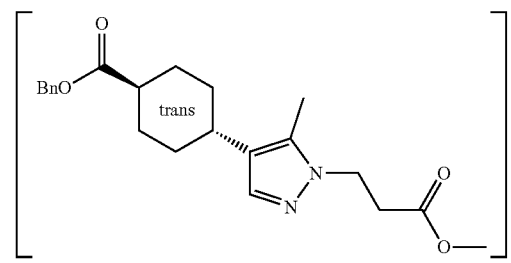

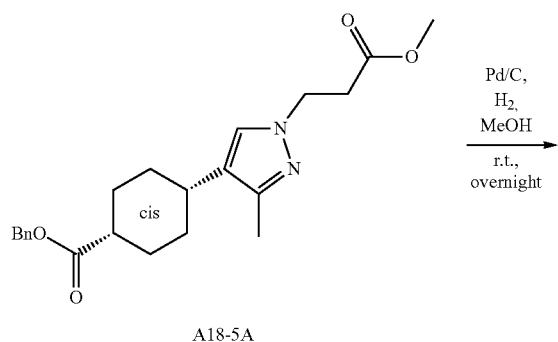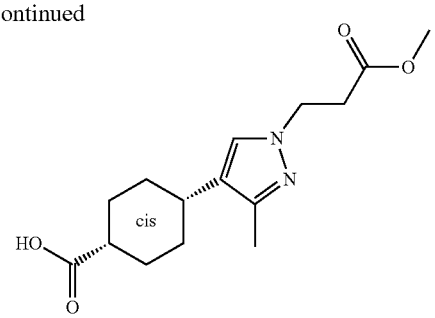

Intermediate A18-2

Benzyl 4-(3-methyl-1H-pyrazol-4-yl)cyclohex-3-enecarboxylate

To the solution of benzyl 4-(((trifluoromethyl)sulfonyl)oxy)cyclohex-3-enecarboxylate A11-1 (1.0 g, 90% purity, 2.47 mmol) and 3-methyl-4-(4,4,5,5-tetramethyl-1,3,2-dioxaborolan-2-yl)-1H-pyrazole A18-1 (857 mg, 4.12 mmol) in 1,4-dioxane (20 mL) and water (4 mL) were added potassium carbonate (1.12 g, 8.10 mmol) and [1,1'-Bis(diphenylphosphino)ferrocene]dichloropalladium(II) (198 mg, 0.27 mmol) at room temperature under nitrogen atmosphere. After stirred at 95° C. overnight, the mixture was concentrated under reduced pressure to give a crude which was diluted with water (10 mL) and extracted with ethyl acetate (20 mL) for three times. The combined organic layers were washed with brine (20 mL), dried over $Na_2SO_{4(s)}$ and filtered. The filtrate was concentrated and purified by silica gel column chromatography (petroleum ether:ethyl acetate=4:1 to 1:1) to give the title compound (670 mg, 73% purity, 67% yield) as colorless oil. LC-MS (ESI): $R_T$=2.350 min, mass calcd. for $C_{18}H_{20}N_2O_2$ 296.2, m/z found 297.1 [M+H]$^+$. $^1$H NMR (400 MHz, CDCl$_3$) δ 7.44 (s, 1H), 7.37-7.31 (m, 5H), 5.78 (s, 1H), 5.16 (s, 2H), 2.71-2.64 (m, 1H), 2.48-2.43 (m, 2H), 2.42-2.37 (m, 2H), 2.35 (s, 3H), 2.20-2.10 (m, 1H), 1.91-1.78 (m, 1H).

Intermediate A18-3

Mixture of benzyl 4-(1-(3-methoxy-3-oxopropyl)-3-methyl-1H-pyrazol-4-yl)cyclohex-3-enecarboxylate and benzyl 4-(1-(3-methoxy-3-oxopropyl)-5-methyl-1H-pyrazol-4-yl)cyclohex-3-enecarboxylate To the solution of benzyl 4-(3-methyl-H-pyrazol-4-yl)cyclohex-3-enecarboxylate A18-2 (500 mg, 73% purity, 1.23 mmol) in N,N-dimethylformamide (10 mL) were added potassium carbonate (466 mg, 3.37 mmol) and methyl acrylate (291 mg, 3.38 mmol) at room temperature under nitrogen atmosphere. After stirred at 50° C. overnight, the mixture was diluted with water (15 mL) and extracted with ethyl acetate (10 mL) for three times. The combined organic layers were washed with brine (10 mL) for three times, dried over $Na_2SO_{4(s)}$ and filtered. The filtrate was concentrated and purified by silica gel column chromatography (petroleum ether:ethyl acetate=4:1 to 1:1) to give crude product and then further purified by C18 column (acetonitrile:water=5% to 80%) to give the title compound (300 mg, 95% purity, 61% yield) as light yellow oil. LC-MS (ESI): $R_T$=2.509 min, mass calcd. for $C_{22}H_{26}N_2O_4$ 382.2, m/z found 383.1 [M+H]$^+$. $^1$H NMR (400 MHz, CDCl$_3$) δ 7.39-7.31 (m, 5H), 7.27 (s, 1H), 5.83-5.77 (m, 0.7H), 5.67-5.62 (m, 0.3H), 5.16 (s, 2H), 4.30 (t, J=6.4 Hz, 2H), 3.68 (s, 3H), 2.89 (t, J=7.2 Hz, 0.5H), 2.86 (t, J=6.4 Hz, 1.5H), 2.71-2.62 (m, 1H), 2.46-2.42 (m, 2H), 2.40-2.33 (m, 2H), 2.31 (s, 1H), 2.30 (s, 2H), 2.17-2.12 (m, 1H), 1.92-1.79 (m, 1H).

Intermediate A18-4

Mixture of 4-(1-(3-methoxy-3-oxopropyl)-3-methyl-1H-pyrazol-4-yl)cyclohexanecarboxylic acid and 4-(1-(3-methoxy-3-oxopropyl)-5-methyl-1H-pyrazol-4-yl)cyclohexanecarboxylic Acid To the solution of mixture of benzyl 4-(1-(3-methoxy-3-oxopropyl)-3-methyl-1H-pyrazol-4-yl)cyclohex-3-enecarboxylate and benzyl 4-(1-(3-methoxy-3-oxopropyl)-5-methyl-1H-pyrazol-4-yl)cyclohex-3-enecarboxylate A18-3 (300 mg, 95% purity, 0.745 mmol) in methanol (5 mL) was added 10% palladium on charcoal wt. (30 mg). The reaction was stirred at room temperature under hydrogen atmosphere of balloon overnight. The completed reaction was filtered and the filtrate was concentrated under reduced pressure to give the title compound (220 mg, 90% purity, 90% yield) as colorless oil. $^1$H NMR (400 MHz, DMSO-d$_6$) δ 12.15 (br s, 1H), 7.33 (s, 0.8H), 7.13 (s, 0.2H), 4.17 (t, J=6.8 Hz, 2H), 3.58 (s, 1.6H), 3.57 (s, 1.4H), 2.83-2.78 (m, 2H), 2.56-2.53 (m, 1H), 2.44-2.35 (m, 0.7H), 2.33-2.23 (m, 0.3H), 2.17 (s, 1H), 2.06 (s, 2H), 2.04-1.91 (m, 2H), 1.67-1.51 (m, 3.4H), 1.47-1.22 (m, 2.6H).

Intermediate A18-5

Mixture of benzyl 4-(1-(3-methoxy-3-oxopropyl)-3-methyl-1H-pyrazol-4-yl)cyclohexanecarboxylate (a Mixture of 2 Stereoisomers) and Benzyl 4-(1-(3-methoxy-3-oxopropyl)-5-methyl-1H-pyrazol-4-yl)cyclohexanecarboxylate (a Mixture of 2 Stereoisomers)

To the solution of mixture of 4-(1-(3-methoxy-3-oxopropyl)-3-methyl-1H-pyrazol-4-yl)cyclohexanecarboxylic acid and 4-(1-(3-methoxy-3-oxopropyl)-5-methyl-1H-pyrazol-4-yl)cyclohexanecarboxylic acid A18-4 (220 mg, 90% purity, 0.673 mmol) in N,N-dimethylformamide (5 mL) were added potassium carbonate (207 mg, 1.49 mmol) and (bromomethyl)benzene (193 mg, 1.13 mmol) at room temperature under nitrogen atmosphere. After stirred at room temperature overnight, the mixture was diluted with water (15 mL) and extracted with ethyl acetate (10 mL) for three times. The combined organic layers were washed with brine (10 mL)

for three times, dried over Na₂SO₄₍ₛ₎ and filtered. The filtrate was concentrated and purified by silica gel column chromatography (petroleum ether:ethyl acetate=5:1 to 1:1) to give the title compound (240 mg, 95% purity from $^1$H NMR, 88% yield) as light yellow oil. LC-MS (ESI): $R_T$=2.556 min, mass calcd. for $C_{22}H_{28}N_2O_4$ 384.2, m/z found 385.1 [M+H]$^+$. $^1$H NMR (400 MHz, CDCl₃) δ 7.39-7.30 (m, 5H), 7.21 (s, 0.3H), 7.09 (s, 0.2H), 7.05 (s, 0.5H), 5.17 (s, 0.5H), 5.16 (s, 1H), 5.13 (s, 0.5H), 4.30-4.25 (m, 2H), 3.67 (s, 3H), 2.91-2.83 (m, 2H), 2.73-2.68 (m, 0.8H), 2.49-2.31 (m, 1.2H), 2.23-2.15 (m, 4H), 2.12-1.87 (m, 1H), 1.76-1.39 (m, 6H).

Intermediates A18-5A, A18-5B and A18-5C (cis)-benzyl 4-(1-(3-methoxy-3-oxopropyl)-3-methyl-1H-pyrazol-4-yl)cyclohexane carboxylate (a Single Stereoisomer), (trans)-benzyl 4-(1-(3-methoxy-3-oxopropyl)-3-methyl-1H-pyrazol-4-yl) cyclohexanecarboxylate (a Single Stereoisomer) and Mixture of (cis)-benzyl 4-(1-(3-methoxy-3-oxopropyl)-5-methyl-1H-pyrazol-4-yl)cyclohexanecarboxylate and (trans)-benzyl 4-(1-(3-methoxy-3-oxopropyl)-5-methyl-1H-pyrazol-4-yl) cyclohexanecarboxylate (a Mixture of 2 Stereoisomers)

Mixture of benzyl 4-(1-(3-methoxy-3-oxopropyl)-3-methyl-1H-pyrazol-4-yl)cyclohexanecarboxylate and benzyl 4-(1-(3-methoxy-3-oxopropyl)-5-methyl-1H-pyrazol-4-yl)cyclohexanecarboxylate A18-5 (7.90 g, 95% purity, 19.5 mmol) was separated by chiral Prep. SFC (separation condition: Column: Chiralpak IE 5 μm 20*250 nm; Mobile Phase: CO₂:MeOH=60:40 at 45 g/min; Temp: 30° C.; Wavelength: 214 nm) to afford the title compounds A18-5A (4.35 g, 88% purity, 51% yield) as light yellow oil, A18-5B (1.04 g, 87% purity, 12% yield) as light yellow oil and A18-5C (1.70 g, 84% purity, 19% yield) as light yellow oil. A18-5A: LC-MS (ESI): $R_T$=2.544 min, mass calcd. for $C_{22}H_{28}N_2O_4$ 384.2, m/z found 385.1 [M+H]$^+$. Chiral analysis (Column: Chiralpak IE 5 μm 4.6*250 mm; Mobile Phase: CO₂:MeOH=60:40 at 3 g/min; Temp: 30° C.; Wavelength: 230 nm, Back pressure: 100 bar, $R_T$=3.03 min). $^1$H NMR (400 MHz, CDCl₃) δ 7.40-7.36 (m, 5H), 7.05 (s, 1H), 5.16 (s, 2H), 4.27 (t, J=6.8 Hz, 2H), 3.67 (s, 3H), 2.84 (t, J=6.8 Hz, 2H), 2.72-2.68 (m, 1H), 2.48-2.41 (m, 1H), 2.19-2.15 (m, 5H), 1.76-1.71 (m, 2H), 1.68-1.60 (m, 2H), 1.52-1.42 (m, 2H).

A18-5B: LC-MS (ESI): $R_T$=2.689 min, mass calcd. for $C_{22}H_{28}N_2O_4$ 384.2, m/z found 385.1 [M+H]$^+$. Chiral analysis (Column: Chiralpak IE 5 μm 4.6*250 mm; Mobile Phase: CO₂:MeOH=60:40 at 3 g/min; Temp: 30° C.; Wavelength: 230 nm, Back pressure: 100 bar, $R_T$=3.71 min). $^1$H NMR (400 MHz, CDCl₃) δ 7.39-7.30 (m, 5H), 7.09 (s, 1H), 5.13 (s, 2H), 4.29 (t, J=6.4 Hz, 2H), 3.67 (s, 3H), 2.85 (t, J=6.4 Hz, 2H), 2.41-2.32 (m, 2H), 2.19 (s, 3H), 2.11-2.06 (m, 2H), 1.98-1.94 (m, 2H), 1.63-1.53 (m, 2H), 1.33-1.23 (m, 2H).

A18-5C: LC-MS (ESI): $R_T$=2.588 min, mass calcd. for $C_{22}H_{28}N_2O_4$ 384.2, m/z found 385.1 [M+H]$^+$. Chiral analysis (Column: Chiralpak IE 5 μm 4.6*250 mm; Mobile Phase: CO₂:MeOH=60:40 at 3 g/min; Temp: 30° C.; Wavelength: 230 nm, Back pressure: 100 bar, $R_T$=4.45 min). $^1$H NMR (400 MHz, CDCl₃) δ 7.37-7.31 (m, 5H), 7.21 (s, 1H), 5.17 (s, 1.6H), 5.13 (s, 0.4H), 4.29-4.25 (m, 2H), 3.67 (s, 3H), 2.91-2.87 (m, 2H), 2.75-2.67 (m, 0.8H), 2.43-2.31 (m, 1.2H), 2.25-2.17 (m, 4.5H), 2.15-2.08 (m, 0.5H), 1.91-1.87 (m, 0.5H), 1.72-1.52 (m, 5H), 1.43-1.37 (m, 0.5H).

Acid 18

(cis)-4-(1-(3-Methoxy-3-oxopropyl)-3-methyl-1H-pyrazol-4-yl)cyclohexanecarboxylic Acid To the solution of (cis)-benzyl 4-(1-(3-methoxy-3-oxopropyl)-3-methyl-1H-pyrazol-4-yl)cyclohexanecarboxylate A18-5A (4.35 g, 88% purity, 9.96 mmol) in methanol (20 mL) was added 10% palladium on charcoal wt. (440 mg). After stirred at room temperature under hydrogen atmosphere (balloon) overnight, the reaction mixture was filtered and the filtrate was concentrated under reduced pressure to give the title compound (3.22 g, 80% purity, 88% yield) as white solids. LC-MS (ESI): $R_T$=1.718 min, mass calcd. for $C_{15}H_{22}N_2O_4$ 294.2, m/z found 295.1 [M+H]$^+$. $^1$H NMR (400 MHz, DMSO-d₆) δ 12.11 (s, 1H), 7.33 (s, 1H), 4.17 (t, J=6.8 Hz, 2H), 3.58 (s, 3H), 2.80 (t, J=6.8 Hz, 2H), 2.59-2.57 (m, 1H), 2.43-2.37 (m, 1H), 2.06 (s, 3H), 2.02-1.98 (m, 2H), 1.67-1.63 (m, 2H), 1.59-1.51 (m, 2H), 1.40-1.34 (m, 2H).

Acid 19

4-(1-(3-(tert-butoxycarbonyl)cyclobutyl)-1H-pyrazol-4-yl)cyclohexane-1-carboxylic Acid (A19)

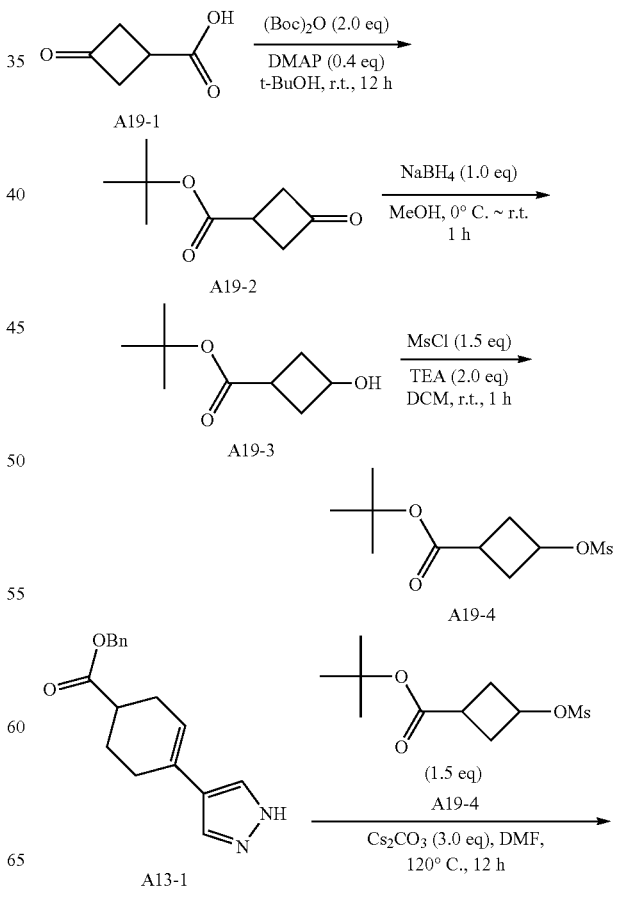

-continued

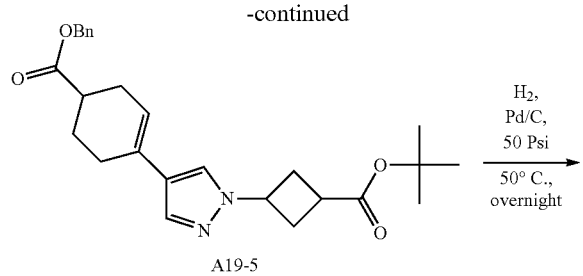

Intermediate A19-2 tert-Butyl 3-oxocyclobutanecarboxylate

To a solution of 3-oxocyclobutanecarboxylic acid A19-1 (20.0 g, 98% purity, 0.172 mol) in 2-methylpropan-2-ol (200 mL) were added N,N-dimethylpyridin-4-amine (8.48 g, 99% purity, 68.7 mmol) and di-tert-butyl dicarbonate (75.5 g, 99.3% purity, 0.344 mol) slowly at room temperature. After stirred at room temperature for 12 hours under nitrogen atmosphere, the reaction mixture was quenched with 1 M hydrochloride aqueous solution (200 mL) slowly and extracted with ethyl acetate (200 mL) for three times. The combined organic layers were washed with brine (200 mL), dried over $Na_2SO_{4(s)}$, filtered and concentrated under reduced pressure to give a residue, which was purified by silica gel column chromatography (petroleum ether:ethyl acetate=50:1 to 30:1) to afford the title compound (17.9 g, 95% purity from $^1$H NMR, 58% yield) as colorless oil. $^1$H NMR (400 MHz, CDCl$_3$) δ 3.39-3.32 (m, 2H), 3.27-3.20 (m, 2H), 3.13-3.07 (m, 1H), 1.47 (s, 9H).

Intermediate A19-3 tert-Butyl 3-hydroxycyclobutanecarboxylate

To a solution of tert-butyl 3-oxocyclobutanecarboxylate A19-2 (17.9 g, 95% purity, 0.100 mol) in methanol (180 mL) was added sodium tetrahydroborate (3.86 g, 98.5% purity, 0.101 mol) at 0° C. After stirred at room temperature for 1 hour under nitrogen atmosphere, the reaction mixture was quenched with saturated aqueous sodium bicarbonate solution (200 mL) slowly and extracted with ethyl acetate (200 mL) for three times. The combined organic layers were washed with brine (200 mL), dried over $Na_2SO_{4(s)}$, filtered and concentrated under reduced pressure to give the title compound (17.9 g, 95% purity from $^1$H NMR, 99% yield) as colorless oil. $^1$H NMR (400 MHz, CDCl$_3$) δ 4.15 (br s, 1H), 2.59-2.46 (m, 3H), 2.24-2.17 (m, 1H), 2.12-2.04 (m, 2H), 1.44 (s, 9H).

Intermediate A19-4 tert-Butyl 3-((methylsulfonyl)oxy)cyclobutanecarboxylate

To a solution of tert-butyl 3-hydroxycyclobutanecarboxylate A19-3 (5.00 g, 95% purity, 27.6 mmol) in dichloromethane (50 mL) were added triethylamine (5.61 g, 99% purity, 54.9 mmol) and methanesulfonyl chloride (4.79 g, 99% purity, 41.4 mmol) at room temperature. After stirred at room temperature for 1 hour under nitrogen atmosphere, the reaction mixture was quenched with saturated aqueous sodium bicarbonate solution (50 mL) slowly and extracted with dichloromethane (50 mL) for three times. The combined organic layers were washed with brine (50 mL), dried over $Na_2SO_{4(s)}$, filtered and concentrated under reduced pressure to afford the title compound (7.10 g, 85% purity, 87% yield) as yellow solids. $^1$H NMR (300 MHz, CDCl$_3$) δ 4.95-4.85 (m, 1H), 3.00 (s, 3H), 2.71-2.61 (m, 3H), 2.55-2.46 (m, 2H), 1.45 (s, 9H).

Intermediate A19-5 Benzyl 4-(1-(3-(tert-butoxycarbonyl)cyclobutyl)-1H-pyrazol-4-yl)cyclohex-3-enecarboxylate To a solution of benzyl 4-(1H-pyrazol-4-yl)cyclohex-3-enecarboxylate A13-1 (3.00 g, 90% purity, 9.56 mmol) in N,N-dimethylformamide (30 mL) were added tert-butyl 3-((methylsulfonyl)oxy)cyclobutanecarboxylate A19-4 (4.22 g, 85% purity, 14.3 mmol) and cesium carbonate (9.44 g, 99% purity, 28.7 mmol) at room temperature. After stirred at 120° C. for 12 hours under nitrogen atmosphere, the reaction mixture was quenched with water (50 mL) slowly and extracted with ethyl acetate (50 mL) for three times. The combined organic layers were washed with brine (50 mL), dried over $Na_2SO_{4(s)}$, filtered and concentrated under reduced pressure to give a residue, which was purified by silica gel column chromatography (petroleum ether:ethyl acetate=20:1 to 10:1) to afford the title compound (980 mg, 95% purity, 22% yield) as yellow oil. LC-MS (ESI): $R_T$=2.100 min, mass calcd. for $C_{26}H_{32}N_2O_4$ 436.2, m/z found 437.2 $[M+H]^+$.

Acid 19

4-(1-(3-(tert-butoxycarbonyl)cyclobutyl)-1H-pyrazol-4-yl)cyclohexane-1-carboxylic Acid To a solution of benzyl 4-(1-(3-(tert-butoxycarbonyl)cyclobutyl)-1H-pyrazol-4-yl)cyclohex-3-enecarboxylate A19-5 (980 mg, 95% purity, 2.13 mmol) in methanol (20 mL) was added 10% palladium on charcoal wt. (100 mg) under nitrogen atmosphere at room temperature. After replacing the inner nitrogen atmosphere with hydrogen gas, the mixture was stirred at 50° C. under hydrogen atmosphere (50 psi) overnight. After cooling down to room temperature and releasing the inside pressure into normal pressure, the catalyst was filtered off and the filtrate was concentrated under reduced pressure to give the title compound (490 mg, 95% purity, 63% yield) as gray solids. $^1$H NMR (400 MHz, CDCl$_3$) δ 7.38-7.17 (m, 2H), 6.43 (br s, 1H), 4.94-4.86 (m, 0.5H), 4.66-4.57 (m, 0.5H), 3.07-3.01 (m, 0.5H), 2.84-2.76 (m, 1.5H), 2.68-2.63 (m, 4H), 2.53-2.50 (m, 0.8H), 2.43-2.37 (m, 0.2H), 2.00-1.98 (m, 2.5H), 1.79-1.74 (m, 1.5H), 1.66-1.58 (m, 3H), 1.48 (s, 4H), 1.45 (s, 5H), 1.32-1.21 (m, 1H).

Acid 20

4-(3-(Methoxycarbonyl)-1-methyl-1H-pyrazol-5-yl)cyclohexane Carboxylic Acid (A20)

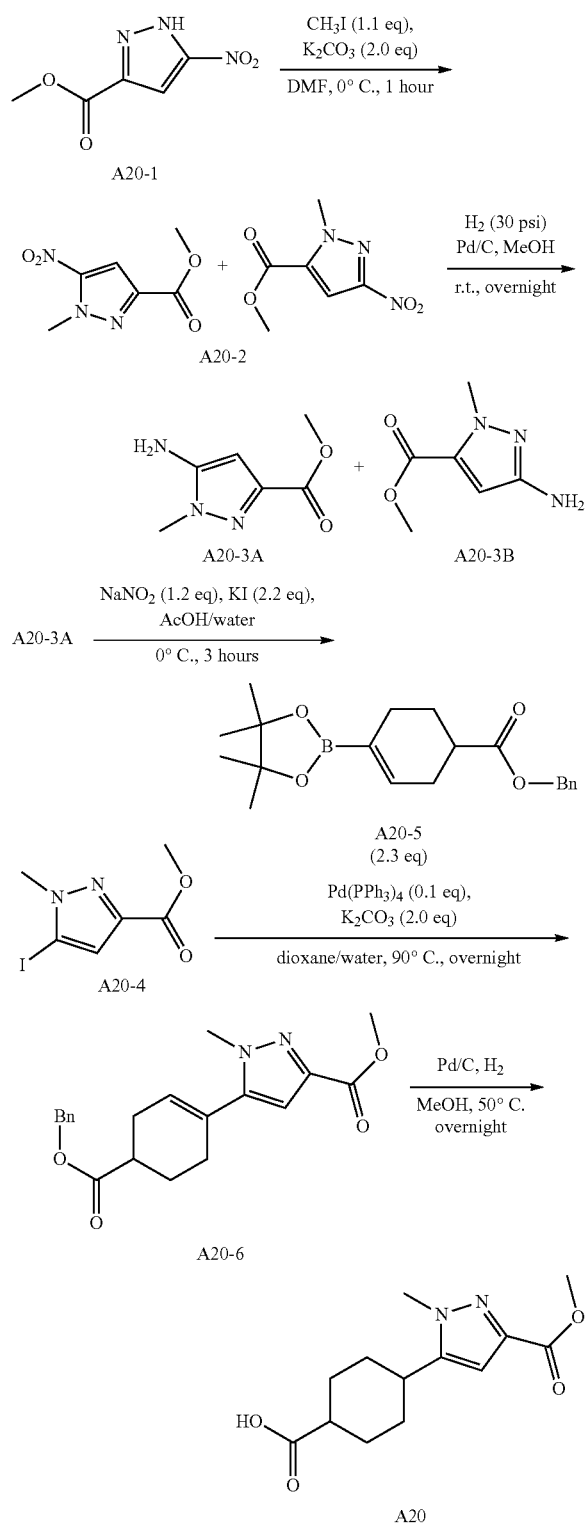

Intermediate A20-2

Mixture of methyl 1-methyl-5-nitro-1H-pyrazole-3-carboxylate and methyl 1-methyl-3-nitro-1H-pyrazole-5-carboxylate To a solution of methyl 5-nitro-1H-pyrazole-3-carboxylate A20-1 (8.4 g, 97% purity, 47.6 mmol) in N,N-dimethylformamide (100 mL) was added potassium carbonate (13.139 g, 95.068 mmol), then iodomethane (7.451 g, 52.495 mmol) was added dropwise at 0° C. The reaction mixture was stirred at 0° C. for 1 hour. The solvent was concentrated under reduced pressure to give the title compound (8.0 g, 88% purity, 80% yield) as yellow solids. LC-MS (ESI): $R_T$=1.11 min and 1.30 min.

Intermediates A20-3A and A20-3B

Methyl 5-amino-1-methyl-1H-pyrazole-3-carboxylate and methyl 3-amino-1-methyl-1H-pyrazole-5-carboxylate To a solution of A20-2 (8.0 g, 88% purity, 38.0 mmol) in ethanol (100 mL) was added 10% palladium on charcoal wt. (1.0 g) at room temperature. The reaction mixture was stirred at room temperature under hydrogen atmosphere (30 psi) overnight. The reaction mixture was filtered and the filtrate was concentrated to give a residue, which was purified by silica gel column chromatography (petroleum ether:ethyl acetate=2:1 to dichloromethane:methanol=20:1) to give the title compound A20-3A (970 mg, 95% purity from $^1$HNMR, 16% yield) and A20-3B (5.26 g, 98% purity from $^1$HNMR, 89% yield) as yellow solids.

A20-3A: LC-MS (ESI): $R_T$=0.32 min, mass calcd. for $C_6H_9N_3O_2$ 155.1, m/z found 156.2[M+H]$^+$. $^1$H NMR (400 MHz, CDCl$_3$) 6.08 (s, 1H), 3.89 (s, 3H), 3.75 (s, 3H), 3.68 (br s, 2H).

A20-3B: LC-MS (ESI): $R_T$=0.38 min, mass calcd. for $C_6H_9N_3O_2$ 155.1, m/z found 156.2[M+H]$^+$. $^1$H NMR (400 MHz, CDCl$_3$) 6.11 (s, 1H), 3.98 (s, 3H), 3.83 (s, 3H), 3.65 (br s, 2H).

Intermediate A20-4

Methyl 5-iodo-1-methyl-1H-pyrazole-3-carboxylate

To a solution of methyl 5-amino-1-methyl-1H-pyrazole-3-carboxylate A20-3A (970 mg, 95% purity, 5.94 mmol) and potassium iodide (2.2 g, 13.3 mmol) in acetic acid (10 mL) and water (3 mL) was added a sodium nitrite (534 mg, 97% purity, 7.51 mmol) in water (7 mL). After addition, the reaction mixture was stirred at 0° C. for 3 hours then the mixture was basified to pH 7-8 with saturated sodium bicarbonate aqueous solution (200 mL). The mixture was extracted by ethyl acetate (100 mL) twice. The combined organic layers were washed by brine (100 mL) twice, dried over Na$_2$SO$_{4(s)}$ and filtered. The filtrate was concentrated under reduced pressure to give a residue, which was purified by silica gel column chromatography (petroleum ether:ethyl acetate=5:1) to give the title compound A20-4 (700 mg, 95% purity, 40% yield) as white solids. LC-MS (ESI): $R_T$=1.26 min, mass calcd. for $C_6H_7IN_2O_2$ 266.0, m/z found 266.9 [M+H]$^+$. $^1$H NMR (400 MHz, CDCl$_3$) 6.97 (s, 1H), 4.00 (s, 3H), 3.91 (s, 3H).

Intermediate A20-6

Methyl 5-(4-((Benzyloxy)carbonyl)cyclohex-1-en-1-yl)-1-methyl-1H-pyrazole-3-carboxylate The mixture of methyl 5-iodo-1-methyl-1H-pyrazole-3-carboxylate A20-4 (550 mg, 95% purity, 1.96 mmol), benzyl 4-(4,4,5,5-tetramethyl-1,3,2-dioxaborolan-2-yl)cyclohex-3-enecarboxylate A20-5 (1.7 g, 91% purity, 4.5 mmol), tetrakis(triphenylphosphine) palladium(0) (232 mg, 0.201 mmol) and potassium carbonate (560 mg, 4.05 mmol) in dioxane (10 mL) and water (0.5 mL) was stirred at 90° C. under nitrogen atmosphere overnight. After cooling down to room temperature, the solvent was removed under reduced pressure, and the residue was purified by silica gel column chromatography (petroleum ether:ethyl acetate=3:1) to give the title compound A20-6 (390 mg, 96% purity, 54% yield) as yellow oil. LC-MS (ESI): $R_T$=1.63 min, mass calcd. for $C_{20}H_{22}N_2O_4$ 354.2, m/z found 355.2[M+H]$^+$. $^1$H NMR (400 MHz, CDCl$_3$) 7.38-7.33 (m, 5H), 6.64 (s, 1H), 5.93-5.90 (m, 1H), 5.16 (s, 2H), 3.91 (s, 3H), 3.87 (s, 3H), 2.74-2.70 (m, 1H), 2.53-2.50 (m, 2H), 2.35-2.32 (m, 2H), 2.17-2.14 (m, 1H), 1.92-1.90 (m, 1H).

Acid 20

4-(3-(Methoxycarbonyl)-1-methyl-1H-pyrazol-5-yl)cyclohexanecarboxylic Acid

To a solution of methyl 5-(4-((benzyloxy)carbonyl)cyclohex-1-en-1-yl)-1-methyl-1H-pyrazole-3-carboxylate A20-6 (810 mg, 97% purity, 2.22 mmol) in methanol (5 mL) was added palladium on charcoal (80 mg, 10% wt) at room temperature. The reaction mixture was stirred at 50° C. under hydrogen atmosphere (50 psi) overnight. The reaction mixture was cooled down to room temperature and filtered. The filtrate was concentrated to give the title compound A20 (550 mg, 90% purity from $^1$HNMR, 84% yield) as white solids. $^1$H NMR (300 MHz, CDCl$_3$) 6.61 (s, 0.8H), 6.59 (s, 0.2H), 3.91-3.89 (m, 6H), 2.79-2.77 (m, 1H), 2.66-2.42 (m, 2H), 2.30-2.18 (m, 2H), 2.05-2.03 (m, 1H), 1.87-1.80 (m, 2H), 1.74-1.66 (m, 2H).

Acid 21

4-(5-(methoxycarbonyl)-1-methyl-1H-pyrazol-3-yl)cyclohexanecarboxylic Acid (A21)

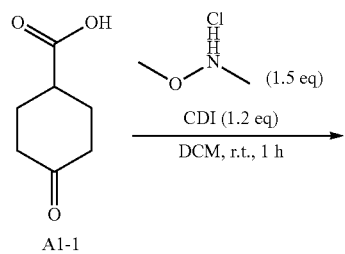

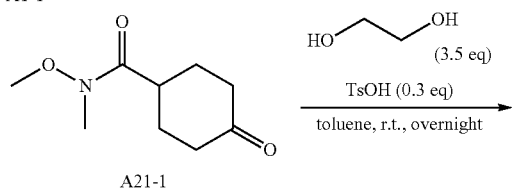

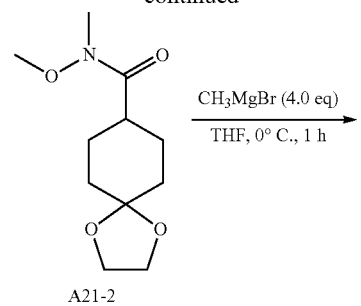

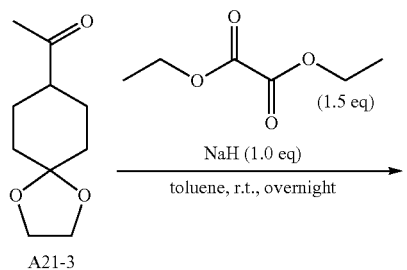

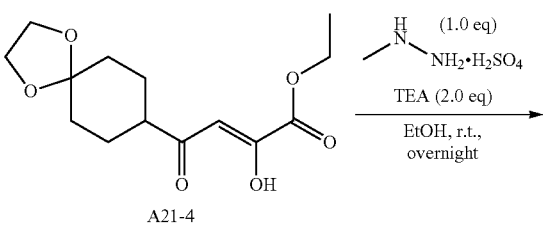

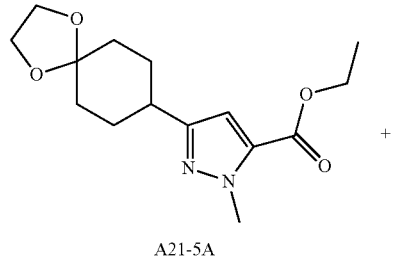

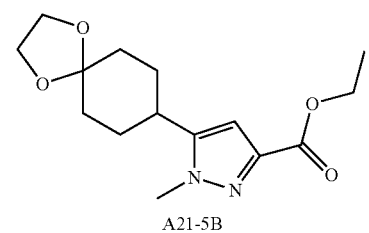

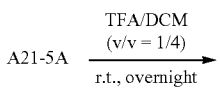

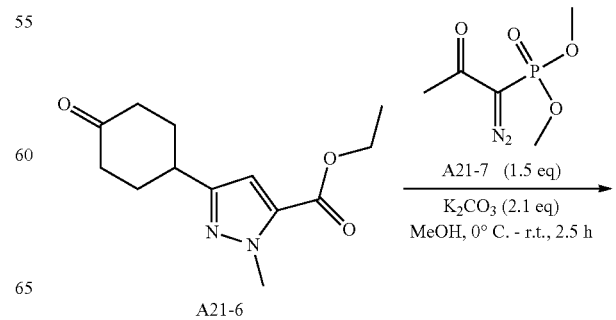

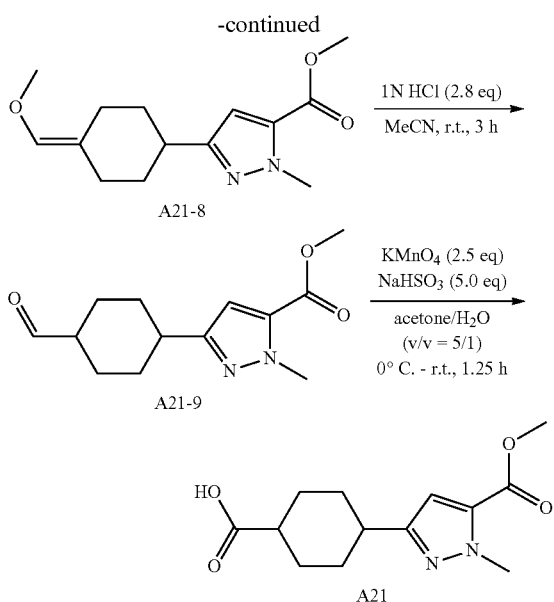

Intermediate A21-1

N-Methoxy-N-methyl-4-oxocyclohexanecarboxamide

To a solution of 4-oxocyclohexanecarboxylic acid A1-1 (20.0 g, 141 mmol) in dichloromethane (400 mL) was added N,O-dimethylhydroxylamine hydrochloride (20.5 g, 211 mmol) and N,N'-carbonyldiimidazole (27.3 g, 169 mmol) at room temperature. After stirred at room temperature for 1 hour, the mixture was diluted with water (300 mL), extracted with dichloromethane (400 mL) twice. The combined organic layers were concentrated under reduced pressure to give the title compound (13.3 g, 51% yield) as yellow oil. LC-MS (ESI): $R_T$=0.63 min, mass calcd. for $C_9H_{15}NO_3$ 185.1, m/z found mass 186.0 [M+H]$^+$. $^1$H NMR (300 MHz, CD$_3$OD) δ 3.75 (s, 3H), 3.14 (s, 3H), 2.54-2.43 (m, 3H), 2.30-2.22 (m, 2H), 2.05-1.99 (m, 2H), 1.80-1.65 (m, 2H)

Intermediate A21-2

N-Methoxy-N-methyl-1,4-dioxaspiro[4.5]decane-8-carboxamide

To a solution of N-methoxy-N-methyl-4-oxocyclohexanecarboxamide A21-1 (13.3 g, 71.8 mmol) and ethane-1,2-diol (15.5 g, 250 mmol) in toluene (150 mL) was added 4-methylbenzenesulfonic acid (3.69 g, 21.4 mmol). After stirred at room temperature overnight, the mixture was concentrated to give a residue, which was dissolved in dichloromethane (100 mL). The resulting solution was washed with water (100 mL) and then concentrated under reduced pressure to give the title compound (9.00 g, 55% yield) as yellow oil. $^1$H NMR (300 MHz, DMSO-d$_6$) δ 3.92-3.86 (m, 4H), 3.66-3.63 (m, 3H), 3.13-3.12 (m, 3H), 2.68-2.62 (m, 1H), 1.86-1.74 (m, 6H), 1.58-1.47 (m, 2H)

Intermediate A21-3

1-(1,4-Dioxaspiro[4.5]decan-8-yl)ethanone

To a solution of N-methoxy-N-methyl-1,4-dioxaspiro[4.5]decane-8-carboxamide A21-2 (9.00 g, 39.2 mmol) in anhydrous tetrahydrofuran (60 mL) at 0° C. was added dropwise 2 M methylmagnesium bromide in tetrahydrofuran (79 mL, 158 mmol). After stirred at 0° C. for 1 hour, the mixture was quenched with saturated aqueous ammonium chloride (79 mL), then extracted with ethyl acetate (100 mL) for three times. The separated combined organic layer was washed with brine (100 mL), dried over Na$_2$SO$_{4(s)}$ and concentrated under reduced pressure to give a residue, which was purified by silica gel column chromatography (petroleum ether:ethyl acetate=10:1) to give the title compound (4.00 g, 55% yield) as yellow oil. LC-MS (ESI): $R_T$=0.88 min, mass calcd. for $C_{10}H_{16}O_3$ 184.1, m/z found mass 185.1 [M+H]$^+$. $^1$H NMR (300 MHz, DMSO-d$_6$) δ 3.83-3.76 (m, 4H), 2.40-2.29 (m, 1H), 2.09-2.02 (m, 3H), 1.78-1.72 (m, 2H), 1.70-1.58 (m, 2H), 1.46-1.40 (m, 4H).

Intermediate A21-4

Ethyl 2-hydroxy-4-oxo-4-(1,4-dioxaspiro[4.5]decan-8-yl)but-2-enoate

To a solution of 1-(1,4-dioxaspiro[4.5]decan-8-yl)ethanone A21-3 (3.30 g, 17.9 mmol) in toluene (40 mL) was added 60% wt. sodium hydride in mineral oil (716 mg, 17.9 mmol) at room temperature. After stirring at room temperature for 1 hour, diethyl oxalate (3.93 g, 26.9 mmol) was added. After stirred at room temperature overnight, the mixture was acidified to pH 3~4 with 10% wt. citric acid aqueous solution and extracted with ethyl acetate (20 mL) twice. The combined organic layers were washed with water (20 mL), brine (10 mL), dried over anhydrous Na$_2$SO$_{4(s)}$, filtered and concentrated to give a residue, which was purified by silica gel column chromatography (petroleum ether:ethyl acetate=15:1) to give the title compound (3.30 g, 65% yield) as yellow oil. LC-MS (ESI): $R_T$=1.45 min, mass calcd. for $C_{14}H_{20}O_6$ 284.1, m/z found mass 285.2 [M+H]$^+$. $^1$H NMR (300 MHz, DMSO-d$_6$) δ 7.24-7.13 (m, 1H), 6.39 (s, 1H), 4.28-4.19 (m, 2H), 3.84-3.80 (m, 4H), 2.4-2.47 (m, 1H), 1.81-1.49 (m, 8H), 1.27-1.16 (m, 3H).

Intermediates A21-5A and A21-5B

Ethyl 1-methyl-3-(1,4-dioxaspiro[4.5]decan-8-yl)-1H-pyrazole-5-carboxylate and ethyl 1-methyl-5-(1,4-dioxaspiro[4.5]decan-8-yl)-1H-pyrazole-3-carboxylate To a solution of triethylamine (2.35 g, 23.2 mmol) in ethanol (300 mL) was added methylhydrazine sulfate (1.67 g, 11.6 mmol) at room temperature. After stirring at room temperature for 1 hour, ethyl 2-hydroxy-4-oxo-4-(1,4-dioxaspiro[4.5]decan-8-yl)but-2-enoate A21-4 (3.30 g, 11.6 mmol) was added.

After stirred at room temperature overnight, the mixture was concentrated to give a residue, which was dissolved in ethyl acetate (150 mL). The resulting solution was washed with water (100 mL), brine (100 mL), dried over Na$_2$SO$_{4(s)}$, filtered and concentrated under reduced pressure to give a residue, which was purified by silica gel column chromatography (petroleum ether:ethyl acetate=4:1 to 2:1) to give the title compounds A21-5A (1.50 g, 44% yield) and A21-5B (520 mg, 15% yield) as yellow oil.

A21-5A: $^1$H NMR (300 MHz, CDCl$_3$) δ 6.67 (s, 1H), 4.32 (q, J=5.4 Hz, 2H), 4.11 (s, 3H), 3.96 (s, 4H), 2.74-2.66 (m, 1H), 1.99-1.95 (m, 2H), 1.85-1.81 (m, 2H), 1.78-1.63 (m, 4H), 1.37 (t, J=5.4 Hz, 3H).

A21-5B: $^1$H NMR (300 MHz, DMSO-d$_6$) δ 6.49 (s, 1H), 4.23 (q, J=5.4 Hz, 2H), 3.88 (s, 4H), 3.85 (s, 3H), 2.84-2.77 (m, 1H), 1.88-1.84 (m, 2H), 1.76-1.73 (m, 2H), 1.67-1.50 (m, 4H), 1.27 (t, J=5.4 Hz, 3H).

Intermediate A21-6

Ethyl 1-methyl-3-(4-oxocyclohexyl)-1H-pyrazole-5-carboxylate

To a solution of ethyl 1-methyl-3-(1,4-dioxaspiro[4.5]decan-8-yl)-1H-pyrazole-5-carboxylate A21-5A (830 mg, 2.82 mmol) in dichloromethane (20 mL) was added trifluoroacetic acid (5 mL) at room temperature. After stirred at room temperature overnight, the reaction mixture was concentrated to give a residue, which was dissolved in ethyl acetate (40 mL). The resulting solution was washed with saturated sodium bicarbonate aqueous solution (50 mL), brine (15 mL), dried over Na$_2$SO$_{4(s)}$ and filtered. The filterate was concentrated under reduced pressure to give the title compound (700 mg, 99% yield) as yellow oil. LC-MS (ESI): R$_T$=1.38 min, mass calcd. for C$_{13}$H$_{18}$N$_2$O$_3$ 250.1, m/z found mass 251.2 [M+H]$^+$. $^1$H NMR (300 MHz, DMSO-d$_6$) δ 6.68-6.64 (m, 1H), 4.35-4.28 (m, 2H), 4.14-4.06 (m, 3H), 3.18-3.06 (m, 1H), 2.48-2.41 (m, 2H), 2.27-2.26 (m, 2H), 2.02-1.86 (m, 2H), 1.68-1.53 (m, 2H), 1.38-1.32 (m, 3H).

Intermediate A21-8

Methyl 3-(4-(methoxymethylene)cyclohexyl)-1-methyl-1H-pyrazole-5-carboxylate

To a solution of ethyl 1-methyl-3-(4-oxocyclohexyl)-1H-pyrazole-5-carboxylate A21-6 (736 mg, 2.94 mmol) and dimethyl (1-diazo-2-oxopropyl)phosphonate A21-7 (840 mg, 4.37 mmol) in dry methanol (15 mL) was added potassium carbonate (845 mg, 6.11 mmol) at 0° C. under nitrogen atmosphere. After stirred at 0° C. for 30 minutes and then at room temperature for 2 hours, the reaction mixture was diluted with water (20 mL) and extracted with ethyl acetate (30 mL) twice. The combined organic layers were washed with water (30 mL), brine (30 mL) twice, dried over Na$_2$SO$_{4(s)}$ and filtered. The filtrate was concentrated under reduced pressure to give a residue, which was purified by silica gel column chromatography (petroleum ether:ethyl acetate=15:1) to give the title compound (380 mg, 49% yield) as yellow oil. LC-MS (ESI): R$_T$=1.78 min, mass calcd. for C14H$_{20}$N$_2$O$_3$ 264.2, m/z found mass 265.2 [M+H]$^+$. $^1$H NMR (300 MHz, DMSO-d$_6$) δ 6.64 (s, 1H), 5.84 (s, 1H), 3.98-3.97 (m, 3H), 3.77-3.76 (m, 3H), 3.45-3.44 (m, 3H), 2.70-2.60 (m, 1H), 1.92-1.60 (m, 4H), 1.32-1.05 (m, 4H).

Intermediate A21-9

Methyl 3-(4-formylcyclohexyl)-1-methyl-1H-pyrazole-5-carboxylate

To a solution of methyl 3-(4-(methoxymethylene)cyclohexyl)-1-methyl-1H-pyrazole-5-carboxylate A21-8 (380 mg, 1.44 mmol) in acetonitrile (18 mL) was added 1 M hydrochloride aqueous solution (4 mL, 4.0 mmol) at 0° C. After stirred at room temperature for 3 hours, the reaction mixture was basified with saturated sodium bicarbonate aqueous solution to pH 7~8 and extracted with ethyl acetate (20 mL) twice. The combined organic layers were washed with brine (20 mL) twice, dried over Na$_2$SO$_{4(s)}$, filtered and concentrated under reduced pressure to give the crude title compound (300 mg, 83% yield) as brown oil. LC-MS (ESI): R$_T$=1.43 min, mass calcd. for C$_{13}$H$_{18}$N$_2$O$_3$ 250.1, m/z found mass 251.2 [M+H]$^+$. $^1$H NMR (300 MHz, DMSO-d$_6$) δ 9.63-9.59 (m, 1H), 6.71-6.65 (m, 1H), 4.05-4.00 (m, 3H), 3.84-3.80 (m, 3H), 2.70-2.62 (m, 1H) 2.34-2.26 (m, 1H), 2.01-1.97 (m, 2H), 1.79-1.59 (m, 2H), 1.49-1.41 (m, 2H), 1.36-1.22 (m, 2H).

Acid 21

4-(5-(methoxycarbonyl)-1-methyl-1H-pyrazol-3-yl)cyclohexanecarboxylic Acid

To a solution of methyl 3-(4-formylcyclohexyl)-1-methyl-1H-pyrazole-5-carboxylate A21-9 (320 mg, 1.28 mmol) in acetone (15 mL) and water (3 mL) was added potassium permanganate (504 mg, 3.19 mmol) at 0° C. After stirring at 0° C. for 1 hour, sodium bisulfite (660 mg, 6.34 mmol) was added. Then the mixture was diluted with acetone (10 mL) and water (5 mL). The resulting suspension was stirred at room temperature for 15 minutes and filtered through a pad of celite. The filtrate was concentrated under reduced pressure at room temperature to remove acetone. The resulting aqueous solution was acidified with citric acid(s) to pH 3~4 and extracted with ethyl acetate (20 mL) twice. The combined organic layers were washed with brine (20 mL), dried over Na$_2$SO$_{4(s)}$, filtered and concentrated under reduced pressure to give the title compound (250 mg, 73% yield) as white solids. $^1$H NMR (300 MHz, DMSO-d$_6$) δ 11.98 (s, 1H), 6.67-6.64 (m, 1H), 4.00-3.99 (m, 3H), 3.79-3.78 (m, 3H), 2.72-2.63 (m, 1H), 2.27-2.11 (m, 0.5H), 1.96-1.91 (m, 0.5H), 1.89-1.78 (m, 2H), 1.71-1.57 (m, 4H), 1.43-1.32 (m, 2H).

Acid 22

4-(1-(3-(tert-butoxy)-2,2-dimethyl-3-oxopropyl)-1H-pyrazol-4-yl)cyclohexane-1-carboxylic Acid (A22)

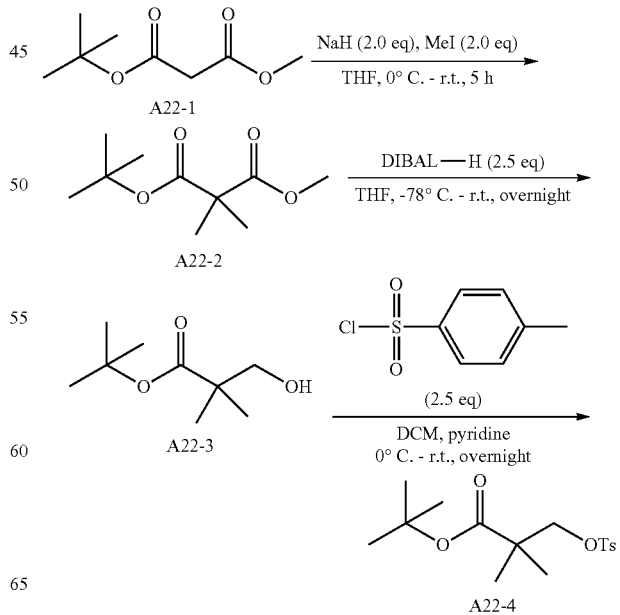

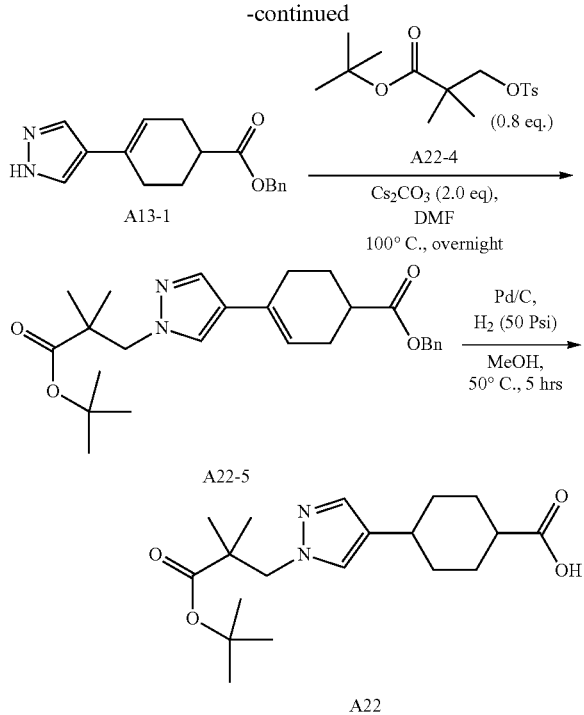

Intermediate A22-2

1-tert-Butyl 3-methyl 2,2-dimethylmalonate

To a suspension of 60% wt. sodium hydride in mineral oil (1.56 g, 39.0 mmol) in tetrahydrofuran (40 mL) was added tert-butyl methyl malonate A22-1 (3.50 g, 20.0 mmol) dropwise at 0° C. After stirring at this temperature for 30 minutes, iodomethane (5.54 g, 39.0 mmol) was added dropwise and it was continued to stir at room temperature for another 5 hours. Then the mixture was quenched with water (30 mL) and extracted with ethyl acetate (50 mL) twice. The combined organic layers were washed with brine (50 mL), dried over $Na_2SO_{4(s)}$ and filtered. The filtrate was concentrated under reduced pressure to give the title compound (3.80 g, 94% yield) as brown oil. $^1$H NMR (300 MHz, CDCl$_3$) δ 3.72 (s, 3H), 1.44 (s, 9H), 1.40 (s, 6H).

Intermediate A22-3 tert-Butyl 3-hydroxy-2,2-dimethylpropanoate

To a solution of 1-tert-butyl 3-methyl 2,2-dimethylmalonate A22-2 (5.00 g, 24.7 mmol) in tetrahydrofuran (30 mL) was added 1.5 M diisobutylaluminum hydride in toluene (41.3 mL, 61.9 mmol) dropwise at −78° C. under nitrogen atmosphere.

After stirred at this temperature under nitrogen atmosphere for 2 hours and then at room temperature overnight, the mixture was quenched with water (50 mL) and extracted with ethyl acetate (100 mL) for three times. The combined organic layers were washed with water (200 mL) for three times and brine (100 mL), dried over $Na_2SO_{4(s)}$ and filtered. The filtrate was concentrated under reduced pressure to give the title compound (2.00 g, 47% yield) as white oil. $^1$H NMR (300 MHz, CDCl$_3$) δ 3.52 (d, J=5.4 Hz, 2H), 2.58 (br s, 1H), 1.47 (s, 9H), 1.16 (s, 6H).

Intermediate A22-4 tert-Butyl 2,2-dimethyl-3-(tosyloxy)propanoate

To a solution of tert-butyl 3-hydroxy-2,2-dimethylpropanoate A22-3 (2.00 g, 11.5 mmol) in pyridine (8 mL) and dichloromethane (20 mL) was added tosyl chloride (5.49 g, 28.7 mmol) at 0° C. After stirred at room temperature under nitrogen atmosphere overnight, the mixture was concentrated and dissolved in ethyl acetate (40 mL) and water (40 mL), then added 0.5 M hydrochloride aqueous solution (24 mL) and separated. The aqueous layer was extracted with ethyl acetate (40 mL) twice. The combined organic layers were washed with 0.5 M hydrochloride aqueous solution (20 mL) and brine (20 mL), dried over $Na_2SO_{4(s)}$ and filtered. The filtrate was concentrated and purified by silica gel column chromatography (petroleum ether:ethyl acetate=10:1) to give the title compound (1.80 g, 48% yield) as white solids. $^1$H NMR (300 MHz, CDCl$_3$) δ 7.79 (d, J=8.1 Hz, 2H), 7.35 (d, J=8.1 Hz, 2H), 3.98 (s, 2H), 2.46 (s, 3H), 1.40 (s, 9H), 1.14 (s, 6H).

Intermediate A22-5

Benzyl 4-(1-(3-(tert-butoxy)-2,2-dimethyl-3-oxopropyl)-1H-pyrazol-4-yl)cyclohex-3-enecarboxylate To a suspension of benzyl 4-(1H-pyrazol-4-yl)cyclohex-3-enecarboxylate A13-1 (1.18 g, 95% purity, 3.97 mmol) and cesium carbonate (2.60 g, 7.98 mmol) in N,N-dimethylformamide (30 mL) was added tert-butyl 2,2-dimethyl-3-(tosyloxy)propanoate A22-4 (1.10 g, 95% purity, 3.18 mmol) at room temperature. After stirred at 100° C. overnight, the reaction mixture was quenched with water (60 mL) and extracted with ethyl acetate (60 mL) for three times. The combined organic layers were washed with water (60 mL), brine (60 mL), dried over $Na_2SO_{4(s)}$ and filtered. The filtrate was concentrated under reduced pressure to give a residue, which was purified by silica gel column chromatography (petroleum ether:ethyl acetate=10:1 to 3:1) to give crude product, which was further purified by C18 column (acetonitrile:water=70% to 100%) to give the title compound (700 mg, 95% purity from $^1$H NMR, 38% yield) as colorless oil. LC-MS (ESI): $R_T$=1.92 min, mass calcd. for $C_{26}H_{34}N_2O_4$ 438.3, m/z found 439.1 [M+H]$^+$. $^1$H NMR (400 MHz, CDCl$_3$) δ 7.50 (s, 1H), 7.39-7.30 (m, 6H), 5.94 (t, J=4.0 Hz, 1H), 5.14 (s, 2H), 4.20 (s, 2H), 2.68-2.61 (m, 1H), 2.46-2.38 (m, 2H), 2.37-2.27 (m, 2H), 2.17-2.11 (m, 1H), 1.88-1.78 (m, 1H), 1.45 (s, 9H), 1.15 (s, 6H).

Acid 22

4-(1-(3-(tert-Butoxy)-2,2-dimethyl-3-oxopropyl)-1H-pyrazol-4-yl)cyclohexane-1-carboxylic Acid To a solution of benzyl 4-(1-(3-(tert-butoxy)-2,2-dimethyl-3-oxopropyl)-1H-pyrazol-4-yl)cyclohex-3-enecarboxylate A22-5 (700 mg, 95% purity, 1.52 mmol) in methanol (30 mL) was added 10% palladium on charcoal wt. (400 mg) at room temperature. The reaction was stirred at 50° C. under hydrogen atmosphere (50 Psi) for 5 hours. The catalyst was filtered off and the filtrate was concentrated to give the title compound (570 mg, 90% purity from $^1$H NMR, 97% yield) as colorless oil. LC-MS (ESI): $R_T$=1.46 and 1.59 min, mass calcd. for $C_{19}H_{30}N_2O_4$ 350.2, m/z found 351.1 [M+H]$^+$. $^1$H NMR (400 MHz, CDCl$_3$) δ 7.31 (d, J=2.8 Hz, 1H), 7.17 (s, 1H), 4.19 (s, 2H), 2.66-2.56 (m, 1.5H), 2.48-

2.42 (m, 0.3H), 2.34-2.28 (m, 0.2H), 2.12-1.98 (m, 2.5H), 1.84-1.74 (m, 1.5H), 1.69-1.53 (m, 3.2H), 1.44-1.43 (m, 9H), 1.35-1.25 (m, 0.8H), 1.13-1.12 (m, 6H).

Acid 23

2-(3-Ethoxy-2,2-dimethyl-3-oxopropyl)-4,5,6,7-tetrahydro-2H-indazole-5-carboxylic Acid (A23)

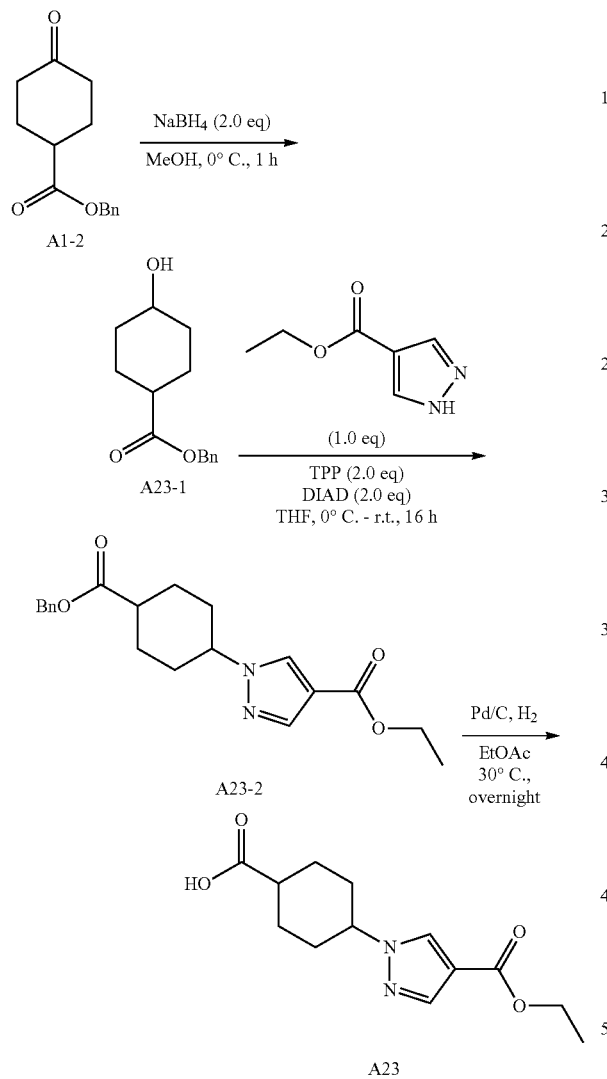

Intermediate A23-1 Benzyl 4-hydroxycyclohexanecarboxylate

To a solution of benzyl 4-oxocyclohexanecarboxylate A1-2 (17.3 g, 93% purity, 70.8 mmol) in methanol (150 mL) was added sodium borohydride (5.40 g, 143 mmol) under nitrogen atmosphere at 0° C. After stirred at 0° C. for 1.0 hour, the mixture was quenched with water (100 mL) and acidified with 2 M hydrochloride aqueous solution to pH ~1, then extracted with ethyl acetate (200 mL) twice. The combined organic layers were washed with brine (100 mL), dried over $Na_2SO_{4(s)}$ and filtered. The filtrate was concentrated under reduced pressure to give a residue, which was purified by silica gel column chromatography (petroleum ether:ethyl acetate=5:1 to 4:1) to give the desired compound (13.5 g, 90% purity from $^1$H NMR, 76% yield) as white solids. LC-MS (ESI): $R_T$=1.53 min, mass calcd. for $C_{14}H_{18}O_3$ 234.1, m/z found 235.0 [M+H]$^+$. $^1$H NMR (400 MHz, CDCl$_3$) δ 7.39-7.30 (m, 5H), 5.13 (s, 0.7H), 5.11 (s, 1.3H), 3.92-3.88 (m, 0.3H), 3.65-3.57 (m, 0.7H), 2.47-2.42 (m, 0.3H), 2.35-2.27 (m, 0.7H), 2.05-2.01 (m, 3H), 1.74-1.61 (m, 2H), 1.58-1.47 (m, 2H), 1.34-1.24 (m, 1H).

Intermediate A23-2

Ethyl 1-(4-((benzyloxy)carbonyl)cyclohexyl)-1H-pyrazole-4-carboxylate

To a solution of benzyl 4-hydroxycyclohexanecarboxylate A23-1 (5.00 g, 90% purity, 19.8 mmol), ethyl 1H-pyrazole-4-carboxylate (2.78 g, 19.8 mmol) and triphenylphosphine (10.4 g, 39.7 mmol) in tetrahydrofuran (70 mL) was added dropwise diisopropyl diazene-1,2-dicarboxylate (8.03 g, 39.7 mmol) at 0° C. under nitrogen atmosphere. After stirred at 0° C. to room temperature under nitrogen atmosphere for 16 hours, the mixture was quenched with water (80 mL) and extracted with ethyl acetate (100 mL) twice. The combined organic layers were washed with brine (80 mL), dried over $Na_2SO_{4(s)}$ and filtered. The filtrate was concentrated under reduced pressure to give a residue, which was purified by silica gel column chromatography (petroleum ether:ethyl acetate=10:1 to 5:1) and further purified by C18 column (acetonitrile:water=65% to 72%) to give the title compound (2.20 g, 90% purity from $^1$H NMR, 28% yield) as white solids. LC-MS (ESI): $R_T$=1.74 min, mass calcd. for $C_{20}H_{24}N_2O_4$ 356.2, m/z found 357.1 [M+H]$^+$. $^1$H NMR (400 MHz, CDCl$_3$) δ 7.91 (s, 0.2H), 7.90 (s, 0.2H), 7.89 (s, 0.8H), 7.87 (s, 0.8H), 7.40-7.32 (m, 5H), 5.17 (s, 1.6H), 5.14 (s, 0.4H), 4.32-4.26 (m, 2H), 4.22-4.16 (m, 1H), 2.75-2.70 (m, 0.8H), 2.46-2.39 (m, 0.2H), 2.28-2.18 (m, 2.5H), 2.09-1.84 (m, 3H), 1.84-1.64 (m, 2.5H), 1.37-1.32 (m, 3H).

Acid 23

2-(3-Ethoxy-2,2-dimethyl-3-oxopropyl)-4,5,6,7-tetrahydro-2H-indazole-5-carboxylic Acid To the solution of ethyl 1-(4-((benzyloxy)carbonyl)cyclohexyl)-1H-pyrazole-4-carboxylate A23-2 (2.15 g, 90% purity, 5.43 mmol) in ethyl acetate (26 mL) was added 10% palladium on charcoal wt. (400 mg). The mixture was stirred at 30° C. under hydrogen atmosphere (balloon) overnight. The catalyst was filtered off and the filtrate was concentrated to give the title compound (1.58 g, 90% purity, 98% yield) as white solids. LC-MS (ESI): $R_T$=1.12 min, mass calcd. for $C_{13}H_{18}N_2O_4$ 266.1, m/z found 267.1 [M+H]$^+$. $^1$H NMR (400 MHz, CDCl$_3$) δ 7.96 (s, 0.8H), 7.93 (s, 0.2H), 7.92 (s, 1H), 4.29 (q, J=7.2 Hz, 2H), 4.24-4.15 (m, 1H), 2.78-2.66 (m, 1H), 2.31-2.22 (m, 2.6H), 2.12-1.99 (m, 3.4H), 1.87-1.69 (m, 2H), 1.34 (t, J=7.2 Hz, 3H).

Acid 24

4-(5-(Ethoxycarbonyl)-1H-pyrazol-1-yl)cyclohexanecarboxylic Acid A24

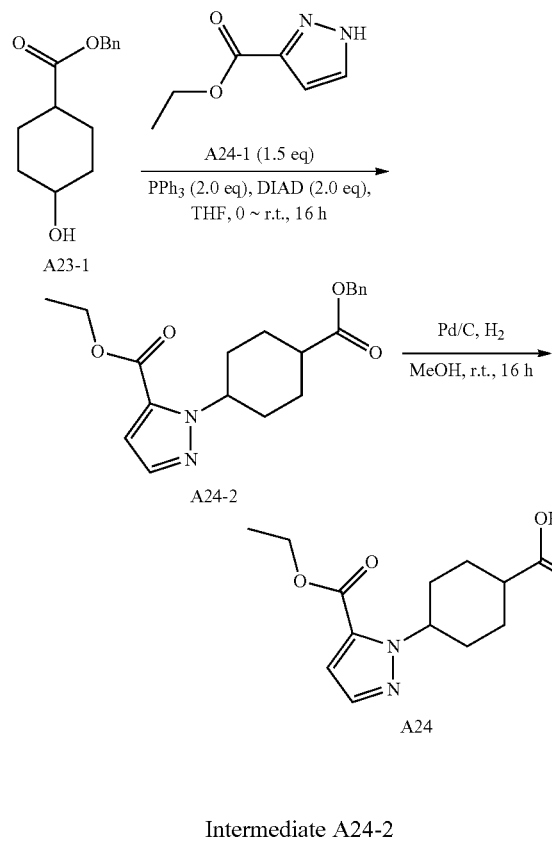

Intermediate A24-2

Ethyl 1-(4-((benzyloxy)carbonyl)cyclohexyl)-1H-pyrazole-5-carboxylate

To a solution of benzyl 4-hydroxycyclohexanecarboxylate A23-1 (5.7 g, 90% purity, 21.9 mmol), ethyl 1H-pyrazole-3-carboxylate A24-1 (4.70 g, 33.5 mmol) and triphenylphosphine (11.7 g, 44.6 mmol) in tetrahydrofuran (100 mL) was added diisopropyl azodicarboxylate (9.04 g, 44.7 mmol) dropwise at 0° C. After stirred at room temperature for 16 hours, the mixture was concentrated and dichloromethane (100 mL) was added. It was washed with water (50 mL) twice, followed by brine (50 mL), dried over $Na_2SO_{4(s)}$ and filtered. The filtrate was concentrated under reduced pressure to leave a yellow oil, which was purified by silica gel column chromatography (petroleum ether:ethyl acetate=50:1 to 30:1) and further purified by C18 column (acetonitrile:water=20% to 80%) to give the title compound (3.66 g, 96% purity, 45% yield) as colorless oil. LC-MS (ESI): $R_T$=1.62 and 1.63 min, mass calcd. for $C_{20}H_{24}N_2O_4$ 356.2, m/z found 357.3 [M+H]$^+$. $^1$H NMR (400 MHz, CDCl$_3$) δ 7.49 (d, J=2.0 Hz, 1H), 7.37-7.30 (m, 5H), 6.83 (d, J=2.0 Hz, 1H), 5.18 (s, 2H), 5.17-5.11 (m, 1H), 4.33 (q, J=7.2 Hz, 2H), 2.78-2.69 (m, 1H), 2.45-2.32 (m, 2H), 2.17-2.06 (m, 2H), 1.98-1.88 (m, 2H), 1.80-1.68 (m, 2H), 1.38 (t, J=7.2 Hz, 3H).

Acid 24

4-(5-(Ethoxycarbonyl)-1H-pyrazol-1-yl)cyclohexanecarboxylic Acid

To a solution of ethyl 1-(4-((benzyloxy)carbonyl)cyclohexyl)-1H-pyrazole-5-carboxylate A24-2 (2.0 g, 96% purity, 5.33 mmol) in methanol (50 mL) was added 10% palladium on charcoal wt. (284 mg, 0.267 mmol) under nitrogen atmosphere at room temperature. After stirred at room temperature under hydrogen atmosphere for 16 hours, the mixture was filtered though a pad of celite. The filtrate was concentrated under reduced pressure to give the title compound (1.45 g, 95% purity from $^1$H NMR, 97% yield) as white solids. $^1$H NMR (400 MHz, CDCl$_3$) δ 7.52 (d, J=1.6 Hz, 1H), 6.83 (d, J=1.6 Hz, 1H), 5.24-5.14 (m, 1H), 4.34 (q, J=7.2 Hz, 2H), 2.79-2.72 (m, 1H), 2.44-2.35 (m, 2H), 2.23-1.12 (m, 2H), 1.99-1.90 (m, 2H), 1.79-1.66 (m, 2H), 1.39 (t, J=7.2 Hz, 3H).

Acid 25

4-(5-(Ethoxycarbonyl)pyrimidin-2-yl)cyclohexanecarboxylic Acid (A25)

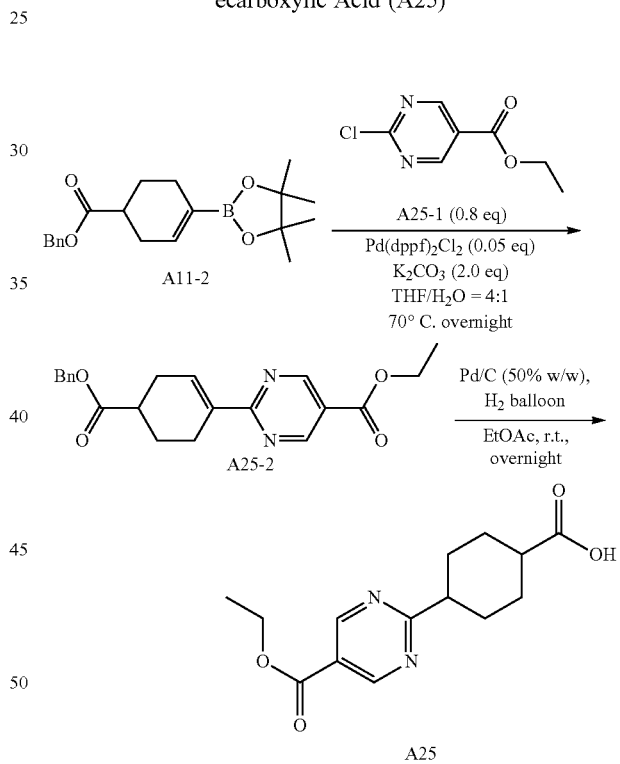

Intermediates A25-2

Ethyl 2-(4-((benzyloxy)carbonyl)cyclohex-1-en-1-yl)pyrimidine-5-carboxylate To a solution of benzyl 4-(4,4,5,5-tetramethyl-1,3,2-dioxaborolan-2-yl)cyclohex-3-enecarboxylate A11-2 (2.00 g, 5.84 mmol) and ethyl 2-chloropyrimidine-5-carboxylate A25-1 (0.90 g, 4.82 mmol) in tetrahydrofuran (20 mL) and water (5 mL) was added potassium carbonate (1.60 g, 11.6 mmol) under nitrogen atmosphere. The resulting mixture was purged with nitrogen for three times, and then [1,1'-bis (diphenylphosphino)ferrocene]dichloropalladium(II) (200 mg, 0.29 mmol) was added. Then it was purged with nitrogen again three times and stirred at 70° C. overnight. After cooled down and quenched with water (20 mL), the mixture was extracted with ethyl acetate (20 mL) for three times. The combined organic layers were washed with brine (20 mL), dried over $Na_2SO_{4(s)}$ and filtered. The filtrate was concentrated under reduced pressure to give a residue, which was purified by silica gel column chromatography (petroleum ether:ethyl acetate=8:1) to give the title compound (230 mg, 13% yield) as yellow solids. LC-MS (ESI): $R_T$=1.80 min, mass calcd. for $C_{21}H_{22}N_2O_4$ 366.2, m/z found 367.1 $[M+H]^+$. $^1H$ NMR (400 MHz, $CDCl_3$) δ 9.18 (s, 2H), 7.47 (s, 1H), 7.38-7.33 (m, 5H), 5.17 (s, 2H), 4.42 (q, J=7.2 Hz, 2H), 2.90-2.84 (m, 1H), 2.76-2.69 (m, 1H), 2.64-2.62 (m, 2H), 2.58-2.49 (m, 1H), 2.29-2.24 (m, 1H), 1.92-1.82 (m, 1H), 1.41 (t, J=7.2 Hz, 3H).

Acid 25

4-(5-(Ethoxycarbonyl)pyrimidin-2-yl)cyclohexanecarboxylic Acid

To a solution of ethyl 2-(4-((benzyloxy)carbonyl)cyclohex-1-en-1-yl)pyrimidine-5-carboxylate A25-2 (600 mg, 1.64 mmol) in ethyl acetate (25 mL) was added 10% palladium on charcoal wt. (300 mg). After stirred at room temperature under hydrogen atmosphere of balloon overnight, the reaction mixture was filtered. The filtrate was concentrated under reduced pressure to give the title compound (400 mg, 87% yield) as white solids. LC-MS (ESI): $R_T$=0.494 min, mass calcd. for $C_{14}H_{18}N_2O_4$ 278.1, m/z found 279.1 $[M+H]^+$.

Acid 26

4-(4-(Ethoxycarbonyl)thiazol-2-yl)cyclohexanecarboxylic Acid (A26)

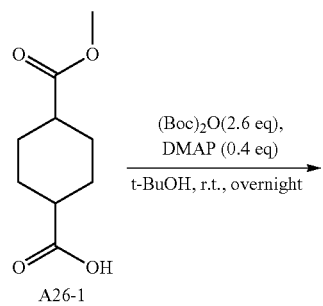

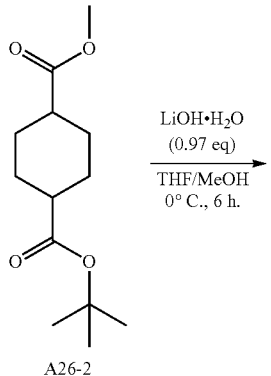

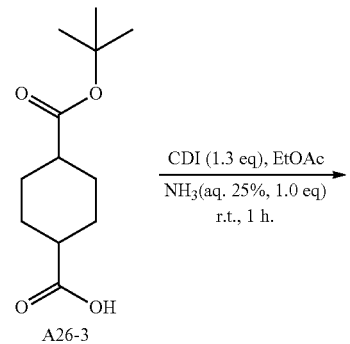

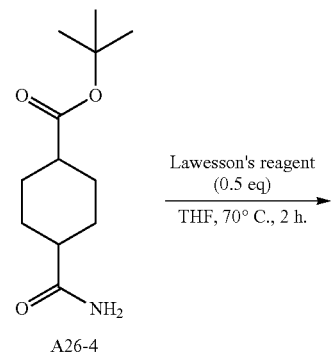

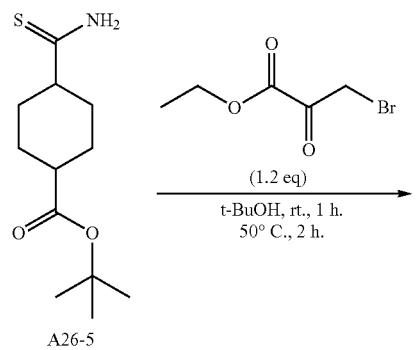

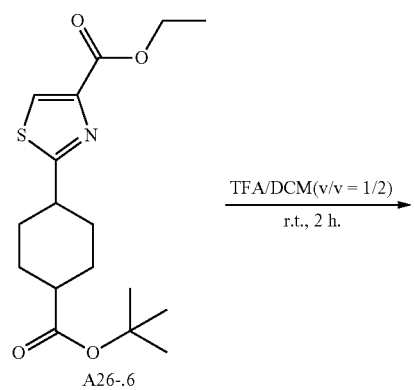

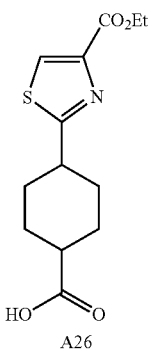

A26

Intermediate A26-2

1-tert-Butyl 4-methyl cyclohexane-1,4-dicarboxylate

To a solution of 4-(methoxycarbonyl)cyclohexanecarboxylic acid A26-1 (14.4 g, 75.8 mmol) in tert-butanol (200 mL) was added di-tert-butyl dicarbonate (43.9 g, 197 mmol) and 4-dimethylaminopyridine (3.78 g, 30.3 mmol). After stirred at room temperature overnight, the reaction mixture was concentrated under reduced pressure to give a residue, which was dissolved in ethyl acetate (200 mL). The resulting solution was washed with 1 M hydrochloride aqueous solution (100 mL), saturated sodium bicarbonate (100 mL), brine (100 mL), dried over $Na_2SO_{4(s)}$ and filtered. The filtrate was concentrated and purified by silica gel column chromatography (petroleum ether:ethyl acetate=100:1 to 20:1) to give the title compound (11.8 g, 58% yield, 90% purity) as colorless oil. $^1$H NMR (300 MHz, DMSO-$d_6$) δ 3.60 (s, 1.8H), 3.59 (s, 1.2H), 2.48-2.45 (m 0.4H), 2.40-2.09 (m, 1.6H), 1.92-1.82 (m, 2H), 1.76-1.53 (m, 4H), 1.39 (s, 9H), 1.34-1.24 (m, 2H).

Intermediate A26-3

4-(tert-Butoxycarbonyl)cyclohexanecarboxylic Acid

To a solution of 1-tert-butyl 4-methyl cyclohexane-1,4-dicarboxylate A26-2 (11.8 g, 90% purity, 43.8 mmol) in tetrahydrofuran (39 mL) and methanol (13 mL) was added a solution of lithium hydroxide monohydrate (1.87 g, 95% purity, 42.3 mmol) in water (13 mL). After stirred at 0° C. for 6 hours, the mixture was poured into water (150 mL) and washed with ethyl acetate (100 mL). The aqueous layer was acidified to pH 2 with 1 M hydrochloride aqueous solution. The solid which formed was collected by filtration and dried under reduced pressure to give the title compound (7.8 g, 77% yield) as white solids. $^1$H NMR (300 MHz, DMSO-$d_6$) δ 12.07 (br s, 1H), 2.40-2.31 (m, 1H), 2.17-2.08 (m, 1H), 1.93-1.83 (m, 2H), 1.75-1.51 (m, 4H), 1.39 (s, 9H), 1.33-1.26 (m, 2H).

Intermediate A26-4 tert-Butyl 4-carbamoylcyclohexanecarboxylate

To a solution of 4-(tert-butoxycarbonyl)cyclohexanecarboxylic acid A26-3 (7.80 g, 34.2 mmol) in ethyl acetate (150 mL) was added N,N-carbonyldiimidazole (7.20 g, 44.5 mmol) at room temperature. After stirring at room temperature for 0.5 hour, 25% wt. ammonium hydroxide aqueous solution (48.0 g, 34.2 mmol) was added. The stirring was continued at room temperature for another 0.5 hour. Then the separated organic layer was adjusted to PH 2-3 with 0.2 M hydrochloride aqueous solution, washed with water (100 mL), brine (100 mL), dried over $Na_2SO_{4(s)}$, filtered and concentrated to give the crude product, which was purified by silica gel column chromatography (petroleum ether:ethyl acetate=10:1 to 6:1, then 100% ethyl acetate) to give the title compound (6.4 g, 82% yield) as white solids. $^1$H NMR (300 MHz, DMSO-$d_6$) δ 7.13 (s, 1H), 6.63 (s, 1H), 2.38-2.35 (m, 0.5H), 2.14-1.94 (m, 1.5H), 1.85-1.71 (m, 3H), 1.55-1.41 (m, 3H), 1.37-1.34 (m, 9H), 1.26-1.18 (m, 2H).

Intermediate A26-5 tert-Butyl 4-carbamothioylcyclohexanecarboxylate

To a solution of tert-butyl 4-carbamoylcyclohexanecarboxylate A26-4 (6.40 g, 28.2 mmol) in tetrahydrofuran (100 mL) was added 2,4-bis-(4-methoxy-phenyl)-[1,3,2,4]dithiadiphosphetane 2,4-disulfide (5.70 g, 14.1 mmol). The reaction mixture was stirred at 70° C. for 2 hours. Then it was allowed to cool down to room temperature and concentrated under reduced pressure to give a residue, which was diluted with ethyl acetate (50 mL). The solution was washed with saturated sodium dicarbonate aqueous solution to PH 7-8, then washed with water (50 mL), brine (50 mL), dried over $Na_2SO_{4(s)}$, filtered and concentrated to give the crude product, which was purified by silica gel column chromatography (petroleum ether:ethyl acetate=10:1 to 2:1) to give the title compound (4.30 g, 62% yield) as white solids. $^1$H NMR (300 MHz, DMSO-$d_6$) δ 9.26 (s, 1H), 9.00 (s, 1H), 2.42-2.35 (m, 1H), 2.09-2.02 (m, 1H), 1.87-1.83 (m, 2H), 1.70-1.66 (m, 2H), 1.55-1.42 (m, 2H), 1.35-1.18 (m, 11H).

Intermediate A26-6

Ethyl 2-(4-(tert-butoxycarbonyl)cyclohexyl)thiazole-4-carboxylate

To a solution of tert-butyl 4-carbamothioylcyclohexanecarboxylate A26-5 (3.20 g, 13.2 mmol) in 2-methylpropan-2-ol (50 mL) was added ethyl 3-bromo-2-oxopropanoate (3.2 g, 16.4 mmol). After stirring at room temperature for 1 hour, it was warmed up to 50° C. and stirred at 50° C. for 2 hours. After cooling down to room temperature, the mixture was concentrated to give a residue, which was diluted with ethyl acetate (25 mL). The solution was adjusted with saturated sodium dicarbonate aqueous solution to PH 7-8. The separated organic layer was washed with water (10 mL), brine (10 mL), dried over $Na_2SO_{4(s)}$, filtered and concentrated to give a residue, which was purified by silica gel column chromatography (petroleum ether:ethyl acetate=10:1 to 6:1) to give the title compound (2.6 g, 58% yield) as yellow solids. $^1$H NMR (400 MHz, DMSO-$d_6$) δ 8.41 (s, 0.5H), 8.40 (s, 0.5H), 4.29 (q, J=7.2 Hz, 2H), 3.18-3.11 (m, 0.5H), 3.04-2.97 (m, 0.5H), 2.56-2.54 (m, 0.5H), 2.29-2.22 (m, 0.5H), 2.12-2.10 (m, 1H), 1.98-1.88 (m, 3H), 1.80-1.72 (m, 1H), 1.67-1.61 (m, 1H), 1.57-1.44 (m, 2H), 1.40 (s, 9H), 1.29 (t, J=7.2 Hz, 3H).

Acid 26

4-(4-(Ethoxycarbonyl)thiazol-2-yl)cyclohexanecarboxylic Acid

To a solution of ethyl 2-(4-(tert-butoxycarbonyl)cyclohexyl)thiazole-4-carboxylate A26-6 (2.60 g, 7.67 mmol) in dichloromethane (20 mL) was added trifluoroacetic acid (10 mL). The reaction mixture was stirred at room temperature for 2 hours. Then the solvent was removed to give a residue, which was purified by silica gel column chromatography (petroleum ether:ethyl acetate=10:1 to 2:1, then 100% ethyl acetate) to give the title compound (2.1 g, 96% yield) as yellow solids. $^1$H NMR (300 MHz, DMSO-d$_6$) δ 8.39-8.36 (m, 1H), 4.30-4.21 (m, 2H), 3.15-3.08 (m, 0.6H), 3.02-2.94 (m, 0.4H), 2.57-2.52 (m, 0.6H), 2.28-2.21 (m, 0.4H), 2.11-2.06 (m, 1H), 1.99-1.86 (m, 3H), 1.78-1.56 (m, 2.5H), 1.52-1.41 (m, 1.5H), 1.29-1.23 (m, 3H).

Acid 27

4-(3-(Methoxycarbonyl)isoxazol-5-yl)cyclohexanecarboxylic Acid (A27)

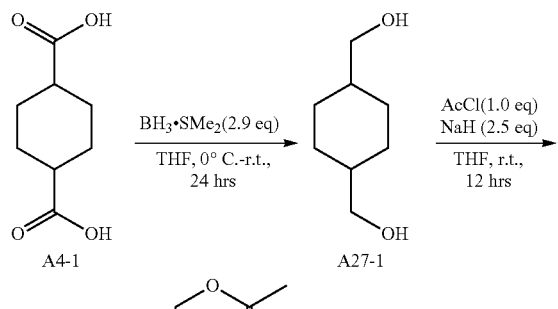

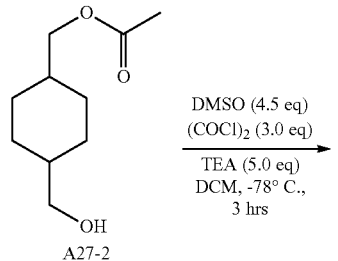

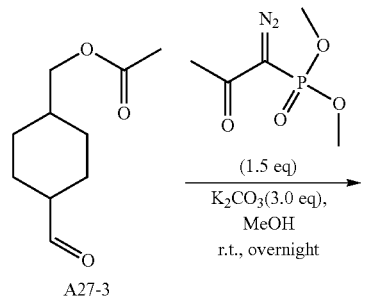

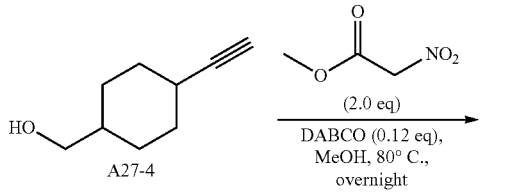

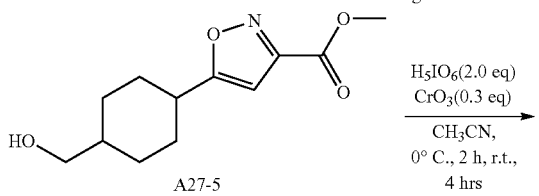

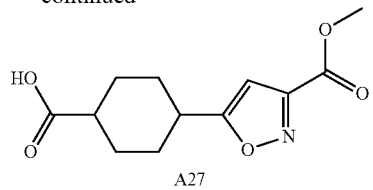

A27-1

Cyclohexane-1,4-diyldimethanol

To a solution of cyclohexane-1,4-dicarboxylic acid A4-1 (50.0 g, 0.276 mol) in tetrahydrofuran (500 mL) was added 10 M borane-methyl sulfide complex (80 mL, 0.800 mol) at 0° C. After stirred at room temperature for 24 hours, the reaction mixture was quenched with methanol (100 mL) slowly and water (200 mL), then extracted with ethyl acetate (200 mL) for three times. The combined organic layers were washed with brine (200 mL), dried over Na$_2$SO$_{4(s)}$, filtered and concentrated under reduced pressure to give a residue, which was purified by silica gel column chromatography (petroleum ether:ethyl acetate=3:1) to give the title compound (42.0 g, 90% purity from $^1$H NMR, 90% yield) as white solids. $^1$H NMR (400 MHz, DMSO-d$_6$) δ 4.28 (br s, 2H), 3.26-3.14 (m, 4H), 1.71-1.69 (m, 3H), 1.35-1.19 (m, 4H), 0.84-0.77 (m, 3H).

Intermediate A27-2

(4-(Hydroxymethyl)cyclohexyl)methyl Acetate

To a solution of cyclohexane-1,4-diyldimethanol A27-1 (80.0 g, 90% purity, 0.499 mol) in tetrahydrofuran (500 mL) was added 60% wt. sodium hydride in mineral oil (30.6 g, 1.25 mol) and acetyl chloride (41.3 g, 95% purity, 0.499 mol) at 0° C. After stirred at room temperature for 12 hours. The reaction mixture was concentrated to dryness under reduced pressure to give a residue, which was purified by silica gel column chromatography (petroleum ether:ethyl acetate=3:1) to give the title compound (21.0 g, 95% purity from $^1$H NMR, 21% yield) as yellow oil. $^1$H NMR (400 MHz, DMSO-d$_6$) δ 4.36 (m, 1H), 3.82 (d, J=6.4 Hz, 1.6H), 3.30-3.27 (m, 0.4H), 3.21-3.18 (m, 1.6H), 1.99 (s, 3H), 1.75-1.70 (m, 3H), 1.53-1.23 (m, 4H), 0.94-0.87 (m, 3H).

Intermediate A27-3

(4-Formylcyclohexyl)methyl Acetate

To a solution of dimethyl sulfoxide (40.0 g, 99% purity, 0.507 mol) in dichloromethane (200 mL) was added a solution of oxalyl chloride (43.8 g, 98% purity, 0.338 mol) in dichloromethane (50 mL) at −78° C. After stirred at −78° C. for 1 hour, a solution of (4-(hydroxymethyl)cyclohexyl)methyl A27-2 (22.1 g, 95% purity, 0.113 mol) was added at −78° C. After stirring at −78° C. for 3 hours, triethylamine (57.6 g, 99% purity, 0.564 mol) was added dropwise at −78° C. to quench the reaction. The reaction mixture was allowed to warm to room temperature and extracted with dichloromethane (200 mL) for three times. The combined organic layers were dried over anhydrous Na$_2$SO$_{4(s)}$, filtered and concentrated to give the title compound (16.0 g, 95% purity from $^1$H NMR, 73% yield) as yellow oil. $^1$H NMR (400

MHz, DMSO-d$_6$) δ 9.57 (s, 0.5H), 5.76 (s, 0.5H), 3.85-3.79 (m, 2H), 2.25-2.19 (m, 0.5H), 2.01 (s, 3H), 1.94-1.92 (m, 1H), 1.79-1.70 (m, 2.5H), 1.58-1.43 (m, 2H), 1.22-1.11 (m, 1.5H), 1.05-0.90 (m, 2.5H).

Intermediate A27-4

(4-Ethynylcyclohexyl)methanol

To a solution of (4-formylcyclohexyl)methyl acetate A27-3 (13.1 g, 95% purity, 67.7 mmol) in methanol (100 mL) were added dimethyl (1-diazo-2-oxopropyl)phosphonate (20.5 g, 95% purity, 101 mmol) and potassium carbonate (28.1 g, 203 mmol) at room temperature. After stirred at room temperature overnight under nitrogen atmosphere, the mixture was allowed to cool down to room temperature and filtered. The filtrate was concentrated under reduced pressure to give a residue, which was purified by silica gel column chromatography (petroleum ether:ethyl acetate=5:1) to afford the title compound (4.00 g, 95% purity from $^1$H NMR, 41% yield) as white solids. $^1$H NMR (400 MHz, DMSO-d$_6$) δ 3.45 (d, J=6.4 Hz, 2H), 2.22-2.16 (m, 1H), 2.06-2.02 (m, 3H), 1.84-1.80 (m, 2H), 1.53-1.38 (m, 5H).

Intermediate A27-5

Methyl 5-(4-(hydroxymethyl)cyclohexyl)isoxazole-3-carboxylate

To a solution of (4-ethynylcyclohexyl)methanol A27-4 (1.16 g, 95% purity, 7.97 mmol) in methanol (10 mL) was added methyl 2-nitroacetate (2.11 g, 90% purity, 15.9 mmol) and triethylenediamine (110 mg, 98% purity, 0.961 mmol). After stirred at 80° C. overnight under nitrogen atmosphere, the mixture was allowed to cool down to room temperature and filtered. The filtrate was concentrated under reduced pressure to give a residue, which was purified by silica gel column chromatography (petroleum ether:ethyl acetate=3:1) to give the title compound (1.30 g, 95% purity from $^1$H NMR, 65% yield) as white solids. LC-MS (ESI): R$_T$=1.484 min, mass calcd. for C$_{12}$H$_{17}$NO$_4$ 239.1, m/z found 240.1 [M+H]$^+$. $^1$H NMR (400 MHz, DMSO-d$_6$) δ 6.67 (s, 1H), 3.88 (s, 3H), 3.24 (d, J=6.0 Hz, 2H), 2.85-2.78 (m, 1H), 2.06-2.01 (m, 2H), 1.84-1.80 (m, 2H), 1.46-1.36 (m, 3H), 1.08-0.98 (m, 2H).

Acid 27

4-(3-(Methoxycarbonyl)isoxazol-5-yl)cyclohexanecarboxylic Acid

To a solution of periodic acid (1.73 g, 99% purity, 7.52 mmol) in acetonitrile (20 mL) was added chromium(VI) oxide (100 mg, 99% purity, 0.990 mmol) at room temperature over 2 hours under nitrogen atmosphere. After that, methyl 5-(4-(hydroxymethyl)cyclohexyl)isoxazole-3-carboxylate A27-5 (928 mg, 95% purity, 3.69 mmol) was added at 0° C. and stirring continued at 0° C. for 2 hours under nitrogen atmosphere. Then the reaction mixture was diluted with water (10 mL) and extracted with ethyl acetate (10 mL) for three times. The combined organic layers were dried over anhydrous Na$_2$SO$_{4(s)}$, filtered and concentrated to give the title compound (800 mg, 90% purity, 77% yield) as white solids. LC-MS (ESI): R$_T$=1.005 min, mass calcd. for C$_{12}$H$_{15}$NO$_5$ 253.1, m/z found 254.1 [M+H]$^+$. $^1$H NMR (400 MHz, DMSO-d$_6$) δ 12.13 (br s, 1H), 6.69 (s, 1H), 3.88 (s, 3H), 2.91-2.84 (m, 1H), 2.28-2.21 (m, 1H), 2.07-1.97 (m, 4H), 1.51-1.40 (m, 4H).

Acid 28

4-(4-(Ethoxycarbonyl)thiazol-2-yl)cyclohexanecarboxylic Acid (A28)

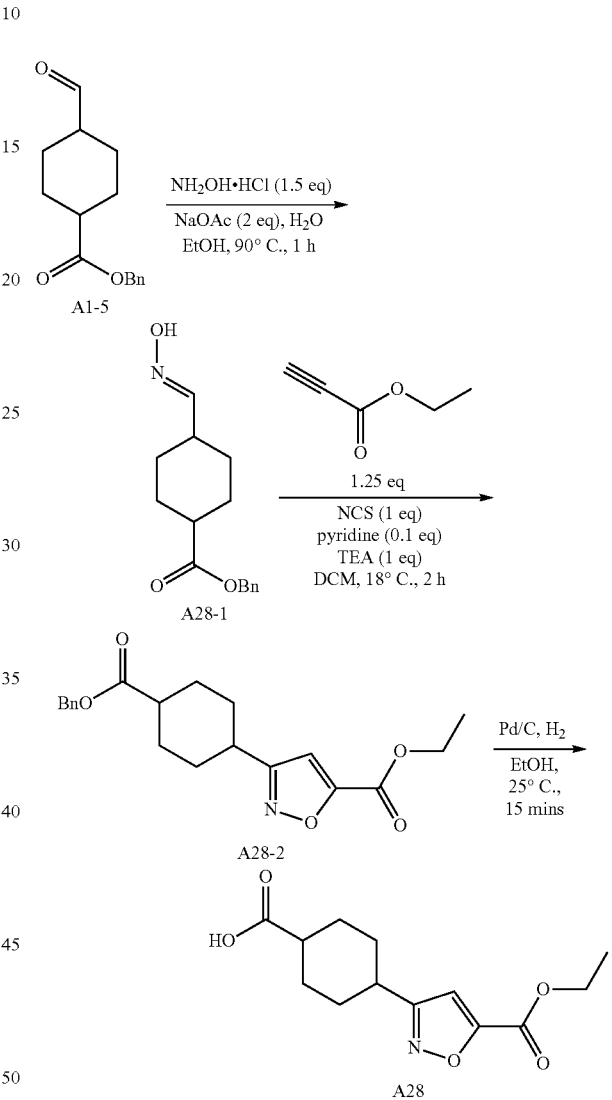

Intermediate A28-1

Benzyl 4-((hydroxyimino)methyl)cyclohexanecarboxylate

To a solution of benzyl 4-formylcyclohexanecarboxylate A1-5 (17.6 g, 71.5 mmol) in ethanol (348 mL) was added sodium acetate (11.7 g, 143 mmol) and a solution of hydroxylamine hydrochloride (7.45 g, 107 mmol) in water (26 mL). After stirred at 90° C. for 1 hour, the mixture was cooled down to room temperature and filtered off and then the filtrate was concentrated to give a residue, which was diluted with ethyl acetate (300 mL). The organic phase was washed with water (60 mL) for three times, dried over Na₂SO₄(s) and filtered. The filtrate was concentrated under reduced pressure to give the title compound (17.5 g, 96% yield) as yellow oil. LC-MS (ESI): $R_T$=2.069 min, mass calcd. for $C_{15}H_{19}NO_3$ 261.1, m/z found 262.1 [M+H]⁺. ¹H NMR (300 MHz, DMSO-d₆) δ 10.97-10.71 (m, 0.3H), 10.42-10.39 (m, 0.7H), 7.34-7.27 (m, 5H), 7.21-7.18 (m, 1H), 5.09-5.05 (m, 2H), 2.34-2.23 (m, 1H), 2.16-2.02 (m, 1H), 1.93-1.87 (m, 2H), 1.79-1.74 (m, 2H), 1.61-1.53 (m, 1H), 1.49-1.21 (m, 3H).

Intermediate A28-2

Ethyl 3-(4-((benzyloxy)carbonyl)cyclohexyl)isoxazole-5-carboxylate

To a solution of 1-chloropyrrolidine-2,5-dione (8.95 g, 67.0 mmol) and pyridine (530 mg, 6.70 mmol) in dichloromethane (150 mL) was added benzyl 4-((hydroxyimino) methyl)cyclohexanecarboxylate A28-1 (17.5 g, 67.0 mmol) at about 5° C. After stirring at room temperature for 10 minutes, ethyl propiolate (8.22 g, 83.0 mmol) and a solution of triethylamine (6.77 g, 67.0 mmol) in dichloromethane (30 mL) were added into the mixture. The mixture was stirred at 18° C. under nitrogen atmosphere for 2 hours. The mixture was washed with water (100 mL) for three times, dried over Na₂SO₄(s) and filtered. The filtrate was concentrated under reduced pressure to give a residue, which was purified by silica gel column chromatography (petroleum ether:ethyl acetate=3:1) to give the title compound (11.0 g, 46% yield) as yellow solids. LC-MS (ESI): $R_T$=2.552 min, mass calcd. for $C_{20}H_{23}NO_5$ 357.2, m/z found 358.1 [M+H]⁺. ¹H NMR (300 MHz, DMSO-d₆) δ 7.38-7.28 (m, 5H), 7.23-7.13 (m, 1H), 5.08 (s, 2H), 4.35-4.19 (m, 2H), 3.10-2.64 (m, 1H), 2.42-2.32 (m, 1H), 2.03-1.95 (m, 2H), 1.91-1.81 (m, 1H), 1.77-1.59 (m, 2H), 1.53-1.44 (m, 3H), 1.32-1.23 (m, 3H).

Acid 28

4-(5-(Ethoxycarbonyl)isoxazol-3-yl)cyclohexanecarboxylic Acid

To a solution of ethyl 3-(4-((benzyloxy)carbonyl)cyclohexyl)isoxazole-5-carboxylate A28-2 (7.00 g, 19.0 mmol) in ethanol (200 mL) was added 10% palladium on charcoal wt. (500 mg) under nitrogen atmosphere at room temperature. After replacing the inner nitrogen atmosphere with hydrogen gas, the mixture was stirred at 25° C. under hydrogen atmosphere for 15 minutes. The catalyst was filtered off and the filtrate was concentrated under reduced pressure to give a residue, which was purified by silica gel column chromatography (petroleum ether:ethylacetate=3:1 to 1:1) to give the title compound (2.30 g, 44% yield) as white solids. LC-MS (ESI): $R_T$=0.720 min, mass calcd. for $C_{13}H_{17}NO_5$ 267.1, m/z found 268.1 [M+H]⁺. ¹H NMR (300 MHz, DMSO-d₆) δ 12.06 (s, 1H), 7.24 (s, 1H), 4.31 (q, J=7.2 Hz, 2H), 2.77-2.67 (m, 1H), 2.25-2.16 (m, 1H), 1.96-1.92 (m, 4H), 1.53-1.34 (m, 4H), 1.30-1.25 (m, 3H).

Acid 29

5-methylisoxazole-4-carbonyl Chloride (A29)

Acid 30

4-(4-(Methoxycarbonyl)phenyl)cyclohexanecarboxylic Acid (A30)

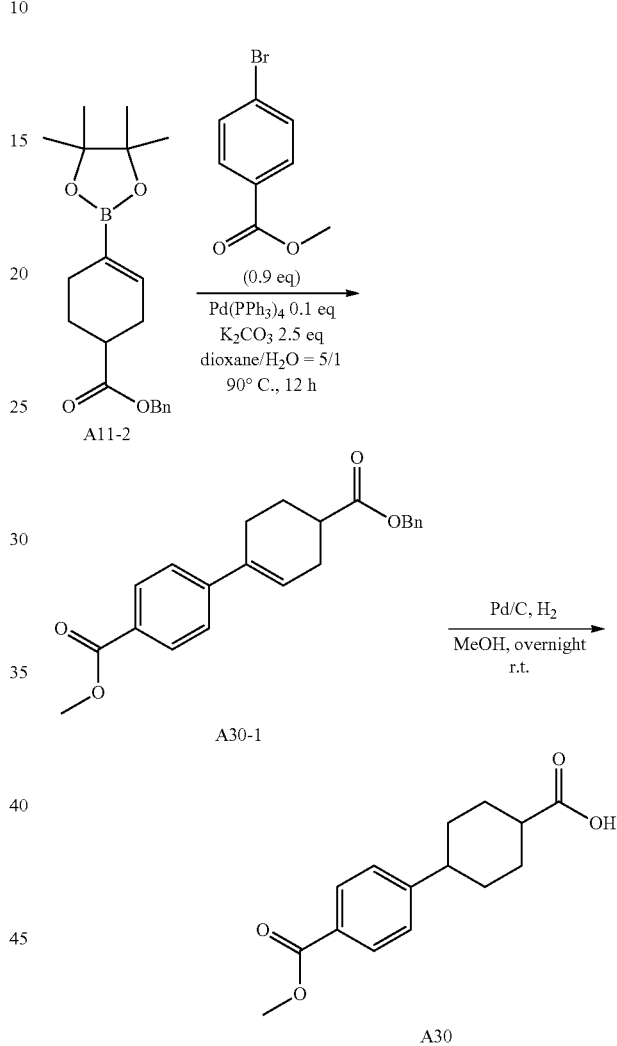

Intermediate A30-1

4-Benzyl 4'-methyl 2,3,4,5-tetrahydro-[1,1'-biphenyl]-4,4'-dicarboxylate

To a solution of methyl 4-bromobenzoate (760 mg, 3.55 mmol), potassium carbonate (1.37 g, 9.93 mmol) and tetrakis(triphenylphosphine)palladium (462 mg, 0.40 mmol) in dioxane (75 mL) and water (15 mL) was added benzyl 4-(4,4,5,5-tetramethyl-1,3,2-dioxaborolan-2-yl)cyclohex-3-enecarboxylate A11-2 (1.49 g, 3.94 mmol) at room temperature. After stirred at 90° C. for 12 hours under nitrogen atmosphere, the reaction mixture was cooled down to room temperature, filtered and concentrated under reduced pressure to give a residue, which was purified by silica gel column chromatography (petroleum ether:ethyl acetate=20:

1) to give the title compound (1.15 g, 83% yield) as a white solids. $^1$H NMR (300 MHz, DMSO-$d_6$) δ 7.95-7.86 (m, 2H), 7.59-7.49 (m, 2H), 7.40-7.33 (m, 5H), 6.34 (s, 1H), 5.14 (s, 2H), 3.85-3.83 (m, 3H), 2.75-2.66 (m, 1H), 2.48-2.38 (m, 4H), 2.14-2.08 (m, 1H), 1.82-1.63 (m, 1H).

Acid 30

4-(4-(Methoxycarbonyl)phenyl)cyclohexanecarboxylic Acid

To a solution of 4-benzyl 4'-methyl 2,3,4,5-tetrahydro-[1,1'-biphenyl]-4,4'-dicarboxylate A30-1 (1.10 g, 3.97 mmol) in methanol (50 mL) was added 10% palladium on charcoal wt. (110 mg) at room temperature. After stirred at room temperature overnight under hydrogen atmosphere, the reaction mixture was filtered and concentrated under reduced pressure to give the title compound (800 mg, 97% yield) as a white solids. LC-MS (ESI): $R_T$=0.27 min, mass calcd. for $C_{15}H_{18}O_4$ 262.1, m/z found 261.2 [M−H]$^-$. $^1$H NMR (300 MHz, DMSO-$d_6$) δ 7.90-7.87 (m, 2H), 7.39-7.32 (m, 2H), 3.83 (s, 3H), 2.63 (s, 1.6H), 2.30-2.22 (m, 0.4H), 2.12-1.98 (m, 2H), 1.85-1.44 (m, 6H).

Acid 31

4-(1-(3-(tert-butoxy)-2,2-dimethyl-3-oxopropyl)-1H-pyrazol-4-yl)cyclohexane-1-carboxylic Acid (A31)

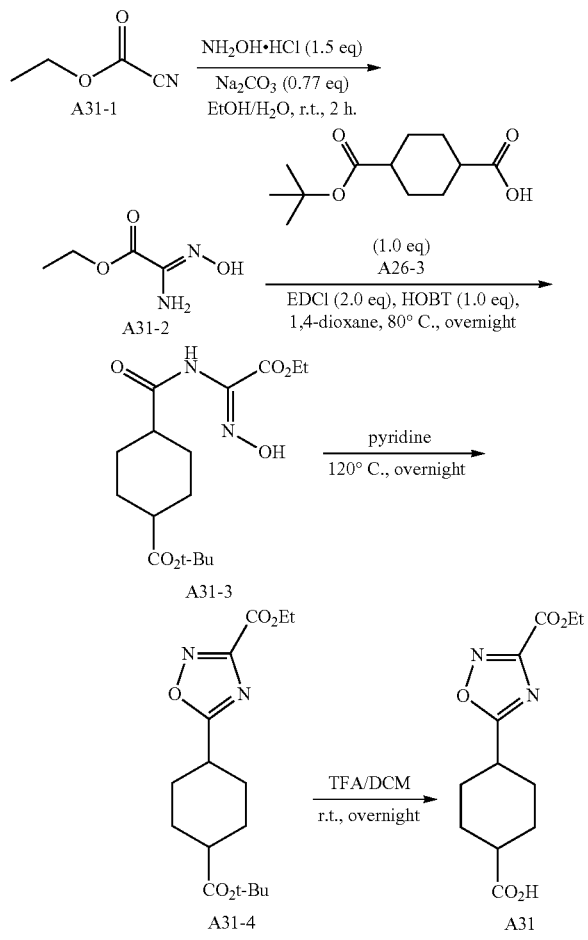

Intermediate A31-2

Ethyl 2-amino-2-(hydroxyimino)acetate

Water (150 mL) was added dropwise to a stirred mixture of ethyl carbonocyanidate A31-1 (25.5 g, 250 mmol), hydroxylamine hydrochloride (26.1 g, 375 mmol) and sodium carbonate (20.5 g, 193 mmol) in ethanol (250 mL). After the mixture was stirred at room temperature for 2 hours, the solvent was removed and the aqueous layer was extracted with dichloromethane (900 mL) for three times. The combined organic layers were dried over $Na_2SO_{4(s)}$, filtered and concentrated to afford the title compound (21.0 g, 88% yield) as white solids. $^1$H NMR (300 MHz, CDCl$_3$) δ 9.52 (br s, 1H), 5.15 (s, 2H), 4.35-4.27 (m, 2H), 1.36-1.31 (m, 3H).

Intermediate A31-3 tert-Butyl 4-((2-ethoxy-1-(hydroxyimino)-2-oxo-ethyl)carbamoyl)cyclohexanecarboxylate To a solution of 4-(tert-butoxycarbonyl)cyclohexanecarboxylic acid A26-3 (1.60 g, 90% purity, 6.31 mmol) in 1,4-dioxane (30 mL) were added 1H-benzo[d][1,2,3]triazol-1-ol (947 mg, 90% purity, 6.31 mmol) and $N_1$-((ethylimino)methylene)-$N_2$,$N_2$-dimethylethane-1,2-diamine hydrochloride (2.50 g, 90% purity, 12.7 mmol) at room temperature. After stirring at room temperature for 1 hour, ethyl 2-amino-2-(hydroxyimino)acetate A31-2 (926 mg, 90% purity, 6.31 mmol) was added. After stirred at 80° C. overnight, it was cooled down to room temperature and concentrated to give a residue, which was diluted with water (50 mL), extracted with ethyl acetate (100 mL) for five times. The combined organic layers were washed with water (50 mL), brine (50 mL), dried over $Na_2SO_{4(s)}$, filtered and concentrated under reduced pressure to give a residue, which was purified by silica gel column chromatography (100% dichloromethane, then dichloromethane:ethyl acetate=6:1) to give the title compound (1.90 g, 95% purity from $^1$H NMR, 84% yield) as yellow solids. LC-MS (ESI): $R_T$=1.58 min, mass calcd. for $C_{16}H_{26}N_2O_6$ 342.2, m/z found 343.3 [M+H]$^+$. $^1$H NMR (300 MHz, DMSO-$d_6$) δ 6.89 (s, 2H), 4.27-4.15 (m, 2H), 2.40-2.31 (m, 1H), 2.15-2.10 (m, 1H), 1.93-1.81 (m, 4H), 1.38-1.29 (m, 12H), 1.25-1.17 (m, 4H)

Intermediate A31-4

Ethyl 5-(4-(tert-butoxycarbonyl)cyclohexyl)-1,2,4-oxadiazole-3-carboxylate

A solution of (tert-butyl 4-((2-ethoxy-1-(hydroxyimino)-2-oxoethyl)carbamoyl)cyclohexanecarboxylate A31-3 (1.90 g, 95% purity, 5.27 mmol) in pyridine (20 mL) was stirred at 120° C. overnight. Then it was cooled down to room temperature, the solvent was removed to give a residue, which was purified by silica gel column chromatography (petroleum ether:ethyl acetate=10:1 to 4:1) to give the title compound (1.50 g, 95% purity from $^1$H NMR, 83% yield) as yellow oil. LC-MS (ESI): $R_T$=1.73 min, mass calcd. for $C_{16}H_{24}N_2O_5$ 324.2, m/z found 325.3 [M+H]$^+$. $^1$H NMR (300 MHz, DMSO-$d_6$) δ 4.51-4.44 (m, 2H), 3.24-3.13 (m, 1H), 2.38-2.30 (m, 1H), 2.23-2.18 (m, 2H), 2.07-2.01 (m, 2H), 1.72-1.45 (m, 13H), 1.43-1.37 (m, 3H)

Acid 31

4-(3-(Ethoxycarbonyl)-1,2,4-oxadiazol-5-yl)cyclohexanecarboxylic Acid

To a solution of ethyl 5-(4-(tert-butoxycarbonyl)cyclohexyl)-1,2,4-oxadiazole-3-carboxylate A31-4 (1.50 g, 95% purity, 4.39 mmol) in dichloromethane (10 mL) was added trifluoroacetic acid (5 mL) at room temperature. After stirred at room temperature overnight, the mixture was concentrated to give a residue, which was purified by silica gel column chromatography (dichloromethane:ethyl acetate=1:1) to give the title compound (1.20 g, 90% purity from $^1$H NMR, 92% yield) as yellow solids. $^1$H NMR (300 MHz, DMSO-$d_6$) δ 12.09 (s, 1H), 4.39-4.30 (m, 2H), 3.10-3.00 (m, 1H), 2.28-2.18 (m, 1H), 2.09-2.05 (m, 2H), 1.96-1.93 (m, 2H), 1.59-1.39 (m, 4H), 1.30-1.23 (m, 3H).

Acid 32

1-(tert-butoxycarbonyl)piperidine-4-carboxylic Acid (A32)

Acid 33

(cis)-1-(tert-butoxycarbonyl)-2-methylpiperidine-4-carboxylic Acid (A33)

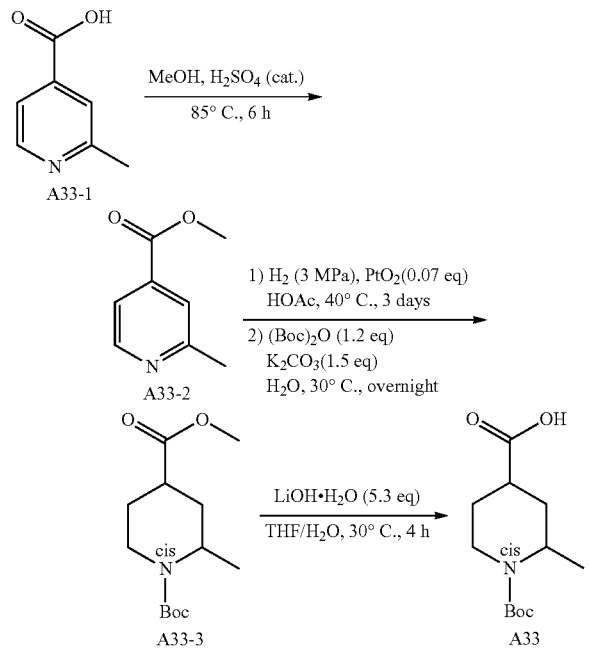

Intermediate A33-2 methyl 2-methylisonicotinate

To a 500 mL flask was added 2-methyl-isonicotinic acid A33-1 (10 g, 72.9 mmol), methanol (200 mL) and concentrated sulfuric acid (10 mL). After stirred at 85° C. for 6 hours, the reaction mixture was cooled down to room temperature. The solvent was evaporated under reduced pressure to give a residue, which was diluted with dichloromethane (100 mL) and washed with saturated sodium bicarbonate solution (100 mL) twice, dried over Na$_2$SO$_{4(s)}$ and filtered. The filtrate was concentrated under reduced pressure to give the title compound (10 g, 90% yield) as colorless liquid. LC-MS (ESI): R$_T$=1.37 min, mass calcd. for C$_8$H$_9$NO$_2$ 151.1, m/z found 151.9 [M+H]$^+$. $^1$H NMR (300 MHz, CDCl$_3$) δ 8.63-8.61 (m, 1H), 7.66 (s, 1H), 7.60-7.57 (m, 1H), 3.85 (s, 3H), 2.53 (s, 3H).

Intermediate A33-3

(cis)-1-tert-butyl 4-methyl 2-methylpiperidine-1,4-dicarboxylate

To a solution of methyl 2-methylisonicotinate A33-2 (6 g, 39.7 mmol) in acetic acid (60 mL) were added and platinum (IV) oxide (600 mg, 2.6 mmol). The mixture was stirred at 40° C. under 3 MPa hydrogen atmosphere for 3 days. The mixture was filtered and the filtrate was concentrated under reduced pressure to give the crude intermediate (11 g, 70.0 mmol). To the mixture of the crude intermediate in water (100 mL) was added di-tert-butyl dicarbonate (18.3 g, 84.0 mmol) and potassium carbonate (14.5 g, 105.0 mmol). The reaction mixture was stirred at room temperature overnight. Then the reaction mixture was extracted with ethyl acetate (70 mL) twice. The combined organic layers were dried over Na$_2$SO$_{4(s)}$ and filtered. The filtrate was concentrated under reduced pressure to leave a residue, which was purified by silica gel column chromatography (petroleum ether:ethyl acetate=10:1 to 9:1) to give the title compound (9.2 g, 90% yield) as colorless oil. LC-MS (ESI): R$_T$=1.839 min, mass calcd. For C$_{13}$H$_{23}$NO$_4$ 257.2, m/z found 258.1 [M+H]$^+$. $^1$H NMR (400 MHz, CDCl$_3$) δ 4.20-4.15 (m, 1H), 3.90-3.81 (m, 1H), 3.71 (s, 3H), 3.13-3.05 (m, 1H), 2.62-2.56 (m, 1H), 2.00-1.87 (m, 3H), 1.79-1.72 (m, 1H), 1.47 (s, 9H), 1.08 (d, J=6.8 Hz, 3H).

Acid 33

(cis)-1-(tert-butoxycarbonyl)-2-methylpiperidine-4-carboxylic Acid

To a solution of 1-tert-butyl 4-methyl 2-methylpiperidine-1,4-dicarboxylate A33-3 (2.5 g, 9.72 mmol) in tetrahydrofuran/water (13 mL/6.5 mL) was added a solution of Lithium hydroxide monohydrate (2.16 g, 51.4 mmol) in water (6 mL) at 0° C. The reaction mixture was stirred at 30° C. for 4 hours. Tetrahydrofuran was removed under reduced pressure. Then the residue was diluted with water (30 mL) and washed with ethyl acetate (20 mL). The aqeuous layer was acidified with 1 M hydrochloride aqueous solution to pH 4~5 and extracted with ethyl acetate (30 mL). The organic layers were dried over Na$_2$SO$_{4(s)}$ and filtered. The filtrate was concentrated under reduced pressure to give the title compound (2.5 g, 90% purity, 95% yield) as white solids. LC-MS (ESI): R$_T$=0.39 min, mass calcd. for C$_{12}$H$_{21}$NO$_4$ 243.1, m/z found 242.0 [M–H]$^-$. $^1$H NMR (400 MHz, DMSO-$d_6$) δ 12.31 (s, 1H), 4.06-3.99 (m, 1H), 3.67-3.61 (m, 1H), 3.06-2.98 (m, 1H), 2.53-2.47 (m, 1H), 1.88-1.76 (m, 3H), 1.62-1.53 (m, 1H), 1.39 (s, 9H), 1.05 (d, J=6.8 Hz, 3H).

Acid 34

1-(tert-butoxycarbonyl)pyrrolidine-3-carboxylic Acid (A34)

Acid 35 tert-Butyl 3-(3-ethoxy-3-oxopropanoyl)azetidine-1-carboxylate (A35)

Acid 36

4-(5-(1-(methoxycarbonyl)cyclopropyl)pyrimidin-2-yl)cyclohexane-1-carboxylic Acid (A36)

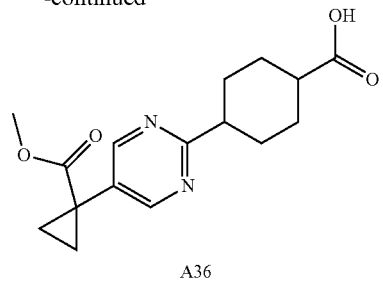

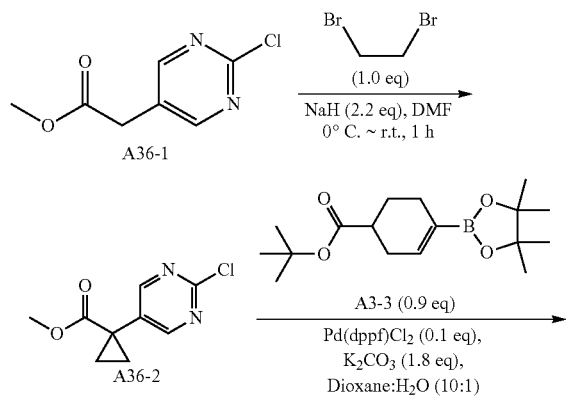

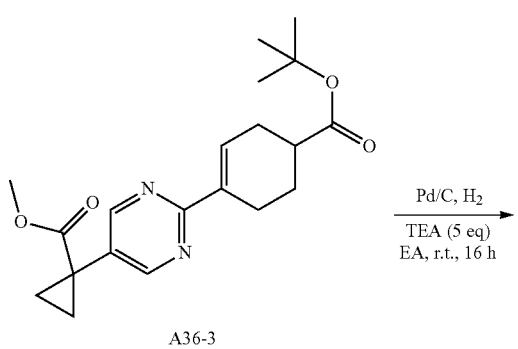

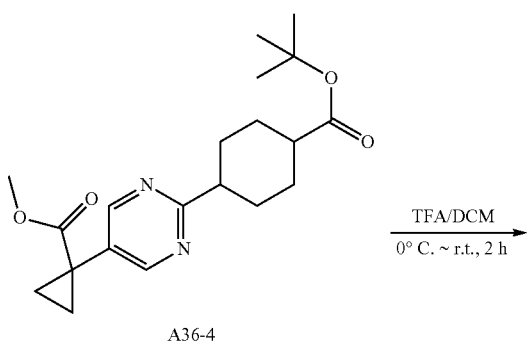

Intermediate A36-2

Methyl 1-(2-chloropyrimidin-5-yl)cyclopropanecarboxylate

To a solution of methyl 2-(2-chloropyrimidin-5-yl)acetate A36-1 (700 mg, 3.75 mmol) in N,N-dimethylformamide (21 mL) was added 60% sodium hydride in mineral oil (330 mg, 8.25 mmol) at 0° C. The resulting mixture was stirred at 0° C. under nitrogen atmosphere for 30 minutes, and then 1,2-dibromoethane (700 mg, 3.73 mmol) was added. After stirred at room temperature for 1 hour, the reaction mixture was quenched with ice water (30 mL) at 0° C. and extracted with ethyl acetate (30 mL) twice. The combined organic layers were washed with water (50 mL) twice and brine (50 mL) twice, dried over $Na_2SO_{4(s)}$ and filtered. The filtrate was concentrated and purified by silica gel column chromatography (petroleum ether:ethyl acetate=20:1 to 9:1) to give the title compound (456 mg, 57% yield) as white solids. LC-MS (ESI): $R_T$=1.36 min, mass calcd. for $C_9H_9ClN_2O_2$ 212.0, m/z found 213.0 [M+H]$^+$. $^1$H NMR (400 MHz, CDCl$_3$) δ 8.59 (s, 2H), 3.67 (s, 3H), 1.75 (dd, J=7.2 Hz, 4.4 Hz, 2H), 1.23 (dd, J=7.2 Hz, 4.4 Hz, 2H).

Intermediate A36-3 tert-butyl 4-(5-(1-(methoxycarbonyl)cyclopropyl)pyrimidin-2-yl)cyclohex-3-enecarboxylate To a solution of tert-butyl 4-(4,4,5,5-tetramethyl-1,3,2-dioxaborolan-2-yl)cyclohex-3-enecarboxylate A3-3 (600 mg, 1.95 mmol) in 1,4-dioxane (38 ml) and water (3.8 mL) was added methyl 1-(2-chloropyrimidin-5-yl)cyclopropanecarboxylate A36-2 (454 mg, 2.14 mmol), potassium carbonate (538 mg, 3.89 mmol) and [1,1'-Bis(diphenylphosphino)ferrocene]dichloropalladium(II) (142 mg, 0.194 mmol) at room temperature. After stirred at 100° C. for 6 hours under nitrogen atmosphere, the reaction mixture was cooled down to room temperature, diluted with water (100 mL) slowly and then extracted with ethyl acetate (50 mL) twice. The combined organic layers were washed with brine (50 mL), dried over $Na_2SO_{4(s)}$ and filtered. The filtrate was concentrated and purified by silica gel column chromatography (petroleum ether:ethyl acetate=10:1 to 4:1) to give the title compound (600 mg, 86% yield) as white solids. LC-MS (ESI): $R_T$=1.80 min, mass calcd. for $C_{19}H_{26}N_2O_4$ 358.2, m/z found 359.2 [M+H]$^+$. $^1$H NMR (400 MHz, CDCl$_3$) δ 8.62 (s, 2H), 7.29-7.27 (m, 1H), 3.65 (s, 3H), 2.87-2.81 (m, 1H), 2.57-2.47 (m, 4H), 2.21-2.15 (m, 1H), 1.83-1.73 (m, 1H), 1.70 (dd, J=7.2 Hz, 4.0 Hz, 2H), 1.47 (s, 9H), 1.20 (dd, J=7.2 Hz, 4.0 Hz, 2H).

Intermediate A36-4 tert-butyl 4-(5-(1-(methoxycarbonyl)cyclopropyl)pyrimidin-2-yl)cyclohexanecarboxylate To a mixture of tert-butyl 4-(5-(1-(methoxycarbonyl)cyclopropyl)pyrimidin-2-yl) cyclohex-3-enecarboxylate A36-3 (600 mg, 1.67 mmol) and triethylamine (846 mg, 8.38 mmol) in ethyl acetate (20 mL) was added 10% palladium on charcoal wt. (200 mg) under nitrogen atmosphere. After stirred at room temperature under hydrogen atmosphere (balloon pressure) for 16 hours, the mixture was filtered. The filtrate was concentrated to give the title compound (500 mg, 83% yield) as brownish oil. LC-MS (ESI): $R_T$=1.76 min, mass calcd. for $C_2H_{28}N_2O_4$ 360.2, m/z found 361.2 $[M+H]^+$. $^1$H NMR (400 MHz, CDCl$_3$) δ 8.61 (s, 2H), 3.65 (s, 3H), 3.00-2.93 (m, 0.8H), 2.90-2.83 (m, 0.2H), 2.55-2.50 (m, 0.8H), 2.30-2.22 (m, 0.2H), 2.14-1.96 (m, 4.4H), 1.92-1.85 (m, 1.6H), 1.71-1.67 (m, 2.6H), 1.63-1.53 (m, 1.6H), 1.45 (s, 9H), 1.20 (dd, J=7.2 Hz, 4.0 Hz, 2H).

Acid 36

4-(5-(1-(methoxycarbonyl)cyclopropyl)pyrimidin-2-yl)cyclohexane-1-carboxylic Acid To a solution of tert-butyl 4-(5-(1-(methoxycarbonyl)cyclopropyl)pyrimidin-2-yl) cyclohexanecarboxylate A36-4 (500 mg, 1.39 mmol) in dichloromethane (10 mL) was added trifluoroacetic acid (5 mL) at 0° C. After stirred at room temperature for 2 hours, the mixture was concentrated under reduced pressure to give the tilte compound (400 mg, 95% yield) as brownish oil. LC-MS (ESI): $R_T$=1.12 min, 1.27 min, mass calcd. for $C_6H_{20}N_2O_4$ 304.1, m/z found 305.1 $[M+H]^+$.

Acid 37

4-(4-(ethoxycarbonyl)-5-methylpyrimidin-2-yl)cyclohexane-1-carboxylic Acid (A37)

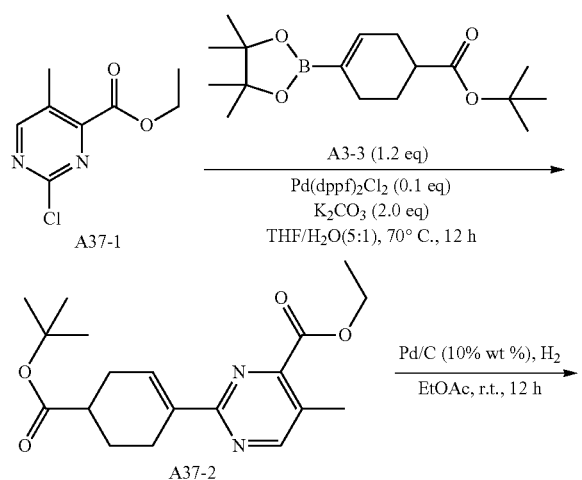

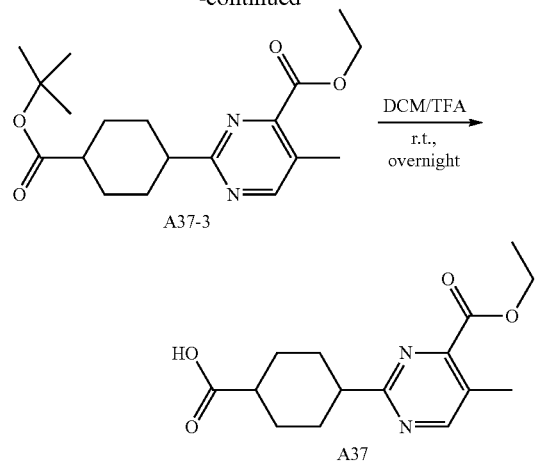

Intermediate A37-2 ethyl 2-(4-(tert-butoxycarbonyl)cyclohex-1-en-1-yl)-5-methylpyrimidine-4-carboxylate To a solution of ethyl 2-chloro-5-methylpyrimidine-4-carboxylate (3 g, 97% purity, 14.5 mmol) A37-1 and tert-butyl 4-(4,4,5,5-tetramethyl-1,3,2-dioxaborolan-2-yl)cyclohex-3-enecarboxylate A3-3 (5.947 g, 93% purity, 17.9 mmol) in tetrahydrofuran (100 mL) was added a solution of potassium carbonate (4.151 g, 30.1 mmol) in water (20 mL), then [1,1'-bis(diphenylphosphino)ferrocene] dichloropalladium(II) (1.094 g, 1.50 mmol) was added under nitrogen atmosphere. After stirred at 70° C. for 12 hours, the reaction mixture was cooled down to room temperature and poured into water (60 mL). The aqueous layer was extracted with ethyl acetate (60 mL) twice. The combined organic layers were dried over $Na_2SO_{4(s)}$ and filtered. The filtrate was concentrated and purified by silica gel column chromatography (petroleum ether:ethyl acetate=10:1) to give the title compound (4.9 g, 95.7% purity, 93% yield) as colorless oil. LC-MS (ESI): $R_T$=2.009 min, mass calcd. for $C_{19}H_{26}N_2O_4$ 346.2, m/z found 347.1 $[M+H]^+$. $^1$H NMR (400 MHz, DMSO-d$_6$) δ 8.80 (s, 1H), 7.19-7.18 (m, 1H), 4.38 (q, J=7.2 Hz, 2H), 2.70-2.66 (m, 1H), 2.56-2.52 (m, 1H), 2.46-2.37 (m, 3H), 2.35 (s, 3H), 2.07-2.03 (m, 1H), 1.70-1.61 (m, 1H), 1.42 (s, 9H), 1.33 (t, J=7.2 Hz, 3H).

Intermediate A37-3

Ethyl 2-(4-(tert-butoxycarbonyl)cyclohexyl)-5-methylpyrimidine-4-carboxylate To a solution of ethyl 2-(4-(tert-butoxycarbonyl)cyclohex-1-en-1-yl)-5-methylpyrimidine-4-carboxylate A37-2 (2 g, 95.7% purity, 5.53 mmol) in ethyl acetate (20 mL) was added 10% palladium on charcoal wt. (600 mg) under nitrogen atmosphere. After stirred at room temperature under hydrogen atmosphere for 12 hours, the mixture was filtered. The filtrate was concentrated to give the title compound (2 g, 90% purity from $^1$H NMR, 94% yield) as colorless oil. $^1$H NMR (400 MHz, DMSO-d$_6$) δ 8.80 (s, 1H), 4.39-4.34 (m, 2H), 2.95-2.87 (m, 0.7H), 2.82-2.75 (m, 0.3H), 2.34 (s, 3H), 1.98-1.85 (m, 4H), 1.77-1.73 (m, 2H), 1.63-1.56 (m, 3H), 1.41 (s, 9H), 1.32 (t, J=7.2 Hz, 3H).

129

Acid 37

4-(4-Ethoxycarbonyl)-5-methylpyrimidin-2-yl)cyclohexanecarboxylic Acid

To a solution of ethyl 2-(4-(tert-butoxycarbonyl)cyclohexyl)-5-methylpyrimidine-4-carboxylate A37-3 (2 g, 90% purity, 5.17 mmol) in dichloromethane (5 mL) was added trifluoroacetic acid (5 mL) at 0° C. After stirred at room temperature overnight, the reaction mixture was concentrated and purified by C18 column (acetonitrile:water=20% to 80%) to give the title compound (1.2 g, 97.7% purity, 78% yield) as colorless oil. LC-MS (ESI): $R_T$=1.111 min, mass calcd. for $C_{15}H_{20}N_2O_4$, 292.1 m/z found 291.1 [M−H]⁻.

Acid 38

4-(4-(2-Methoxy-2-oxoethyl)-5-methyloxazol-2-yl)cyclohexanecarboxylic Acid (A38)

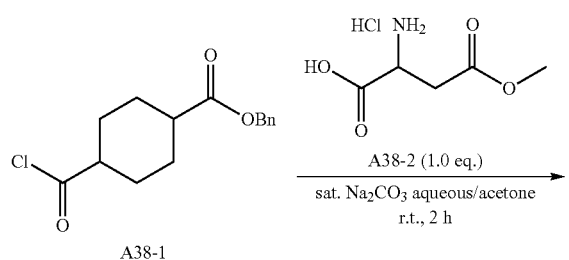

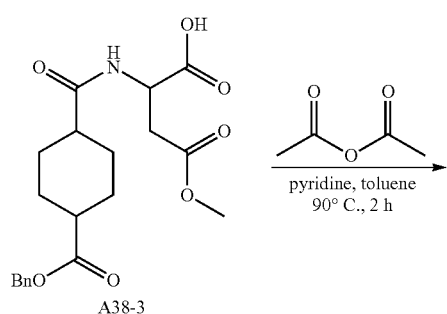

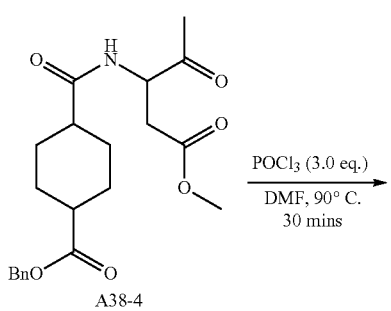

130

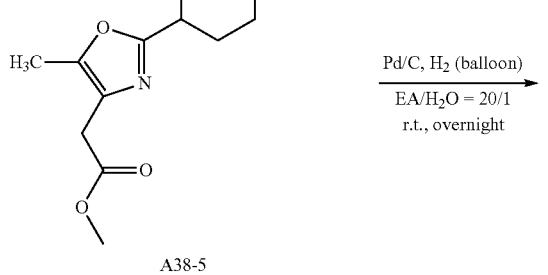

Intermediate A38-3

2-(4-((Benzyloxy)carbonyl)cyclohexanecarboxamido)-4-methoxy-4-oxobutanoic Acid To a solution of 2-amino-4-methoxy-4-oxobutanoic acid hydrochloride A38-2 (600 mg, 98% purity, 3.20 mmol) in acetone (25 mL) and saturated sodium bicarbonate aqueous solution (25 mL) was added dropwise a solution of benzyl 4-(chlorocarbonyl)cyclohexanecarboxylate A38-1 (1 g, 95% purity, 3.38 mmol) in tetrahydrofuran (5 mL) at room temperature over 30 minutes. After stirred at room temperature for 2 hours, the mixture was concentrated under reduced pressure at room temperature to give a residue, which was diluted with water (100 mL) and acidified with 1 M hydrochloride aqueous solution to pH=3~4. The resulting mixture was extracted with ethyl acetate (100 mL) twice. The combined organic layers were washed with water (50 mL) twice and brine (50 mL), dried over $Na_2SO_{4(s)}$ and filtered. The filtrate was concentrated and purified by C18 column (acetonitril:water=50% to 70%) to afford the title compound (500 mg, 90% purity from ¹H NMR, 36% yield) as yellow oil. LC-MS (ESI): $R_T$=1.48 min, mass calcd. for $C_2H_{25}NO_7$ 391.2, m/z found 391.9 [M+H]⁺. ¹H NMR (400 MHz, DMSO-$d_6$) δ 12.73 (br s, 1H), 8.08-8.04 (m, 1H), 7.40-7.30 (m, 5H), 5.11 (s, 1.2H), 5.08 (m, 0.8H), 4.56-4.50 (m, 1H), 3.58 (s, 1.2H), 3.57 (s, 1.8H), 2.79-2.73 (m, 1H), 2.65-2.59 (m, 1H), 2.36-2.24 (m, 1H), 2.16-2.07 (m, 0.5H), 1.95-1.90 (m, 2H), 1.77-1.72 (m, 1H), 1.64-1.53 (m, 3.5H), 1.41-1.24 (m, 2H).

Intermediate A38-4

Benzyl 4-((1-methoxy-1,4-dioxopentan-3-yl)carbamoyl)cyclohexanecarboxylate

To a solution of 2-(4-((benzyloxy)carbonyl)cyclohexanecarboxamido)-4-methoxy-4-oxobutanoic acid A38-3 (2.4 g, 95% purity, 5.8 mmol) in toluene (20 mL) was added pyridine (11 mL) and acetic anhydride (9 mL) at room temperature. After stirred at 90° C. for 2 hours, the mixture was cooled to room temperature and concentrated under reduced pressure to give a residue, which was dissolved in water (20 mL) and extracted with ethyl acetate (20 mL) twice. The combined organic layers were washed with water (10 mL) twice and brine (10 mL), dried over $Na_2SO_{4(s)}$ and filtered. The filtrate was concentrated and purified by C18 column (acetonitril:water=50% to 70%) to afford the title compound (1.0 g, 95% purity from $^1$H NMR, 42% yield) as yellow oil. LC-MS (ESI): $R_T$=1.52 min, mass calcd. for $C_{21}H_{27}NO_6$ 389.2, m/z found 390.0 $[M+H]^+$. $^1$H NMR (400 MHz, DMSO-$d_6$) δ 7.40-7.30 (m, 6H), 5.11 (s, 1.2H), 5.08 (s, 0.8H), 4.50-4.45 (m, 1H), 3.58 (s, 1H), 3.57 (s, 2H), 2.79-2.74 (m, 1H), 2.68-2.62 (m, 1H), 2.34-2.27 (m, 1H), 2.06 (s, 1H), 2.05 (s, 2H), 1.96-1.91 (m, 2H), 1.78-1.75 (m, 1H), 1.62-1.53 (m, 4H), 1.43-1.32 (m, 2H).

Intermediate A38-5

Benzyl 4-(4-(2-methoxy-2-oxoethyl)-5-methyloxazol-2-yl)cyclohexanecarboxylate

To a solution of benzyl 4-((1-methoxy-1,4-dioxopentan-3-yl)carbamoyl)cyclohexanecarboxylate A38-4 (860 mg, 95% purity, 2.10 mmol) in N,N-dimethylformamide (8 mL) was added phosphoryl trichloride (985 mg, 6.3 mmol) at 0° C. After stirred at 90° C. for 30 minutes, the mixture was cooled down to room temperature, dissolved in water (50 mL) and extracted with ethyl acetate (100 mL) twice. The combined organic layers were washed with water (50 mL) twice and brine (50 mL), dried over $Na_2SO_{4(s)}$ and filtered. The filtrate was concentrated and purified by C18 column (acetonitril:water=50% to 70%) to afford the title compound (530 mg, 95% purity from $^1$H NMR, 65% yield) as yellow oil. LC-MS (ESI): $R_T$=1.72 min, mass calcd. for $C_{21}H_{25}NO_5$ 371.2, m/z found 372.1 $[M+H]^+$. $^1$H NMR (400 MHz, DMSO-$d_6$) δ 7.39-7.29 (m, 5H), 5.10 (s, 2H), 3.60 (s, 3H), 3.49 (s, 1.2H), 3.48 (s, 0.8H), 2.92-2.86 (m, 0.6H), 2.72-2.61 (m, 1H), 2.43-2.38 (m, 0.4H), 2.21 (s, 3H), 2.03-1.95 (m, 1.6H), 1.84-1.75 (m, 3.4H), 1.70-1.62 (m, 1.4H), 1.52-1.41 (m, 1.6H).

Acid 38

4-(4-(2-Methoxy-2-oxoethyl)-5-methyloxazol-2-yl)cyclohexanecarboxylic acid

To a solution of benzyl 4-(4-(2-methoxy-2-oxoethyl)-5-methyloxazol-2-yl)cyclohexanecarboxylate A38-5 (400 mg, 95% purity, 1.02 mmol) in ethyl acetate (20 mL) and water (1 mL) was added 10% palladium on charcoal (40 mg, wt. %) at room temperature. After stirred at room temperature under hydrogen atmosphere (balloon) overnight, the mixture was filtered. The filtrate was concentrated under reduced pressure to afford the title compound (300 mg, 95% purity from $^1$H NMR, 99% yield) as colorless oil. $^1$H NMR (400 MHz, DMSO-$d_6$) δ 12.09 (br s, 1H), 3.60 (s, 3H), 3.48 (s, 1.2H), 3.47 (s, 0.8H), 2.89-2.85 (m, 0.6H), 2.70-2.62 (m, 0.4H), 2.45-2.42 (m, 0.6H), 2.25-2.14 (m, 3.4H), 2.05-2.00 (m, 0.6H), 1.96-1.94 (m, 0.8H), 1.83-1.69 (m, 3.6H), 1.65-1.59 (m, 1.3H), 1.49-1.34 (m, 1.7H).

Acid 39

4-(5-(2-methoxy-2-oxoethyl)pyrimidin-2-yl)cyclohexane-1-carboxylic Acid (A39)

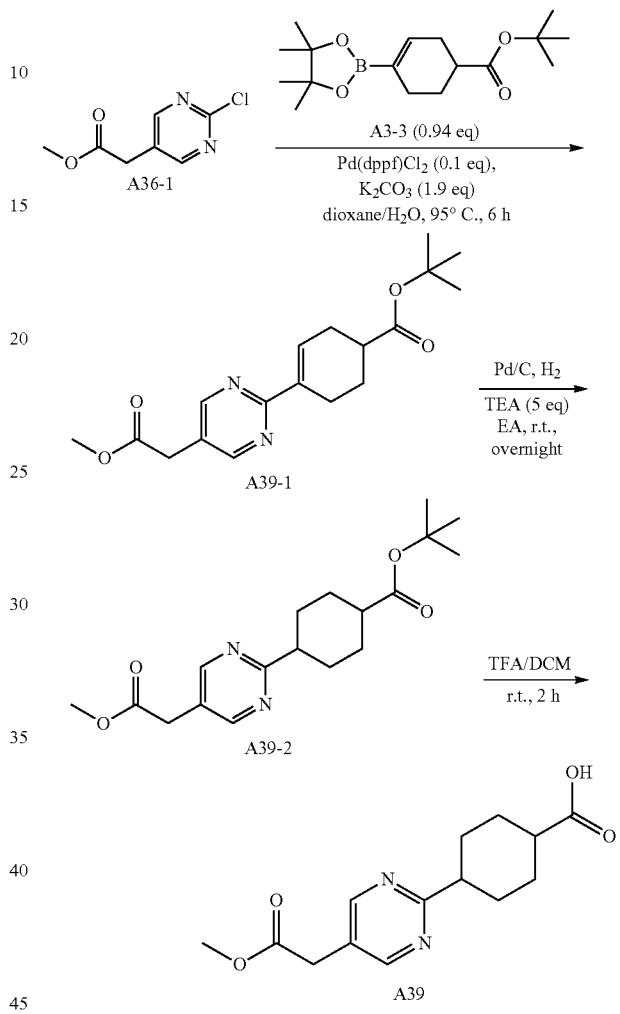

Intermediate A39-1 tert-butyl 4-(5-(2-methoxy-2-oxoethyl)pyrimidin-2-yl)cyclohex-3-enecarboxylate

The mixture of methyl 2-(2-chloropyrimidin-5-yl)acetate A36-1 (1.8 g, 9.65 mmol), tert-butyl 4-(4,4,5,5-tetramethyl-1,3,2-dioxaborolan-2-yl)cyclohex-3-ene carboxylate A3-3 (2.79 g, 9.05 mmol), potassium carbonate (2.47 g, 7.9 mmol) and [1,1'-bis(diphenylphosphino)ferrocene]dichloropalladium(II) (0.76 g, 1.04 mmol) in dioxane (25 mL) and water (2.5 mL) was stirred at 95° C. under nitrogen atmosphere for 6 hours. After cooled down to room temperature, the mixture was filtered, concentrated under reduced pressure and purified by silica chromatography (petroleum ether:ethyl acetate=10:1) to give the title compound (1.88 g, 95% purity from $^1$H NMR, 59% yield) as brown oil. LC-MS (ESI): $R_T$=1.70 min, mass calcd. for $C_{18}H_{24}N_2O_4$ 332.2, m/z found 333.2 $[M+H]^+$. $^1$H NMR (400 MHz, DMSO-$d_6$) δ 8.66 (s, 2H), 7.20 (s, 1H), 3.77 (s, 2H), 3.65 (s, 3H), 2.71-2.67 (m, 1H), 2.54-2.53 (m, 1H), 2.47-2.32 (m, 3H), 2.07-2.04 (m, 1H), 1.69-1.63 (m, 1H), 1.42 (s, 9H).

Intermediate A39-2 tert-butyl 4-(5-(2-methoxy-2-oxoethyl)pyrimidin-2-yl)cyclohexanecarboxylate

To a solution of tert-butyl 4-(5-(2-methoxy-2-oxoethyl)pyrimidin-2-yl)cyclohex-3-enecarboxylate A39-1 (1.42 g, 95% purity, 4.06 mmol) in ethyl acetate (10 mL) and triethylamine (2.1 g, 20.8 mmol) at room temperature was added 10% palladium on charcoal wt. (0.42 g). After stirred at room temperature hydrogen atmosphere overnight, the mixture was filtered. The filtrate was concentrated under reduced pressure to give the title compound (1.4 g, 90% purity from $^1$H NMR, 93% yield) as brown oil. LC-MS (ESI): $R_T$=1.67 min, mass calcd. for $C_{18}H_{26}N_2O_4$ 334.2, m/z found 335.2 [M+H]$^+$. $^1$H NMR (400 MHz, DMSO-$d_6$) δ 8.64 (s, 2H), 3.75 (s, 2H), 3.65 (s, 3H), 2.93-2.86 (m, 0.8H), 2.78-2.74 (m, 0.2H), 2.56-2.53 (m, 0.7H), 2.23-2.18 (m, 0.3H), 2.01-1.93 (m, 0.4H), 1.90-1.87 (m, 3.6H), 1.79-1.75 (m, 2H), 1.64-1.56 (m, 2H), 1.40 (s, 9H).

Acid 39

4-(5-(2-methoxy-2-oxoethyl)pyrimidin-2-yl)cyclohexanecarboxylic Acid

To a solution of tert-butyl 4-(5-(2-methoxy-2-oxoethyl)pyrimidin-2-yl)cyclohexane carboxylate A39-2 (1.4 g, 90% purity, 3.77 mmol) in dichloromethane (10 mL) was added trifluoroacetic acid (5 mL). The mixture was stirred at room temperature for 2 hours. The mixture was concentrated under reduced pressure to give the compound (1.2 g, 90% purity from $^1$H NMR, 100% yield) as brown oil. LC-MS (ESI): $R_T$=1.10 min, mass calcd. for $C_{14}H_{18}N_2O_4$ 278.1, m/z found 279.2 [M+H]$^+$. $^1$H NMR (400 MHz, CDCl$_3$) δ 8.63 (s, 2H), 3.75 (s, 2H), 3.65 (s, 3H), 2.93-2.86 (m, 1H), 2.31-2.15 (m, 1H), 1.99-1.93 (m, 2H), 1.89-1.83 (m, 1H), 1.78-1.72 (m, 2H), 1.63-1.56 (m, 2H), 1.50-1.39 (m, 1H).

Acid 40

1-(5-(4-(ethoxycarbonyl)piperidin-1-yl)pyrimidin-2-yl)piperidine-4-carboxylic Acid (A40)

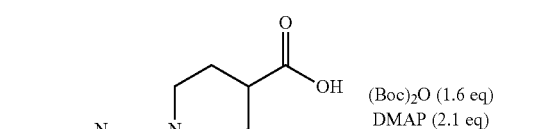

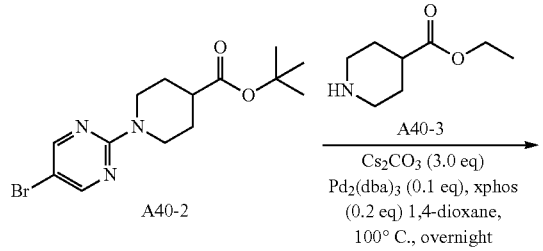

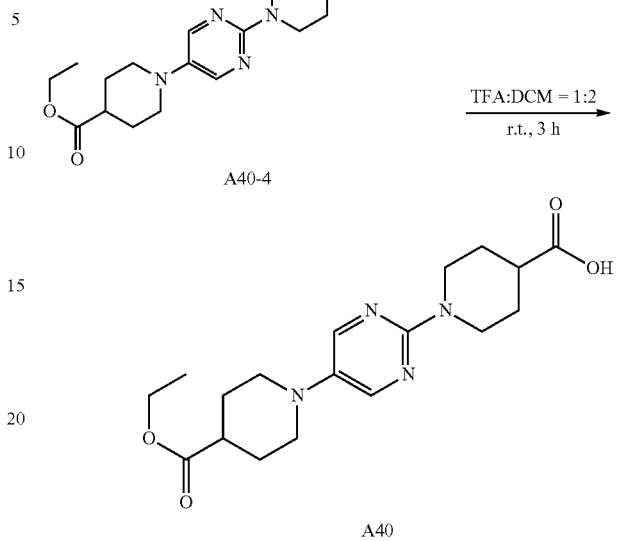

Intermediate A40-2 tert-butyl 1-(5-bromopyrimidin-2-yl)piperidine-4-carboxylate

To a solution of 1-(5-bromopyrimidin-2-yl)piperidine-4-carboxylic acid A40-1 (14.8 g, 90% purity, 46.6 mmol) in tert-butanol (150 mL) was added di-tert-butyl dicarbonate (16.0 g, 73.3 mmol) and 4-dimethylaminopyridine (12.0 g, 98.2 mmol) at room temperature. After stirred at room temperature overnight, the reaction mixture was concentrated and purified by silica gel column chromatography (petroleum ether:ethyl acetate=20:1) to afford the title compound (13.0 g, 90% purity from $^1$H NMR, 73% yield) as white solids. $^1$H NMR (400 MHz, CDCl$_3$) δ 8.27 (s, 2H), 4.57-4.52 (m, 2H), 3.08-3.01 (m, 2H), 2.51-2.43 (m, 1H), 1.95-1.91 (m, 2H), 1.70-1.60 (m, 2H), 1.45 (s, 9H).

Intermediate A40-3 tert-butyl 1-(5-(4-(ethoxycarbonyl)piperidin-1-yl)pyrimidin-2-yl)piperidine-4-carboxylate To a solution of tert-butyl 1-(5-bromopyrimidin-2-yl)piperidine-4-carboxylate A40-2 (1.2 g, 90% purity, 3.16 mmol), ethyl piperidine-4-carboxylate A40-3 (600 mg, 3.82 mmol) and cesium carbonate (3.10 g, 9.51 mmol) in 1,4-dioxane (60 mL) was added dicyclohexyl(2',4',6'-triisopropyl-[1,1'-biphenyl]-2-yl) phosphine (300 mg, 0.629 mmol) and tris(dibenzylideneacetone)dipalladium(0) (290 mg, 0.317 mmol) at room temperature under nitrogen atmosphere. After stirred at 100° C. under nitrogen atmosphere overnight, the reaction mixture was cooled down to room temperature, concentrated and purified by silica gel column chromatography (petroleum ether:ethyl acetate=12:1 to 3:1) to give the title compound (980 mg, 90% purity from $^1$H NMR, 67% yield) as yellow solids. LC-MS (ESI): $R_T$=1.990 min, mass calcd. for $C_{22}H_{34}N_4O_4$ 418.3, m/z found 419.2 [M+H]$^+$. $^1$H NMR (400 MHz, CDCl$_3$) δ 8.10 (s, 2H), 4.54-4.49 (m, 2H), 4.16 (q, J=7.2 Hz, 2H), 3.35-3.30 (m, 2H), 3.02-2.95 (m, 2H), 2.73-2.67 (m, 2H), 2.47-2.35 (m, 2H), 2.05-2.01 (m, 2H), 1.94-1.87 (m, 4H), 1.71-1.62 (m, 2H), 1.44 (s, 9H), 1.27 (t, J=7.2 Hz, 3H).

Acid 40

1-(5-(4-(ethoxycarbonyl)piperidin-1-yl)pyrimidin-2-yl)piperidine-4-carboxylic Acid To a solution of tert-butyl 1-(5-(4-(ethoxycarbonyl)piperidin-1-yl)pyrimidin-2-yl) piperidine-4-carboxylate A40-4 (980 mg, 90% purity, 2.11 mmol) in dichloromethane (6 mL) was added trifluoroacetic acid (3 mL) at 0° C. After stirred at room temperature for 3 hours, the mixture was poured into water (15 mL) and extracted with ethyl acetate (15 mL) twice. The combined organic layers were washed with brine (20 mL), dried over $Na_2SO_{4(s)}$ and filtered. The filtrate was concentrated under reduced pressure to give the title compound (840 mg, 90% purity from $^1$H NMR, 98% yield) as yellow solids. LC-MS (ESI): $R_T$=1.269 min, mass calcd. for $C_{18}H_{26}N_4O_4$ 362.2, m/z found 363.1 [M+H]$^+$. $^1$H NMR (400 MHz, CDCl$_3$) δ 8.23 (s, 2H), 4.56-4.51 (m, 2H), 4.17 (q, J=7.2 Hz, 2H), 3.41-3.36 (m, 2H), 3.17-3.10 (m, 2H), 2.84-2.78 (m, 2H), 2.65-2.60 (m, 1H), 2.47-2.41 (m, 1H), 2.12-1.92 (m, 6H), 1.80-1.70 (m, 2H), 1.28 (t, J=7.2 Hz, 3H).

Acid 41

1-(5-(3-(tert-butoxy)-3-oxopropyl)pyridin-2-yl)piperidine-4-carboxylic Acid (A41)

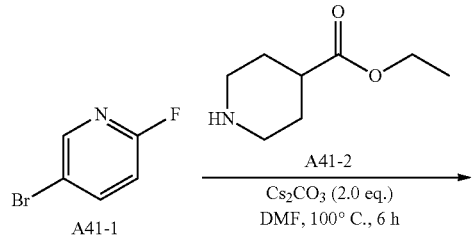

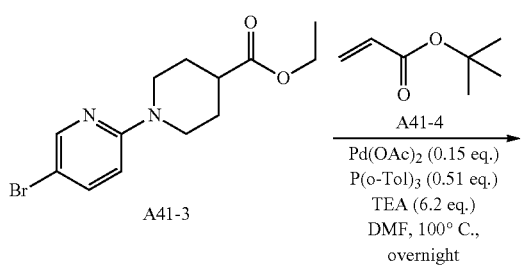

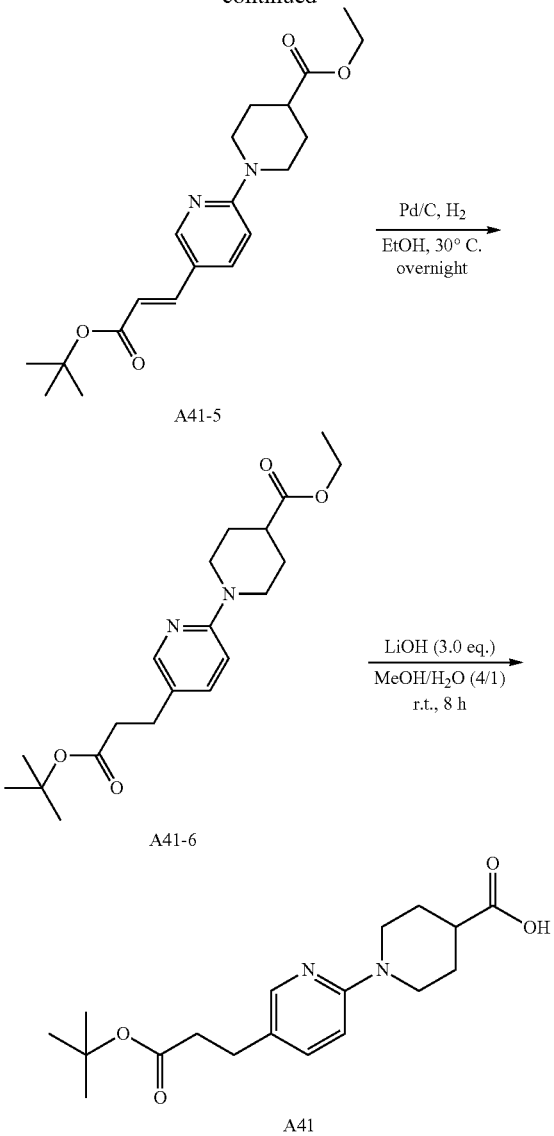

Intermediate A41-3

Ethyl 1-(5-bromopyridin-2-yl)piperidine-4-carboxylate

To the solution of ethyl piperidine-4-carboxylate A41-2 (5.9 g, 37.5 mmol) in N,N-dimethylformamide (80 mL) was added cesium carbonate (19.0 g, 58.3 mmol) and 5-bromo-2-fluoropyridine A41-1 (5.0 g, 28.4 mmol) under nitrogen atmosphere at room temperature. After stirred at 100° C. for 6 hours, the mixture was cooled down to room temperature and filtered. The filtrate was poured into water (100 mL) and extracted with ethyl acetate (150 mL) for three times. The combined organic layers were washed with water (200 mL) and brine (200 mL), dried over $Na_2SO_{4(s)}$ and filtered. The filtrate was concentrated and purified by silica gel column chromatography (petroleum ether:ethyl acetate=50:1 to 20:1) to give the title compound (7.1 g, 95% purity from $^1$H NMR, 76% yield) as colorless oil. LC-MS (ESI): $R_T$=1.66 min, mass calcd. for $C_{13}H_{17}BrN_2O_2$ 312.0, m/z found 313.0 [M+H]$^+$. $^1$H NMR (400 MHz, CDCl$_3$) δ 8.17 (d, J=2.4 Hz, 1H), 7.51 (dd, J=9.2 Hz, 2.8 Hz, 1H), 6.56 (d, J=9.2 Hz, 1H), 4.15 (q, J=7.2 Hz, 4H), 3.00-2.93 (m, 2H), 2.56-2.49 (m, 1H), 2.01-1.95 (m, 2H), 1.80-1.70 (m, 2H), 1.26 (t, J=7.2 Hz, 3H).

Intermediate A41-5

(E)-Ethyl 1-(5-(3-(tert-butoxy)-3-oxoprop-1-en-1-yl)pyridin-2-yl)piperidine-4-carboxylate To the solution of ethyl 1-(5-bromopyridin-2-yl)piperidine-4-carboxylate A41-3 (3 g, 9.1 mmol) and tert-butyl acrylate A41-4 (2.40 g, 18.7 mmol) in N,N-dimethylformamide (90 mL) was added tri-o-tolylphosphine (1.40 g, 4.60 mmol), triethylamine (5.70 g, 56.3 mmol) and diacetoxypalladium (0.30 g, 1.34 mmol) at room temperature under nitrogen atmosphere. After stirred at 100° C. under nitrogen atmosphere overnight, the mixture was cooled down to room temperature, poured into water (100 mL) and extracted with ethyl acetate (150 mL) for three times. The combined organic layers were washed with water (250 mL) and brine (250 mL), dried over $Na_2SO_{4(s)}$ and filtered. The filtrate was concentrated and purified by silica gel column chromatography (petroleum ether:ethyl acetate=20:1 to 8:1) to give the title compound (3.6 g, 90% purity from $^1$H NMR, 99% yield) as light green solids. LC-MS (ESI): $R_T$=1.78 min, mass calcd. for $C_{20}H_{28}N_2O_4$ 360.2, m/z found 361.1 [M+H]$^+$. $^1$H NMR (400 MHz, CDCl$_3$) δ 8.24 (d, J=2.4 Hz, 1H), 7.63 (dd, J=9.2 Hz, 2.4 Hz, 1H), 7.48 (d, J=15.6 Hz, 1H), 6.64 (d, J=8.8 Hz, 1H), 6.17 (d, J=16.0 Hz, 1H), 4.29 (dt, J=13.6 Hz, 3.6 Hz, 2H), 4.15 (q, J=7.2 Hz, 2H), 3.09-3.02 (m, 2H), 2.60-2.53 (m, 1H), 2.02-1.98 (m, 2H), 1.80-1.71 (m, 2H), 1.53 (s, 9H), 1.26 (t, J=7.2 Hz, 3H).

Intermediate A41-6

Ethyl 1-(5-(3-(tert-butoxy)-3-oxopropyl)pyridin-2-yl)piperidine-4-carboxylate

To the solution of ethyl 1-(5-(3-(tert-butoxy)-3-oxoprop-1-en-1-yl)pyridin-2-yl)piperidine-4-carboxylate A41-5 (1.50 g, 90% purity, 3.75 mmol) in ethanol (40 mL) was added 10% palladium on charcoal (450 mg, wt.). After stirred at 30° C. under hydrogen atmosphere overnight, the mixture was filtered and the filtrate was concentrated to give the title compound (1.37 g, 90% purity from $^1$H NMR, 91% yield) as brown oil. LC-MS (ESI): $R_T$=1.68 min, mass calcd. for $C_{20}H_{30}N_2O_4$ 362.2, m/z found 363.1 [M+H]$^+$. $^1$H NMR (400 MHz, CDCl$_3$) δ 8.03 (d, J=2.4 Hz, 1H), 7.33 (dd, J=8.8 Hz, 2.4 Hz, 1H), 6.61 (d, J=8.8 Hz, 1H), 4.19-4.12 (m, 4H), 2.95-2.89 (m, 2H), 2.77 (t, J=8.0 Hz, 2H), 2.53-2.45 (m, 3H), 2.02-1.96 (m 2H), 1.81-1.72 (m 2H), 1.42 (s, 9H), 1.26 (t, J=7.2 Hz, 3H).

Acid 41

1-(5-(3-(tert-Butoxy)-3-oxopropyl)pyridin-2-yl)piperidine-4-carboxylic Acid

To the solution of ethyl 1-(5-(3-(tert-butoxy)-3-oxopropyl)pyridin-2-yl)piperidine-4-carboxylate A41-6 (1.37 g, 90% purity, 3.40 mmol) in methanol (32 mL) and water (8 mL) was added lithium hydroxide monohydrate (430 mg, 10.2 mmol) under nitrogen atmosphere at room temperature. After stirred at room temperature for 8 hours, the mixture was poured into ethyl acetate (80 mL). The mixture was acidified with 1 M hydrochloride aqueous solution to pH=5 6, then washed with water (40 mL) twice and brine (50 mL), dried over $Na_2SO_{4(s)}$ and filtered. The filtrate was concentrated under reduced pressure to give the title compound (1.1 g, 95% purity from $^1$H NMR, 92% yield) as brown solids. LC-MS (ESI): $R_T$=0.94 min, mass calcd. for $C_{18}H_{26}N_2O_4$ 334.2, m/z found 335.0 [M+H]$^+$. $^1$H NMR (400 MHz, CDCl$_3$) δ 8.04 (d, J=2.0 Hz, 1H), 7.36 (dd, J=8.8 Hz, 2.4 Hz, 1H), 6.64 (d, J=8.8 Hz, 1H), 4.17-4.12 (m, 2H), 3.00-2.94 (m, 2H), 2.78 (t, J=8.0 Hz, 2H), 2.61-2.53 (m, 1H), 2.47 (t, J=8.0 Hz, 2H), 2.05-2.02 (m, 2H), 1.85-1.75 (m, 2H), 1.42 (s, 9H).

Part II: Preparation of Ketoesters of General Formula IV-1 and IV-2

Intermediate KT1: (Exemplified with Method A)

methyl 2-(4-(3-methoxy-3-oxopropanoyl)cyclohexyl)oxazole-4-carboxylate

To a solution of 4-(4-(methoxycarbonyl)oxazol-2-yl)cyclohexanecarboxylic acid A1 (1.30 g, 5.14 mmol) in acetonitrile (18 mL) was added N,N'-carbonyldiimidazole (998 mg, 6.17 mmol) at room temperature. The solution was stirred at room temperature under nitrogen atmosphere for 2 hours (mixture A). To the suspension of potassium 3-methoxy-3-oxopropanoate (1.67 g, 10.7 mmol) and magnesium chloride (1.21 g, 12.8 mmol) in acetonitrile (25 mL) was added triethylamine (1.65 g, 16.3 mmol). After stirred at room temperature under nitrogen atmosphere for 1 hour, the suspension was added mixture A and stirring continued at 80° C. under nitrogen atmosphere for 3 hours. Then it was cooled down and concentrated under reduced pressure to give a residue, which was taken up into water (100 mL) and ethyl acetate (100 mL). The mixture was acidified with 0.5 M hydrochloride aqueous solution to give a clear solution and then the organic phase was separated. The aqueous layer was extracted with ethyl acetate (50 mL) twice. The combined organic layers were washed with brine (50 mL), dried over $Na_2SO_4$ (and filtered. The filtrate was concentrated under reduced pressure to give the title compound (1.55 g, 98.1% yield) as colorless oil. LC-MS (ESI): $R_T$=1.399 min, mass calcd. for $C_{15}H_{19}NO_6$ 309.1, m/z found 310.1 [M+H]$^+$. $^1$H NMR (400 MHz, CDCl$_3$) δ 8.16 (s, 1H), 3.91 (s, 1.2H), 3.90 (s, 1.8H), 3.75 (s, 1.2H), 3.73 (s, 1.8H), 3.53 (s, 1.08H), 3.51 (s, 0.72H), 3.10-3.05 (m, 0.4H), 2.87-2.77 (m, 0.6H), 2.69-2.63 (m, 0.4H), 2.56-2.50 (m, 0.6H), 2.28-2.23 (m, 1H), 2.-2.03 (m, 2H), 1.89-1.83 (m, 1H), 1.79-1.61 (m, 3H), 1.54-1.44 (m, 1H).

Spectral Analyses of Ketoesters

Intermediate KT2 methyl 2-(4-(3-ethoxy-3-oxopropanoyl)cyclohexyl)oxazole-4-carboxylate

By utilizing the analogous procedure of Method A, the title compound was synthesized from A1 as colorless oil. LC-MS (ESI): $R_T$=1.454 min, mass calcd. for $C_{16}H_{21}NO_6$ 323.1, m/z found 324.1 [M+H]$^+$. $^1$H NMR (400 MHz, CDCl$_3$) δ 8.16 (s, 1H), 4.23-4.16 (m, 2H), 3.91 (s, 1.5H), 3.90 (s, 1.5H), 3.51-3.45 (m, 2H), 3.09-3.05 (m, 0.4H), 2.86-2.78 (m, 0.6H), 2.69-2.63 (m, 0.4H), 2.58-2.50 (m, 0.6H), 2.23-2.02 (m, 3H), 1.88-1.77 (m, 2H), 1.68-1.54 (m, 2H), 1.47-1.39 (m, 1H), 1.30-1.26 (m, 3H).

Intermediate KT3 methyl 2-(3-(3-methoxy-3-oxopropanoyl)bicyclo[1.1.1]pentan-1-yl)oxazole-4-carboxylate By utilizing the analogous procedure of Method A, the title compound was synthesized from A2 as gray solids. LC-MS (ESI): $R_T$=1.815 min, mass calcd. for $C_{14}H_{15}NO_6$ 293.1, m/z found 293.9 [M+H]$^+$. $^1$H NMR (300 MHz, CDCl$_3$) δ 11.75 (s, 0.4H), 8.17 (s, 1H), 5.02 (s, 0.4H), 3.91 (s, 3H), 3.74 (s, 3H), 3.52 (s, 1.2H), 2.52 (s, 3.8H), 2.44 (m, 2.2H).

Intermediate KT4

Ethyl 2-(4-(3-ethoxy-3-oxopropanoyl)cyclohex-1-en-1-yl)oxazole-4-carboxylate

By utilizing the analogous procedure of Method A, the title compound was synthesized from A3 as gray solids.
LC-MS (ESI): $R_T$=1.53 min, mass calcd. for $C_{17}H_{21}NO_6$ 335.1, m/z found 336.3 [M+H]$^+$. $^1$H NMR (400 MHz, CDCl$_3$) δ 8.13 (s, 1H), 6.86 (s, 1H), 4.39 (q, J=7.2 Hz, 2H), 4.21 (q, J=7.2 Hz, 2H), 3.61 (s, 0.5H), 3.56 (s, 1.5H), 2.87-2.77 (m, 2H), 2.55-2.42 (m, 3H), 2.20-2.16 (m, 1H), 1.76-1.68 (m, 1H), 1.38 (t, J=7.2 Hz, 3H), 1.29 (t, J=7.2 Hz, 3H).

Intermediate KT5

Methyl 2-(4-(3-ethoxy-3-oxopropanoyl)cyclohexyl)-5-methyloxazole-4-carboxylate

By utilizing the analogous procedure of Method A, the title compound was synthesized from A4 as white solids.
LC-MS (ESI): $R_T$=1.57 min, mass calcd. for $C_{17}H_{23}NO_6$ 337.2, m/z found 338.3 [M+H]$^+$. $^1$H NMR (400 MHz, CDCl$_3$) δ 12.21 (s, 0.1H), 5.02 (s, 0.1H), 4.22 (s, 2H), 3.92 (d, J=1.6 Hz, 3H), 3.53 (s, 1.8H), 3.02 (s, 0.4H), 2.78-2.56 (m, 4.6H), 2.26-2.09 (m, 4H), 1.79-1.49 (m, 4H), 1.34-1.28 (m, 3H).

Intermediate KT6

Methyl 2-((4-(3-ethoxy-3-oxopropanoyl)cyclohexyl)methyl)oxazole-4-carboxylate

By utilizing the analogous procedure of Method A, the title compound was synthesized from A5 as yellow oil which was directly used without further purification. LC-MS (ESI): $R_T$=1.65 min, mass calcd. for $C_{17}H_{23}NO_6$ 337.2, m/z found 338.1 [M+H]$^+$. $^1$H NMR (400 MHz, DMSO-d$_6$) δ 8.73 (s, 1H), 4.09-4.04 (m, 2H), 3.79 (s, 3H), 3.64-3.63 (m, 2H), 2.73-2.69 (m, 2H), 2.65-2.60 (m, 0.6H), 2.44-2.37 (m, 0.4H), 1.99-1.68 (m, 4H), 1.59-1.48 (m, 2.7H), 1.26-1.22 (m, 1.3H), 1.19-1.16 (m, 3H), 1.09-1.02 (m, 1H).

Intermediate KT7 methyl 3-(4-(4-(2-ethoxy-2-oxoethyl)oxazol-2-yl)cyclohexyl)-3-oxopropanoate

By utilizing the analogous procedure of Method A, the title compound was synthesized from A6 as yellow oil. $^1$H NMR (400 MHz, CDCl$_3$) δ 7.54 (s, 1H), 4.22-4.16 (m, 2H), 3.74-3.73 (m, 3H), 3.60-3.56 (m, 2H), 3.53-3.48 (m, 2H), 3.03-3.00 (m, 0.3H), 2.78-2.71 (m, 0.7H), 2.62-2.61 (m, 0.3H), 2.56-2.47 (m, 0.7H), 2.24-2.12 (m, 2H), 2.11-2.01 (m, 1.5H), 1.84-1.76 (m, 1.5H), 1.65-1.43 (m, 3H), 1.30-1.24 (m, 3H).

Intermediate KT8

Methyl 3-(4-(4-(2-ethoxy-2-oxoethyl)-5-methyloxazol-2-yl)cyclohexyl)-3-oxopropanoate By utilizing the analogous procedure of Method A, the title compound was synthesized from A7 as yellow oil.
LC-MS (ESI): $R_T$=1.55 min, mass calcd. for $C_{18}H_{25}NO_6$ 351.2, m/z found 352.0 [M+H]$^+$. $^1$H NMR (400 MHz, CDCl$_3$) δ 4.16 (q, J=6.8 Hz, 2H), 3.75-3.73 (m, 3H), 3.53 (s, 1.5H), 3.51 (s, 0.5H), 3.45 (s, 2H), 2.96-2.93 (m, 0.2H), 2.71-2.65 (m, 1H), 2.54-2.48 (m, 0.8H), 2.24 (s, 2H), 2.19 (s, 1H), 2.07-2.04 (m, 2H), 1.86-1.74 (m, 2H), 1.62-1.44 (m, 4H), 1.26 (t, J=7.2 Hz, 3H).

Intermediate KT9

Ethyl 3-(4-(4-(2-methoxy-2-oxoethyl)oxazol-2-yl)cyclohexyl)-3-oxopropanoate (a Mixture of 2 Stereoisomers)

By utilizing the analogous procedure of Method A, the title compound was synthesized from A6 as yellow oil.
LC-MS (ESI): $R_T$=1.49 min, mass calcd. for $C_{18}H_{25}NO_6$ 351.2, m/z found 352.2 [M+H]$^+$. $^1$H NMR (400 MHz, CDCl$_3$) δ 12.2 (s, 0.1H), 7.54 (s, 1H), 4.99 (s, 0.1H), 4.23-4.16 (m, 4H), 3.61-3.58 (m, 1.8H), 3.51-3.48 (m, 2H), 3.04-2.99 (m, 0.3H), 2.78-2.71 (m, 0.7H), 2.65-2.60 (m, 0.3H), 2.57-2.48 (m, 0.7H), 2.24-1.98 (m, 4H), 1.84-1.74 (m, 1H), 1.65-1.47 (m, 3H), 1.30-1.26 (m, 6H).

Intermediate KT10 ethyl 3-(4-(4-(3-methoxy-3-oxopropyl)oxazol-2-yl)cyclohexyl)-3-oxopropanoate

By utilizing the analogous procedure of Method A, the title compound was synthesized from A9 as yellow oil. $^1$H NMR (300 MHz, DMSO-d$_6$) δ 7.65 (s, 1H), 4.06 (q, J=7.2 Hz, 2H), 3.63 (s, 2H), 3.56 (s, 3H), 2.71-2.67 (m, 1H), 2.65-2.63 (m, 2H), 2.58-2.56 (m, 2H), 2.05-2.01 (m, 2H), 1.95-1.90 (m, 2H), 1.70-1.55 (m, 1H), 1.48-1.24 (m, 4H), 1.15 (t, J=7.2 Hz, 3H).

Intermediate KT11

Ethyl 3-(2-(4-(3-methoxy-3-oxopropanoyl)cyclohexyl)oxazol-4-yl)-2,2-dimethylpropanoate By utilizing the analogous procedure of Method A, the title compound was synthesized from A10 as yellow oil. $^1$H NMR (300 MHz, CDCl$_3$) δ 7.24 (s, 1H), 4.11 (q, J=6.9 Hz, 2H), 3.73-3.72 (m, 3H), 3.52-3.50 (m, 2H), 2.73 (s, 2H), 2.71-2.64 (m, 1H), 2.58-2.43 (m, 1H), 2.24-2.19 (m, 1H), 2.11-1.99 (m, 2H), 1.84-1.38 (m, 5H), 1.26-1.20 (m, 9H).

Intermediate KT12

Ethyl 2-(4-(3-ethoxy-3-oxopropanoyl)cyclohexyl) oxazole-5-carboxylate (a Mixture of 2 Stereoisomers)

Intermediate KT12-1

Mixture of ethyl 2-(4-(3-ethoxy-3-oxopropanoyl) cyclohexyl)oxazole-5-carboxylate and ethyl 2-(4-(3-ethoxy-3-oxopropanoyl)cyclohex-1-en-1-yl)oxazole-5-carboxylate By utilizing the analogous procedure of Method A, the title compound was synthesized as yellow oil. LC-MS (ESI): $R_T$=1.635 min, mass calcd. for $C_{17}H_{23}NO_6$ and $C_{17}H_{21}NO_6$ 337.2 and 335.1, m/z found 338.1 [M+H]$^+$ and 336.1 [M+H]$^+$, respectively.

Intermediate KT12

Ethyl 2-(4-(3-ethoxy-3-oxopropanoyl)cyclohexyl) oxazole-5-carboxylate (a Mixture of 2 Stereoisomers)

To a mixture of ethyl 2-(4-(3-ethoxy-3-oxopropanoyl) cyclohex-1-en-1-yl)oxazole-5-carboxylate and ethyl 2-(4-(3-ethoxy-3-oxopropanoyl)cyclohexyl)oxazole-5-carboxylate KT12-1 (3.48 g, 90% purity, about 9.34 mmol)) in methanol (100 mL) was added 10% palladium on charcoal wt. (1.00 g) under nitrogen atmosphere at room temperature. After replacing the inert nitrogen atmosphere with hydrogen gas, the mixture was stirred at 25° C. under hydrogen atmosphere of balloon for 1.5 hours. The catalyst was filtered off and the filtrate was concentrated under reduced pressure to give the title compound (3.05 g, 90% purity from $^1$H NMR, 87% yield) as yellow oil. LC-MS (ESI): $R_T$=1.498 min, mass calcd. for $C_{17}H_{23}NO_6$ 337.2, m/z found 338.1 [M+H]$^+$. $^1$H NMR (400 MHz, DMSO-d$_6$) δ 7.89 (s, 0.5H), 7.88 (s, 0.5H), 4.31 (q, J=7.2 Hz, 2H), 4.12-4.05 (m, 2H), 3.68 (s, 1H), 3.65 (s, 1H), 3.17-3.14 (m, 0.6H), 2.94-2.85 (m, 0.4H), 2.72-2.63 (m, 0.5H), 2.13-2.09 (m, 0.5H), 1.99-1.97 (m, 2H), 1.85-1.74 (m, 2H), 1.64-1.57 (m, 2H), 1.47-1.36 (m, 2H), 1.29 (t, J=7.2 Hz, 3H), 1.21-1.16 (m, 3H).

Intermediate KT13

Ethyl 3-(4-(4-(1-ethoxy-2-methyl-1-oxopropan-2-yl) oxazol-2-yl)cyclohexyl)-3-oxopropanoate By utilizing the analogous procedure of Method A, the title compound was synthesized from A12 as colorless oil. LC-MS (ESI): $R_T$=2.138 min, mass calcd. for $C_{20}H_{29}NO_6$ 379.2, m/z found 380.1 [M+H]$^+$. $^1$H NMR (400 MHz, CDCl$_3$) δ 7.37 (s, 1H), 4.23-4.12 (m, 4H), 3.50-3.48 (m, 2H), 3.04-3.00 (m, 0.2H), 2.81-2.72 (m, 0.8H), 2.62-2.51 (m, 1H), 2.20-2.00 (m, 3.5H), 1.86-1.55 (m, 4.5H), 1.51 (s, 6H), 1.30-1.21 (m, 6H).

Intermediate KT14

Ethyl 3-(4-(1-(2-ethoxy-2-oxoethyl)-1H-pyrazol-4-yl)cyclohexyl)-3-oxopropanoate

By utilizing the analogous procedure of Method A, the title compound was synthesized from A13 as pink oil. LC-MS (ESI): $R_T$=1.918 min, mass calcd. for $C_{18}H_{26}N_2O_5$ 350.2, m/z found 351.1 [M+H]$^+$. $^1$H NMR (400 MHz, CDCl$_3$) δ 12.24 (s, 0.1H), 12.17 (s, 0.1H), 7.41 (s, 1H), 7.25 (s, 1H), 4.87 (s, 0.6H), 4.85 (s, 1.4H), 4.25-4.18 (m, 4H), 3.51 (s, 0.5H), 3.49 (s, 1.3H), 2.75-2.65 (m, 1H), 2.53-2.46 (m, 0.3H), 2.11-1.67 (m, 6.7H), 1.57-1.35 (m, 2H), 1.30-1.26 (m, 6H).

Intermediate KT15 methyl 3-(4-(1-(3-methoxy-3-oxopropyl)-1H-pyrazol-4-yl)cyclohexyl)-3-oxopropanoate By utilizing the analogous procedure of Method A, the title compound was synthesized from A14 which was directly used without further purification. LC-MS (ESI): $R_T$=1.46 min, mass calcd. for $C_{17}H_{24}N_2O_5$ 336.2, m/z found 337.0 [M+H]$^+$.

Intermediates KT16

Methyl 3-(4-(4-(3-ethoxy-3-oxopropanoyl)cyclohexyl)-1H-pyrazol-1-yl)-3-methylbutanoate By utilizing the analogous procedure of Method A, the title compound was synthesized from A15 as yellow oil. LC-MS (ESI): $R_T$=1.867 min, mass calcd. for $C_{20}H_{30}N_2O_5$ 378.2, m/z found 379.2 [M+H]$^+$. $^1$HNMR (400 MHz, CDCl$_3$) δ 7.37 (s, 0.4H), 7.35 (s, 0.6H), 7.29 (s, 0.4H), 7.28 (s, 0.6H), 4.23-4.15 (m, 2H), 3.57 (s, 1.2H), 3.56 (s, 1.8H), 3.51 (s, 0.8H), 3.50 (s, 1.2H), 2.88 (s, 0.8H), 2.87 (s, 1.2H), 2.72-2.64 (m, 1.4H), 2.53-2.43 (m, 0.6H), 2.12-1.92 (m, 3H), 1.83-1.73 (m, 3H), 1.71-1.67 (m, 6H), 1.53-1.30 (m, 1.5H), 1.27-1.24 (m, 3.5H).

Intermediate KT17

Methyl 3-(4-(4-(3-ethoxy-3-oxopropanoyl)cyclohexyl)-1H-pyrazol-1-yl)butanoate

By utilizing the analogous procedure of Method A, the title compound was synthesized from A16 as brown oil which was directly used without further purification. $^1$H NMR (400 MHz, CDCl$_3$) δ 7.36-7.33 (m, 1H), 7.21-7.20 (m, 1H), 4.77-4.68 (m, 1H), 4.19 (q, J=7.2 Hz, 2H), 3.64 (s, 3H), 3.51-3.49 (m, 2H), 3.06-2.95 (m, 1.4H), 2.78-2.68 (m, 2.5H), 2.09-1.91 (m, 2H), 1.82-1.66 (m, 4H), 1.58-1.53 (m, 4H), 1.49-1.33 (m, 1H), 1.30-1.26 (m, 3H).

Intermediate KT18

Ethyl 3-(4-(1-(3-methoxy-3-oxopropyl)-1H-pyrazol-4-yl)cyclohexyl)-3-oxopropanoate By utilizing the analogous procedure of Method A, the title compound was synthesized from A17 as colorless oil. LC-MS (ESI): $R_T$=2.134 min, mass calcd. for $C_{18}H_{26}N_2O_5$ 350.2, m/z found 351.2 [M+H]$^+$.

Intermediate KT19

Ethyl 3-(4-(1-(3-methoxy-3-oxopropyl)-3-methyl-1H-pyrazol-4-yl)cyclohexyl)-3-oxopropanoate By utilizing the analogous procedure of Method A, the title compound was synthesized from A18 as light yellow oil. LC-MS (ESI): $R_T$=2.592 min. mass calcd. for $C_{19}H_{28}N_2O_5$ 364.2, m/z found 365.1 [M+H]$^+$. $^1$H NMR (400 MHz, CDCl$_3$) δ 12.34 (s, 0.1H), 7.12 (s, 1H), 5.07 (s, 0.1H), 4.28 (t, J=6.8 Hz, 2H), 4.23-4.18 (m, 2H), 3.68 (s, 3H), 3.52 (s, 1.8H), 2.84 (t, J=6.8 Hz, 2H), 2.77-2.71 (m, 0.7H), 2.55-2.46 (m, 1H), 2.40-2.30 (m, 0.3H), 2.19 (s, 1H), 2.18 (s, 2H), 2.09-1.97 (m, 2.5H), 1.77-1.64 (m, 3.5H), 1.56-1.44 (m, 2H), 1.29 (t, J=7.2 Hz, 3H).

Intermediate KT20 tert-Butyl 3-(4-(4-(3-ethoxy-3-oxopropanoyl)cyclohexyl)-1H-pyrazol-1-yl)cyclobutanecarboxylate By utilizing the analogous procedure of Method A, the title compound was synthesized from A19 as colorless oil. $^1$H NMR (400 MHz, CDCl$_3$) δ 7.40-7.29 (m, 2H), 5.00-4.90 (m, 0.5H), 4.70-4.62 (m, 0.5H), 4.21-4.16 (m, 2H), 3.61 (s, 0.3H), 3.51-3.49 (m, 1.5H), 3.36 (s, 0.2H), 3.08-3.01 (m, 0.4H), 2.87-2.78 (m, 1.6H), 2.72-2.64 (m, 4H), 2.17 (s, 1H), 2.09-1.93 (m, 2H), 1.84-1.76 (m, 1.5H), 1.73-1.67 (m, 2.5H), 1.49 (s, 4H), 1.46 (s, 5H), 1.33-1.25 (m, 5H).

Intermediate KT21

Methyl 5-(4-(3-ethoxy-3-oxopropanoyl)cyclohexyl)-1-methyl-1H-pyrazole-3-carboxylate By utilizing the analogous procedure of Method A, the title compound was synthesized from A20 as colorless oil. LC-MS (ESI): R$_T$=1.38 and 1.43 min, mass calcd. for C$_{17}$H$_{24}$N$_2$O$_5$ 336.2, m/z found 337.2[M+H]$^+$.

Intermediate KT22

Methyl 3-(4-(3-ethoxy-3-oxopropanoyl)cyclohexyl)-1-methyl-1H-pyrazole-5-carboxylate By utilizing the analogous procedure of Method A, the title compound was synthesized from A21 as yellow oil. LC-MS (ESI): R$_T$=1.52 min, mass calcd. for C$_{17}$H$_{24}$N$_2$O$_5$ 336.2, m/z found mass 337.3 [M+H]$^+$. $^1$H NMR (300 MHz, DMSO-d$_6$) δ 6.68-6.66 (m, 1H), 4.12-4.04 (m, 2H), 4.02-3.99 (m, 3H), 3.80-3.79 (m, 3H), 3.66-3.61 (m, 2H), 2.80-2.64 (m, 1H), 2.01-1.98 (m, 1H), 1.95-1.91 (m, 2H), 1.82-1.61 (m, 4H), 1.42-1.33 (m, 2H), 1.18-1.12 (m, 3H).

Intermediate KT23 tert-Butyl 3-(4-(4-(3-ethoxy-3-oxopropanoyl)cyclohexyl)-1H-pyrazol-1-yl)-2,2-dimethylpropanoate By utilizing the analogous procedure of Method A, the title compound was synthesized from A22 as colorless oil. LC-MS (ESI): R$_T$=1.80 min, mass calcd. for C$_{23}$H$_{36}$N$_2$O$_5$ 420.3, m/z found 421.1 [M+H]$^+$. $^1$H NMR (400 MHz, CDCl$_3$) δ 12.22-12.16 (m, 0.1H), 7.32-7.27 (m, 1H), 7.22-7.15 (m, 1H), 4.98-4.97 (m, 0.1H), 4.29-4.10 (m, 4H), 3.60 (s, 0.1H), 3.50 (s, 0.4H), 3.47 (s, 1H), 3.36 (s, 0.3H), 2.88-2.44 (m, 1.5H), 2.14-1.59 (m, 8.5H), 1.45-1.44 (m, 9H), 1.30-1.23 (m, 3H), 1.14-1.13 (m, 6H).

Intermediate KT24

Ethyl 1-(4-(3-ethoxy-3-oxopropanoyl)cyclohexyl)-1H-pyrazole-4-carboxylate

By utilizing the analogous procedure of Method A, the title compound was synthesized from A23 as white solids. LC-MS (ESI): R$_T$=1.55 min, mass calcd. for C$_{17}$H$_{24}$N$_2$O$_5$ 336.2, m/z found 337.1 [M+H]$^+$. $^1$H NMR (400 MHz, CDCl$_3$) δ 12.35 (s, 0.1H), 7.93 (s, 0.8H), 7.92 (s, 0.2H), 7.91 (s, 0.2H), 7.90 (s, 0.8H), 6.36 (s, 0.1H), 4.29 (q, J=7.2 Hz, 2H), 4.24-4.20 (m, 3H), 3.53 (s, 1.5H), 3.52 (s, 0.3H), 2.82-2.77 (m, 0.7H), 2.63-2.55 (m, 0.3H), 2.30-2.03 (m, 5H), 1.84-1.73 (m, 2H), 1.63-1.56 (m, 1H), 1.36-1.29 (m, 6H).

Intermediate KT25

Ethyl 1-(4-(3-ethoxy-3-oxopropanoyl)cyclohexyl)-1H-pyrazole-5-carboxylate

By utilizing the analogous procedure of Method A, the title compound was synthesized from A24 as colorless oil. LC-MS (ESI): R$_T$=1.88 min, mass calcd. for C$_{17}$H$_{24}$N$_2$O$_5$ 336.2, m/z found 337.4 [M+H]$^+$. $^1$H NMR (300 MHz, CDCl$_3$) δ 12.41 (s, 0.1H), 7.54-7.45 (m, 1H), 6.87-6.80 (m, 1H), 5.27-5.09 (m, 1.1H), 4.38-4.29 (m, 2H), 4.24-4.17 (m, 2H), 3.61-3.48 (m, 1.8H), 2.81-2.72 (m, 0.7H), 2.64-2.53 (m, 0.3H), 2.37-2.18 (m, 1.8H), 2.14-1.99 (m, 2.4H), 1.94-1.86 (m, 1.8H), 1.84-1.71 (m, 2H), 1.38 (t, J=7.2 Hz, 3H), 1.29 (t, J=7.2 Hz, 3H).

Intermediate KT26

Ethyl 2-(4-(3-ethoxy-3-oxopropanoyl)cyclohexyl)pyrimidine-5-carboxylate

By utilizing the analogous procedure of Method A, the title compound was synthesized from A25 as yellow solids. LC-MS (ESI): R$_T$=1.671 min and 1.987 min, mass calcd. for C$_{18}$H$_{24}$N$_2$O$_5$ 348.2, m/z found 349.1 [M+H]$^+$.

Intermediate KT27

(trans)-Ethyl 2-(4-(3-ethoxy-3-oxopropanoyl)cyclohexyl)thiazole-4-carboxylate

By utilizing the analogous procedure of Method A, the title compound was synthesized from A26 as yellow oil. $^1$H NMR (400 MHz, DMSO-d$_6$) δ 12.15 (s, 0.1H), 8.40 (s, 1H), 5.10 (m, 0.1H), 4.29 (q, J=7.2 Hz, 2H), 4.12 (q, J=7.2 Hz, 2H), 3.68 (s, 1.8H), 3.01 (tt, J=12.0, 3.6 Hz, 1H), 2.57 (tt, J=12.0, 3.6 Hz, 1H), 2.16-2.13 (m, 2H), 2.02-1.99 (m, 2H), 1.58-1.48 (m, 2H), 1.45-1.35 (m, 2H), 1.30 (t, J=7.2 Hz, 3H), 1.19 (t, J=7.2 Hz, 3H).

Intermediate KT28

Methyl 5-(4-(3-ethoxy-3-oxopropanoyl)cyclohexyl)isoxazole-3-carboxylate

By utilizing the analogous procedure of Method A, the title compound was synthesized from A27 as yellow oil. LC-MS (ESI): R$_T$=1.721 min, mass calcd. for C$_{16}$H$_{21}$NO$_6$ 323.1, m/z found 324.1 [M+H]$^+$. $^1$H NMR (400 MHz, DMSO-d$_6$) δ 6.70 (s, 0.7H), 6.68 (s, 0.3H), 4.12-4.07 (m, 2H), 3.88 (s, 3H), 3.68 (s, 2H), 2.90-2.84 (m, 1H), 2.57-2.51 (m, 1H), 2.10-2.07 (m, 2H), 2.00-1.96 (m, 2H), 1.51-1.36 (m, 4H), 1.19 (t, J=7.0 Hz, 3H).

Intermediate KT29

Ethyl 3-(4-(3-ethoxy-3-oxopropanoyl)cyclohexyl)isoxazole-5-carboxylate

By utilizing the analogous procedure of Method A, the title compound was synthesized from A28 as yellow oil.

LC-MS (ESI): $R_T$=2.114 min, mass calcd. for $C_{17}H_{23}NO_6$ 337.2, m/z found 338.1 [M+H]$^+$. $^1$H NMR (300 MHz, DMSO-d$_6$) δ 7.25 (s, 1H), 4.32 (q, J=7.2 Hz, 2H), 4.06 (q, J=7.2 Hz, 2H), 3.65 (s, 2H), 2.77-2.66 (m, 1H), 2.55-2.48 (m, 1H), 2.03-1.89 (m, 4H), 1.53-1.31 (m, 4H), 1.28 (t, J=7.2 Hz, 3H), 1.16 (t, J=7.2 Hz, 3H).

Intermediate KT30 tert-Butyl 4-(4-(3-ethoxy-3-oxopropanoyl)piperidin-1-yl)benzoate

By utilizing the analogous procedure of Method A, the title compound was synthesized from A8 as yellow solids.
$^1$H NMR (400 MHz, CDCl$_3$) δ 12.18 (br s, 0.1H), 7.86 (d, J=8.8 Hz, 2H), 6.84 (d, J=8.8 Hz, 2H), 5.00 (s, 0.1H), 4.23-4.18 (m, 2H), 3.92-3.84 (m, 2H), 3.52 (s, 1.8H), 2.93-2.82 (m, 2H), 2.72-2.64 (m, 1H), 2.00-1.93 (m, 2H), 1.81-1.71 (m, 2H), 1.57 (s, 9H), 1.31-1.24 (m, 3H).

Intermediate KT31

Methyl 4-(4-(3-ethoxy-3-oxopropanoyl)cyclohexyl)benzoate

By utilizing the analogous procedure of Method A, the title compound was synthesized from A30 as colorless oil.
$^1$H NMR (300 MHz, DMSO-d$_6$) δ 7.91-7.88 (m, 2H), 7.41-7.32 (m, 2H), 4.15-4.07 (m, 2H), 3.84 (s, 3H), 3.70 (s, 2H), 2.86-2.58 (m, 2H), 2.13-1.98 (m, 2H), 1.89-1.37 (m, 6H), 1.25-1.18 (m, 3H).

Intermediate KT32

(trans)-Ethyl 5-(4-(3-ethoxy-3-oxopropanoyl)cyclohexyl)-1,2,4-oxadiazole-3-carboxylate By utilizing the analogous procedure of Method A, the title compound was synthesized from A31 as yellow solids.
$^1$H NMR (400 MHz, DMSO-d$_6$) δ 4.40 (q, J=7.2 Hz, 2H), 4.10 (q, J=7.2 Hz, 2H), 3.68 (s, 2H), 3.11 (tt, J=11.6, 4.0 Hz, 1H), 2.56 (tt, J=12.0, 3.6 Hz, 1H), 2.19-2.15 (m, 2H), 2.02-1.98 (m, 2H), 1.57 (qd, J=12.4, 3.6 Hz, 2H), 1.40 (qd, J=12.0, 3.2 Hz, 2H), 1.32 (t, J=7.2 Hz, 3H), 1.19 (t, J=7.2 Hz, 3H).

Intermediate KT33 tert-butyl 4-(3-methoxy-3-oxopropanoyl)piperidine-1-carboxylate

By utilizing the analogous procedure of Method A, the title compound was synthesized from A32.
LC-MS (ESI): $R_T$=2.484 min, mass calcd. for $C_{14}H_{23}NO_5$ 285.2, m/z found 230.0 [M+H-t-Bu]$^+$. $^1$H NMR (300 MHz, CDCl$_3$) δ 4.96 (s, 0.2H), 4.10-4.06 (m, 2H), 3.71 (s, 3H), 3.49 (s, 1.8H), 3.77 (t, J=16 Hz, 2H), 2.60 (tt, J=11.3, 3.83 Hz, 1H), 1.84-1.80 (m, 2H), 1.58-1.46 (m, 2H), 1.44 (s, 9H).

Intermediate KT34

4-(2-Ethoxycarbonyl-acetyl)-piperidine-1-carboxylic acid tert-butyl ester

By utilizing the analogous procedure of Method A, the title compound was synthesized from A32.

$^1$H NMR (300 MHz, CDCl$_3$) δ 12.17 (s, 0.2H), 4.99 (s, 0.2H), 4.26-4.03 (m, 4H), 3.50 (s, 1.6H), 2.87-2.72 (m, 2H), 2.68-2.58 (m, 1H), 1.94-1.76 (m, 2H), 1.63-1.49 (m, 2H), 1.46 (s, 9H), 1.28 (t, J=10.5 Hz, 3H).

Intermediate KT35 tert-butyl 4-(3-ethoxy-3-oxopropanoyl)-2-methylpiperidine-1-carboxylate

By utilizing the analogous procedure of Method A, the title compound was synthesized from A33 as colorless oil.
LC-MS (ESI): $R_T$=2.043 min, mass calcd. for $C_{16}H_{27}NO_5$ 313.2, m/z found 314.1 [M+H]$^+$. $^1$HNMR (400 MHz, CDCl$_3$) δ 12.24 (s, 0.1H), 12.17 (s, 0.1H), 5.02 (s, 0.1H), 4.97 (s, 0.1H), 4.20 (q, J=7.2 Hz, 2H), 4.10-4.05 (m, 1H), 3.87-3.81 (m, 1H), 3.52 (s, 1H), 3.49 (s, 0.6H) 3.08-3.00 (m, 0.8H), 2.86-2.70 (m, 1.2H), 2.05-1.98 (m, 0.7H), 1.89-1.85 (m, 2H), 1.72-1.67 (m, 1.3H), 1.46 (s, 9H), 1.30-1.26 (m, 3H), 1.14-1.11 (m, 3H).

Intermediate KT36 tert-Butyl 3-(3-ethoxy-3-oxopropanoyl)pyrrolidine-1-carboxylate

By utilizing the analogous procedure of Method A, the title compound was synthesized from A34.
LC-MS (ESI): $R_T$=1.939 min, mass calcd. for $C_{14}H_{23}NO_5$ 285.2, m/z found 230.1 [M-Boc+H]$^+$. $^1$H NMR (400 MHz, CDCl$_3$) δ 12.12 (br s, 0.2H), 6.17 (br s, 0.2H), 4.17 (q, J=7.2 Hz, 2H), 3.64-3.58 (m, 1.4H), 3.49 (s, 1.6H), 3.39-3.27 (m, 3.6H), 2.09-2.05 (m, 2H), 1.42 (s, 9H), 1.25 (t, J=7.2 Hz, 3H).

Intermediate KT37 tert-Butyl 3-(3-ethoxy-3-oxopropanoyl)azetidine-1-carboxylate

By utilizing the analogous procedure of Method A, the title compound was synthesized from A35 as red oil. $^1$H NMR (300 MHz, CDCl$_3$) δ 12.17 (br s, 0.2H), 5.06 (s, 0.2H), 4.18 (q, J=7.2 Hz, 2H), 4.10-4.00 (m, 4H), 3.64-3.55 (m, 0.8H), 3.45 (s, 1.6H), 3.26-3.20 (m, 0.2H), 1.41 (s, 9H), 1.27 (t, J=7.2 Hz, 3H).

Intermediate KT38 tert-Butyl 3-(3-methoxy-3-oxopropanoyl)azetidine-1-carboxylate

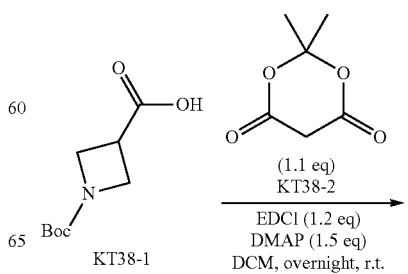

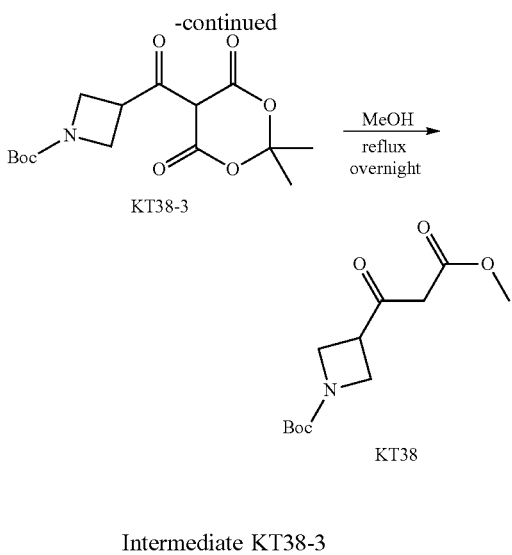

Intermediate KT38-3 tert-Butyl 3-(2,2-dimethyl-4,6-dioxo-1,3-dioxane-5-carbonyl)azetidine-1-carboxylate To a solution of 1-(tert-butoxycarbonyl)azetidine-3-carboxylic acid KT38-1 (4.00 g, 19.9 mmol), 2,2-dimethyl-1,3-dioxane-4,6-dione KT38-2 (3.15 g, 21.9 mmol) and 4-dimethylaminopyridine (3.64 g, 29.8 mmol) in dichloromethane (80 mL) was added N-(3-dimethylaminopropyl)-N'-ethylcarbodiimide hydrochloride (4.58 g, 23.9 mmol). The reaction mixture was stirred at room temperature under nitrogen atmosphere overnight. Then the mixture was diluted with dichloromethane (100 mL) and washed with 5% potassium bisulfate aqueous solution (200 mL) for three times. The combined organic layers were dried over $Na_2SO_{4(s)}$ and filtered. The filtrate was concentrated to give the title compound (6.3 g, 97% yield) as yellow oil. $^1$H NMR (300 MHz, CDCl$_3$) δ 4.60-4.50 (m, 1H), 4.27 (t, J=8.7 Hz, 2H), 4.16-4.11 (m, 3H), 1.75 (s, 6H), 1.45 (s, 9H).

Intermediate KT38 tert-Butyl 3-(3-methoxy-3-oxopropanoyl)azetidine-1-carboxylate

The solution of tert-butyl 3-(2,2-dimethyl-4,6-dioxo-1,3-dioxane-5-carbonyl)azetidine-1-carboxylate KT38-3 (6.30 g, 19.3 mmol) in methanol (80 mL) was heated to 80° C. After stirred at 80° C. overnight, the mixture was allowed to cool down to room temperature, concentrated under reduced pressure and purified by silica gel column chromatography (petroleum ether:ethyl acetate=4:1 to 2:1) to give the title compound (3.3 g, 67% yield) as yellow oil. LC-MS (ESI): $R_T$=1.44 min, mass calcd. for $C_{12}H_{19}NO_5$ 257.1, m/z found 258.2 [M+H]$^+$. $^1$H NMR (400 MHz, CDCl$_3$) δ 12.11 (s, 0.2H), 5.09 (s, 0.2H), 4.13-4.03 (m, 4H), 3.75 (s, 3H), 3.65-3.57 (m, 1H), 3.49 (s, 1.6H), 1.43 (s, 9H).

Intermediate KT39

Methyl 1-(2-(4-(3-methoxy-3-oxopropanoyl)cyclohexyl)pyrimidin-5-yl)cyclopropane-1-carboxylate By utilizing the analogous procedure of Method A, the title compound was synthesized from A36 as red oil. $^1$H NMR (300 MHz, CDCl$_3$) δ 12.17 (br s, 0.2H), 5.06 (s, 0.2H), 4.18 (q, J=7.2 Hz, 2H), 4.10-4.00 (m, 4H), 3.64-3.55 (m, 0.8H), 3.45 (s, 1.6H), 3.26-3.20 (m, 0.2H), 1.41 (s, 9H), 1.27 (t, J=7.2 Hz, 3H).

Intermediate KT40

Ethyl 2-(4-(3-methoxy-3-oxopropanoyl)cyclohexyl)-5-methylpyrimidine-4-carboxylate By utilizing the analogous procedure of Method A, the title compound was synthesized from A37 as brown oil. LC-MS (ESI): $R_T$=1.599 min, mass calcd. for $C_{18}H_{24}N_2O_5$ 348.2, m/z found 349.1 [M+H]$^+$. $^1$H NMR (400 MHz, DMSO-d$_6$) 8.80 (s, 1H), 4.37 (q, J=7.2 Hz, 2H), 3.72 (s, 0.5H), 3.69 (s, 1.5H), 3.63 (s, 0.8H), 3.62 (s, 2.2H), 2.99-2.94 (m, 0.7H), 2.82-2.73 (m, 1H), 2.58-2.55 (m, 0.3H), 2.34 (s, 3H), 2.01-1.99 (m, 0.8H), 1.91-1.85 (m, 3H), 1.76-1.54 (m, 4.2H), 1.32 (t, J=7.2H, 3H).

Intermediate KT41

Methyl 3-(4-(4-(2-methoxy-2-oxoethyl)-5-methyloxazol-2-yl)cyclohexyl)-3-oxopropanoate By utilizing the analogous procedure of Method A, the title compound was synthesized from A38 as colorless oil. $^1$H NMR (400 MHz, DMSO-d$_6$) δ 3.69-3.65 (m, 2H), 3.63-3.60 (m, 6H), 3.49 (s, 1.2H), 3.48 (s, 0.8H), 2.94-2.89 (m, 0.5H), 2.69-2.62 (m, 1H), 2.56-2.52 (m, 0.3H), 2.49-2.47 (m, 0.2H), 2.21 (s, 3H), 2.05-1.84 (m 3H), 1.74-1.65 (m 3H), 1.46-1.31 (m 2H).

Intermediate KT42

Methyl 3-(4-(5-(2-methoxy-2-oxoethyl)pyrimidin-2-yl)cyclohexyl)-3-oxopropanoate

By utilizing the analogous procedure of Method A, the title compound was synthesized from A39 as colorless oil. $^1$H NMR (400 MHz, CDCl$_3$) δ 8.61-8.59 (m, 2H), 3.75-3.73 (m, 6H), 3.60-3.29 (m, 2H), 3.54-3.53 (m, 2H), 3.06-3.02 (m, 0.5H), 2.89-2.87 (m, 0.5H), 2.73-2.70 (m, 0.5H), 2.59-2.53 (m, 0.5H), 2.18-2.07 (m, 3H), 2.03-1.97 (m, 1H), 1.91-1.85 (m, 1H), 1.78-1.73 (m, 2H), 1.58-1.53 (m, 1H).

Intermediate KT43

Ethyl 1-(2-(4-(3-methoxy-3-oxopropanoyl)piperidin-1-yl)pyrimidin-5-yl)piperidine-4-carboxylate By utilizing the analogous procedure of Method A, the title compound was synthesized from A40 as yellow solid. LC-MS (ESI): $R_T$=1.671 min, mass calcd. For $C_{21}H_{30}N_4O_5$ 418.2, m/z found 419.2 [M+H]$^+$. $^1$H NMR (300 MHz, CDCl$_3$) δ 8.10 (s, 2H), 4.74-4.63 (m, 2H), 4.16 (q, J=7.2 Hz, 2H), 3.75 (s, 3H), 3.54 (s, 2H), 3.35-3.31 (m, 2H), 2.98-2.87 (m, 2H), 2.75-2.67 (m, 3H), 2.43-2.34 (m, 1H), 2.05-2.01 (m, 2H), 1.95-1.82 (m, 4H), 1.69-1.55 (m, 2H), 1.27 (t, J=7.2 Hz, 3H).

Intermediate KT44

Methyl 3-(1-(5-(3-(tert-butoxy)-3-oxopropyl)pyridin-2-yl)piperidin-4-yl)-3-oxopropanoate By utilizing the analogous procedure of Method A, the title compound was synthesized from A41 as brown oil.

LC-MS (ESI): $R_T$=1.56 min, mass calcd. for $C_{21}H_{30}N_2O_5$ 390.2, m/z found 391.1 [M+H]$^+$. $^1$H NMR (400 MHz, CDCl$_3$) δ 12.09 (s, 0.2H), 8.02 (d, J=2.4 Hz, 1H), 7.34 (dd, J=8.8 Hz, 2.4 Hz, 1H), 6.61 (d, J=8.8 Hz, 1H), 5.01 (s, 0.2H), 4.32-4.23 (m, 2H), 3.75-3.73 (m, 3H), 3.54 (s, 1.6H), 2.92-2.82 (m, 2H), 2.77 (t, J=8.0 Hz, 2H), 2.73-2.65 (m, 1H), 2.47 (t, J=7.2 Hz, 2H), 1.97-1.91 (m, 2H), 1.71-1.67 (m, 2H), 1.42 (s, 9H).

Part III: Preparation of Aryl Aldehydes of General Formula V (P1)

Aldehyde 1, AL1: 2-Chloro-4-fluoro-benzaldehyde
Aldehyde 2, AL2: 2-Chloro-3-fluoro-benzaldehyde
Aldehyde 3, AL3: 4-Fluoro-2-methylbenzaldehyde
Aldehyde 4, AL4: 2-Bromo-4-fluorobenzaldehyde
Aldehyde 5, AL5: 3-Fluoro-2-methyl-benzaldehyde
Aldehyde 6, AL6: 2-Bromo-3,4-difluorobenzaldehyde
Aldehyde 7, AL7: 4-Fluoro-2-methyl-benzaldehyde
Aldehyde 8, AL8: 2-Bromo-3-fluoro-benzaldehyde
Aldehyde 9, AL9: 2-Chloro-3,4-difluorobenzaldehyde
Aldehyde 10, AL10: 3,4-Difluoro-2-methylbenzaldehyde
Aldehyde 11, AL11: 4-bromo-2-chlorobenzaldehyde Aldehyde 6, AL6:
2-Bromo-3,4-difluorobenzaldehyde

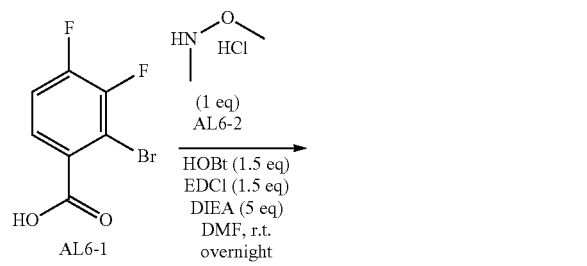

Intermediate AL6-3

2-Bromo-3,4-difluoro-N-methoxy-N-methyl-benzamide

To a solution of 2-bromo-3,4-difluoro-benzoic acid AL6-1 (2.50 g, 10.6 mmol) in N,N-dimethylformamide (25 Ml) was added 1-hydroxybenzotriazole (2.15 g, 15.9 mmol), N,N-diisopropylethylamine (6.84 g, 53.0 mmol) and N-ethyl-N'-(3-dimethylaminopropyl)carbodiimide hydrochloride (3.05 g, 15.9 mmol) under nitrogen atmosphere at room temperature. The mixture was stirred for 10 minutes and N,O-dimethylhydroxylamine hydrochloride AL6-2 (1.04 g, 10.6 mmol) was added. After stirred at room temperature overnight, the mixture was poured into water (80 Ml) and extracted with ethyl acetate (75 Ml) twice. The separated organic layers were washed with water (100 Ml) twice, brine (50 Ml) twice, dried over Na$_2$SO$_{4(s)}$, filtered, concentrated and purified by silica gel column chromatography (petroleum ether:ethyl acetate=10:1 to 5:1) to give the title compound (1.9 g, 66% yield) as yellow solids. $^1$H NMR (300 MHz, CDCl$_3$) δ 7.26-7.17 (m, 1H), 7.14-7.09 (m, 1H), 3.93-3.16 (m, 6H).

Aldehyde 6

2-Bromo-3,4-difluoro-benzaldehyde

To a solution of 2-bromo-3,4-difluoro-N-methoxy-N-methyl-benzamide AL6-3 (1.90 g, 6.81 mmol) in tetrahydrofuran (30 Ml) was added 1.5 M diisobutylaluminum hydride in toluene (5.90 Ml. 8.85 mmol) at −78° C. dropwise under nitrogen atmosphere. After stirred at −78° C. for 1 hour, the mixture was quenched with water (40 Ml), extracted with ethyl acetate (75 Ml) three times. The separated organic layers were washed with 2 M hydrochloride aqueous solution (30 Ml), water (40 Ml), brine (20 Ml) twice, dried over Na$_2$SO$_{4(s)}$ and filtered. The filtrate was concentrated under reduced pressure to give a residue, which was purified by silica gel column chromatography (petroleum ether:ethyl acetate=10:1 to 5:1) to give the title compound (1.0 g, 67% yield) as yellow solids. $^1$H NMR (300 MHz, DMSO-d$_6$) δ 10.12 (s, 1H), 7.81-7.65 (m, 2H).

Aldehyde 9, AL9:
2-Chloro-3,4-difluorobenzaldehyde

Intermediate AL9-1: 2-Chloro-3,4-difluorobenzoic Acid

A solution of $N^1,N^1,N^2,N^2$-tetramethylethane-1,2-diamine (3.7 g, 69.6 mmol) in tetrahydrofuran (45 Ml) was cooled to −70° C. under nitrogen atmosphere before dropwise addition of 1.3 M sec-butyllithium in hexane (60 Ml, 75.9 mmol) followed by a solution of 3,4-difluorobenzoic acid (5.0 g, 31.6 mmol) in tetrahydrofuran (20 Ml) over 10 minutes. The resulting mixture was stirred at −70° C. for 1 hour and then a solution of 1,1,1,2,2,2-hexachloroethane (26 g, 110.8 mmol) in THF (45 Ml) was added dropwise. Stirring continued at −70° C. for 2 hours. The mixture was warmed to −10° C., quenched with water (125 Ml), added diethyl ether (60 Ml) and then separated two phases. The aqueous layer was acidified to Ph 1 by using concentrated hydrochloride aqueous solution and extracted with diethyl ether (125 Ml) twice. The combined organic extracts were concentrated in vacuo to give yellow solids, which was recrystallized with ethyl acetate (30 Ml) to afford the title

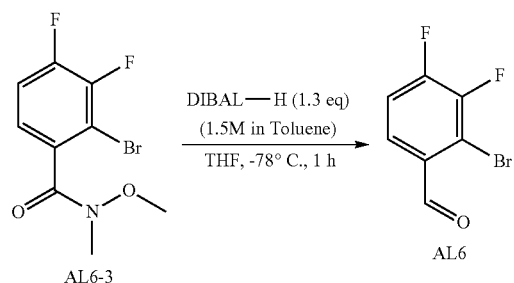

compound (2.7 g, 45% yield) as yellow solids. $^1$H NMR (400 MHz, DMSO-$d_6$) δ 13.69 (br s, 1H), 7.75-7.71 (m, 1H), 7.55-7.48 (m, 1H).

Intermediate AL9-2

2-Chloro-3,4-difluoro-N-methoxy-N-methyl-benzamide

To a solution of 2-chloro-3,4-difluorobenzoic acid Intermediate AL9-1 (1.0 g, 5.2 mmol) in N, N-dimethylformamide (10 Ml) were added 1-hydroxybenzotriazole (1.1 g, 7.8 mmol), N,N-diisopropylethylamine (4.6 Ml, 26 mmol) and N-(3-Dimethylaminopropyl)-N'-ethylcarbodiimide hydrochloride (1.5 g, 7.8 mmol) under nitrogen atmosphere at room temperature. The resulting mixture was stirred at room temperature for 10 minutes. O, N-dimethyl-hydroxylamine hydrochloride (0.5 g, 5.2 mmol) was added and stirring continued at room temperature overnight. After quenched with water (20 Ml), the mixture was extracted with ethyl acetate (20 Ml) for three times. The combined organic layers were washed with water (20 Ml), brine (20 Ml), dried over Na$_2$SO$_{4(s)}$, filtered and concentrated to leave a residue, which was purified by silica gel column chromatography (petroleum ether:ethyl acetate=4:1 to 2:1) to give the title compound (1.06 g, 87% yield) as yellow solids. $^1$H NMR (400 MHz, DMSO-$d_6$) δ 7.60-7.53 (m, 1H), 7.42-7.38 (m, 1H), 3.80-3.45 (m, 3H), 3.39-3.06 (m, 3H).

Aldehyde 9

2-Chloro-3,4-difluorobenzaldehyde

To a solution of 2-chloro-3,4-difluoro-N-methoxy-N-methyl-benzamide Intermediate AL9-2 (500 mg, 2.13 mmol) in tetrahydrofuran (8 Ml) was added 1 M diisobutylaluminium hydride in toluene (2.8 Ml, 2.8 mmol) dropwise at –78° C. under nitrogen atmosphere. After the addition, the mixture was stirred at –78° C. for 1 hour. It was then quenched with water (15 Ml) and extracted with ethyl acetate (25 Ml) for three times. The combined organic layers were washed with 1 M hydrochloric acid aqueous solution (10 Ml), dried over Na$_2$SO$_{4(s)}$, filtered and evaporated under reduced pressure to leave a yellow residue, which was purified by silica gel column chromatography (petroleum ether:ethyl acetate=20:1) to give the title compound (200 mg, 53% yield) as yellow solids. $^1$H NMR (400 MHz, DMSO-$d_6$) δ 10.23 (s, 1H), 7.80-7.76 (m, 1H), 7.69-7.62 (m, 1H).

Aldehyde 10, AL10

3,4-Difluoro-2-methylbenzaldehyde

Intermediate AL10-1

3,4-Difluoro-N-methoxy-N,2-dimethylbenzamide

To a solution of 3,4-difluoro-2-methylbenzoic acid (3.0 g, 17.4 mmol) in N, N-dimethylformamide (30 Ml) were added 1-hydroxybenzotriazole (3.5 g, 26.2 mmol), N,N-diisopropylethylamine (15.4 Ml, 87.0 mmol) and N$^1$-((ethylimino)methylene)-N$^3$,N$^3$-dimethylpropane-1,3-diamine hydrochloride (5.0 g, 26.2 mmol) under nitrogen atmosphere at room temperature. Having stirred at room temperature for 10 minutes, the resulting mixture was added N,O-dimethylhydroxylamine hydrochloride (1.7 g, 17.4 mmol) and stirring continued at room temperature overnight. After quenched with water (50 Ml), the mixture was extracted with ethyl acetate (50 Ml) for three times. The combined organic layers were washed with water (50 Ml), brine (50 Ml), dried over Na$_2$SO$_{4(s)}$, and concentrated to leave a residue, which was purified by silica gel column chromatography (petroleum ether:ethyl acetate=8:1 to 5:1) to give the title compound (3.1 g, 84% yield) as yellow oil. $^1$H NMR (300 MHz, CDCl$_3$) δ 7.07-6.96 (m, 2H), 3.47 (s, 3H), 3.30 (s, 3H), 2.26 (s, 3H).

Aldehyde 10

3,4-Difluoro-2-methylbenzaldehyde

To a solution of 3,4-difluoro-N-methoxy-N,2-dimethylbenzamide AL10-1 (3.1 g, 14.4 mmol) in tetrahydrofuran (40 Ml) was added 1.5 M diisobutylaluminium hydride in toluene (12.5 Ml, 18.7 mmol) dropwise at –78° C. under nitrogen atmosphere. After the addition, the mixture was stirred at –78° C. for 1.5 hour. It was then quenched with water (15 Ml) and extracted with ethyl acetate (50 Ml) for three times. The combined organic layers were washed with water (50 Ml) for three times, brine (50 Ml), dried over Na$_2$SO$_{4(s)}$ and evaporated under reduced pressure to leave a yellow residue, which was purified by silica gel column chromatography (petroleum ether:ethyl acetate=20:1 to 10:1) to give the title compound (1.87 g, 85% yield) as colorless oil. $^1$H NMR (400 MHz, CDCl$_3$) δ 10.15 (s, 1H), 7.61-7.57 (m, 1H), 7.18-7.12 (m, 1H), 2.61 (s, 3H).

Part IV: Preparation of Carboxamidines of General Formula VI (P2)

Carboxamidine 1: Thiazole-2-carboxamidine Hydrochloride (Ca1)

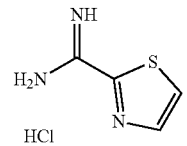

Carboxamidine 2: 3,5-Difluoropicolinimidamide Hydrochloride (Ca2)

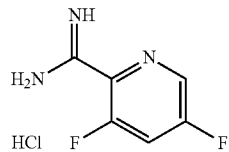 [SMILES: Cl ; N=C(N)c1ncc(F)cc1F]

To a stirred suspension of ammonium chloride (1.89 g, 35.7 mmol) in toluene (100 M) was added 2M trimethylaluminum in toluene (21 M, 42.8 mmol) dropwise at 0° C. under nitrogen atmosphere. The resulting mixture was then brought up to room temperature and stirring continued for 30 minutes. A solution of 3,5-difluoropicolinonitrile (5.00 g, 35.7 mmol) in toluene (50 Ml) was added and the reaction mixture was subsequently stirred at 80° C. overnight. After cooled down to room temperature, the mixture was poured into slurry of silica gel in dichloromethane (50 Ml). After stirring for 10 minutes, the slurry was filtered and washed with methanol. The filtrate was concentrated in vacuum to give the title compound (1.90 g, 34% yield) as white solids. LC-MS (ESI): $R_T$=0.357 min, mass calcd. For $C_6H_6ClF_2N_3$ 193.0, m/z found 157.9 [M+H−HCl]$^+$. $^1$H NMR (400 MHz, DMSO-$d_6$) δ 9.77 (br s, 2H), 9.60 (br s, 2H), 8.79 (d, J=1.6 Hz, 1H), 8.41-8.35 (m, 1H).

Part V: Assembly of Dihydropyrimidines of General Formula VII and VIII

Compound VII-1-X: (Exemplified with Method B)

(trans)-Methyl 2-(4-(6-(2-chloro-3,4-difluorophenyl)-5-(methoxycarbonyl)-2-(thiazol-2-yl)-3,6-dihydropyrimidin-4-yl)cyclohexyl)oxazole-4-carboxylate (a Single Stereoisomer)

Intermediates VII-1-P and VII-1-Q (cis)-Methyl 2-(-4-(6-(2-chloro-3,4-difluorophenyl)-5-(methoxycarbonyl)-2-(thiazol-2-yl)-3,6-dihydropyrimidin-4-yl)cyclohexyl)oxazole-4-carboxylate (a Mixture of 2 Stereoisomers) and (trans)-methyl 2-(-4-(6-(2-chloro-3,4-difluorophenyl)-5-(methoxycarbonyl)-2-(thiazol-2-yl)-3,6-dihydropyrimidin-4-yl)cyclohexyl)oxazole-4-carboxylate (a Mixture of 2 Stereoisomers)

To a solution of methyl 2-(4-(3-ethoxy-3-oxopropanoyl)cyclohexyl)oxazole-4-carboxylate KT1 (1.55 g, 5.02 mmol), 2-chloro-3,4-difluorobenzaldehyde AL9 (893 mg, 5.02 mmol) and thiazole-2-carboximidamide hydrochloride Ca1 (823 mg, 5.02 mmol) in methanol (40 Ml) was added sodium acetate (412 mg, 5.02 mmol). The mixture was heated to 70° C. for 16 hours. The reaction mixture was allowed to cool down to room temperature and concentrated under reduced pressure to give a residue, which was purified by silica gel column chromatography (petroleum ether:ethyl acetate=5:1 to 2:1) and further purified by C18 column (acetonitrile:water=30% to 75%) to give the title compound VII-1-P (320 mg, 12% yield) as yellow solids and VII-1-Q (700 mg, 26% yield) as yellow solids.

VII-1-P: LC-MS (ESI): $R_T$=1.63 min, mass calcd. For $C_{26}H_{23}ClF_2N_4O_5S$, 576.1, m/z found 576.9 [M+H]$^+$. $^1$HNMR (400 MHz, DMSO-$d_6$) δ 9.55 (d, J=4.0 Hz, 1H), 8.87-8.86 (m, 0.8H), 8.71 (s, 0.2H), 7.98-7.92 (m, 2H), 7.48-7.41 (m, 1H), 7.18-7.14 (m, 1H), 6.02 (s, 0.3H), 5.89 (d, J=3.6 Hz, 0.7H), 3.90-3.86 (m, 0.3H), 3.83 (s, 2.1H), 3.82 (s, 0.9H), 3.73-3.68 (m, 0.7H), 3.53 (s, 2.1H), 3.52 (s, 0.9H), 3.31 (s, 0.3H), 3.28 (br s, 0.7H), 2.42-2.31 (m, 2H), 1.96-1.44 (m, 6H).

VII-1-Q: LC-MS (ESI): $R_T$=1.967 min, mass calcd. For $C_{26}H_{23}ClF_2N_4O_5S$, 576.1, m/z found 577.0 [M+H]$^+$. $^1$HNMR (400 MHz, DMSO-$d_6$) δ 9.58 (d, J=3.6 Hz, 0.6H), 9.07 (s, 0.4H), 8.78 (d, J=4.0 Hz, 1H), 8.01 (s, 1.5H), 7.95 (d, J=3.2 Hz, 0.5H), 7.50-7.41 (m, 1H), 7.23-7.15 (m, 1H), 6.03 (s, 0.4H), 5.93 (d, J=4.0 Hz, 0.6H), 3.96-3.87 (m, 0.4H), 3.80 (s, 3H), 3.70-3.61 (m, 0.6H), 3.54 (s, 1.8H), 3.53 (s, 1.2H), 3.10-3.01 (m, 0.4H), 2.93-2.86 (m, 0.6H), 2.26-2.14 (m, 2H), 2.10-2.01 (m, 0.4H), 1.95-1.50 (m, 5.6H).

A stereoisomeric mixture of (trans)-methyl 2-(4-(6-(2-chloro-3,4-difluorophenyl)-5-(methoxycarbonyl)-2-(thiazol-2-yl)-3,6-dihydropyrimidin-4-yl)cyclohexyl)oxazole-4-carboxylate VII-1-Q (700 mg, 1.15 mmol, 90% purity) was purified by chiral Prep. SFC (Column: Chiralpak IC 5 μm 20*250 mm; Mobile Phase: CO$_2$:MeOH=70:30 at 50 g/min; Col. Temp: 40° C.; Wavelength: 254 nm; Back pressure: 100 bar) to give VII-1-X (280 mg, 41% yield, 98.0% purity, 100% stereopure) as yellow solids and VII-1-Y (300 mg, 44% yield, 98.2% purity, 98.0% stereopure) as yellow solids.

VII-1-X: LC-MS (ESI): $R_T$=2.028 min, mass calcd. For $C_{26}H_{23}ClF_2N_4O_5S$, 576.1, m/z found 577.1 [M+H]$^+$. Chiral analysis (Column: Chiralpak IC 5 μm 4.6*250 mm; Mobile Phase: CO$_2$:MeOH=70:30 at 3 g/min; Col. Temp: 40° C.; Wavelength: 254 nm, Back pressure: 100 bar, $R_T$=6.41 min). $^1$H NMR (400 MHz, CDCl$_3$) δ 8.18 (s, 1H), 8.17 (s, 0.5H), 7.83 (t, J=2.8 Hz, 1H), 7.51 (d, J=2.8 Hz, 0.4H), 7.46 (d, J=3.2 Hz, 0.6H), 7.39 (d, J=1.6 Hz, 0.5H), 7.10-7.01 (m, 2H), 6.19 (s, 0.6H), 6.06 (d, J=2.4 Hz, 0.4H), 4.09-4.02 (m, 0.6H), 3.92 (s, 3H), 3.86-3.78 (m, 0.4H), 3.63 (s, 1.2H), 3.60 (s, 1.8H), 3.01-2.93 (m, 1H), 2.36-2.11 (m, 2.5H), 2.05-2.01 (m, 1.5H), 1.92-1.78 (m, 3H), 1.72-1.62 (m, 1H).

VII-1-Y: LC-MS (ESI): $R_T$=2.026 min, mass calcd. For $C_{26}H_{23}ClF_2N_4O_5S$, 576.1, m/z found 577.1 [M+H]$^+$. Chiral analysis (Column: Chiralpak IC 5 μm 4.6*250 mm; Mobile Phase: CO$_2$:MeOH=70:30 at 3 g/min; Col. Temp: 40° C.; Wavelength: 254 nm, Back pressure: 100 bar, $R_T$=7.98 min). $^1$H NMR (400 MHz, CDCl$_3$) δ 8.18 (s, 1H), 8.17 (s, 0.5), 7.83 (d, J=2.8 Hz, 1H), 7.51 (d, J=3.2 Hz, 0.5H), 7.46 (d, J=3.2 Hz, 0.5H), 7.39 (d, J=1.2 Hz, 0.5H), 7.10-6.99 (m, 2H), 6.19 (s, 0.6H), 6.06 (d, J=2.4 Hz, 0.4H), 4.10-4.03 (m, 0.6H), 3.92 (s, 3H), 3.86-3.77 (m, 0.4H), 3.63 (s, 1.2H), 3.60 (s, 1.8H), 3.01-2.95 (m, 1H), 2.36-2.10 (m, 2.6H), 2.05-2.01 (m, 1.4H), 1.92-1.71 (m, 3H), 1.68-1.61 (m, 1H).

Assembles of dihydropyrimidines of general formula VII/VIII incorporated with acids of general formula III-1 or III-2, aryl aldehydes (P1) and carboxamidines (P2) via sequential two reaction steps are shown below in Table 1:

TABLE 1
| acid of general formula III-1/III-2 | ketoester of general formula IV-1/IV-2 | P1 | P2 | dihydropyrimidine of general formula VII/VIII |
|---|---|---|---|---|
| A1 | KT1 | AL9 | Ca1 | 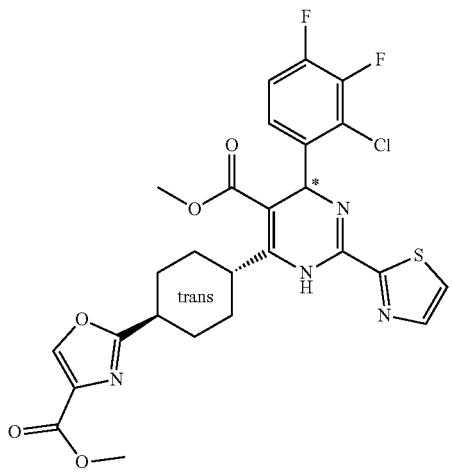<br>Compound VII-1-X |
| A1 | KT2 | AL9 | Ca1 | 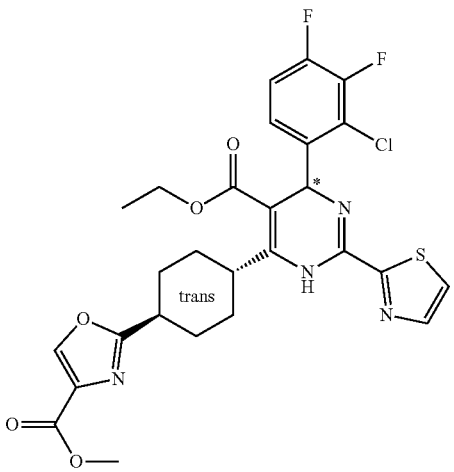<br>Compound VII-2-Y |
| A1 | KT1 | AL5 | Ca1 | 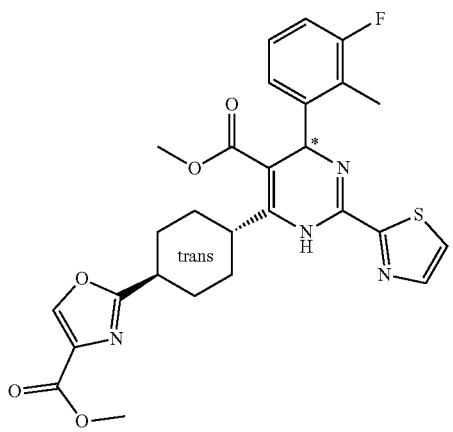<br>Compound VII-3-H |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A1 | KT1 | AL1 | Ca1 | 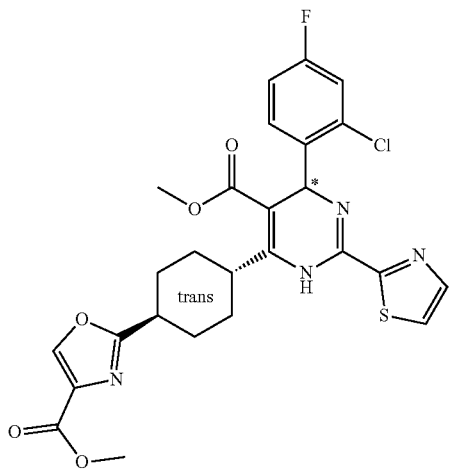<br>Compound VII-4-N |
| A1 | KT1 | AL2 | Ca1 | 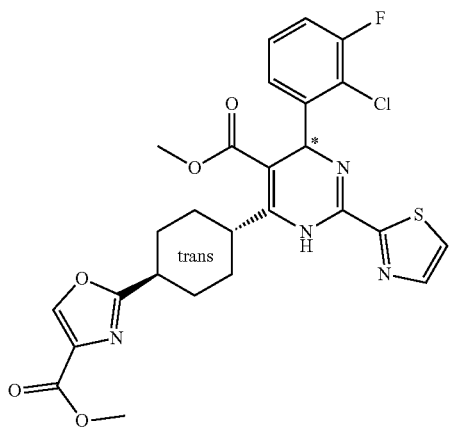<br>Compound VII-5-Q |
| A1 | KT1 | AL7 | Ca1 | 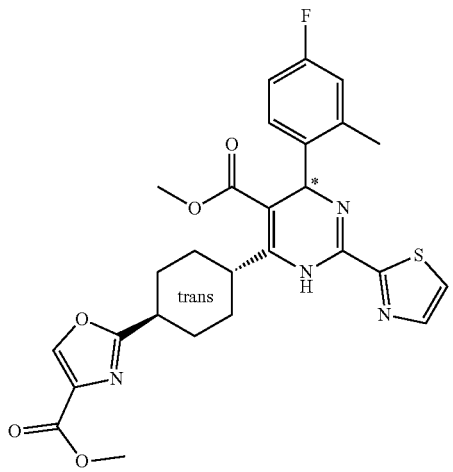<br>Compound VII-6-Q |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A1 | KT1 | AL9 | Ca2 | 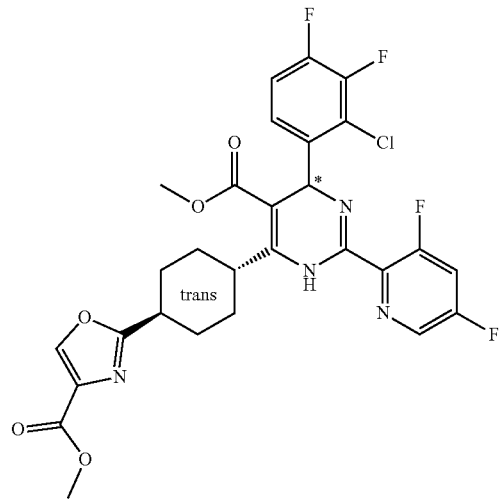<br>Compound VII-7-N |
| A2 | KT3 | AL9 | Ca1 | 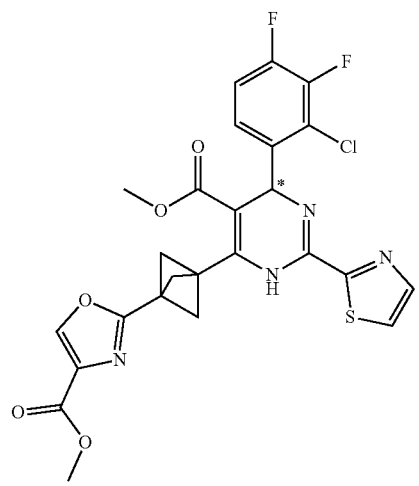<br>Compound VII-8-N |
| A1 | KT2 | AL2 | Ca1 | 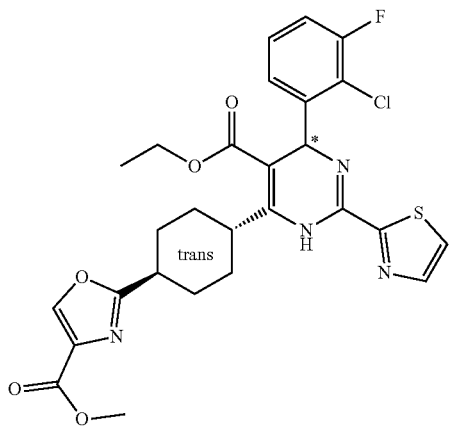<br>Compound VII-9-F |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A1 | KT2 | AL1 | Ca1 | 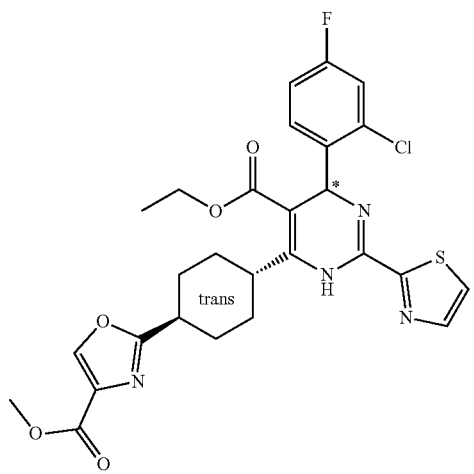<br>Compound VII-10-P |
| A1 | KT2 | AL5 | Ca1 | 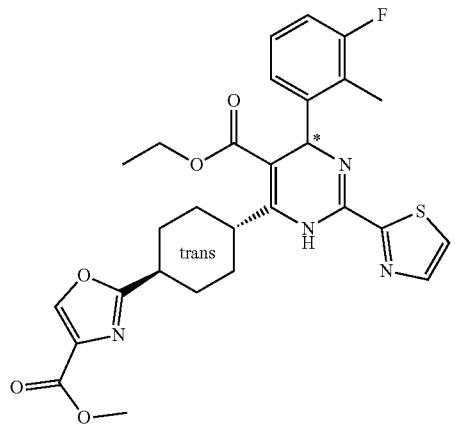<br>Compound VII-11-Q |
| A1 | KT2 | AL7 | Ca1 | 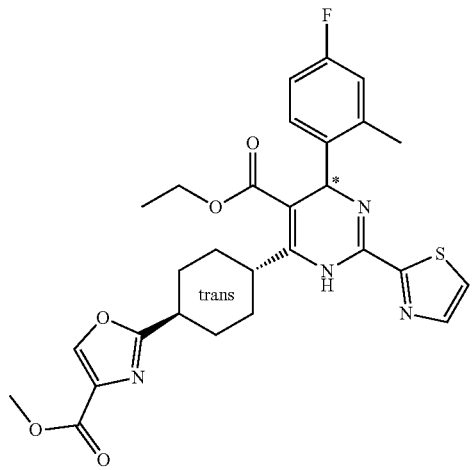<br>Compound VII-12-P |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A3 | KT4 | AL9 | Ca1 | 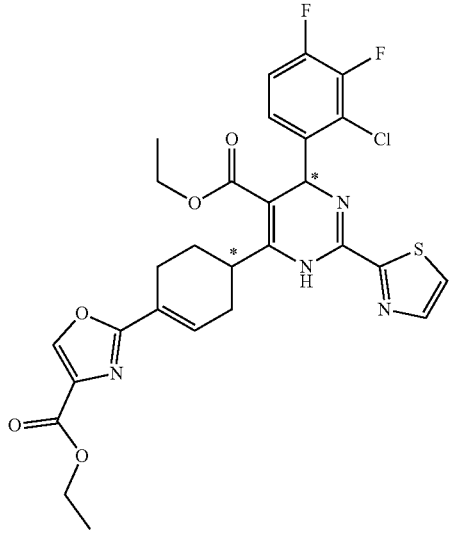<br>Compound VII-13-P<br>Compound VII-13-Q |
| A4 | KT5 | AL9 | Ca1 | 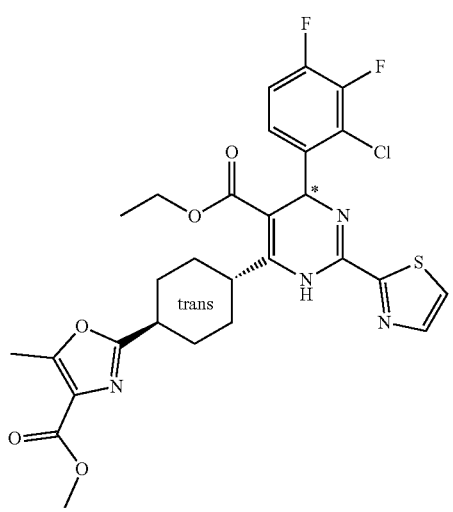<br>Compound VII-14-N |
| A5 | KT6 | AL9 | Ca1 | 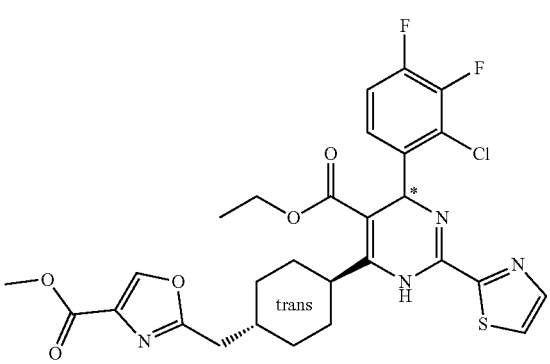<br>Compound VII-15-M |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A6 | KT7 | AL9 | Ca1 | 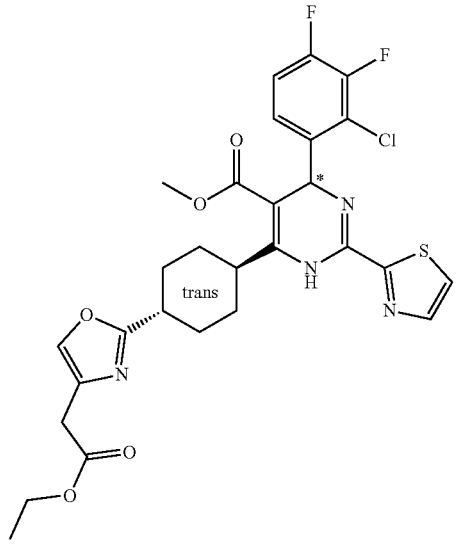<br>Compound VII-16-N |
| A6 | KT7 | AL1 | Ca1 | 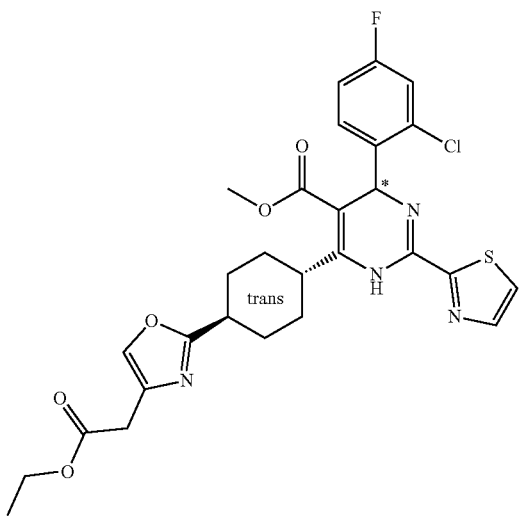<br>Compound VII-17-M |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A6 | KT7 | AL4 | Ca1 | 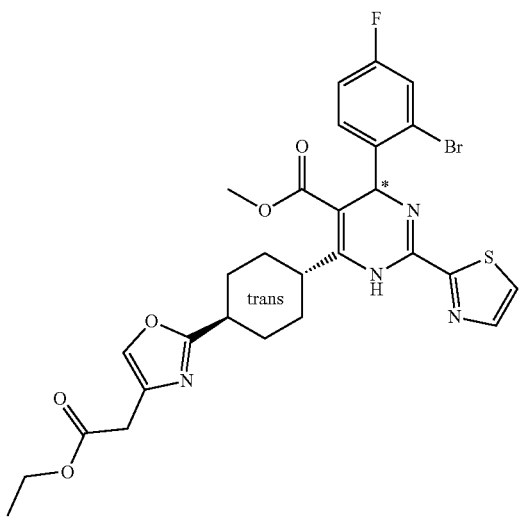<br>Compound VII-18-M |
| A6 | KT7 | AL8 | Ca1 | 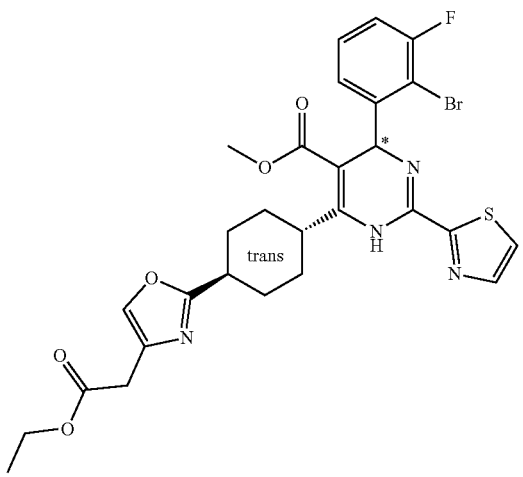<br>Compound VII-19-M |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A6 | KT7 | AL2 | Ca1 | 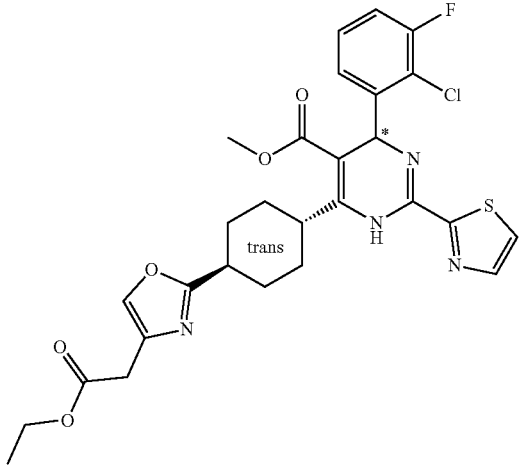<br>Compound VII-20-N |
| A6 | KT7 | AL5 | Ca1 | 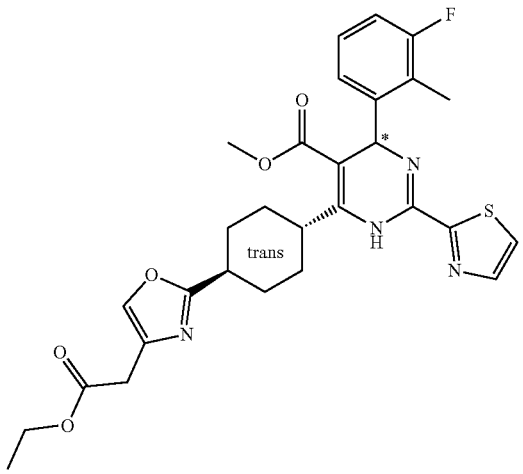<br>Compound VII-21-N |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A7 | KT8 | AL9 | Ca1 | 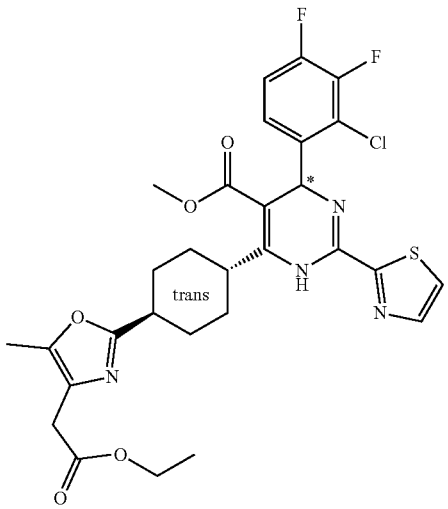<br>Compound VII-22-S |
| A8 | KT9 | AL9 | Ca1 | 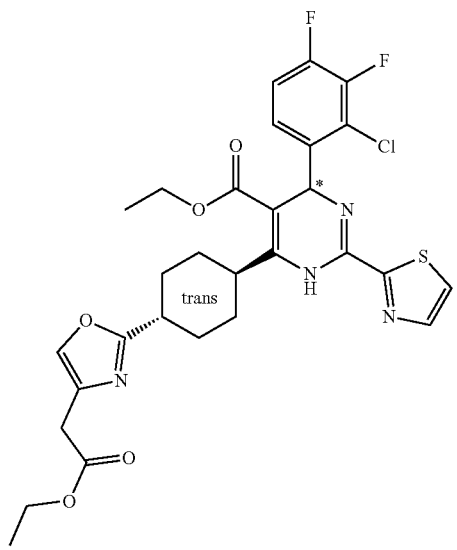<br>Compound VII-23-Y |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A9 | KT10 | AL9 | Ca1 | 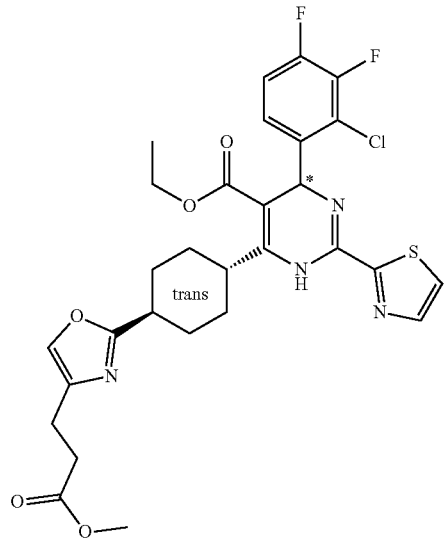<br>Compound VII-24-M |
| A10 | KT11 | AL9 | Ca1 | 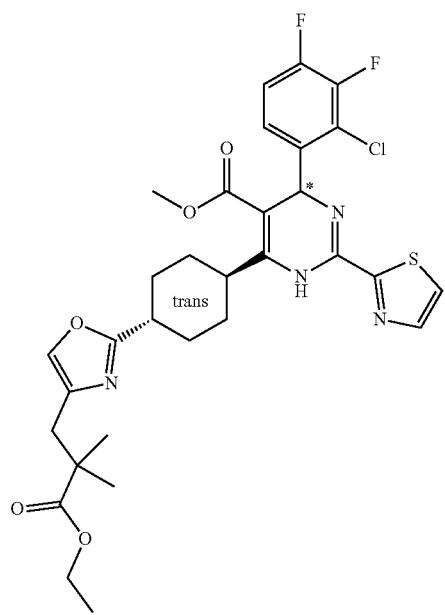<br>Compound VII-25-N |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A11 | KT12 | AL9 | Ca1 | 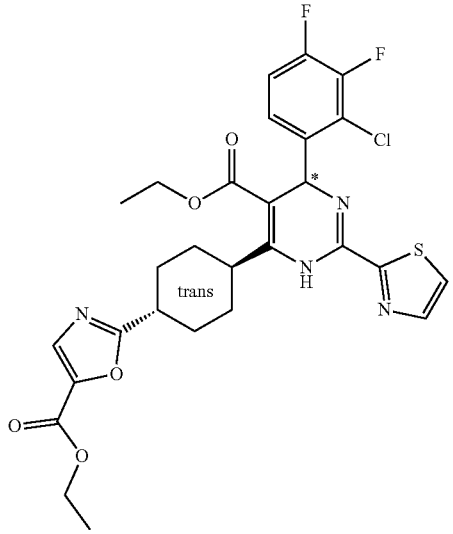<br>Compound VII-26-S |
| A12 | KT13 | AL9 | Ca1 | 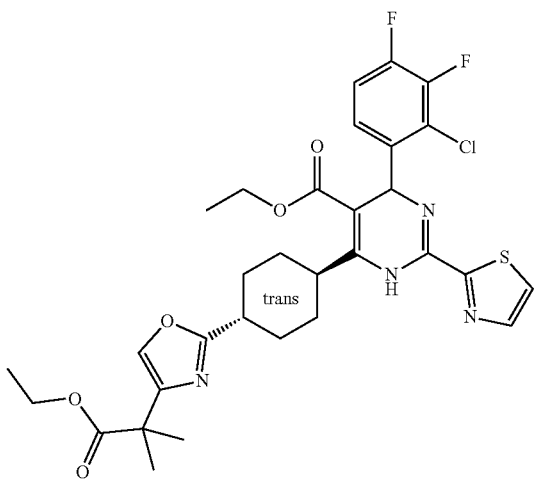<br>Compound VII-27-R |
| A13 | KT14 | AL9 | Ca1 | 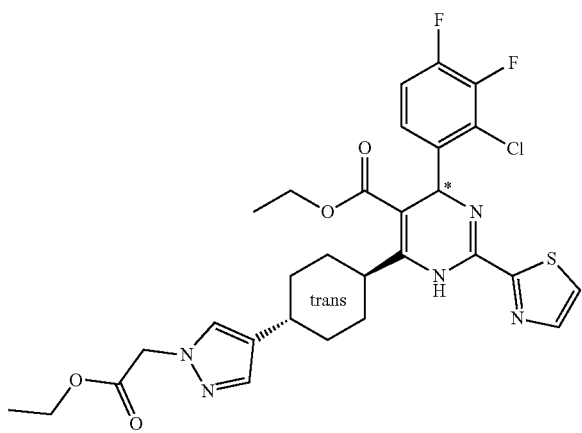<br>Compound VII-28-N |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A14 | KT15 | AL1 | Ca1 | 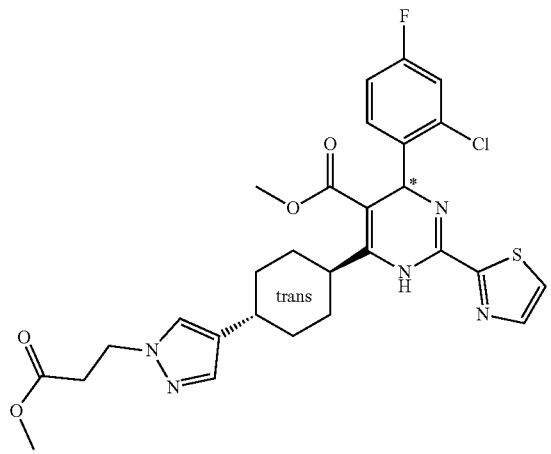<br>Compound VII-29-P |
| A15 | KT16 | AL9 | Ca1 | 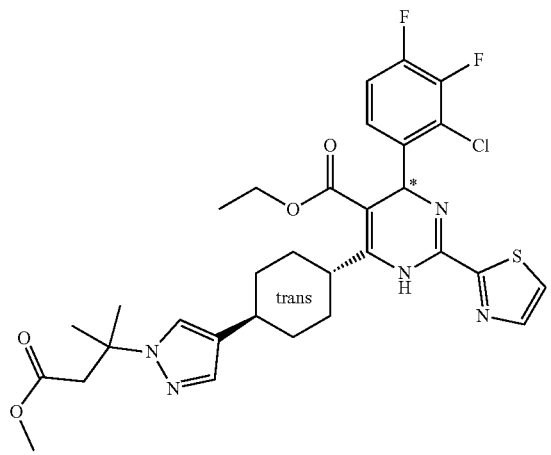<br>Compound VII-30-10 |
| A16 | KT17 | AL9 | Ca1 | 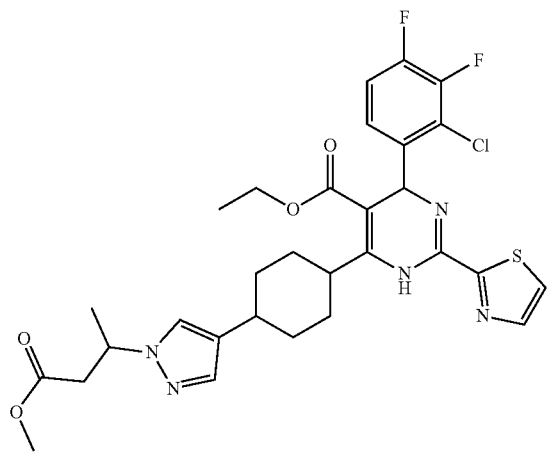<br>Compound VII-31 |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A17 | KT18 | AL9 | Ca1 | 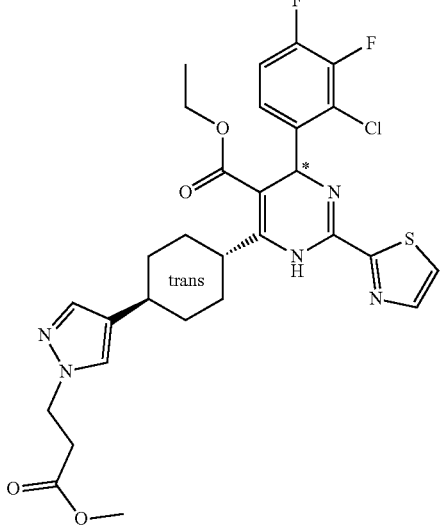<br>Compound VII-32-N |
| A18 | KT19 | AL9 | Ca1 | 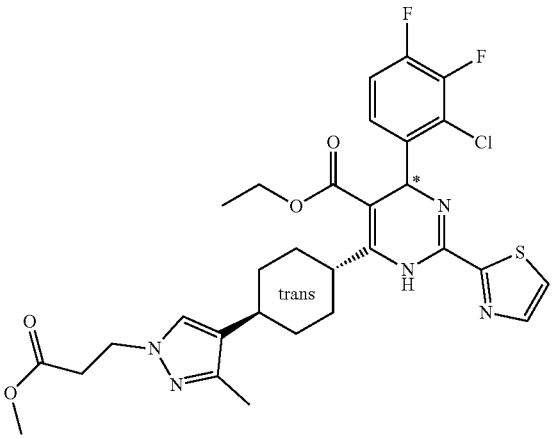<br>Compound VII-33-10 |
| A19 | KT20 | AL9 | Ca1 | 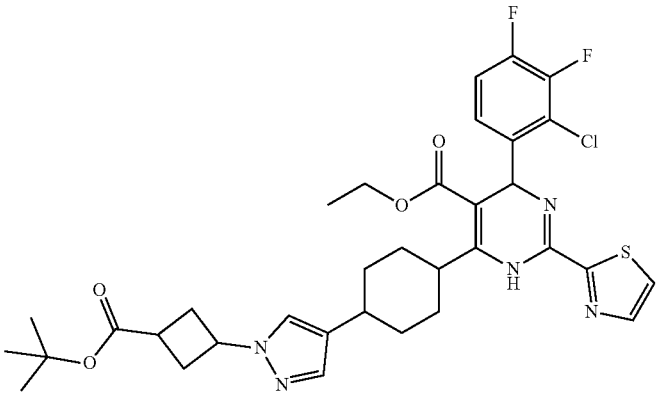<br>Compound VII-34 |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A20 | KT21 | AL9 | Ca1 | 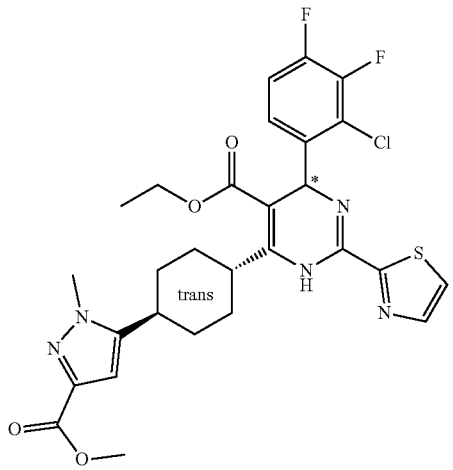<br>Compound VII-35-P |
| A21 | KT22 | AL9 | Ca1 | 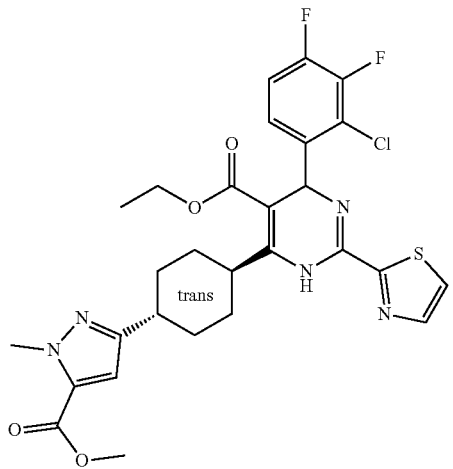<br>Compound VII-36-N |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A22 | KT23 | AL9 | Ca1 | 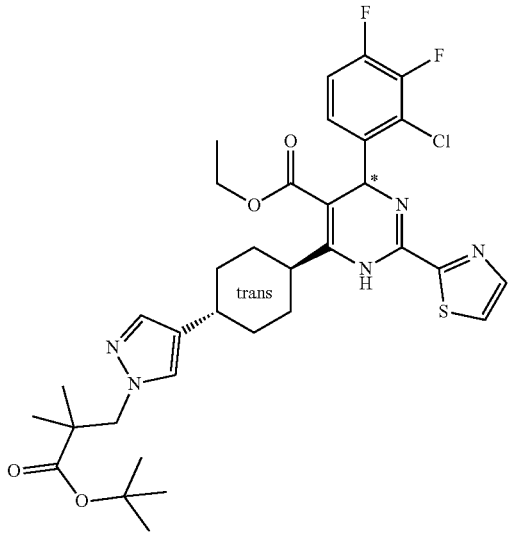<br>Compound VII-37-4C |
| A23 | KT24 | AL9 | Ca1 | 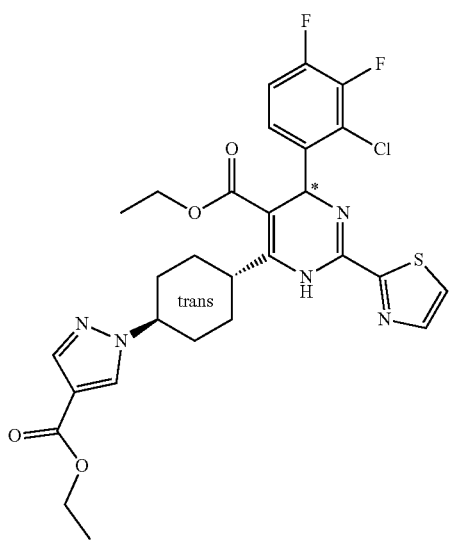<br>Compound VII-38-N |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A24 | KT25 | AL9 | Ca1 | 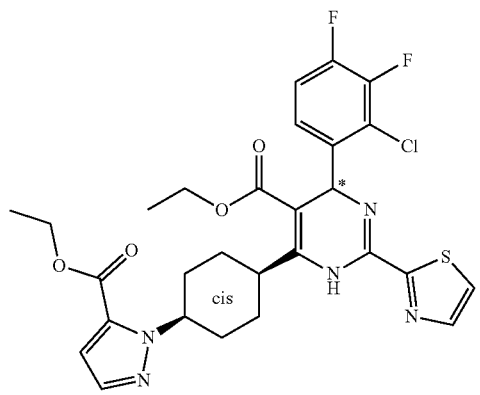<br>Compound VII-39-N |
| A24 | KT25 | AL9 | Ca1 | 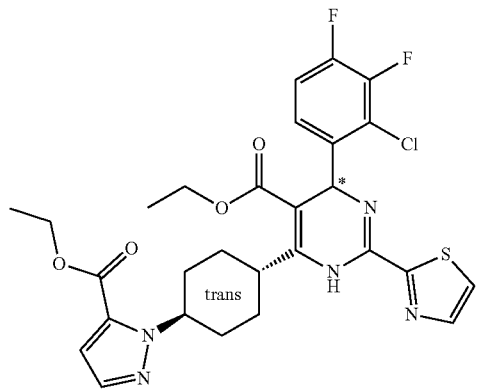<br>Compound VII-39-P |
| A25 | KT26 | AL9 | Ca1 | 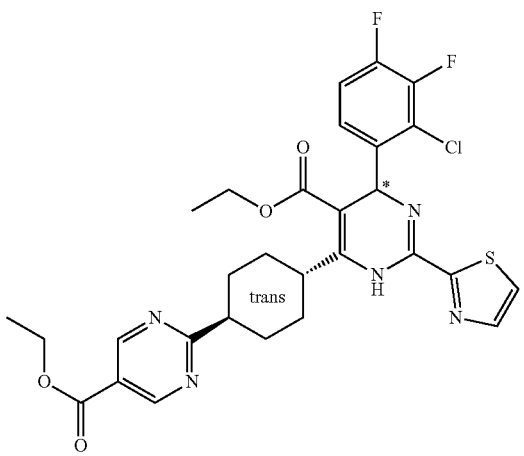<br>Compound VII-40-M |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A26 | KT27 | AL9 | Ca1 | 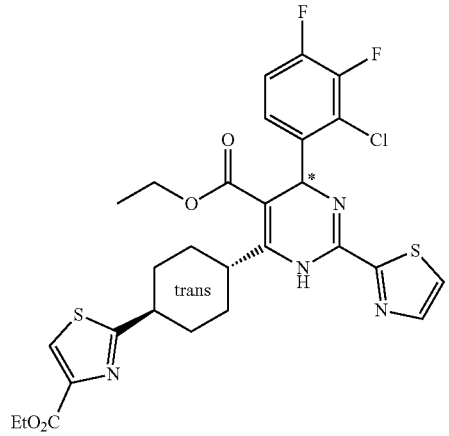<br>Compound VII-41-N |
| A27 | KT28 | AL9 | Ca1 | 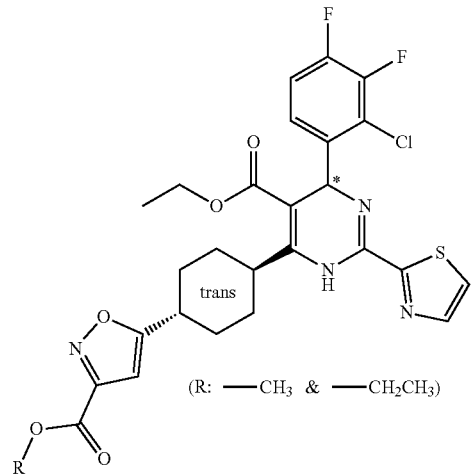<br>Compound VII-42-11 |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A28 | KT29 | AL9 | Ca1 | 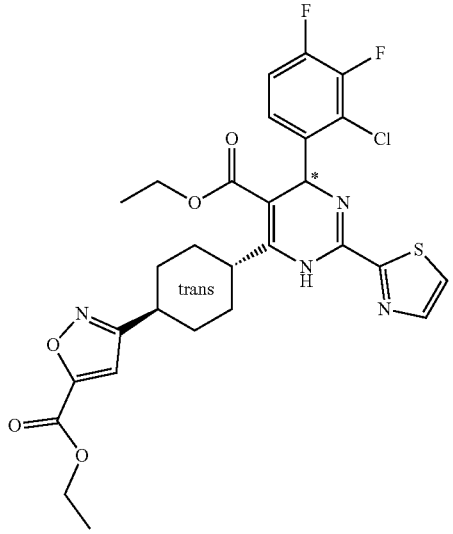<br>Compound VII-43-N |
| A30 | KT31 | AL9 | Ca1 | 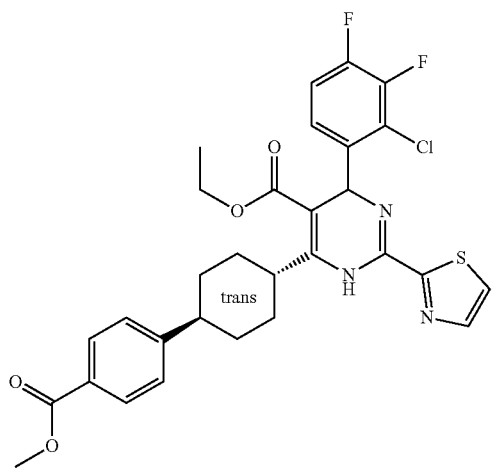<br>Compound VII-44-X |
| A31 | KT32 | AL9 | Ca1 | 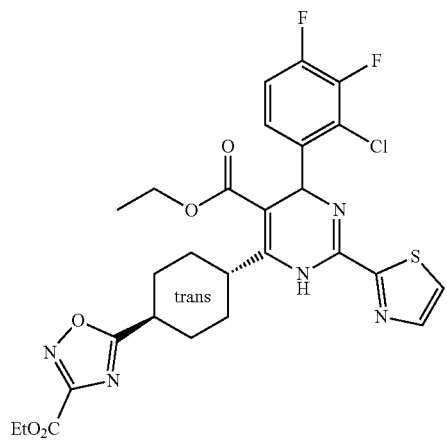<br>Compound VII-45-R |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A36 | KT39 | AL9 | Ca1 | 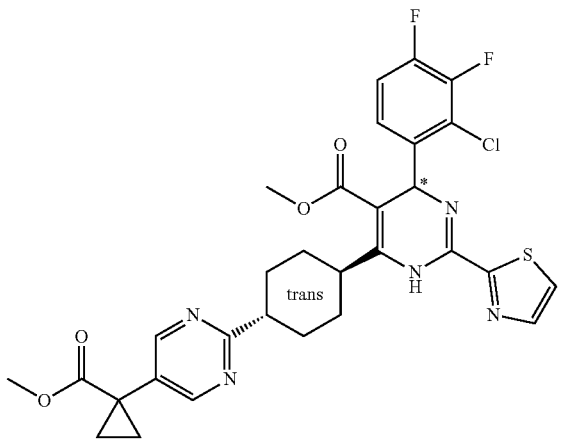<br>Compound VII-46-P |
| A37 | KT40 | AL6 | Ca1 | 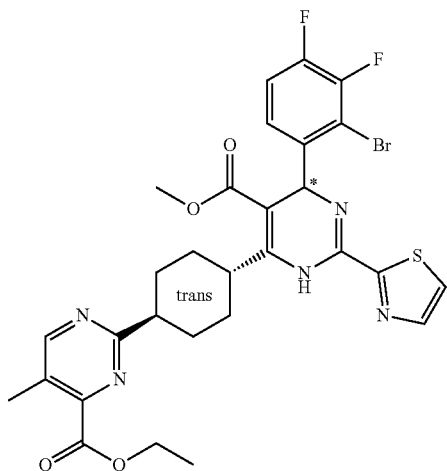<br>Compound VII-47-N |
| A38 | KT41 | AL1 | Ca1 | 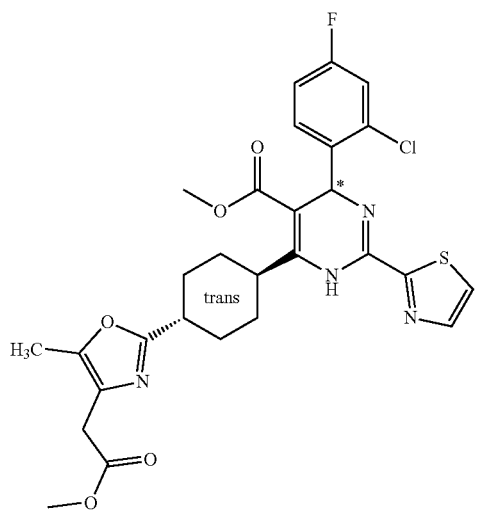<br>Compound VII-48-B |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A39 | KT42 | AL9 | Ca1 | |
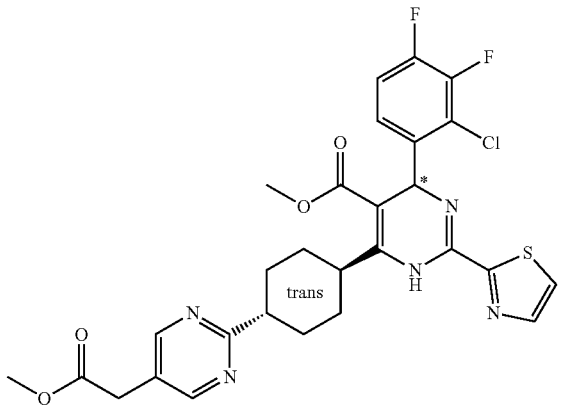
Compound VII-49-A
| A39 | KT42 | AL1 | Ca1 | |
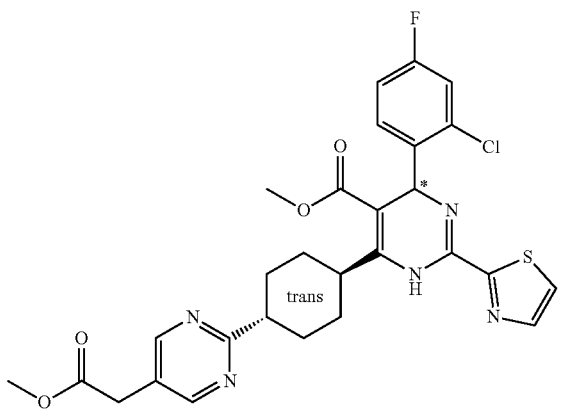
Compound VII-50-A
| A32 | KT33 | AL10 | Ca1 | |
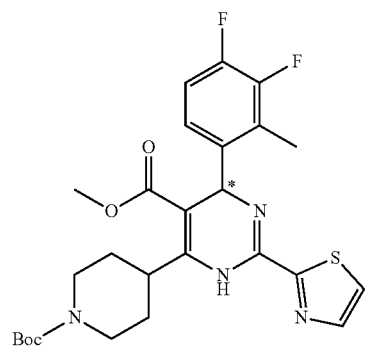
Compound VIII-1-B TABLE 1-continued
| acid of general formula III-1/III-2 | ketoester of general formula IV-1/IV-2 | P1 | P2 | dihydropyrimidine of general formula VII/VIII |
|---|---|---|---|---|
| A32 | KT34 | AL5 | Ca1 | 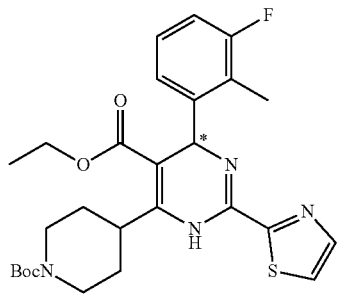<br>Compound VIII-2-B |
| A32 | KT34 | AL3 | Ca1 | 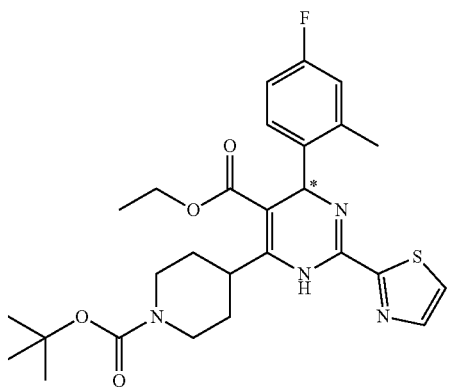<br>Compound VIII-3-B |
| A32 | KT33 | AL5 | Ca1 | 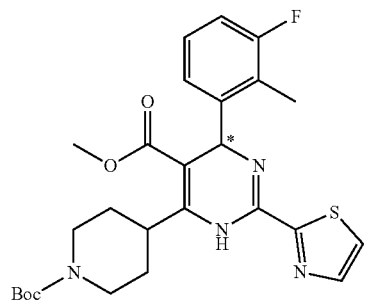<br>Compound VIII-4-A |
| A32 | KT33 | AL7 | Ca1 | 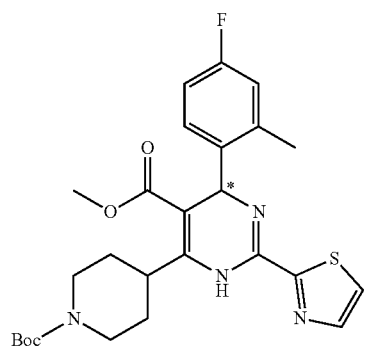<br>Compound VIII-5-B |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A32 | KT33 | AL2 | Ca1 | 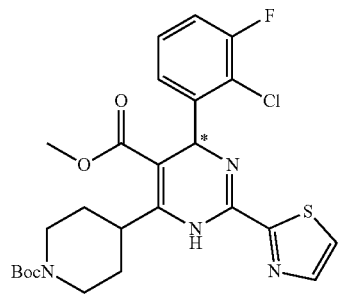<br>Compound VIII-6-B |
| A32 | KT33 | AL1 | Ca1 | 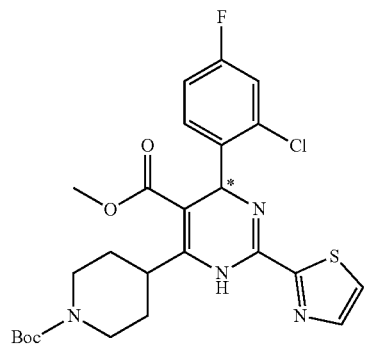<br>Compound VIII-7-B |
| A32 | KT34 | AL1 | Ca1 | 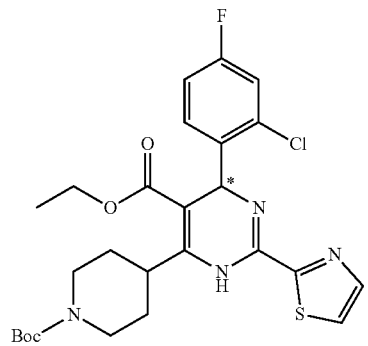<br>Compound VIII-8-B |
| A32 | KT34 | AL2 | Ca1 | 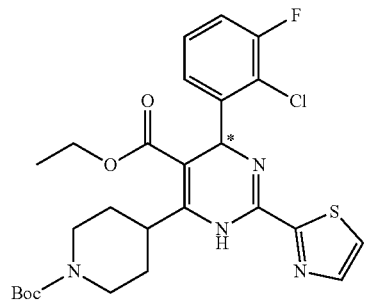<br>Compound VIII-9-B |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A32 | KT33 | AL9 | Ca1 | 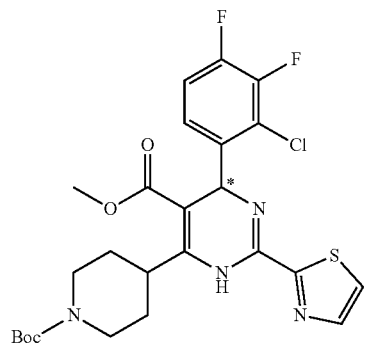<br>Compound VIII-10-B |
| A33 | KT35 | AL9 | Ca1 | 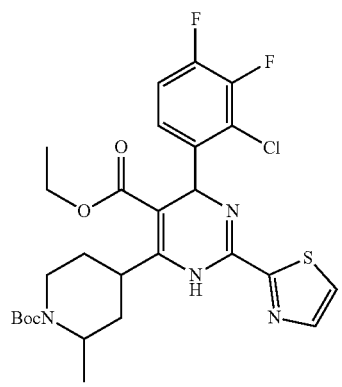<br>Compound VIII-11-6 |
| A32 | KT34 | AL9 | Ca1 | 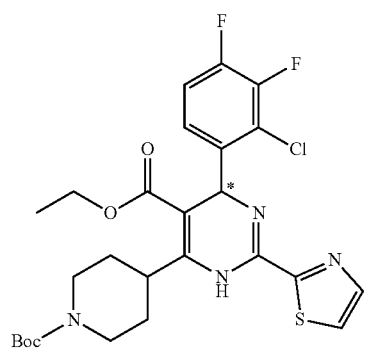<br>Compound VIII-12-B |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A32 | KT33 | AL11 | Ca1 | 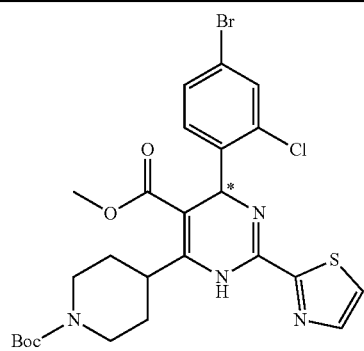Compound VIII-13-2b |
| A32 | KT33 | AL6 | Ca1 | 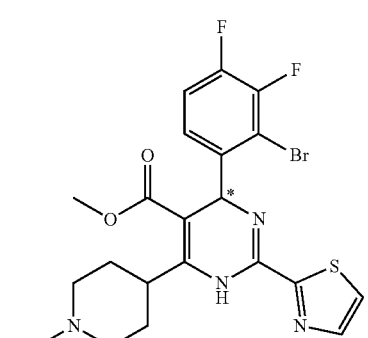Compound VIII-14-B |
| A32 | KT33 | AL8 | Ca1 | 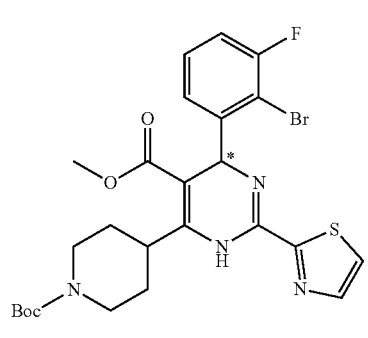Compound VIII-15-B |
| A32 | KT33 | AL11 | Ca1 | 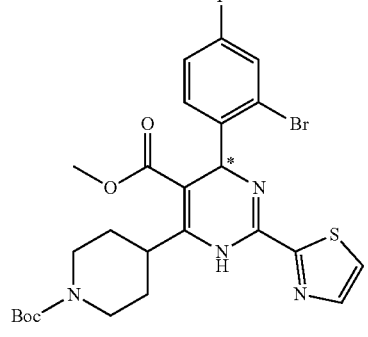VIII-16-2B |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A34 | KT36 | AL9 | Ca1 | 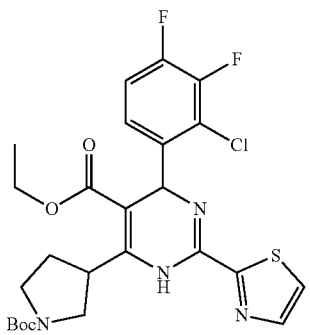<br>Compound VIII-17 |
| A29 | KT37 | AL9 | Ca1 | 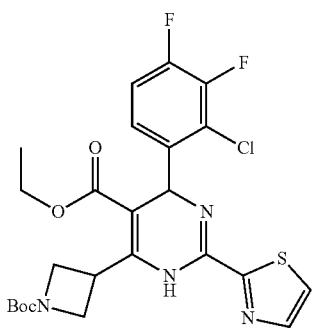<br>Compound VIII-18-2 |
| A35 | KT38 | AL1 | Ca1 | 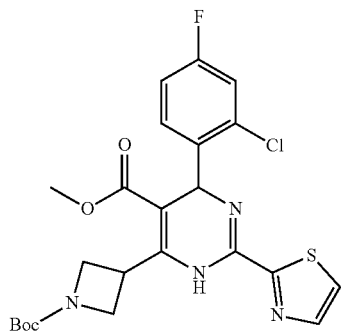<br>Compound VIII-19-4 |

TABLE 1-continued
| acid of general formula III-1/III-2 | ketoester of general formula IV-1/IV-2 | P1 | P2 | dihydropyrimidine of general formula VII/VIII |
|---|---|---|---|---|
| A40 | KT43 | AL1 | Ca1 | 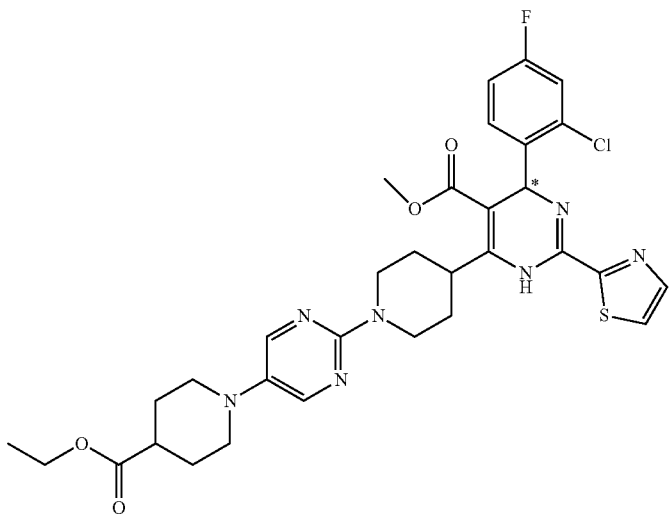 Compound VIII-20-6B |
| A32 | KT34 | AL8 | Ca1 | 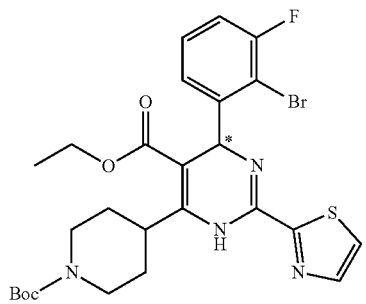 Compound VIII-21-B |
| A32 | KT34 | AL11 | Ca1 | 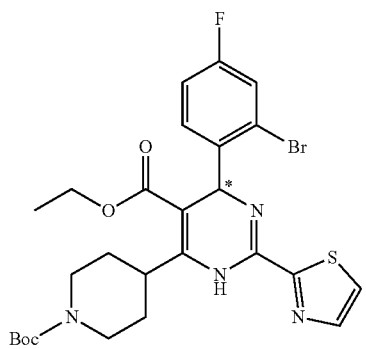 Compound VIII-22-2 |

TABLE 1-continued

| acid of general formula III-1/III-2 | ketoester of general formula IV-1/IV-2 | P1 | P2 | dihydropyrimidine of general formula VII/VIII |
|---|---|---|---|---|
| A41 | KT44 | AL1 | Ca1 | |

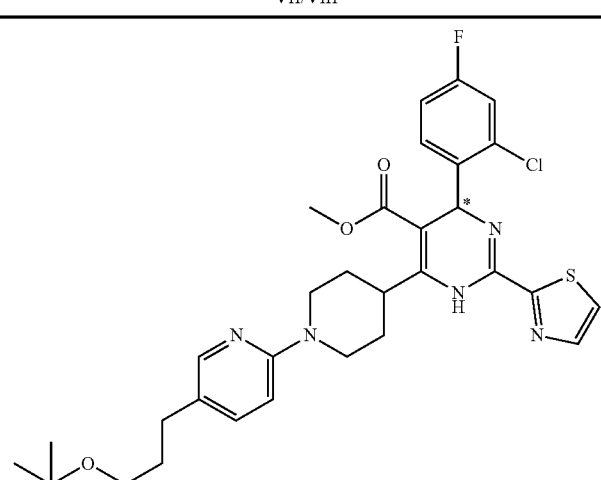

Compound VIII-23-B

Spectral Analyses of Assembled Dihydropyrimidines of General Formula VII/VIII

Compound VII-2-Y (trans)-methyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-4-carboxylate (a Single Stereoisomer)

Intermediates VII-2-P and VII-2-Q (cis)-Methyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers) and (trans)-methyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compounds were synthesized.

Compound VII-2-P: LC-MS (ESI): $R_T$=3.919 min, mass calcd. for $C_{27}H_{25}ClF_2N_4O_5S$, 590.1, m/z found 591.1 [M+H]$^+$. $^1$H NMR (400 MHz, CDCl$_3$) δ 8.26 (s, 1H), 8.17 (s, 1H), 7.80-7.78 (m, 1H), 7.45 (d, J=3.2 Hz, 0.3H), 7.42 (d, J=2.8 Hz, 0.7H), 7.09-6.96 (m, 2H), 6.20 (s, 0.7H), 6.06 (d, J=2.8 Hz, 0.3H), 4.11-3.99 (m, 3H), 3.94 (s, 2.1H), 3.92 (s, 0.9H), 3.38-3.33 (m, 0.7H), 3.31-3.26 (m, 0.3H), 2.57-2.43 (m, 2H), 2.1-1.65 (m, 6H), 1.14 (t, J=7.2 Hz, 3H).

Compound VII-2-Q: LC-MS (ESI): $R_T$=4.351 min, mass calcd. for $C_{27}H_{25}ClF_2N_4O_5S$, 590.1, m/z found 591.1 [M+H]$^+$. $^1$H NMR (400 MHz, CDCl$_3$) δ 8.18 (s, 1H), 8.14 (s, 0.5H), 7.83-7.82 (m, 1H), 7.51 (d, J=3.2 Hz, 0.4H), 7.46 (d, J=3.2 Hz, 0.6H), 7.33 (s, 0.5H), 7.12-6.99 (m, 2H), 6.21 (s, 0.6H), 6.08 (d, J=2.8 Hz, 0.4H), 4.10-4.00 (m, 2.6H), 3.92 (s, 3H), 3.85-3.78 (m, 0.4H), 3.02-2.93 (m, 1H), 2.38-2.21 (m, 2.8H), 2.15-2.01 (m, 1.2H), 1.91-1.65 (m, 4H), 1.17-1.12 (m, 3H).

A stereoisomeric mixture of (trans)-methyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-4-carboxylate VII-2-Q (160 mg, 0.270 mmol, 98.6% purity) was separated by chiral Prep. HPLC (Column: Chiralpak IE 5 μm 20*250 mm; Mobile Phase: Hex:EtOH:DEA=50:50:0.2 at 25 mL/min; Temp: 30° C.; Wavelength: 230 nm) to give compounds VII-2-X (70 mg, 43% yield, 100% stereopure) and VII-2-Y (65 mg, 40% yield, 99.6% stereopure).

Compound VII-2-X: LC-MS (ESI): $R_T$=2.878 min, mass calcd. for $C_{27}H_{25}ClF_2N_4O_5S$, 590.1, m/z found 591.1 [M+H]$^+$. Chiral analysis (Column: Chiralpak IE 5 μm 4.6*250 mm; Mobile Phase: Hex:EtOH:DEA=50:50:0.2 at 1 mL/min; Wavelength: 230 nm, $R_T$=5.865 min). $^1$H NMR (400 MHz, CDCl$_3$) δ 8.18 (s, 1H), 8.14 (s, 0.6H), 7.83 (d, J=3.6 Hz, 1H), 7.51 (d, J=3.2 Hz, 0.4H), 7.46 (d, J=3.2 Hz, 0.6H), 7.33 (s, 0.4H), 7.12-6.99 (m, 2H), 6.21 (s, 0.6H), 6.08 (d, J=2.8 Hz, 0.4H), 4.12-3.98 (m, 2.8H), 3.92 (s, 3H), 3.86-3.77 (m, 0.2H), 3.03-2.92 (m, 1H), 2.36-2.17 (m, 2.6H), 2.10-2.01 (m, 1.2H), 1.93-1.65 (m, 4.2H), 1.17-1.12 (m, 3H).

Compound VII-2-Y: LC-MS (ESI): $R_T$=2.849 min, mass calcd. for $C_{27}H_{25}ClF_2N_4O_5S$, 590.1, m/z found 591.1 [M+H]$^+$. Chiral analysis (Column: Chiralpak IE 5 μm 4.6*250 mm; Mobile Phase: Hex:EtOH:DEA=50:50:0.2 at 1 mL/min; Wavelength: 230 nm, $R_T$=6.610 min). $^1$H NMR (400 MHz, CDCl$_3$) δ 8.18 (s, 1H), 8.15 (s, 0.5H), 7.83-7.82 (m, 1H), 7.51 (d, J=3.2 Hz, 0.4H), 7.46 (d, J=2.8 Hz, 0.6H), 7.33 (s, 0.5H), 7.12-6.99 (m, 2H), 6.21 (s, 0.6H), 6.08 (d, J=2.4 Hz, 0.4H), 4.10-4.00 (m, 2.8H), 3.92 (s, 3H), 3.85-3.78 (m, 0.2H), 3.01-2.92 (m, 1H), 2.38-2.17 (m, 2.8H), 2.10-1.98 (m, 1.2H), 1.92-1.65 (m, 4H), 1.17-1.12 (m, 3H).

Compound VII-3-H (trans)-Methyl 2-(4-(6-(3-fluoro-2-methylphenyl)-5-(methoxycarbonyl)-2-(thiazol-2-yl)-3,6-dihydropyrimidin-4-yl)cyclohexyl)oxazole-4-carboxylate (a Single Stereoisomer)

Intermediate VII-3-1

Methyl 2-(4-(3-(3-fluoro-2-methylphenyl)-2-(methoxycarbonyl)acryloyl)cyclohexyl)oxazole-4-carboxylate To a solution of methyl 2-(4-(3-methoxy-3-oxopropanoyl)cyclohexyl)oxazole-4-carboxylate KT1 (700 mg, 1.86 mmol) and 3-fluoro-2-methylbenzaldehyde AL5 (307 mg, 2.22 mmol) in propan-2-ol (30 mL) was added one drop of piperidine and one drop of acetic acid at room temperature. After stirred at 70° C. under nitrogen atmosphere overnight, the reaction mixture was cooled down and concentrated under reduced pressure to give a residue, which was purified by C18 column (acetonitrile:water=62% to 69%) to give the title compound (510 mg, 64% yield) as yellow solids. LC-MS (ESI): $R_T$=1.72 min, mass calcd. for $C_{23}H_{24}FNO_6$ 429.1, m/z found 429.9 [M+H]$^+$. $^1$H NMR (400 MHz, CDCl$_3$) δ 8.18-8.11 (m, 1H), 7.97-7.94 (m, 0.7H), 7.79-7.75 (m, 0.3H), 7.15-6.94 (m, 3H), 3.91 (s, 2H), 3.89 (s, 1H), 3.85 (s, 1.3H), 3.83 (s, 0.7H), 3.70 (s, 0.7H), 3.68 (s, 0.3H), 3.13-3.05 (m, 0.3H), 2.97-2.78 (m, 0.7H), 2.73-2.66 (m, 0.3H), 2.30-1.63 (m, 9.7H), 1.46-1.24 (m, 2H).

Intermediate VII-3-Q and VII-3-P (trans)-Methyl 2-(4-(6-(3-fluoro-2-methylphenyl)-5-(methoxycarbonyl)-2-(thiazol-2-yl)-3,6-dihydropyrimidin-4-yl)cyclohexyl)oxazole-4-carboxylate (a Mixture of 2 Stereoisomers) and (cis)-Methyl 2-(4-(6-(3-fluoro-2-methylphenyl)-5-(methoxycarbonyl)-2-(thiazol-2-yl)-3,6-dihydropyrimidin-4-yl)cyclohexyl)oxazole-4-carboxylate (a Mixture of 2 Stereoisomers)

To a solution of methyl 2-(4-(3-(3-fluoro-2-methylphenyl)-2-(methoxycarbonyl)acryloyl)cyclohexyl)oxazole-4-carboxylate VII-3-1 (500 mg, 1.08 mmol) and thiazole-2-carboximidamide hydrochloride Ca1 (212 mg, 1.30 mmol) in N,N-dimethylformamide (26 mL) was added sodium bicarbonate (273 mg, 3.25 mmol) at room temperature. After stirred at 90° C. under nitrogen atmosphere overnight, the reaction mixture was cooled down and diluted with water (100 mL), extracted with ethyl acetate (100 mL) twice. The combined organic layers were washed with water (30 ml), brine (50 mL), dried over Na$_2$SO$_{4(s)}$ and filtered.

The filtrate was concentrated under reduced pressure and purified by silica gel column chromatography (petroleum ether:ethyl acetate=4:1 to 3:1 to 2:1) to give the compound VII-3-P (53 mg, 8% yield) as yellow solids and VII-3-Q (82 mg, 14% yield) as yellow solids.

VII-3-P: LC-MS (ESI): $R_T$=1.78 min, mass calcd. for $C_{27}H_{27}FN_4O_5S$, 538.2, m/z found 539.0 [M+H]$^+$. $^1$H NMR (400 MHz, CDCl$_3$) δ 8.27 (s, 1H), 8.13 (s, 0.8H), 7.76 (d, J=3.2 Hz, 1H), 7.52 (s, 0.2H), 7.40 (d, J=2.8 Hz, 1H), 7.08-7.00 (m, 2H), 6.91-6.85 (m, 1H), 5.98 (s, 1H), 4.10-4.04 (m, 0.8H), 3.94 (s, 3H), 3.76-3.73 (m, 0.2H), 3.59 (s, 3H), 3.38-3.31 (m, 1H), 2.58-2.49 (m, 5H), 2.05-1.77 (m, 6H).

VII-3-Q: LC-MS (ESI): $R_T$=1.76 min, mass calcd. for $C_{27}H_{27}FN_4O_5S$, 538.2, m/z found 539.0 [M+H]$^+$. $^1$H NMR (400 MHz, CDCl$_3$) δ 8.18 (d, J=3.2 Hz, 1H), 8.11 (s, 0.7H), 7.80 (d, J=2.8 Hz, 1H), 7.52 (s, 0.3H), 7.50 (d, J=3.2 Hz, 0.2H), 7.43 (d, J=3.6 Hz, 0.8H), 7.15-7.00 (m, 2H), 6.95-6.88 (m, 1H), 6.01 (s, 0.8H), 5.91 (d, J=2.0 Hz, 0.2H), 4.09-4.05 (m, 0.8H), 3.93 (s, 2.4H), 3.92 (s, 0.6H), 3.75-3.70 (m, 0.2H), 3.60 (s, 2.4H), 3.59 (s, 0.6H), 3.02-2.94 (m, 1H), 2.55 (d, J=2.0 Hz, 2.4H), 2.40-2.21 (m, 3.6H), 2.10-1.62 (m, 5H).

A stereoisomeric mixture of trans-methyl 2-(4-(6-(3-fluoro-2-methylphenyl)-5-(methoxycarbonyl)-2-(thiazol-2-yl)-3,6-dihydropyrimidin-4-yl)cyclohexyl)oxazole-4-carboxylate VII-3-Q (98 mg, 0.164 mmol) was separated by chiral Prep. HPLC (the separation condition: Column: Chiralpak IE 5 μm 20*250 mm; Mobile Phase: Hex:EtOH:DEA=80:20:0.3 at 15 mL/min; Temp: 30° C.; Wavelength: 214 nm) to afford the compounds VII-3-G (41 mg, 42% yield, 100% stereopure) and VII-3-H (38 mg, 39% yield, 97.7% stereopure) as yellow solids.

VII-3-G: LC-MS (ESI): $R_T$=1.72 min, mass calcd. for $C_{27}H_{27}FN_4O_5S$, 538.2, m/z found 539.2 [M+H]$^+$. Chiral HPLC (Column: Chiralpak IE 5 μm 4.6*250 mm; Mobile Phase: Hex:EtOH:DEA=80:20:0.2 at 1 mL/min; Temp: 30° C.; Wavelength: 230 nm, $R_T$=18.513 min). $^1$H NMR (400 MHz, CDCl$_3$) δ 8.18 (d, J=3.2 Hz, 1H), 8.11 (s, 0.8H), 7.80 (d, J=3.2 Hz, 1H), 7.50 (d, J=3.2 Hz, 0.2H), 7.43 (d, J=3.6 Hz, 1H), 7.17-7.00 (m, 2H), 6.95-6.88 (m, 1H), 6.01 (s, 0.8H), 5.91 (d, J=2.0 Hz, 0.2H), 4.13-4.04 (m, 0.8H), 3.93 (s, 2.4H), 3.92 (s, 0.6H), 3.75-3.69 (m, 0.2H), 3.60 (s, 2.4H), 3.59 (s, 0.6H), 3.03-2.94 (m, 1H), 2.55 (d, J=2.0 Hz, 2.4H), 2.40-2.22 (m 3.6H), 2.10-1.62 (m, 5H).

VII-3-H: LC-MS (ESI): $R_T$=1.72 min, mass calcd. for $C_{27}H_{27}FN_4O_5S$, 538.2, m/z found 539.2 [M+H]$^+$. Chiral HPLC (Column: Chiralpak IE 5 μm 4.6*250 mm; Mobile Phase: Hex:EtOH:DEA=80:20:0.2 at 1 mL/min; Temp: 30° C.; Wavelength: 230 nm, $R_T$=20.813 min). $^1$H NMR (400 MHz, CDCl$_3$) δ 8.18 (d, J=3.2 Hz, 1H), 8.11 (s, 0.8H), 7.80 (d, J=2.8 Hz, 1H), 7.50 (d, J=2.8 Hz, 0.2H), 7.43 (d, J=2.8 Hz, 1H), 7.17-7.00 (m, 2H), 6.95-6.88 (m, 1H), 6.01 (s, 0.8H), 5.91 (d, J=2.0 Hz, 0.2H), 4.13-4.04 (m, 0.8H), 3.93 (s, 3H), 3.74-3.69 (m, 0.2H), 3.60 (s, 3H), 3.02-2.94 (m, 1H), 2.55 (d, J=2.0 Hz, 2.4H), 2.41-2.22 (m, 3.6H), 2.10-1.62 (m, 5H).

Compound VII-4-N (trans)-methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate (a Single Stereoisomer)

Intermediate VII-4-R

Methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate (a Mixture of 4 Stereoisomers)

By utilizing the analogous procedure of Method B, the title compound was synthesized as yellow solids. $^1$HNMR (400 MHz, CDCl$_3$) δ 8.26 (s, 0.5H), 8.18 (s, 0.5H), 7.86 (t, J=2.8 Hz, 1H), 7.54 (d, J=2.8 Hz, 1H), 7.33-7.28 (m, 1H), 7.16-7.11 (m, 1H), 6.96-6.89 (m, 1H), 6.20 (s, 0.5H), 6.17 (s, 0.5H), 3.93 (s, 1.5H), 3.92 (s, 1.5H), 3.62 (s, 1.5H), 3.61 (s, 1.5H), 3.39-3.30 (m, 1H), 2.38-2.19 (m, 2H), 2.00-1.64 (m, 6H), 1.36-1.14 (m, 1H).

Intermediates VII-4-M, VII-4-N and VII-4-P (trans)-Methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate (a Single Stereoisomer), (trans)-methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate (a Single Stereoisomer) and (cis)-methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate (a Mixture of 2 Stereoisomers)

A stereoisomeric mixture of methyl 2-(4-(6-(2-chloro-4-fluorophenyl)-5-(methoxycarbonyl)-2-(thiazol-2-yl)-3,6-dihydropyrimidin-4-yl)cyclohexyl)oxazole-4-carboxylate VII-4-R (710 mg, 1.27 mmol) was separated by chiral Prep. HPLC (Column: Chiralpak IE 5 μm 20*250 mm; Mobile Phase: Hex:EtOH:DEA=60:40:0.2 at 13 mL/min; Temp: 30° C.; Wavelength: 214 nm) to give the title compounds VII-4-M (100 mg, 14% yield, 100% stereopure), VII-4-N (100 mg, 14% yield, 100% stereopure) and VII-4-P (190 mg, 27% yield) as a yellow solids.

VII-4-M: LC-MS (ESI): $R_T$=1.72 min, mass calcd. for $C_{26}H_{24}ClFN_4O_5S$, 558.1, m/z found 559.0 [M+H]$^+$. Chiral analysis (Column: Chiralpak IE 5 μm 4.6*250 mm; Mobile Phase: Hex:EtOH:DEA=60:40:0.2 at 1 mL/min; Wavelength: 230 nm, $R_T$=10.485 min). $^1$H NMR (400 MHz, DMSO-$d_6$) δ 9.48-9.44 (m, 0.6H), 9.02 (s, 0.4H), 8.79 (s, 0.4H), 8.78 (s, 0.6H), 8.01-7.99 (m, 1.5H), 7.95-7.94 (m, 0.4H), 7.46-7.40 (m, 1H), 7.39-732 (m, 1H), 7.26-7.18 (m, 1H), 6.02 (s, 0.4H), 5.92 (d, J=3.6 Hz, 0.6H), 3.94-3.85 (m, 0.4H), 3.80 (s, 3H), 3.70-3.61 (m, 0.7H), 3.53 (d, J=5.2 Hz, 3H), 3.10-3.01 (m, 0.4H), 2.95-2.85 (m, 0.6H), 2.24-2.16 (m, 2H), 2.07-1.76 (m, 3.4H), 1.73-1.51 (m, 2.6H).

VII-4-N: LC-MS (ESI): $R_T$=1.73 min, mass calcd. for $C_{26}H_{24}ClFN_4O_5S$, 558.1, m/z found 559.0 [M+H]$^+$. Chiral analysis (Column: Chiralpak OJ-H 5 μm 4.6*250 mm; Mobile Phase: Hex:EtOH:DEA=60:40:0.2 at 1 mL/min; Wavelength: 230 nm, $R_T$=13.163 min). $^1$H NMR (400 MHz, DMSO-$d_6$) δ 9.47-9.46 (m, 0.6H), 9.01 (s, 0.4H), 8.79 (s, 0.4H), 8.78 (s, 0.6H), 8.00-7.99 (m, 1.6H), 7.95-7.94 (m, 0.4H), 7.45-7.41 (m, 1H), 7.38-7.33 (m, 1H), 7.25-7.19 (m, 1H), 6.02 (s, 0.4H), 5.92 (d, J=3.2 Hz, 0.6H), 3.96-3.86 (m, 0.4H), 3.80 (s, 3H), 3.71-3.61 (m, 0.6H), 3.53 (d, J=5.6 Hz, 3H), 3.11-3.00 (m, 0.4H), 2.95-2.85 (m, 0.6H), 2.25-2.12 (m, 2H), 2.09-1.77 (m, 3.4H), 1.73-1.50 (m, 2.6H).

VII-4-P: LC-MS (ESI): $R_T$=1.74 min, mass calcd. for $C_{26}H_{24}ClFN_4O_5S$, 558.1, m/z found 559.0 [M+H]$^+$. Chiral analysis (Column: Chiralpak OJ-H 5 μm 4.6*250 mm; Mobile Phase: Hex:EtOH:DEA=60:40:0.2 at 1 mL/min; Wavelength: 230 nm, $R_T$=7.430 min and 7.778 min). $^1$H NMR (400 MHz, DMSO-$d_6$) δ 9.43 (s, 0.7H), 9.42 (s, 0.3H), 8.86-8.85 (m, 1H), 7.97-7.92 (m, 2H), 7.42-7.39 (m, 1H), 7.32-7.29 (m, 1H), 7.20-7.19 (m, 1H), 6.01 (s, 0.3H), 5.88 (d, J=3.6 Hz, 0.7H), 3.83 (s, 3H), 3.75-3.66 (m, 1H), 3.53 (s, 2.1H), 3.52 (s, 0.9H), 3.29-3.25 (m, 1H), 2.44-2.29 (m, 2H), 2.00-1.78 (m, 4H), 1.72-1.58 (m, 1.3H), 1.52-1.38 (m, 0.7H).

Compound VII-5-Q (trans)-methyl 2-(4-(6-(2-chloro-3-fluorophenyl)-5-(methoxycarbonyl)-2-(thiazol-2-yl)-3,6-dihydropyrimidin-4-yl)cyclohexyl)oxazole-4-carboxylate (a Single Stereoisomer)

Intermediates VII-5-M and VII-5-N (cis)-Methyl-2-(4-(6-(2-chloro-3-fluorophenyl)-5-(methoxycarbonyl)-2-(thiazol-2-yl)-3,6-dihydropyrimidin-4-yl)cyclohexyl)oxazole-4-carboxylate (a Mixture of 2 Stereoisomers) and (trans)-methyl-2-(4-(6-(2-chloro-3-fluorophenyl)-5-(methoxycarbonyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compounds were synthesized.

VII-5-M: $^1$H NMR (400 MHz, CDCl$_3$) δ 8.29-8.24 (m, 1H), 8.20-8.13 (m, 0.7H), 7.83-7.74 (m, 1H), 7.48-7.44 (m, 0.4H), 7.43-7.41 (m, 0.6H), 7.38-7.35 (m, 0.3H), 7.19-7.08 (m, 2H), 7.07-6.99 (m, 1H), 6.25 (s, 0.6H), 6.09 (d, J=2.8 Hz, 0.4H), 4.15-4.02 (m, 1H), 3.94 (s, 1.9H), 3.92 (s, 1.1H), 3.61 (s, 1.1H), 3.59 (s, 1.9H), 3.89-3.33 (m, 0.6H), 3.31-3.26 (m, 0.4H), 2.58-2.43 (m, 2H), 2.00-1.90 (m, 3H), 1.89-1.83 (m, 2H), 1.77-1.65 (m, 1H).

VII-5-N: $^1$H NMR (400 MHz, CDCl$_3$) δ 8.20-8.14 (m, 1.5H), 7.81 (d, J=2.8 Hz, 1H), 7.49 (d, J=3.2 Hz, 0.5H), 7.45-7.42 (m, 1H), 7.22-7.10 (m, 2H), 7.08-6.99 (m, 1H), 6.24 (s, 0.5H), 6.10 (d, J=2.8 Hz, 0.5H), 4.09-4.02 (m, 0.5H), 3.91 (s, 3H), 3.86-3.78 (m, 0.5H), 3.60 (s, 1.4H), 3.58 (s, 1.6H), 3.04-2.94 (m, 1H), 2.37-2.26 (m, 2H), 2.23-2.20 (m, 1H), 2.12-2.03 (m, 2H), 1.98-1.85 (m, 2H), 1.72-1.58 (m, 1H).

A stereoisomeric mixture of (trans)-methyl 2-(4-(6-(2-chloro-3-fluorophenyl)-5 (methoxycarbonyl)-2-(thiazol-2-yl)-3,6-dihydropyrimidin-4-yl)cyclohexyl)oxazole-4-carboxylate VII-5-N (300 mg, 90% purity, 0.483 mmol) was separated by chiral HPLC (separation condition: Column: Chiralpak IA 5 μm 20*250 mm, Mobile Phase: Hex:EtOH: DEA=60:40:0.3 at 20 ml/min; Temp: 30° C.; Wavelength: 214 nm) to afford the title compounds VII-5-P (119 mg, 95% purity from NMR, 42% yield, 99.8% stereopure) and VII-5-Q (129 mg, 95% purity from NMR, 45% yield, 96.9% stereopure) as yellow solids.

VII-5-P: $^1$H NMR (400 MHz, CDCl$_3$) δ 8.18 (s, 1H), 8.14 (s, 0.5H), 7.86-7.80 (m, 1H), 7.50 (d, J=3.2 Hz, 0.5H), 7.45 (d, J=2.8 Hz, 0.5H), 7.43 (m, 0.5H), 7.22-7.20 (m, 0.6H), 7.16-7.11 (m, 1.4H), 7.10-7.00 (m, 1H), 6.26 (s, 0.5H), 6.12 (d, J=2.4 Hz, 0.5H), 4.12-4.03 (m, 0.5H), 3.92 (s, 3H), 3.87-3.79 (m, 0.5H), 3.62 (s, 1.5H), 3.60 (s, 1.5H), 3.03-2.92 (m, 1H), 2.38-2.26 (m, 1.7H), 2.26-2.14 (m, 1.2H), 2.11-1.97 (m, 1.7H), 1.86-1.71 (m 3.4H). Chiral analysis (Column: Chiralpak IA 5 μm 4.6*250 mm; Mobile Phase: Hex:EtOH:DEA=60:40:0.2 at 1 ml/min; Col. Temp: 30° C.; Wavelength: 230 nm, Back pressure: 100 bar; $R_T$=6.960 min).

VII-5-Q: $^1$H NMR (400 MHz, CDCl$_3$) δ 8.19-8.18 (m, 1.5H), 7.84-7.82 (m, 1H), 7.50 (d, J=3.2 Hz, 0.5H), 7.46 (d, J=3.2 Hz, 1H), 7.22-7.15 (m, 2H), 7.10-7.02 (m, 1H), 6.26 (s, 0.5H), 6.12 (s, 0.5H), 4.10-4.04 (m, 0.5H), 3.92 (s, 3H), 3.86-3.81 (m, 0.5H), 3.62 (s, 1.4H), 3.60 (s, 1.6H), 3.01-2.95 (m, 1H), 2.35-2.28 (m, 1.6H), 2.24-2.18 (m, 1.1H), 2.10-2.01 (m, 1.7H), 1.92-1.77 (m, 3.6H). Chiral analysis (Column: Chiralpak IA 5 μm 4.6*250 mm; Mobile Phase:

Hex:EtOH:DEA=60:40:0.2 at 1 ml/min; Col. Temp: 30° C.; Wavelength: 230 nm, Back pressure: 100 bar; $R_T$=9.952 min).

Compound VII-6-Q (trans)-methyl 2-(4-(6-(4-fluoro-2-methylphenyl)-5-(methoxycarbonyl)-2-(thiazol-2-yl)-3,6-dihydropyrimidin-4-yl)cyclohexyl)oxazole-4-carboxylate (a Single Stereoisomer)

Intermediates: VII-6-M and VII-6-N (cis)-Methyl 2-(4-(6-(4-fluoro-2-methylphenyl)-5-(methoxycarbonyl)-2-(thiazol-2-yl)-3,6-dihydropyrimidin-4-yl)cyclohexyl)oxazole-4-carboxylate (a Mixture of 2 Stereoisomers) and (trans)-methyl 2-(4-(6-(4-fluoro-2-methylphenyl)-5-(methoxycarbonyl)-2-(thiazol-2-yl)-3,6-dihydropyrimidin-4-yl) cyclohexyl)oxazole-4-carboxylate (a Mixture of 2 Stereoisomers)

By utilizing the analogous procedure of Method B, the title compounds were synthesized.

VII-6-M: $^1$H NMR (400 MHz, CDCl$_3$) δ 8.27 (s, 1H), 8.12 (s, 0.8H), 7.76 (d, J=3.2 Hz, 1H), 7.43 (d, J=3.2 Hz, 0.2H), 7.39 (d, J=3.2 Hz, 0.8H), 7.32-7.28 (m, 0.2H), 7.18-7.10 (m, 0.8H), 7.00-6.96 (m, 0.2H), 6.92-6.82 (m, 1.2H), 6.79-6.72 (m, 0.8H), 5.94 (s, 0.8H), 5.85-5.81 (m, 0.2H), 4.14-4.03 (m, 0.8H), 3.94 (s, 2.3H), 3.93 (s, 0.7H), 3.81-3.73 (m, 0.2H), 3.60 (s, 2.3H), 3.59 (s, 0.7H), 3.40-3.33 (m, 0.8H), 3.31-3.26 (m, 0.2H), 2.62 (s, 2.5H), 2.58-2.49 (m, 2H), 2.47 (s, 0.5H), 2.08-1.91 (m, 3H), 1.90-1.79 (m, 2H), 1.75-1.68 (m, 1H).

VII-6-N: $^1$H NMR (400 MHz, CDCl$_3$) δ 8.21-8.17 (m, 1H), 8.12 (s, 0.7H), 7.82-7.79 (m, 1H), 7.50 (d, J=3.2 Hz, 0.3H), 7.43 (d, J=3.2 Hz, 0.7H), 7.35-7.29 (m, 0.3H), 7.20-7.15 (m, 0.7H), 7.09-7.05 (m, 0.3H), 6.92-6.83 (m, 1.3H), 6.82-6.75 (m, 0.7H), 5.96 (s, 0.7H), 5.88-5.85 (m, 0.3H), 4.12-4.02 (m, 0.7H), 3.93 (s, 2.2H), 3.92 (s, 0.8H), 3.73-3.70 (m 0.3H), 3.61 (s, 2.2H), 3.60 (s, 0.8H), 3.02-2.97 (m, 1H), 2.64 (s, 2.2H), 2.49 (s, 0.8H), 2.41-2.30 (m, 1.8H), 2.25-2.22 (m, 1.4H), 2.12-2.01 (m, 1.2H), 1.97-1.84 (m, 2H), 1.71-1.57 (m, 1.6H).

A stereoisomeric mixture of (trans)-methyl 2-(4-(6-(2-chloro-3-fluorophenyl)-5-(methoxycarbonyl)-2-(thiazol-2-yl)-3,6-dihydropyrimidin-4-yl)cyclohexyl)oxazole-4-carboxylate VII-6-N (365 mg, 80% purity, 0.542 mmol) was separated by chiral Prep. HPLC (separation condition: Column: Chiralpak IA 5 μm 20*250 mm, Mobile Phase: Hex:EtOH:DEA=60:40:0.3 at 22 mL/min; Temp: 30° C.; Wavelength: 214 nm) to afford the title compounds VII-6-P (105 mg, 95% purity from $^1$H NMR, 34% yield, 100% stereopure) and VII-6-Q (110 mg, 95% purity from $^1$H NMR, 36% yield, 94.5% stereopure) as yellow solids.

VII-6-P: $^1$H NMR (400 MHz, CDCl$_3$) δ 8.23-8.16 (m, 1H), 8.11 (s, 0.7H), 7.80 (d, J=3.2 Hz, 1H), 7.50 (d, J=3.2 Hz, 0.3H), 7.42 (d, J=2.8 Hz, 0.7H), 7.35-7.30 (m, 0.3H), 7.21-7.14 (m, 0.7H), 7.02 (s, 0.3H), 6.92-6.87 (m, 1.2H), 6.84-6.75 (m, 0.8H), 5.96 (s, 0.7H), 5.89-5.83 (m, 0.3H), 4.12-4.02 (m, 0.7H), 3.93 (s, 3H), 3.74-3.67 (m, 0.3H), 3.60 (s, 3H), 3.03-2.92 (m, 1H), 2.64 (s, 2.2H), 2.49 (s, 0.8H), 2.39-2.33 (m, 1.7H), 2.27-2.17 (m, 1.3H), 2.12-1.99 (m, 1.4H), 1.97-1.83 (m, 2H), 1.82-1.65 (m, 1.6H). Chiral analysis: (column: Chiralpak IA 5 μm 4.6*250 mm; Mobile Phase: Hex:EtOH:DEA=60:40:0.2 at 1 mL/min; Col. Temp: 30° C.; Wavelength: 230 nm; $R_T$=6.321 min).

VII-6-Q: $^1$H NMR (400 MHz, CDCl$_3$) δ 8.20-8.16 (m, 1H), 8.10 (s, 0.7H), 7.80 (d, J=2.8 Hz, 1H), 7.50 (d, J=3.2 Hz, 0.3H), 7.42 (d, J=3.2 Hz, 0.7H), 7.34-7.29 (m, 0.3H), 7.18-7.15 (m, 0.7H), 7.01 (s, 0.3H), 6.91-6.87 (m, 1.2H), 6.83-6.75 (m, 0.8H), 5.95 (s, 0.7H), 5.88-5.85 (m, 0.3H), 4.12-4.02 (m, 0.7H), 3.92 (s, 3H), 3.72-3.66 (m, 0.3H), 3.60 (s, 3H), 3.02-2.93 (m, 1H), 2.64 (s, 2.2H), 2.49 (s, 0.8H), 2.40-2.33 (m, 1.7H), 2.27-2.22 (m, 1.3H), 2.11-1.99 (m, 1.4H), 1.95-1.83 (m, 2H), 1.80-1.62 (m, 1.6H). Chiral analysis: (column: Chiralpak IA 5 μm 4.6*250 mm; Mobile Phase: Hex:EtOH:DEA=60:40:0.2 at 1 mL/min; Col. Temp: 30° C.; Wavelength: 230 nm; $R_T$=8.167 min).

Compound VII-7-N (trans)-methyl 2-(4-(6-(2-chloro-3,4-difluorophenyl)-2-(3,5-difluoropyridin-2-yl)-5-(methoxycarbonyl)-3,6-dihydropyrimidin-4-yl)cyclohexyl)oxazole-4-carboxylate (a Single Stereoisomer)

Intermediate VII-7-S (trans)-Methyl 2-(4-(6-(2-chloro-3,4-difluorophenyl)-2-(3,5-difluoropyridin-2-yl)-5-(methoxycarbonyl)-3,6-dihydropyrimidin-4-yl)cyclohexyl)oxazole-4-carboxylate (a Mixture of 2 Stereoisomers)

By utilizing the analogous procedure of Method B, the title compound was synthesized.

LC-MS (ESI): $R_T$=2.052 min, mass calcd. for $C_{28}H_{23}ClF_4N_4O_5$ 606.0, m/z found 607.1 [M+H]$^+$. $^1$H NMR (300 MHz, CDCl$_3$) δ 8.70 (s, 1H), 8.34-8.20 (m, 2H), 7.09-6.97 (m, 2H), 6.30 (d, J=6.0 Hz, 0.8H), 6.05-6.02 (m, 0.2H), 4.17-4.08 (m, 1H), 3.95 (s, 2.4H), 3.93 (s, 0.6H), 3.61 (s, 3H), 3.41-3.34 (m, 1H), 2.54-2.46 (m, 1H), 2.38-2.11 (m, 1H), 2.05-1.91 (m, 3H), 1.86-1.82 (m, 2H), 1.71-1.58 (m, 1H).

A stereoisomeric mixture of (trans)-methyl 2-(4-(6-(2-chloro-3,4-difluorophenyl)-2-(3,5-difluoropyridin-2-yl)-(methoxycarbonyl)-3,6-dihydropyrimidin-4-yl)cyclohexyl) oxazole-4-carboxylate VII-7-S (340 mg, 90% purity, 0.504 mmol) was separated by chiral Prep. HPLC (separation condition: Column: Chiralpak IC 5 μm 20*250 mm; Mobile Phase: Hex:EtOH=50:50 at 11 mL/min; Temp: 30° C.; Wavelength: 214 nm) to afford the desired compounds VII-7-M (36 mg, 90% purity from $^1$H NMR, 11% yield, 100% stereopure) and VII-7-N (101 mg, 90% purity from $^1$H NMR, 30% yield, 98.5% stereopure) as yellow solids.

VII-7-M: Chiral analysis: (Column: Chiralpak IC 5 μm 4.6*250 mm; Mobile Phase: Hex:EtOH:DEA=50:50:0.2 at 1 mL/min; Temp: 40° C.; Wavelength: 230 nm, Back pressure: 100 bar, $R_T$=7.887 min). $^1$H NMR (400 MHz, DMSO-d$_6$) δ 9.32 (s, 0.7H), 9.21 (s, 0.3H), 8.79 (s, 0.7H), 8.77 (s, 0.3H), 8.58 (d, J=7.2 Hz, 1H), 8.10-8.04 (m, 1H), 7.54-7.44 (m, 1H), 7.25-7.16 (m, 1H), 6.04 (s, 0.7H), 5.94 (d, J=2.4 Hz, 0.3H), 4.00-3.92 (m, 0.6H), 3.80 (s, 3H), 3.70-3.64 (m, 0.4H), 3.53 (s, 2H), 3.51 (s, 1H), 2.95-2.84 (m, 1H), 2.29-2.16 (m, 2H), 1.98-1.77 (m, 4H), 1.68-1.54 (m, 2H).

VII-7-N: Chiral analysis: (Column: Chiralpak IC 5 μm 4.6*250 mm; Mobile Phase: Hex:EtOH=50:50 at 1 mL/min; Temp: 30° C.; Wavelength: 230 nm, Back pressure: 100 bar, $R_T$=12.115 min). $^1$H NMR (400 MHz, DMSO-d$_6$) δ 9.31 (s, 0.7H), 9.21 (s, 0.3H), 8.79 (s, 0.7H), 8.77 (s, 0.3H), 8.59-8.57 (m, 1H), 8.10-8.05 (m, 1H), 7.53-7.44 (m, 1H), 7.25-7.17 (m, 1H), 6.05 (s, 0.7H), 5.94 (d, J=3.2 Hz, 0.3H), 3.99-3.93 (m, 0.7H), 3.80 (s, 3H), 3.71-3.63 (m, 0.3H), 3.54

(s, 2H), 3.51 (s, 1H), 2.95-2.85 (m, 1H), 2.23-2.13 (m, 2H), 1.97-1.80 (m, 4H), 1.70-1.53 (m 2H).

Compound VII-8-N methyl 2-(3-(6-(2-chloro-3,4-difluorophenyl)-5-(methoxycarbonyl)-2-(thiazol-2-yl)-3,6-dihydropyrimidin-4-yl)bicyclo[1.1.1]pentan-1-yl)oxazole-4-carboxylate (a Single Stereoisomer)

Intermediate VII-8-R

Methyl 2-(3-(6-(2-chloro-3,4-difluorophenyl)-5-(methoxycarbonyl)-2-(thiazol-2-yl)-3,6-dihydropyrimidin-4-yl)bicyclo[1.1.1]pentan-1-yl)oxazole-4-carboxylate (a Mixture of 2 Stereoisomers)

By utilizing the analogous procedure of Method B, the title compound was synthesized as yellow solids. LC-MS (ESI): $R_T$=1.77 min, mass calcd. for $C_{25}H_{19}ClF_2N_4O_5S$, 560.1, m/z found 561.2 $[M+H]^+$. $^1H$ NMR (400 MHz, DMSO-$d_6$) δ 9.62 (d, J=3.2 Hz, 0.6H), 8.83 (s, 0.4H), 8.80 (s, 0.6H), 8.49 (s, 0.4H), 8.03-8.01 (m, 1.6H), 7.97-7.96 (m, 0.4H), 7.51-7.44 (m, 1H), 7.23-7.17 (m, 1H), 6.00 (s, 0.4H), 5.91 (d, J=3.2 Hz, 0.6H), 3.80 (s, 3H), 3.58-3.57 (m, 3H), 2.68 (s, 2.3H), 2.52 (s, 3.7H).

A stereoisomeric mixture of methyl 2-(3-(6-(2-chloro-3,4-difluorophenyl)-5-(methoxycarbonyl)-2-(thiazol-2-yl)-3,6-dihydropyrimidin-4-yl)bicyclo[1.1.1]pentan-1-yl)oxazole-4-carboxylate VII-8-R (150 mg, 95% purity, 0.254 mmol) was separated by chiral Prep. HPLC (separation condition: Column: Chiralpak IE 5 μm 20*250 mm; Mobile Phase: Hex:EtOH:DEA=70:30:0.2 at 12 mL/min; Temp: 30° C.; Wavelength: 230 nm) to afford the title compounds VII-8-M (60 mg, 95% purity, 40% yield, 100% stereopure) and VII-8-N (60 mg, 95% purity, 40% yield, 100% stereopure) as yellow solids.

VII-8-M: LC-MS (ESI): $R_T$=1.80 min, mass calcd. for $C_{25}H_{19}ClF_2N_4O_5S$, 560.1, m/z found 561.0 $[M+H]^+$. Chiral HPLC (Column: Chiralpak IE 5 μm 4.6*250 mm; Mobile Phase: Hex:EtOH:DEA=70:30:0.2 at 1.0 mL/min; Temp: 30° C.; Wavelength: 230 nm, $R_T$=11.217 min). $^1H$ NMR (400 MHz, CDCl$_3$) δ 8.19 (d, J=2.0 Hz, 1H), 7.93 (s, 0.7H), 7.84-7.82 (m, 1H), 7.51 (d, J=3.2 Hz, 0.3H), 7.46 (d, J=3.2 Hz, 0.7H), 7.42 (s, 0.3H), 7.10-7.01 (m, 2H), 6.17 (s, 0.7H), 6.05 (d, J=1.6 Hz, 0.3H), 3.93 (s, 3H), 3.66 (s, 1H), 3.62 (s, 2H), 2.76 (s, 4H), 2.70 (s, 2H).

VII-8-N: LC-MS (ESI): $R_T$=1.80 min, mass calcd. for $C_{25}H_{19}ClF_2N_4O_5S$, 560.1, m/z found 561.0 $[M+H]^+$. Chiral HPLC (Column: Chiralpak IE 5 μm 4.6*250 mm; Mobile Phase: Hex:EtOH:DEA=70:30:0.2 at 1.0 mL/min; Temp: 30° C.; Wavelength: 230 nm, $R_T$=15.313 min). $^1H$ NMR (400 MHz, CDCl$_3$) δ 8.19 (d, J=2.0 Hz, 1H), 7.93 (s, 0.7H), 7.84-7.82 (m, 1H), 7.51 (d, J=3.2 Hz, 0.3H), 7.46 (d, J=3.2 Hz, 0.7H), 7.42 (s, 0.3H), 7.10-7.01 (m, 2H), 6.17 (s, 0.7H), 6.05 (d, J=2.4 Hz, 0.3H), 3.93 (s, 3H), 3.66 (s, 1H), 3.62 (s, 2H), 2.76 (s, 4H), 2.70 (s, 2H).

Compound VII-9-F (trans)-methyl 2-(4-(6-(2-chloro-3-fluorophenyl)-5-(ethoxycarbonyl)-2-(thiazol-2-yl)-3,6-dihydropyrimidin-4-yl)cyclohexyl)oxazole-4-carboxylate (a Single Stereoisomer)

Intermediates VII-9-M and VII-9-N (cis)-methyl 2-(4-(6-(2-chloro-3-fluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers)

And (trans)-methyl 2-(4-(6-(2-chloro-3-fluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compound was synthesized as yellow solids.

VII-9-M: LC-MS (ESI): $R_T$=4.322 min, mass calcd. for $C_{27}H_{26}ClFN_4O_5S$, 572.1, m/z found 572.9 $[M+H]^+$. $^1H$ NMR (400 MHz, CDCl$_3$) δ 8.29 (s, 0.6H), 8.26 (s, 0.4H), 8.14 (s, 0.6H), 7.81-7.76 (m, 1H), 7.44 (d, J=3.2 Hz, 0.4H), 7.41 (d, J=3.2 Hz, 0.6H), 7.31-7.29 (m, 0.4H), 7.21-7.09 (m, 2H), 7.09-6.98 (m, 1H), 6.27 (s, 0.6H), 6.14-6.09 (d, J=8.0 Hz, 0.4H), 4.14-3.97 (m, 3H), 3.94 (s, 2H), 3.92 (s, 1H), 3.38-3.33 (m, 0.6H), 3.31-3.26 (m, 0.4H), 2.58-2.43 (m, 2H), 2.15-2.03 (m, 0.5H), 1.99-1.89 (m, 2.5H), 1.89-1.77 (m, 2H), 1.77-1.63 (m, 1H), 1.16-1.08 (m, 3H).

VII-9-N: LC-MS (ESI): $R_T$=4.420 min, mass calcd. for $C_{27}H_{26}ClFN_4O_5S$, 572.1, m/z found 573.1 $[M+H]^+$. $^1H$ NMR (400 MHz, DMSO-$d_6$) δ 9.50 (d, J=3.6 Hz, 0.6H), 8.98 (s, 0.4H), 8.79 (s, 0.4H), 8.78 (s, 0.6H), 8.01-7.94 (m, 2H), 7.42-7.28 (m, 2H), 7.24-7.17 (m, 1H), 6.09 (s, 0.4H), 5.98 (d, J=3.6 Hz, 0.6H), 4.01-3.94 (m, 2H), 3.93-3.88 (m, 0.3H), 3.80 (s, 3H), 3.71-3.60 (m, 0.7H), 3.10-3.03 (m, 0.4H), 2.94-2.85 (m, 0.6H), 2.26-2.11 (m, 2H), 2.01-1.86 (m, 2.3H), 1.86-1.67 (m, 1.7H), 1.66-1.48 (m, 2H), 1.11-1.00 (m, 3H).

A stereoisomeric mixture of VII-9-N (740 mg, 99.7% purity, 1.29 mmol) was separated by chiral Prep. HPLC (Column: Chiralpak IE 5 μm 20*250 mm; Mobile Phase: Hex:EtOH:DEA=60:40:0.3 at 10 ml/min; Temp: 30° C.; Wavelength: 214 nm) to afford the title compounds VII-9-E (210 mg, 98.8% purity, 28% yield, 100% ee) as yellow solids and VII-9-F (229 mg, 98.1% purity, 31% yield, 99.7% ee) as yellow solids.

VII-9-E: LC-MS (ESI): $R_T$=4.253 min, mass calcd. for $C_{27}H_{26}ClFN_4O_5S$, 572.1, m/z found 573.1 $[M+H]^+$. $^1H$ NMR (400 MHz, CDCl$_3$) δ 8.18 (s, 1H), 8.13 (s, 0.5H), 7.83 (s, 0.5H), 7.82 (s, 0.5H), 7.50 (d, J=3.2 Hz, 0.5H), 7.45 (d, J=3.2 Hz, 0.5H), 7.36 (s, 0.5H), 7.24-7.12 (m, 2H), 7.11-6.99 (m, 1H), 6.28 (s, 0.5H), 6.14 (d, J=2.4 Hz, 0.5H), 4.10-3.98 (m, 2.5H), 3.92 (s, 3H), 3.88-3.79 (m, 0.5H), 3.03-2.93 (m, 1H), 2.38-2.16 (m, 2.8H), 2.12-2.00 (m, 1.5H), 1.94-1.65 (m, 3.7H), 1.16-1.09 (m, 3H).

VII-9-F: LC-MS (ESI): $R_T$=2.265 min, mass calcd. for $C_{27}H_{26}ClFN_4O_5S$, 572.1, m/z found 573.1 $[M+H]^+$. $^1H$ NMR (400 MHz, CDCl$_3$) δ 8.18 (s, 1H), 8.13 (s, 0.5H), 7.84-7.81 (m, 1H), 7.50 (d, J=3.2 Hz, 0.5H), 7.45 (d, J=2.8 Hz, 0.5H), 7.37 (d, J=2.4 Hz, 0.5H), 7.24-7.13 (m, 2H), 7.10-7.00 (m, 1H), 6.28 (s, 0.5H), 6.14 (d, J=2.8 Hz, 0.5H), 4.09-4.01 (m, 2.5H), 3.92 (s, 3H), 3.87-3.79 (m, 0.5H), 3.03-2.93 (m, 1H), 2.38-2.16 (m, 2.8H), 2.12-2.02 (m, 1.4H), 1.96-1.74 (m, 3.1H), 1.74-1.64 (m, 0.7H), 1.17-1.09 (m, 3H).

Compound VII-10-P (trans)-Methyl 2-(4-(6-(2-chloro-4-fluorophenyl)-5-(ethoxycarbonyl)-2-(thiazol-2-yl)-3,6-dihydropyrimidin-4-yl)cyclohexyl)oxazole-4-carboxylate (a Single Stereoisomer)

Intermediates: VII-10-X and VII-10-Y (cis)-Methyl 2-(4-(6-(2-chloro-4-fluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers) & (trans)-methyl 2-(4-(6-(2-chloro-4-fluorophenyl)-5-(ethoxycarbonyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compounds were synthesized as yellow solids.

VII-10-X: LC-MS (ESI): $R_T$=3.644 min, mass calcd. for $C_{27}H_{26}ClFN_4O_5S$, 572.1, m/z found 572.9 [M+H]$^+$. $^1$H NMR (400 MHz, $CD_3OD$) δ 8.55 (d, J=3.2 Hz, 1H), 7.86-7.84 (m, 1H), 7.71-6.68 (m, 1H), 7.40-7.34 (m, 1H), 7.25-7.20 (m, 1H), 7.06-7.00 (m, 1H), 6.13 (s, 0.5H), 6.05 (s, 0.5H), 4.07-4.01 (m, 2.5H), 3.91-3.81 (m, 3.5H), 3.37-3.31 (m, 0.5H), 3.30-3.24 (m, 0.5H), 2.55-2.42 (m, 2H), 2.10-1.79 (m 4H), 1.77-1.72 (m, 1.5H), 1.57-1.53 (m 0.5H), 1.14 (t, J=7.2 Hz, 3H).

VII-10-Y: LC-MS (ESI): $R_T$=2.496 min, mass calcd. for $C_{27}H_{26}ClFN_4O_5S$, 572.1, m/z found 572.9 [M+H]$^+$. $^1$H NMR (400 MHz, $CD_3OD$) δ 8.48 (s, 1H), 8.29-8.26 (m, 2H), 7.57-7.53 (m, 1H), 7.4-27.40 (m, 1H), 7.24-7.19 (m, 1H), 6.32 (s, 1H), 4.17-4.10 (m, 2H), 3.99-3.92 (m, 1H), 3.88 (s, 3H), 3.05-2.97 (m, 1H), 2.32-2.29 (m, 2H), 2.06-1.83 (m, 4H), 1.76-1.68 (m, 2H), 1.18 (t, J=7.2 Hz, 3H).

A stereoisomeric mixture of (trans)-methyl 2-(4-(6-(2-chloro-4-fluorophenyl)-5-(ethoxycarbonyl)-2-(thiazol-2-yl)-3,6-dihydropyrimidin-4-yl)cyclohexyl)oxazole-4-carboxylate VII-10-Y (200 mg, 90% purity, 0.314 mmol) was separated by chiral Prep. HPLC (Column: Chiralpak S-OJ 5 μm 21*250 mm; Mobile Phase: Hex:EtOH:DEA=70:30:0.05 at 20 mL/min; Temp: 35° C.; Wavelength: 254 nm) to give the title compounds VII-10-P (80 mg, 99% purity, 44% yield, 98.6% stereopure) as yellow solids and VII-10-Q (75 mg, 99.2% purity, 41% yield, 99.9% stereopure) as yellow solids.

VII-10-P: LC-MS (ESI): $R_T$=4.289 min, mass calcd. for $C_{27}H_{26}ClFN_4O_5S$, 572.1, m/z found 572.9 [M+H]$^+$. Chiral analysis (Column: Chiralpak S-OJ 5 μm 4.6*150 mm; Mobile Phase: Hex:EtOH:DEA=70:30:0.05 at 1 mL/min; Wavelength: 254 nm, $R_T$=5.657 min). $^1$H NMR (400 MHz, $CD_3OD$) δ 8.37 (s, 0.5H), 8.36 (s, 0.5H), 7.84-7.83 (m, 0.5H), 7.80-7.79 (m, 0.5H), 7.66-7.65 (m, 1H), 7.34-7.29 (m, 1H), 7.16-7.11 (m, 1H), 6.99-6.92 (m, 1H), 6.06 (s, 0.5H), 5.99 (s, 0.5H), 3.98-3.92 (m, 2.5H), 3.79 (s, 3H), 3.74-3.67 (m, 0.5H), 2.98-2.80 (m, 1H), 2.24-2.03 (m, 2H), 1.93-1.60 (m, 6H), 1.07-1.02 (m, 3H).

VII-10-Q: LC-MS (ESI): $R_T$=4.289 min, mass calcd. for $C_{27}H_{26}ClFN_4O_5S$, 572.1, m/z found 572.9 [M+H]$^+$. Chiral analysis (Column: Chiralpak S-OJ 5 μm 4.6*150 mm; Mobile Phase: Hex:EtOH:DEA=70:30:0.05 at 1 mL/min; Wavelength: 254 nm, $R_T$=7.812 min). $^1$H NMR (400 MHz, $CD_3OD$) δ 8.50 (s, 0.5H), 8.49 (s, 0.5H), 7.97-7.96 (m, 0.5H), 7.92-7.92 (m, 0.5H), 7.78-7.77 (m, 0.5H), 7.46-7.42 (m, 1H), 7.28-7.23 (m, 1H), 7.11-7.04 (m, 1H), 6.18 (s, 0.5H), 6.11 (s, 0.5H), 4.10-4.05 (m, 2.5H), 3.91 (s, 3H), 3.86-3.80 (m, 0.5H), 3.14-2.93 (m, 1H), 2.37-2.21 (m, 2H), 2.14-1.73 (m, 6H), 1.17 (t, J=7.2 Hz, 3H).

Compound VII-11-Q (trans)-methyl 2-(4-(5-(ethoxycarbonyl)-6-(3-fluoro-2-methylphenyl)-2-(thiazol-2-yl)-3,6-dihydropyrimidin-4-yl)cyclohexyl)oxazole-4-carboxylate (a Single Stereoisomer)

Intermediates VII-11-M and VII-11-N (cis)-Methyl 2-(4-(5-(ethoxycarbonyl)-6-(3-fluoro-2-methylphenyl)-2-(thiazol-2-yl)-3,6-dihydropyrimidin-4-yl)cyclohexyl)oxazole-4-carboxylate (a Mixture of 2 Stereoisomers) and (trans)-methyl 2-(4-(5-(ethoxycarbonyl)-6-(3-fluoro-2-methylphenyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compound was synthesized as yellow solids.

VII-11-M: $^1$H NMR (400 MHz, $CDCl_3$) δ 8.27 (s, 1H), 8.12 (s, 1H), 7.76 (d, J=3.2 Hz, 1H), 7.46-7.43 (m, 0.2H), 7.42-7.37 (m, 0.8H), 7.14-6.99 (m, 2H), 6.97-6.84 (m, 1H), 6.01 (s, 0.8H), 5.90 (s, 0.2H), 4.16-3.98 (m, 3H), 3.94 (s, 3H), 3.40-3.33 (m, 0.8H), 3.31-3.25 (m, 0.2H), 2.57-2.45 (m, 4.5H), 2.41-2.36 (m, 0.5H), 1.98-1.91 (m, 1H), 1.86-1.80 (m, 2H), 1.75-1.67 (m, 3H), 1.13 (t, J=7.2 Hz, 3H).

VII-11-N: $^1$H NMR (300 MHz, $CDCl_3$) δ 8.24 (s, 1H), 8.19-8.11 (m, 1H), 7.89-7.83 (m, 1H), 7.57-7.45 (m, 1H), 7.19-7.05 (m, 2H), 7.01-6.91 (m, 1H), 6.07 (s, 0.8H), 5.99 (s, 0.2H), 4.13-4.04 (m, 3H), 3.98 (s, 3H), 3.02-2.99 (m, 1H), 2.64-2.55 (m, 2H), 2.52-2.22 (m, 4H), 2.03-1.83 (m, 3H), 1.81-1.58 (m, 2H), 1.81 (t, J=7.2 Hz, 3H).

A stereoisomeric mixture of (trans)-methyl 2-(4-(5-(ethoxycarbonyl)-6-(3-fluoro-2-methylphenyl)-2-(thiazol-2-yl)-3,6-dihydropyrimidin-4-yl)cyclohexyl)oxazole-4-carboxylate VII-11-N (376 mg, 90% purity, 0.612 mmol) was separated by chiral Prep. SFC (Column: Chiralpak IC 5 μm 20*250 mm; Mobile Phase: $CO_2$:EtOH:DEA=70:30:0.3 at 50 g/min; Col. Temp: 40° C.; Wavelength: 214 nm; Back pressure: 100 bar) to afford the compounds VII-11-P (165 mg, 95% purity from 25 $^1$H NMR, yield 46%, 100% stereopure) and VII-11-Q (150 mg, 95% purity from $^1$H NMR, yield 42% 100% stereopure) as yellow solids.

VII-11-P: Chiral analysis (Column: Chiralpak IC 5 μm 4.6*250 mm; Mobile Phase: $CO_2$:EtOH:DEA=70:30:0.2 at 3 g/min; Col. Temp: 40° C.; Wavelength: 280 nm, Back pressure: 100 bar; $R_T$=4.38 min). $^1$H NMR (300 MHz, $CDCl_3$) δ 8.19 (s, 1H), 8.10 (s, 0.7H), 7.83-7.78 (m, 1H), 7.52-7.40 (m, 1H), 7.16-7.00 (m, 2.3H), 6.96-6.87 (m, 1H), 6.02 (s, 0.8H), 5.97-5.91 (m, 0.2H), 4.09-4.02 (m, 2.8H), 3.92 (s, 3H), 3.77-3.69 (m, 0.2H), 2.94-2.91 (m, 1H), 2.54 (s, 2.5H), 2.45-2.41 (m, 0.5H), 2.37-2.18 (m, 3H), 2.13-2.08 (m, 0.5H), 1.94-1.79 (m, 2.5H), 1.76-1.54 (m 2H), 1.13 (t, J=7.2 Hz, 3H).

VII-11-Q: Chiral analysis (Column: Chiralpak IC 5 μm 4.6*250 mm; Mobile Phase: $CO_2$:EtOH:DEA=70:30:0.2 at 3 g/min; Col. Temp: 40° C.; Wavelength: 280 nm, Back pressure: 100 bar; $R_T$=5.03 min). $^1$H NMR (300 MHz, $CDCl_3$) δ 8.19 (s, 1H), 8.10 (s, 0.7H), 7.83-7.78 (m, 1H), 7.53-7.49 (m, 0.2H), 7.49-7.41 (m, 0.8H), 7.18-7.15 (m, 0.3H), 7.13-7.01 (m, 2H), 6.99-6.86 (m, 1H), 6.03 (s, 0.8H), 5.96-5.91 (m, 0.2H), 4.11-4.03 (m, 2.7H), 3.93 (s, 3H), 3.78-3.67 (m, 0.3H), 2.97-2.94 (m, 1H), 2.55 (s, 2.5H), 2.42-2.41 (m, 0.5H), 2.37-2.18 (m, 3H), 2.13-2.05 (m, 1.3H), 1.95-1.78 (m, 2.7H), 1.71-1.60 (m, 1H), 1.14 (t, J=7.2 Hz, 3H).

Compound VII-12-P (trans)-Methyl 2-(4-(5-(ethoxycarbonyl)-6-(4-fluoro-2-methylphenyl)-2-(thiazol-2-yl)-3,6-dihydropyrimidin-4-yl)cyclohexyl)oxazole-4-carboxylate (a Single Stereoisomer)

Intermediates VII-12-X & VII-12-Y (cis)-Methyl 2-(4-(5-(ethoxycarbonyl)-6-(4-fluoro-2-methylphenyl)-2-(thiazol-2-yl)-3,6-dihydropyrimidin-4-yl)cyclohexyl)oxazole-4-carboxylate (a Mixture of 2 Stereoisomers) & (trans)-methyl 2-(4-(5-(ethoxycarbonyl)-6-(4-fluoro-2-methylphenyl)-2-(thiazol-2-yl)-3,6-dihydropyrimidin-4-yl)cyclohexyl)oxazole-4-carboxylate (a Mixture of 2 Stereoisomers)

By utilizing the analogous procedure of Method B, the title compound was synthesized as yellow solids.

VII-12-X: LC-MS (ESI): $R_T$=3.737 min, mass calcd. for $C_{28}H_{29}FN_4O_5S$, 552.2, m/z found 553.0 [M+H]$^+$. $^1$H NMR (400 MHz, CDCl$_3$) δ 8.27 (s, 1H), 8.10 (s, 0.7H), 7.76 (d, J=3.2 Hz, 1H), 7.45 (d, J=3.2 Hz, 0.3H), 7.39 (d, J=3.2 Hz, 0.8H), 7.30-7.26 (m, 0.2H), 7.17-7.14 (m, 0.8H), 6.92-6.74 (m, 2.2H), 5.95 (s, 0.8H), 5.84 (d, J=2.0 Hz, 0.2H), 4.11-3.99 (m, 3H), 3.94 (s, 2H), 3.93 (s, 1H), 3.36 (s, 0.8H), 3.28 (s, 0.2H), 2.62 (s, 2.3H), 2.55-2.47 (m, 2.7H), 2.04-1.69 (m, 6H), 1.15-1.10 (m, 3H).

VII-12-Y: LC-MS (ESI): $R_T$=4.521 min, mass calcd. for $C_{28}H_{29}FN_4O_5S$, 552.2, m/z found 553.1 [M+H]$^+$. $^1$H NMR (400 MHz, CDCl$_3$) δ 8.19 (s, 0.7H), 8.18 (s, 0.3H), 8.08 (s, 0.7H), 7.81-7.80 (m, 1H), 7.50 (d, J=3.2 Hz, 0.3H), 7.42 (d, J=2.8 Hz, 0.7H), 7.33-7.29 (m, 0.3H), 7.20-7.17 (m, 0.7H), 6.97-6.90 (m, 0.3H), 6.84-6.77 (m, 2H), 5.97 (s, 0.7H), 5.87 (d, J=2.0 Hz, 0.3H), 4.11-4.01 (m, 3H), 3.92 (d, J=2.0 Hz, 3H), 3.02-2.94 (m, 1H), 2.64 (s, 2H), 2.49 (s, 1H), 2.38-2.22 (m, 2.7H), 2.10-1.62 (m, 5.3H), 1.13 (d, J=7.2 Hz, 3H).

A stereoisomeric mixture of (trans)-methyl 2-(4-(5-(ethoxycarbonyl)-6-(4-fluoro-2-methylphenyl)-2-(thiazol-2-yl)-3,6-dihydropyrimidin-4-yl)cyclohexyl)oxazole-4-carboxylate VII-12-Y (120 mg, 95% purity, 0.206 mmol) was separated by chiral Prep. HPLC (Column: Chiralpak IC 5 μm 20*250 mm; Mobile Phase: Hex:EtOH:DEA=80:20:0.3 at 25 mL/min; Temp: 30° C.; Wavelength: 214 nm) to give the title compounds VII-12-P (65 mg, 95.5% purity, 54% yield, 100% stereopure) and VII-12-Q (50 mg, 97.8% purity, 43% yield, 95.3% stereopure) as yellow solids.

VII-12-P: LC-MS (ESI): $R_T$=2.037 min, mass calcd. for $C_{28}H_{29}FN_4O_5S$, 552.2, m/z found 553.1 [M+H]$^+$. Chiral analysis (Column: Chiralpak IC 5 μm 4.6*250 mm; Mobile Phase: Hex:EtOH:DEA=80:20:0.2 at 1 mL/min; Wavelength: 230 nm, $R_T$=12.418 min). $^1$H NMR (400 MHz, CDCl$_3$) δ 8.18 (d, J=2.8 Hz, 1H), 8.08 (s, 0.7H), 7.81-7.80 (m, 1H), 7.50 (d, J=2.8 Hz, 0.3H), 7.42 (d, J=3.6 Hz, 0.7H), 7.34-7.30 (m, 0.3H), 7.20-7.17 (m, 0.8H), 6.98-6.97 (m, 0.2H), 6.89-6.75 (m, 2H), 5.97 (s, 0.7H), 5.87 (d, J=2.0 Hz, 0.3H), 4.12-4.00 (m, 3H), 3.93 (s, 2H), 3.92 (s, 1H), 3.03-2.93 (m, 1H), 2.63 (s, 2H), 2.49 (s, 1H), 2.37-2.21 (m, 3H), 2.04-1.67 (m, 5H), 1.13 (t, J=7.2 Hz, 3H).

VII-12-Q: LC-MS (ESI): $R_T$=2.037 min, mass calcd. for $C_{28}H_{29}FN_4O_5S$, 552.2, m/z found 553.1 [M+H]$^+$. Chiral analysis (Column: Chiralpak IC 5 μm 4.6*250 mm; Mobile Phase: Hex:EtOH:DEA=80:20:0.2 at 1 mL/min; Wavelength: 230 nm, $R_T$=13.758 min). $^1$H NMR (400 MHz, CDCl$_3$) δ 8.18 (d, J=3.2 Hz, 1H), 8.08 (s, 0.7H), 7.81-7.80 (m, 1H), 7.50 (d, J=3.2 Hz, 0.3H), 7.42 (d, J=3.2 Hz, 0.7H), 7.34-7.30 (m, 0.3H), 7.20-7.17 (m, 0.8H), 6.97-6.95 (m, 0.2H), 6.90-6.77 (m, 2H), 5.97 (s, 0.7H), 5.87 (d, J=2.0 Hz, 0.3H), 4.11-4.00 (m, 3H), 3.93 (s, 2H), 3.92 (s, 1H), 3.01-2.93 (m, 1H), 2.63 (s, 2.2H), 2.49 (s, 0.8H), 2.37-2.22 (m, 3H), 2.10-1.65 (m, 5H), 1.13 (d, J=7.2 Hz, 3H).

Compound VII-13-P and Compound VII-13-Q 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylate (a Single Stereoisomer) and 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylate (a Single Stereoisomer)

Intermediates VII-13-R

Ethyl 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylate (a Mixture of 4 Stereoisomers)

By utilizing the analogous procedure of Method B, the title compounds were synthesized.

Intermediate VII-13-R: LC-MS (ESI): $R_T$=4.032 min, mass calcd. for $C_{28}H_{25}ClF_2N_4O_5S$, 602.1, m/z found 602.9 [M+H]$^+$. $^1$H NMR (400 MHz, DMSO-d$_6$) δ 9.64-9.61 (m, 0.8H), 9.15 (s, 0.1H), 9.08 (s, 0.1H), 8.81-8.78 (m, 1H), 8.00-7.94 (m, 2H), 7.51-7.45 (m, 1H), 7.28-7.20 (m, 1H), 6.94-6.90 (m, 1H), 6.07 (s, 0.1H), 6.05 (s, 0.1H), 5.97-5.95 (m, 0.8H), 4.29 (q, J=7.2 Hz, 2H), 4.14 (br s, 0.2H), 4.00-3.89 (m, 2.8H), 2.75-2.58 (m, 2H), 2.49-2.26 (m, 2H), 2.08-1.83 (m, 2H), 1.30 (t, J=7.2 Hz, 3H), 1.08-1.01 (m, 3H).

A stereoisomeric mixture of ethyl 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylate VII-13-R (420 mg, 99.7% purity, 0.69 mmol) was separated by chiral prep. HPLC (the first separation condition: Column: Chiralpak ID 5 μm 20*250 mm; Mobile Phase: Hex:EtOH:DEA=70:30:0.3 at 15 mL/min; Wavelength: 214 nm; the second separation condition: Column: Chiralpak IF 5 μm 20*250 mm; Mobile Phase: CO$_2$:MeOH=60:40 at 45 g/min; Col. Temp 40° C.; Wavelength: 254 nm; Back pressure: 100 bar; the third separation condition: Column: Chiralpak ID 5 μm 20*250 mm; Mobile Phase: Hex:EtOH:DEA=70:30:0.3 at 15 mL/min; Wavelength: 214 nm) to give the title compounds VII-13-M (60 mg, 96.5% purity, 34% yield, 98.2% de), VII-13-N (80 mg, 95.2% purity, 45% yield, 98.4% de), VII-13-P (60 mg, 99.1% purity, 38% yield, 100% de) and VII-13-Q (70 mg, 99.7% purity, 44% yield, 99.5% de).

VII-13-M: LC-MS (ESI): $R_T$=4.227 min, mass calcd. for $C_{28}H_{25}ClF_2N_4O_5S$, 602.1, m/z found 603.1 [M+H]$^+$. Chiral HPLC (Column: Chiralpak IF 5 μm 4.6*250 mm; Mobile Phase: CO$_2$:MeOH=60:40 at 3 g/min; Temp: 40° C.; Wavelength: 254 nm, $R_T$=3.85 min). $^1$H NMR (400 MHz, DMSO-d$_6$) δ 9.63 (d, J=3.2 Hz, 0.7H), 9.17 (s, 0.3H), 8.81-8.79 (m, 1H), 8.01-7.93 (m, 2H), 7.51-7.45 (m, 1H), 7.26-7.20 (m, 1H), 6.93-6.90 (m, 1H), 6.07 (s, 0.3H), 5.97 (d, J=3.6 Hz, 0.7H), 4.29 (q, J=7.2 Hz, 2H), 4.13 (br s, 0.3H), 4.00-3.88 (m, 2.7H), 2.78-2.59 (m, 2H), 2.46-2.36 (m, 2H), 2.10-1.82 (m, 2H), 1.29 (t, J=7.2 Hz, 3H), 1.08-1.01 (m, 3H).

VII-13-N: LC-MS (ESI): R$_T$=4.113 min, mass calcd. for C$_{28}$H$_{25}$ClF$_2$N$_4$O$_5$S, 602.1, m/z found 602.9 [M+H]$^+$. Chiral HPLC (Column: Chiralpak IF 5 μm 4.6*250 mm; Mobile Phase: CO$_2$:MeOH=60:40 at 3 g/min; Temp: 40° C.; Wavelength: 254 nm, R$_T$=5.43 min). $^1$H NMR (400 MHz, DMSO-d$_6$) δ 9.65 (d, J=3.2 Hz, 0.7H), 9.09 (s, 0.3H), 8.81-8.79 (m, 1H), 8.02-7.94 (m, 2H), 7.53-7.47 (m, 1H), 7.28-7.25 (m, 1H), 6.91-6.88 (m, 1H), 6.05 (s, 0.2H), 5.96 (d, J=3.2 Hz, 0.8H), 4.29 (q, J=7.2 Hz, 2H), 4.13 (br s, 0.3H), 4.00-3.89 (m, 2.7H), 2.76-2.58 (m, 2H), 2.44-2.26 (m, 2H), 2.20-1.99 (m, 2H), 1.30 (t, J=7.2 Hz, 3H), 1.08-1.01 (m, 3H).

VII-13-P: LC-MS (ESI): R$_T$=3.346 min, mass calcd. for C$_{28}$H$_{25}$ClF$_2$N$_4$O$_5$S, 602.1, m/z found 603.1 [M+H]$^+$. Chiral HPLC (Column: Chiralpak ID 5 μm 4.6*250 mm; Mobile Phase: Hex:EtOH:DEA=70:30:0.2 at 1.0 mL/min; Temp: 30° C.; Wavelength: 230 nm, R$_T$=8.847 min). $^1$H NMR (400 MHz, DMSO-d$_6$) δ 9.62 (d, J=3.2 Hz, 0.6H), 9.16 (s, 0.4H), 8.81-8.78 (m, 1H), 8.01-7.93 (m, 2H), 7.51-7.45 (m, 1H), 7.26-7.20 (m, 1H), 6.93-6.89 (m, 1H), 6.07 (s, 0.3H), 5.97 (d, J=2.8 Hz, 0.7H), 4.29 (q, J=7.2 Hz, 2H), 4.16-4.09 (m, 0.3H), 4.00-3.87 (m, 2.7H), 2.79-2.58 (m, 2H), 2.46-2.33 (m, 2H), 2.08-1.82 (m, 2H), 1.29 (t, J=7.2 Hz, 3H), 1.08-1.01 (m, 3H).

VII-13-Q: LC-MS (ESI): R$_T$=3.604 min, mass calcd. for C$_{28}$H$_{25}$ClF$_2$N$_4$O$_5$S, 602.1, m/z found 603.1 [M+H]$^+$. Chiral HPLC (Column: Chiralpak ID 5 μm 4.6*250 mm; Mobile Phase: Hex:EtOH:DEA=70:30:0.2 at 1.0 mL/min; Temp: 30° C.; Wavelength: 230 nm, R$_T$=13.800 min). $^1$H NMR (400 MHz, DMSO-d$_6$) δ 9.64 (d, J=3.2 Hz, 0.7H), 9.08 (s, 0.3H), 8.81-8.78 (m, 1H), 8.01-7.93 (m, 2H), 7.53-7.45 (m, 1H), 7.28-7.25 (m, 1H), 6.91-6.88 (m, 1H), 6.05 (s, 0.2H), 5.96 (d, J=3.6 Hz, 0.8H), 4.29 (q, J=7.2 Hz, 2H), 4.16-4.10 (m, 0.3H), 4.00-3.89 (m, 2.7H), 2.75-2.57 (m, 2H), 2.44-2.26 (m, 2H), 2.19-1.99 (m, 2H), 1.30 (t, J=7.2 Hz, 3H), 1.08-1.01 (m, 3H).

Compound VII-14-N (trans)-methyl 2-(4-(6-(2-chloro-3,4-difluorophenyl)-5-(ethoxycarbonyl)-2-(thiazol-2-yl)-3,6-dihydropyrimidin-4-yl)cyclohexyl)-5-methyloxazole-4-carboxylate (a Single Stereoisomer)

Intermediate VII-14-8

(trans)-Methyl 2-(4-(6-(2-chloro-3,4-difluorophenyl)-5-(ethoxycarbonyl)-2-(thiazol-2-yl)-3,6-dihydropyrimidin-4-yl)cyclohexyl)-5-methyloxazole-4-carboxylate (a Mixture of 2 Stereoisomers)

By utilizing the analogous procedure of Method B, the title compounds were synthesized as yellow solids. LC-MS (ESI): R$_T$=1.723 min, mass calcd. for C$_{28}$H$_{27}$ClF$_2$N$_4$O$_5$S, 604.1, m/z found 605.1 [M+H]$^+$. $^1$H NMR (400 MHz, CDCl$_3$) δ 8.14 (s, 0.6H), 7.83 (d, J=2.8 Hz, 1H), 7.51 (d, J=3.2 Hz, 0.4H), 7.46 (d, J=3.2 Hz, 0.6H), 7.32 (s, 0.4H), 7.12-7.01 (m, 2H), 6.21 (s, 0.6H), 6.08 (d, J=2.8 Hz, 0.4H), 4.10-4.02 (m, 2.6H), 3.91 (s, 3H), 3.81 (br s, 0.4H), 2.93-2.87 (m, 1H), 2.61 (s, 3H), 2.29-1.63 (m, 8H), 1.17-1.12 (m, 3H).

A stereoisomeric mixture of (trans)-methyl 2-(4-(6-(2-chloro-3,4-difluorophenyl)-5-(ethoxycarbonyl)-2-(thiazol-2-yl)-3,6-dihydropyrimidin-4-yl)cyclohexyl)-5-methyloxazole-4-carboxylate VII-14-8 (630 mg, 99% purity, 1.03 mmol) was separated by chiral Prep. HPLC (separation condition: Column: Chiralpak IA 5 μm 30*250 mm; Mobile Phase: Hex:EtOH:DEA=60:40:0.3 at 22 mL/min; Wavelength: 214 nm) to give the title compound VII-14-M (200 mg, 98.7% purity, 32% yield, 100% stereopure) as yellow solids and another isomer (190 mg, 88% stereopure), which was further purified by chiral Prep. HPLC (Column: Chiralpak IA 5 μm 30*250 mm; Mobile Phase: Hex:EtOH:DEA=80:20:0.3 at 22 mL/min; Wavelength: 214 nm) to give the title compound VII-14-N (60 mg, 99.9% purity, 9.6% yield, 99.6% stereopure) as yellow solids.

VII-14-M: LC-MS (ESI): R$_T$=3.051 min, mass calcd. for C$_{28}$H$_{27}$ClF$_2$N$_4$O$_5$S, 604.1, m/z found 604.9 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, R$_T$=9.303 min). $^1$H NMR (400 MHz, DMSO-d$_6$) δ 9.56 (d, J=3.6 Hz, 0.6H), 9.00 (s, 0.4H), 8.01-8.00 (m, 1.6H), 7.95 (d, J=3.2 Hz, 0.4H), 7.51-7.43 (m, 1H), 7.22-7.17 (m, 1H), 6.04 (s, 0.4H), 5.93 (d, J=3.6 Hz, 0.6H), 4.02-3.87 (m, 2.4H), 3.79 (s, 3H), 3.68-3.62 (m, 0.6H), 3.01-2.94 (m, 0.4H), 2.84-2.78 (m, 0.6H), 2.56-2.55 (m, 3H), 2.19-1.54 (m, 8H), 1.11-1.04 (m, 3H).

VII-14-N: LC-MS (ESI): R$_T$=4.134 min, mass calcd. for C$_{28}$H$_{27}$ClF$_2$N$_4$O$_5$S, 604.1, m/z found 605.0 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, R$_T$=11.057 min). $^1$H NMR (400 MHz, DMSO-d$_6$) δ 9.55 (d, J=3.2 Hz, 0.6H), 9.00 (s, 0.4H), 8.01-8.00 (m, 1.6H), 7.95 (d, J=3.2 Hz, 0.4H), 7.51-7.43 (m, 1H), 7.23-7.17 (m, 1H), 6.04 (s, 0.4H), 5.93 (d, J=3.6 Hz, 0.6H), 4.02-3.86 (m, 2.4H), 3.79 (s, 3H), 3.67-3.61 (m, 0.6H), 3.01-2.95 (m, 0.4H), 2.84-2.77 (m, 0.6H), 2.56-2.55 (m, 3H), 2.16-1.51 (m, 8H), 1.10-1.04 (m, 3H).

Compound VII-15-M (trans)-Methyl-2-((4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylate (a Single Stereoisomer)

Intermediate VII-15-R

Methyl 2-((4-(6-(2-chloro-3,4-difluorophenyl)-5-(ethoxycarbonyl)-2-(thiazol-2-yl)-3,6-dihydro pyrimidin-4-yl)cyclohexyl)methyl)oxazole-4-carboxylate (a Mixture of 4 Stereoisomers)

By utilizing the analogous procedure of Method B, the title compounds were synthesized as yellow solids.
LC-MS (ESI): R$_T$=1.94 min, mass calcd. for C$_{28}$H$_{27}$ClF$_2$N$_4$O$_5$S, 604.1, m/z found 604.9 [M+H]$^+$. $^1$H NMR (400 MHz, DMSO-d$_6$) δ 9.57-9.48 (m, 0.7H), 8.96 (s, 0.3H), 8.80-8.78 (m, 1H), 8.03-7.93 (m, 2H), 7.50-7.42 (m, 1H), 7.23-7.15 (m, 1H), 6.03-6.02 (m, 0.4H), 5.92-5.91 (m, 0.6H), 3.99-3.92 (m, 2H), 3.88-3.80 (m, 3.5H), 3.74-3.66 (m, 0.2H), 3.62-3.54 (m, 0.3H), 3.21-3.19 (m, 0.3H), 3.00-0.97 (m, 0.4H), 2.75-2.74 (m, 1.3H), 2.30-2.25 (m, 0.3H), 2.09-1.38 (m, 7.7H), 1.17-1.11 (m, 1H), 1.09-1.02 (m, 3H).

Intermediates VII-15-X and VII-15-Y (trans)-Methyl 2-((4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylate (a Mixture of 2 Stereoisomers) and (cis)-methyl 2-((4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylate (a Mixture of 2 Stereoisomers)

A mixture of methyl 2-((4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylate VII-15-R (480 mg, 95% purity, 0.75 mmol) was separated by chiral prep. HPLC (Column: Chiralpak IC 5 μm 20*250 mm; Mobile Phase: Hex:EtOH:DEA=80:20:0.3 at 15 mL/min; Temp: 30° C.; Wavelength: 254 nm) to give the title compounds VII-15-X (140 mg, 98% purity, 29% yield) and VII-15-Y (260 mg, 98% purity, 54% yield) as yellow solids.

Intermediate VII-15-X: Chiral analysis (Chiralpak IC 5 μm 4.6*250 mm; Mobile Phase: Hex:EtOH:DEA=80:20:0.2 at 1 mL/min; Temp: 30° C.; Wavelength: 254 nm, $R_T$=11.072 min and 11.491 min). $^1$H NMR (400 MHz, DMSO-$d_6$) δ 9.53 (d, J=3.6 Hz, 0.5H), 8.96 (br s, 0.5H), 8.79-8.78 (m, 1H), 8.00-7.94 (m, 2H), 7.49-7.42 (m, 1H), 7.21-7.14 (m, 1H), 6.02 (s, 0.5H), 5.91 (d, J=3.6 Hz, 0.5H), 3.99-3.92 (m, 2H), 3.86-3.80 (m, 3.5H), 3.62-3.55 (m, 0.5H), 2.79-2.70 (m, 2H), 2.02-1.57 (m, 7H), 1.18-1.02 (m, 5H).

Intermediate VII-15-Y: Chiral analysis (Chiralpak IC 5 μm 4.6*250 mm; Mobile Phase: Hex:EtOH:DEA=80:20:0.2 at 1 mL/min; Temp: 30° C.; Wavelength: 254 nm, $R_T$=14.629 min). $^1$H NMR (400 MHz, DMSO-$d_6$) δ 9.57 (d, J=3.2 Hz, 0.5H), 9.48 (s, 0.5H), 8.80-8.79 (m, 1H), 8.03-7.93 (m, 2H), 7.51-7.44 (m, 1H), 7.24-7.15 (m, 1H), 6.03 (s, 0.5H), 5.93-5.92 (d, J=3.6 Hz, 0.5H), 3.99-3.92 (m, 2H), 3.99-3.80 (m, 3.5H), 3.73-3.64 (m, 0.5H), 3.21-3.19 (m, 1H), 3.04-3.93 (m, 1H), 2.33-2.27 (m, 1H), 2.09-1.86 (m, 2H), 1.63-1.38 (m, 6H), 1.09-1.03 (m, 3H).

A stereoisomeric mixture of (trans)-methyl-4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylate VII-15-X (240 mg, 98% purity, 0.377 mmol) was separated by chiral prep. SFC (Column: Chiralpak IA 5 μm 20*250 mm; Mobile Phase: CO$_2$: IPA=75:25 at 50 g/min; Col. Temp: 40° C.; Wavelength: 214 nm, Back pressure: 100 bar) to give the compounds VII-15-M (110 mg, 95% purity, 46% yield, 100% stereopure) and VII-15-N (80 mg, 95% purity, 33% yield, 99% stereopure) as yellow solids.

VII-15-M: Chiral analysis (Chiralpak IA 5 μm 4.6*250 mm; Mobile Phase: CO$_2$: IPA=75:25 at 3 g/min; Col. Temp: 40° C.; Wavelength: 220 nm, Back pressure: 100 bar, $R_T$=4.98 min).

VII-15-N: Chiral analysis (Chiralpak IA 5 μm 4.6*250 mm; Mobile Phase: CO$_2$: IPA=75:25 at 3 g/min; Col. Temp: 40° C.; Wavelength: 220 nm, Back pressure: 100 bar, $R_T$=5.87 min).

Compound VII-16-N (trans)-Methyl 4-(2-chloro-3,4-difluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Single Stereoisomer)

Intermediates VII-16-X and VII-16-Y (trans)-Methyl 4-(2-chloro-3,4-difluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers) and (cis)-methyl 4-(2-chloro-3,4-difluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compounds were synthesized.

Intermediate VII-16-X: $^1$H NMR (400 MHz, DMSO-$d_6$) δ 9.59 (d, J=3.6 Hz, 0.7H), 9.07 (s, 0.3H), 8.01-8.00 (m, 1.5H), 7.96-7.95 (m, 0.5H), 7.86-7.85 (m, 1H), 7.50-7.43 (m, 1H), 7.22-7.15 (m, 1H), 6.02 (s, 0.4H), 5.93 (d, J=3.6 Hz, 0.6H), 4.13-4.08 (m, 2H), 3.94-3.89 (m, 0.5H), 3.69-3.62 (m, 2.5H), 3.54 (s, 1.8H), 3.53 (m, 1.2H), 3.00-2.94 (m, 0.4H), 2.83-2.76 (m, 0.6H), 2.18-2.10 (m, 2H), 2.06-1.66 (m, 4H), 1.62-1.48 (m, 2H), 1.22-1.18 (m, 3H).

Intermediate VII-16-Y: $^1$H NMR (400 MHz, DMSO-$d_6$) δ 9.54 (d, J=3.6 Hz, 0.7H), 8.49 (s, 0.3H), 7.98-7.91 (m, 3H), 7.48-7.40 (m, 1H), 7.18-7.14 (m, 1H), 6.02 (s, 0.3H), 5.89 (d, J=3.6 Hz, 0.7H), 4.12-4.06 (m, 2H), 3.93-3.88 (m, 0.3H), 3.71-3.66 (m, 1.4H), 3.62 (s, 1.3H), 3.53 (s, 1.8H), 3.52 (s, 1.2H), 3.29-2.27 (m, 0.3H), 3.18-3.16 (m, 0.7H), 2.34-2.24 (m, 2H), 1.97-1.58 (m, 5.3H), 1.44-1.41 (m, 0.7H), 1.19-1.15 (m, 3H).

A stereoisomeric mixture of (trans)-methyl 4-(2-chloro-3,4-difluorophenyl)-6-(4-(4-(2-ethoxy-2-oxoethyl)oxazol-2-yl)cyclohexyl)-2-(thiazol-2-yl)-1,4-dihydropyrimidine-5-carboxylate VII-16-X (300 mg, 95% purity, 0.471 mmol) was separated by chiral prep. HPLC (Column: Chiralpak IE 5 μm 20*250 mm; Mobile Phase: Hex:EtOH:DEA=50:50:0.3 at 10 mL/min, Temp: 30° C., Wavelength: 230 nm) to afford VII-16-M (110 mg, 95% purity from $^1$H NMR, 37% yield, 100% stereopure) and VII-16-N (110 mg, 95% purity from $^1$H NMR, 37% yield, 99.8% stereopure) as yellow solids.

VII-16-M: Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=6.781 min). $^1$H NMR (400 MHz, DMSO-$d_6$) δ 9.58-9.57 (m, 0.6H), 9.05 (s, 0.4H), 8.01 (s, 1.5H), 7.96-7.95 (m, 0.5H), 7.86-7.84 (m, 1H), 7.50-7.43 (m, 1H), 7.21-7.14 (m, 1H), 6.02 (s, 0.4H), 5.93-5.92 (m, 0.6H), 4.10 (q, J=7.2 Hz, 2H), 3.94-3.88 (m, 0.5H), 3.68-3.61 (m, 0.5H), 3.57 (s, 2H), 3.54 (s, 1.8H), 3.53 (s, 1.2H), 3.00-2.94 (m, 0.4H), 2.84-2.76 (m, 0.6H), 2.18-2.10 (m, 2H), 2.04-1.66 (m, 4H), 1.61-1.51 (m, 2H), 1.20 (t, J=7.2 Hz, 3H).

VII-16-N: Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=12.009 min). $^1$H NMR (400 MHz, DMSO-$d_6$) δ 9.58-9.57 (m, 0.6H), 9.05 (s, 0.4H), 8.01 (s, 1.5H), 7.96-7.95 (m, 0.5H), 7.85-7.84 (m, 1H), 7.50-7.43 (m, 1H), 7.22-7.16 (m, 1H), 6.02 (s, 0.4H), 5.93-5.92 (m, 0.6H), 4.10 (q, J=7.2 Hz, 2H), 3.95-3.88 (m, 0.5H), 3.67-3.61 (m, 0.5H), 3.57 (s, 2H), 3.54

(s, 1.8H), 3.53 (s, 1.2H), 3.00-2.94 (m, 0.4H), 2.83-2.76 (m, 0.6H), 2.18-2.11 (m, 2H), 2.04-1.67 (m, 4H), 1.61-1.51 (m, 2H), 1.20 (t, J=7.2 Hz, 3H).

Compound VII-17-M (trans)-Methyl 4-(2-chloro-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Single Stereoisomer)

Intermediates VII-17-X and VII-17-Y (trans)-Methyl 4-(2-chloro-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers) and (cis)-methyl 4-(2-chloro-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compounds were synthesized.

VII-17-X: $^1$H NMR (400 MHz, CDCl$_3$) δ 8.16 (s, 0.4H), 7.83-7.82 (m, 1H), 7.56-7.54 (m, 1H), 7.50 (d, J=3.2 Hz, 0.4H), 7.46-7.45 (d, J=2.8 Hz, 0.6H), 7.40 (br s, 0.6H), 7.32-7.28 (m, 1H), 7.14-7.12 (m, 1H), 6.96-6.89 (m, 1H), 6.19 (s, 0.6H), 6.06-6.05 (m, 0.4H), 4.23-4.18 (m, 2H), 4.08-4.01 (m, 0.6H), 3.84-3.78 (m, 0.4), 3.62-3.60 (m, 4H), 2.93-2.86 (m, 1H), 2.33-2.14 (m, 3H), 2.10-2.07 (m, 1H), 1.88-1.64 (m, 4H), 1.31-1.24 (m, 3H).

VII-17-Y $^1$H NMR (400 MHz, CDCl$_3$) δ 8.27 (s, 0.7H), 7.83-7.82 (d, J=3.2 Hz, 0.7H), 7.80-7.79 (d, J=2.8 Hz, 0.3H), 7.65 (s, 0.7H), 7.63 (s, 0.3H), 7.47-7.46 (d, J=3.2 Hz, 0.3H), 7.43-7.42 (d, J=3.2 Hz, 0.7H), 7.35 (br s, 0.3H), 7.30-7.25 (m, 1H), 7.13-7.10 (m, 1H), 6.94-6.86 (m, 1H), 6.18 (s, 0.7H), 6.04-6.03 (d, J=3.2 Hz, 0.3H), 4.23-4.16 (m, 2H), 4.13-4.05 (m, 0.7H), 3.89-3.83 (m, 0.3H), 3.73 (s, 1.4H), 3.66 (s, 0.6H), 3.61 (s, 0.5H), 3.60 (s, 2.5H), 3.29 (s, 0.7H), 3.22-3.21 (m, 0.3H), 2.50-2.35 (m, 2H), 2.13-2.07 (m, 0.3H), 1.98-1.78 (m, 5.7H), 1.30-1.26 (m, 3H).

A stereoisomeric mixture of (trans)-methyl 4-(2-chloro-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate VII-17-X (130 mg, 0.221 mmol) was separated by chiral Prep. SFC (Column: Chiralpak IG 5 μm 20*250 mm; Mobile Phase: CO$_2$:EtOH:DEA=65:35:0.3 at 50 g/min; Col. Temp: 40° C.; Wavelength: 230 nm; Back pressure: 100 bar) to give the compounds VII-17-M (50 mg, 38% yield, 100% stereopure) and VII-17-N (60 mg, 46% yield, 99.2% stereopure).

VII-17-M: Chiral analysis (Column: Chiralpak IG 5 μm 4.6*250 mm; Mobile Phase: CO$_2$:EtOH:DEA=65:35:0.3 at 3 g/min; Col. Temp: 40° C.; Wavelength: 230 nm, Back pressure: 100 bar, R$_T$=3.51 min).

VII-17-N: Chiral analysis (Column: Chiralpak IG 5 μm 4.6*250 mm; Mobile Phase: CO$_2$:EtOH:DEA=65:35:0.3 at 3 g/min; Col. Temp: 40° C.; Wavelength: 230 nm, Back pressure: 100 bar, R$_T$=4.28 min).

Compound VII-18-M (trans)-Methyl 4-(2-bromo-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Single Stereoisomer)

Intermediates VII-18-X and VII-18-Y (trans)-Methyl 4-(2-bromo-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers) and (cis)-methyl 4-(2-bromo-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compounds were synthesized.

Intermediate VII-18-Y: $^1$H NMR (400 MHz, CDCl$_3$) δ 8.25 (s, 0.7H), 7.82 (d, J=3.2 Hz, 0.7H), 7.80 (d, J=3.2 Hz, 0.3H), 7.65 (s, 0.7H), 7.63 (s, 0.3H), 7.46 (d, J=3.2 Hz, 0.3H), 7.42 (d, J=3.2 Hz, 0.7H), 7.41-7.38 (m, 0.3H), 7.32-7.30 (m, 1H), 7.00-6.91 (m, 1H), 6.15 (s, 0.7H), 5.99 (d, J=2.8 Hz, 0.3H), 4.23-4.16 (m, 2H), 4.13-4.07 (m, 0.7H), 3.89-3.84 (m, 0.3H), 3.73 (s, 1.3H), 3.66 (s, 0.7H), 3.61 (s, 1H), 3.60 (s, 2H), 3.30 (br s, 0.7H), 3.22-3.21 (m, 0.3H), 2.43-2.34 (m, 1.8H), 2.13-2.07 (m, 0.3H), 1.96-1.87 (m, 4.5H), 1.83-1.76 (m, 1.4H), 1.30-126 (m, 3H).

Intermediate VII-18-X: $^1$H NMR (400 MHz, CDCl$_3$) δ 8.16 (s, 0.5H), 7.83 (t, J=3.2 Hz, 1H), 7.59-7.56 (m, 1H), 7.53-7.50 (m, 0.5H), 7.49-7.46 (m, 0.5H), 7.45-7.43 (m, 0.5H), 7.35-7.30 (m, 2H), 7.03-6.91 (m, 1H), 6.17 (s, 0.5H), 6.02 (d, J=2.4 Hz, 0.5H), 4.20 (q, J=7.2 Hz, 2H), 4.10-4.02 (m, 0.5H), 3.86-3.77 (m, 0.5H), 3.62 (s, 2H), 3.60 (s, 3H), 2.95-2.82 (m, 1H), 2.37-2.25 (m, 1.5H), 2.19-2.16 (m, 1H), 2.08-2.01 (m, 1.5H), 1.86-1.75 (m, 3H), 1.70-1.57 (m, 1H), 1.33-1.26 (m, 3H).

A stereoisomeric mixture of (trans)-methyl 4-(2-bromo-4-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate VII-18-X (560 mg, 95% purity, 0.842 mmol) was separated by chiral Prep. SFC (Column: Chiralpak IF 5 μm 20*250 mm, Mobile Phase: CO$_2$: EtOH:DEA=70:30:0.3 at 50 g/min; Col. Temp: 40° C.; Wavelength: 214 nm; Back pressure: 100 bar) to afford the title compounds VII-18-M (103 mg, 90% purity, 17% yield, 100% stereopure) and VII-18-N (145 mg, 90% purity, 25% yield, 99.5% stereopure) as yellow solids.

VII-18-M: LC-MS (ESI): R$_T$=1.92 min, mass calcd. for C$_{28}$H$_{28}$BrFN$_4$O$_5$S, 631.5, m/z found 632.8 [M+H]$^+$. Chiral analysis (Column: Chiralpak IF 5 μm 4.6*250 mm; Mobile Phase: CO$_2$:EtOH:DEA=70:30:0.2 at 5 g/min; Col. Temp: 40° C.; Wavelength: 214 nm, Back pressure: 100 bar, R$_T$=5.82 min). $^1$H NMR (400 MHz, CDCl$_3$) δ 8.14 (s, 0.5H), 7.83-7.82 (m, 1H), 7.56 (s, 1H), 7.50-7.49 (m, 0.5H), 7.44 (d, J=3.2 Hz, 1H), 7.33-7.28 (m, 2H), 7.03-6.90 (m, 1H), 6.17 (s, 0.5H), 6.02 (d, J=2.8 Hz, 0.5H), 4.20 (q, J=7.2 Hz, 2H), 4.10-4.00 (m, 0.5H), 3.86-3.76 (m, 0.5H), 3.62-3.60 (m, 5H), 2.96-2.83 (m, 1H), 2.37-2.02 (m, 4H), 1.92-1.64 (m, 4H), 1.29 (t, J=7.2 Hz, 3H).

VII-18-N: LC-MS (ESI): R$_T$=1.90 min, mass calcd. for C$_{28}$H$_{28}$BrFN$_4$O$_5$S, 631.5, m/z found 632.8 [M+H]$^+$. Chiral analysis (Column: Chiralpak IF 5 μm 4.6*250 mm; Mobile Phase: CO$_2$:EtOH:DEA=70:30:0.2 at 5 g/min; Col. Temp: 40° C.; Wavelength: 214 nm, Back pressure: 100 bar, $R_T$=8.02 min). $^1$H NMR (400 MHz, CDCl$_3$) δ 8.15 (s, 0.5H), 7.83-7.82 (m, 1H), 7.56 (s, 1H), 7.50-7.49 (m, 0.5H), 7.44 (d, J=3.2 Hz, 1H), 7.33-7.28 (m, 2H), 7.01-6.91 (m, 1H), 6.17 (s, 0.5H), 6.02 (d, J=2.8 Hz, 0.5H), 4.20 (q, J=7.2 Hz, 2H), 4.10-4.01 (m, 0.5H), 3.86-3.76 (m, 0.5H), 3.62-3.60 (m, 5H), 2.94-2.84 (m, 1H), 2.36-2.02 (m, 4H), 1.93-1.64 (m, 4H), 1.29 (t, J=7.2 Hz, 3H).

Compound VII-19-M (trans)-Methyl 4-(2-bromo-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate
(a Single Stereoisomer)

Intermediate VII-19-1

(trans)-Methyl 4-(2-bromo-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate
(a Mixture of 2 Stereoisomers)

By utilizing the analogous procedure of Method B, the title compounds were synthesized.

LC-MS (ESI): $R_T$=2.097 min, mass calcd. for C$_{28}$H$_{28}$BrFN$_4$O$_5$S, 630.1, m/z found 631.0 [M+H]$^+$. $^1$H NMR (400 MHz, CD$_3$OD) δ 7.92 (s, 0.5H), 7.88 (s, 0.5H), 7.75-7.72 (m, 2H), 7.34-7.28 (m, 1H), 7.21 (d, J=8.0 Hz, 1H), 7.14-7.07 (m, 1H), 6.20 (s, 0.5H), 6.10 (s, 0.5H), 4.18 (q, J=6.8 Hz, 2H), 4.09-4.03 (m, 0.5H), 3.85-3.81 (m, 0.5H), 3.60-3.58 (m, 5H), 3.00-2.84 (m, 1H), 2.29-2.18 (m, 2H), 2.13-2.06 (m, 1H), 1.88-1.67 (m, 5H), 1.29-1.23 (m, 3H).

A stereoisomeric mixture of (trans)-methyl 4-(2-bromo-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate VII-19-1 (352 mg, 95% purity, 0.530 mmol) was separated by chiral Prep. HPLC (Column: Chiralpak IE 5 μm 20*250 mm; Mobile Phase: Hex:EtOH:DEA=50:50:0.3 at 12 mL/min; Temp: 30° C.; Wavelength: 214 nm) to afford the title compounds VII-19-M (148 mg, 95% purity from $^1$H NMR, 42% yield) and VII-19-N (144 mg, 95% purity from $^1$H NMR, 41% yield) as yellow solids.

VII-19-M: $^1$H NMR (400 MHz, DMSO-d$_6$) δ 9.49 (br s, 0.5H), 9.03 (s, 0.5H), 8.00 (d, J=3.2 Hz, 1.5H), 7.94 (d, J=3.2 Hz, 0.5H), 7.85 (d, J=4.8 Hz, 1H), 7.44-7.39 (m, 1H), 7.31-7.25 (m, 1H), 7.21 (d, J=8.0 Hz, 0.5H), 7.16 (d, J=8.0 Hz, 0.5H), 6.06 (s, 0.5H), 5.97 (s, 0.5H), 4.11 (q, J=7.2 Hz, 2H), 3.95-3.90 (m, 0.5H), 3.68-3.62 (m, 0.5H), 3.58 (s, 2H), 3.53 (s, 1.5H), 3.52 (s, 1.5H), 3.00-2.94 (m, 0.5H), 2.84-2.78 (m, 0.5H), 2.18-2.11 (m, 2H), 2.05-2.02 (m, 0.5H), 1.94-1.89 (m, 2H), 1.82-1.76 (m, 1H), 1.70-1.67 (m, 0.5H), 1.63-1.51 (m, 2H), 1.20 (t, J=7.2 Hz, 3H).

VII-19-N: $^1$H NMR (400 MHz, DMSO-d$_6$) δ 9.49 (br s, 0.5H), 9.05 (s, 0.5H), 8.00 (d, J=2.8 Hz, 1.5H), 7.95 (d, J=2.8 Hz, 0.5H), 7.86 (d, J=4.8 Hz, 1H), 7.45-7.39 (m, 1H), 7.32-7.25 (m, 1H), 7.21 (d, J=7.6 Hz, 0.5H), 7.16 (d, J=7.6 Hz, 0.5H), 6.06 (s, 0.5H), 5.97 (s, 0.5H), 4.11 (q, J=7.2 Hz, 2H), 3.96-3.90 (m, 0.5H), 3.69-3.63 (m, 0.5H), 3.58 (s, 2H), 3.53 (s, 2H), 3.52 (s, 1H), 3.00-2.94 (m, 0.5H), 2.84-2.78 (m, 0.5H), 2.18-2.10 (m, 2H), 2.06-2.00 (m, 0.5H), 1.94-1.88 (m, 2H), 1.82-1.77 (m, 1H), 1.70-1.67 (m, 0.5H), 1.60-1.51 (m, 2H), 1.20 (t, J=7.2 Hz, 3H).

Compound VII-20-N (trans)-Methyl 4-(2-chloro-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate
(a Single Stereoisomer)

Intermediate VII-20-3

(trans)-Methyl 4-(2-chloro-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate
(a Mixture of 2 Stereoisomers)

By utilizing the analogous procedure of Method B, the title compound was synthesized.

LC-MS (ESI): $R_T$=1.89 min, mass calcd. for C$_{28}$H$_{28}$ClFN$_4$O$_5$S, 586.2, m/z found 586.9 [M+H]$^+$. $^1$H NMR (400 MHz, CDCl$_3$) δ 8.17 (s, 0.5H), 7.83 (d, J=3.2 Hz, 1H), 7.56 (s, 1H), 7.51-7.50 (m, 0.5H), 7.46-7.45 (m, 0.5H), 7.42 (s, 0.5H), 7.23-7.12 (m, 2H), 7.10-7.00 (m, 1H), 6.26 (s, 0.6H), 6.11 (s, 0.4H), 4.20 (q, J=7.2 Hz, 2H), 4.10-4.02 (m, 0.5H), 3.89-3.78 (m, 0.5H), 3.62-3.60 (m, 5H), 2.95-2.87 (m, 1H), 2.36-1.99 (m, 4H), 1.91-1.67 (m, 3.6H), 1.61-1.54 (m, 0.4H), 1.30 (t, J=7.2 Hz, 3H).

A stereoisomeric mixture of (trans)-methyl 4-(2-chloro-3-fluorophenyl)-6-(4-(4-(2-ethoxy-2-oxoethyl)oxazol-2-yl)cyclohexyl)-2-(thiazol-2-yl)-1,4-dihydropyrimidine-5-carboxylate VII-20-3 (400 mg, 90% purity, 0.613 mmol) was separated by chiral Prep. HPLC (Column: Chiralpak IE 5 μm 20*250 mm; Mobile Phase: Hex:EtOH:DEA=50:50:0.3 at 13 mL/min; Temp: 30° C.; Wavelength: 230 nm) to give the title compounds VII-20-M (148 mg, 90% purity, 37% yield, 100% stereopure) and VII-20-N (150 mg, 90% purity, 37% yield, 99.7% stereopure) as yellow solids.

VII-20-M: Chiral analysis (Column: Chiralpak IE 5 μm 4.6*250 mm; Mobile Phase: Hex:EtOH:DEA=50:50:0.2 at 1 mL/min; Temp: 30° C.; Wavelength: 230 nm, $R_T$=7.675 min). $^1$H NMR (400 MHz, CDCl$_3$) δ 7.83 (d, J=3.2 Hz, 1H), 7.56 (s, 1H), 7.47 (br s, 1H), 7.23-7.13 (m, 2H), 7.11-7.01 (m, 1H), 6.32-6.09 (m, 1H), 4.20 (q, J=7.2 Hz, 2H), 3.98 (br s, 0.6H), 3.86-3.73 (m, 0.4H), 3.60 (s, 5H), 2.93-2.85 (m, 1H), 2.35-2.04 (m, 4H), 2.02-1.72 (m, 4H), 1.31 (t, J=7.2 Hz, 3H).

VII-20-N: Chiral analysis (Column: Chiralpak IE 5 μm 4.6*250 mm; Mobile Phase: Hex:EtOH:DEA=50:50:0.2 at 1 mL/min; Temp: 30° C.; Wavelength: 230 nm, $R_T$=10.297 min). $^1$H NMR (400 MHz, CDCl$_3$) δ 7.83 (d, J=3.2 Hz, 1H), 7.56 (s, 1H), 7.47 (br s, 1H), 7.21-7.13 (m, 2H), 7.09-7.00 (m, 1H), 6.29-6.10 (m, 1H), 4.20 (q, J=7.2 Hz, 2H), 3.98 (br s, 0.6H), 3.88-3.71 (m, 0.4H), 3.60 (s, 5H), 2.94-2.84 (m, 1H), 2.36-2.07 (m, 4H), 2.04-1.74 (m, 3H), 1.68-1.57 (m, 1H), 1.30 (t, J=7.2 Hz, 3H).

Compound VII-21-N (trans)-Methyl 6-(4-(4-(2-ethoxy-2-oxoethyl)oxazol-2-yl)cyclohexyl)-4-(3-fluoro-2-methylphenyl)-2-(thiazol-2-yl)-1,4-dihydropyrimidine-5-carboxylate
(a Single Stereoisomer)

Intermediate VII-21-1

(trans)-Methyl 6-(4-(4-(2-ethoxy-2-oxoethyl)oxazol-2-yl)cyclohexyl)-4-(3-fluoro-2-methylphenyl)-2-(thiazol-2-yl)-1,4-dihydropyrimidine-5-carboxylate
(a Mixture of 2 Stereoisomers)

By utilizing the analogous procedure of Method B, the title compound was synthesized.

LC-MS (ESI): $R_T$=1.87 min, mass calcd. for $C_{29}H_{31}FN_4O_5S$, 566.2, m/z found 566.9 [M+H]$^+$. $^1$H NMR (400 MHz, CDCl$_3$) δ 8.12 (s, 1H), 7.80 (d, J=2.8 Hz, 1H), 7.56-7.55 (m, 1H), 7.50 (d, J=2.8 Hz, 0.2H), 7.42 (d, J=2.8 Hz, 0.8H), 7.16-7.02 (m, 2H), 6.90-6.88 (m, 1H), 6.01 (s, 0.8H), 5.91 (d, J=2.4 Hz, 0.2H), 4.21 (q, J=7.2 Hz, 2H), 4.12-4.04 (m, 1H), 3.60 (s, 5H), 2.93-2.87 (m, 1H), 2.54 (d, J=2.0 Hz, 2.4H), 2.40 (d, J=2.0 Hz, 0.6H), 2.35-2.27 (m, 3H), 2.09-1.98 (m, 1H), 1.93-1.65 (m, 3.5H), 1.59-1.55 (m, 0.5H), 1.29 (t, J=7.2 Hz, 3H).

A stereoisomeric mixture of (trans)-methyl 6-(4-(4-(2-ethoxy-2-oxoethyl)oxazol-2-yl)cyclohexyl)-4-(3-fluoro-2-methylphenyl)-2-(thiazol-2-yl)-1,4-dihydropyrimidine-5-carboxylate VII-21-1 (400 mg, 90% purity, 0.635 mmol) was separated by chiral Prep. HPLC (Column: Chiralpak IE 5 μm 20*250 mm; Mobile Phase: Hex:EtOH:DEA=70:30:0.3 at 13 mL/min; Temp: 30° C.; Wavelength: 230 nm) to give the title compounds VII-21-M (60 mg, 90% purity, 15% yield, 100% stereopure) and VII-21-N (100 mg, 90% purity, 25% yield, 99.6% stereopure), as yellow solids VII-21-M: Chiral analysis (Column: Chiralpak IE 5 μm 4.6*250 mm; Mobile Phase: Hex:EtOH:DEA=70:30:0.2 at 1 mL/min; Temp: 30° C.; Wavelength: 230 nm, $R_T$=9.911 min). $^1$H NMR (400 MHz, CDCl$_3$) δ 8.12 (s, 1H), 7.80 (d, J=2.8 Hz, 1H), 7.56 (s, 1H), 7.50 (d, J=3.2 Hz, 0.2H), 7.42 (d, J=3.2 Hz, 0.8H), 7.16-7.02 (m, 2H), 6.95-6.88 (m, 1H), 6.01 (s, 0.8H), 5.91 (d, J=2.4 Hz, 0.2H), 4.20 (q, J=7.2 Hz, 2H), 4.12-4.04 (m, 1H), 3.60 (s, 5H), 2.93-2.87 (m, 1H), 2.54 (d, J=2.0 Hz, 2.4H), 2.40 (d, J=2.0 Hz, 0.6H), 2.35-2.17 (m, 3H), 2.09-1.98 (m, 1H), 1.93-1.65 (m, 3.5H), 1.59-1.55 (m, 0.5H), 1.29 (t, J=7.2 Hz, 3H).

VII-21-N: Chiral analysis (Column: Chiralpak IE 5 μm 4.6*250 mm; Mobile Phase: Hex:EtOH:DEA=70:30:0.2 at 1 mL/min; Temp: 30° C.; Wavelength: 230 nm, $R_T$=12.043 min). $^1$H NMR (400 MHz, CDCl$_3$) δ 8.12 (s, 1H), 7.80 (d, J=2.8 Hz, 1H), 7.56 (s, 1H), 7.50 (d, J=3.2 Hz, 0.2H), 7.42 (d, J=3.2 Hz, 0.8H), 7.16-7.00 (m, 2H), 6.94-6.87 (m, 1H), 6.01 (s, 0.8H), 5.91 (d, J=2.0 Hz, 0.2H), 4.20 (q, J=7.2 Hz, 2H), 4.11-4.03 (m, 1H), 3.60 (s, 5H), 2.94-2.85 (m, 1H), 2.54 (d, J=2.0 Hz, 2.4H), 2.40 (d, J=2.0 Hz, 0.6H), 2.36-2.17 (m, 3H), 2.09-1.98 (m, 1H), 1.93-1.65 (m, 3.5H), 1.58-1.55 (m, 0.5H), 1.29 (t, J=7.2 Hz, 3H).

Compound VII-22-S (trans)-Methyl 4-(2-chloro-3,4-difluorophenyl)-6-(4-(4-(2-ethoxy-2-oxoethyl)-5-methyloxazol-2-yl)cyclohexyl)-2-(thiazol-2-yl)-1,4-dihydropyrimidine-5-carboxylate (a Single Stereoisomer)

Intermediate VII-22

Methyl 4-(2-chloro-3,4-difluorophenyl)-6-(4-(4-(2-ethoxy-2-oxoethyl)-5-methyloxazol-2-yl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized.

LC-MS (ESI): $R_T$=2.172 min, mass calcd. for $C_{29}H_{29}ClF_2N_4O_5S$, 618.2, m/z found 619.1 [M+H]$^+$. $^1$H NMR (400 MHz, CDCl$_3$) δ 8.18 (s, 0.6H), 7.83 (d, J=3.2 Hz, 1H), 7.51 (d, J=3.2 Hz, 0.3H), 7.46 (d, J=2.8 Hz, 0.7H), 7.37 (s, 0.4H), 7.10-7.00 (m, 2H), 6.19 (s, 0.7H), 6.05 (d, J=2.8 Hz, 0.3H), 4.21-4.10 (m, 2H), 4.06-4.00 (m, 0.6H), 3.83-3.77 (m, 0.4H), 3.63 (s, 1H), 3.60 (s, 2H), 3.47 (s, 2H), 2.86-2.80 (m, 1H), 2.32-2.30 (m, 1H), 2.28 (s, 3H), 2.16-2.13 (m, 1H), 2.07-1.99 (m, 2H), 1.86-1.62 (m, 4H), 1.28 (t, J=7.2 Hz, 3H).

A stereoisomeric mixture of methyl 4-(2-chloro-3,4-difluorophenyl)-6-(4-(4-(2-ethoxy-2-oxoethyl)-5-methyloxazol-2-yl)cyclohexyl)-2-(thiazol-2-yl)-1,4-dihydropyrimidine-5-carboxylate VII-22 (300 mg, 90% purity, 0.436 mmol) was separated by chiral Prep. HPLC (Colum: Chiralpak IE 5 μm 20 mm*250 mm; Mobile Phase: Hex:EtOH:DEA=75:25:0.3 at 15 mL/min; Temp: 30° C.; Wavelength: 214 nm) to afford the title compounds VII-22-R (85 mg, 90% purity from $^1$H NMR, 28% yield, 96.4% stereopure) and VII-22-S (90 mg, 90% purity from $^1$H NMR, 30% yield, 98.4% stereopure) as yellow solids.

VII-22-R: LC-MS (ESI): $R_T$=2.281 min, mass calcd. for $C_{29}H_{29}ClF_2N_4O_5S$, 618.2, m/z found 619.1 [M+H]$^+$. Chiral analysis (Colum: Chiralpak IE 5 μm 4.6 mm*250 mm; Mobile Phase: Hex:EtOH:DEA=75:25:0.2 at 1.0 mL/min; Temp: 30° C.; Wavelength: 254 nm, $R_T$=10.938 min). $^1$H NMR (400 MHz, CDCl$_3$) δ 8.18 (s, 0.6H), 7.83 (d, J=3.2 Hz, 1H), 7.51 (d, J=3.2 Hz, 0.3H), 7.46 (d, J=3.2 Hz, 0.7H), 7.38 (s, 0.4H), 7.10-7.01 (m, 2H), 6.19 (s, 0.7H), 6.05 (s, 0.3H), 4.18 (q, J=7.2 Hz, 2H), 4.05-4.00 (m, 0.7H), 3.83-3.77 (m, 0.3H), 3.63 (s, 1H), 3.60 (s, 2H), 3.47 (s, 2H), 2.86-2.80 (m, 1H), 2.31-2.28 (m, 1H), 2.26 (s, 3H), 2.19-1.99 (m, 2.7H), 1.87-1.70 (m, 4.3H), 1.28 (t, J=7.2 Hz, 3H).

VII-22-S: LC-MS (ESI): $R_T$=2.241 min, mass calcd. for $C_{29}H_{29}ClF_2N_4O_5S$, 618.2, m/z found 619.1 [M+H]$^+$. Chiral analysis (Colum: Chiralpak IE 5 μm 4.6 mm*250 mm; Mobile Phase: Hex:EtOH:DEA=75:25:0.2 at 1.0 mL/min; Temp: 30° C.; Wavelength: 254 nm, $R_T$=12.525 min). $^1$H NMR (400 MHz, CDCl$_3$) δ 8.18 (s, 0.6H), 7.83 (d, J=3.6 Hz, 1H), 7.51 (d, J=3.2 Hz, 0.4H), 7.46 (d, J=3.2 Hz, 0.6H), 7.38 (s, 0.4H), 7.10-7.00 (m, 2H), 6.19 (s, 0.6H), 6.05 (d, J=2.0 Hz, 0.4H), 4.18 (q, J=6.8 Hz, 2H), 4.06-4.00 (m, 0.7H), 3.83-3.78 (m, 0.3H), 3.63 (s, 1H), 3.60 (s, 2H), 3.47 (s, 2H), 2.86-2.80 (m, 1H), 2.30-2.28 (m, 1H), 2.26 (s, 3H), 2.16-1.98 (m, 2.5H), 1.84-1.64 (m, 4.5H), 1.28 (t, J=6.8 Hz, 3H).

Compound VII-23-Y (trans)-Ethyl 4-(2-chloro-3,4-difluorophenyl)-(4-(4-(2-ethoxy-2-oxoethyl)oxazol-2-yl)cyclohexyl)-2-(thiazol-2-yl)-1,4-dihydropyrimidine-5-carboxylate (a Single Stereoisomer)

Intermediates VII-23-M and VII-23-N (trans)-Ethyl 4-(2-chloro-3,4-difluorophenyl)-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers) and (cis)-ethyl 4-(2-chloro-3,4-difluorophenyl)-(4-(4-(2-ethoxy-2-oxoethyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized.

VII-23-M: LC-MS (ESI): $R_T$=3.140 min, mass calcd. for $C_{29}H_{29}ClF_2N_4O_5S$, 618.2, m/z found 619.1 [M+H]$^+$. $^1$H NMR (400 MHz, DMSO-d$_6$) δ 9.54 (d, J=2.8 Hz, 0.6H), 8.98 (s, 0.4H), 8.00 (d, J=3.6 Hz, 0.6H), 7.99 (s, 1H), 7.95 (d, J=3.2 Hz, 0.4H), 7.84 (d, J=4.4 Hz, 1H), 7.50-7.43 (m, 1H), 7.23-7.17 (m, 1H), 6.03 (s, 0.4H), 5.93 (d, J=3.6 Hz, 0.6H), 4.13-4.08 (m, 2H), 4.01-3.94 (m, 2H), 3.93-3.86 (m, 0.4H), 3.68-3.61 (m, 0.6H), 3.57 (s, 2H), 3.01-2.92 (m, 0.4H), 2.83-2.76 (m, 0.6H), 2.20-2.10 (m, 2H), 2.06-1.68 (m, 4H), 1.61-1.47 (m, 2H), 1.20 (t, J=7.2 Hz, 3H), 1.10-1.03 (m, 3H).

VII-23-N: LC-MS (ESI): $R_T$=3.644 min, mass calcd. for $C_{29}H_{29}ClF_2N_4O_5S$, 618.2, m/z found 619.1 [M+H]$^+$. $^1$H NMR (400 MHz, DMSO-$d_6$) δ 9.48 (d, J=3.6 Hz, 0.7H), 8.41 (s, 0.3H), 7.97-7.90 (m, 3H), 7.48-7.40 (m, 1H), 7.19-7.14 (m, 1H), 6.03 (s, 0.3H), 5.90 (d, J=3.6 Hz, 0.7H), 4.12-4.04 (m, 2H), 4.01-3.94 (m, 2H), 3.97-3.94 (m, 0.3H), 3.72-3.66 (m, 1.4H), 3.61 (s, 1.3H), 3.28-3.26 (m, 0.3H), 3.19-3.15 (m, 0.7H), 2.36-2.22 (m, 2H), 1.98-1.69 (m, 4.7H), 1.64-1.59 (m, 0.7H), 1.46-1.41 (m, 0.6H), 1.19-1.13 (m, 3H), 1.10-1.04 (m, 3H).

A stereoisomeric mixture of (trans)-ethyl 4-(2-chloro-3,4-difluorophenyl)-4-(4-(2-ethoxy-2-oxoethyl)oxazol-2-yl)cyclohexyl)-2-(thiazol-2-yl)-1,4-dihydropyrimidine-5-carboxylate VII-23-M (400 mg, 0.647 mmol) was separated by chiral Prep. HPLC (Column: Chiralpak IE 5 μm 20*250 mm; Mobile Phase: Hex:EtOH:DEA=40:60:0.2 at 25 mL/min; Temp: 30° C.; Wavelength: 254 nm) to give the title compounds VII-23-X (150 mg, 38% yield, 99.8% purity, 100% stereopure) and VII-23-Y (150 mg, 38% yield, 99.9% purity, 100% stereopure) as yellow solids.

VII-23-X: LC-MS (ESI): $R_T$=4.463 min, mass calcd. for $C_{29}H_{29}ClF_2N_4O_5S$, 618.2, m/z found 618.9 [M+H]$^+$. Chiral analysis (Column: Chiralpak IE 5 μm 4.6*250 mm; Mobile Phase: Hex:EtOH:DEA=40:60:0.2 at 1.0 mL/min; Temp: 30° C.; Wavelength: 230 nm, $R_T$=6.153 min). $^1$H NMR (400 MHz, DMSO-$d_6$) δ 9.54 (d, J=3.2 Hz, 0.6H), 8.98 (s, 0.4H), 8.01-8.00 (m, 1.6H), 7.95 (d, J=3.2 Hz, 0.4H), 7.85 (d, J=4.4 Hz, 1H), 7.50-7.43 (m, 1H), 7.23-7.17 (m, 1H), 6.03 (s, 0.4H), 5.93 (d, J=3.6 Hz, 0.6H), 4.13-4.08 (m, 2H), 4.01-3.94 (m, 2H), 3.93-3.86 (m, 0.4H), 3.68-3.61 (m, 0.6H), 3.57 (s, 2H), 3.00-2.93 (m, 0.4H), 2.83-2.77 (m, 0.6H), 2.19-2.10 (m, 2H), 2.03-1.50 (m, 6H), 1.20 (t, J=7.2 Hz, 3H), 1.10-1.04 (m, 3H).

VII-23-Y: LC-MS (ESI): $R_T$=4.466 min, mass calcd. for $C_{29}H_{29}ClF_2N_4O_5S$, 618.2, m/z found 618.9 [M+H]$^+$. Chiral analysis (Column: Chiralpak IE 5 μm 4.6*250 mm; Mobile Phase: Hex:EtOH:DEA=40:60:0.2 at 1.0 mL/min; Temp: 30° C.; Wavelength: 230 nm, $R_T$=9.894 min). $^1$H NMR (400 MHz, DMSO-$d_6$) δ 9.54 (d, J=3.6 Hz, 0.6H), 8.98 (s, 0.4H), 8.01-8.00 (m, 1.6H), 7.95 (d, J=3.6 Hz, 0.4H), 7.85 (d, J=4.0 Hz, 1H), 7.50-7.43 (m, 1H), 7.23-7.17 (m, 1H), 6.03 (s, 0.4H), 5.93 (d, J=3.6 Hz, 0.6H), 4.10 (q, J=7.2 Hz, 2H), 4.01-3.94 (m, 2H), 3.93-3.87 (m, 0.4H), 3.67-3.60 (m, 0.6H), 3.57 (s, 2H), 2.99-2.93 (m, 0.4H), 2.83-2.76 (m, 0.6H), 2.18-2.10 (m, 2H), 2.04-1.67 (m, 4H), 1.61-1.46 (m, 2H), 1.20 (t, J=7.2 Hz, 3H), 1.10-1.03 (m, 3H).

Compound VII-24-M (trans)-ethyl 4-(2-chloro-3,4-difluorophenyl)-6-(4-(4-(3-methoxy-3-oxopropyl)oxazol-2-yl)cyclohexyl)-2-(thiazol-2-yl)-1,4-dihydropyrimidine-5-carboxylate (a Single Stereoisomer)

Intermediate VII-24-R (trans)-Ethyl 4-(2-chloro-3,4-difluorophenyl)-6-(4-(4-(3-methoxy-3-oxopropyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=3.193 min, mass calcd. for $C_{29}H_{29}ClF_2N_4O_5S$, 618.2, m/z found mass 619.1 [M+H]$^+$. $^1$H NMR (400 MHz, DMSO-$d_6$) δ 9.55-9.54 (d, J=4.0 Hz, 0.6H), 8.98 (s, 0.4H), 8.00-7.95 (m, 2H), 7.71-7.70 (d, J=4.0 Hz, 1H), 7.50-7.43 (m, 1H), 7.22-7.17 (m, 1H), 6.03 (s, 0.4H), 5.93 (d, J=3.6 Hz, 0.6H), 3.99 (q, J=7.2 Hz, 2H), 3.87-3.78 (m, 0.6H), 3.67-3.64 (m, 0.4H), 3.60 (s, 3H), 2.97-2.91 (m, 0.4H), 2.79-2.74 (m, 0.6H), 2.70-2.68 (m, 2H), 2.63-2.59 (m, 2H), 2.16-2.10 (m, 2H), 1.97-1.86 (m, 2H), 1.81-1.66 (m, 2H) 1.57-1.46 (m, 2H), 1.10-1.03 (m, 3H).

A stereoisomeric mixture of VII-24-R (396 mg, 0.640 mmol) was separated by chiral Prep. SFC (Column: Chiralpak IE 5 μm 20*250 mm; Mobile Phase: $CO_2$:MeOH=60:40 at 50 g/min; Temp: 30° C.; Wavelength: 230 nm; Back pressure: 100 bar) to give the title compounds VII-24-M (80 mg, 20% yield, 100% stereopure) and VII-24-N (90 mg, 23% yield, 100% stereopure) as yellow solids.

VII-24-M: LC-MS (ESI): $R_T$=4.857 min, mass calcd. for $C_{29}H_{29}ClF_2N_4O_5S$, 618.2, m/z found 619.1 [M+H]$^+$. Chiral analysis (Column: Chiralpak IE 5 μm 4.6*250 mm; Mobile Phase: $CO_2$: EtOH=60:40 at 3.0 g/min; Col. Temp: 40° C.; Wavelength: 230 nm, Back pressure: 100 bar, $R_T$=3.92 min). $^1$H NMR (400 MHz, $CD_3OD$) δ 7.93 (d, J=3.2 Hz, 0.6H), 7.89 (d, J=2.8 Hz, 0.4H), 7.76-7.74 (m, 1H), 7.55 (d, J=4.8 Hz, 1H), 7.25-7.20 (m, 2H), 6.15 (s, 0.6H), 6.08 (s, 0.4H), 4.06-4.03 (m, 2H), 4.03-4.02 (m, 0.6H), 3.84-3.76 (m, 0.4H), 3.67 (s, 3H), 2.98-2.92 (m, 0.6H), 2.88-2.85 (m, 0.4H), 2.81 (t, J=7.6 Hz, 2H), 2.66 (t, J=7.6 Hz, 2H), 2.29-2.15 (m, 2H), 2.12-1.97 (m, 2H), 1.94-1.79 (m, 2H), 1.76-1.65 (m, 2H), 1.17-1.12 (m, 3H).

VII-24-N: LC-MS (ESI): $R_T$=4.860 min, mass calcd. for $C_{29}H_{29}ClF_2N_4O_5S$, 618.2, m/z found 619.1 [M+H]$^+$. Chiral analysis (Column: Chiralpak IE 5 μm 4.6*250 mm; Mobile Phase: $CO_2$: EtOH=60:40 at 3.0 g/min; Col. Temp: 40° C.; Wavelength: 230 nm, Back pressure: 100 bar, $R_T$=6.65 min). $^1$H NMR (400 MHz, $CD_3OD$) δ 7.93 (d, J=3.2 Hz, 0.6H), 7.89 (d, J=2.8 Hz, 0.4H), 7.76-7.74 (m, 1H), 7.55 (d, J=4.8 Hz, 1H), 7.27-7.18 (m, 2H), 6.15 (s, 0.6H), 6.08 (s, 0.4H), 4.08-4.04 (m, 2H), 4.03-4.02 (m, 0.5H), 3.85-3.76 (m, 0.5H), 3.67 (s, 3H), 2.98-2.95 (m, 0.6H), 2.89-2.84 (m, 0.4H), 2.81 (t, J=7.6 Hz, 2H), 2.66 (t, J=7.6 Hz, 2H), 2.29-2.15 (m, 2H), 2.12-1.97 (m, 2H), 1.94-1.88 (m, 2H), 1.79-1.65 (m, 2H), 1.17-1.12 (m, 3H).

Compound VII-25-N (trans)-Methyl 4-(2-chloro-3,4-difluorophenyl)-6-(4-(4-(3-ethoxy-2,2-dimethyl-3-oxopropyl)oxazol-2-yl)cyclohexyl)-2-(thiazol-2-yl)-1,4-dihydropyrimidine-5-carboxylate (a Single Stereoisomer)

Intermediate VII-25-7

(trans)-Methyl 4-(2-chloro-3,4-difluorophenyl)-6-(4-(4-(3-ethoxy-2,2-dimethyl-3-oxopropyl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=2.10 min, mass calcd. for $C_{31}H_{33}ClF_2N_4O_5S$, 646.2, m/z found 646.9 [M+H]$^+$. $^1$H NMR (400 MHz, $CDCl_3$) δ 8.18 (s, 0.6H), 7.83 (d, J=3.2 Hz, 1H), 7.51 (d, J=3.2 Hz, 0.4H), 7.46 (d, J=3.2 Hz, 0.6H), 7.38 (s, 0.4H), 7.28 (s, 1H), 7.11-6.99 (m, 2H), 6.19 (s, 0.6H), 6.05 (d, J=2.8 Hz, 0.4H), 4.14 (q, J=6.8 Hz, 2H), 4.04-4.00

(m, 0.6H), 3.85-3.78 (m, 0.4H), 3.63 (s, 1H), 3.60 (s, 2H), 2.90-2.81 (m, 1H), 2.77-2.76 (m, 2H), 2.31-2.07 (m, 3H), 2.05-1.98 (m, 1H), 1.90-1.69 (m, 3H), 1.66-1.52 (m, 1H), 1.28-1.23 (m, 9H).

A stereoisomeric mixture of (trans)-methyl 4-(2-chloro-3,4-difluorophenyl)-6-(4-(4-(3-ethoxy-2,2-dimethyl-3-oxopropyl)oxazol-2-yl)cyclohexyl)-2-(thiazol-2-yl)-1,4-dihydropyrimidine-5-carboxylate VII-25-7 (500 mg, 90% purity, 0.695 mmol) was separated by chiral Prep. HPLC (Column: Chiralpak IE 5 μm 20*250 mm; Mobile Phase: Hex:EtOH:DEA=80:20:0.2 at 10 mL/min; Temp: 30° C.; Wavelength: 230 nm) to give the title compounds VII-25-M (200 mg, 90% purity, 40% yield, 100% stereopure) and VII-25-N (210 mg, 90% purity, 42% yield, 100% stereopure) as yellow solids.

VII-25-M: Chiral analysis (Column: Chiralpak IE 5 μm 4.6*250 mm; Mobile Phase: Hex:EtOH:DEA=80:20:0.2 at 1.0 mL/min; Temp: 30° C.; Wavelength: 230 nm, $R_T$=8.385 min). $^1$H NMR (400 MHz, DMSO-$d_6$) δ 9.60 (d, J=3.6 Hz, 0.6H), 9.06 (s, 0.4H), 8.01 (s, 1.6H), 7.96-7.95 (m, 0.4H), 7.67-7.66 (m, 1H), 7.50-7.43 (m, 1H), 7.24-7.13 (m, 1H), 6.02 (s, 0.4H), 5.93 (d, J=3.6 Hz, 0.6H), 4.06 (q, J=7.2 Hz, 2H), 3.93-3.86 (m, 0.5H), 3.68-3.61 (m, 0.5H), 3.53 (s, 1.8H), 3.52 (s, 1.2H), 2.97-2.89 (m, 0.5H), 2.79-2.72 (m, 0.5H), 2.66 (s, 2H), 2.19-1.45 (m, 8H), 1.20-1.14 (m, 9H).

VII-25-N: Chiral analysis (Column: Chiralpak IE 5 μm 4.6*250 mm; Mobile Phase: Hex:EtOH:DEA=80:20:0.2 at 1.0 mL/min; Temp: 30° C.; Wavelength: 230 nm, $R_T$=10.968 min). $^1$H NMR (400 MHz, DMSO-$d_6$) δ 9.60 (d, J=3.2 Hz, 0.6H), 9.06 (s, 0.4H), 8.01 (s, 1.5H), 7.96-7.95 (m, 0.5H), 7.67-7.66 (m, 1H), 7.51-7.43 (m, 1H), 7.26-7.13 (m, 1H), 6.02 (s, 0.4H), 5.93 (d, J=3.6 Hz, 0.6H), 4.06 (q, J=7.2 Hz, 2H), 3.94-3.85 (m, 0.5H), 3.70-3.60 (m, 0.5H), 3.53 (s, 1.8H), 3.52 (s, 1.2H), 3.00-2.89 (m, 0.5H), 2.83-2.72 (m, 0.5H), 2.66 (s, 2H), 2.15-1.46 (m, 8H), 1.20-1.14 (m, 9H).

Compound VII-26-8

(trans)-Ethyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-5-carboxylate (a Single Stereoisomer)

Intermediates VII-26-5 and VII-26-6

(trans)-Ethyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-5-carboxylate (a Mixture of 2 Stereoisomers) and (cis)-ethyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-5-carboxylate (a Mixture of 2 Stereoisomers)

By utilizing the analogous procedure of Method B, the title compound was synthesized.

VII-26-5: $^1$H NMR (400 MHz, DMSO-$d_6$) δ 9.58-9.53 (m, 0.7H), 9.00 (s, 0.3H), 8.02-7.92 (m, 2H), 7.90 (d, J=2.8 Hz, 1H), 7.51-7.44 (m, 1H), 7.24-7.18 (m, 1H), 6.04-6.03 (m, 0.4H), 5.95-5.90 (m, 0.6H), 4.32 (q, J=6.8 Hz, 2H), 4.02-3.96 (m, 2H), 3.94-3.87 (m, 0.4H), 3.72-3.63 (m, 0.6H), 3.15-3.07 (m, 0.4H), 2.98-2.91 (m, 0.6H), 2.23-2.04 (m, 2H), 1.99-1.47 (m, 6H), 1.30 (t, J=6.8 Hz, 3H), 1.10-1.03 (m, 3H).

VII-26-6: $^1$H NMR (400 MHz, DMSO-$d_6$) δ 9.53 (d, J=3.2 Hz, 0.7H), 8.63 (s, 0.3H), 8.01-7.93 (m, 3H), 7.49-7.41 (m, 1H), 7.19-7.16 (m, 1H), 6.04 (s, 0.3H), 5.91 (d, J=3.6 Hz, 0.7H), 4.34 (q, J=7.2 Hz, 2H), 4.01-3.95 (m, 2H), 3.92-3.86 (m 0.3H), 3.75-3.69 (m 0.7H), 3.42-3.35 (m 0.3H), 3.33-3.27 (m 0.7H), 2.40-2.33 (m, 2H), 1.96-1.75 (m, 4H), 1.70-1.47 (m, 2H), 1.31 (t, J=6.8 Hz, 3H), 1.11-1.05 (m, 3H).

A stereoisomeric mixture of (trans)-ethyl 2-(4-(6-(2-chloro-3,4-difluorophenyl)-5-(ethoxycarbonyl)-2-(thiazol-2-yl)-3,6-dihydropyrimidin-4-yl)cyclohexyl)oxazole-5-carboxylate VII-26-5 (220 mg, 95% purity, 0.345 mmol) was separated by chiral Prep. HPLC (Column: Chiralpak IE 5 μm 20*250 mm, Mobile Phase: Hex:EtOH:DEA=70:30:0.3 at 15 mL/min, Temp: 30° C., Wavelength: 230 nm) to afford the title compounds VII-26-7 (100 mg, 96% purity from $^1$H NMR, 46% yield, 100% stereopure), VII-26-8 (98 mg, 97% purity from $^1$H NMR, 45% yield, 98.7% stereopure) as yellow solid.

VII-26-7: LC-MS (ESI): $R_T$=1.98 min, mass calcd. for $C_{28}H_{27}ClF_2N_4O_5S$, 604.1, m/z found 604.8 [M+H]$^+$. Chiral analysis (Column: Chiralpak IE 5 μm 4.6*250 mm, Mobile Phase: Hex:EtOH:DEA=70:30:0.2 at 1.0 mL/min, Temp: 30° C., Wavelength: 230 nm, $R_T$=9.657 min). $^1$H NMR (400 MHz, CD$_3$OD) δ 7.93 (d, J=3.2 Hz, 0.5H), 7.89 (d, J=3.2 Hz, 0.5H), 7.76-7.74 (m, 2H), 7.28-7.19 (m, 2H), 6.15 (s, 0.6H), 6.09 (s, 0.4H), 4.37 (q, J=7.2 Hz, 2H), 4.11-4.02 (m, 2.6H), 3.85-3.78 (m, 0.4H), 3.12-2.93 (m, 1H), 2.36-2.22 (m, 2H), 2.15-1.71 (m, 6H), 1.37 (t, J=6.8 Hz, 3H), 1.17-1.12 (m, 3H).

VII-26-8: LC-MS (ESI): $R_T$=1.98 min, mass calcd. for $C_{28}H_{27}ClF_2N_4O_5S$, 604.1, m/z found 604.8 [M+H]$^+$. Chiral analysis (Column: Chiralpak IE 5 μm 4.6*250 mm, Mobile Phase: Hex:EtOH:DEA=70:30:0.2 at 1.0 mL/min, Temp: 30° C., Wavelength: 230 nm, $R_T$=11.066 min). $^1$H NMR (400 MHz, CD$_3$OD) δ 7.93 (d, J=3.2 Hz, 0.5H), 7.89 (d, J=2.8 Hz, 0.5H), 7.76-7.74 (m, 2H), 7.28-7.19 (m, 2H), 6.15 (s, 0.6H), 6.08 (s, 0.4H), 4.37 (q, J=7.2 Hz, 2H), 4.11-4.02 (m, 2.5H), 3.86-3.77 (m, 0.5H), 3.11-2.92 (m, 1H), 2.36-2.22 (m, 2H), 2.15-1.66 (m, 6H), 1.37 (t, J=7.2 Hz, 3H), 1.17-1.12 (m, 3H).

Compound VII-27-R (trans)-Ethyl 4-(2-chloro-3,4-difluorophenyl)-6-(4-(4-(1-ethoxy-2-methyl-1-oxopropan-2-yl)oxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

LC-MS (ESI): $R_T$=2.274 min, mass calcd. for $C_{29}H_{28}ClF_2N_5O_4S$, 646.2, m/z found 647.1 [M+H]$^+$.

Compound VII-28-N (trans)-ethyl 4-(2-chloro-3,4-difluorophenyl)-6-(4-(1-(2-ethoxy-2-oxoethyl)-1H-pyrazol-4-yl)cyclohexyl)-2-(thiazol-2-yl)-1,4-dihydropyrimidine-5-carboxylate (a Single Stereoisomer)

Intermediate VII-28-R

Ethyl 4-(2-chloro-3,4-difluorophenyl)-6-(4-(1-(2-ethoxy-2-oxoethyl)-1H-pyrazol-4-yl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

LC-MS (ESI): $R_T$=2.136 min, mass calcd. for $C_{29}H_{30}ClF_2N_5O_4S$, 617.2, m/z found 618.1 [M+H]$^+$.

The stereoisomeric mixture of VII-28-R (800 mg, 1.29 mmol) was separated by chiral Prep. HPLC (the first separation condition: Column: Chiralpak IE (5 μm 20*250 mm); Mobile Phase: Hex:EtOH:DEA=60:40:0.3 at 11 mL/min; Temp: 30° C.; Wavelength: 214 nm; the second separation condition: Column: Chiralpak IG (5 μm 20*250 mm); Mobile Phase: Hex:EtOH:DEA=80:20:0.3 at 15 mL/min; Temp: 30° C.; Wavelength: 230 nm) to afford VII-28-M (184 mg, 23% yield, 96.9% stereopure), VII-28-N (123 mg, 15% yield, 99.7% stereopure) VII-28-P (143 mg, 18% yield, 100% stereopure) and VII-28-Q (120 mg, 15% yield, 96.4% stereopure) as yellow solids.

VII-28-M: Chiral analysis (Column: Chiralpak IE 5 μm 4.6*250 mm; Mobile Phase: Hex:EtOH:DEA=50:50:0.2 at 1 mL/min; Temp: 30° C.; Wavelength: 230 nm; $R_T$=8.072 min). $^1$H NMR (400 MHz, DMSO-d$_6$) δ 9.54 (d, J=3.6 Hz, 0.6H), 8.93 (s, 0.4H), 8.01-8.00 (m, 1.6H), 7.96 (d, J=3.2 Hz, 0.4H), 7.55 (d, J=5.2 Hz, 1H), 7.51-7.46 (m, 1H), 7.38 (s, 1H), 7.23-7.18 (m, 1H), 6.04 (s, 0.4H), 5.93 (d, J=2.8 Hz, 0.6H), 4.98 (d, J=2.0 Hz, 2H), 4.15-4.10 (m, 2H), 4.01-3.94 (m, 2H), 3.89-3.85 (m, 0.4H), 3.70-3.65 (m, 0.6H), 2.67-2.64 (m, 0.4H), 2.44-2.39 (m, 0.6H), 2.06-1.81 (m, 5.4H), 1.67-1.64 (m, 0.6H), 1.45-1.34 (m, 2H), 1.23-1.19 (m, 3H), 1.10-1.05 (m, 3H).

VII-28-N: Chiral analysis (Column: Chiralpak IE 5 μm 4.6*250 mm; Mobile Phase: Hex:EtOH:DEA=50:50:0.2 at 1 mL/min; Temp: 30° C.; Wavelength: 230 nm; $R_T$=10.392 min). $^1$H NMR (400 MHz, DMSO-d$_6$) δ 9.54 (d, J=3.6 Hz, 0.6H), 8.93 (s, 0.4H), 8.01-7.99 (m, 1.6H), 7.96 (d, J=3.2 Hz, 0.4H), 7.55 (d, J=5.2 Hz, 1H), 7.50-7.43 (m, 1H), 7.38 (s, 1H), 7.23-7.18 (m, 1H), 6.04 (s, 0.4H), 5.93 (d, J=3.6 Hz, 0.6H), 4.98 (d, J=2.0 Hz, 2H), 4.14 (q, J=7.2 Hz, 2H), 4.01-3.94 (m, 2H), 3.89-3.80 (m, 0.4H), 3.70-3.62 (m, 0.6H), 2.67-2.61 (m, 0.5H), 2.47-2.40 (m, 0.5H), 2.06-1.80 (m, 5.4H), 1.68-1.63 (m, 0.6H), 1.44-1.34 (m, 2H), 1.21 (t, J=7.2 Hz, 3H), 1.10-1.03 (m, 3H).

VII-28-P: Chiral analysis (Column: Chiralpak IG 5 μm 4.6*250 mm; Mobile Phase: Hex:EtOH:DEA=80:20:0.2 at 1 mL/min; Temp: 30° C.; Wavelength: 254 nm; $R_T$=10.892 min). $^1$H NMR (400 MHz, DMSO-d$_6$) δ 9.50 (br s, 0.7H), 8.37 (s, 0.3H), 7.99-7.94 (m, 2H), 7.70 (s, 0.3H), 7.66 (s, 0.7H), 7.51 (s, 1H), 7.49-7.41 (m, 1H), 7.21-7.17 (m, 1H), 6.03 (s, 0.3H), 5.91 (s, 0.7H), 5.04 (s, 2H), 4.14 (q, J=7.2 Hz, 2H), 4.01-3.94 (m, 2H), 3.87-3.81 (m, 0.3H), 3.76-3.70 (m, 0.7H), 3.07-3.03 (m, 0.3H), 3.01-2.97 (m, 0.7H), 2.10-1.59 (m, 7.4H), 1.43-1.39 (m, 0.6H), 1.22-1.17 (m, 3H), 1.09-1.06 (m, 3H).

VII-28-Q: Chiral analysis (Column: Chiralpak IG 5 μm 4.6*250 mm; Mobile Phase: Hex:EtOH:DEA=80:20:0.2 at 1 mL/min; Temp: 30° C.; Wavelength: 254 nm; $R_T$=13.657 min). $^1$H NMR (400 MHz, DMSO-d$_6$) δ 9.54 (d, J=3.2 Hz, 0.7H), 8.37 (s, 0.3H), 7.99-7.94 (m, 2H), 7.70 (s, 0.3H), 7.65 (s, 0.7H), 7.50 (s, 1H), 7.49-7.40 (m, 1H), 7.20-7.16 (m, 1H), 6.03 (s, 0.3H), 5.91 (d, J=3.6 Hz, 0.7H), 5.04 (s, 1.4H), 5.03 (s, 0.6H), 4.14 (q, J=7.2 Hz, 2H), 4.00-3.97 (m, 2H), 3.88-3.82 (m, 0.3H), 3.75-3.69 (m, 0.7H), 3.07-3.03 (m, 0.3H), 3.01-2.97 (m, 0.7H), 2.09-1.58 (m, 7.3H), 1.42-1.39 (m, 0.7H), 1.21-1.17 (m, 3H), 1.10-1.06 (m, 3H).

Compound VII-29-P (trans)-Methyl 4-(2-chloro-4-fluorophenyl)-6-(4-(1-(3-methoxy-3-oxopropyl)-1H-pyrazol-4-yl)cyclohexyl)-2-(thiazol-2-yl)-1,4-dihydropyrimidine-5-carboxylate (a Single Stereoisomer)

Intermediate VII-29-5

Methyl 4-(2-chloro-4-fluorophenyl)-6-(4-(1-(3-methoxy-3-oxopropyl)-1H-pyrazol-4-yl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

LC-MS (ESI): $R_T$=1.87 min, mass calcd. for $C_{28}H_{29}ClFN_5O_4S$, 585.2, m/z found 585.9 [M+H]$^+$. $^1$H NMR (400 MHz, DMSO-d$_6$) δ 9.44 (d, J=3.2 Hz, 0.6H), 8.93 (s, 0.2H), 8.38 (s, 0.2H), 8.01-7.95 (m, 2H), 7.69 (s, 0.2H), 7.63 (s, 0.5H), 7.54-7.53 (m, 0.3H), 7.45-7.31 (m, 3H), 7.24-7.16 (m, 1H), 6.02-6.01 (m, 0.3H), 5.92-5.89 (m, 0.7H), 4.36-4.26 (m, 2H), 3.92-3.66 (m, 1H), 3.59 (d, J=7.6 Hz, 3H), 3.53 (s, 3H), 3.02-2.96 (m, 1H), 2.90-2.84 (m, 2H), 2.12-1.54 (m, 7H), 1.39-1.36 (m, 1H).

A stereoisomeric mixture of methyl 4-(2-chloro-4-fluorophenyl)-6-(4-(1-(3-methoxy-3-oxopropyl)-1H-pyrazol-4-yl)cyclohexyl)-2-(thiazol-2-yl)-1,4-dihydropyrimidine-5-carboxylate VII-29-5 (350 mg, 0.579 mmol) was separated by chiral Prep. HPLC (Column: Chiralpak IE 5 μm 20*250 mm; Mobile Phase: Hex:EtOH:DEA=50:50:0.3 at 15 mL/min; Temp: 30° C.; Wavelength: 230 nm) to give the title compounds Group 1 (200 mg, 29% yield), VII-29-P (40 mg, 95% purity from $^1$H NMR, 11% yield, 99.7% stereopure) and VII-29-Q (40 mg, 95% purity from NMR, 11% yield, 99.6% stereopure) as yellow solids. Group 1 (200 mg, 0.34 mmol) was separated by chiral Prep. HPLC (Column: Chiralpak OJ-H 5 μm 50*250 mm; Mobile Phase: MeOH:DEA=100:0.1 at 60 mL/min; Temp.: 35° C.; Wavelength: 254 nm) to afford the title compounds VII-29-M (80 mg, 99% purity, 42% yield, 100% stereopure) and VII-29-N (80 mg, 99% purity, 42% yield, 99.9% stereopure).

VII-29-M: LC-MS (ESI): $R_T$=1.974 min, mass calcd. for $C_{28}H_{29}CFN_5O_4S$, 585.2, m/z found 586.1 [M+H]$^+$. Chiral analysis (Column: Chiralpak OJ-H 5 μm 4.6*250 mm; Mobile Phase: MeOH:DEA=100:0.2 at 1 mL/min; Temp.: 30° C.; Wavelength: 230 nm, $R_T$=5.320 min). $^1$H NMR (400 MHz, CDCl$_3$) δ 8.07 (s, 0.5H), 7.81 (d, J=3.2 Hz, 0.4H), 7.78 (d, J=3.2 Hz, 0.6H), 7.56 (s, 0.6H), 7.49 (d, J=3.2 Hz, 0.4H), 7.47-7.45 (m, 1H), 7.41 (d, J=3.6 Hz, 0.5H), 7.37 (s, 1H), 7.31-7.27 (m, 0.7H), 7.24 (s, 0.3H), 7.14-7.10 (m, 1H), 6.95-6.86 (m, 1H), 6.17 (s, 0.6H), 6.04 (d, J=2.8 Hz, 0.4H), 4.47-4.42 (m, 2H), 4.05-3.99 (m, 0.6H), 3.92-3.85 (m, 0.4H), 3.67 (s, 3H), 3.61-3.59 (m, 3H), 3.11 (s, 0.6H), 3.05 (s, 0.4H), 2.98-2.92 (m, 2H), 2.19-2.14 (m, 1.6H), 2.06-1.80 (m, 3.4H), 1.76-1.69 (m, 2H), 1.60-1.48 (m, 1H).

VII-29-N: LC-MS (ESI): $R_T$=1.973 min, mass calcd. for $C_{28}H_{29}CFN_5O_4S$, 585.2, m/z found 586.1 [M+H]$^+$. Chiral analysis (Column: Chiralpak OJ-H 5 μm 4.6*250 mm; Mobile Phase: MeOH:DEA=100:0.2 at 1 mL/min; Temp.: 30° C.; Wavelength: 230 nm, $R_T$=6.864 min). $^1$H NMR (400 MHz, CDCl$_3$) δ 8.07 (s, 0.5H), 7.81 (d, J=2.8 Hz, 0.4H), 7.78 (d, J=2.8 Hz, 0.6H), 7.56 (s, 0.6H), 7.49 (d, J=2.8 Hz, 0.4H), 7.47-7.45 (m, 1H), 7.41 (d, J=3.2 Hz, 0.5H), 7.37 (s, 1H), 7.31-7.27 (m, 0.7H), 7.24 (s, 0.3H), 7.14-7.10 (m, 1H), 6.95-6.86 (m, 1H), 6.17 (s, 0.6H), 6.04 (d, J=2.8 Hz, 0.4H), 4.47-4.43 (m, 2H), 4.06-3.98 (m, 0.6H), 3.92-3.85 (m 0.4H), 3.67 (s, 3H), 3.61-3.59 (m 3H), 3.11 (s, 0.6H), 3.05 (s, 0.4H), 2.97-2.92 (m, 2H), 2.19-2.12 (m, 1.6H), 2.03-1.84 (m, 3.4H), 1.76-1.67 (m, 2H), 1.61-1.48 (m, 1H).

VII-29-P: LC-MS (ESI): $R_T$=1.83 min, mass calcd. for $C_{28}H_{29}ClFN_5O_4S$, 585.2, m/z found 585.9 [M+H]$^+$. Chiral analysis (Column: Chiralpak IE 5 μm 4.6*250 mm; Mobile Phase: Hex:EtOH:DEA=50:50:0.2 at 1 mL/min; Temp.: 30° C.; Wavelength: 230 nm, $R_T$=9.064 min). $^1$H NMR (400 MHz, DMSO-d$_6$) δ 9.44 (d, J=3.2 Hz, 0.6H), 8.92 (s, 0.4H), 8.01-7.98 (m, 1.6H), 7.95 (d, J=3.2 Hz, 0.4H), 7.53 (d, J=5.6 Hz, 1H), 7.45-7.41 (m, 1H), 7.38-7.33 (m, 2H), 7.24-7.19 (m, 1H), 6.02 (s, 0.4H), 5.91 (d, J=3.2 Hz, 0.6H), 4.30-4.26 (m, 2H), 3.93-3.84 (m, 0.4H), 3.69-3.60 (m, 3.6H), 3.52 (d, J=4.8 Hz, 3H), 2.87-2.83 (m, 2H), 2.68-2.55 (m, 0.6H), 2.46-2.43 (m, 0.4H), 2.05-1.74 (m, 5.4H), 1.65-1.61 (m, 0.6H), 1.44-1.30 (m, 2H).

VII-29-Q: LC-MS (ESI): $R_T$=1.83 min, mass calcd. for $C_{28}H_{29}CFN_5O_4S$, 585.2, m/z found 585.9 [M+H]$^+$. Chiral analysis (Column: Chiralpak IE 5 μm 4.6*250 mm; Mobile Phase: Hex:EtOH:DEA=50:50:0.2 at 1 mL/min; Temp.: 30° C.; Wavelength: 230 nm, $R_T$=12.766 min). $^1$H NMR (400 MHz, DMSO-d$_6$) δ 9.44 (d, J=3.2 Hz, 0.6H), 8.92 (s, 0.4H), 8.01-7.98 (m, 1.6H), 7.95 (d, J=3.2 Hz, 0.4H), 7.53 (d, J=5.6 Hz, 1H), 7.45-7.41 (m, 1H), 7.38-7.33 (m, 2H), 7.24-7.19 (m, 1H), 6.02 (s, 0.4H), 5.91 (d, J=3.2 Hz, 0.6H), 4.30-4.26 (m, 2H), 3.93-3.84 (m, 0.4H), 3.69-3.60 (m, 3.6H), 3.52 (d, J=4.8 Hz, 3H), 2.87-2.83 (m, 2H), 2.68-2.55 (m, 0.6H), 2.46-2.43 (m, 0.4H), 2.05-1.74 (m, 5.4H), 1.65-1.61 (m, 0.6H), 1.44-1.30 (m, 2H).

Compound VII-30-10

(trans)-Ethyl 4-(2-chloro-3,4-difluorophenyl)-6-(4-(1-(4-methoxy-2-methyl-4-oxobutan-2-yl)-1H-pyrazol-4-yl)cyclohexyl)-2-(thiazol-2-yl)-1,4-dihydropyrimidine-5-carboxylate (a Single Stereoisomer)

Intermediates VII-30-5 and VII-30-6: (cis)-Ethyl 4-(2-chloro-3,4-difluorophenyl)-6-(4-(1-(4-methoxy-2-methyl-4-oxobutan-2-yl)-1H-pyrazol-4-yl)cyclohexyl)-2-(thiazol-2-yl)-1,4-dihydropyrimidine-5-carboxylate (a Mixture of 2 Stereoisomers) and (trans)-ethyl 4-(2-chloro-3,4-difluorophenyl)-6-(4-(1-(4-methoxy-2-methyl-4-oxobutan-2-yl)-1H-pyrazol-4-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

VII-30-5: LC-MS (ESI): $R_T$=2.327 min, mass calcd. for $C_{31}H_{34}ClF_2N_5O_4S$, 645.2, m/z found 646.1 [M+H]$^+$. $^1$H NMR (400 MHz, CDCl$_3$) δ 8.08 (s, 0.7H), 7.81 (d, J=3.2 Hz, 0.3H), 7.74 (d, J=3.2 Hz, 0.7H), 7.56 (s, 0.3H), 7.49-7.46 (m, 2H), 7.41 (d, J=3.2 Hz, 0.7H), 7.30-7.28 (s, 0.3H), 7.10-6.97 (m, 2H), 6.18 (s, 0.7H), 6.06 (d, J=2.8 Hz, 0.3H), 4.11-3.97 (m, 2.8H), 3.91-3.83 (m, 0.2H), 3.58 (s, 0.6H), 3.57 (s, 2.4H), 3.15-3.10 (m, 0.8H), 3.07-3.02 (m, 0.2H), 2.96 (s, 1.6H), 2.93 (s, 0.4H), 2.22-2.09 (m, 2H), 2.04-1.92 (m, 2.7H), 1.89-1.81 (m, 1.3H), 1.78 (s, 4.4H), 1.75 (s, 1.6H), 1.74-1.65 (m, 2H), 1.17-1.13 (m, 3H).

VII-30-6: LC-MS (ESI): $R_T$=2.167 min, mass calcd. for $C_{31}H_{34}ClF_2N_5O_4S$, 645.2, m/z found 646.1 [M+H]$^+$. $^1$H NMR (400 MHz, CDCl$_3$) δ 8.19 (s, 0.8H), 7.83 (d, J=3.6 Hz, 1H), 7.52-7.49 (m, 0.2H), 7.46 (d, J=3.2 Hz, 0.8H), 7.43-7.41 (m, 1H), 7.33 (s, 1.2H), 7.13-6.99 (m, 2H), 6.21 (s, 0.7H), 6.08 (d, J=2.0 Hz, 0.3H), 4.12-3.95 (m, 2.8H), 3.83-3.76 (m, 0.2H), 3.58 (s, 3H), 2.89 (s, 2H), 2.66-2.55 (m, 1H), 2.18-1.92 (m, 4H), 1.86-1.75 (m, 0.7H), 1.71-1.68 (m, 6.3H), 1.65-1.63 (m, 0.4H), 1.61-1.46 (m, 2.6H), 1.14 (t, J=6.8 Hz, 3H).

A stereoisomeric mixture of (trans)-ethyl 4-(2-chloro-3,4-difluorophenyl)-6-(4-(1-(4-methoxy-2-methyl-4-oxobutan-2-yl)-1H-pyrazol-4-yl)cyclohexyl)-2-(thiazol-2-yl)-1,4-dihydropyrimidine-5-carboxylate VII-30-6 (265 mg, 90% purity, 0.369 mmol) was separated by chiral Prep. HPLC (separation condition: Column: Chiralpak IC 5 μm 20*250 mm; Mobile Phase: Hex:EtOH:DEA=80:20:0.1 at 60 mL/min; Temp: 35° C.; Wavelength: 214 nm) to give the title compounds VII-30-9 (110 mg, 95% purity from $^1$H NMR, 44% yield, 99.9% stereopure) as yellow solids and the title compound VII-30-10 (80 mg, 95% purity from $^1$H NMR, 32% yield, 99.9% stereopure) as yellow solids.

VII-30-9: LC-MS (ESI): $R_T$=2.156 min, mass calcd. for $C_{31}H_{34}ClF_2N_5O_4S$, 645.2, m/z found 646.2 [M+H]$^+$. Chiral analysis (Column: Chiralpak IE 5 μm 4.6*250 mm; Mobile Phase: Hex:EtOH:DEA=80:20:0.2 at 1 mL/min; Wavelength: 230 nm, $R_T$=13.343 min). $^1$H NMR (400 MHz, CDCl$_3$) δ 8.20 (s, 0.8H), 7.83 (d, J=2.8 Hz, 1H), 7.51 (d, J=3.2 Hz, 0.3H), 7.46 (d, J=2.8 Hz, 0.7H), 7.44 (s, 0.3H), 7.41 (s, 0.7H), 7.33-7.32 (m, 1.2H), 7.13-6.98 (m, 2H), 6.21 (s, 0.7H), 6.08 (d, J=2.0 Hz, 0.3H), 4.11-3.98 (m, 2.8H), 3.83-3.72 (m, 0.2H), 3.58 (s, 3H), 2.90 (s, 2H), 2.67-2.55 (m, 1H), 2.18-2.11 (m, 2.5H), 2.05-1.92 (m, 2.5H), 1.87-1.78 (m, 1H), 1.72 (s, 6H), 1.56-1.47 (m 2H), 1.16-1.13 (m 3H).

VII-30-10: LC-MS (ESI): $R_T$=2.157 min, mass calcd. for $C_{31}H_{34}ClF_2N_5O_4S$, 645.2, m/z found 646.2 [M+H]$^+$. Chiral analysis (Column: Chiralpak IE 5 μm 4.6*250 mm; Mobile Phase: Hex:EtOH:DEA=80:20:0.2 at 1 mL/min; Wavelength: 230 nm, $R_T$=15.752 min). $^1$H NMR (400 MHz, CDCl$_3$) δ 8.20 (s, 0.8H), 7.83 (d, J=3.2 Hz, 1H), 7.51 (d, J=2.8 Hz, 0.3H), 7.46 (d, J=3.2 Hz, 0.7H), 7.43 (s, 0.3H), 7.41 (s, 0.7H), 7.33-7.31 (m, 1.2H), 7.13-6.98 (m, 2H), 6.21 (s, 0.7H), 6.08 (d, J=2.0 Hz, 0.3H), 4.13-3.95 (m, 2.8H), 3.84-3.71 (m, 0.2H), 3.58 (s, 3H), 2.89 (s, 2H), 2.66-2.54 (m, 1H), 2.18-2.09 (m, 2.5H), 2.05-1.91 (m, 2H), 1.88-1.75 (m, 1.5H), 1.72 (s, 1.8H), 1.71 (s, 4.2H), 1.61-1.56 (m, 2H), 1.16-1.12 (m, 3H).

Compound VII-31

Ethyl 4-(2-chloro-3,4-difluorophenyl)-6-(4-(1-(4-methoxy-4-oxobutan-2-yl)-1H-pyrazol-4-yl)cyclohexyl)-2-(thiazol-2-yl)-1,4-dihydropyrimidine-5-carboxylate (a Mixture of 8 Stereoisomers)

By utilizing the analogous procedure of Method B, the title compound was synthesized as yellow solids.

$^1$H NMR (400 MHz, DMSO-d$_6$) δ 9.55-9.53 (m, 0.5H), 8.93 (s, 0.2H), 8.28-8.27 (m, 0.3H), 8.01-7.99 (m, 1.3H), 7.96-7.94 (m, 0.4H), 7.91-7.90 (m, 0.3H), 7.74-7.73 (m, 0.2H), 7.66 (s, 0.4H), 7.59-7.58 (m, 0.4H), 7.49-7.42 (m, 1.6H), 7.32 (s, 0.4H), 7.24-7.16 (m, 1H), 6.04-6.02 (m, 0.4H), 5.93-5.90 (m, 0.6H), 4.78-4.64 (m, 1H), 4.06-3.96 (m, 2H), 3.89-3.82 (m, 0.4H), 3.75-3.65 (m, 0.6H), 3.56-3.53 (m, 3H), 3.02-2.76 (m, 3H), 2.13-1.54 (m, 7H), 1.48-1.32 (m, 4H), 1.10-1.03 (m, 3H).

Compound VII-32-N (trans)-ethyl 4-(2-chloro-3,4-difluorophenyl)-6-(4-(1-(3-methoxy-3-oxopropyl)-1H-pyrazol-4-yl)cyclohexyl)-2-(thiazol-2-yl)-1,4-dihydropyrimidine-5-carboxylate (a Single Stereoisomer)

Compound VII-32 ethyl 4-(2-chloro-3,4-difluorophenyl)-6-(4-(1-(3-methoxy-3-oxopropyl)-1H-pyrazol-4-yl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

LC-MS (ESI): $R_T$=2.803 min, mass calcd. for $C_{29}H_{30}ClF_2N_5O_4S$, 617.2, m/z found 618.1 [M+H]$^+$. $^1$H NMR (400 MHz, CDCl$_3$) δ 8.19 (s, 0.3H), 8.06 (s, 0.3H), 7.83-7.79 (m, 1H), 7.56-7.36 (m 2.5H), 7.34-7.26 (m 0.4H), 7.24 (s, 0.5H), 7.13-6.97 (m, 2H), 6.21 (s, 0.3H), 6.19 (s, 0.4H), 6.08-6.06 (m, 0.3H), 4.44 (q, J=7.2 Hz, 1H), 4.39 (q, J=6.8 Hz, 1H), 4.10-3.99 (m, 3H), 3.70 (s, 1H), 3.67 (s, 2H), 3.11 (br s, 0.4H), 3.04 (br s, 0.2H), 2.96 (t, J=6.4 Hz, 1H), 2.90 (t, J=6.8 Hz, 1H), 2.64-2.55 (m, 0.4H), 2.17-2.10 (m, 2H), 2.03-1.84 (m, 3H), 1.77-1.65 (m, 2H), 1.57-1.46 (m, 1H), 1.16-1.12 (m, 3H).

A stereoisomeric mixture of VII-32 (770 mg, 1.25 mmol) was separated by chiral Prep. HPLC (the first separation condition: Column: Chiralpak IA 5 μm 20*250 mm; Mobile Phase: Hex:EtOH:DEA=60:40:0.2 at 25 mL/min; Temp: 30° C.; Wavelength: 214 nm) to afford the VII-32-F (170 mg, 22% yield) and VII-32-E (280 mg, 36% yield) as yellow solids.

A stereoisomeric mixture of VII-32-F (170 mg, 0.28 mmol) was separated by chiral Prep. HPLC (the second separation condition: Column: Chiralpak IE 5 μm 20*250 mm; Mobile Phase: Hex:EtOH:DEA=40:60:0.2 at 10 mL/min; Temp: 30° C.; Wavelength: 230 nm) to afford the VII-32-M (60 mg, 35% yield, 100% stereopure) and VII-32-N (29 mg, 29% yield, 100% stereopure); Compound VII-32-F: LC-MS (ESI): $R_T$=2.760 min, mass calcd. for $C_{29}H_{30}ClF_2N_5O_4S$, 617.2, m/z found 618.2 [M+H]$^+$. $^1$H NMR (400 MHz, CDCl$_3$) δ 8.18 (s, 0.7H), 7.82 (d, J=3.2 Hz, 1H), 7.50 (d, J=2.8 Hz, 0.3H), 7.45 (d, J=3.2 Hz, 0.7H), 7.40 (s, 0.3H), 7.37 (s, 0.7H), 7.32 (s, 0.3H), 7.24 (s, 1H), 7.14-7.09 (m, 1H), 7.07-6.99 (m, 1H), 6.21 (s, 0.7H), 6.08 (d, J=2.4 Hz, 0.3H), 4.38 (t, J=6.4 Hz, 2H), 4.11-3.97 (m, 2.8H), 3.83-3.76 (m, 0.2H), 3.70 (s, 3H), 2.90 (t, J=6.4 Hz, 2H), 2.64-2.55 (m, 1H), 2.17-2.01 (m, 4H), 1.92-1.65 (m, 1.5H), 1.59-1.44 (m, 2.5H), 1.16-1.12 (m, 3H).

Compound VII-32-E: LC-MS (ESI): $R_T$=4.450 min, mass calcd. for $C_{29}H_{30}ClF_2N_5O_4S$, 617.2, m/z found 617.9 [M+H]$^+$. $^1$H NMR (400 MHz, CDCl$_3$) δ 8.06 (s, 0.7H), 7.81 (d, J=2.8 Hz, 0.3H), 7.79 (d, J=3.2 Hz, 0.7H), 7.56 (s, 0.3H), 7.50 (d, J=3.2 Hz, 0.3H), 7.47 (s, 0.7H), 7.45 (s, 0.3H), 7.42 (d, J=3.2 Hz, 0.7H), 7.36 (s, 0.7H), 7.28 (s, 0.3H), 7.12-6.97 (m, 1H), 6.19 (s, 0.7H), 6.06 (d, J=2.4 Hz, 0.3H), 4.44 (q, J=6.8 Hz, 2H), 4.11-3.93 (m, 2.7H), 3.90-3.85 (m, 0.3H), 3.67 (s, 3H), 3.11 (s, 0.7H), 3.04 (s, 0.3H), 2.94 (q, J=6.4 Hz, 2H), 2.17-2.12 (m, 1.5H), 2.06-1.83 (m, 3.5H), 1.76-1.61 (m, 2.5H), 1.56-1.48 (m, 0.5H), 1.16-1.12 (m, 3H).

Compound VII-32-M: LC-MS (ESI): $R_T$=3.872 min, mass calcd. for $C_{29}H_{30}ClF_2N_5O_4S$, 617.2, m/z found 618.1 [M+H]$^+$. $^1$H NMR (400 MHz, CDCl$_3$) δ 8.22 (s, 0.7H), 7.87-7.86 (m, 1H), 7.54 (d, J=3.2 Hz, 0.3H), 7.49 (d, J=3.2 Hz, 0.7H), 7.44 (s, 0.3H), 7.42 (s, 0.7H), 7.35 (s, 0.3H), 7.28 (s, 1H), 7.18-7.13 (m, 1H), 7.11-7.03 (m, 1H), 6.25 (s, 0.7H), 6.12 (d, J=3.2 Hz, 0.3H), 4.42 (t, J=6.8 Hz, 2H), 4.15-4.02 (m, 2.8H), 3.88-3.79 (m, 0.2H), 3.74 (s, 3H), 2.94 (t, J=6.8 Hz, 2H), 2.68-2.59 (m, 1H), 2.21-2.02 (m, 4H), 1.96-1.65 (m, 2H), 1.61-1.50 (m, 2H), 1.20-1.16 (m, 3H).

Compound VII-32-N: LC-MS (ESI): $R_T$=3.876 min, mass calcd. for $C_{29}H_{30}ClF_2N_5O_4S$, 617.2, m/z found 618.1 [M+H]$^+$. $^1$H NMR (400 MHz, CDCl$_3$) δ 8.22 (s, 0.7H), 7.87-7.86 (m, 1H), 7.54 (d, J=3.2 Hz, 0.3H), 7.49 (d, J=2.8 Hz, 0.7H), 7.44 (s, 0.3H), 7.42 (s, 0.7H), 7.36 (s, 0.3H), 7.28 (s, 1H), 7.18-7.13 (m, 1H), 7.11-7.03 (m, 1H), 6.25 (s, 0.7H), 6.12 (d, J=2.8 Hz, 0.3H), 4.42 (t, J=6.4 Hz, 2H), 4.15-4.02 (m, 2.8H), 3.87-3.80 (m, 0.2H), 3.74 (s, 3H), 2.94 (t, J=6.4 Hz, 2H), 2.68-2.58 (m, 1H), 2.21-2.02 (m, 4H), 1.96-1.66 (m, 2H), 1.60-1.47 (m, 2H), 1.20-1.16 (m, 3H).

Compound VII-33-10

(trans)-ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate (a Single Stereoisomer)

Intermediate VII-33-8

Ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids. LC-MS (ESI): $R_T$=2.998 min, mass calcd. for $C_{30}H_{32}ClF_2N_5O_4S$, 631.2, m/z found 632.1 [M+H]$^+$. $^1$H NMR (400 MHz, CDCl$_3$) δ 8.21-8.20 (m, 0.7H), 7.84-7.83 (m, 1H), 7.64 (s, 0.1H), 7.57-7.55 (m, 0.2H), 7.51 (d, J=3.2 Hz, 0.1H), 7.47-7.45 (m, 1H), 7.39-7.34 (m, 0.3H), 7.14 (s, 0.6H), 7.12-6.99 (m, 2H), 6.22-6.21 (m, 0.7H), 6.08 (d, J=2.4 Hz, 0.3H), 4.39 (t, J=7.2 Hz, 1H), 4.31 (t, J=6.8 Hz, 1H), 4.15-3.90 (m, 3H), 3.69 (s, 1.5H), 3.67 (s, 1.5H), 3.06-3.03 (m, 0.5H), 2.99-2.92 (m, 1H), 2.89-2.85 (m, 1H), 2.53-2.47 (m, 0.5H), 2.26 (s, 0.4H), 2.24 (s, 2.6H), 2.19-1.42 (m, 8H), 1.17-1.13 (m, 3H).

Intermediates VII-33-9, VII-33-10 and VII-33-11

(cis)-Ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate (a Mixture of 2 Stereoisomers), (trans)-ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate (a Single Stereoisomer) and (trans)-ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate (a Single Stereoisomer)

A stereoisomeric mixture of ethyl 4-(2-chloro-3,4-difluorophenyl)-6-(4-(1-(3-methoxy-3-oxopropyl)-3-methyl-1H-pyrazol-4-yl)cyclohexyl)-2-(thiazol-2-yl)-1,4-dihydropyrimidine-5-carboxylate VII-33-8 (1.26 g, 90% purity, 1.79 mmol) was separated by chiral Prep. HPLC (condition: Column: Chiralpak IG 5 μm 20*250 nm; Mobile Phase: Hex:EtOH:DEA=70:30:0.3 at 15 mL/min; Temp: 30° C.; Wavelength: 230 nm) to afford the title compounds VII-33-9

(450 mg, 36% yield, 90% purity, 97.5% stereopure) as yellow solids, VII-33-10 (220 mg, 17% yield, 90% purity, 95.1% stereopure) as yellow solids and VII-33-11 (210 mg, 17% yield, 90% purity, 99.2% stereopure) as yellow solids.

VII-33-9: LC-MS (ESI): $R_T$=2.866 min, mass calcd. for $C_{30}H_{32}ClF_2N_5O_4S$, 631.2, m/z found 632.2 [M+H]$^+$. $^1$H NMR (400 MHz, CDCl$_3$) δ 8.20 (s, 0.6H), 7.84 (d, J=3.2 Hz, 1H), 7.64 (s, 0.5H), 7.56 (d, J=2.8 Hz, 0.5H), 7.46-7.44 (m, 1H), 7.32 (s, 0.4H), 7.13-6.99 (m, 2H), 6.21 (s, 0.6H), 6.08 (d, J=2.8 Hz, 0.4H), 4.39 (t, J=7.2 Hz, 2H), 4.15-3.88 (m, 3H), 3.67 (s, 3H), 3.05-2.99 (m, 0.7H), 2.97-2.92 (m, 2.3H), 2.24 (s, 3H), 2.05-1.70 (m, 7.4H), 1.60-1.41 (m, 0.6H), 1.15 (t, J=7.2 Hz, 3H).

VII-33-10: LC-MS (ESI): $R_T$=2.823 min, mass calcd. for $C_{30}H_{32}ClF_2N_5O_4S$, 631.2, m/z found 632.2 [M+H]$^+$. $^1$H NMR (400 MHz, CDCl$_3$) 8.19 (s, 0.8H), 7.84 (d, J=3.2 Hz, 1H), 7.51 (d, J=2.8 Hz, 0.2H), 7.46 (d, J=3.2 Hz, 0.8H), 7.33 (s, 0.2H), 7.14-7.10 (m, 2H), 7.07-6.99 (m, 1H), 6.21 (s, 0.8H), 6.08 (d, J=2.4 Hz, 0.2H), 4.31 (t, J=6.4 Hz, 2H), 4.12-4.05 (m, 2.8H), 3.98-3.85 (m, 0.2H), 3.69 (s, 3H), 2.87 (d, J=6.8 Hz, 2H), 2.53-2.47 (m, 1H), 2.26 (s, 0.7H), 2.24 (s, 2.3H), 2.14-1.98 (m, 4H), 1.75-1.41 (m, 4H), 1.14 (t, J=7.2 Hz, 3H).

VII-33-11: LC-MS (ESI): $R_T$=2.819 min, mass calcd. for $C_{30}H_{32}ClF_2N_5O_4S$, 631.2, m/z found 632.2 [M+H]$^+$. $^1$H NMR (400 MHz, CDCl$_3$) 8.20 (s, 0.8H), 7.84 (d, J=2.8 Hz, 1H), 7.51 (d, J=2.4 Hz, 0.2H), 7.46 (d, J=3.2 Hz, 0.8H), 7.32 (s, 0.2H), 7.14 (s, 1H), 7.12-7.10 (m, 1H), 7.07-6.99 (m, 1H), 6.22 (s, 0.8H), 6.08 (s, 0.2H), 4.31 (t, J=6.8 Hz, 2H), 4.15-3.98 (m, 2.8H), 3.85-3.77 (m, 0.2H), 3.69 (s, 3H), 2.87 (d, J=6.4 Hz, 2H), 2.53-2.47 (m, 1H), 2.26 (s, 0.7H), 2.24 (s, 2.3H), 2.14-1.95 (m, 4H), 1.75-1.42 (m, 4H), 1.14 (t, J=7.2 Hz, 3H).

Compound VII-34

Ethyl 6-(4-(1-(3-(tert-butoxycarbonyl)cyclobutyl)-1H-pyrazol-4-yl)cyclohexyl)-4-(2-chloro-3,4-difluorophenyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

$^1$H NMR (300 MHz, CDCl$_3$) δ 8.19 (br s, 0.2H), 8.08 (br s, 0.3H), 7.84-7.82 (m, 0.6H), 7.78-7.76 (m, 0.4H), 7.57-7.33 (m, 3.5H), 7.10-6.98 (m, 2H), 6.21-6.19 (m, 0.7H), 6.09-6.05 (m, 0.3H), 5.06-4.93 (m, 0.4H), 4.76-4.64 (m, 0.6H), 4.11-4.02 (m, 3H), 3.15-3.04 (m, 1H), 2.88-2.73 (m, 4H), 2.14-1.89 (m, 5H), 1.78-1.72 (m, 2H), 1.52-1.46 (m, 11H), 1.17-1.12 (m, 3H).

Compound VII-35-P (trans)-Ethyl 4-(2-chloro-3,4-difluorophenyl)-6-(4-(3-(methoxycarbonyl)-1-methyl-1H-pyrazol-5-yl)cyclohexyl)-2-(thiazol-2-yl)-1,4-dihydropyrimidine-5-carboxylate (a Single Stereoisomer)

Intermediates VII-35-X and VII-35-Y (cis)-Ethyl 4-(2-chloro-3,4-difluorophenyl)-6-(4-(3-(methoxycarbonyl)-1-methyl-1H-pyrazol-5-yl)cyclohexyl)-2-(thiazol-2-yl)-1,4-dihydropyrimidine-5-carboxylate (a Mixture of 2 Stereoisomers) and (trans)-Ethyl 4-(2-chloro-3,4-difluorophenyl)-6-(4-(3-(methoxycarbonyl)-1-methyl-1H-pyrazol-5-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

VII-35-X: LC-MS (ESI): $R_T$=1.81 min, mass calcd. for $C_{28}H_{28}ClF_2N_5O_4S$, 603.2, m/z found 604.2[M+H]$^+$. $^1$H NMR (400 MHz, DMSO-d$_6$) 9.60 (d, J=3.6 Hz, 0.8H), 8.74 (s, 0.2H), 8.06-7.95 (m, 2H), 7.50-7.43 (m, 1H), 7.24-7.20 (m, 1H), 6.92 (s, 1H), 6.05 (s, 0.2H), 5.93 (d, J=3.2 Hz, 0.8H), 4.01-3.96 (m, 2H), 3.88 (s, 3H), 3.80 (s, 3H), 3.78-3.74 (m, 1H), 3.24-3.22 (m, 1H), 2.14-2.11 (m, 1H), 2.00-1.92 (m, 3H), 1.85-1.76 (m, 2H), 1.67-1.62 (m, 1H), 1.52-1.48 (m, 1H), 1.10-1.05 (m, 3H).

VII-35-Y: LC-MS (ESI): $R_T$=1.79 min, mass calcd. for $C_{28}H_{28}ClF_2N_5O_4S$, 603.2, m/z found 604.2[M+H]$^+$. $^1$H NMR (400 MHz, DMSO-d$_6$) 9.56 (d, J=3.6 Hz, 0.6H), 8.92 (s, 0.4H), 8.01-7.96 (m, 2H), 7.51-7.43 (m, 1H), 7.23-7.20 (m, 1H), 6.60-6.58 (m, 1H), 6.04 (s, 0.4H), 5.94 (d, J=3.6 Hz, 0.6H), 4.01-3.95 (m, 2H), 3.89 (s, 3H), 3.77 (s, 3H), 3.72-3.66 (m, 1H), 2.97-2.91 (m, 0.5H), 2.81-2.75 (m, 0.5H), 2.04-1.85 (m, 5H), 1.82-1.79 (m, 0.5H), 1.71-1.67 (m, 0.5H), 1.52-1.43 (m, 2H), 1.11-1.04 (m, 3H).

A stereoisomeric mixture of ethyl 4-(2-chloro-3,4-difluorophenyl)-6-((trans)-4-(3-(methoxycarbonyl)-1-methyl-1H-pyrazol-5-yl)cyclohexyl)-2-(thiazol-2-yl)-1,4-dihydropyrimidine-5-carboxylate VII-35-Y (180 mg, 90% purity, 0.268 mmol) was separated by chiral Prep. HPLC (separation condition: Column: Chiralpak ID 5 μm 30*250 mm; Mobile Phase: Hex:EtOH:DEA=60:40:0.3 at 13 mL/min; Temp: 30° C.; Wavelength: 230 nm) to afford VII-35-P (63 mg, 95% purity from $^1$HNMR, 37% yield, 100% ee) and VII-35-Q (78 mg, 97% purity from $^1$HNMR, 47% yield, 97% ee) as yellow solids.

VII-35-P: Chiral HPLC (Column: Chiralpak ID 5 μm 4.6*250 mm; Mobile Phase: Hex:EtOH:DEA=60:40:0.2 at 1.0 mL/min; Temp: 30° C.; Wavelength: 230 nm, $R_T$=8.464 min). $^1$H NMR (300 MHz, CDCl$_3$) 8.15 (s, 0.5H), 7.85-7.82 (m, 1H), 7.52-7.46 (m, 1H), 7.34 (s, 0.5H), 7.10-7.01 (m, 2H), 6.62 (s, 1H), 6.21 (s, 0.6H), 6.09 (s, 0.4H), 4.16-4.07 (m, 2H), 4.05-4.00 (m, 1H), 3.94-3.92 (m, 6H), 2.73-2.65 (m, 1H), 2.22-1.99 (m, 5H), 1.91-1.79 (m, 1H), 1.72-1.64 (m, 2H), 1.16-1.11 (m, 3H).

VII-35-Q: LC-MS (ESI): $R_T$=1.79 min, mass calcd. for $C_{28}H_{28}ClF_2N_5O_4S$, 603.2, m/z found 604.1 [M+H]$^+$. Chiral HPLC (Column: Chiralpak ID 5 μm 4.6*250 mm; Mobile Phase: Hex:EtOH:DEA=60:40:0.2 at 1.0 mL/min; Temp: 30° C.; Wavelength: 230 nm, $R_T$=10.400 min). $^1$H NMR (300 MHz, CDCl$_3$) 8.15 (s, 0.5H), 7.85-7.82 (m, 1H), 7.52-7.46 (m, 1H), 7.34 (s, 0.5H), 7.12-7.01 (m, 2H), 6.62 (s, 1H), 6.21 (s, 0.6H), 6.08 (s, 0.4H), 4.13-4.09 (m, 1H), 4.06-4.00 (m, 2H), 3.94-3.92 (m, 6H), 2.74-2.67 (m, 1H), 2.19-2.03 (m, 5H), 1.87-1.80 (m, 1H), 1.73-1.66 (m, 2H), 1.17-1.11 (m, 3H).

Compound VII-36-N (trans)-Ethyl 4-(2-chloro-3,4-difluorophenyl)-6-(4-(5-(methoxycarbonyl)-1-methyl-1H-pyrazol-3-yl)cyclohexyl)-2-(thiazol-2-yl)-1,4-dihydropyrimidine-5-carboxylate (a Single Stereoisomer)

Intermediate VII-36-R (trans)-Ethyl 4-(2-chloro-3,4-difluorophenyl)-6-(4-(5-(methoxycarbonyl)-1-methyl-1H-pyrazol-3-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

LC-MS (ESI): $R_T$=1.95 min, mass calcd. for $C_{28}H_{28}ClF_2N_5O_4S$, 603.2, m/z found mass 604.0 [M+H]$^+$. $^1$H NMR (400 MHz, DMSO-$d_6$) δ 9.53 (br s, 0.5H), 8.97 (br s, 0.5H), 8.01-7.98 (m, 2H), 7.50-7.44 (m, 1H), 7.22-7.19 (m, 1H), 6.74 (s, 1H), 5.96 (br s, 1H), 4.03 (s, 3H), 3.98 (q, J=7.2 Hz, 2H), 3.82 (s, 3H), 3.69-3.63 (m, 0.6H), 3.31 (s, 0.4H), 2.77-2.60 (m, 1H), 2.08-2.05 (m, 2H), 1.92-1.85 (m, 2H), 1.80-1.72 (m, 2H), 1.55-1.49 (m, 2H), 1.07 (t, J=7.2 Hz, 3H).

A stereoisomeric mixture of VII-36-R (100 mg, 0.166 mg) was separated by chiral Prep. HPLC (Column: Chiralpak IE 5 μm 20*250 mm; Mobile Phase: Hex:EtOH:DEA=70:30:0.3 at 12 mL/min; Temp: 30° C.; Wavelength: 230 nm) to give the compounds VII-36-M (30 mg, 30% yield) and VII-36-N (30 mg, 30% yield) as yellow solids.

VII-36-M: $^1$H NMR (400 MHz, DMSO-$d_6$) δ 9.53 (br s, 0.5H), 8.97 (br s, 0.5H), 8.01-7.98 (m, 2H), 7.50-7.44 (m, 1H), 7.22-7.19 (m, 1H), 6.74 (s, 1H), 5.96 (br s, 1H), 4.03 (s, 3H), 3.98 (q, J=7.2 Hz, 2H), 3.82 (s, 3H), 3.69-3.63 (m, 0.6H), 3.31 (s, 0.4H), 2.77-2.60 (m, 1H), 2.08-2.05 (m, 2H), 1.93-1.85 (m, 2H), 1.80-1.72 (m, 2H), 1.55-1.45 (m, 2H), 1.07 (t, J=7.2 Hz, 3H).

VII-36-N: $^1$H NMR (400 MHz, DMSO-$d_6$) δ 9.53 (br s, 0.5H), 8.97 (br s, 0.5H), 8.01-7.98 (m, 2H), 7.50-7.44 (m, 1H), 7.22-7.19 (m, 1H), 6.74 (s, 1H), 5.96 (br s, 1H), 4.03 (s, 3H), 3.98 (q, J=7.2 Hz, 2H), 3.82 (s, 3H), 3.69-3.63 (m, 0.6H), 3.31 (s, 0.4H), 2.77-2.60 (m, 1H), 2.08-2.05 (m, 2H), 1.93-1.85 (m, 2H), 1.80-1.72 (m, 2H), 1.55-1.45 (m, 2H), 1.07 (t, J=7.2 Hz, 3H).

Compound VII-37-4C (trans)-Ethyl 6-(4-(1-(3-(tert-butoxy)-2,2-dimethyl-3-oxopropyl)-1H-pyrazol-3-yl)cyclohexyl)-4-(2-chloro-3,4-difluorophenyl)-2-(thiazol-2-yl)-1,4-dihydropyrimidine-5-carboxylate (a Single Stereoisomer)

Intermediate VII-37

Ethyl 6-(4-(1-(3-(tert-butoxy)-2,2-dimethyl-3-oxopropyl)-1H-pyrazol-3-yl)cyclohexyl)-4-(2-chloro-3,4-difluorophenyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

LC-MS (ESI): $R_T$=1.88 and 1.91 min, mass calcd. for $C_{34}H_{40}ClF_2N_5O_4S$, 687.2, m/z found 688.0 [M+H]$^+$. $^1$H NMR (400 MHz, CD$_3$OD) δ 7.94-7.93 (m, 0.3H), 7.90-7.85 (m, 0.7H), 7.76-7.72 (m, 1H), 7.54-7.53 (m, 0.8H), 7.47 (s, 0.3H), 7.41 (s, 0.3H), 7.39-7.36 (m 0.6H), 7.24-7.18 (m 2H), 6.15-6.13 (m 0.6H), 6.08-6.06 (m, 0.4H), 4.29-4.27 (m, 1H), 4.22 (s, 1H), 4.08-3.99 (m, 2.8H), 3.87-3.79 (m, 0.2H), 3.12-3.04 (m, 0.6H), 2.69-2.57 (m, 0.4H), 2.26-1.54 (m, 8H), 1.47 (s, 4H), 1.41 (s, 5H), 1.17-1.12 (m, 9H).

A stereoisomeric mixture of ethyl 6-(4-(1-(3-(tert-butoxy)-2,2-dimethyl-3-oxopropyl)-1H-pyrazol-3-yl)cyclohexyl)-4-(2-chloro-3,4-difluorophenyl)-2-(thiazol-2-yl)-1,4-dihydropyrimidine-5-carboxylate VII-37 (290 mg, 90% purity, 0.379 mmol) was separated by chiral Prep. HPLC (the first separation condition: Column: Chiralpak IE 5 μm 20*250 mm; Mobile Phase: CO$_2$:EtOH:DEA=70:30:0.3 at 50 g/min; Col. Temp: 30° C.; Wavelength: 230 nm; Back pressure 100 bar; the second separation condition: Column: Chiralpak IE 5 μm 20*250 mm; Mobile Phase: CO$_2$:EtOH:DEA=70:30:0.3 at 50 g/min; Col. Temp: 30° C.; Wavelength: 214 nm; Back pressure 100 bar; the third separation condition: Column: Chiralpak IA 5 μm 20*250 mm; Mobile Phase: CO$_2$:EtOH:DEA=70:30:0.3 at 45 g/min; Col. Temp: 30° C.; Wavelength: 214 nm; Back pressure 100 bar) to afford VII-37-4A (55 mg, 90% purity from $^1$H NMR, 19% yield, 100% stereopure), VII-37-4B (68 mg, 90% purity from $^1$H NMR, 23% yield, 97.1% stereopure), VII-37-4C (36 mg, 90% purity from $^1$H NMR, 12% yield, 100% stereopure) and VII-37-4D (45 mg, 90% purity from $^1$H NMR, 16% yield, 93.3% stereopure) as yellow solids.

VII-37-4A: LC-MS (ESI): $R_T$=1.93 min, mass calcd. for $C_{34}H_{40}ClF_2N_5O_4S$, 687.2, m/z found 687.9 [M+H]$^+$. Chiral analysis (Column: Chiralpak IE 5 μm 4.6*250 mm; Mobile Phase: CO$_2$:EtOH:DEA=70:30:0.2 at 3.0 g/min; Col. Temp: 40° C.; Wavelength: 230 nm; Back pressure 100 bar, $R_T$=4.05 min). $^1$H NMR (400 MHz, CD$_3$OD) δ 7.88 (d, J=3.2 Hz, 0.4H), 7.86 (d, J=3.2 Hz, 0.6H), 7.75-7.73 (m, 1H), 7.55-7.53 (m, 1.4H), 7.47 (s, 0.6H), 7.24-7.16 (m, 2H), 6.13 (s, 0.6H), 6.06 (s, 0.4H), 4.29-4.27 (m, 2H), 4.08-4.01 (m, 2.6H), 3.88-3.81 (m, 0.4H), 3.15-3.09 (m, 0.6H), 3.07-3.02 (m, 0.4H), 2.26-1.65 (m, 7.5H), 1.50-1.43 (m, 0.5H), 1.41 (s, 9H), 1.17-1.12 (m, 9H).

VII-37-4B: LC-MS (ESI): $R_T$=1.92 min, mass calcd. for $C_{34}H_{40}ClF_2N_5O_4S$, 687.2, m/z found 687.9 [M+H]$^+$. Chiral analysis (Column: Chiralpak IE 5 μm 4.6*250 mm; Mobile Phase: CO$_2$:EtOH:DEA=70:30:0.2 at 3.0 g/min; Col. Temp: 40° C.; Wavelength: 230 nm; Back pressure 100 bar, $R_T$=4.77 min). $^1$H NMR (400 MHz, CD$_3$OD) δ 7.88 (d, J=3.2 Hz, 0.4H), 7.86 (d, J=2.8 Hz, 0.6H), 7.75-7.73 (m, 1H), 7.55-7.53 (m, 1.4H), 7.47 (s, 0.6H), 7.24-7.15 (m, 2H), 6.13 (s, 0.6H), 6.06 (s, 0.4H), 4.29-4.27 (m 2H), 4.08-4.00 (m 2.6H), 3.89-3.81 (m 0.4H), 3.15 -3.09 (m, 0.6H), 3.06-3.01 (m, 0.4H), 2.25-1.65 (m, 7.5H), 1.50-1.44 (m, 0.5H), 1.41 (s, 9H), 1.17-1.12 (m, 9H).

VII-37-4C: LC-MS (ESI): $R_T$=1.88 min, mass calcd. for $C_{34}H_{40}ClF_2N_5O_4S$, 687.2, m/z found 687.9 [M+H]$^+$. Chiral analysis (Column: Chiralpak IA 5 μm 4.6*250 mm; Mobile Phase: CO$_2$:EtOH:DEA=80:20:0.2 at 3.0 g/min; Col. Temp: 40° C.; Wavelength: 230 nm; Back pressure 100 bar, $R_T$=5.03 min). $^1$H NMR (400 MHz, CD$_3$OD) δ 7.94 (d, J=3.2 Hz, 0.7H), 7.90 (d, J=3.2 Hz, 0.3H), 7.76 (d, J=2.8 Hz, 1H), 7.42 (s, 0.7H), 7.39-7.36 (m, 1.3H), 7.24-7.22 (m, 2H), 6.15 (s, 0.7H), 6.08 (s, 0.3H), 4.22 (s, 2H), 4.08-3.99 (m, 2.7H), 3.81-3.73 (m, 0.3H), 2.70-2.53 (m, 1H), 2.18-1.71 (m, 6.3H), 1.62-1.50 (m, 1.7H), 1.47 (s, 9H), 1.17-1.12 (m, 9H).

VII-37-4D: LC-MS (ESI): $R_T$=1.89 min, mass calcd. for $C_{34}H_{40}ClF_2N_5O_4S$, 687.2, m/z found 687.9 [M+H]$^+$. Chiral analysis (Column: Chiralpak IA 5 μm 4.6*250 mm; Mobile Phase: CO$_2$:EtOH:DEA=80:20:0.2 at 3.0 g/min; Col. Temp: 40° C.; Wavelength: 230 nm; Back pressure 100 bar, $R_T$=6.37 min). $^1$H NMR (400 MHz, CD$_3$OD) δ 7.94 (d, J=3.2 Hz, 0.7H), 7.90 (d, J=2.8 Hz, 0.3H), 7.76 (d, J=3.2 Hz, 1H), 7.42 (s, 0.7H), 7.39-7.36 (m, 1.3H), 7.26-7.22 (m, 2H), 6.15 (s, 0.7H), 6.08 (s, 0.3H), 4.22 (s, 2H), 4.08-3.98 (m, 2.7H), 3.81-3.74 (m, 0.3H), 2.70-2.54 (m, 1H), 2.17-1.70 (m, 6.2H), 1.62-1.51 (m, 1.8H), 1.47 (s, 9H), 1.18-1.11 (m, 9H).

Compound VII-38-N (trans)-ethyl 4-(2-chloro-3,4-difluorophenyl)-6-(4-(4-(ethoxycarbonyl)-1H-pyrazol-1-yl)cyclohexyl)-2-(thiazol-2-yl)-1,4-dihydropyrimidine-5-carboxylate (a Single Stereoisomer)

Intermediates VII-38-X and VII-38-Y (cis)-Ethyl 4-(2-chloro-3,4-difluorophenyl)-6-(4-(4-(ethoxycarbonyl)-1H-pyrazol-1-yl)cyclohexyl)-2-(thiazol-2-yl)-1,4-dihydropyrimidine-5-carboxylate (a Mixture of 2 Stereoisomers) and (trans)-ethyl 4-(2-chloro-3,4-difluorophenyl)-6-(4-(4-(ethoxycarbonyl)-1H-pyrazol-1-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

VII-38-X: LC-MS (ESI): $R_T$=4.266 min, mass calcd. for $C_{28}H_{28}ClF_2N_5O_4S$, 603.2, m/z found 604.1 [M+H]$^+$. $^1$H NMR (400 MHz, CDCl$_3$) δ 8.34 (s, 0.5H), 8.21 (s, 0.5H), 8.08 (s, 0.5H), 8.05 (s, 0.5H), 7.98 (s, 0.5H), 7.83 (d, J=3.2 Hz, 0.6H), 7.80 (d, J=3.2 Hz, 0.4H), 7.47 (d, J=3.2 Hz, 0.5H), 7.43 (d, J=3.2 Hz, 0.5H), 7.35-7.29 (m, 0.5H), 7.12-6.97 (m, 2H), 6.20 (s, 0.5H), 6.08 (d, J=2.4 Hz, 0.5H), 4.55-4.45 (m, 1H), 4.36-4.28 (m, 2H), 4.24-4.13 (m, 0.5H), 4.08-3.97 (m, 2.5H), 2.68-2.44 (m, 2H), 2.19-1.78 (m, 6H), 1.39-1.33 (m, 3H), 1.14 (t, J=7.2 Hz, 3H).

VII-38-Y: LC-MS (ESI): $R_T$=4.148 min, mass calcd. for $C_{28}H_{28}ClF_2N_5O_4S$, 603.2, m/z found 604.1 [M+H]$^+$. $^1$H NMR (400 MHz, CDCl$_3$) δ 8.15 (s, 0.5H), 7.98 (s, 0.5H), 7.95 (s, 0.5H), 7.93 (s, 1H), 7.86-7.82 (m, 1H), 7.52 (d, J=3.2 Hz, 0.6H), 7.47 (d, J=2.8 Hz, 0.4H), 7.34 (d, J=2.0 Hz, 0.5H), 7.13-7.00 (m, 2H), 6.21 (s, 0.4H), 6.09 (d, J=2.8 Hz, 0.6H), 4.34-4.26 (m, 3H), 4.16-3.98 (m, 2.4H), 3.92-3.82 (m, 0.6H), 2.43-2.21 (m, 2.6H), 2.17-2.09 (m, 1.4H), 2.03-1.79 (m, 3.2H), 1.74-1.66 (m, 0.8H), 1.36 (t, J=6.4 Hz, 3H), 1.18-1.11 (m, 3H).

A stereoisomeric mixture of (trans)-ethyl 4-(2-chloro-3,4-difluorophenyl)-6-(4-(4-(ethoxycarbonyl)-1H-pyrazol-1-yl)cyclohexyl)-2-(thiazol-2-yl)-1,4-dihydropyrimidine-5-carboxylate VII-38-Y (150 mg, 97% purity, 0.249 mmol) was separated by chiral Prep. HPLC (the separation condition: Column: Chiralpak IA 5 μm 20*250 mm; Mobile Phase: Hex:EtOH:DEA=80:20:0.2 at 1.0 mL/min; Temp: 30° C.; Wavelength: 230 nm), then further purified by C18 column (acetonitrile:water=50% to 71%) to give the title compounds VII-38-M (59 mg, 96.7% purity, 39% yield, 100% stereopure) and VII-38-N (54 mg, 98.6% purity, 36% yield, 96.9% stereopure) as yellow solids.

VII-38-M: LC-MS (ESI): $R_T$=4.475 min, mass calcd. for $C_{28}H_{28}ClF_2N_5O_4S$, 603.2, m/z found 604.1 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, $R_T$=10.844 min). $^1$H NMR (400 MHz, CDCl$_3$) δ 8.15 (br s, 0.5H), 8.00-7.95 (m, 1H), 7.93 (s, 1H), 7.85 (d, J=3.2 Hz, 1H), 7.57-7.44 (m, 1H), 7.37-7.32 (m, 0.5H), 7.12-7.00 (m, 2H), 6.21 (s, 0.5H), 6.09 (s, 0.5H), 4.33-4.28 (m, 3H), 4.17-4.10 (m, 2.5H), 3.93-3.82 (m, 0.5H), 2.43-1.74 (m, 8H), 1.35 (t, J=6.8 Hz, 3H), 1.14 (t, J=7.2 Hz, 3H).

VII-38-N: LC-MS (ESI): $R_T$=4.471 min, mass calcd. for $C_{28}H_{28}ClF_2N_5O_4S$, 603.2, m/z found 604.0 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, $R_T$=13.803 min). $^1$H NMR (400 MHz, CDCl$_3$) δ 8.15 (s, 0.5H), 7.97 (s, 0.5H), 7.95 (s, 0.5H), 7.93 (s, 1H), 7.83-7.82 (m, 1H), 7.51 (d, J=3.2 Hz, 0.5H), 7.47 (d, J=2.8 Hz, 0.5H), 7.34 (br s, 0.5H), 7.13-6.99 (m, 2H), 6.21 (s, 0.5H), 6.09 (d, J=2.8 Hz, 0.5H), 4.33-4.27 (m, 3H), 4.16-3.99 (m, 2.5H), 3.93-3.82 (m, 0.5H), 2.45-2.03 (m, 4H), 1.97-1.67 (m, 4H), 1.36 (t, J=6.8 Hz, 3H), 1.14 (t, J=6.8 Hz, 3H).

Compound VII-39-N and Compound VII-39-P (cis)-ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate (a Single Stereoisomer) and (trans)-Ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate (a Single Stereoisomer)

Intermediates VII-39-X and VII-39-Y (cis)-Ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate (a Mixture of 2 Stereoisomers) and (trans)-ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

VII-39-X: LC-MS (ESI): $R_T$=3.843 min, mass calcd. for $C_{28}H_{28}ClF_2N_5O_4S$, 603.2, m/z found 603.9 [M+H]$^+$. $^1$H NMR (400 MHz, DMSO-d$_6$) δ 9.57 (d, J=3.6 Hz, 0.6H), 8.55 (s, 0.4H), 8.07 (d, J=2.8 Hz, 0.4H), 8.02-7.97 (m, 1.6H), 7.75 (d, J=2.4 Hz, 0.4H), 7.60 (d, J=2.0 Hz, 0.6H), 7.51-7.40 (m, 1H), 7.26-7.18 (m, 1H), 6.97 (d, J=2.0 Hz, 0.4H), 6.92 (d, J=2.0 Hz, 0.6H), 6.05 (s, 0.4H), 5.94 (d, J=3.6 Hz, 0.6H), 5.51-5.45 (m, 0.4H), 5.28-5.21 (m, 0.6H), 4.31 (qd, J=7.2, 2.8 Hz, 2H), 4.10-4.03 (m, 0.4H), 3.98 (q, J=7.2 Hz, 2H), 3.83-3.75 (m, 0.6H), 2.40-2.26 (m, 2H), 2.23-1.99 (m, 3H), 1.95-1.78 (m, 1.4H), 1.74-1.65 (m, 1H), 1.59-1.50 (m, 0.6H), 1.32 (t, J=7.2 Hz, 3H), 1.12-1.03 (m, 3H).

VII-39-Y: LC-MS (ESI): $R_T$=4.435 min, mass calcd. for $C_{28}H_{28}ClF_2N_5O_4S$, 603.2, m/z found 603.9 [M+H]$^+$. $^1$H NMR (400 MHz, DMSO-d$_6$) δ 9.59 (d, J=3.2 Hz, 0.6H), 9.32 (s, 0.4H), 8.04-7.99 (m, 1.6H), 7.95 (d, J=2.8 Hz, 0.4H), 7.62-7.59 (m, 1H), 7.51-7.43 (m, 1H), 7.25-7.16 (m, 1H), 6.88 (d, J=1.6 Hz, 1H), 6.04 (s, 0.4H), 5.94 (d, J=3.6 Hz, 0.6H), 5.31-5.22 (m, 0.4H), 5.18-5.09 (m, 0.6H), 4.33 (q, J=7.2 Hz, 2H), 4.04-3.93 (m, 2.4H), 3.77-3.68 (m, 0.6H), 2.25-2.15 (m, 0.4H), 2.12-1.88 (m, 6.4H), 1.85-1.79 (m, 0.6H), 1.77-1.71 (m, 0.6H), 1.34 (td, J=7.2, 2.0 Hz, 3H), 1.13-1.03 (m, 3H).

The racemic mixture of (cis)-ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate VII-39-X (390 mg, 99.5% purity, 0.639 mmol) was separated by chiral prep. SFC (separation condition: Column: Chiralpak IE 5 μm 20*250 mm; Mobile Phase: CO$_2$:MeOH=75:25 at 50 g/min; Col. Temp: 40° C.; Wavelength: 214 nm, Back pressure: 100 bar) to afford VII-39-M (160 mg, 98.7% purity, 41% yield, 100% stereopure) and VII-39-N (165 mg, 98.8% purity, 42% yield, 100% stereopure) as yellow solids.

VII-39-M: LC-MS (ESI): $R_T$=4.170 min, mass calcd. for $C_{28}H_{28}ClF_2N_5O_4S$, 603.2, m/z found 603.9 [M+H]⁺. Chiral analysis (Column: Chiralpak IE 5 μm 4.6*250 mm; Mobile Phase: $CO_2$:MeOH=75:25 at 3.00 g/min; Col. Temp: 40° C.; Wavelength: 230 nm; Back pressure: 100 bar, $R_T$=6.15 min). ¹H NMR (400 MHz, DMSO-$d_6$) δ 9.58 (d, J=3.6 Hz, 0.6H), 8.55 (s, 0.4H), 8.07 (d, J=2.8 Hz, 0.4H), 8.02-7.96 (m, 1.6H), 7.74 (d, J=2.0 Hz, 0.4H), 7.60 (d, J=1.6 Hz, 0.6H), 7.50-7.40 (m, 1H), 7.26-7.17 (m, 1H), 6.96 (d, J=2.0 Hz, 0.4H), 6.91 (d, J=2.0 Hz, 0.6H), 6.05 (s, 0.4H), 5.94 (d, J=3.6 Hz, 0.6H), 5.51-5.45 (m, 0.4H), 5.28-5.20 (m, 0.6H), 4.30 (qd, J=7.2, 2.4 Hz, 2H), 4.11-4.02 (m, 0.4H), 3.98 (q, J=6.8 Hz, 2H), 3.83-3.74 (m, 0.6H), 2.40-2.26 (m, 2H), 2.22-1.98 (m, 2.8H), 1.95-1.78 (m, 1.6H), 1.74-1.64 (m, 1H), 1.58-1.49 (m, 0.6H), 1.31 (t, J=7.2 Hz, 3H), 1.12-1.02 (m, 3H).

VII-39-N: LC-MS (ESI): $R_T$=4.172 min, mass calcd. for $C_{28}H_{28}ClF_2N_5O_4S$, 603.2, m/z found 603.9 [M+H]⁺. Chiral analysis (Column: Chiralpak IE 5 μm 4.6*250 mm; Mobile Phase: $CO_2$:MeOH=75:25 at 3.00 g/min; Col. Temp: 40° C.; Wavelength: 230 nm; Back pressure: 100 bar, $R_T$=7.12 min). ¹H NMR (400 MHz, DMSO-$d_6$) δ 9.58 (d, J=3.6 Hz, 0.6H), 8.55 (s, 0.4H), 8.07 (d, J=3.6 Hz, 0.4H), 8.01-7.97 (m, 1.6H), 7.75 (d, J=2.0 Hz, 0.4H), 7.61 (d, J=2.0 Hz, 0.6H), 7.51-7.40 (m, 1H), 7.25-7.19 (m, 1H), 6.97 (d, J=2.0 Hz, 0.4H), 6.92 (d, J=2.0 Hz, 0.6H), 6.06 (s, 0.4H), 5.94 (d, J=3.6 Hz, 0.6H), 5.51-5.46 (m, 0.4H), 5.28-5.21 (m, 0.6H), 4.31 (qd, J=7.2, 2.4 Hz, 2H), 4.11-4.03 (m, 0.4H), 3.98 (q, J=6.8 Hz, 2H), 3.83-3.75 (m, 0.6H), 2.40-2.26 (m, 2H), 2.23-1.98 (m, 2.8H), 1.95-1.78 (m, 1.6H), 1.74-1.64 (m, 1H), 1.59-1.49 (m, 0.6H), 1.31 (t, J=7.2 Hz, 3H), 1.12-1.03 (m, 3H).

The racemic mixture of (trans)-ethyl 4-(2-chloro-3,4-difluorophenyl)-6-(4-(5-(ethoxycarbonyl)-1H-pyrazol-1-yl)cyclohexyl)-2-(thiazol-2-yl)-1,4-dihydropyrimidine-5-carboxylate VII-39-Y (410 mg, 99.5% purity, 0.672 mmol) was separated by chiral prep. HPLC (separation condition: Column: Chiralpak IG 5 μm 20*250 mm; Mobile Phase: Hex:IPA:DEA=90:10:0.3 at 15 mL/min; Wavelength: 230 nm) to afford VII-39-P (170 mg, 99.5% purity, 42% yield, 100% stereopure) and VII-39-Q (175 mg, 99.5% purity, 43% yield, 99.8% stereopure) as yellow solids.

VII-39-P: LC-MS (ESI): $R_T$=3.868 min, mass calcd. for $C_{28}H_{28}ClF_2N_5O_4S$, 603.2, m/z found 603.9 [M+H]⁺. Chiral analysis (Column: Chiralpak IG 5 μm 4.6*250 mm; Mobile Phase: Hex:IPA:DEA=90:10:0.2 at 1.0 mL/min; Temp: 30° C.; Wavelength: 254 nm, $R_T$=9.987 min). ¹H NMR (400 MHz, DMSO-$d_6$) δ 9.60 (d, J=3.2 Hz, 0.6H), 9.32 (s, 0.4H), 8.04-7.99 (m, 1.6H), 7.95 (d, J=3.6 Hz, 0.4H), 7.63-7.58 (m, 1H), 7.51-7.44 (m, 1H), 7.25-7.16 (m, 1H), 6.88 (d, J=2.0 Hz, 1H), 6.04 (s, 0.4H), 5.94 (d, J=3.6 Hz, 0.6H), 5.32-5.22 (m, 0.4H), 5.18-5.09 (m, 0.6H), 4.33 (q, J=7.2 Hz, 2H), 4.04-3.93 (m, 2.4H), 3.77-3.68 (m, 0.6H), 2.25-2.15 (m, 0.4H), 2.12-1.88 (m, 6.4H), 1.86-1.79 (m, 0.6H), 1.78-1.71 (m, 0.6H), 1.34 (td, J=7.2, 2.0 Hz, 3H), 1.13-1.03 (m, 3H).

VII-39-Q: LC-MS (ESI): $R_T$=3.980 min, mass calcd. for $C_{28}H_{28}ClF_2N_5O_4S$, 603.2, m/z found 603.9 [M+H]⁺. Chiral analysis (Column: Chiralpak IG 5 μm 4.6*250 mm; Mobile Phase: Hex:IPA:DEA=90:10:0.2 at 1.0 mL/min; Temp: 30° C.; Wavelength: 254 nm, $R_T$=13.321 min). ¹H NMR (400 MHz, DMSO-$d_6$) δ 9.60 (d, J=3.2 Hz, 0.6H), 9.32 (s, 0.4H), 8.05-7.98 (m, 1.6H), 7.95 (d, J=2.8 Hz, 0.4H), 7.63-7.58 (m, 1H), 7.51-7.44 (m, 1H), 7.26-7.16 (m, 1H), 6.88 (d, J=2.0 Hz, 1H), 6.04 (s, 0.4H), 5.94 (d, J=3.6 Hz, 0.6H), 5.32-5.22 (m, 0.4H), 5.18-5.08 (m, 0.6H), 4.33 (q, J=7.2 Hz, 2H), 4.05-3.93 (m, 2.4H), 3.77-3.67 (m, 0.6H), 2.26-2.14 (m, 0.4H), 2.12-1.88 (m, 6.4H), 1.85-1.79 (m, 0.6H), 1.78-1.71 (m, 0.6H), 1.34 (t, J=7.2 Hz, 3H), 1.13-1.03 (m, 3H).

Compound VII-40-M (trans)-Ethyl 2-(4-(6-(2-chloro-3,4-difluorophenyl)-5-(methoxycarbonyl)-2-(thiazol-2-yl)-3,6-dihydropyrimidin-4-yl)cyclohexyl)pyrimidine-5-carboxylate (a Single Stereoisomer)

Intermediates VII-40-X and VII-40-Y (cis)-Ethyl 2-(4-(6-(2-chloro-3,4-difluorophenyl)-5-(methoxycarbonyl)-2-(thiazol-2-yl)-3,6-dihydropyrimidin-4-yl)cyclohexyl)pyrimidine-5-carboxylate (a Mixture of 2 Stereoisomers) and (trans)-ethyl 2-(4-(6-(2-chloro-3,4-difluorophenyl)-5-(methoxycarbonyl)-2-(thiazol-2-yl)-3,6-dihydropyrimidin-4-yl)cyclohexyl)pyrimidine-5-carboxylate (a Mixture of 2 Stereoisomers)

By utilizing the analogous procedure of Method B, the title compounds were synthesized as yellow solids.

VII-40-X: LC-MS (ESI): $R_T$=3.614 min, mass calcd. for $C_{29}H_{28}ClF_2N_5O_4S$, 615.2, m/z found 615.9 [M+H]⁺. ¹H NMR (400 MHz, CDCl₃) δ 9.37 (s, 1.5H), 9.28 (s, 0.5H), 8.34 (s, 1H), 7.84 (d, J=3.2 Hz, 0.8H), 7.78 (d, J=3.2 Hz, 0.2H), 7.44 (d, J=2.8 Hz, 1H), 7.11-6.96 (m, 2H), 6.20 (s, 0.8H), 6.05 (d, J=3.2 Hz, 0.2H), 4.47 (q, J=7.2 Hz, 2H), 4.22-4.17 (m, 0.8H), 4.11-4.00 (m, 2H), 3.96-3.91 (m, 0.2H), 3.48 (s, 0.8H), 3.40-3.36 (m, 0.2H), 2.70-2.62 (m, 0.5H), 2.53-2.47 (m, 1.5H), 2.05-1.88 (m, 5H), 1.80-1.78 (m, 1H), 1.45 (t, J=7.2 Hz, 3H), 1.15 (t, J=7.2 Hz, 3H).

VII-40-Y: LC-MS (ESI): $R_T$=1.97 min, mass calcd. for $C_{29}H_{28}ClF_2N_5O_4S$, 615.2, m/z found 616.1 [M+H]⁺. ¹H NMR (400 MHz, CDCl₃) δ 9.22 (s, 2H), 8.21 (s, 0.6H), 7.84 (d, J=2.8 Hz, 1H), 7.51 (d, J=2.8 Hz, 0.4H), 7.46 (d, J=3.2 Hz, 0.6H), 7.32 (s, 0.4H), 7.14-6.99 (m, 2H), 6.22 (s, 0.6H), 6.08 (d, J=2.8 Hz, 0.4H), 4.44 (q, J=7.2 Hz, 2H), 4.15-4.01 (m, 2.8H), 3.91-3.85 (m, 0.2H), 3.12-3.05 (m, 1H), 2.29-2.08 (m, 4H), 1.97-1.64 (m, 4H), 1.42 (t, J=7.2 Hz, 3H), 1.15 (t, J=7.2 Hz, 3H).

A stereoisomeric mixture of (trans)-ethyl 2-(4-(6-(2-chloro-3,4-difluorophenyl)-5-(methoxycarbonyl)-2-(thiazol-2-yl)-3,6-dihydropyrimidin-4-yl)cyclohexyl)pyrimidine-5-carboxylate VII-40-Y (210 mg, 95% purity, 0.324 mmol) was separated by chiral Prep. HPLC (Column: Chiralpak ID 5 μm 20*250 mm; Mobile Phase: Hex:EtOH:DEA=40:60:0.3 at 10 mL/min; Temp: 30° C.; Wavelength: 214 nm) to afford the title compounds VII-40-M (50 mg, 95.6% purity, 24% yield, 100% stereopure) and VII-40-N (55 mg, 99.7% purity, 27% yield, 100% stereopure) as yellow solids.

VII-40-M: LC-MS (ESI): $R_T$=4.462 min, mass calcd. for $C_{29}H_{28}ClF_2N_5O_4S$, 615.2, m/z found 616.1 [M+H]⁺. Chiral analysis (Column: Chiralpak ID 5 μm 4.6*250 mm; Mobile Phase: Hex:EtOH:DEA=40:60:0.2 at 1.0 mL/min; Temp: 30° C.; Wavelength: 230 nm, $R_T$=7.153 min). ¹H NMR (400 MHz, CDCl₃) δ 9.27-9.26 (m, 2H), 8.26 (s, 0.7H), 7.88-7.87 (m, 1H), 7.55 (d, J=2.8 Hz, 0.3H), 7.50 (d, J=3.2 Hz, 0.7H), 7.36 (s, 0.3H), 7.18-7.04 (m, 2H), 6.26 (s, 0.6H), 6.13 (d, J=2.4 Hz, 0.4H), 4.48 (q, J=6.8 Hz, 2H), 4.19-4.05 (m, 2.5H), 3.95-3.89 (m, 0.5H), 3.18-3.10 (m, 1H), 2.33-2.13 (m, 4H), 2.00-1.66 (m, 4H), 1.46 (t, J=6.8 Hz, 3H), 1.22-1.17 (m, 3H).

VII-40-N: LC-MS (ESI): $R_T$=3.396 min, mass calcd. for $C_{29}H_{28}ClF_2N_5O_4S$, 615.2, m/z found 615.9 [M+H]$^+$. Chiral analysis (Column: Chiralpak ID 5 μm 4.6*250 mm; Mobile Phase: Hex:EtOH:DEA=40:60:0.2 at 1.0 mL/min; Temp: 30° C.; Wavelength: 230 nm, $R_T$=11.243 min). $^1$H NMR (400 MHz, CDCl$_3$) δ 9.26-9.25 (m, 2H), 8.26 (s, 0.6H), 7.88-7.87 (m, 1H), 7.55 (d, J=2.8 Hz, 0.4H), 7.49 (d, J=3.2 Hz, 0.6H), 7.36 (s, 0.3H), 7.18-7.04 (m, 2H), 6.26 (s, 0.7H), 6.12 (d, J=2.4 Hz, 0.3H), 4.48 (q, J=7.2 Hz, 2H), 4.19-4.04 (m, 2.7H), 3.95-3.89 (m, 0.3H), 3.17-3.10 (m, 1H), 2.32-2.13 (m, 4H), 2.01-1.69 (m, 4H), 1.46 (t, J=7.8 Hz, 3H), 1.22-1.17 (m, 3H).

Compound VII-41-N (trans)-ethyl 2-(4-(6-(2-chloro-3,4-difluorophenyl)-5-(ethoxycarbonyl)-2-(thiazol-2-yl)-3,6-dihydropyrimidin-4-yl)cyclohexyl)thiazole-4-carboxylate (a Single Stereoisomer)

Intermediate VII-41-R (trans)-Ethyl 2-(4-(6-(2-chloro-3,4-difluorophenyl)-5-(ethoxycarbonyl)-2-(thiazol-2-yl)-3,6-dihydropyrimidin-4-yl)cyclohexyl)thiazole-4-carboxylate (a Mixture of 2 Stereoisomers)

By utilizing the analogous procedure of Method B, the title compound was synthesized as yellow solids.

LC-MS (ESI): $R_T$=3.965 min, mass calcd. for $C_{28}H_{27}ClF_2N_4O_4S_2$ 620.1, m/z found 621.1 [M+H]$^+$. $^1$H NMR (400 MHz, DMSO-d$_6$) δ 9.55 (d, J=3.6 Hz, 0.6H), 8.98 (s, 0.4H), 8.42 (d, J=4.8 Hz, 1H), 8.02-8.01 (m, 1.6H), 7.95 (d, J=2.8 Hz, 0.4H), 7.51-7.44 (m, 1H), 7.24-7.18 (m, 1H), 6.05 (s, 0.4H), 5.94 (d, J=3.2 Hz, 0.6H), 4.30 (q, J=7.2 Hz, 2H), 4.02-3.91 (m, 2.4H), 3.73-3.65 (m, 0.6H), 3.27-3.19 (m, 0.4H), 3.13-3.05 (m, 0.6H), 2.27-2.18 (m, 2H), 2.10-1.82 (m, 3.5H), 1.74-1.71 (m, 0.5H), 1.64-1.56 (m, 2H), 1.31 (t, J=7.2 Hz, 3H), 1.10-1.03 (m, 3H).

A stereoisomeric mixture of VII-41-R (300 mg, 0.48 mmol) was separated by chiral Prep. HPLC (Column: Chiralpak AD 5 μm 20*250 mm; Mobile Phase: Hex:EtOH:DEA=70:30:0.3 at 15 mL/min; Temp: 30° C.; Wavelength: 214 nm) to give the peak 1 (122 mg, 41% yield, about 90% purity, 100% stereopure) and the peak 2 (110 mg, 37% yield, about 90% purity, 98.6% stereopure). Parts of the peak 1 (30 mg, 90% purity) and the peak 2 (30 mg, 90% purity) were further purified by Prep. HPLC (Column: Gilson Xbrige C18 (5 μm 19*150 mm), Mobile Phase A: water (0.1% ammonium bicarbonate), Mobile Phase B: acetonitrile, UV: 214 nm, Flow rate: 15 mL/min, Gradient: 70-98% (% B)) to give the title compounds VII-41-M (6.1 mg, 20% yield, 98.3% purity, 100% stereopure) and VII-41-N (6.8 mg, 23% yield, 99.7% purity, 98.6% stereopure).

VII-41-M: LC-MS (ESI): $R_T$=3.001 min, mass calcd. for $C_{28}H_{27}ClF_2N_4O_4S_2$ 620.1, m/z found 621.1 [M+H]$^+$. Chiral analysis (Column: Chiralpak AD-H 5 μm 4.6*250 mm; Mobile Phase: Hex:EtOH:DEA=70:30:0.2 at 1 mL/min; Temp: 30° C.; Wavelength: 230 nm; $R_T$=6.075 min). $^1$H NMR (400 MHz, DMSO-d$_6$) δ 9.56 (d, J=3.2 Hz, 0.6H), 8.99 (s, 0.4H), 8.42 (d, J=5.2 Hz, 1H), 8.02-8.01 (m, 1.6H), 7.96 (d, J=3.2 Hz, 0.4H), 7.51-7.44 (m, 1H), 7.24-7.18 (m, 1H), 6.05 (s, 0.4H), 5.94 (d, J=3.6 Hz, 0.6H), 4.30 (q, J=7.2 Hz, 2H), 4.02-3.91 (m, 2.4H), 3.72-3.66 (m, 0.6H), 3.27-3.19 (m, 0.4H), 3.13-3.05 (m, 0.6H), 2.28-2.18 (m, 2H), 2.08-1.82 (m, 3.5H), 1.75-1.71 (m, 0.5H), 1.65-1.53 (m, 2H), 1.31 (t, J=7.2 Hz, 3H), 1.10-1.03 (m, 3H).

VII-41-N: LC-MS (ESI): $R_T$=3.952 min, mass calcd. for $C_{28}H_{27}ClF_2N_4O_4S_2$ 620.1, m/z found 621.1 [M+H]$^+$. Chiral analysis (Column: Chiralpak AD-H 5 μm 4.6*250 mm; Mobile Phase: Hex:EtOH:DEA=70:30:0.2 at 1 mL/min; Temp: 30° C.; Wavelength: 230 nm; $R_T$=8.428 min). $^1$H NMR (400 MHz, DMSO-d$_6$) δ 9.56 (d, J=3.6 Hz, 0.6H), 8.98 (s, 0.4H), 8.42 (d, J=3.2 Hz, 1H), 8.02-8.01 (m, 1.6H), 7.95 (d, J=3.6 Hz, 0.4H), 7.51-7.44 (m, 1H), 7.24-7.18 (m, 1H), 6.05 (s, 0.4H), 5.94 (d, J=3.2 Hz, 0.6H), 4.30 (q, J=7.2 Hz, 2H), 4.02-3.90 (m, 2.4H), 3.73-3.65 (m, 0.6H), 3.27-3.20 (m, 0.4H), 3.13-3.06 (m, 0.6H), 2.28-2.18 (m, 2H), 2.08-1.82 (m, 3.5H), 1.75-1.71 (m, 0.5H), 1.67-1.54 (m, 2H), 1.31 (t, J=7.2 Hz, 3H), 1.10-1.05 (m, 3H).

Compound VII-42-11

Mixture of (trans)-methyl 5-(4-(6-(2-chloro-3,4-difluorophenyl)-5-(ethoxycarbonyl)-2-(thiazol-2-yl)-3,6-dihydropyrimidin-4-yl)cyclohexyl)isoxazole-3-carboxylate (a Single Stereoisomer) and (trans)-ethyl 5-(4-(6-(2-chloro-3,4-difluorophenyl)-5-(ethoxycarbonyl)-2-(thiazol-2-yl)-3,6-dihydropyrimidin-4-yl)cyclohexyl)isoxazole-3-carboxylate (a Single Stereoisomer)

Intermediates VII-42-9A and VII-42-9B (trans)-Ethyl 5-(4-(6-(2-chloro-3,4-difluorophenyl)-5-(ethoxycarbonyl)-2-(thiazol-2-yl)-3,6-dihydropyrimidin-4-yl)cyclohexyl)isoxazole-3-carboxylate (a Mixture of 2 Stereoisomers) and (trans)-methyl 5-(4-(6-(2-chloro-3,4-difluorophenyl)-5-(ethoxycarbonyl)-2-(thiazol-2-yl)-3,6-dihydropyrimidin-4-yl) cyclohexyl)isoxazole-3-carboxylate (a Mixture of 2 Stereoisomers)

By utilizing the analogous procedure of Method B, the title compound was synthesized as yellow solids. Transesterification reaction was observed when using ethanol as solvent.

VII-42-9A: LC-MS (ESI): $R_T$=2.03 min, mass calcd. for $C_{28}H_{27}ClF_2N_4O_5S$, 604.1, m/z found 604.8 [M+H]$^+$. $^1$H NMR (400 MHz, DMSO-d$_6$) δ 9.59 (d, J=3.2 Hz, 0.6H), 9.04 (s, 0.4H), 8.01-7.95 (m, 2H), 7.51-7.44 (m, 1H), 7.23-7.18 (m, 1H), 6.74 (d, J=10.0 Hz, 1H), 6.04 (s, 0.4H), 5.94 (d, J=3.2 Hz, 0.6H), 4.39-4.34 (m, 2H), 4.01-3.94 (m, 2.5H), 3.71-3.65 (m, 0.5H), 3.12-3.06 (m, 0.4H), 2.99-2.92 (m, 0.6H), 2.19-2.12 (m, 2.3H), 2.07-1.78 (m, 3H), 1.73-1.69 (m, 0.7H), 1.60-1.50 (m, 2H), 1.32 (t, J=7.2 Hz, 3H), 1.10-1.03 (m, 3H).

VII-42-9B: LC-MS (ESI): $R_T$=2.00 min, mass calcd. for $C_{27}H_{25}ClF_2N_4O_5S$, 590.1, m/z found 590.8 [M+H]$^+$. $^1$H NMR (400 MHz, DMSO-d$_6$) δ 9.59 (s, 0.6H), 9.04 (s, 0.4H), 8.02-7.96 (m, 2H), 7.51-7.44 (m, 1H), 7.22-7.19 (m, 1H), 6.77-6.74 (m, 1H), 6.03 (s, 0.4H), 5.95 (s, 0.6H), 4.00-3.95 (m, 2.5H), 3.89 (s, 3H), 3.73-3.65 (m, 0.5H), 3.13-3.07 (m, 0.4H), 3.00-2.94 (m, 0.6H), 2.19-2.12 (m, 2H), 1.97-1.72 (m, 4H), 1.61-1.47 (m, 2H), 1.07-1.06 (m, 3H).

A stereoisomeric mixture of (trans)-methyl 5-(4-(6-(2-chloro-3,4-difluorophenyl)-5-(ethoxycarbonyl)-2-(thiazol-2-yl)-3,6-dihydropyrimidin-4-yl)cyclohexyl)isoxazole-3-carboxylate VII-42-9B (200 mg, 90% purity, 0.305 mmol) was separated by chiral Prep. HPLC (Column: Chiralpak IE 5 μm 20*250 mm; Mobile Phase: Hex:EtOH:DEA=50:50:0.3 at 11 mL/min; Temp: 30° C.; Wavelength: 230 nm) to give the compounds VII-42-10 (45 mg, 23% yield, 100% stereopure) and VII-42-11 (65 mg, 33% yield, 99.8% stereopure) as yellow solids.

Transesterification reaction was observed when using ethanol as solvent.

VII-42-10: LC-MS (ESI): $R_T$=1.97 min and 2.02 min, mass calcd. for $C_{27}H_{25}ClF_2N_4O_5S$, 590.1 and $C_{28}H_{27}ClF_2N_4O_5S$, 604.1, m/z found 590.8 and 604.9 [M+H]$^+$. Chiral analysis (Column: Chiralpak IE 5 μm 4.6*250 mm; Mobile Phase: Hex:EtOH:TEA=50:50:0.2 at 1.0 mL/min; Temp: 30° C.; Wavelength: 230 nm, $R_T$=7.355 and 8.163 min).

VII-42-11: LC-MS (ESI): $R_T$=1.97 min and 2.02 min, mass calcd. for $C_{27}H_{25}ClF_2N_4O_5S$, 590.1 and $C_{28}H_{27}ClF_2N_4O_5S$, 604.1, m/z found 590.9 and 604.9 [M+H]$^+$. Chiral analysis (Column: Chiralpak IE 5 μm 4.6*250 mm; Mobile Phase: Hex:EtOH:TEA=50:50:0.2 at 1.0 mL/min; Temp: 30° C.; Wavelength: 230 nm, $R_T$=11.346 and 13.670 min).

Compound VII-43-N (trans)-ethyl 3-4-(6-(2-chloro-3,4-difluorophenyl)-5-(ethoxycarbonyl)-2-(thiazol-2-yl)-3,6-dihydropyrimidin-4-yl)cyclohexyl)isoxazole-5-carboxylate (a Single Stereoisomer)

Intermediate VII-43-R (trans)-Ethyl 3-(4-(6-(2-chloro-3,4-difluorophenyl)-5-(ethoxycarbonyl)-2-(thiazol-2-yl)-3,6-dihydropyrimidin-4-yl)cyclohexyl)isoxazole-5-carboxylate (a Mixture of 2 Stereoisomers)

By utilizing the analogous procedure of Method B, the title compound was synthesized as yellow solids.

LC-MS (ESI): $R_T$=3.918 min, mass calcd. for $C_{28}H_{27}ClF_2N_4O_5S$, 604.1, m/z found 605.1 [M+H]$^+$. $^1$H NMR (400 MHz, DMSO-d$_6$) δ 9.56 (d, J=3.2 Hz, 0.6H), 9.02 (s, 0.4H), 8.01 (d, J=3.2 Hz, 1.6H), 7.95 (d, J=3.2 Hz, 0.4H), 7.51-7.46 (m, 1H), 7.38 (s, 0.4H), 7.35 (s, 0.6H), 7.24-7.18 (m, 1H), 6.04 (s, 0.4H), 5.94 (d, J=3.6 Hz, 0.6H), 4.36 (q, J=7.2 Hz, 2H), 3.99 (q, J=7.2 Hz, 2H), 3.93-3.90 (m, 0.4H), 3.74-3.66 (m, 0.6H), 3.04-2.96 (m, 0.4H), 2.87-2.79 (m, 0.6H), 2.10-1.81 (m, 6H), 1.72-1.54 (m, 2H), 1.32 (t, J=7.2 Hz, 3H), 1.11-1.04 (m, 3H).

A stereoisomeric mixture of VII-43-R (1.20 g, 1.98 mmol) was separated by chiral Prep. HPLC (Column: Chiralpak IE 5 μm 20*250 mm, Mobile Phase: Hex:EtOH:DEA=50:50:0.2 at 1.0 mL/min, Temp: 30° C., Wavelength: 214 nm) to afford the compounds VII-43-M (436 mg, 36% yield, 100% stereopure) and VII-43-N (376 mg, 31% yield, 99.8% stereopure).

VII-43-M: LC-MS (ESI): $R_T$=3.207 min, mass calcd. for $C_{28}H_{27}ClF_2N_4O_5$ 604.1, m/z found 605.1 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=6.378 min). $^1$H NMR (400 MHz, DMSO-d$_6$) δ 9.55 (d, J=3.6 Hz, 0.6H), 9.02 (s, 0.4H), 8.01 (d, J=3.2 Hz, 1.6H), 7.95 (d, J=3.2 Hz, 0.4H), 7.51-7.43 (m, 1H), 7.38 (s, 0.4H), 7.35 (s, 0.6H), 7.24-7.18 (m, 1H), 6.04 (s, 0.4H), 5.94 (d, J=3.2 Hz, 0.6H), 4.36 (q, J=7.2 Hz, 2H), 3.99 (q, J=7.2 Hz, 2H), 3.94-3.91 (m, 0.4H), 3.73-3.65 (m, 0.6H), 3.03-2.95 (m, 0.4H), 2.86-2.79 (m, 0.6H), 2.11-1.78 (m, 6H), 1.73-1.53 (m, 2H), 1.32 (t, J=7.2 Hz, 3H), 1.11-1.04 (m, 3H).

VII-43-N: LC-MS (ESI): $R_T$=4.047 min, mass calcd. for $C_{28}H_{27}ClF_2N_4O_5$ 604.1, m/z found 605.1 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=9.388 min). $^1$H NMR (400 MHz, DMSO-d$_6$) δ 9.55 (d, J=3.6 Hz, 0.6H), 9.02 (s, 0.4H), 8.01 (d, J=3.2 Hz, 1.6H), 7.95 (d, J=3.2 Hz, 0.4H), 7.51-7.43 (m, 1H), 7.38 (s, 0.4H), 7.35 (s, 0.6H), 7.24-7.18 (m, 1H), 6.04 (s, 0.4H), 5.94 (d, J=3.6 Hz, 0.6H)), 4.36 (q, J=7.2 Hz, 2H), 3.99 (q, J=7.2 Hz, 2H), 3.94-3.91 (m 0.4H), 3.73-3.66 (m 0.6H), 3.04-2.96 (m 0.4H), 2.87-2.79 (m, 0.6H), 2.11-1.72 (m, 6H), 1.60-1.53 (m, 2H), 1.32 (t, J=7.2 Hz, 3H), 1.11-1.04 (m, 3H).

Compound VII-44-X (trans)-Ethyl 4-(2-chloro-3,4-difluorophenyl)-6-(4-(4-(methoxycarbonyl)phenyl)cyclohexyl)-2-(thiazol-2-yl)-1,4-dihydropyrimidine-5-carboxylate (a Mixture of 2 Stereoisomers)

Intermediate VII-44-R

Ethyl 4-(2-chloro-3,4-difluorophenyl)-6-(4-(4-(methoxycarbonyl)phenyl)cyclohexyl)-2-(thiazol-2-yl)-1,4-dihydropyrimidine-5-carboxylate (a Mixture of 4 Stereoisomers)

By utilizing the analogous procedure of Method B, the title compound was synthesized as yellow solids.

LC-MS (ESI): $R_T$=2.17 min, 2.21 min, mass calcd. for $C_{30}H_2ClF_2N_3O_4S$, 599.2, m/z found 600.2 [M+H]$^+$. $^1$H NMR (400 MHz, DMSO-d$_6$) δ 9.56-9.53 (m, 0.7H), 8.96 (s, 0.3H), 8.02-7.89 (m, 4H), 7.60-7.44 (m, 3H), 7.23-7.19 (m, 1H), 6.05 (s, 0.4H), 5.95-5.93 (m, 0.6H), 4.02-3.95 (m, 2H), 3.85-3.84 (m, 3.5H), 3.75-3.68 (m, 0.5H), 2.93-2.68 (m, 1H), 1.99-1.54 (m, 8H), 1.11-1.05 (m, 3H).

A stereoisomeric mixture of ethyl 4-(2-chloro-3,4-difluorophenyl)-6-(4-(4-(methoxycarbonyl)phenyl)cyclohexyl)-2-(thiazol-2-yl)-1,4-dihydropyrimidine-5-carboxylate VII-44-R (300 mg, 0.50 mmol) was separated by chiral Prep. SFC (separation condition: Column: Chiralpak IA 5 μm 20*250 mm; Mobile Phase: CO$_2$:MeOH=70:30 at 50 g/min; Col. Temp: 41.1° C.; Wavelength: 230 nm; Back pressure: 100 bar) to afford the compounds VII-44-X (a mixture of 2 stereoisomers) (200 mg, 67% yield) and VII-44-Y (a mixture of 2 stereoisomers) (85 mg, 28% yield) as yellow solids.

Intermediate VII-44-X: LC-MS (ESI): $R_T$=2.07 min, mass calcd. for $C_{30}H_{28}ClF_2N_3O_4S$ 599.2, m/z found 600.2 [M+H]$^+$. $^1$H NMR (400 MHz, DMSO-d$_6$) δ 9.54 (d, J=3.6 Hz, 0.6H), 8.96 (s, 0.4H), 8.02-8.00 (m, 1.5H), 7.96 (d, J=2.8 Hz, 0.5H), 7.92-7.89 (m, 2H), 7.51-7.42 (m, 3H), 7.24-7.18 (m, 1H), 6.05 (s, 0.4H), 5.94 (d, J=3.2 Hz, 0.6H), 4.02-3.95 (m, 2.4H), 3.84 (s, 3H), 3.75-3.68 (m, 0.6H), 2.86-2.78 (m, 0.4H), 2.72-2.63 (m, 0.6H), 2.03-1.81 (m, 5.4H), 1.74-1.68 (m, 0.6H), 1.63-1.53 (m, 2H), 1.10-1.04 (m, 3H).

Intermediate VII-44-Y: LC-MS (ESI): $R_T$=3.121 min, mass calcd. for $C_{30}H_2ClF_2N_3O_4S$, 599.2, m/z found 600.1 [M+H]$^+$. $^1$H NMR (400 MHz, DMSO-d$_6$) δ 9.56 (d, J=4.0 Hz, 0.8H), 8.52 (s, 0.2H), 7.99-7.93 (m, 4H), 7.60-7.54 (m, 2H), 7.50-7.40 (m, 1H), 7.23-7.20 (m, 1H), 6.04 (s, 0.2H), 5.93 (d, J=3.6 Hz, 0.8 H), 4.01-3.94 (m, 2H), 3.86-3.85 (m, 4H), 3.13-3.10 (m, 0.2H), 2.96-2.91 (m, 0.8H), 2.35-2.25 (m, 2H), 2.03-1.59 (m, 6H), 1.10-1.04 (m, 3H).

Compound VII-45-R (trans)-Ethyl 5-(-4-(6-(2-chloro-3,4-difluorophenyl)-5-(ethoxycarbonyl)-2-(thiazol-2-yl)-3,6-dihydropyrimidin-4-yl)cyclohexyl)-1,2,4-oxadiazole-3-carboxylate (a Mixture of 2 Stereoisomers)

By utilizing the analogous procedure of Method B, the title compound was synthesized as yellow solids.

LC-MS (ESI): $R_T$=4.364 min, mass calcd. for $C_{27}H_{26}ClF_2N_5O_5S$, 605.13, m/z found 606.2 [M+H]$^+$. $^1$H NMR (400 MHz, CDCl$_3$) δ 8.14 (s, 0.5H), 7.84-7.82 (m, 1H), 7.52 (d, J=2.8 Hz, 0.5H), 7.47 (d, J=3.2 Hz, 0.5H), 7.35 (s, 0.5H), 7.12-7.00 (m, 2H), 6.21 (s, 0.5H), 6.09 (d, J=2.4 Hz, 0.5H), 4.52 (q, J=7.2 Hz, 2H), 4.14-4.00 (m, 2.5H), 3.89-3.82 (m, 0.5H), 3.19-3.12 (m, 1H), 2.41-2.22 (m, 2.5H), 2.15-2.04 (m, 1.5H), 1.97-1.83 (m, 3H), 1.75-1.62 (m, 1H), 1.45 (t, J=7.2 Hz, 3H), 1.17-1.12 (m, 3H).

Compound VII-46-P methyl 4-(2-chloro-3,4-difluorophenyl)-6-((trans)-4-(5-(1-(methoxycarbonyl)cyclopropyl)pyrimidin-2-yl)cyclohexyl)-2-(thiazol-2-yl)-1,4-dihydropyrimidine-5-carboxylate (a Single Stereoisomer)

Intermediate VII-46-Y methyl 4-(2-chloro-3,4-difluorophenyl)-6-((trans)-4-(5-(1-(methoxycarbonyl)cyclopropyl)pyrimidin-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

LC-MS (ESI): $R_T$=1.92 min, mass calcd. for $C_{30}H_{28}ClF_2N_5O_4S$, 627.2, m/z found 628.4 [M+H]$^+$. $^1$H NMR (400 MHz, CDCl$_3$) δ 8.65 (s, 0.6H), 8.64 (s, 1.4H), 8.24 (s, 0.7H), 7.85-7.83 (m, 1H), 7.52 (d, J=3.2 Hz, 0.3H), 7.47 (d, J=2.8 Hz, 0.7H), 7.38 (d, J=2.4 Hz, 0.3H), 7.12-7.10 (m, 1H), 7.06-6.99 (m, 1H), 6.20 (s, 0.7H), 6.06 (d, J=2.4 Hz, 0.3H), 4.13-4.06 (m, 0.7H), 3.87-3.85 (m, 0.3H), 3.67 (s, 3H), 3.64 (s, 0.9H), 3.61 (s, 2.1H), 3.06-2.98 (m, 1H), 2.25-2.08 (m, 4H), 1.99-1.84 (m, 3H), 1.73-1.71 (m, 3H), 1.24-1.21 (m, 2H). A racemic mixture of methyl 4-(2-chloro-3,4-difluorophenyl)-6-((trans)-4-(5-(1-(methoxycarbonyl)cyclopropyl)pyrimidin-2-yl)cyclohexyl)-2-(thiazol-2-yl)-1,4-dihydropyrimidine-5-carboxylate VII-46-Y (170 mg, 0.271 mmol) was separated by chiral Prep. HPLC (separation condition: Column: Chiralpak IE 5 μm 20*250 mm; Mobile Phase: MeOH:IPA:DEA=90:10:0.3 at 10 mL/min; Temp: 30° C.; Wavelength: 214 nm) to give VII-46-P (50 mg, 95% purity from $^1$H NMR, 28% yield, 100% stereopure) and VII-46-Q (50 mg, 95% purity from $^1$H NMR, 28% yield, 99.8% stereopure) as yellow solids.

VII-46-P: LC-MS (ESI): $R_T$=1.87 min, mass calcd. for $C_{30}H_2ClF_2N_5O_4S$, 627.2, m/z found 628.3 [M+H]$^+$. Chiral analysis (Column: Chiralpak ID 5 μm 4.6*250 mm; Mobile Phase: MeOH:DCM:DEA=90:10:0.2 at 1 mL/min; Temp: 30° C.; Wavelength: 230 nm, Rt=5.543 min). $^1$H NMR (400 MHz, CDCl$_3$) δ 8.65 (s, 0.6H), 8.64 (s, 1.4H), 8.25 (s, 0.6H), 7.84-7.83 (m, 1H), 7.51 (d, J=3.2 Hz, 0.3H), 7.46 (d, J=3.2 Hz, 0.7H), 7.39 (br s, 0.4H), 7.12-7.09 (m, 1H), 7.05-7.01 (m, 1H), 6.20 (s, 0.7H), 6.07 (d, J=2.4 Hz, 0.3H), 4.11-4.06 (m, 1H), 3.67 (s, 3H), 3.64 (s, 0.9H), 3.61 (s, 2.1H), 3.04-2.99 (m, 1H), 2.28-2.21 (m, 3H), 2.11-2.07 (m, 2H), 1.95-1.90 (m, 2H), 1.72-1.70 (m, 3H), 1.26-1.24 (m, 2H).

VII-46-Q: LC-MS (ESI): $R_T$=1.87 min, mass calcd. for $C_{30}H_2ClF_2N_5O_4S$, 627.2, m/z found 628.3 [M+H]$^+$. Chiral analysis (Column: Chiralpak ID 5 μm 4.6*250 mm; Mobile Phase: MeOH:DCM:DEA=90:10:0.2 at 1 mL/min; Temp: 30° C.; Wavelength: 230 nm, Rt=9.079 min). $^1$H NMR (400 MHz, CDCl$_3$) δ 8.64 (s, 2H), 8.24 (s, 0.7H), 7.84 (d, J=3.2 Hz, 1H), 7.51 (d, J=2.8 Hz, 0.3H), 7.46 (d, J=3.2 Hz, 0.7H), 7.39 (br s, 0.3H), 7.12-7.09 (m, 1H), 7.05-7.01 (m, 1H), 6.20 (s, 0.7H), 6.07 (s, 0.3H), 4.12-4.06 (m, 0.7H), 3.88-3.83 (m, 0.3H), 3.67 (s, 3H), 3.64 (s, 0.9H), 3.61 (s, 2.1H), 3.05-2.99 (m, 1H), 2.28-2.22 (m, 3H), 2.11-2.08 (m, 2H), 1.97-1.90 (m, 2H), 1.73-1.70 (m, 3H), 1.26-1.24 (m, 2H).

Compound VII-47-N

Ethyl 2-((trans)-4-(6-(2-bromo-3,4-difluorophenyl)-5-(methoxycarbonyl)-2-(thiazol-2-yl)-3,6-dihydropyrimidin-4-yl)cyclohexyl)-5-methylpyrimidine-4-carboxylate (a Single Stereoisomer)

Intermediate VII-47-B

Ethyl 2-((trans)-4-(6-(2-bromo-3,4-difluorophenyl)-5-(methoxycarbonyl)-2-(thiazol-2-yl)-3,6-dihydropyrimidin-4-yl)cyclohexyl)-5-methylpyrimidine-4-carboxylate (a Mixture of 2 Stereoisomers)

By utilizing the analogous procedure of Method B, the title compound was synthesized as yellow solids.

LC-MS (ESI): $R_T$=1.97 min, mass calcd. for $C_{29}H_{28}BrF_2N_5O_4S$, 659.1, m/z found 660.1 [M+H]$^+$. $^1$H NMR (400 MHz, CDCl$_3$) δ 8.67 (s, 0.4H), 8.66 (s, 0.6H), 8.25 (s, 0.6H), 7.83 (d, J=3.2 Hz, 1H), 7.51 (d, J=3.2 Hz, 0.4H), 7.45 (d, J=3.2 Hz, 0.6H), 7.43 (s, 0.4H), 7.12-7.02 (m, 2H), 6.19 (s, 0.6H), 6.03 (d, J=2.8 Hz, 0.4H), 4.52-4.46 (m, 2H), 4.17-4.07 (m, 1H), 3.63 (s, 1H), 3.61 (s, 2H), 3.12-3.03 (m, 1H), 2.46 (s, 3H), 2.28-2.18 (m, 2H), 2.18-2.04 (m, 2H), 2.03-1.90 (m, 2H), 1.87-1.64 (m, 2H), 1.45 (t, J=6.8 Hz, 3H).

A racemic mixture of Ethyl 2-((trans)-4-(6-(2-bromo-3,4-difluorophenyl)-5-(methoxycarbonyl)-2-(thiazol-2-yl)-3,6-dihydropyrimidin-4-yl)cyclohexyl)-5-methylpyrimidine-4-carboxylate VII-47-B (127 mg, 95% purity, 0.183 mmol) was separated by chiral Prep. HPLC (separation condition: Column: Chiralpak IG 5 μm 30*250 mm, Mobile Phase: CO$_2$: EtOH=70:30 at 60 g/min; Col. Temp: 40° C.; Wavelength: 230 nm, Back pressure: 100 bar) to afford VII-47-M (40 mg, 90% purity from $^1$H NMR, 30% yield, 99.6% stereopure) and VII-47-N (35 mg, 90% purity from $^1$H NMR, 26% yield, 99.6% stereopure).

Intermediate VII-47-M: LC-MS (ESI): $R_T$=1.98 min, mass calcd. for $C_{29}H_{28}BrF_2N_5O_4S$, 659.1, m/z found 660.2 [M+H]$^+$. Chiral analysis (Column: Chiralpak IG 5 μm 4.6*250 mm; Mobile Phase: CO$_2$: EtOH=70:30 at 3.0 g/min; Col. Temp: 40° C.; Wavelength: 230 nm; Back pressure 100 bar, $R_T$=7.78 min). $^1$H NMR (400 MHz, CDCl$_3$) δ 8.66 (s, 1H), 8.24 (s, 0.6H), 7.83 (d, J=3.2 Hz, 1H), 7.52-7.51 (m, 0.4H), 7.45 (d, J=2.8 Hz, 0.6H), 7.42 (s, 0.4H), 7.12-7.04 (m, 2H), 6.19 (s, 0.7H), 6.03 (s, 0.3H), 4.48 (q, J=6.8 Hz, 2H), 4.15-4.08 (m, 1H), 3.63 (s, 0.5H), 3.60 (s, 2.5H), 3.13-3.03 (m, 1H), 2.46 (s, 3H), 2.29-2.06 (m, 4H), 2.03-1.89 (m, 2H), 1.85-1.66 (m, 2H), 1.45 (t, J=6.8 Hz, 3H).

Intermediate VII-47-N: LC-MS (ESI): $R_T$=1.97 min, mass calcd. for $C_{29}H_2BrF_2N_5O_4S$, 659.1, m/z found 660.2 [M+H]$^+$. Chiral analysis (Column: Chiralpak IG 5 μm 4.6*250 mm; Mobile Phase: CO$_2$: EtOH=70:30 at 3.0 g/min; Col. Temp: 40° C.; Wavelength: 230 nm; Back pressure 100 bar, $R_T$=8.83 min). $^1$H NMR (400 MHz, CDCl$_3$) δ 8.67 (s, 0.3H), 8.66 (s, 0.7H), 8.24 (s, 0.6H), 7.83 (d, J=2.8 Hz, 1H), 7.51 (d, J=6.4 Hz, 0.4H), 7.46 (d, J=3.2 Hz, 0.6H), 7.43 (s, 0.4H), 7.12-7.03 (m, 2H), 6.19 (s, 0.7H), 6.04 (d, J=2.8 Hz, 0.3H), 4.52-4.46 (m, 2H), 4.17-4.06 (m, 1H), 3.63 (s, 1H), 3.61 (s, 2H), 3.12-3.05 (m, 1H), 2.46 (s, 3H), 2.27-2.11 (m, 4H), 2.08-1.93 (m, 2H), 1.90-1.66 (m, 2H), 1.45 (t, J=7.2 Hz, 3H).

Compound VII-48-B (trans)-Methyl 4-(2-chloro-4-fluorophenyl)-6-(4-(4-(2-methoxy-2-oxoethyl)-5-methyloxazol-2-yl)cyclohexyl)-2-(thiazol-2-yl)-1,4-dihydropyrimidine-5-carboxylate (a Single Stereoisomer)

Intermediate VII-48

(trans)-Methyl 4-(2-chloro-4-fluorophenyl)-6-(4-(4-(2-methoxy-2-oxoethyl)-5-methyloxazol-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.
LC-MS (ESI): $R_T$=1.86 min, mass calcd. for C$_{28}$H$_{28}$ClFN$_4$O$_5$S, 586.1, m/z found 586.9 [M+H]$^+$. $^1$H NMR (400 MHz, DMSO-d$_6$) δ 9.41 (d, J=3.6 Hz, 0.6H), 8.95 (s, 0.4H), 8.00-7.93 (m, 2H), 7.44-7.40 (m, 1H), 7.37-7.32 (m, 1H), 7.24-7.18 (m, 1H), 6.02 (s, 0.4H), 5.91 (d, J=3.6 Hz, 0.6H), 3.90-3.84 (m, 0.4H), 3.65-3.60 (m, 3.6H), 3.53-3.50 (m, 5H), 2.89-2.87 (m, 0.4H), 2.76-2.69 (m, 0.6H), 2.23 (s, 3H), 2.17-2.07 (m, 2H), 1.94-1.77 (m, 3H), 1.68-1.62 (m, 1H), 1.58-1.45 (m, 2H).

A racemic mixture of (trans)-methyl 4-(2-chloro-4-fluorophenyl)-6-(4-(4-(2-methoxy-2-oxoethyl)-5-methyloxazol-2-yl)cyclohexyl)-2-(thiazol-2-yl)-1,4-dihydropyrimidine-5-carboxylate VII-48 (180 mg, 95% purity, 0.291 mmol) was separated by chiral Prep. HPLC (separation condition: Superchiral S-AD 5 m 21*250 mm; Mobile phase: Hex: EtOH:formic acid=75:25:0.05 at 20 mL/min; Temp: 35° C.; Wavelength: 220 nm) to give compound VII-48-A (65 mg, 95% purity from $^1$H NMR, 36% yield, 98.6% stereopure) as yellow solids and the title compound VII-48-B (70 mg, 95% purity from $^1$H NMR, 39% yield, 96.4% stereopure) as yellow solids.

Intermediate VII-48-A: LC-MS (ESI): $R_T$=1.84 min, mass calcd. for C$_{28}$H$_{28}$ClFN$_4$O$_5$S, 586.1, m/z found 587.1 [M+H]$^+$. Chiral analysis (analytical condition: Column: Chiralpak column: IE 5 μm 4.6*250 mm; Mobile Phase: Hex EtOH:DEA=70:30:0.2 at 1 mL/min; Temp.: 30° C.; Wavelength: 254 nm, $R_T$=10.302 min). $^1$H NMR (400 MHz, DMSO-d$_6$) δ 9.44 (br s, 0.6H), 8.97 (s, 0.4H), 7.99 (s, 1.6H), 7.94 (s, 0.4H), 7.43-7.41 (m, 1H), 7.37-7.32 (m, 1H), 7.23-7.19 (m, 1H), 6.02 (s, 0.4H), 5.91 (s, 0.6H), 3.91-3.85 (m, 0.4H), 3.68-3.57 (m, 3.6H), 3.53-3.50 (m, 5H), 2.92-2.86 (m, 0.4H), 2.75-2.69 (m, 0.6H), 2.23 (s, 3H), 2.14-2.07 (m, 2H), 2.01-1.74 (m, 3.4H), 1.68-1.65 (m, 0.6H), 1.59-1.45 (m, 2H).

Intermediate VII-48-B: LC-MS (ESI): $R_T$=1.84 min, mass calcd. for C$_2$H$_2$ClFN$_4$O$_5$S, 586.1, m/z found 587.1 [M+H]$^+$. Chiral analysis (analytical condition: Column: Chiralpak column: IE 5 μm 4.6*250 mm; Mobile Phase: Hex EtOH:DEA=70:30:0.2 at 1 mL/min; Temp.: 30° C.; Wavelength: 254 nm, $R_T$=11.581 min). $^1$H NMR (400 MHz, DMSO-d$_6$) δ 9.43 (br s, 0.6H), 8.97 (s, 0.4H), 7.99 (s, 1.6H), 7.94 (s, 0.4H), 7.43-7.41 (m, 1H), 7.37-7.32 (m, 1H), 7.23-7.19 (m, 1H), 6.02 (s, 0.4H), 5.91 (s, 0.6H), 3.90-3.85 (m, 0.4H), 3.65-3.62 (m, 3.6H), 3.53-3.50 (m, 5H), 2.92-2.86 (m, 0.4H), 2.75-2.69 (m, 0.6H), 2.23 (s, 3H), 2.14-2.07 (m, 2H), 2.01-1.74 (m, 3.4H), 1.68-1.65 (m, 0.6H), 1.59-1.46 (m, 2H).

Compound VII-49-A methyl 4-(2-chloro-3,4-difluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate (a Single Stereoisomer)

Intermediate VII-49

Methyl 4-(2-chloro-3,4-difluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. $^1$H NMR (400 MHz, CDCl$_3$) δ 8.63-8.62 (m, 1.7H), 8.60-8.58 (m, 0.3H), 8.24 (br s, 0.7H), 7.84-7.83 (m, 1H), 7.52-7.51 (m, 0.3H), 7.46-7.45 (m, 0.7H), 7.39-7.37 (m, 0.3H), 7.12-7.09 (m, 1H), 7.05-7.00 (m, 1H), 6.20 (s, 0.7H), 6.06 (d, J=2.4 Hz, 0.3H), 4.10-4.05 (m, 0.7H), 3.87-3.84 (m, 0.3H), 3.75 (s, 3H), 3.64 (s, 1H), 3.62 (s, 2H), 3.61 (s, 2H), 3.07-2.97 (m, 1H), 2.24-2.20 (m, 3H), 2.12-2.07 (m, 1H), 1.94-1.87 (m, 2H), 1.83-1.74 (m, 1H), 1.69-1.64 (m, 1H).

A racemic mixture of methyl 4-(2-chloro-3,4-difluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate VII-49 (100 mg, 95% purity, 0.158 mmol) was separated by chiral Prep. HPLC (separation condition: Column: Chiralpak IG 4.6 μm 20*250 mm; Mobile Phase: MeOH:DCM:DEA=90:10:0.3 at 18 mL/min; Temp: 30° C.; Wavelength: 254 nm) to give VII-49-A (40 mg, 95% purity from $^1$H NMR, 40% yield, 100% stereopure) and VII-49-B (40 mg, 95% purity from $^1$H NMR, 40% yield, 100% stereopure) as yellow solids.

Intermediate VII-49-A: LC-MS (ESI): $R_T$=1.82 min, mass calcd. for C$_{28}$H$_{26}$ClF$_2$N$_5$O$_4$S, 601.1, m/z found 602.3 [M+H]$^+$. Chiral analysis (Column: Chiralpak IG 5 μm 4.6*250 mm; Mobile Phase: MeOH:DCM:DEA=90:10:0.2 at 1 mL/min; Temp: 30° C.; Wavelength: 254 nm, $R_T$=7.300 min). $^1$H NMR (400 MHz, CDCl$_3$) δ 8.63-8.62 (m, 2H), 8.24 (s, 0.7H), 7.84-7.83 (m, 1H), 7.52-7.50 (m, 0.3H), 7.46-7.45 (m, 0.7H), 7.38-7.37 (m, 0.3H), 7.12-7.09 (m, 1H), 7.03-6.98 (m, 1H), 6.20 (s, 0.7H), 6.06 (d, J=2.8 Hz, 0.3H), 4.10-4.05 (m, 0.7H), 3.87-3.84 (m, 0.3H), 3.75 (s, 3H), 3.64 (s, 1H), 3.62 (s, 2H), 3.61 (s, 2H), 3.07-3.04 (m, 1H), 2.28-2.20 (m, 3H), 2.12-2.07 (m, 1H), 1.96-1.89 (m, 2H), 1.84-1.75 (m, 1H), 1.67-1.58 (m, 1H).

Intermediate VII-49-B: LC-MS (ESI): $R_T$=1.81 min, mass calcd. for C$_{28}$H$_{26}$ClF$_2$N$_5$O$_4$S, 601.1, m/z found 602.3 [M+H]$^+$. Chiral analysis (Column: Chiralpak IG 5 μm 4.6*250 mm; Mobile Phase: MeOH:DCM:DEA=90:10:0.2 at 1 mL/min; Temp: 30° C.; Wavelength: 254 nm, $R_T$=10.123 min). $^1$H NMR (400 MHz, CDCl$_3$) δ 8.63-8.62 (m, 2H), 8.24 (br s, 0.7H), 7.84-7.83 (m, 1H), 7.52-7.50 (m, 0.3H), 7.46-7.45 (m, 0.7H), 7.38-7.37 (m, 0.3H), 7.12-7.09 (m, 1H), 7.03-6.98 (m, 1H), 6.20 (s, 0.7H), 6.06 (d, J=2.8 Hz, 0.3H), 4.10-4.05 (m, 0.7H), 3.87-3.84 (m, 0.3H), 3.75 (s, 3H), 3.64 (s, 1H), 3.62 (s, 2H), 3.61 (s, 2H), 3.07-3.04 (m, 1H), 2.28-2.20 (m, 3H), 2.12-2.07 (m, 1H), 1.96-1.89 (m, 2H), 1.84-1.75 (m, 1H), 1.67-1.58 (m, 1H).

Compound VII-50-A methyl 4-(2-chloro-4-fluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate (a Single Stereoisomer+Acid+Ethyl Ester

Intermediate VII-50 methyl 4-(2-chloro-4-fluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids.

$^1$H NMR (400 MHz, CDCl$_3$) δ 8.63 (s, 0.8H), 8.62 (s, 1.2H), 8.22 (br s, 0.7H), 7.84-7.82 (m, 1H), 7.50 (d, J=3.2 Hz, 0.4H), 7.44 (d, J=3.2 Hz, 0.6H), 7.40 (br s, 0.3H), 7.33-7.27 (m, 1H), 7.14-7.12 (m, 1H), 6.96-6.89 (m, 1H), 6.20 (s, 0.6H), 6.06 (d, J=5.2 Hz, 0.4H), 4.09-4.03 (m, 0.6H), 3.87-3.83 (m, 0.4H), 3.75 (s, 3H), 3.63 (s, 1H), 3.62 (s, 2H), 3.61 (s, 2H), 3.07-3.00 (m, 1H), 2.24-2.08 (m, 4H), 1.97-1.88 (m, 2H), 1.82-1.76 (m, 1H), 1.73-1.65 (m, 1H).

A racemic mixture of methyl 4-(2-chloro-4-fluorophenyl)-6-((trans)-4-(5-(2-methoxy-2-oxoethyl)pyrimidin-2-yl)cyclohexyl)-2-(thiazol-2-yl)-1,4-dihydropyrimidine-5-carboxylate VII-50 (120 mg, 95% purity, 0.195 mmol) was separated by chiral Prep. HPLC (separation condition: Column: Chiralpak IA 4.6 μm 20*250 mm; Mobile Phase: Hex:EtOH:DEA=40:60:0.3 at 10 mL/min; Temp: 30° C.; Wavelength: 254 nm) to give VII-50-A (a Mixture of acid and ethyl ester, 30 mg, 25% yield, 100% stereopure) and VII-50-B (50 mg, 95% purity from $^1$H NMR, 42% yield, 98% stereopure) as yellow solids.

Mixture VII-50-A: Chiral analysis (Column: Chiralpak IA 5 μm 4.6*250 mm; Mobile Phase: Hex:EtOH:DEA=40:60:0.2 at 1 mL/min; Temp: 30° C.; Wavelength: 254 nm, R$_T$=3.223 min, 7.171 min). LC-MS (ESI): R$_T$=1.40 min, 1.83 min, mass calcd. for C$_{28}$H$_{27}$ClFN$_5$O$_4$S, 584.1, m/z found 570.1 [M+H−14]$^+$, 598.2 [M+H+14]$^+$.

Intermediate VII-50-B: LC-MS (ESI): R$_T$=1.78 min, mass calcd. for C$_{28}$H$_{27}$CFN$_5$O$_4$S, 583.1, m/z found 584.2 [M+H]$^+$. Chiral analysis (Column: Chiralpak IA 5 μm 4.6*250 mm; Mobile Phase: Hex:EtOH:DEA=40:60:0.2 at 1 mL/min; Temp: 30° C.; Wavelength: 254 nm, R$_T$=13.619 min). $^1$H NMR (400 MHz, CDCl$_3$) δ 8.63 (s, 0.8H), 8.62 (s, 1.2H), 8.22 (br s, 0.7H), 7.84-7.83 (m, 1H), 7.50 (d, J=6.0 Hz, 0.4H), 7.45 (d, J=3.2 Hz, 0.6H), 7.40 (br s, 0.3H), 7.35-7.31 (m, 1H), 7.14-7.12 (m, 1H), 6.96-6.89 (m, 1H), 6.20 (s, 0.6H), 6.06 (d, J=2.8 Hz, 0.4H), 4.10-4.04 (m, 0.6H), 3.89-3.82 (m, 0.4H), 3.75 (s, 3H), 3.64 (s, 1H), 3.62 (s, 2H), 3.61 (s, 2H), 3.06-2.98 (m, 1H), 2.27-2.08 (m, 4H), 1.97-1.67 (m, 4H).

Compound VIII-1

Methyl 6-(1-(tert-butoxycarbonyl)piperidin-4-yl)-4-(3,4-difluoro-2-methylphenyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): R$_T$=1.96 min, mass calcd. For C$_{26}$H$_{30}$F$_2$N$_4$O$_4$S, 532.2 m/z found 533.3 [M+H]$^+$. $^1$H NMR (400 MHz, DMSO-d$_6$) δ 9.56 (d, J=3.2 Hz, 0.8H), 9.13 (s, 0.2H), 7.99-7.91 (m, 2H), 7.25-7.18 (m, 1H), 7.11-7.08 (m, 0.8H), 6.97-6.94 (m, 0.2H), 5.82 (s, 0.2H), 5.69 (d, J=3.2 Hz, 0.8H), 4.14-4.00 (m, 2.2H), 3.81-3.75 (m, 0.8H), 3.52 (s, 3H), 2.85-2.68 (m, 2H), 2.43 (s, 3H), 1.91-1.64 (m, 3H), 1.52-1.48 (m, 1H), 1.44 (s, 9H).

A stereoisomeric mixture of VIII-1 (600 mg, 1.13 mmol) was separated by chiral Prep. SFC (separation condition: Column: Chiralpak IG 5 μm 20*250 mm; Mobile Phase: CO$_2$:MeOH:DEA=80:20:0.2 at 50 g/min; Col. Temp 40° C.; Wavelength: 214 nm; Back pressure: 100 bar) to afford the title compounds VIII-1-A (260 mg, 43% yield, 100% stereopure) and VIII-1-B (270 mg, 45% yield, 98.6% stereopure) as yellow solids.

VIII-1-A: LC-MS (ESI): R$_T$=1.87 min, mass calcd. For C$_{26}$H$_{30}$F$_2$N$_4$O$_4$S, 532.2 m/z found 533.6 [M+H]$^+$. Chiral analysis (Column: Chiralpak IG; Mobile Phase: CO$_2$:MeOH:DEA=80:20:0.2 at 3.0 g/min; Col. Temp: 40.1° C.; Wavelength: 230 nm, Back pressure: 100 bar, R$_T$=3.08 min). $^1$H NMR (300 MHz, CDCl$_3$) δ 8.10 (s, 0.7H), 7.80 (s, 1H), 7.51 (d, J=2.1 Hz, 0.3H), 7.43 (d, J=2.4 Hz, 0.7H), 7.09-7.06 (m, 0.3H), 7.04 (s, 0.2H), 6.97-6.85 (m, 1.8H), 5.93 (s, 0.8H), 5.85 (s, 0.2H), 4.39-4.16 (m, 2.8H), 3.85-3.78 (m, 0.2H), 3.60 (s, 3H), 2.94-2.79 (m, 2H), 2.57 (s, 2.3H), 2.42 (s, 0.7H), 2.00-1.97 (m, 1H), 1.87-1.63 (m, 3H), 1.50 (s, 9H).

VIII-1-B: LC-MS (ESI): R$_T$=1.87 min, mass calcd. For C$_{26}$H$_{30}$F$_2$N$_4$O$_4$S, 532.2 m/z found 533.7 [M+H]$^+$. Chiral analysis (Column: Chiralpak IG; Mobile Phase: CO$_2$:MeOH:DEA=80:20:0.2 at 3.0 g/min; Col. Temp: 39.9° C.; Wavelength: 230 nm, R$_T$=3.96 min). $^1$H NMR (300 MHz, CDCl$_3$) δ 8.10 (s, 0.7H), 7.80-7.79 (m, 1H), 7.51 (d, J=2.1 Hz, 0.3H), 7.43 (d, J=2.1 Hz, 0.7H), 7.09-7.07 (m, 0.3H), 7.05 (s, 0.2H), 6.95-6.87 (m, 1.8H), 5.93 (s, 0.8H), 5.85 (s, 0.2H), 4.37-4.15 (m, 2.7H), 3.84-3.78 (m, 0.3H), 3.60 (s, 3H), 2.94-2.80 (m, 2H), 2.57 (s, 2.3H), 2.43 (s, 0.7H), 2.01-1.97 (m, 1H), 1.75-1.60 (m, 3H), 1.50 (s, 9H).

Compound VIII-2

Ethyl 6-(1-(tert-butoxycarbonyl)piperidin-4-yl)-4-(3-fluoro-2-methylphenyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): R$_T$=2.143 min, mass calcd. for C$_{27}$H$_{33}$FN$_4$O$_4$S, 528.2, m/z found 529.1 [M+H]$^+$. $^1$H NMR (400 MHz, CDCl$_3$) δ 8.08 (s, 1H), 7.80-7.78 (m, 1H), 7.49 (d, J=2.8 Hz, 0.3H), 7.42 (d, J=2.8 Hz, 0.7H), 7.08-7.01 (m, 2H), 6.95-6.88 (m, 1H), 6.01 (s, 0.7H), 5.92 (d, J=2.0 Hz, 0.3H), 4.31-4.17 (m, 3H), 4.08-3.99 (m, 2H), 2.89-2.82 (m, 2H), 2.54 (d, J=2.0 Hz, 2H), 2.39 (d, J=1.6 Hz, 1H), 2.03-2.00 (m, 1H), 1.87-1.84 (m, 1H), 1.69-1.56 (m, 2H), 1.50 (s, 9H), 1.13-1.09 (m, 3H).

A stereoisomeric mixture of ethyl 6-(1-(tert-butoxycarbonyl)piperidin-4-yl)-4-(3-fluoro-2-methylphenyl)-2-(thiazol-2-yl)-1,4-dihydropyrimidine-5-carboxylate VIII-2 (3.0 g, 85% purity, 4.82 mmol) was separated by Chiral Prep. HPLC (Column: Chiralpak IC 5 μm 20 mm*250 mm; Mobile Phase: Hex:EtOH:DEA=98:2:0.3 at 22 mL/min Temp: 30° C.; Wavelength: 214 nm) to afford the title compounds VIII-2-A (950 mg, 32% yield, 90% purity, 100% stereopure) and VIII-2-B (650 mg, 23% yield, 90% purity, 99.3% stereopure) as yellow solids.

VIII-2-A: Chiral HPLC (Colum: Chiralpak IC 5 μm 4.6 mm*250 mm; Mobile Phase: Hex:EtOH:DEA=98:2:0.2 at 1 mL/min; Col. Temp: 40° C.; Wavelength: 254 nm, $R_T$=17.28 min). $^1$H NMR (400 MHz, CDCl$_3$) δ 8.06 (s, 0.7H), 7.79 (d, J=3.2 Hz, 1H), 7.49 (d, J=3.2 Hz, 0.3H), 7.42 (d, J=3.2 Hz, 0.7H), 7.16-7.01 (m, 2.3H), 6.95-6.88 (m, 1H), 6.01 (s, 0.7H), 5.92 (d, J=2.4 Hz, 0.3H), 4.38-4.17 (m, 2.7H), 4.09-3.99 (m, 2H), 3.86-3.80 (m, 0.3H), 2.93-2.82 (m, 2H), 2.53 (s, 2.2H), 2.39 (s, 0.8H), 2.06-2.00 (m, 1H), 1.87-1.68 (m, 2H), 1.62-1.55 (m, 1H), 1.50 (s, 9H), 1.13-1.09 (m, 3H).

VIII-2-B: Chiral HPLC(Colum: Chiralpak IC 5 μm 4.6 mm*250 mm; Mobile Phase: Hex:EtOH:DEA=98:2:0.2 at 1 mL/min; Col. Temp: 40° C.; Wavelength: 254 nm, $R_T$=19.61 min). $^1$H NMR (400 MHz, CDCl$_3$) δ 8.06 (s, 0.7H), 7.79 (d, J=2.8 Hz, 1H), 7.50 (d, J=3.2 Hz, 0.3H), 7.42 (d, J=3.2 Hz, 0.7H), 7.15-7.01 (m, 2.3H), 6.95-6.88 (m, 1H), 6.01 (s, 0.7H), 5.92 (d, J=2.0 Hz, 0.3H), 4.35-4.17 (m, 2.7H), 4.10-3.99 (m, 2H), 3.86-3.81 (m, 0.3H), 2.89-2.83 (m, 2H), 2.54 (s, 2.2H), 2.40 (s, 0.8H), 2.03-2.00 (m, 1H), 1.87-1.84 (m, 1H), 1.73-1.68 (m, 1H), 1.62-1.56 (m, 1H), 1.50 (s, 9H), 1.14-1.09 (m, 3H).

Compound VIII-3

Ethyl 6-(1-(tert-butoxycarbonyl)piperidin-4-yl)-4-(4-fluoro-2-methylphenyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=2.169 min, mass calcd. for C$_{27}$H$_{33}$FN$_4$O$_4$S, 528.2, m/z found 529.1 [M+H]$^+$. $^1$H NMR (400 MHz, CDCl$_3$) δ 8.07 (s, 1H), 7.80-7.78 (m, 1H), 7.50 (d, J=3.2 Hz, 0.3H), 7.42 (d, J=3.2 Hz, 0.7H), 7.06-6.79 (m, 3H), 5.96 (s, 0.7H), 5.87 (d, J=2.0 Hz, 0.3H), 4.34-4.15 (m, 2.7H), 4.07-4.00 (m, 2H), 3.85-3.79 (m, 0.3H), 2.89-2.86 (m, 2H), 2.63 (s, 2H), 2.48 (s, 1H), 2.03-2.00 (m, 1H), 1.87-1.83 (m, 1H), 1.70-1.55 (m, 2H), 1.50 (s, 9H), 1.14-1.10 (m, 3H).

A stereoisomeric mixture of VIII-3 (6.00 g, 90% purity, 10.2 mmol) was separated by chiral Prep. SFC (Column: Chiralpak IG 5 μm 20 mm*250 mm; Mobile Phase: CO$_2$:MeOH:DEA=75:25:0.3 at 50 g/min; Col. Temp: 40° C.; Wavelength: 214 nm, Back pressure: 100 bar) to afford the title compounds VIII-3-A (2.70 g, 90% purity, 45% yield, 100% stereopure) and VIII-3-B (2.60 g, 90% purity, 43% yield, 99.2% stereopure) as yellow solids.

VIII-3-A: Chiral analysis (Colum: Chiralpak IG 5 μm 4.6 mm*250 mm; Mobile Phase: CO$_2$:MeOH:DEA=75:25:0.2 at 3.00 g/min; Col. Temp: 40° C.; Wavelength: 214 nm, Back pressure: 100 bar, $R_T$=2.73 min). $^1$H NMR (400 MHz, CDCl$_3$) δ 8.05 (s, 0.7H), 7.80-7.79 (m, 1H), 7.50 (d, J=3.2 Hz, 0.3H), 7.42 (d, J=3.2 Hz, 0.7H), 7.32-7.28 (m, 0.3H), 7.18-7.15 (m, 0.7H), 7.00 (s, 0.3H), 6.90-6.76 (m, 2H), 5.96 (s, 0.7H), 5.87 (s, 0.3H), 4.35-4.16 (m, 2.7H), 4.09-3.99 (m, 2H), 3.84-3.79 (m, 0.3H), 2.92-2.83 (m, 2H), 2.63 (s, 2H), 2.48 (s, 1H), 2.03-2.00 (m, 1H), 1.87-1.84 (m, 1H), 1.72-1.59 (m, 2H), 1.50 (s, 9H), 1.14-1.09 (m, 3H).

VIII-3-B: Chiral analysis (Colum: Chiralpak IG 5 μm 4.6 mm*250 mm; Mobile Phase: CO$_2$:MeOH:DEA=75:25:0.2 at 3.00 g/min; Col. Temp: 40° C.; Wavelength: 214 nm, Back pressure: 100 bar, $R_T$=3.59 min). $^1$H NMR (400 MHz, CDCl$_3$) δ 8.05 (s, 0.7H), 7.79 (d, J=2.8 Hz, 1H), 7.50 (d, J=3.2 Hz, 0.3H), 7.42 (d, J=2.8 Hz, 0.7H), 7.32-7.28 (m, 0.3H), 7.18-7.15 (m, 0.7H), 6.99 (s, 0.3H), 6.90-6.76 (m, 2H), 5.96 (s, 0.7H), 5.87 (d, J=2.0 Hz, 0.3H), 4.36-4.16 (m, 2.7H), 4.09-3.99 (m, 2H), 3.84-3.78 (m, 0.3H), 2.92-2.83 (m, 2H), 2.63 (s, 2H), 2.49 (s, 1H), 2.03-2.00 (m, 1H), 1.87-1.79 (m, 1H), 1.73-1.69 (m, 1H), 1.61-1.56 (m, 1H), 1.50 (s, 9H), 1.15-1.10 (m, 3H).

Compound VIII-4

Methyl 6-(1-(tert-butoxycarbonyl)piperidin-4-yl)-4-(3-fluoro-2-methylphenyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=2.133 min, mass calcd. for C$_{26}$H$_{31}$FN$_4$O$_4$S, 514.6, m/z found 515.1 [M+H]$^+$. $^1$H NMR (400 MHz, CDCl$_3$) δ 8.10 (br s, 1H), 7.79-7.78 (m, 1H), 7.49 (d, J=3.2 Hz, 0.3H), 7.42 (d, J=3.2 Hz, 0.7H), 7.17-7.00 (m, 2H), 6.95-6.88 (m, 1H), 6.01 (s, 0.7H), 5.91 (s, 0.3H), 4.40-4.17 (m, 2.7H), 3.88-3.80 (m, 0.3H), 3.59-3.58 (m, 3H), 2.99-2.79 (m, 2H), 2.54 (d, J=2 Hz, 2.2H), 2.38 (d, J=2 Hz, 0.8H), 2.04-1.59 (m, 4H), 1.50 (s, 9H).

A stereoisomeric mixture of methyl 6-(1-(tert-butoxycarbonyl)piperidin-4-yl)-4-(3-fluoro-2-methylphenyl)-2-(thiazol-2-yl)-1,4-dihydropyrimidine-5-carboxylate VIII-4 (5.0 g, 90% purity, 8.77 mmol) was separated by chiral Prep. HPLC (separation condition: Column: Chiralpak IG 5 μm 20*250 mm; Mobile Phase: CO$_2$:MeOH:DEA=75:25:0.3 at 50 g/min; Temp: 30° C.; Wavelength: 230 nm) to give the title compounds VIII-4-A (2.2 g, 90% purity, 44% yield, 99.1% stereopure) and VIII-4-B (2.0 g, 90% purity, 40% yield, 100% stereopure) as yellow solids.

VIII-4-A: chiral analytical: (Column: Chiralpak IG 5 μm 4.6*250 mm; Mobile Phase: CO$_2$:MeOH=75:25 at 3 g/min; Col. Temp: 40° C.; Wavelength: 214 nm, Back pressure: 100 bar, $R_T$=3.38 min). $^1$H NMR (400 MHz, CDCl$_3$) δ 8.09 (s, 1H), 7.79-7.78 (m, 1H), 7.50 (d, J=3.2 Hz, 0.3H), 7.42 (d, J=3.2 Hz, 0.7H), 7.16-7.04 (m, 2H), 6.99-6.88 (m, 1H), 6.00 (s, 0.7H), 5.91 (s, 0.3H), 4.43-4.16 (m, 2.7H), 3.87-3.81 (m, 0.3H), 3.59-3.58 (m, 3H), 2.98-2.78 (m, 2H), 2.54 (d, J=2 Hz, 2.2H), 2.37 (d, J=2.4 Hz, 0.8H), 2.03-1.59 (m, 4H), 1.50 (s, 9H).

VIII-4-B: chiral analytical: (Column: Chiralpak IG 5 μm 4.6*250 mm; Mobile Phase: CO$_2$:MeOH=75:25 at 3 g/min; Col. Temp: 40° C.; Wavelength: 214 nm, Back pressure: 100 bar, $R_T$=2.91 min). $^1$H NMR (400 MHz, CDCl$_3$) δ 8.10 (s, 1H), 7.79-7.78 (m, 1H), 7.49 (d, J=3.2 Hz, 0.3H), 7.42 (d, J=3.2 Hz, 0.7H), 7.17-7.12 (m, 2H), 7.00-6.88 (m, 1H), 6.01 (s, 0.7H), 5.91 (d, J=3.2 Hz, 0.3H), 4.43-4.17 (m, 2.7H), 3.88-3.80 (m, 0.3H), 3.59-3.58 (m, 3H), 2.98-2.79 (m, 2H), 2.54 (d, J=2 Hz, 2.2H), 2.39 (d, J=2 Hz, 0.8H), 2.04-1.56 (m, 4H), 1.50 (s, 9H).

Compound VIII-5-B methyl 6-(1-(tert-butoxycarbonyl)piperidin-4-yl)-4-(4-fluoro-2-methylphenyl)-2-(thiazol-2-yl)-1,4-dihydropyrimidine-5-carboxylate (a Single Stereoisomer)

Intermediate VIII-5-2

Methyl 6-(1-(tert-butoxycarbonyl)piperidin-4-yl)-4-(4-fluoro-2-methylphenyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): R$_T$=1.79 min, mass calcd. for C$_{26}$H$_{31}$FN$_4$O$_4$S, 514.2, m/z found 515.4 [M+H]$^+$. $^1$H NMR (400 MHz, CDCl$_3$) δ 8.09 (s, 0.7H), 7.79 (d, J=2.8 Hz, 1H), 7.49 (d, J=3.2 Hz, 0.3H), 7.42 (d, J=2.8 Hz, 0.7H), 7.32-7.28 (m, 0.3H), 7.17-7.13 (m, 0.7H), 7.07 (s, 0.3H), 6.90-6.76 (m, 2H), 5.95 (s, 0.7H), 5.85 (s, 0.3H), 4.40-4.20 (m, 2H), 3.59 (s, 2H), 3.58 (s, 1H), 2.97-2.79 (m, 2H), 2.63 (s, 2H), 2.47 (s, 1H), 2.02-1.97 (m, 1H), 1.90-1.81 (m, 1H), 1.72-1.59 (m, 3H), 1.50 (s, 9H).

A stereoisomeric mixture of methyl 6-(1-(tert-butoxycarbonyl)piperidin-4-yl)-4-(4-fluoro-2-methylphenyl)-2-(thiazol-2-yl)-1,4-dihydropyrimidine-5-carboxylate VIII-5-2 (2.00 g, 3.88 mmol) was separated by chiral Prep. SFC (Column: Chiralpak IG 5 μm 20*250 mm; Mobile Phase: C$_2$:MeOH:DEA=75:25:0.3 at 50 g/min; Col. Temp 40° C.; Wavelength: 214 nm; Back pressure: 100 bar) to afford title compounds VIII-5-2A (684 mg, 34% yield, 99.3% stereopure) as yellow solids and VIII-5-2B (607 mg, 30% yield, 100% stereopure) as yellow solids.

VIII-5-2A: LC-MS (ESI): R$_T$=1.89 min, mass calcd. for C$_{26}$H$_{31}$FN$_4$O$_4$S, 514.2, m/z found 515.1 [M+H]$^+$. Chiral analysis (Column: Chiralpak IG 5 μm 4.6*250 mm; Mobile Phase: CO$_2$:MeOH:DEA=75:25:0.2 at 3.0 g/min; Col. Temp: 40° C.; Wavelength: 280 nm, Back pressure: 100 bar; R$_T$=3.81 min).

VIII-5-2B: LC-MS (ESI): R$_T$=1.88 min, mass calcd. for C$_{26}$H$_{31}$FN$_4$O$_4$S, 514.2, m/z found 515.1 [M+H]$^+$. Chiral analysis (Column: Chiralpak IG 5 μm 4.6*250 mm; Mobile Phase: CO$_2$:MeOH:DEA=75:25:0.2 at 3.0 g/min; Col. Temp: 40° C.; Wavelength: 280 nm, Back pressure: 100 bar; R$_T$=2.93 min).

Compound VIII-6 methyl 6-(1-(tert-butoxycarbonyl)piperidin-4-yl)-4-(2-chloro-3-fluorophenyl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): R$_T$=1.55 min, mass calcd. For C$_{25}$H$_{28}$ClFN$_4$O$_4$S, 534.2 m/z found 535.5 [M+H]$^+$. $^1$H NMR (400 MHz, DMSO-d$_6$) δ 9.55 (d, J=3.6 Hz, 0.8H), 9.14 (s, 0.2H), 8.00-7.98 (m, 1.7H), 7.93 (d, J=3.2 Hz, 0.3H), 7.40-7.31 (m, 2H), 7.21-7.15 (m, 1H), 6.07 (s, 0.2H), 5.97 (d, J=3.6 Hz, 0.8H), 4.15-3.98 (m, 2.2H), 3.84-3.76 (m, 0.8H), 3.52 (s, 2.4H), 3.51 (s, 0.6H), 2.82-2.71 (m, 2H), 1.99-1.65 (m, 4H), 1.44 (s, 9H).

A stereoisomeric mixture of VIII-6 (1.95 g, 3.65 mmol) was separated by chiral Prep. SFC (Column: Chiralpak IG 5 μm 20*250 mm; Mobile Phase: CO$_2$:MeOH=70:30 at 50 g/min; Col. Temp 41.1° C.; Wavelength: 214 nm; Back pressure: 100 bar) to afford the title compounds VIII-6-A (910 mg, 47% yield, 100% stereopure) and VIII-6-B (960 mg, 49% yield, 99.1% stereopure) as yellow solids.

VIII-6-A: LC-MS (ESI): R$_T$=1.96 min, mass calcd. for C$_{25}$H$_{28}$ClFN$_4$O$_4$S, 534.2 m/z found 535.2 [M+H]$^+$. Chiral analysis (Column: Chiralpak IG 5 μm 4.6*250 mm; Mobile Phase: CO$_2$:MeOH=70:30 at 2.999 g/min; Temp: 40° C.; Wavelength: 230 nm, R$_T$=2.74 min).

VIII-6-B: LC-MS (ESI): R$_T$=1.96 min, mass calcd. for C$_{25}$H$_{28}$ClFN$_4$O$_4$S, 534.2 m/z found 535.3 [M+H]$^+$. Chiral analysis (Column: Chiralpak IG 5 μm 4.6*250 mm; Mobile Phase: CO$_2$:MeOH=70:30 at 2.999 g/min; Temp: 40.4° C.; Wavelength: 230 nm, R$_T$=3.60 min).

Compound VIII-7 methyl 6-(1-(tert-butoxycarbonyl)piperidin-4-yl)-4-(2-chloro-4-fluorophenyl)-2-(thiazol-2-yl)-1,4-dihydro-pyrimidine-5-carboxylate (a Mixture of 2 Stereoisomers)

By utilizing the analogous procedure of Method B, the title compound was synthesized.

A stereoisomeric mixture of VIII-7 (7.00 g, 13.1 mmol) was further separated by chiral Prep. HPLC (Column: Chiralpak IA 5 μm 20*250 mm; Mobile Phase: Hex:EtOH=90:10 at 23 mL/min; Temp: 30° C.; Wavelength: 230 nm) to afford stereoisomers VIII-7-A (2.44 g, 35% yield) and VIII-7-B (1.56 g, 22% yield).

VIII-7-A: SFC (analytical condition: Column: Chiralpak IG; Mobile Phase: CO$_2$:MeOH=70:30 at 1.0 mL/min; Temp: 41° C.; Wavelength: 230 nm, R$_T$=2.59 min). $^1$H NMR (400 MHz, CDCl$_3$) δ 8.12 (s, 0.5H), 7.81 (t, J=3.2 Hz, 1H), 7.48 (d, J=3.2 Hz, 0.6H), 7.44 (d, J=3.6 Hz, 0.4H), 7.41 (br s, 0.5H), 7.30-7.27 (m, 1H), 7.15-7.11 (m, 1H), 6.96-6.88 (m, 1H), 6.19 (s, 0.4H), 6.06 (d, J=2.8 Hz, 0.6H), 4.35-4.21 (m, 2H), 4.20-4.12 (m, 0.4H), 3.96-3.89 (m, 0.6H), 3.60 (s, 2.4H), 3.59 (s, 0.6H), 2.94-2.78 (m, 2H), 2.10-1.79 (m, 3H), 1.74-1.63 (m, 1H), 1.50 (s, 9H).

VIII-7-B: LC-MS (ESI): R$_T$=2.191 min, mass calcd. For C$_{25}$H$_{28}$ClFN$_4$O$_4$S, 534.2 m/z found 534.9 [M+H]$^+$. Chiral HPLC (Column: Chiralpak IA 5 μm 4.6*250 mm; Mobile Phase: Hex:EtOH=85:15 at 1.0 mL/min; Temp: 30° C.; Wavelength: 230 nm, R$_T$=6.154 min). $^1$H NMR (400 MHz, CDCl$_3$) δ 8.12 (s, 0.5H), 7.82 (t, J=3.2 Hz, 1H), 7.47 (dd, J=20.4, 3.0 Hz, 1H), 7.41 (br s, 0.5H), 7.30-7.28 (m, 1H), 7.15-7.11 (m, 1H), 6.96-6.88 (m, 1H), 6.19 (s, 0.4H), 6.06 (d, J=2.4 Hz, 0.6H), 4.36-4.22 (m, 2H), 4.20-4.12 (m, 0.4H), 3.96-3.88 (m, 0.6H), 3.60 (s, 2.4H), 3.59 (s, 0.6H), 2.95-2.79 (m, 2H), 2.09-1.74 (m, 3H), 1.63-1.58 (m, 1H), 1.50 (s, 9H).

Compound VIII-8

Ethyl 6-(1-(tert-butoxycarbonyl)piperidin-4-yl)-4-(2-chloro-4-fluorophenyl)-2-(thiazol-2-yl)-1,4-dihydro-pyrimidine-5-carboxylate (a Mixture of 2 Stereoisomers)

By utilizing the analogous procedure of Method B, the title compound was synthesized.

LC-MS (ESI): R$_T$=2.01 min, mass calcd. for C$_{26}$H$_{30}$ClFN$_4$O$_4$S, 548.2, m/z found 549.5 [M+H]$^+$. $^1$H NMR (400 MHz, DMSO-d$_6$) δ 9.47 (d, J=2.4 Hz, 0.7H), 9.04 (s, 0.3H), 8.01-7.99 (m, 1.7H), 7.93-7.92 (m, 0.3H), 7.43-7.34 (m, 2H), 7.24-7.18 (m, 1H), 6.03 (s, 0.2H), 5.92 (d, J=3.2 Hz, 0.8H), 4.11-4.01 (m, 2H), 3.99-3.94 (m, 2H), 3.83-3.75 (m, 1H), 2.84-2.69 (m, 2H), 1.91-1.66 (m, 3H), 1.57-1.49 (m, 1H), 1.43 (s, 9H), 1.10-1.02 (m 3H).

A stereoisomeric mixture of ethyl 6-(1-(tert-butoxycarbonyl)piperidin-4-yl)-4-(2-chloro-4-fluorophenyl)-2-(thiazol-2-yl)-1,4-dihydropyrimidine-5-carboxylate VIII-8 (2.50 g, 4.55 mmol) was separated by Chiral Prep. HPLC (separation condition: Column: Chiralpak IG 5 μm 20*250 mm; Mobile Phase: CO$_2$:MeOH=70:30 at 50 g/min; Temp: 30° C.; Wavelength: 214 nm; Back Pressure: 100 bar) to give the compounds VIII-8-A (1.00 g, 40% yield, 100% stereopure) and VIII-8-B (1.20 g, 48% yield, 99.8% stereopure) as yellow solids.

VIII-8-A: Chiral analysis (Column: Chiralpak IG 5 μm 4.6*250 mm; Mobile Phase: $CO_2$:MeOH=70:30 at 3 g/min; Temp: 30° C.; Wavelength: 230 nm, Back Pressure: 100 bar; $R_T$=2.5 min).

VIII-8-B: Chiral analysis (Column: Chiralpak IG 5 μm 4.6*250 mm; Mobile Phase: $CO_2$:MeOH=70:30 at 3 g/min; Temp: 30° C.; Wavelength: 230 nm, Back Pressure: 100 bar; $R_T$=3.4 min).

Compound VIII-9

Ethyl 6-(1-(tert-butoxycarbonyl)piperidin-4-yl)-4-(2-chloro-3-fluorophenyl)-2-(thiazol-2-yl)-1,4-dihydropyrimidine-5-carboxylate (a Mixture of 2 Stereoisomers)

By utilizing the analogous procedure of Method B, the title compound was synthesized. $^1$H NMR (400 MHz, $CDCl_3$) δ 8.11 (br s, 0.4H), 7.82 (d, J=3.2 Hz, 1H), 7.54-7.41 (m, 1H), 7.35-7.29 (m, 0.6H), 7.25-7.12 (m, 2H), 7.10-7.00 (m, 1H), 6.27 (s, 0.5H), 6.14 (s, 0.5H), 4.38-4.18 (m, 3H), 4.08-3.90 (m, 2H), 2.95-2.76 (m, 2H), 2.01-1.61 (m, 4H), 1.50 (s, 9H), 1.11 (t, J=7.2 Hz, 3H).

A stereoisomeric mixture of ethyl 6-(1-(tert-butoxycarbonyl)piperidin-4-yl)-4-(2-chloro-3-fluorophenyl)-2-(thiazol-2-yl)-1,4-dihydropyrimidine-5-carboxylate VIII-9 (1.00 g, 1.82 mmol) was separated by chiral Prep. SFC (Column: Chiralpak IG 5 μm 20*250 mm; Mobile Phase: $CO_2$: MeOH=75:25 at 50 g/min; Col. Temp: 39.8° C.; Wavelength: 214 nm; Back pressure: 100 bar) to afford the compounds VIII-9-A (410 mg, 41% yield, 100% stereopure) and VIII-9-B (450 mg, 45% yield, 100% stereopure) as a yellow solids.

VIII-9-A: Chiral analysis (Column: Chiralpak IG 5 μm 4.6*250 mm; Mobile Phase: $CO_2$:MeOH=80:20 at 3 g/min; Col. Temp: 40° C.; Wavelength: 214 nm; Back pressure: 100 bar; $R_T$=4.69 min).

VIII-9-B: Chiral analysis (Column: Chiralpak IG 5 μm 4.6*250 mm; Mobile Phase: $CO_2$:MeOH=80:20 at 3 g/min; Col. Temp: 40° C.; Wavelength: 214 nm; Back pressure: 100 bar; $R_T$=5.92 min).

Compound VIII-10

Methyl 6-(1-(tert-butoxycarbonyl)piperidin-4-yl)-4-(2-chloro-3,4-difluorophenyl)-2-(thiazol-2-yl)-1,4-dihydropyrimidine-5-carboxylate (a Mixture of 2 Stereoisomers)

By utilizing the analogous procedure of Method B, the title compound was synthesized.
$^1$H NMR (400 MHz, $CDCl_3$) δ 8.16 (br s, 0.5H), 7.82 (d, J=3.2 Hz, 1H), 7.51 (d, J=2.8 Hz, 0.5H), 7.46 (d, J=3.2 Hz, 1H), 7.10-6.98 (m, 2H), 6.18 (s, 0.5H), 6.06 (s, 0.5H), 4.41-4.16 (m, 2H), 3.97-3.91 (m, 0.4H), 3.74-3.69 (m, 0.6H), 3.61 (s, 1.2H), 3.60 (s, 1.8H), 3.02-2.78 (m, 2H), 2.08-1.80 (m, 2H), 1.73-1.58 (m, 2H), 1.50 (s, 9H).

A stereoisomeric mixture of VIII-10 (18.0 g, 32.6 mmol) was separated by chiral Prep. SFC (Column: chiralpak IG 5 μm 20*250 mm; Mobile Phase: $CO_2$:MeOH=70:30 at 50 g/min; Co-solvent: MeOH; Col. Temp 40° C.; Wavelength: 230 nm; Back pressure: 100 bar) to give the title compounds VIII-10-A (8.0 g, 40% yield, 100% stereopure) and VIII-10-B (8.0 g, 40%, 100% stereopure).

VIII-10-A: Chiral SFC: (Column: Chiralpak IG 5 μm 4.6*250 mm; Mobile Phase: $CO_2$:MeOH:DEA=70:30:0.2 at 2.999 g/min; Col. Temp: 39.6° C.; Wavelength: 230 nm, Back pressure: 100 bar, $R_T$=2.37 min). $^1$H NMR (400 MHz, DMSO-$d_6$) δ 9.62 (br s, 0.7H), 9.20 (s, 0.3H), 8.01-7.99 (m, 1.7H), 7.94 (d, J=3.6 Hz, 0.3H), 7.49-7.42 (m, 1H), 7.23-7.15 (m, 1H), 6.03 (s, 0.3H), 5.94 (s, 0.7H), 4.18-3.99 (m, 2.3H), 3.85-3.76 (m, 0.7H), 3.54 (s, 2H), 3.53 (s, 1H), 2.92-2.65 (m, 2H), 1.96-1.51 (m, 4H), 1.44 (s, 9H).

VIII-10-B: Chiral SFC: (Column: Chiralpak IG 5 μm 4.6*250 mm; Mobile Phase: $CO_2$:MeOH:DEA=70:30:0.2 at 2.999 g/min; Col. Temp: 40° C.; Wavelength: 230 nm, Back pressure: 100 bar, $R_T$=3.44 min). $^1$H NMR (400 MHz, DMSO-$d_6$) δ 9.62 (br s, 0.7H), 9.20 (s, 0.3H), 8.01-7.99 (m, 1.7H), 7.94 (d, J=3.6 Hz, 0.3H), 7.49-7.42 (m, 1H), 7.23-7.15 (m, 1H), 6.03 (s, 0.3H), 5.94 (s, 0.7H), 4.18-3.99 (m, 2.3H), 3.85-3.76 (m, 0.7H), 3.54 (s, 1H), 3.53 (s, 2H), 2.92-2.65 (m, 2H), 1.96-1.51 (m, 4H), 1.44 (s, 9H).

Compound VIII-11-6 ethyl 6-(1-(tert-butoxycarbonyl)-2-methylpiperidin-4-yl)-4-(2-chloro-3,4-difluorophenyl)-2-(thiazol-2-yl)-1,4-dihydropyrimidine-5-carboxylate (a mixture of 4 Stereoisomers)

By utilizing the analogous procedure of Method B, the title compound was synthesized as yellow solids. LC-MS (ESI): $R_T$=2.13 min. mass calcd. For $C_{27}H_{31}ClF_2N_4O_4S$, 580.2, m/z found 581.0 [M+H]$^+$. $^1$HNMR (400 MHz, DMSO-$d_6$) δ 9.61-9.59 (m, 1H), 8.00-7.98 (m, 1.7H), 7.94 (d, J=3.2 Hz, 0.3H), 7.49-7.43 (m, 1H), 7.21-7.16 (m, 1H), 6.05-6.02 (m, 0.3H), 5.95-5.91 (m, 0.7H), 4.47-4.29 (m, 1H), 4.07-3.94 (m, 4H), 3.02-2.82 (m, 1H), 1.99-1.55 (m, 3H), 1.43 (s, 9H), 1.36-1.23 (m, 1H), 1.18-1.16 (m, 3H), 1.10-1.07 (m, 3H).

Compound VIII-12

Ethyl 6-(1-(tert-butoxycarbonyl)piperidin-4-yl)-4-(2-chloro-3,4-difluorophenyl)-2-(thiazol-2-yl)-1,4-dihydropyrimidine-5-carboxylate (a Mixture of 2 Stereoisomers)

By utilizing the analogous procedure of Method B, the title compound was synthesized.
LC-MS (ESI): $R_T$=2.05 min, mass calcd. for $C_{26}H_{29}ClF_2N_4O_4S$, 566.2, m/z found 567.7 [M+H]$^+$. $^1$H NMR (400 MHz, $CDCl_3$) δ 8.36 (s, 0.5H), 7.82 (d, J=3.2 Hz, 1H), 7.51 (d, J=2.8 Hz, 0.5H), 7.46 (d, J=3.2 Hz, 0.5H), 7.38 (s, 0.5H), 7.10-6.99 (m, 2H), 6.20 (s, 0.5H), 6.08 (s, 0.5H), 4.30 (br s, 1.5H), 4.09-3.99 (m, 2H), 3.97-3.89 (m, 0.5H), 2.91-2.79 (m, 2H), 1.80-1.74 (m, 3H), 1.61-1.58 (m, 2H), 1.50 (s, 9H), 1.13 (t, J=6.8 Hz, 3H).

A stereoisomeric mixture of VIII-12 (13.0 g, 22.9 mmol) was separated by chiral Prep. HPLC (Column: Chiralpak IA 5 μm 20*250 mm; Mobile Phase: Hex:EtOH=95:5 at 25 mL/min, Temp: 30° C.; Wavelength: 214 nm) to afford the compounds VIII-12-A (5 g, 38% yield, 99.7% stereopure) and VIII-12-B (5 g, 38% yield, 98.4% stereopure).

VIII-12-A: LC-MS (ESI): $R_T$=2.05 min, mass calcd. for $C_{26}H_{29}ClF_2N_4O_4S$, 566.2, m/z found 567.6 [M+H]$^+$. Chiral analysis (Column: Chiralpak IA 5 μm 4.6*250 mm; Mobile Phase: Hex:EtOH=95:5 at 1.0 mL/min; Temp: 30° C.; Wavelength: 230 nm; $R_T$=7.937 min). $^1$H NMR (400 MHz, $CDCl_3$) δ 8.12 (s, 0.5H), 7.83-7.82 (m, 1H), 7.51 (d, J=3.2 Hz, 0.4H), 7.46 (d, J=3.2 Hz, 0.6H), 7.34 (s, 0.5H), 7.10-6.99 (m, 2H), 6.20 (s, 0.6H), 6.08 (d, J=2.4 Hz, 0.4H), 4.36-4.14 (m, 2.6H), 4.10-3.99 (m, 2H), 3.97-3.89 (m, 0.4H), 2.91-2.78 (m, 2H), 2.10-1.63 (m, 3.5H), 1.58-1.56 (m, 0.5H), 1.50 (s, 9H), 1.14 (t, J=7.2 Hz, 3H).

VIII-12-B: LC-MS (ESI): $R_T$=2.05 min, mass calcd. for $C_{26}H_{29}ClF_2N_4O_4S$, 566.2, m/z found 567.6 [M+H]$^+$. Chiral analysis (Column: Chiralpak IA 5 μm 4.6*250 mm; Mobile Phase: Hex:EtOH=95:5 at 1.0 mL/min; Temp: 30° C.; Wavelength: 230 nm; $R_T$=8.930 min). $^1$H NMR (400 MHz, CDCl$_3$) δ 8.12 (s, 0.5H), 7.83-7.82 (m, 1H), 7.51 (d, J=3.2 Hz, 0.4H), 7.46 (d, J=3.2 Hz, 0.6H), 7.34 (s, 0.5H), 7.10-6.99 (m 2H), 6.20 (s, 0.6H), 6.08 (d, J=2.4 Hz, 0.4H), 4.36-4.14 (m 2.6H), 4.10-3.99 (m, 2H), 3.97-3.89 (m, 0.4H), 2.91-2.78 (m, 2H), 2.10-1.63 (m, 3.5H), 1.58-1.56 (m, 0.5H), 1.50 (s, 9H), 1.14 (t, J=7.2 Hz, 3H).

Compound VIII-13

Methyl 4-(4-bromo-2-chlorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=2.13 min, mass calcd. for $C_{25}H_{28}BrClN_4O_4S$, 594.1, m/z found 594.8 [M+H]$^+$. $^1$H NMR (400 MHz, CDCl$_3$) δ 8.13 (s, 0.4H), 7.82 (t, J=2.8 Hz, 1H), 7.56-7.54 (m, 1H), 7.50 (d, J=2.8 Hz, 0.6H), 7.46-7.42 (m, 1H), 7.36-7.31 (m, 1H), 7.19-7.16 (m, 1H), 6.18 (s, 0.5H), 6.04 (d, J=2.4 Hz, 0.5H), 4.35-4.17 (m, 2.4H), 3.97-3.90 (m, 0.6H), 3.61 (s, 1.5H), 3.59 (s, 1.5H), 2.90-2.81 (m, 2H), 1.96-1.62 (m, 4H), 1.50 (s, 9H).

A stereoisomeric mixture of VIII-13 (1.30 g, 90% purity, 1.96 mmol) was separated by chiral Prep-HPLC (Column: Chiralpak AD 5 μm 20*250 mm; Mobile Phase: Hex:EtOH:DEA=70:30:0.3 at 15 mL/min; Col. Temp: 40° C.; Wavelength: 214 nm) to afford the title compounds VIII-13-2a (460 mg, 35% yield, 90% purity from HNMR, 100% stereopure) and VIII-13-2b (480 mg, 39% yield, 95% purity from HNMR, 96.2% stereopure) as yellow solids.

VIII-13-2a: LC-MS (ESI): $R_T$=2.18 min, mass calcd. for $C_{25}H_{28}BrClN_4O_4S$, 594.1, m/z found 594.8 [M+H]$^+$. Chiral HPLC(Colum: Chiralpak AD 5 μm 4.6*250 mm; Mobile Phase: Hex:EtOH:DEA=70:30:0.2 at 1 mL/min; Col. Temp: 40° C.; Wavelength: 230 nm, $R_T$=4.34 min). $^1$H NMR (400 MHz, CDCl$_3$) δ 8.13 (s, 0.5H), 7.82 (t, J=3.2 Hz, 1H), 7.56 (t, J=2.4 Hz, 1H), 7.50 (d, J=3.2 Hz, 0.5H), 7.45 (d, J=3.2 Hz, 0.5H), 7.43 (d, J=2.4 Hz, 0.5H), 7.36-7.30 (m, 1H), 7.19-7.16 (m, 1H), 6.18 (s, 0.5H), 6.04 (d, J=2.4 Hz, 0.5H), 4.34-4.13 (m, 2.5H), 3.96-3.90 (m, 0.5H), 3.61 (s, 1.5H), 3.59 (s, 1.5H), 2.91-2.82 (m, 2H), 1.96-1.67 (m, 3H), 1.62-1.57 (m, 1H), 1.50 (s, 9H).

VIII-13-2b: LC-MS (ESI): $R_T$=2.15 min, mass calcd. for $C_{25}H_{28}BrClN_4O_4S$, 594.1, m/z found 594.8 [M+H]$^+$. Chiral HPLC(Colum: Chiralpak AD 5 μm 4.6*250 mm; Mobile Phase: Hex:EtOH:DEA=70:30:0.2 at 1 mL/min; Col. Temp: 40° C.; Wavelength: 230 nm, $R_T$=5.60 min). $^1$H NMR (400 MHz, CDCl$_3$) δ 8.13 (s, 0.5H), 7.82 (t, J=3.6 Hz, 1H), 7.56 (t, J=2.4 Hz, 1H), 7.50 (d, J=3.2 Hz, 0.5H), 7.45 (d, J=2.8 Hz, 0.5H), 7.42 (d, J=2.4 Hz, 0.5H), 7.37-7.31 (m, 1H), 7.19-7.16 (m, 1H), 6.18 (s, 0.5H), 6.04 (d, J=2.4 Hz, 0.5H), 4.35-4.14 (m, 2.5H), 3.96-3.90 (m, 0.5H), 3.61 (s, 1.5H), 3.59 (s, 1.5H), 2.92-2.81 (m, 2H), 2.12-2.04 (m, 0.5H), 1.96-1.64 (m, 3.5H), 1.50 (s, 9H).

Compound VIII-14

Methyl 4-(2-bromo-3,4-difluorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=1.96 min, mass calcd. for $C_{25}H_{27}BrF_2N_4O_4S$, 596.1, m/z found 599.3 [M+H]$^+$. $^1$H NMR (400 MHz, DMSO-d$_6$) δ 9.58 (d, J=3.2 Hz, 0.7H), 9.16 (s, 0.3H), 8.00-7.98 (m, 1.7H), 7.93-7.92 (m, 0.3H), 7.51-7.36 (m, 1H), 7.23-7.12 (m, 1H), 6.00 (s, 0.3H), 5.92 (d, J=3.6 Hz, 0.7H), 4.16-4.02 (m, 2.3H), 3.82-3.76 (m, 0.7H), 3.52 (s, 2.1H), 3.51 (s, 0.9H), 2.78 (br s, 2H), 1.97-1.50 (m, 4H), 1.44 (s, 9H).

A stereoisomeric mixture of VIII-14 (950 mg, 1.59 mmol) was separated by chiral Prep. SFC (Column: Chiralpak IG 5 μm 20*250 mm; Mobile Phase: CO$_2$:MeOH:DEA=70:30:0.2 at 50 g/min; Col. Temp 41.1° C.; Wavelength: 214 nm; Back pressure: 100 bar) to afford the title compounds VIII-14-A (450 mg, 47% yield, 100% stereopure) and VIII-14-B (460 mg, 48% yield, 100% stereopure) as yellow solids.

VIII-14-A: LC-MS (ESI): $R_T$=1.85 min, mass calcd. for $C_{25}H_{27}BrF_2N_4O_4S$, 596.1, m/z found 597.5 [M+H]$^+$. Chiral analysis (Column: Chiralpak IG 5 μm 4.6*250 mm; Mobile Phase: CO$_2$:MeOH:DEA=70:30:0.2 at 2.999 g/min; Temp: 40° C.; Wavelength: 230 nm, $R_T$=2.72 min). $^1$H NMR (400 MHz, DMSO-d$_6$) δ 9.52 (br s, 0.7H), 9.15 (s, 0.3H), 8.00-7.92 (m, 2H), 7.51-7.45 (m, 1H), 7.23-7.13 (m, 1H), 6.01 (s, 0.3H), 5.92 (s, 0.7H), 4.14-3.99 (m, 2.3H), 3.82-3.76 (m, 0.7H), 3.52 (s, 3H), 2.86-2.71 (m, 2H), 1.96-1.50 (m, 4H), 1.44 (s, 9H).

VIII-14-B: LC-MS (ESI): $R_T$=1.85 min, mass calcd. for $C_{25}H_{27}BrF_2N_4O_4S$, 596.1, m/z found 597.5 [M+H]$^+$. Chiral analysis (Column: Chiralpak IG 5 μm 4.6*250 mm; Mobile Phase: CO$_2$:MeOH:DEA=70:30:0.2 at 2.999 g/min; Temp: 40° C.; Wavelength: 230 nm, $R_T$=3.99 min). $^1$H NMR (400 MHz, DMSO-d$_6$) δ 9.57 (d, J=3.6 Hz, 0.7H), 9.15 (s, 0.3H), 8.00-7.92 (m, 2H), 7.51-7.44 (m, 1H), 7.23-7.12 (m, 1H), 6.01 (s, 0.3H), 5.92 (d, J=3.2 Hz, 0.7H), 4.16-3.99 (m, 2.3H), 3.82-3.75 (m, 0.7H), 3.52-3.51 (m, 3H), 2.92-2.71 (m, 2H), 1.96-1.49 (m, 4H), 1.44 (s, 9H).

Compound VIII-15

Methyl 4-(2-bromo-3-fluorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized. $^1$H NMR (400 MHz, CDCl$_3$) δ 8.13 (s, 0.5H), 7.85-7.80 (m, 1H), 7.52-7.47 (m, 1H), 7.47-7.43 (m, 0.5H), 7.25-7.18 (m, 1H), 7.14-6.98 (m, 2H), 6.25 (s, 0.5H), 6.12-6.07 (m, 0.5H), 4.41-4.16 (m, 2.5H), 4.01-3.90 (m, 0.5H), 3.65-3.56 (m, 3H), 2.97-2.78 (m, 2H), 2.02-1.80 (m, 2H), 1.75-1.64 (m, 2H), 1.54-1.47 (m, 9H).

A stereoisomeric mixture of methyl 4-(2-bromo-3-fluorophenyl)-6-(1-(tert-butoxycarbonyl)piperidin-4-yl)-2-(thiazol-2-yl)-1,4-dihydropyrimidine-5-carboxylate VIII-15 (6.40 g, 107 mmol) was separated by chiral Prep. SFC (Column: Chiralpak IG 5 μm 20*250 mm; Mobile Phase: CO$_2$:MeOH=70:30 at 50 g/min; Col. Temp: 30° C.; Wavelength: 214 nm, Back pressure: 100 bar) to afford the title compounds VIII-15-A (2.60 g, 38% yield, 100% stereopure) and VIII-15-B (2.90 g, 38% yield, 99.5% stereopure) as yellow solids.

VIII-15-A: Chiral analysis (Column: Chiralpak IG 5 μm 4.6*250 mm; $CO_2$:MeOH=70:30 at 3.0 g/min; Col. Temp: 40° C.; Wavelength: 254 nm, Back pressure: 100 bar, $R_T$=3.25 min). $^1$H NMR (400 MHz, $CDCl_3$) δ 8.13 (s, 0.5H), 7.83-7.81 (m, 1H), 7.50-7.49 (m, 1H), 7.45-7.44 (m, 0.5H), 7.26-7.14 (m, 1H), 7.10-6.98 (m, 2H), 6.25 (s, 0.5H), 6.10 (s, 0.5H), 4.41-4.13 (m, 2.5H), 4.00-3.92 (m, 0.5H), 3.60-3.58 (m, 3H), 2.97-2.77 (m, 2H), 2.00-1.74 (m, 2H), 1.64-1.55 (m, 2H), 1.54-1.45 (m, 9H).

VIII-15-B: Chiral analysis (Column: Chiralpak IG 5 μm 4.6*250 mm; $CO_2$:MeOH=70:30 at 3.0 g/min; Temp: 40° C.; Wavelength: 254 nm, $R_T$=4.31 min). $^1$H NMR (400 MHz, $CDCl_3$) δ 8.13 (s, 0.5H), 7.83-7.81 (m, 1H), 7.52-7.48 (m, 1H), 7.44-7.43 (m, 0.5H), 7.26-7.17 (m, 1H), 7.12-6.97 (m, 2H), 6.25 (s, 0.5H), 6.10 (s, 0.5H), 4.37-4.09 (m, 2.5H), 4.98-3.94 (m, 0.5H), 3.63-3.59 (m, 3H), 2.96-2.79 (m, 2H), 2.01-1.81 (m, 2H), 1.74-1.58 (m, 2H), 1.51-1.45 (m, 9H).

Compound VIII-16-2B methyl 4-(2-bromo-4-fluorophenyl)-6-(1-(tert-butoxycarbonyl)piperidin-4-yl)-2-(thiazol-2-yl)-1,4-dihydropyrimidine-5-carboxylate (a Single Stereoisomer)

Intermediate VIII-16-1

Methyl 4-(2-bromo-4-fluorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized.

LC-MS (ESI): $R_T$=2.207 min, mass calcd. for $C_{25}H_{28}BrFN_4O_4S$, 578.1, m/z found 579.0 [M+H]$^+$. $^1$H NMR (400 MHz, $CDCl_3$) δ 8.12 (s, 0.4H), 7.83-7.81 (m, 1H), 7.51-7.45 (m, 1.6H), 7.34-7.30 (m, 1H), 7.01-6.94 (m, 1H), 6.17 (s, 0.4H), 6.02 (d, J=2.8 Hz, 0.6H), 4.32-4.17 (m, 2H), 3.94-3.93 (m, 0.3H), 3.61-3.60 (m, 3H), 3.50-3.49 (m, 0.7H), 2.86 (br s, 2H), 2.10-1.66 (m, 3.3H), 1.51 (s, 9H), 1.46-1.35 (m, 0.7H).

A stereoisomeric mixture of methyl 4-(2-bromo-4-fluorophenyl)-6-(1-(tert-butoxycarbonyl)piperidin-4-yl)-2-(thiazol-2-yl)-1,4-dihydropyrimidine-5-carboxylate VIII-16-1 (5.00 g, 8.65 mmol) was separated by chiral SFC (Column: Chiralpak IG 5 μm 20*250 mm; Mobile Phase: $CO_2$:MeOH=70:30 at 50 g/min, Temp: 30° C.; Wavelength: 214 nm, Back pressure: 100 bar) to get VIII-16-2A (1.6 g, 32% yield, 100% stereopure) as yellow solids and VIII-16-2B (1.8 g, 36% yield, 100% stereopure) as yellow solids.

VIII-16-2A: Chiral HPLC analysis (Column: Chiralpak IG 5 μm 4.6*250 mm; Mobile Phase:$CO_2$:MeOH=70:30, at 3.0 g/min; Temp: 40° C.; Wavelength: 220 nm; $R_T$=2.98 min). $^1$H NMR (400 MHz, $CDCl_3$) δ 8.12 (s, 0.4H), 7.84-7.81 (m, 1H), 7.55-7.45 (m, 1.6H), 7.33-7.31 (m, 1H), 7.01-6.93 (m, 1H), 6.17 (s, 0.4H), 6.02 (d, J=2.8 Hz, 0.6H), 4.36-4.14 (m, 2.4H), 3.96-3.91 (m, 0.6H), 3.61-3.60 (m, 3H), 2.89 (br s, 2H), 2.12-1.64 (m, 3.5H), 1.58 (s, 0.5H), 1.51 (s, 9H).

VIII-16-2B: Chiral HPLC analysis (Column: Chiralpak IG 5 μm 4.6*250 mm; Mobile Phase: $CO_2$:MeOH=70:30 at 3.0 g/min; Temp: 40° C.; Wavelength: 230 nm; $R_T$=4.46 min). $^1$H NMR (400 MHz, $CDCl_3$) δ 8.12 (s, 0.4H), 7.83-7.81 (m, 1H), 7.50-7.44 (m, 1.6H), 7.35-7.33 (m, 1H), 7.01-6.93 (m, 1H), 6.17 (s, 0.4H), 6.02 (d, J=2.8 Hz, 0.6H), 4.37-4.14 (m, 2.4H), 3.96-3.91 (m, 0.6H), 3.61-3.60 (m, 3H), 2.96-2.77 (m, 2H), 2.11-1.63 (m, 3.5H), 1.58 (s, 0.5H), 1.51 (s, 9H).

Compound VIII-17

Ethyl-6-(1-(tert-butoxycarbonyl)pyrrolidin-3-yl)-4-(2-chloro-3,4-difluorophenyl)-2-(thiazol-2-yl)-1,4-dihydropyrimidine-5-carboxylate (a Mixture of 4 Stereoisomers)

By utilizing the analogous procedure of Method B, the title compound was synthesized.

LC-MS (ESI): $R_T$=2.144 min, mass calcd. for $C_{25}H_{27}ClF_2N_4O_4S$, 552.1, m/z found 553.1 [M+H]$^+$. $^1$H NMR (300 MHz, $CDCl_3$) δ 8.27 (s, 0.3H), 7.77-7.73 (m, 1H), 7.46-7.35 (m, 1.7H), 7.09-6.97 (m 2H), 6.15 (s, 0.3H), 6.06-6.01 (m 0.7H), 4.76 -4.65 (m, 0.3H), 4.47-4.40 (m, 0.7H), 4.04-3.95 (m, 2H), 3.71-3.31 (m, 4H), 2.39-1.99 (m, 2H), 1.47-1.42 (m, 9H), 1.10-1.04 (m, 3H).

Compound VIII-18-2

Ethyl 6-(1-(tert-butoxycarbonyl)azetidin-3-yl)-4-(2-chloro-3,4-difluorophenyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=1.657 min, mass calcd. for $C_{24}H_{25}ClF_2N_4O_4S$, 538.1, m/z found 539.1 [M+H]$^+$. $^1$H NMR (400 MHz, $CDCl_3$) δ 8.57 (s, 0.1H), 7.85-7.83 (m, 1H), 7.54 (d, J=2.8 Hz, 0.9H), 7.47-7.45 (m, 1H), 7.10-7.07 (m, 2H), 6.21 (s, 0.1H), 6.10 (d, J=2.8 Hz, 0.9H), 4.89-4.85 (m, 0.1H), 4.64-4.56 (m, 0.9H), 4.40-4.25 (m, 3H), 4.17-4.13 (m, 1H), 4.06 (q, J=7.2 Hz, 2H), 1.49 (s, 9H), 1.13 (t, J=7.2 Hz, 3H).

Compound VIII-19-4

Methyl 6-(1-(tert-butoxycarbonyl)azetidin-3-yl)-4-(2-chloro-4-fluorophenyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=1.56 min, mass calcd. for $C_{23}H_{24}ClFN_4O_4S$, 506.1, m/z found 507.4 [M+H]$^+$.

A stereoisomeric mixture of VIII-19-4 (9.00 g, 17.8 mmol) was separated by chiral Prep. HPLC (Column: Chiralpak IC 5 μm 20*250 mm, Mobile Phase: MeOH:EtOH=70:30 at 20 mL/min, Temp: 30° C., Wavelength: 214 nm) to afford the compounds VIII-19-4A (3.5 g, 39% yield, 100% ee) and VIII-19-4B (3.58 g, 40% yield, 99.4% ee).

Compound VIII-19-4A: LC-MS (ESI): $R_T$=1.55 min, mass calcd. for $C_{23}H_{24}CFN_4O_4S$, 506.1, m/z found 507.6 [M+H]$^+$. Chiral HPLC (Column: Chiralpak IC 5 μm 4.6*250 mm; Mobile Phase: Hex:EtOH=70:30 at 1.0 mL/min; Temp: 30° C.; Wavelength: 230 nm, $R_T$=6.015 min); $^1$H NMR (400 MHz, DMSO-$d_6$) δ 9.65 (d, J=3.6 Hz, 1H), 8.04-7.93 (m, 2H), 7.42-7.38 (m, 2H), 7.21 (dt, J=8.8, 3.2 Hz, Hz, 1H), 5.94 (d, J=3.2 Hz, 1H), 4.48-4.40 (m, 1H), 4.14-3.99 (m, 4H), 3.52 (s, 3H), 1.42 (s, 9H).

Compound VIII-19-4B: LC-MS (ESI): $R_T$=1.56 min, mass calcd. for $C_{23}H_{24}CFN_4O_4S$, 506.1, m/z found 507.6 [M+H]$^+$. Chiral HPLC (Column: Chiralpak IC 5 μm 4.6*250 mm; Mobile Phase: Hex:EtOH=70:30 at 1.0 mL/min; Temp: 30° C.; Wavelength: 230 nm, $R_T$=7.158 min); $^1$H NMR (400 MHz, DMSO-d$_6$) δ 9.66-9.65 (d, J=2.8 Hz, 1H), 8.04-8.02 (m, 2H), 7.42-7.38 (m, 2H), 7.21 (dt, J=8.8, 3.2 Hz, 1H), 5.94 (d, J=2.8 Hz, 1H), 4.48-4.41 (m, 1H), 4.13-3.97 (m, 4H), 3.52 (s, 3H), 1.42 (s, 9H).

Compound VIII-20-6B methyl 4-(2-chloro-4-fluorophenyl)-6-(1-(5-(4-(ethoxycarbonyl)piperidin-1-yl)pyrimidin-2-yl)piperidin-4-yl)-2-(thiazol-2-yl)-1,4-dihydropyrimidine-5-carboxylate (a Single Stereoisomer)

Intermediate VIII-20-6

Methyl 4-(2-chloro-4-fluorophenyl)-6-(1-(5-(4-(ethoxycarbonyl)piperidin-1-yl)pyrimidin-2-yl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=1.933 min, mass calcd. for $C_{32}H_{35}ClFN_7O_4S$, 667.2, m/z found 668.1 [M+H]$^+$. $^1$H NMR (400 MHz, CDCl$_3$) 8.15 (s, 1H), 8.14 (s, 1H), 7.80 (d, J=3.2 Hz, 0.5H), 7.76 (d, J=3.2 Hz, 0.5H), 7.46 (d, J=3.2 Hz, 0.5H), 7.42 (d, J=3.2 Hz, 0.5H), 7.33-7.29 (m, 1H), 7.14-7.11 (m, 1H), 6.97-6.89 (m, 1H), 6.20 (s, 0.5H), 6.07 (d, J=2.4 Hz, 0.5H), 4.91-4.75 (m, 2H), 4.30-4.24 (m, 0.5H), 4.17 (q, J=7.2 Hz, 2H), 4.05-3.99 (m, 0.5H), 3.62 (s, 1.5H), 3.61 (s, 1.5H), 3.38-3.32 (m, 2H), 3.05-2.93 (m, 2H), 2.75-2.69 (m, 2H), 2.42-2.36 (m, 1H), 2.06-2.03 (m, 3H), 1.96-1.89 (m, 3H), 1.79-1.69 (m, 2H), 1.27 (t, J=7.2 Hz, 3H).

A racemic mixture of methyl 4-(2-chloro-4-fluorophenyl)-6-(1-(5-(4-(ethoxycarbonyl) piperidin-1-yl)pyrimidin-2-yl)piperidin-4-yl)-2-(thiazol-2-yl)-1,4-dihydropyrimidine-5-carboxylate VIII-20-6 (200 mg, 90% purity, 0.269 mmol) was separated by chiral Prep. HPLC (separation condition: Column: Chiralpak IE 5 μm 20*250 mm; Mobile Phase: MeOH:DCM:DEA=80:20:0.3 at 14 mL/min; Temp: 30° C.; Wavelength: 254 nm) to give VIII-20-6A (90 mg, 90% purity from 1H NMR, 45% yield, 100% stereopure) and VIII-20-6B (80 mg, 90% purity from 1H NMR, 40% yield, 99.7% stereopure) as yellow solids.

VIII-20-6A: Chiral analysis (Column: Chiralpak IE 5 μm 4.6*250 mm; Mobile Phase: MeOH:DCM:DEA=80:20:0.2 at 1 mL/min; Temp: 30° C.; Wavelength: 254 nm, $R_T$=8.560 min). 1H NMR (400 MHz, CDCl$_3$) δ 8.15 (s, 1H), 8.14 (s, 1H), 7.81 (d, J=3.2 Hz, 0.5H), 7.76 (d, J=3.2 Hz, 0.5H), 7.47 (d, J=3.2 Hz, 0.5H), 7.43 (d, J=3.2 Hz, 0.5H), 7.32-7.29 (m, 1H), 7.15-7.12 (m, 1H), 6.97-6.89 (m, 1H), 6.20 (s, 0.5H), 6.07 (d, J=2.8 Hz, 0.5H), 4.90-4.75 (m, 2H), 4.31-4.25 (m 0.5H), 4.17 (q, J=7.2 Hz, 2H), 4.05-3.99 (m 0.5H), 3.63 (s, 1.5H), 3.61 (s, 1.5H), 3.39-3.33 (m, 2H), 2.98-2.94 (m, 2H), 2.76-2.69 (m, 2H), 2.43-2.37 (m, 1H), 2.08-2.02 (m, 3H), 1.96-1.89 (m, 3H), 1.79-1.70 (m, 2H), 1.28 (t, J=7.2 Hz, 3H).

VIII-20-6B: Chiral analysis (Column: Chiralpak IE 5 μm 4.6*250 mm; Mobile Phase: MeOH:DCM:DEA=80:20:0.2 at 1 mL/min; Temp: 30° C.; Wavelength: 254 nm, $R_T$=12.299 min). 1H NMR (400 MHz, CDCl$_3$) δ 8.18 (s, 1H), 8.17 (s, 1H), 7.84 (d, J=4.0 Hz, 0.5H), 7.78 (d, J=4.0 Hz, 0.5H), 7.50 (d, J=4.0 Hz, 0.5H), 7.46 (d, J=4.0 Hz, 0.5H), 7.36-7.31 (m, 1H), 7.19-7.14 (m, 1H), 7.01-6.91 (m, 1H), 6.23 (s, 0.5H), 6.10 (d, J=3.2 Hz, 0.5H), 4.93-4.82 (m, 2H), 4.34-4.26 (m, 0.5H), 4.20 (q, J=9.6 Hz, 2H), 4.08-4.02 (m, 0.5H), 3.65 (s, 1.5H), 3.64 (s, 1.5H), 3.41-3.29 (m, 2H), 3.00-2.95 (m, 2H), 2.84-2.72 (m, 2H), 2.46-2.39 (m, 1H), 2.11-1.91 (m, 6H), 1.78-1.69 (m, 2H), 1.31 (t, J=9.6 Hz, 3H).

Compound VIII-21-B ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate (a Single Stereoisomer)

Intermediate VIII-21

Ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=2.11 min, mass calcd. for $C_{26}H_{30}BrFN_4O_4S$, 592.1, m/z found 594.9 [M+H]$^+$. $^1$H NMR (300 MHz, CDCl$_3$) δ 8.10 (s, 0.4H), 7.82-7.80 (m, 1H), 7.50-7.47 (m, 0.6H), 7.44-7.39 (m, 1H), 7.24-7.17 (m, 1H), 7.13-7.11 (m, 1H), 7.10-6.95 (m, 1H), 6.26 (s, 0.5H), 6.11 (d, J=2.4 Hz, 0.5H), 4.36-4.14 (m, 2.4H), 4.08-3.90 (m, 2.6H), 2.94-2.77 (m, 2H), 2.08-1.71 (m, 3H), 1.62-1.54 (m, 1H), 1.50 (s, 9H), 1.13-1.08 (m, 3H).

A racemic mixture of VIII-21 (7.60 g, 95% purity, 12.2 mmol) was separated by chiral Prep. SFC (separation condition: Column: Chiralpak IG 5 μm 20*250 mm; Mobile Phase: CO$_2$:MeOH=75:25 at 50 g/min; Col. Temp.: 40° C.; Wavelength: 254 nm; Back Pressure: 100 Bar) to afford the title compounds VIII-21-A (3.20 g, 95% purity, 42% yield, 100% stereopure) as yellow solids and VIII-21-B (3.20 g, 95% purity, 42% yield, 99.3% stereopure) as yellow solids.

VIII-21-A: LC-MS (ESI): $R_T$=2.268 min, mass calcd. for $C_{26}H_{30}BrFN_4O_4S$, 592.1, m/z found 593.1 [M+H]$^+$. Chiral analysis (Column: Chiralpak IG 5 μm 20*250 mm; Mobile Phase: CO$_2$:MeOH=75:25 at 3.0 g/min; Col. Temp.: 40° C.; Wavelength: 254 nm; Back Pressure: 100 Bar, $R_T$=3.98 min). $^1$H NMR (300 MHz, CDCl$_3$) δ 8.09 (s, 0.4H), 7.82-7.80 (m, 1H), 7.49-7.40 (m, 1.6H), 7.24-7.17 (m, 1H), 7.17-7.11 (m, 1H), 7.07-6.98 (m, 1H), 6.26 (s, 0.5H), 6.12 (s, 0.5H), 4.35-3.91 (m, 5H), 2.93-2.78 (m, 2H), 2.01-1.81 (m, 2H), 1.71-1.56 (m, 2H), 1.50 (s, 9H), 1.10 (t, J=7.2 Hz, 3H).

VIII-21-B: LC-MS (ESI): $R_T$=2.249 min, mass calcd. for $C_{26}H_{30}BrFN_4O_4S$, 592.1, m/z found 593.0 [M+H]$^+$. Chiral analysis (Column: Chiralpak IG 5 μm 20*250 mm; Mobile Phase: CO$_2$:MeOH=75:25 at 3.0 g/min; Col. Temp.: 40° C.; Wavelength: 254 nm; Back Pressure: 100 Bar, $R_T$=4.84 min). $^1$H NMR (300 MHz, CDCl$_3$) δ 8.14-8.08 (m, 0.3H), 7.81 (d, J=3.0 Hz, 1H), 7.51-7.34 (m, 1.7H), 7.24-7.20 (m, 1H), 7.07-7.00 (m, 1H), 6.27-6.10 (m, 1H), 4.39-3.90 (m, 5H), 2.98-2.76 (m, 2H), 2.06-1.77 (m, 2.5H), 1.68-1.57 (m, 1.5H), 1.50 (s, 9H), 1.10 (t, J=7.2 Hz, 3H).

Compound VIII-22-2

Ethyl 4-(2-bromo-4-fluorophenyl)-6-(1-(tert-butoxycarbonyl)piperidin-4-yl)-2-(thiazol-2-yl)-1,4-dihydropyrimidine-5-carboxylate (a Single Stereoisomer)

Intermediate VIII-22

Ethyl 4-(2-bromo-4-fluorophenyl)-6-(1-(tert-butoxycarbonyl)piperidin-4-yl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=2.06 min, mass calcd. for $C_{26}H_{30}BrFN_4O_4S$, 592.1, m/z found 595.5 [M+H]$^+$. $^1$H NMR (300 MHz, CDCl$_3$) δ 8.10 (s, 0.4H), 7.86-7.80 (m, 1H), 7.53-7.49 (m, 0.6H), 7.47-7.44 (m, 0.4H), 7.42-7.38 (m, 0.6H), 7.35-7.30 (m, 2H), 7.05-6.92 (m, 1H), 6.20 (s, 0.4H), 6.06 (d, J=1.2 Hz, 0.6H), 4.39-4.16 (m, 2.4H), 4.11-3.89 (m, 2.6H), 2.97-2.76 (m, 2H), 2.14-1.70 (m, 3H), 1.61-1.56 (m, 1H), 1.52 (s, 9H), 1.18-1.09 (m, 3H).

A racemic mixture of ethyl 4-(2-bromo-4-fluorophenyl)-6-(1-(tert-butoxycarbonyl)piperidin-4-yl)-2-(thiazol-2-yl)-1,4-dihydropyrimidine-5-carboxylate VIII-22 (820 mg, 90% purity, 1.24 mmol) was separated by Chiral Prep. HPLC (Column: Chiralpak IG 5 μm 30 mm*250 mm; Mobile Phase: CO$_2$:MeOH=70:30 at 55 g/min; Col. Temp: 40° C.; Wavelength: 214 nm, Back pressure: 100 bar) to afford the title compound VIII-22-1 (380 mg, 90% purity from $^1$H NMR, 46% yield, 100% stereopure) and VIII-22-2 (370 mg, 90% purity from $^1$H NMR, 45% yield, 99.8% stereopure) as yellow solids.

VIII-22-1: LC-MS (ESI): $R_T$=2.128 min, mass calcd. for $C_{26}H_{30}BrFN_4O_4S$, 592.1, m/z found 593.0 [M+H]$^+$. Chiral analysis (Column: Chiralpak IG 5 μm 4.6*250 mm; Mobile Phase: CO$_2$:MeOH=70:30 at 3 g/min; Col. Temp: 40° C.; Wavelength: 230 nm; Back pressure: 100 bar, $R_T$=3.09 min). $^1$H NMR (400 MHz, CDCl$_3$) δ 8.08 (br s, 0.4H), 7.82-7.80 (m, 1H), 7.49 (d, J=2.8 Hz, 0.6H), 7.43 (d, J=3.2 Hz, 0.4H), 7.38 (s, 0.6H), 7.33-7.28 (m, 2H), 7.01-6.93 (m, 1H), 6.18 (s, 0.4H), 6.05 (d, J=2.4 Hz, 0.6H), 4.37-4.14 (m, 2.4H), 4.08-4.00 (m, 2H), 3.95-3.89 (m, 0.6H), 2.91-2.79 (m, 2H), 2.07-1.81 (m, 2.6H), 1.74-1.68 (m, 0.4H), 1.64-1.58 (m, 1H), 1.50 (s, 9H), 1.15-1.10 (m, 3H).

VIII-22-2: LC-MS (ESI): $R_T$=2.128 min, mass calcd. for $C_{26}H_{30}BrFN_4O_4S$, 592.1, m/z found 593.0 [M+H]$^+$. Chiral analysis (Column: Chiralpak IG 5 μm 4.6*250 mm; Mobile Phase: CO$_2$:MeOH=70:30 at 3 g/min; Col. Temp: 40° C.; Wavelength: 230 nm; Back pressure: 100 bar, $R_T$=4.32 min). $^1$H NMR (400 MHz, CDCl$_3$) δ 8.08 (br s, 0.4H), 7.82-7.80 (m, 1H), 7.49 (d, J=3.2 Hz, 0.6H), 7.43 (d, J=3.2 Hz, 0.4H), 7.38 (s, 0.6H), 7.33-7.28 (m, 2H), 7.01-6.93 (m, 1H), 6.18 (s, 0.4H), 6.05 (d, J=2.4 Hz, 0.6H), 4.36-4.14 (m, 2.4H), 4.08-4.00 (m, 2H), 3.95-3.89 (m, 0.6H), 2.91-2.79 (m, 2H), 2.07-1.81 (m, 2.6H), 1.73-1.68 (m, 0.4H), 1.64-1.58 (m, 1H), 1.50 (s, 9H), 1.14-1.10 (m, 3H).

Compound VIII-23-B

Methyl 6-(1-(5-(3-(tert-butoxy)-3-oxopropyl)pyridin-2-yl)piperidin-4-yl)-4-(2-chloro-4-fluorophenyl)-2-(thiazol-2-yl)-1,4-dihydropyrimidine-5-carboxylate (a Single Stereoisomer)

Intermediate VIII-23

Methyl 6-(1-(5-(3-(tert-butoxy)-3-oxopropyl)pyridin-2-yl)piperidin-4-yl)-4-(2-chloro-4-fluorophenyl)-2-(thiazol-2-yl)-1,4-dihydropyrimidine-5-carboxylate (a Mixture of 2 Stereoisomers)

By utilizing the analogous procedure of Method B, the title compound was synthesized as yellow solids. LC-MS (ESI): $R_T$=1.99 min, mass calcd. for $C_{32}H_{35}ClFN_5O_4S$, 639.2, m/z found 640.1 [M+H]$^+$. $^1$H NMR (400 MHz, CDCl$_3$) δ 8.18 (s, 0.5H), 8.07 (s, 1H), 7.81 (d, J=2.8 Hz, 0.5H), 7.77 (d, J=3.2 Hz, 0.5H), 7.48-7.29 (m, 3.5H), 7.15-7.12 (m, 1H), 6.98-6.89 (m, 1H), 6.70-6.66 (m, 1H), 6.20 (s, 0.5H), 6.07 (d, J=2.8 Hz, 0.5H), 4.49-4.20 (m, 2.5H), 4.03-3.95 (m, 0.5H), 3.62 (s, 1.5H), 3.61 (s, 1.5H), 3.00-2.89 (m, 2H), 2.82-2.77 (m, 2H), 2.52-2.47 (m, 2H), 2.30-2.20 (m, 0.5H), 2.12-2.06 (m, 1H), 2.00-1.94 (m, 1H), 1.88-1.72 (m, 1.5H), 1.44 (s, 9H).

A racemic mixture of methyl 6-(1-(5-(3-(tert-butoxy)-3-oxopropyl)pyridin-2-yl)piperidin-4-yl)-4-(2-chloro-4-fluorophenyl)-2-(thiazol-2-yl)-1,4-dihydropyrimidine-5-carboxylate VIII-23 (220 mg, 95% purity, 0.326 mmol) was separated by chiral Prep. HPLC (Column: Chiralpak IE 5 μm 20*250 mm; Mobile Phase: Hex:EtOH:DEA=50:50:0.3 at 10 mL/min; Temp: 30° C.; Wavelength: 254 nm) to give the title compound VIII-23-A (89 mg, 95% purity from $^1$H NMR, 40% yield, 100% stereopure) as yellow solids and VIII-23-B (80 mg, 95% purity from $^1$H NMR, 36% yield, 99.9% stereopure) as yellow solids.

VIII-23-A: LC-MS (ESI): $R_T$=1.86 min, mass calcd. for $C_{32}H_{35}ClFN_5O_4S$, 639.2, m/z found 640.0 [M+H]$^+$. Chiral analysis (Column: Chiralpak IE 5 μm 4.6*250 mm; Mobile Phase: Hex:EtOH:DEA=50:50:0.2 at 1 mL/min; Temp: 30° C.; Wavelength: 254 nm, $R_T$=7.100 min). $^1$H NMR (400 MHz, CDCl$_3$) δ 8.18 (s, 0.5H), 8.07 (s, 1H), 7.81 (d, J=3.2 Hz, 0.5H), 7.77 (d, J=2.8 Hz, 0.5H), 7.47 (d, J=3.2 Hz, 0.5H), 7.43-7.29 (m, 3H), 7.15-7.12 (m, 1H), 6.98-6.89 (m, 1H), 6.69-6.66 (m, 1H), 6.20 (s, 0.5H), 6.07 (d, J=2.4 Hz, 0.5H), 4.49-4.33 (m, 2H), 4.27-4.21 (m, 0.5H), 4.02-3.95 (m, 0.5H), 3.62 (s, 1.5H), 3.61 (s, 1.5H), 2.99-2.88 (m, 2H), 2.82-2.77 (m, 2H), 2.52-2.47 (m, 2H), 2.30-2.20 (m, 0.5H), 2.12-1.72 (m, 3.5H), 1.44 (s, 9H).

VIII-23-B: LC-MS (ESI): $R_T$=1.85 min, mass calcd. for $C_{32}H_{35}ClFN_5O_4S$, 639.2, m/z found 640.0 [M+H]$^+$. Chiral analysis (Column: Chiralpak IE 5 μm 4.6*250 mm; Mobile Phase: Hex:EtOH:DEA=50:50:0.2 at 1 mL/min; Temp: 30° C.; Wavelength: 254 nm, $R_T$=11.757 min). $^1$H NMR (400 MHz, CDCl$_3$) δ 8.18 (s, 0.5H), 8.07 (s, 1H), 7.81 (d, J=3.2 Hz, 0.5H), 7.77 (d, J=3.2 Hz, 0.5H), 7.47 (d, J=3.2 Hz, 0.5H), 7.43-7.29 (m, 3H), 7.15-7.12 (m, 1H), 6.98-6.89 (m, 1H), 6.69-6.66 (m, 1H), 6.20 (s, 0.5H), 6.07 (d, J=2.4 Hz, 0.5H), 4.49-4.33 (m, 2H), 4.27-4.21 (m, 0.5H), 4.03-3.95 (m, 0.5H), 3.62 (s, 1.5H), 3.61 (s, 1.5H), 2.99-2.88 (m, 2H), 2.82-2.77 (m, 2H), 2.52-2.47 (m, 2H), 2.30-2.20 (m, 0.5H), 2.13-1.72 (m, 3.5H), 1.44 (s, 9H).

Part VI: Preparation of Free Amine (FA) Products of General Formula IX

Free Amine 1

Exemplified with Method D methyl 4-(3,4-difluoro-2-methylphenyl)-6-(piperidin-4-yl)-2-(thiazol-2-yl)-1,4-dihydropyrimidine-5-carboxylate (FA1, a Single Stereoisomer)

To a solution of methyl 6-(1-(tert-butoxycarbonyl)piperidin-4-yl)-4-(3,4-difluoro-2-methylphenyl)-2-(thiazol-2-yl)-1,4-dihydropyrimidine-5-carboxylate VIII-1-B (270 mg, 0.510 mmol) in dichloromethane (3 mL) was added trifluoroacetic acid (3 mL) at room temperature. After stirred at room temperature for 0.5 hour, the mixture was concentrated under reduced pressure to give a residue, which was dissolved in ethyl acetate (50 mL) and washed with saturated sodium bicarbonate aqueous solution (25 mL) for three times, water (25 mL) for three times, and brine (25 mL) for three times, dried over $Na_2SO_{4(s)}$ and filtered. The filtrate was concentrated under reduced pressure to give the title compound (220 mg, 100% yield) as yellow solids. LC-MS (ESI): $R_T$=1.896 min, mass calcd. for $C_{21}H_{22}F_2N_4O_2S$, 432.1, m/z found 432.9 [M+H]$^+$.

Spectral Analyses of Free Amines of General Formula IX

Free Amine 2 ethyl 4-(3-fluoro-2-methylphenyl)-6-(piperidin-4-yl)-2-(thiazol-2-yl)-1,4-dihydropyrimidine-5-carboxylate (FA2, a Single Stereoisomer)

By utilizing the analogous procedure of Method D, the title compound was synthesized from compound VIII-2-B. LC-MS (ESI): $R_T$=1.53 min, mass calcd. for $C_{22}H_{25}FN_4O_2S$, 428.2, m/z found 429.0 [M+H]$^+$. $^1$H NMR (400 MHz, CDCl$_3$) δ 8.37 (s, 0.4H), 7.79 (d, J=3.2 Hz, 1H), 7.52 (d, J=3.2 Hz, 0.6H), 7.40 (d, J=3.2 Hz, 0.4H), 7.14-7.01 (m, 2.6H), 6.97-6.88 (m, 1H), 6.01 (s, 0.3H), 5.93 (s, 0.7H), 4.35-4.29 (m, 0.4H), 4.06-3.93 (m, 2.6H), 3.59-3.42 (m, 2H), 3.10-2.93 (m, 2H), 2.53 (s, 1H), 2.39 (s, 2H), 2.37-2.26 (m, 1H), 2.15-2.08 (m, 1.3H), 2.01-1.82 (m, 1.7H), 1.13-1.08 (m, 3H).

Free Amine 3 ethyl 4-(4-fluoro-2-methylphenyl)-6-(piperidin-4-yl)-2-(thiazol-2-yl)-1,4-dihydropyrimidine-5-carboxylate (FA3, a Single Stereoisomer)

By utilizing the analogous procedure of Method D, the title compound was synthesized from compound VIII-3-B. LC-MS (ESI): $R_T$=1.536 min, mass calcd. for $C_{22}H_{25}FN_4O_2S$, 428.2, m/z found 429.1 [M+H]$^+$. $^1$H NMR (400 MHz, CDCl$_3$) δ 8.49 (s, 0.3H), 7.81-7.79 (m, 1H), 7.53 (d, J=3.2 Hz, 0.7H), 7.39 (d, J=2.8 Hz, 0.3H), 7.30-7.28 (m, 0.7H), 7.17-7.13 (m, 0.7H), 7.09 (s, 0.7H), 6.90-6.84 (m, 1.7H), 6.81-6.76 (m, 0.3H), 5.95 (s, 0.3H), 5.88 (d, J=1.6 Hz, 0.7H), 4.41-4.35 (m, 0.3H), 4.06-3.92 (m, 2.7H), 3.60- 3.53 (m, 2H), 3.11-3.00 (m, 2H), 2.62 (s, 1H), 2.48 (s, 2H), 2.45-2.08 (m, 3H), 2.01-1.97 (m, 0.3H), 1.86-1.83 (m, 0.7H), 1.13-1.08 (m, 3H).

Free Amine 4 methyl 4-(3-fluoro-2-methylphenyl)-6-(piperidin-4-yl)-2-(thiazol-2-yl)-1,4-dihydropyrimidine-5-carboxylate (FA4, a Single Stereoisomer)

By utilizing the analogous procedure of Method D, the title compound was synthesized from compound VIII-4-A. LC-MS (ESI): $R_T$=1.481 min, mass calcd. for $C_{21}H_{23}FN_4O_2S$, 414.5, m/z found 415.1 [M+H]$^+$. $^1$H NMR (400 MHz, CDCl$_3$) δ 8.26 (s, 1H), 7.76 (d, J=2.8 Hz, 1H), 7.50 (d, J=2.8 Hz, 0.4H), 7.39 (d, J=3.2 Hz, 0.6H), 7.26-7.06 (m, 2H), 7.00-6.87 (m, 1H), 5.99 (s, 0.6H), 5.90 (s, 0.4H), 4.25-4.17 (m, 0.6H), 3.97-3.88 (m, 0.4H), 3.58 (s, 3H), 3.52-3.44 (m, 0.7H), 3.32-3.25 (m, 1.3H), 3.04-2.82 (m, 2H), 2.53 (s, 2H), 2.38 (s, 1H), 2.35-2.19 (m, 1H), 2.00-1.73 (m, 3H).

Free Amine 5 methyl 4-(4-fluoro-2-methylphenyl)-6-(piperidin-4-yl)-2-(thiazol-2-yl)-1,4-dihydropyrimidine-5-carboxylate (FA5, a Single Stereoisomer)

By utilizing the analogous procedure of Method D, the title compound was synthesized from compound VIII-5-2B. LC-MS (ESI): $R_T$=1.38 min, mass calcd. for $C_{21}H_{23}FN_4O_2S$, 414.2, m/z found 415.1 [M+H]$^+$. $^1$H NMR (400 MHz, CD$_3$OD) δ 7.80 (d, J=3.2 Hz, 1H), 7.64 (d, J=3.2 Hz, 1H), 7.22-7.19 (m, 1H), 6.83-6.73 (m, 2H), 5.78 (m, 1H), 4.00-3.80 (m, 1H), 3.50 (s, 3H), 3.19-3.13 (m, 2H), 2.78-2.69 (m, 2H), 2.46 (s, 3H), 2.12-1.81 (m, 3H), 1.65-1.62 (m, 1H).

Free Amine 6 methyl 4-(2-chloro-3-fluorophenyl)-6-(piperidin-4-yl)-2-(thiazol-2-yl)-1,4-dihydropyrimidine-5-carboxylate (FA6, a Single Stereoisomer)

By utilizing the analogous procedure of Method D, the title compound was synthesized from compound VIII-6-B. $^1$H NMR (300 MHz, DMSO-d$_6$) 8.01 (s, 2H), 7.38-7.18 (m, 3H), 6.00 (s, 0.8H), 5.76-5.74 (m, 0.2H), 3.83-3.74 (m, 1H), 3.53-3.48 (m, 3H), 3.29-3.18 (m, 2H), 2.86-2.71 (m, 2H), 2.06-1.59 (m, 4H).

Free Amine 7 methyl 4-(2-chloro-4-fluorophenyl)-6-(piperidin-4-yl)-2-(thiazol-2-yl)-1,4-dihydropyrimidine-5-carboxylate (FA7, a Single Stereoisomer)

By utilizing the analogous procedure of Method D, the title compound was synthesized from compound VIII-7-B. LC-MS (ESI): $R_T$=1.444 min, mass calcd. For $C_{20}H_{21}Cl_2FN_4O_2S$, 470.1, m/z found 434.9 [M−HCl+H]$^+$. $^1$H NMR (400 MHz, DMSO-d$_6$) δ 9.00 (br s, 1H), 8.60 (br s, 1H), 8.02 (dd, J=4.4, 3.2 Hz, 1H), 7.43 (dd, J=8.8, 2.8 Hz, 1H), 7.36 (dd, J=8.8, 6.0 Hz, 1H), 7.21 (td, J=8.4, 2.8 Hz, 1H), 5.94 (s, 1H), 3.86-3.79 (m, 1H), 3.54 (s, 3H), 3.40-3.35

(m, 2H), 3.02-2.89 (m, 2H), 2.19-2.02 (m, 2H), 1.88 (d, J=14.4 Hz, 1H), 1.72 (d, J=14.4 Hz, 1H).

Free Amine 8 ethyl 4-(2-chloro-4-fluorophenyl)-6-(piperidin-4-yl)-2-(thiazol-2-yl)-1,4-dihydropyrimidine-5-carboxylate (FA8, a Single Stereoisomer)

By utilizing the analogous procedure of Method D, the title compound was synthesized from compound VIII-8-B.
LC-MS (ESI): $R_T$=1.897 min, mass calcd. for $C_{21}H_{22}ClFN_4O_2S$, 448.1, m/z found 449.1 [M+H]$^+$.

Free Amine 9 ethyl 4-(2-chloro-3-fluorophenyl)-6-(piperidin-4-yl)-2-(thiazol-2-yl)-1,4-dihydropyrimidine-5-carboxylate (FA9, a Single Stereoisomer)

By utilizing the analogous procedure of Method D, the title compound was synthesized from compound VIII-9-B.
$^1$H NMR (300 MHz, CDCl$_3$) δ 8.33 (s, 0.5H), 7.86-7.78 (m, 1H), 7.58-7.38 (m, 1.5H), 7.20-6.96 (m, 3H), 6.24 (s, 0.4H), 6.10 (s, 0.6H), 4.10-3.95 (m, 3H), 3.56-3.39 (m, 2H), 3.08-2.85 (m, 2H), 2.38-2.15 (m, 1H), 2.15-2.08 (m, 1H), 1.92-1.74 (m, 2H), 1.16-1.06 (m, 3H).

Free Amine 10 methyl 4-(2-chloro-3,4-difluorophenyl)-6-(piperidin-4-yl)-2-(thiazol-2-yl)-1,4-dihydropyrimidine-5-carboxylate (FA10, a Single Stereoisomer)

By utilizing the analogous procedure of Method D, the title compound was synthesized from compound VIII-10-B.
$^1$H NMR (400 MHz, CDCl$_3$) δ 8.40 (s, 0.4H), 7.85-7.78 (m, 1H), 7.53 (d, J=2.8 Hz, 1H), 7.44 (d, J=3.2 Hz, 0.6H), 7.12-6.96 (m, 2H), 6.18 (s, 0.4H), 6.07 (s, 0.6H), 4.32-4.17 (m, 1H), 4.07-3.92 (m, 2H), 3.61 (s, 2H), 3.60 (s, 1H), 3.39-3.29 (m, 1H), 3.11-2.85 (m, 2H), 2.45-2.17 (m, 1.4H), 2.04-1.81 (m, 2.6H).

Free Amine 11 ethyl 4-(2-chloro-3,4-difluorophenyl)-6-(2-methylpiperidin-4-yl)-2-(thiazol-2-yl)-1,4-dihydropyrimidine-5-carboxylate (FA11, a mixture of 4 Stereoisomers)

By utilizing the analogous procedure of Method D, the title compound was synthesized from compound VIII-11-6.
LC-MS (ESI): $R_T$=1.774 min, mass calcd. for $C_{22}H_{23}ClF_2N_4O_2S$, 480.1, m/z found 481.1 [M+H]$^+$. $^1$H NMR (400 MHz, DMSO-d$_6$) δ 8.01 (d, J=6.8 Hz, 2H), 7.50-7.42 (m, 1H), 7.24-7.18 (m, 1H), 5.96 (d, J=10.8 Hz, 1H), 4.13-4.04 (m, 1H), 4.00-3.94 (m, 2H), 3.67-3.53 (m, 1H), 3.16-2.95 (m, 2H), 2.12-1.92 (m, 2H), 1.82-1.76 (m, 0.6H), 1.66-1.61 (m, 1H), 1.55-1.50 (m, 0.4H), 1.25-1.23 (m, 3H), 1.07 (t, J=7.2 Hz, 3H).

Free Amine 12 ethyl 4-(2-chloro-3,4-difluorophenyl)-6-(piperidin-4-yl)-2-(thiazol-2-yl)-1,4-dihydropyrimidine-5-carboxylate (FA12, a Single Stereoisomer)

By utilizing the analogous procedure of Method D, the title compound was synthesized from compound VIII-12-B.
LC-MS (ESI): $R_T$=1.55 min, mass calcd. for $C_{21}H_{21}ClF_2N_4O_2S$, 466.1, m/z found 467.1 [M+H]$^+$.

Free Amine 13 methyl 4-(4-bromo-2-chlorophenyl)-6-(piperidin-4-yl)-2-(thiazol-2-yl)-1,4-dihydropyrimidine-5-carboxylate (FA13, a Single Stereoisomer)

By utilizing the analogous procedure of Method D, the title compound was synthesized from compound VIII-13-2b.
LC-MS (ESI): $R_T$=1.61 min, mass calcd. for $C_{20}H_{20}BrClN_4O_2S$, 494.0, m/z found 494.7 [M+H]$^+$. $^1$H NMR (400 MHz, CDCl$_3$) δ 8.26 (s, 0.6H), 7.83-7.79 (m, 1H), 7.56-7.55 (m, 1H), 7.50 (d, J=3.2 Hz, 0.4H), 7.44 (d, J=3.2 Hz, 0.8H), 7.37 (d, J=2.0 Hz, 0.2H), 7.35-7.30 (m, 1H), 7.21-7.17 (m, 1H), 6.17 (s, 0.6H), 6.04 (s, 0.4H), 4.18-4.12 (m, 0.6H), 3.97-3.91 (m, 0.4H), 3.61 (s, 1H), 3.59 (s, 2H), 3.30-3.20 (m, 2H), 2.90-2.79 (m, 2H), 2.19-2.13 (m, 0.5H), 1.98-1.86 (m, 2.5H), 1.83-1.62 (m, 2H).

Free Amine 14 methyl 4-(2-bromo-3,4-difluorophenyl)-6-(piperidin-4-yl)-2-(thiazol-2-yl)-1,4-dihydropyrimidine-5-carboxylate (FA14, a Single Stereoisomer)

By utilizing the analogous procedure of Method D, the title compound was synthesized from compound VIII-14-B.
LC-MS (ESI): $R_T$=1.64 min, mass calcd. for $C_{20}H_{19}BrF_2N_4O_2S$, 496.0, m/z found 497.4 [M+1]$^+$.

Free Amine 15 methyl 4-(2-bromo-3-fluorophenyl)-6-(piperidin-4-yl)-2-(thiazol-2-yl)-1,4-dihydropyrimidine-5-carboxylate (FA15, a Single Stereoisomer)

By utilizing the analogous procedure of Method D, the title compound was synthesized from compound VIII-15-B.
$^1$H NMR (400 MHz, CDCl$_3$) δ 9.59-9.01 (m, 1H), 7.82 (s, 1H), 7.58-7.37 (m, 2H), 7.30-7.27 (m, 0.5H), 7.25-7.23 (m, 0.5H), 7.11-7.02 (m, 2H), 6.24 (s, 0.2H), 6.14-6.09 (m, 0.8H), 4.09-4.01 (m, 0.8H), 3.74 (s, 0.2H), 3.67-3.51 (m, 5H), 3.17-3.02 (m, 2H), 2.53-2.38 (m, 1H), 2.34-2.23 (m, 1H), 2.13-2.07 (m, 1H), 1.93-1.83 (m, 1H).

Free Amine 16 methyl 4-(2-bromo-4-fluorophenyl)-6-(piperidin-4-yl)-2-(thiazol-2-yl)-1,4-dihydropyrimidine-5-carboxylate (FA16, a Single Stereoisomer)

By utilizing the analogous procedure of Method D, the title compound was synthesized from compound VIII-16-2B.
LC-MS (ESI): $R_T$=1.903 min, mass calcd. for $C_{20}H_{20}BrFN_4O_2S$, 478.1, m/z found 479.0 [M+H]$^+$. $^1$H NMR (400 MHz, CDCl$_3$) δ 8.34 (s, 0.3H), 7.84-7.80 (m, 1H), 7.53-7.52 (m, 1H), 7.43-7.42 (m, 0.3H), 7.34-7.31 (m, 1.2H), 7.26-7.25 (m, 0.5H), 7.03-6.93 (m, 1H), 6.16 (s, 0.3H), 6.04 (s, 0.7H), 4.25-4.21 (m, 0.3H), 4.06-4.00 (m, 0.7H), 3.61-3.60 (m, 3H), 3.56-3.49 (m, 1H), 3.37-3.30 (m, 0.7H), 3.09-2.85 (m, 3H), 2.48-2.39 (m, 1.2H), 2.35-2.21 (m, 0.8H), 2.02-1.99 (m, 0.6H), 1.92-1.81 (m, 1.4H).

Free Amine 17 ethyl 4-(2-chloro-3,4-difluorophenyl)-6-(pyrrolidin-3-yl)-2-(thiazol-2-yl)-1,4-dihydropyrimidine-5-carboxylate (FA17, a mixture of 4 Stereoisomers)

By utilizing the analogous procedure of Method D, the title compound was synthesized from compound VIII-17.

LC-MS (ESI): $R_T$=1.531 min, mass calcd. for $C_{20}H_{19}ClF_2N_4O_2S$, 452.1, m/z found 453.0 [M+H]$^+$. $^1$H NMR (300 MHz, CDCl$_3$) δ 10.45-10.33 (m, 1H), 7.84 (s, 1H), 7.41 (s, 1H), 7.12-7.02 (m, 2H), 6.17-6.15 (m, 1H), 4.67 (br s, 1H), 4.15-4.01 (m, 2H), 3.36-3.19 (m, 2H), 3.01-2.94 (m, 2H), 2.46-2.10 (m, 1.5H), 1.99-1.77 (m, 1.5H), 1.15-1.10 (m, 3H).

Free Amine 18 ethyl 6-(azetidin-3-yl)-4-(2-chloro-3,4-difluorophenyl)-2-(thiazol-2-yl)-1,4-dihydropyrimidine-5-carboxylate (FA18, a Mixture of 2 Stereoisomers)

By utilizing the analogous procedure of Method D, the title compound was synthesized from compound VIII-18-2.

LC-MS (ESI): $R_T$=1.555 min, mass calcd. for $C_{19}H_{17}ClF_2N_4O_2S$, 438.1, m/z found 439.0 [M+H]$^+$.

Free Amine 19 methyl 6-(azetidin-3-yl)-4-(2-chloro-4-fluorophenyl)-2-(thiazol-2-yl)-1,4-dihydropyrimidine-5-carboxylate (FA19, a Mixture of 2 Stereoisomers)

By utilizing the analogous procedure of Method D, the title compound was synthesized from compound VIII-19-4.

LC-MS (ESI): $R_T$=1.32 min, mass calcd. for $C_{18}H_{16}ClFN_4O_2S$, 406.1, m/z found 407.4 [M+H]$^+$. $^1$H NMR (400 MHz, DMSO-d$_6$+D$_2$O) δ 8.01 (d, J=3.2 Hz, 1H), 7.95 (s, 1H), 7.44-7.40 (m, 2H), 7.22-7.17 (m, 1H), 5.98 (s, 1H), 4.58 (s, 1H), 3.96-3.88 (m, 4H), 3.51 (s, 3H).

Free Amine 19-1B

Methyl 6-(azetidin-3-yl)-4-(2-chloro-4-fluorophenyl)-2-(thiazol-2-yl)-1,4-dihydropyrimidine-5-carboxylate hydrochloride (FA19-1B, a Single Stereoisomer)

To a suspension of methyl 6-(1-(tert-butoxycarbonyl)azetidin-3-yl)-4-(2-chloro-4-fluorophenyl)-2-(thiazol-2-yl)-1,4-dihydropyrimidine-5-carboxylate VIII-19-4B (3.58 g, 7.07 mmol) in methanol (35 mL) was added 4M hydrochloride in methanol (35 mL, 14 mmol), which was stirred at room temperature for 1.5 hours. The mixture was concentrated to give a residue, which was purified by silica gel chromatography column (dichloromethane:methanol=10:1) to give the title compound (2.76 g, 98% yield) as yellow solids. $^1$H NMR (400 MHz, DMSO-d$_6$) δ 9.37 (br s, 2H), 8.08 (d, J=2.8 Hz, 1H), 8.04 (d, J=2.8 Hz, 1H), 7.49-7.46 (m, 2H), 7.42 (dd, J=8.8, 2.4 Hz, 1H), 7.19 (td, J=11.2, 2.4 Hz, 1H), 5.95 (s, 1H), 4.58-4.49 (m, 1H), 4.33-4.04 (m, 4H), 3.52 (s, 3H).

Free Amine 20

Ethyl 4-(2-bromo-3-fluorophenyl)-6-(piperidin-4-yl)-2-(thiazol-2-yl)-1,4-dihydropyrimidine-5-carboxylate (FA20, a Single Stereoisomer)

By utilizing the analogous procedure of Method D, the title compound was synthesized from compound VIII-21-B.

LC-MS (ESI): $R_T$=1.58 min, mass calcd. for $C_{21}H_{22}BrFN_4O_2S$, 492.1, m/z found 494.8 [M+H]$^+$. $^1$H NMR (300 MHz, CDCl$_3$) δ 8.25 (s, 0.5H), 7.83 (d, J=3.0 Hz, 0.4H), 7.80 (d, J=2.7 Hz, 0.6H), 7.51 (d, J=3.0 Hz, 0.4H), 7.44 (d, J=3.0 Hz, 0.6H), 7.23-7.14 (m, 1.5H), 7.09-6.98 (m, 1H), 6.27 (s, 0.6H), 6.13 (s, 0.4H), 4.24-3.97 (m, 3H), 3.34-3.20 (m, 2H), 2.94-2.80 (m, 2H), 2.20-2.09 (m, 0.8H), 1.93-1.63 (m, 3.2H), 1.13 (t, J=7.2 Hz, 3H).

Free Amine 21

Ethyl 4-(2-bromo-4-fluorophenyl)-6-(piperidin-4-yl)-2-(thiazol-2-yl)-1,4-dihydropyrimidine-5-carboxylate (FA21, a Single Stereoisomer)

By utilizing the analogous procedure of Method D, the title compound was synthesized from compound VIII-22-2.

$^1$H NMR (400 MHz, CDCl$_3$) δ 8.22 (br s, 0.5H), 7.82 (d, J=3.2 Hz, 0.5H), 7.79 (d, J=3.2 Hz, 0.5H), 7.49 (d, J=2.8 Hz, 0.5H), 7.42 (d, J=3.2 Hz, 0.5H), 7.38 (br s, 0.5H), 7.33-7.28 (m, 2H), 7.02-6.93 (m, 1H), 6.18 (s, 0.5H), 6.05 (s, 0.5H), 4.19-4.13 (m, 0.5H), 4.08-4.00 (m, 2H), 3.97-3.92 (m, 0.5H), 3.36-3.20 (m, 2H), 2.92-2.79 (m, 2H), 2.23-2.17 (m, 0.6H), 1.91-1.83 (m, 2H), 1.77-1.66 (m, 1.4H), 1.15-1.10 (m, 3H).

Part VII: Preparation of Building Blocks (BB) of General Formula X for Coupling Step

Building Block 1 ethyl 2-(2-chloropyrimidin-5-yl)acetate (BB1)

Building Block 2 methyl 2-chloro-5-methylpyrimidine-4-carboxylate (BB2)

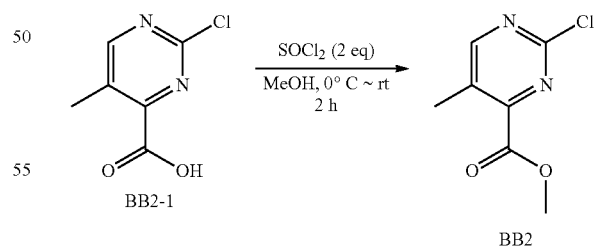

To a solution of 2-chloro-5-methylpyrimidine-4-carboxylic acid BB2-1 (500 mg, 95% purity, 2.75 mmol) in methanol (10 mL) was added thionyl chloride (662 mg, 99% purity, 5.51 mmol) at 0° C. under nitrogen atmosphere. After stirred at 0° C. for 30 minutes and at room temperature for 2 hours, the mixture was diluted with ethyl acetate (200 mL). The mixture was washed with saturated sodium bicarbonate aqueous solution (40 ml) for three times. The organic layers were dried over Na$_2$SO$_{4(s)}$ and filtered. The filtrate was concentrated under reduced pressure to give the title compound (415 mg, 99% purity, 80% yield) as yellow solid. LC-MS (ESI): R$_T$=0.837 min, mass calcd. for C$_7$H$_7$ClN$_2$O$_2$ 186.0, m/z found 187.0 [M+H]$^+$. 0.1H NMR (300 MHz, DMSO-d$_6$) δ 8.64 (s, 1H), 3.89 (s, 3H), 2.39 (s, 3H).

Building Block 3 methyl 2-bromothiazole-5-carboxylate (BB3)

Building Block 4

Ethyl 2-chloro-5-methylpyrimidine-4-carboxylate (BB4)

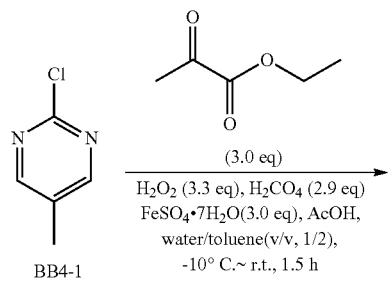

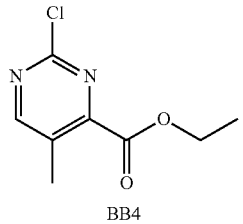

A round bottom flask A was charged with ethyl 2-oxopropanoate (27.0 g, 232.6 mmol) and the flask was cooled to −10° C. Acetic acid (80 mL) was added while maintaining the temperature below −5° C. 30% hydrogen peroxide aqueous solution (26.4 mL, 258.4 mmol) was added dropwise as to maintaining the temperature at −5° C. Another flask B was charged with 2-chloro-5-methylpyrimidine BB4-1 (10.0 g, 77.8 mmol), toluene (80 mL) and water (40 mL). After the flask B was cooled to −10° C., sulfic acid (12.4 mL, 228.2 mmol) was added followed by ferrous sulfate heptahydrate (64.8 g, 233.1 mmol). To the flask B was added the peroxide solution over 1 hour while keeping the temperature at 0° C.-5° C. After the addition, the reaction mixture was further stirred for 30 minutes. Then it was poured into ice water (1 L). The mixture was extracted with ethyl acetate (500 mL) for three times. The combined organic layers were washed with 0.5 M solution bisulfate aqueous solution (500 mL) and brine (500 mL), dried over Na$_2$SO$_{4(s)}$ and filtered. The filtrate was concentrated in vacuo to give a residue, which was purified by C18 column (acetonitrile:water=30% to 90%) to give the title compound (8.50 g, 95% purity, 52% yield) as yellow solids. LC-MS (ESI): R$_T$=2.04 min, mass calcd. for C$_8$H$_9$ClN$_2$O$_2$ 200.0, m/z found mass 200.9 [M+H]$^+$. $^1$H NMR (400 MHz, CDCl$_3$) δ 8.63 (s, 1H), 4.48 (q, J=7.2 Hz, 2H), 2.51 (s, 3H), 1.44 (t, J=7.2 Hz, 3H).

Building Block 5

1-Methyl-1H-pyrazole-4-carboxylic Acid (BB5)

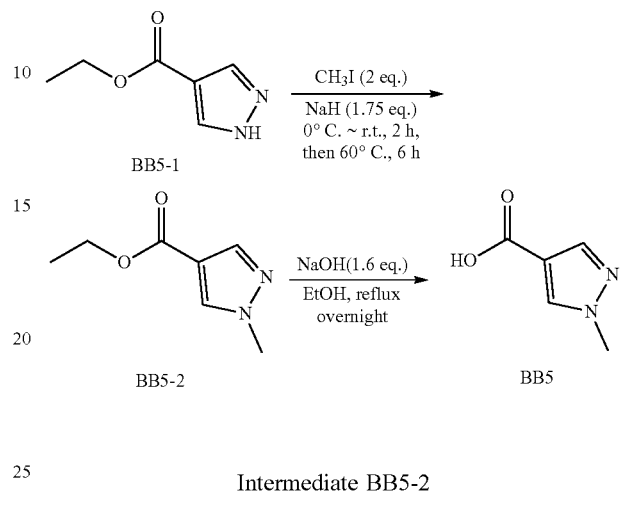

Intermediate BB5-2

Ethyl 1-methyl-1H-pyrazole-4-carboxylate

To a solution of ethyl 1H-pyrazole-4-carboxylate BB5-1 (5.00 g, 35.7 mmol) in tetrahydrofuran (20 mL) was added 60% wt. sodium hydride in mineral oil (2.50 g, 62.5 mmol) at 0° C. under nitrogen atmosphere. The reaction mixture was stirred room temperature for 1 hour and then iodomethane (10.0 g, 70.5 mmol) was added. After stirred at 60° C. for 6 hours, the reaction mixture was cooled down, quenched with water (40 mL) and extracted with ethyl acetate (60 mL) for three times. The combined organic layers were washed with brine (20 mL), dried over Na$_2$SO$_{4(s)}$ and concentrated to afford the title compound (5.6 g, 80% purity from $^1$H NMR, 83% yield) as colourless oil. $^1$H NMR (300 MHz, CDCl$_3$) δ 7.83 (s, 2H), 4.26-4.19 (m, 2H), 3.87 (s, 3H), 1.36-1.26 (m, 3H).

Building Block 5

1-Methyl-1H-pyrazole-4-carboxylic Acid

To a solution of ethyl 1-methyl-1H-pyrazole-4-carboxylate BB5-2 (3.0 g, 80% purity, 15.6 mmol) in ethanol (10 mL) was added sodium hydroxide (1.0 g, 25 mmol) in water (30 mL) at room temperature. After refluxed overnight, the reaction mixture was cooled down, acidified with 1 M hydrochloride aqueous solution (20 mL) till PH 3 and extracted with ethyl acetate (40 mL) for three times. The combined organic layers were washed with water (20 mL) for three times, dried over Na$_2$SO$_{4(s)}$ and concentrated to afford the title compound (1.8 g, 92% yield) as white solids. LC-MS (ESI): R$_T$=0.24 min. mass calcd. for C$_5$H$_6$N$_2$O$_2$ 126.1, m/z found 127.3 [M+H]$^+$ 0.1H NMR (300 MHz, DMSO-d$_6$) δ 12.2 (br s, 1H), 8.20 (s, 1H), 7.77 (s, 1H), 3.86 (s, 3H).

Building Block 6 ethyl 2-chlorooxazole-4-carboxylate (BB6)

Building Block 7

2-chloropyrimidine-5-carboxylic acid (BB7)

Building Block 8

Ethyl 2-chloro-4-methylpyrimidine-5-carboxylate (BB8)

Building Block 9

Ethyl 2-(2-chloropyrimidin-4-yl)acetate (BB9)

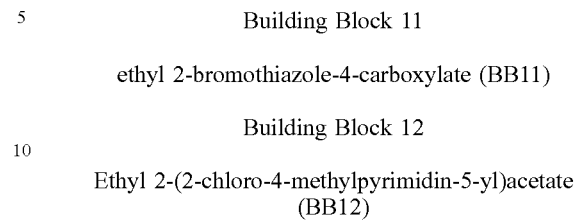

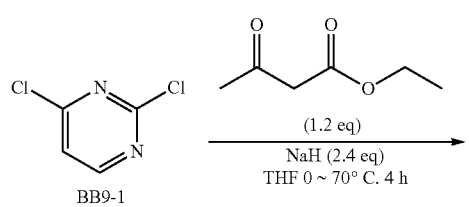

At a temperature between 0 and 5° C., sodium hydride (1.22 g, 60% wt. in mineral oil, 30.5 mmol) was added portionwise to a solution of ethyl 3-oxobutanoate (1.96 g, 98% purity, 14.8 mmol) in tetrahydrofuran (100 mL). The reaction mixture was stirred allowing the temperature to rise to room temperature slowly. Then 2,4-dichloropyrimidine BB9-1 (2.00 g, 95% purity, 12.7 mmol) was added portionwise and the reaction was stirred at 70° C. for 4 hours. After cooling to room temperature, the reaction mixture was poured onto ice-water (80 mL) and extracted with ethyl acetate (100 mL) twice. The combined organic layers were dried over $Na_2SO_{4(s)}$, filtered and concentrated to afford a residue, which was purified by silica gel column chromatography (petroleum ether:ethyl acetate=4:1) to give the title compound BB9 (700 mg, 90% purity, 25% yield) as colorless oil. $^1$H NMR (400 MHz, $CDCl_3$) δ 8.59-8.57 (m, 1H), 7.33-7.32 (m, 0.7H), 7.27-7.26 (m, 0.3H), 4.23-4.16 (m, 2H), 3.99 (s, 0.5H), 3.82-3.81 (m, 1.5H), 1.30-1.23 (m, 3H).

Building Block 10 ethyl 2-chlorooxazole-5-carboxylate (BB10)

Building Block 11 ethyl 2-bromothiazole-4-carboxylate (BB11)

Building Block 12

Ethyl 2-(2-chloro-4-methylpyrimidin-5-yl)acetate (BB12)

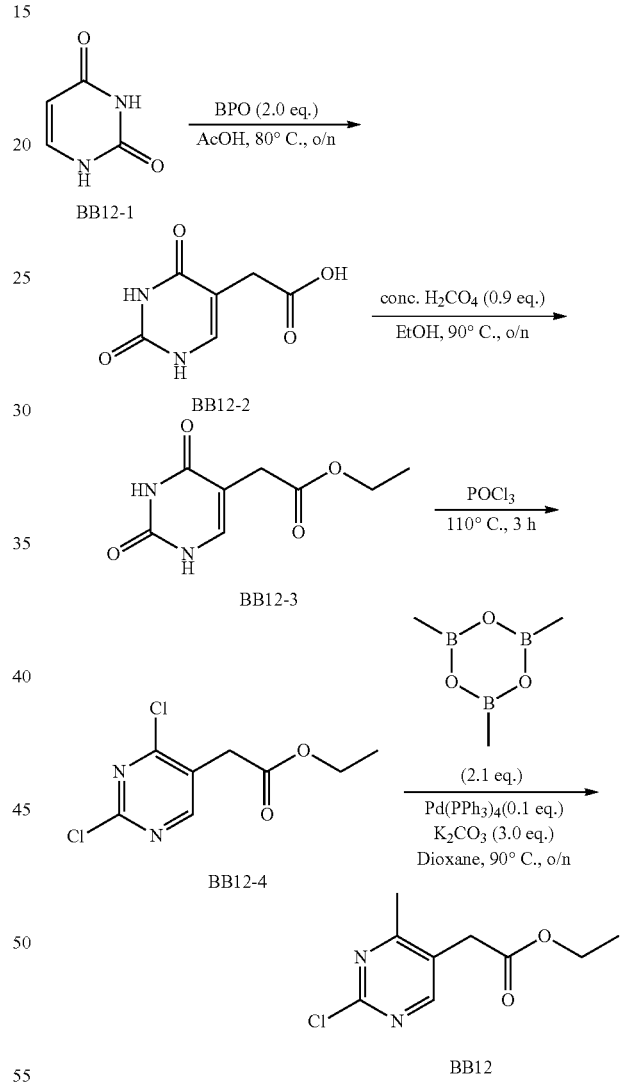

Intermediate BB12-2

2-(2,4-Dioxo-1,2,3,4-tetrahydropyrimidin-5-yl)acetic Acid

To the solution of uracil BB12-1 (23.0 g, 205 mmol) in acetic acid glacial (800 mL) was added benzoyl peroxide (100 g, 413 mmol) at room temperature. After stirred at 80° C. overnight and cooled down to room temperature, the mixture was concentrated under reduced pressure to remove the volatile, then the residue was washed with ethyl acetate (200 mL) to give the title compound (22 g, 35% purity from $^1$H NMR (including un-reacted BB12-1), 22% yield) as white solids. LC-MS (ESI): $R_T$=0.22 min, mass calcd. for $C_6H_6N_2O_4$ 170.0, m/z found 168.9 [M−H]$^−$. $^1$H NMR (400 MHz, DMSO-$d_6$) δ 12.28 (br s, 1H), 11.12 (s, 1H), 10.76 (s, 1H), 7.36 (s, 1H), 3.14 (s, 2H).

Intermediate BB12-3

Ethyl 2-(2,4-dioxo-1,2,3,4-tetrahydropyrimidin-5-yl)acetate

To the solution of 2-(2,4-dioxo-1,2,3,4-tetrahydropyrimidin-5-yl)acetic acid BB12-2 (22.0 g, 35% purity, 45.3 mmol) in ethanol (220 mL) was added sulfuric acid (conc., 4.0 g, 40.8 mmol) at room temperature. After stirred at 90° C. overnight and cooled down to room temperature, the mixture was concentrated under reduced pressure to remove the volatile, then the residue was washed with ethyl acetate (150 mL) to give the title compound (19 g, 35% purity from $^1$H NMR, 74% yield) as white solids. $^1$H NMR (400 MHz, DMSO-$d_6$) δ 11.14 (s, 1H), 10.78 (s, 1H), 7.38 (s, 1H), 4.04 (q, J=7.2 Hz, 2H), 3.21 (s, 2H), 1.17 (t, J=7.2 Hz, 3H).

Intermediate BB12-4

Ethyl 2-(2,4-dichloropyrimidin-5-yl)acetate

The mixture of ethyl 2-(2,4-dioxo-1,2,3,4-tetrahydropyrimidin-5-yl)acetate BB12-3 (19.0 g, 35% purity, 33.6 mmol) in phosphorus oxychloride (300 mL) was stirred at 110° C. for 3 hours. It was cooled down to room temperature and concentrated under reduced pressure to remove the volatile, and the residue was dissolved in ethyl acetate (500 mL). Ice water (200 mL) was added, followed by extraction with ethyl acetate (200 mL) three times. The combined organic layers were washed with brine (100 mL) and dried over Na$_2$SO$_{4(s)}$ and filtered. The filtrate was concentrated under reduced pressure to give a crude product, which was purified by C18 column (acetonitrile:water=40% to 80%) to give the title compound (4.40 g, 90% purity from $^1$H NMR, 51% yield) as yellow oil. LC-MS (ESI): $R_T$=1.50 min, mass calcd. for $C_8H_8Cl_2N_2O_2$ 234.0, m/z found 232.9 [M−H]$^−$. $^1$H NMR (300 MHz, CDCl$_3$) δ 8.81 (s, 1H), 4.13 (q, J=7.2 Hz, 2H), 3.90 (s, 2H), 1.19 (t, J=7.2 Hz, 3H).

Building Block 12

Ethyl 2-(2-chloro-4-methylpyrimidin-5-yl)acetate

To the solution of ethyl 2-(2,4-dichloropyrimidin-5-yl)acetate BB12-4 (100 mg, 90% purity, 0.383 mmol) in 1,4-dioxane (2 mL) was added 2,4,6-trimethyl-1,3,5,2,4,6-trioxatriborinane (98.0 mg, 0.781 mmol), potassium carbonate (159 mg, 1.15 mmol) and tetrakis(triphenylphosphine)palladium (44 mg, 0.038 mmol) under nitrogen atmosphere at room temperature. After stirred at 90° C. under nitrogen atmosphere overnight and cooled down to room temperature, the reaction mixture was poured into water (10 mL) and extracted with ethyl acetate (20 mL) for three times. The combined organic layers were washed with brine (20 mL) and dried over Na$_2$SO$_{4(s)}$ and filtered. The filtrate was concentrated under reduced pressure to give a crude product, which was purified by C18 column (acetonitrile:water=40% to 90%) to give the title compound (27.0 mg, 95% purity, 31% yield) as brown oil. LC-MS (ESI): $R_T$=0.89 min, mass calcd. for $C_9H_{11}ClN_2O_2$ 214.1, m/z found 214.9 [M+H]$^+$. $^1$H NMR (300 MHz, DMSO-$d_6$) δ 8.53 (s, 1H), 4.11 (q, J=7.2 Hz, 2H), 3.84 (s, 2H), 2.41 (s, 3H), 1.19 (t, J=7.2 Hz, 3H).

Building Block 13

Ethyl 2,5-dichloropyrimidine-4-carboxylate (BB13)

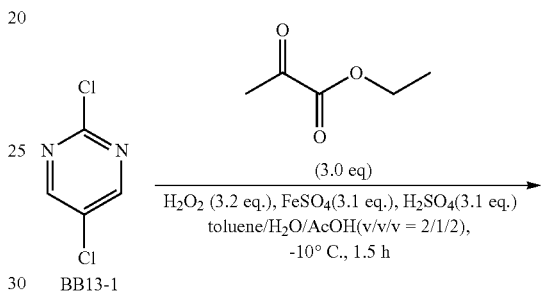

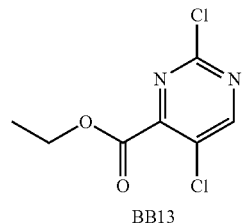

A round bottom flask A was charged with ethyl 2-oxopropanoate (4.70 g, 40.5 mmol) and the flask was cooled to −10° C., acetic acid (13 mL) was added while maintaining the temperature below −5° C. 33% hydrogen peroxide aqueous solution (1.3 mL, 42.4 mmol) was added dropwise as to maintain the temperature below −5° C. Another flask B was charged with 2,5-dichloropyrimidine BB13-1 (2.00 g, 13.2 mmol), toluene (13 mL) and water (7 mL). After the flask was cooled to −15° C., sulfuric acid (2.2 mL, 41.3 mmol) was added followed by ferrous sulfate heptahydrate (11.2 g, 40.3 mmol). To the flask of B was added the peroxide solution which had been prepared in flask A over 1 hour while keeping the temperature below −10° C., the resulting mixture was stirred at the same temperature for 30 minutes. The reaction mixture was poured into ice water (200 mL) and neutralized to pH ~7 with 1 M sodium hydroxide aqueous solution and filtered. The cake was washed with dichloridemethane (200 mL) twice. The filtrate was combined and the aqueous layer was separated and extracted with dichloridemethane (200 mL) twice. The combined organic layers were washed with water (200 mL), brine (200 mL), dried over Na$_2$SO$_{4(s)}$ and filtered. The filtrate was concentrated under reduced pressure to give a residue, which was purified by silica gel chromatography column (petroleum ether:ethyl acetate=100:1 to 50:1) to afford the title compound (300 mg, 96% purity, 10% yield) as colorless oil. LC-MS (ESI): R$_T$=1.682 min, mass calcd. for C$_7$H$_6$C$_{12}$N$_2$O$_2$ 220.0, m/z found 221.0 [M+H]$^+$. $^1$H NMR (300 MHz, CDCl$_3$) δ 8.73 (s, 1H), 4.49 (q, J=7.2 Hz, 2H), 1.43 (t, J=7.2 Hz, 3H).

Building Block 14

(cis)-tert-Butyl 3-(2-chloropyrimidin-5-yl)-3-hydroxycyclobutanecarboxylate (BB14)

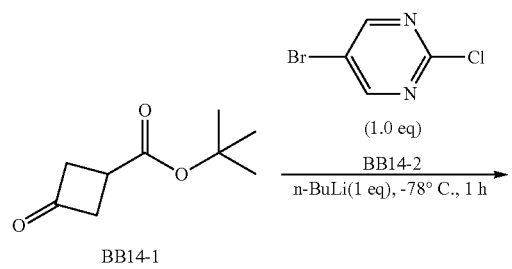

To a solution of tert-butyl 3-oxocyclobutanecarboxylate BB14-1 (2.00 g, 98% purity, 11.5 mmol) and 5-bromo-2-chloropyrimidine BB14-2 (2.27 g, 98% purity, 1.50 mmol) in dry tetrahydrofuran (120 mL) was added 2.5 M n-butyllithium in hexane (4.8 mL, 12.0 mmol) dropwise over 25 minutes at −78° C. under nitrogen atmosphere. After stirred at −78° C. for 1 hour, the reaction mixture was quenched with saturated ammonium chloride aqueous solution (30 mL). The resulting mixture was warmed to room temperature, diluted with water (80 mL) and extracted with ethyl acetate (80 mL) twice. The combined organic layers were washed with brine (100 mL), dried over Na$_2$SO$_{4(s)}$ and filtered. The filtrate was concentrated to give a residue, which was purified by silica gel column chromatography (petroleum ether:ethyl acetate=10:1 to 5:1) to give the title compound (1.40 g, 90% purity, 38% yield) as light yellow solids. LC-MS (ESI): R$_T$=1.51 min, mass calcd. for C$_{13}$H$_{17}$ClN$_2$O$_3$ 284.1, m/z found 284.8 [M+H]$^+$. $^1$H NMR (400 MHz, CDCl$_3$) δ 8.76 (s, 2H), 4.37 (br s, 1H), 3.01-2.94 (m, 1H), 2.87-2.81 (m, 2H), 2.60-2.55 (m, 2H), 1.50 (s, 9H).

Building Block 15 ethyl 2-chloro-4-(trifluoromethyl)thiazole-5-carboxylate (BB15)

Building Block 16 ethyl 5-bromo-1,3,4-thiadiazole-2-carboxylate (BB16)

Building Block 18

Methyl 2-fluoroisonicotinate (BB18)

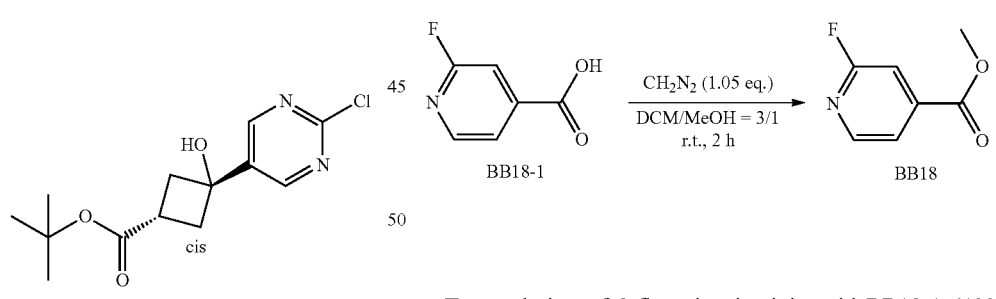

To a solution of 2-fluoroisonicotinic acid BB18-1 (400 mg, 2.84 mmol) in methanol (3 mL) and dichloromethane (9 mL) was added dropwise 2 M diazomethane in tetrahydrofuran (1.5 mL, 3.00 mmol) at 0° C. After stirred at room temperature for 2 hours, the mixture was poured into water (10 mL) and the resulting mixture was extracted with dichloromethane (10 mL) for three times. The combined organic layers were concentrated under reduced pressure to give a residue, which was purified by silica gel column chromatography (petroleum ether:ethyl acetate=10:1) to give the title compound (140 mg, 26% yield) as yellow oil. $^1$H NMR (400 MHz, DMSO-d$_6$) δ 8.47 (d, J=5.2 Hz, 1H), 7.82-7.79 (m, 1H), 7.60-7.59 (m, 1H), 3.92 (s, 3H).

Building Block 19 methyl 6-fluoronicotinate (BB19)

Building Block 20 methyl 6-fluoropicolinate (BB20)

Building Block 21 methyl 6-chloropyrimidine-4-carboxylate (BB21)

Building Block 22

5-chloropyrazine-2-carboxylic Acid (BB22)

Building Block 23

2-chloropyrimidine-4-carboxylic Acid (BB23)

Building Block 24 ethyl 2-bromo-5-methyloxazole-4-carboxylate (BB24)

Building Block 25 ethyl 2-chlorooxazole-5-carboxylate (BB25)

Building Block 26

2-(2-Ethoxy-2-oxoacetamido)acetic Acid (BB26)

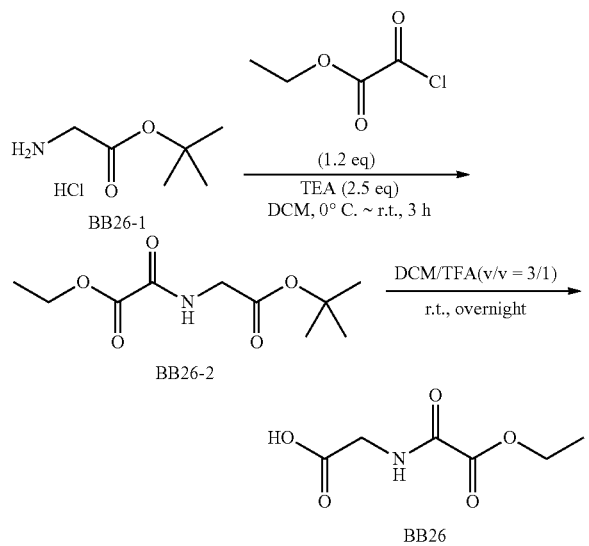

Intermediate BB26-2

Ethyl 2-((2-(tert-butoxy)-2-oxoethyl)amino)-2-oxoacetate

To the solution of tert-butyl 2-aminoacetate hydrochloride BB26-1 (2.00 g, 11.7 mmol) and triethylamine (3.02 g, 29.2 mmol) in dichloromethane (30 mL) was added ethyl oxalyl monochloride (1.6 mL, 14.0 mmol) dropwise at 0° C. After the addition, the mixture was stirred at room temperature for 3 hours. Then it was diluted with dichloromethane (50 mL) and washed with 1 M hydrochloride aqueous solution (40 mL) twice, saturated sodium bicarbonate aqueous solution (40 mL) and brine (40 mL), dried over $Na_2SO_{4(s)}$ and filtered. The filtrate was concentrated to give the title compound (2.10 g, 95% purity from $^1$H NMR, 74% yield) as light yellowish oil. LC-MS (ESI): $R_T$=1.49 min, mass calcd. for $C_{10}H_{17}NO_5$ 231.1, m/z found 176.0 [M+H−56]$^+$. $^1$H NMR (400 MHz, CDCl$_3$) δ 7.52 (br s, 1H), 4.37 (q, J=7.2 Hz, 2H), 4.02 (d, J=5.6 Hz, 2H), 1.49 (s, 9H), 1.39 (t, J=7.2 Hz, 3H).

Building Block 26

2-(2-Ethoxy-2-oxoacetamido)acetic Acid

To a solution of ethyl 2-((2-(tert-butoxy)-2-oxoethyl) amino)-2-oxoacetate BB26-2 (2.10 g, 95% purity, 8.63 mmol) in dichloromethane (21 mL) was added trifluoroacetic acid (7 mL). After stirred at room temperature overnight, the mixture was concentrated to give the title compound (2.10 g, 70% purity from $^1$H NMR, 97% yield) as brown oil. LC-MS (ESI): $R_T$=0.32 min, mass calcd. for $C_6H_9NO_5$ 175.0, m/z found 176.1 [M+H]$^+$. $^1$H NMR (400 MHz, CDCl$_3$) δ 7.72 (s, 1H), 4.38 (q, J=7.2 Hz, 2H), 4.20 (d, J=5.6 Hz, 2H), 1.39 (t, J=7.2 Hz, 3H).

Building Block 27

Methyl 6-chloro-4-methylpyridazine-3-carboxylate (BB27)

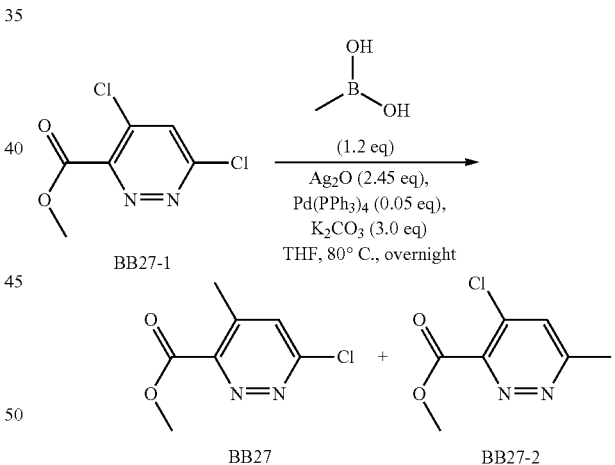

A mixture of methyl 4,6-dichloropyridazine-3-carboxylate BB27-1 (400 mg, 95% purity, 1.84 mmol), methylboronic acid (135 mg, 98% purity, 2.21 mmol) and potassium carbonate (768 mg, 99% purity, 5.50 mmol) in tetrahydrofuran (10 mL) was degassed for 10 minutes with nitrogen. Then tetrakis(triphenylphosphine) palladium(0) (112 mg, 95% purity, 0.092 mmol) and silver oxide (1.10 g, 95% purity, 4.51 mmol) were added, and the solution was further degassed with nitrogen for an additional 5 minutes. The vial was sealed and the reaction was heated at 80° C. overnight under nitrogen atmosphere. Then the mixture was cooled down to room temperature and concentrated. The obtained residue was purified by silica gel column chromatography (petroleum ether:ethyl acetate=3:1) to give the title compound BB27 (30 mg, 74% purity, 6% yield) and methyl 4-chloro-6-methylpyridazine-3-carboxylate BB27-2 (53 mg, 53% purity, 8% yield) as yellow oil.

BB27: $^1$H NMR (400 MHz, CDCl$_3$) δ 7.46 (s, 1H), 4.04 (s, 3H), 2.59 (s, 3H).

BB27-2: $^1$H NMR (400 MHz, CDCl$_3$) δ 7.48 (s, 1H), 4.04 (s, 3H), 2.77 (s, 3H).

Building Block 28

Methyl 6-chloro-2-methylpyrimidine-4-carboxylate (B28)

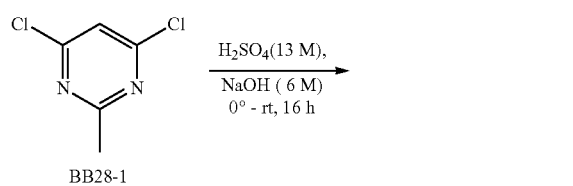

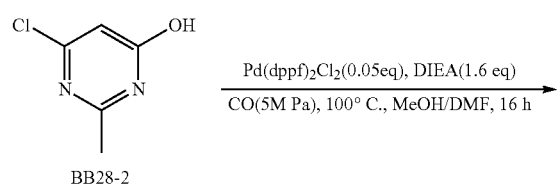

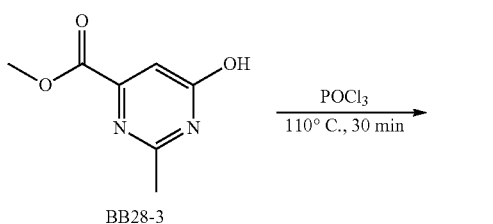

Intermediate BB28-2

6-Chloro-2-methylpyrimidin-4-ol

To 13 M sulfuric acid aqueous solution (25 mL, 32.5 mmol) was added portionwise 4,6-dichloro-2-methylpyrimidine BB28-1 (4.00 g, 97% purity, 23.8 mmol) at 0° C. over 20 minutes. After stirred at 0° C. for 1.5 hours and at room temperature overnight, the reaction mixture was poured into 6 M sodium hydroxide aqueous solution (80 mL) in an ice bath. The resulting solids were then collected by filtration, washed with warm water (100 mL) and dried under high vacuum to provide the desired product (3.00 g, 95% purity from $^1$H NMR, 83% yield) as white solids. $^1$H NMR (400 MHz, DMSO-d$_6$) δ 12.87 (br s, 1H), 6.34 (s, 1H), 2.30 (s, 3H).

Intermediate BB28-3

Methyl 6-hydroxy-2-methylpyrimidine-4-carboxylate

A suspension of 6-chloro-2-methylpyrimidin-4-ol BB28-2 (2.50 g, 95% purity, 16.4 mmol), N,N-diisopropylethylamine (3.30 g, 25.5 mmol) and [1,1'-bis(diphenylphosphino)ferrocene]dichloropalladium(II) (605 mg, 0.827 mmol) in methanol (10 mL) and N,N-dimethylformamide (10 mL) was heated at 100° C. under carbon monoxide atmosphere (5 MPa) for 16 hours. The resulting solids were then collected by filtration, washed with methanol (30 mL), followed by diethyl ether (60 mL) and dried under vacuum to give the title compound (2.10 g, 95% purity from $^1$H NMR, 72% yield) as brown solids. $^1$H NMR (400 MHz, DMSO-d$_6$) δ 12.85 (br s, 1H), 6.72 (s, 1H), 3.82 (s, 3H), 2.33 (s, 3H).

Building Block 28

Methyl 6-chloro-2-methylpyrimidine-4-carboxylate

A mixture of methyl 6-hydroxy-2-methylpyrimidine-4-carboxylate BB28-3 (300 mg, 95% purity, 1.70 mmol) in phosphoryl trichloride (10 mL) was stirred at 110° C. for 30 minutes. Then the mixture was cooled down to room temperature and concentrated to give a residue, which was purified by prep. TLC (petroleum ether:ethyl acetate=8:1) to give the title compound (60 mg, 96% purity from $^1$H NMR, 18% yield) as colorless oil. $^1$H NMR (400 MHz, DMSO-d$_6$) δ 7.96 (s, 1H), 3.92 (s, 3H), 2.70 (s, 3H).

Building Block 29 and Building Block 30

Methyl 5-chloro-3-methylpyrazine-2-carboxylate (BB29) and methyl 6-chloro-3-methylpyrazine-2-carboxylate (BB30)

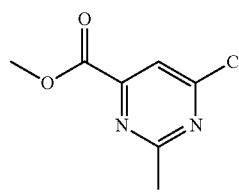

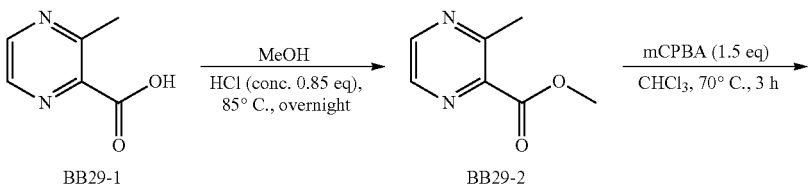

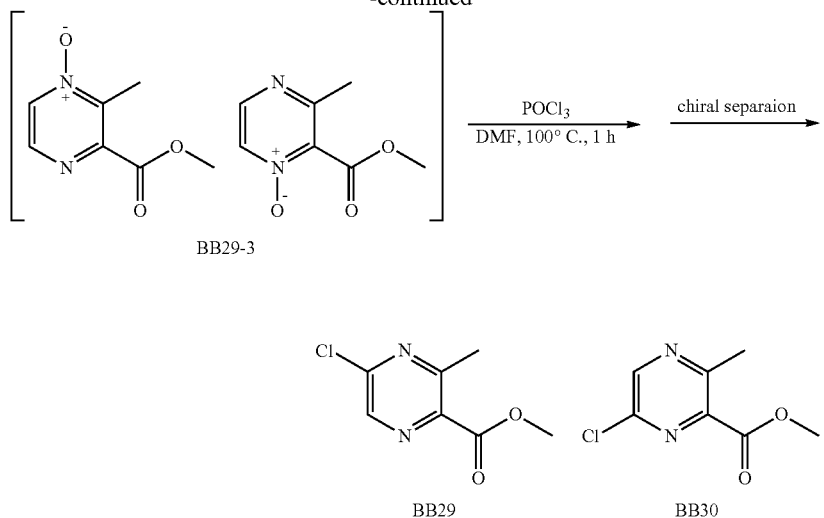

BB29-3

BB29

BB30

Intermediate BB29-2

Methyl 3-methylpyrazine-2-carboxylate

To a solution of 3-methylpyrazine-2-carboxylic acid BB29-1 (1.0 g, 7.10 mmol) in methanol (30 mL) was added concentrated hydrochoride aqueous solution (0.5 mL, 6 mmol) at room temperature. After stirred at 85° C. overnight, the mixture was concentrated under reduced pressure to give a residue, which was dissolved in ethyl acetate (5 mL) and washed with saturated sodium bicarbonate aqueous solution (15 mL) twice. Then the combined aqueous layers were extracted with ethyl acetate (60 mL) twice. The combined organic layers were washed with water (30 mL) twice and brine (30 mL), dried over anhydrous $Na_2SO_{4(s)}$ and filtered. The filtrate was concentrated under reduced pressure to give the title compound (850 mg, 85% purity, 67% yield) as white solids. LC-MS (ESI): $R_T$=0.738 min, mass calcd. for $C_7H_8N_2O_2$ 152.1, m/z found 153.0 $[M+H]^+$. $^1H$ NMR (300 MHz, $CDCl_3$) δ 8.64-8.61 (m, 1H), 8.55-8.51 (m, 1H), 4.05-4.00 (m, 3H), 2.90-2.85 (m, 3H).

Intermediate BB29-3

Mixture of 3-(methoxycarbonyl)-2-methylpyrazine 1-oxide and 2-(methoxycarbonyl)-3-methylpyrazine 1-oxide To a solution of methyl 3-methylpyrazine-2-carboxylate BB29-2 (100 mg, 85% purity, 0.560 mmol) in chloroform (4 mL) was added meta-chloroperoxybenzoic acid (168 mg, 85% purity, 0.83 mmol) at room temperature. After 70° C. for 3 hours, the mixture was diluted with waster (10 mL), then basified with saturated bicarbonate aqueous sodium to pH 8~9 and extracted with dichloromethane (30 mL) twice. The combined organic layers were washed with water (10 mL) twice and brine (10 mL), dried over $Na_2SO_{4(s)}$ and filtered. The filtrate was concentrated under reduced pressure to leave a residue, which was purified by column chromatography on silica gel (dichloromethane:methanol=10:1) to give the title compound (90 mg, 90% purity, 87% yield) as white solids. LC-MS (ESI): $R_T$=0.541 min, mass calcd. for $C_7H_8N_2O_3$ 168.1, m/z found 169.0 $[M+H]^+$.

Building Block 29 and Building Block 30

Methyl 5-chloro-3-methylpyrazine-2-carboxylate (BB29) and methyl 6-chloro-3-methylpyrazine-2-carboxylate (BB30)

To a solution of mixture of 3-(methoxycarbonyl)-2-methylpyrazine 1-oxide and 2-(methoxycarbonyl)-3-methylpyrazine 1-oxide BB29-3 (680 mg, 90% purity, 3.64 mmol) in N,N-dimethylformamide (10 mL) was added phosphoryl trichloride (1 mL) at room temperature. After stirred at 100° C. for 1 hour, the reaction mixture was cooled down and added 1 M sodium carbonate aqueous solution (10 mL) slowly at 0° C., then extracted with ethyl acetate (50 mL) twice. The combine organic layers were washed with water (30 mL) twice and brine (30 mL), dried over $Na_2SO_{4(s)}$ and filtered. The filtrate was concentrated under reduced pressure to leave a residue, which was purified by column chromatography on silica gel (ethyl acetate:methanol=10:1) to give the white solids, which was separated by Chiral Prep. HPLC (Column: Chiralpak ID 5 μm 20 mm*250 mm; Mobile Phase: $CO_2$:MeOH=70:30 at 50 g/min; Temp: 40° C.; Wavelength: 230 nm) to afford the title compounds BB29 (250 mg, 95% purity, 39% yield, 100% stereopure) and BB30 (300 mg, 95% purity, 46% yield, 98.9% stereopure) as yellow solids.

BB29: Chiral HPLC (Column: Chiralpak ID 5 μm 4.6*250 mm; Mobile Phase: $CO_2$:MeOH=70:30 at 3 g/min; Temp: 40° C.; Wavelength: 280 nm, $R_T$=3.17 min). 1H NMR (400 MHz, $CDCl_3$) δ 8.74 (s, 1H), 3.91 (s, 3H), 2.71 (s, 3H).

BB30: Chiral HPLC (Column: Chiralpak ID 5 μm 4.6*250 mm; Mobile Phase: $CO_2$:MeOH=70:30 at 3 g/min; Temp: 40° C.; Wavelength: 280 nm, $R_T$=4.31 min). $^1H$ NMR (400 MHz, $CDCl_3$) δ 8.91 (s, 1H), 3.92 (s, 3H), 2.73 (s, 3H).

Building Block 31

Ethyl 2-chloro-6-methylpyrimidine-4-carboxylate (BB31)

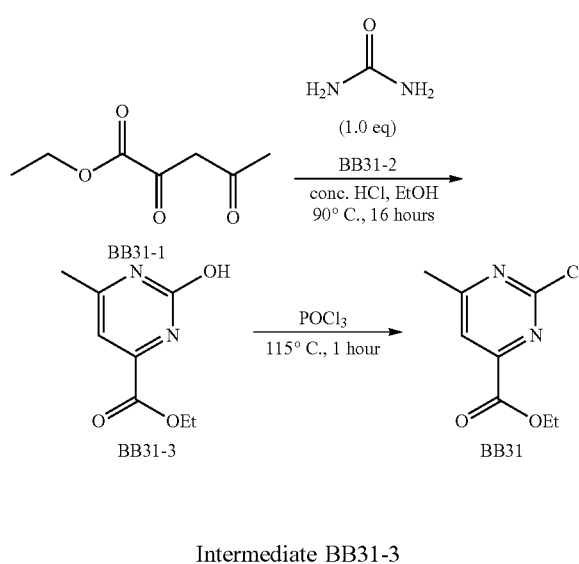

Intermediate BB31-3

Ethyl 2-hydroxy-6-methylpyrimidine-4-carboxylate

To a solution of ethyl 2,4-dioxopentanoate BB31-1 (5.00 g, 31.6 mmol) and urea BB31-2 (1.90 g, 31.6 mmol) in ethanol (40 mL) was added concentrated hydrochloride aqueous solution (4.3 mL) at room temperature. After stirring at 90° C. for 16 hours, the reaction mixture was cooled down to room temperature, adjusted to PH 7-8 with 10 M saturated sodium hydroxide aqueous solution and concentrated to give a residue, which was purified by C18 column (acetonitrile water=1% to 25%) to give the title compound BB31-3 (650 mg, 11% yield) as yellow solids. $^1$H NMR (400 MHz, DMSO-$d_6$) δ 6.47 (s, 1H), 4.31 (q, J=7.2 Hz, 2H), 2.26 (s, 3H), 1.30 (t, J=7.2 Hz, 3H).

Building Block 31

Ethyl 2-chloro-6-methylpyrimidine-4-carboxylate

A mixture of ethyl 2-hydroxy-6-methylpyrimidine-4-carboxylate BB31-3 (550 mg, 3.02 mmol) in phosphorus oxychloride (10 mL) was stirred at 115° C. for 1 hour. Then it was allowed to cool down to room temperature and the solvent was removed under reduced pressure to give a residue, which was basified to pH 8-9 with saturated sodium bicarbonate aqueous solution (20 mL, and extracted with ethyl acetate (10 mL) for three times. The combined organic layers were washed with brine (10 mL), dried over $Na_2SO_{4(s)}$ and filtered. The filtrate was concentrated under reduced pressure to give a residue, which was purified by silica gel column chromatography (petroleum ether:ethyl acetate=10:1 to 1:3) to give the title compound (85 mg, 14% yield) as yellow solids. $^1$H NMR (400 MHz, CDCl$_3$) δ 7.80 (s, 1H), 4.49 (q, J=7.2 Hz, 2H), 2.65 (s, 3H), 1.44 (t, J=7.2 Hz, 3H).

Building Block 32 tert-Butyl 6-chloro-4-((4-methoxybenzyl)oxy)nicotinate (BB32)

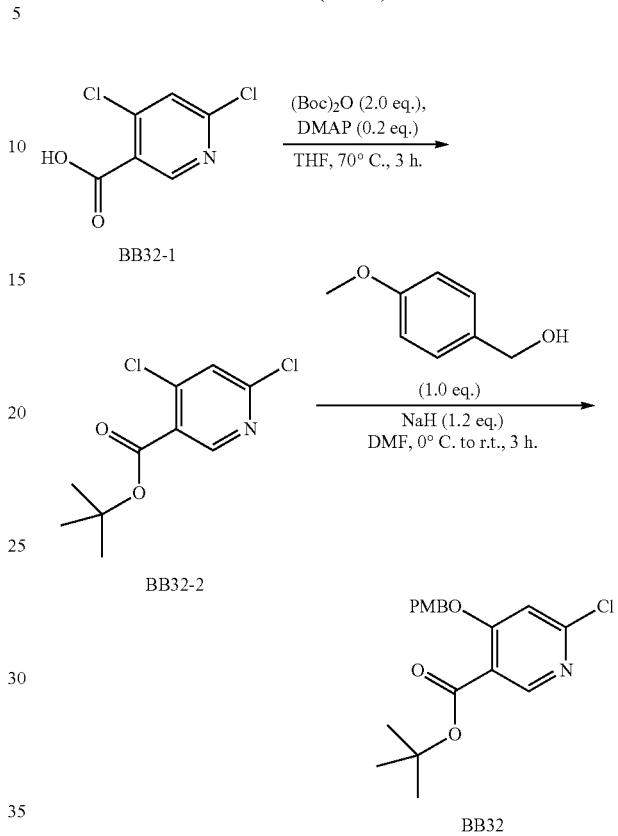

Intermediate BB32-2 tert-Butyl 4,6-dichloronicotinate

To a solution of 4,6-dichloronicotinic acid BB32-1 (10.0 g, 0.05 mol) in tetrahydrofuran (100 mL) was added di-tert-butyl dicarbonate (22.7 g, 0.10 mol) and 4-dimethylaminopyridine (1.20 g, 0.01 mol) at room temperature. After stirred at 70° C. for 3 hours, the mixture was cooled down to room temperature and concentrated under reduced pressure to give a residue, which was purified by silica gel column chromatography (petroleum ether:ethyl acetate=30:1 to 20:1) to afford the title compound (11.0 g, 89% yield) as colorless oil. LC-MS (ESI): $R_T$=1.84 min, mass calcd. for $C_{10}H_{11}Cl_2NO_2$ 247.0, m/z found 247.9 [M+H]$^+$. $^1$H NMR (300 MHz, CDCl$_3$) δ 8.76 (s, 1H), 7.44 (s, 1H), 1.61 (s, 9H).

Building Block 32 tert-Butyl 6-chloro-4-((4-methoxybenzyl)oxy)nicotinate

To a solution of (4-methoxyphenyl)methanol (2.80 g, 20.3 mmol) in N,N-dimethylformamide (35 mL) was added 60% wt. sodium hydride in mineral oil (970 mg, 24.3 mmol) portionwise at 0° C. under nitrogen atmosphere. After stirring for 1 hours at 0° C., tert-butyl 4,6-dichloronicotinate BB32-2 (5.00 g, 20.2 mmol) was added. The resulting mixture was stirred at room temperature for 3 hours. Then it was quenched with ice (50 g) and extracted with ethyl acetate (100 mL) twice. The combined organic layers were washed with brine (100 mL), dried over $Na_2SO_{4(s)}$ and filtered. The filtrate was concentrated under reduced pressure to give a residue, which was purified by silica gel column chromatography (petroleum ether:ethyl acetate=20:1 to 10:1) the afford the crude product, which was further purified by C18 column (acetonitrile:water=30% to 70%) to give the title compound (2.50 g, 35% yield) as white solids. LC-MS (ESI): $R_T$=1.83 min, mass calcd. for $C_{18}H_{20}ClNO_4$ 349.1, m/z found 349.9 $[M+H]^+$. $^1$H NMR (400 MHz, CDCl$_3$) δ 8.62 (s, 1H), 7.38-7.36 (m, 2H), 6.95-6.91 (m, 3H), 5.11 (s, 2H), 3.83 (s, 3H), 1.50 (s, 9H).

Building Block 33 tert-Butyl 6-chloro-5-fluoronicotinate (BB33)

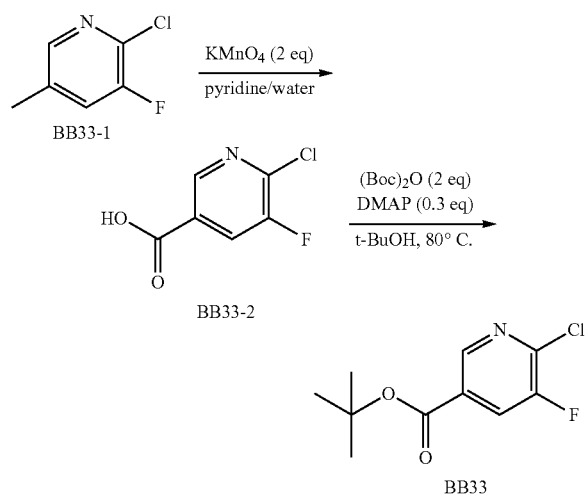

Intermediate BB33-2

6-Chloro-5-fluoronicotinic Acid

To a solution of 2-chloro-3-fluoro-5-methylpyridine BB33-1 (1.00 g, 6.86 mmol) in water (5 mL) and pyridine (5 mL) was added potassium permanganate (2.20 g, 13.7 mmol) at room temperature. After stirring at 100° C. under nitrogen atmosphere for 4 hours, the reaction mixture was cool down to room temperature and filtered. The filtrate was concentrated under reduced pressure to give the title compound (700 mg, 58% yield) as white solids. LC-MS (ESI): $R_T$=0.30 min, mass calcd. for $C_6H_3ClFNO_2$ 175.0, m/z found 174.0 $[M-H]^-$. $^1$H NMR (400 MHz, CD$_3$OD) δ 8.70 (d, J=1.2 Hz, 1H), 8.06 (dd, J=8.8, 1.6 Hz, 1H).

Building Block 33 tert-Butyl 6-chloro-5-fluoronicotinate

To a solution of 6-chloro-5-fluoronicotinic acid BB33-2 (600 mg, 3.43 mmol) in tert-butanol (20 mL) was added 4-dimethylaminopyridine (126 mg, 1.03 mmol) and di-tert-butyl dicarbonate (1.50 g, 6.86 mmol) at room temperature. After stirring at 80° C. overnight, the reaction mixture was cool down to room temperature and filtered. The filtrate was concentrated under reduced pressure to give a residue, which was purified by silica gel column chromatography (petroleum ether:ethyl acetate=50:1) to give the title compound (300 mg, 38% yield) as white solids. LC-MS (ESI): $R_T$=1.80 min, mass calcd. for $C_{10}H_{11}ClFNO_2$ 231.1, m/z found 232.1 $[M+H]^+$. $^1$H NMR (400 MHz, DMSO-d$_6$) δ 8.73 (d, J=1.6 Hz, 1H), 8.27 (dd, J=8.4, 2.0 Hz, 1H), 1.57 (s, 9H).

Building Block 34

Methyl 2-chloro-3-fluoroisonicotinate (BB34)

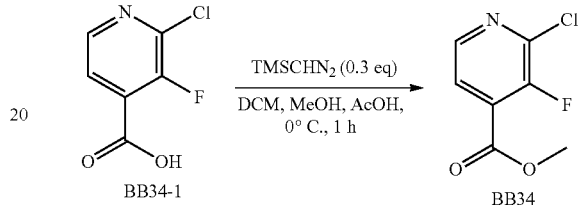

To a solution of 2-chloro-3-fluoroisonicotinic acid BB34-1 (200 mg, 95% purity, 1.08 mmol) in dichloromethane (3 mL) at 0° C. was added dropwise methanol (1 mL) and 0.6 M (diazomethyl)trimethylsilane in dichloromethane (0.6 mL, 0.360 mmol). After stirred at 0° C. for 1 hour, the mixture was quenched with acetic acid (0.5 mL) and concentrated in vacuo. Then the residue was partitioned between water (10 mL) and dichloromethane (1BB34-1. The combined organic layers were washed with brine (10 mL), dried over anhydrous $Na_2SO_{4(s)}$, filtered and concentrated to give the title compound (205 mg, 90% purity from $^1$H NMR, yield 90%) as pale solids. $^1$H NMR (300 MHz, CDCl$_3$) δ 8.30 (d, J=4.8 Hz, 1H), 7.70 (t, J=4.8 Hz, 1H), 4.00-3.97 (m, 3H).

Building Block 35

Ethyl 2-chloro-5-fluoropyrimidine-4-carboxylate (BB35)

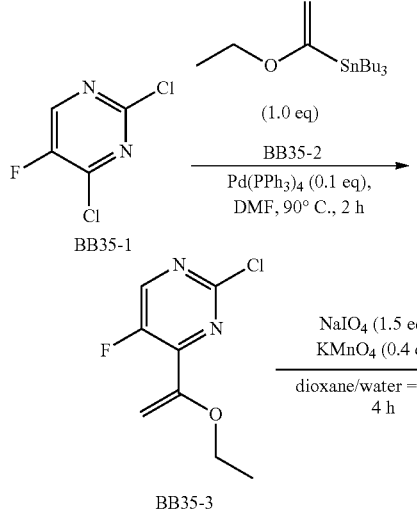

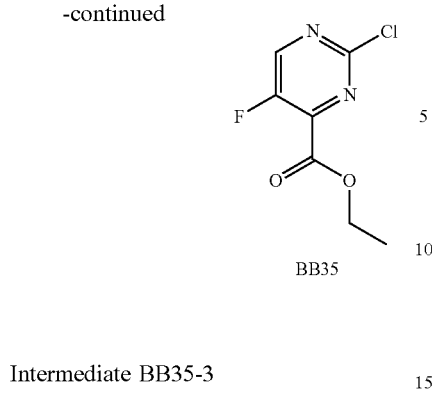

Intermediate BB35-3

2-Chloro-4-(1-ethoxyvinyl)-5-fluoropyrimidine

To a solution of 2,4-dichloro-5-fluoropyrimidine BB35-1 (500 mg, 3.00 mmol) and tributyl (1-ethoxyvinyl) tin BB35-2 (1.08 g, 3.00 mmol) in N,N-dimethylformamide (5 mL) was added tetrakis(triphenylphosphine) palladium (347 mg, 0.300 mmol) at room temperature under nitrogen atmosphere. The mixture was stirred at 90° C. for 2 hours. Another batch (500 mg) was combined to work-up. The mixture was cooled down to room temperature and poured into water (30 mL). It was extracted with ethyl acetate (20 mL) twice. The combined organic layers were washed with water (20 mL), brine (20 mL), dried over $Na_2SO_{4(s)}$ and filtered. The filtrate was concentrated under reduced pressure to give a residue, which was purified by silica gel column chromatography (petroleum ether:ethyl acetate=50:1 to 10:1) to give the title compound (1.7 g, 60% purity from $^1$H NMR, 86% yield, 0.3 eq SnBu$_3$Cl by $^1$H NMR) as colorless oil. $^1$H NMR (400 MHz, CDCl$_3$) δ 8.47 (d, J=2.8 Hz, 1H), 5.31 (d, J=2.8 Hz, 1H), 4.73 (d, J=2.8 Hz, 1H), 3.97 (q, J=7.2 Hz, 2H), 1.43 (t, J=7.2 Hz, 3H).

Building Block 35

Ethyl 2-chloro-5-fluoropyrimidine-4-carboxylate

To a solution of 2-chloro-4-(1-ethoxyethenyl)-5-fluoropyrimidine BB35-3 (1.70 g, 60% purity, 5.03 mmol) in dioxane (50 mL) and water (30 mL) was added sodium periodate (1.61 g, 7.53 mmol) and potassium permanganate (0.32 g, 2.03 mmol) at room temperature. The mixture was stirred at room temperature for 4 hours. Then insoluble solids from the mixture were filtered off and the filtrate was extracted with ethyl acetate (30 mL) for three times. The combined organic layers were washed with brine (30 mL), dried over $Na_2SO_{4(s)}$ and filtered. The filtrate was concentrated under reduced pressure to give a residue, which was purified by silica gel column chromatography (petroleum ether:ethyl acetate=30:1 to 8:1) to give the title compound (700 mg, 94.5% purity, 64% yield) as colorless oil. LC-MS (ESI): R$_T$=1.521 min, mass calcd. for C$_7$H$_6$ClFN$_2$O$_2$ 204.0, m/z found 205.0 [M+H]$^+$. $^1$H NMR (400 MHz, CDCl$_3$) δ 8.70 (d, J=1.6 Hz, 1H), 4.51 (q, J=7.2 Hz, 2H), 1.44 (t, J=7.2 Hz, 3H).

Building Block 36

Ethyl 2-chloro-4,6-dimethylpyrimidine-5-carboxylate (BB36)

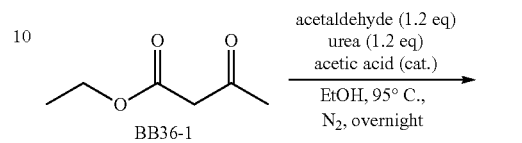

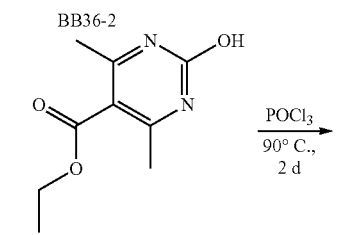

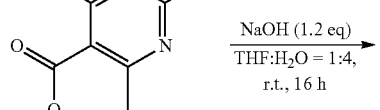

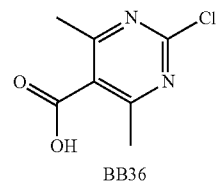

Intermediate BB36-2

Ethyl 2-hydroxy-4,6-dimethyl-1,2-dihydropyrimidine-5-carboxylate

To a solution of ethyl acetoacetate BB36-1 (20.0 g, 0.154 mol), acetaldehyde (7.50 g, 0.170 mol) and urea (10.2 g, 0.170 mol) in anhydrous ethanol (50 mL) was added acetic acid (30 drops) at room temperature. After stirred at 95° C. under nitrogen atmosphere overnight, the mixture was allowed to cool down to room temperature and diluted with water (200 mL). The appeared precipitate was collected by filtration and washed with water (200 mL), followed by a mixed solvent of petroleum ether (167 mL) and ethyl acetate (33 mL) to give the desired product (11.4 g, 36% yield) as white solids. LC-MS (ESI): R$_T$=1.65 min, mass calcd. for C$_9$H$_{14}$N$_2$O$_3$ 198.1, m/z found 199.0 [M+H]$^+$. $^1$H NMR (400

MHz, DMSO-$d_6$) δ 8.98 (s, 1H), 7.21 (s, 1H), 4.13-4.03 (m, 3H), 2.16 (s, 3H), 1.19 (t, J=7.6 Hz, 3H), 1.10 (d, J=6.0 Hz, 3H).

Intermediate BB36-3

Ethyl 2-hydroxy-4,6-dimethylpyrimidine-5-carboxylate

To a solution of concentrated nitric acid (20 mL) and water (8 mL) was added ethyl 2-hydroxy-4,6-dimethyl-1,2-dihydropyrimidine-5-carboxylate BB36-2 (5.00 g, 25.3 mmol) portionwise at 0° C. After stirred at 0° C. for 1 hour, the reaction mixture was basified by sodium bicarbonate (15 g, 17.9 mmol) to pH ~6. The aqueous solution was extracted with a mixed solvent dichloromethane and methanol (v/v=20/1, 50 mL) for four times. The combined organic layers were concentrated to give the desired product (3.00 g, 61% yield) as yellow solids. LC-MS (ESI): $R_T$=1.22 min, mass calcd. for $CH_{12}N_2O_3$ 196.1, m/z found 197.0 $[M+H]^+$. $^1$H NMR (400 MHz, DMSO-$d_6$) δ 12.13 (br s, 1H), 4.26 (q, J=6.8 Hz, 2H), 2.35 (s, 6H), 1.29 (t, J=6.8 Hz, 3H).

Intermediate BB36-4

Ethyl 2-chloro-4,6-dimethylpyrimidine-5-carboxylate

A mixture of ethyl 2-hydroxy-4,6-dimethylpyrimidine-5-carboxylate BB36-3 (3.00 g, 15.3 mmol) in phosphorus oxychloride was stirred at 90° C. under nitrogen atmosphere for 2 days. After cooled down to room temperature, the mixture was concentrated to give a residue, which was purified by silica gel column chromatography (petroleum ether:ethyl acetate=15:1) to give the desired product (1.60 g, 49% yield) as pale yellow oil. LC-MS (ESI): $R_T$=2.12 min, mass calcd. for $C_9H_{11}ClN_2O_2$ 214.1, m/z found 214.9 $[M+H]^+$. $^1$H NMR (400 MHz, CDCl$_3$) δ 4.47-4.44 (m, 2H), 2.56 (s, 6H), 1.44-1.40 (m, 3H).

Building Block 36

2-Chloro-4,6-dimethylpyrimidine-5-carboxylic Acid

To a solution of ethyl 2-chloro-4,6-dimethylpyrimidine-5-carboxylate BB36-4 (100 mg, 0.443 mmol) in water (4 mL) and tetrahydrofuran (1 mL) was added sodium hydroxide (22 mg, 0.550 mmol) at room temperature. After stirred at room temperature for 16 hours, the mixture was concentrated under reduced pressure to give the crude title compound (110 mg, 60% purity, 80% yield) as white solids, which was used for the next step without further purification. LC-MS (ESI): $R_T$=0.27 min, mass calcd. for $C_7H_7ClN_2O_2$ 186.0, m/z found 186.9 $[M+H]^+$.

Building Block 37

Ethyl 2-chloro-5,6-dimethylpyrimidine-4-carboxylate (BB37)

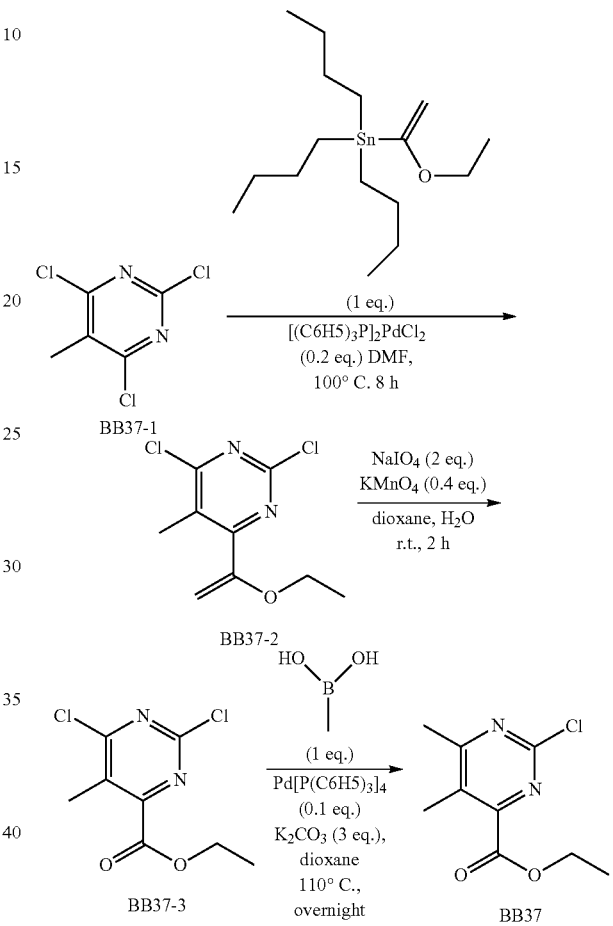

Intermediate BB37-2

2,4-Dichloro-6-(1-ethoxyvinyl)-5-methylpyrimidine

To the solution of 2,4,6-trichloro-5-methylpyrimidine BB37-1 (5.50 g, 27.9 mmol) in N,N-dimethylformamide (30 mL) was added tributyl(1-ethoxyvinyl)stannane (10.0 g, 27.7 mmol) and bis(triphenylphosphine)palladium(II) chloride (410 mg, 5.61 mmol) under nitrogen atmosphere. After stirred at 100° C. under nitrogen atmosphere for 8 hours, the reaction mixture was cooled to room temperature, diluted with water (30 mL) and extracted with ethyl acetate (30 mL) twice. The combined organic layers were washed with brine (30 mL), dried over $Na_2SO_{4(s)}$, filtered and concentrated to give a residue, which was purified by silica gel column chromatography (petroleum ether:ethyl acetate=20:1) to give the desired compound (4.00 g, 90% purity from $^1$H NMR, 55% yield) as white solids. $^1$H NMR (400 MHz, CDCl$_3$) δ 4.78 (d, J=3.2 Hz, 1H), 4.57 (d, J=3.2 Hz, 1H), 3.93 (q, J=6.8 Hz, 2H), 2.40 (s, 3H), 1.39 (t, J=6.8 Hz, 3H).

Intermediate BB37-3

Ethyl 2,6-dichloro-5-methylpyrimidine-4-carboxylate

The suspension of sodium periodate (1.34 g, 8.49 mmol) in water (5 mL) was sonicated until a clear solution was obtained. Then a solution of 2,4-dichloro-6-(1-ethoxyvinyl)-5-methylpyrimidine BB37-2 (5.50 g, 90% purity, 21.2 mmol) in 1,4-dioxane (25 mL) and potassium permanganate (9.28 g, 43.4 mmol) was added at room temperature. After stirred at room temperature under nitrogen atmosphere for 2 hours, the reaction mixture was diluted with water (60 mL) and extracted with ethyl acetate (60 mL) twice. The combined organic layers were washed with brine (60 mL), dried over $Na_2SO_{4(s)}$, filtered and concentrated to give a residue, which was purified by silica gel column chromatography (petroleum ether:ethyl acetate=20:1) to give the title compound (4.00 g, 90% purity from $^1H$ NMR, 72% yield) as white solids. $^1H$ NMR (400 MHz, $CDCl_3$) δ 4.46 (q, J=6.8 Hz, 2H), 2.47 (s, 3H), 1.41 (t, J=6.8 Hz, 3H).

Building Block 37

Ethyl 2-chloro-5,6-dimethylpyrimidine-4-carboxylate

To a solution of ethyl 2,6-dichloro-5-methylpyrimidine-4-carboxylate BB37-3 (2.00 g, 90% purity, 7.66 mmol) and methylboronic acid (460 mg, 7.69 mmol) in 1,4-dioxane (10 mL) was added tetrakis(triphenylphosphine)palladium (890 mg, 0.770 mmol) and potassium carbonate anhydrous (3.20 g, 23.2 mmol) at room temperature. After stirred at 110° C. under nitrogen atmosphere overnight, the reaction mixture was cooled to room temperature, diluted with water (20 mL) and extracted with ethyl acetate (20 mL) twice. The combined organic layers were washed with brine (20 mL), dried over $Na_2SO_{4(s)}$, filtered and concentrated to give a residue, which was purified by C18 column (acetonitrile:water=40% to 70%) to give the title compound (600 mg, 90% purity from $^1H$ NMR, 33% yield) as white solids. $^1H$ NMR (400 MHz, $CDCl_3$) δ 4.45 (q, J=7.2 Hz, 2H), 2.58 (s, 3H), 2.38 (s, 3H), 1.43 (t, J=7.2 Hz, 3H).

Building Block 38

Ethyl 2-chloro-5-ethylpyrimidine-4-carboxylate (BB38)

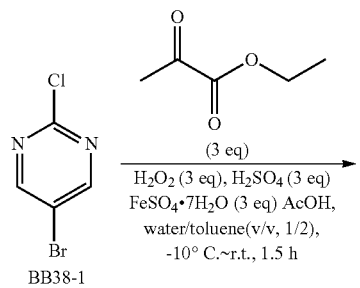

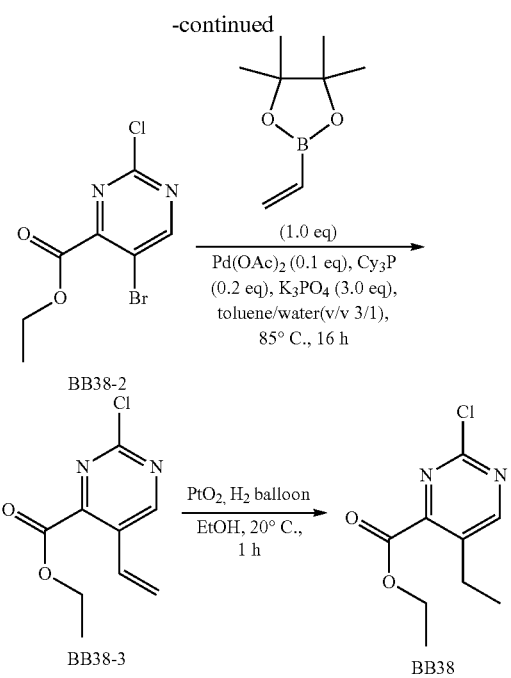

Intermediate BB38-2

Ethyl 5-bromo-2-chloropyrimidine-4-carboxylate

A round bottom flask A was charged with ethyl 2-oxopropanoate (5.40 g, 98% purity, 45.6 mmol) and the flask was cooled to −10° C.

Acetic acid (20 mL) was added while maintaining the temperature below −5° C. 30% hydrogen peroxide aqueous solution (4.7 mL, 46.0 mmol) was added dropwise as to maintain the temperature at −5° C. Another flask B was charged with 5-bromo-2-chloropyrimidine (3.0 g, 98% purity, 15.2 mmol), toluene (20 mL) and water (10 mL). After the flask was cooled to −10° C., sulfuric acid (2.5 mL, 46.0 mmol) was added followed by ferrous sulfate heptahydrate (13.2 g, 98% purity, 46.5 mmol). To the flask B was added the peroxide solution which had been prepared in flask A over 1 hour while keeping the temperature at −10° C. After the addition, the reaction mixture was further stirred for 30 minutes. Then it was poured into ice water (100 mL), neutralized to pH ~7 with 1 N sodium hydroxide aqueous solution and filtered over celite. The celite was washed with dichloromethane (200 mL). The organic layer was separated and the aqueous layer was extracted with dichloromethane (200 mL). The combined organic layers were washed with 0.5 M sodium bisulfite aqueous solution (200 mL) and brine (200 mL), dried over $Na_2SO_{4(s)}$ and filtered. The filtrate was concentrated to give a residue, which was purified by silica gel chromatography (petroleum ether:ethyl acetate=100:1 to 50:1) to give the title compound (850 mg, 90% purity, 19% yield) as colorless oil and recover 5-bromo-2-chloropyrimidine (1.5 g, 90% purity, 46% yield) as white solids. LC-MS (ESI): $R_T$=1.39 min, mass calcd. for $C_7H_6BrClN_2O_2$ 263.9, 265.9, m/z found 265.0, 267.0 $[M+H]^+$. $^1H$ NMR (400 MHz, $CDCl_3$) δ 8.85 (s, 1H), 4.50 (q, J=7.2 Hz, 2H), 1.44 (t, J=7.2 Hz, 3H).

303

Intermediate BB38-3

Ethyl 2-chloro-5-vinylpyrimidine-4-carboxylate

To a mixture of ethyl 5-bromo-2-chloropyrimidine-4-carboxylate BB38-2 (300 mg, 90% purity, 1.02 mmol), 4,4,5,5-tetramethyl-2-vinyl-1,3,2-dioxaborolane (160 mg, 98% purity, 1.02 mmol) and potassium phosphate (661 mg, 98% purity, 3.05 mmol) in toluene (9 mL) and water (3 mL) was added palladium acetate (24 mg, 99% purity, 0.106 mmol) and tricyclohexyl phosphine (61 mg, 95% purity, 0.207 mmol) under nitrogen atmosphere. After stirred at 85° C. under nitrogen atmosphere for 16 hours, the mixture was diluted with water (20 mL). The organic phase was separated and the aqueous layer was extracted with ethyl acetate (10 mL) for three times. The combined organic layers were washed with brine (10 mL), dried over $Na_2SO_{4(s)}$ and filtered. The filtrate was concentrated to give a residue, which was purified by silica gel column chromatography (petroleum ether:ethyl acetate=100:1 to 10:1) to give the title compound (100 mg, 90% purity, 41.6% yield) as white solids. LC-MS (ESI): $R_T$=1.67 min, mass calcd. for $C_9H_9ClN_2O_2$ 212.0, m/z found 212.9 $[M+H]^+$. $^1$H NMR (400 MHz, $CDCl_3$) δ 8.89 (s, 1H), 7.17-7.10 (m, 1H), 5.84 (d, J=17.6 Hz, 1H), 5.61 (d, J=11.2 Hz, 1H), 4.48 (q, J=7.2 Hz, 2H), 1.44 (t, J=7.2 Hz, 3H).

Building Block 38

Ethyl 2-chloro-5-ethylpyrimidine-4-carboxylate

To a solution of ethyl 2-chloro-5-vinylpyrimidine-4-carboxylate BB38-3 (100 mg, 90% purity, 0.423 mmol) in ethanol (5 mL) was added platinum dioxide (25 mg, 99% purity, 0.109 mmol) under nitrogen atmosphere. After stirred at 20° C. under hydrogen atmosphere of balloon for 1 hour, the reaction mixture was filtered and the filtrate was concentrated to give the title compound (90 mg, 90% purity, 89.1% yield) as black solids. LC-MS (ESI): $R_T$=1.677 min, mass calcd. for $C_9H_{11}ClN_2O_2$ 214.1, m/z found 215.0 $[M+H]^+$.

Building Block 39

Methyl 3-(2-chloropyrimidin-5-yl)propanoate (BB39)

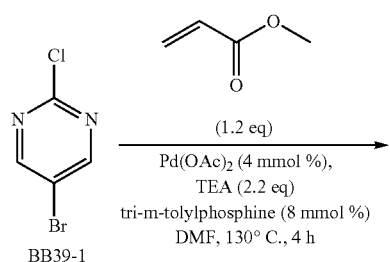

304

-continued

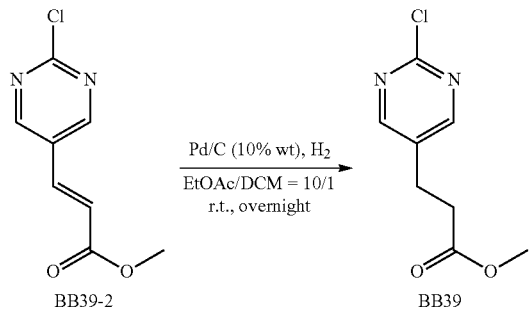

Intermediate BB39-2

Methyl 3-(2-chloropyrimidin-5-yl)acrylate

A suspension of 5-bromo-2-chloropyrimidine BB39-1 (5.0 g, 26 mmol), methyl acrylate (2.6 g, 31 mmol), triethylamine (5.7 g, 57 mmol), wt. palladium acetate (4 mmol %, 243 mg) and tri-m-tolylphosphine (8 mmol %, 630 mg) in N,N-dimethylformamide (30 mL) was stirred at 130° C. for 4 hours. After cooling down to room temperature, the mixture was quenched with water (300 mL), extracted with ethyl acetate (100 mL) twice. The combined organic layers were concentrated under reduced pressure to give a crude product, which was purified by silica gel column chromatography (petroleum ether:ethyl acetate=12:1 to 10:1) to give the title compound (600 mg, 12% yield) as yellow solids. $^1$H NMR (300 MHz, $CDCl_3$) δ 8.76 (s, 2H), 7.59 (d, J=15.9 Hz, 1H), 6.58 (d, J=16.2 Hz, 1H), 3.84 (s, 3H).

Building Block 39

Methyl 3-(2-chloropyrimidin-5-yl)propanoate

To a solution of methyl 3-(2-chloropyrimidin-5-yl)acrylate BB39-2 (150 mg, 0.758 mmol) in ethyl acetate (20 mL) and dichloromethane (2 ml) was added 10% palladium on charcoal wt. (100 mg) at room temperature. After stirred at room temperature under hydrogen atmosphere overnight, the reaction mixture was filtered and the filtrate was concentrated under reduced pressure to give the title compound (15 mg, 10% yield) as yellow solids. $^1$H NMR (300 MHz, $CDCl_3$) δ 8.63 (s, 0.5H), 8.52 (s, 1.5H), 3.68 (s, 3H), 2.95 (d, J=7.2 Hz, 2H), 2.67 (d, J=7.2 Hz, 2H).

Building Block 40 methyl 6-chloro-2-methoxypyrimidine-4-carboxylate (BB40)

Building Block 41 methyl 6-fluoro-3-methoxypyrazine-2-carboxylate (BB41)

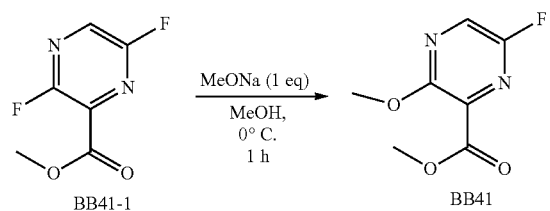

To a solution of methyl 3,6-difluoropyrazine-2-carboxylate BB41-1 (400 mg, 2.30 mmol) in methanol (4 mL) was added sodium methoxide (122 mg, 2.26 mmol) at −20° C., then the reaction was stirred at 0° C. for 1 hours. The mixture was quenched with saturated ammonium chloride aqueous solution (30 ml) at 0° C. and then extracted with ethyl acetate (30 mL) twice. The combined organic layers were washed with brine (20 mL), dried over $Na_2SO_{4(s)}$ and filtered. The filtrate was concentrated under reduced pressure and purified by silica gel column chromatography (petroleum ether:ethyl acetate=10:1 to 5:1) to give the title compound (80 mg, 18% yield, 96% purity) as white solids. LC-MS (ESI): $R_T$=1.34 min, mass calcd. for $C_7H_7FN_2O_3$ 186.0, m/z found 186.9 [M+H]$^+$. $^1$H NMR (400 MHz, CDCl$_3$) δ 8.10 (d, J=8.4 Hz, 1H), 4.09 (s, 3H), 3.99 (s, 3H).

Building Block 42 methyl 2-chloro-6-methoxypyrimidine-4-carboxylate (BB42)

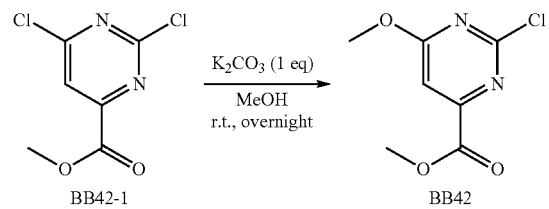

To a solution of methyl 2,6-dichloropyrimidine-4-carboxylate BB42-1 (1.00 g, 4.83 mmol) in methanol (20 mL) was added potassium carbonate (669 mg, 4.84 mmol) at room temperature. After stirred at room temperature overnight, the mixture was concentrated under reduced pressure to give a residue. The residue was diluted with water (20 mL) and extracted with ethyl acetate (20 mL) twice. The combined organic layers were washed with brine (20 mL), dried over $Na_2SO_{4(s)}$ and filtered. The filtrate was concentrated under reduced pressure to give the title compound (200 mg, 21% yield) as white solids. LC-MS (ESI): $R_T$=1.53 min, mass calcd. for $C_7H_7ClN_2O_3$ 202.0, m/z found 203.0 [M+H]$^+$. $^1$H NMR (400 MHz, DMSO-d$_6$) δ 7.45 (s, 1H), 4.02 (s, 3H), 3.90 (s, 3H).

Building Block 43

Mixture of ethyl 2-chloro-4-methoxypyrimidine-5-carboxylate and ethyl 4-chloro-2-methoxypyrimidine-5-carboxylate (BB43)

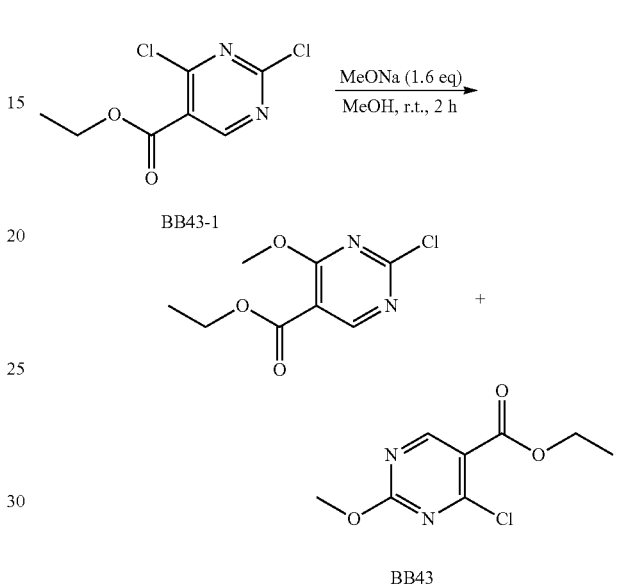

To a solution of ethyl 2,4-dichloropyrimidine-5-carboxylate BB43-1 (1.00 g, 99% purity, 5.52 mmol) in methanol (10 mL) was added sodium methoxide (488 mg, 96% purity, 8.67 mmol) at room temperature. After stirred at this temperature for 2 hours, the mixture was concentrated under reduced pressure to give a residue, which was partitioned between ethyl acetate (15 mL) and water (15 mL). The aqueous layer was separated and extracted with ethyl acetate (15 mL) twice. The combined organic layers were dried over $Na_2SO_{4(s)}$, filtered and concentrated under reduced pressure to give a residue, which was purified by silica gel column chromatography (petroleum ether:ethyl acetate=100:1 to 10:1) to give the title compound (640 mg, 65% yield, 1:1 by $^1$H NMR) as white solids. $^1$H NMR (400 MHz, CDCl$_3$) δ 9.01 (s, 1H), 8.86 (s, 1H), 4.44-4.36 (m, 4H), 4.14 (s, 3H), 4.10 (s, 3H), 1.43-1.37 (m, 6H).

Building Block 44

Methyl tert-butyl 6-chloro-5-fluoropicolinate (BB44)

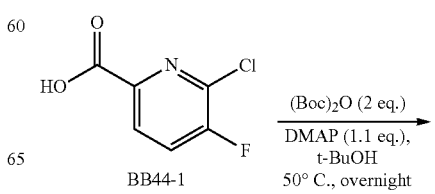

-continued

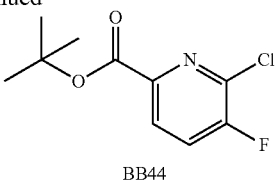

BB44

To the solution of 6-chloro-5-fluoropicolinic acid BB44-1 (200 mg, 1.09 mmol, 96% purity) in tert-butanol (4 mL) was added 4-dimethylaminopyridine (500 mg, 2.25 mmol, 98% purity) and di-tert-butyl dicarbonate (150 mg, 1.20 mmol, 98% purity) at room temperature. After stirred at 50° C. under nitrogen atmosphere overnight, the mixture was washed with water (10 mL) and extracted with ethyl acetate (20 mL) twice. The combined organic layers were dried over $Na_2SO_{4(s)}$ and filtered. The filtrate was and concentrated to give a residue, which was purified by silica gel column chromatography (petroleum ether:ethyl acetate=25:1 to 20:1) to give the title compound (180 mg, 90% purity, 64% yield) as white solids. $^1$H NMR (300 MHz, CDCl$_3$) δ 8.03-7.99 (m, 1H), 7.58-7.53 (m, 1H), 1.63 (s, 9H).

Building Block 45

Ethyl 2-chloro-5-ethylpyrimidine-4-carboxylate (BB45)

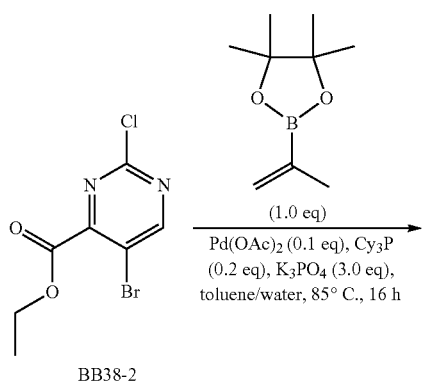

Intermediate BB45-1

Ethyl 2-chloro-5-(prop-1-en-2-yl)pyrimidine-4-carboxylate

To a mixture of ethyl 5-bromo-2-chloropyrimidine-4-carboxylate BB38-2 (300 mg, 90% purity, 1.02 mmol), 4,4,5,5-tetramethyl-2-(prop-1-en-2-yl)-1,3,2-dioxaborolane (175 mg, 98% purity, 1.02 mmol) and potassium phosphate (661 mg, 98% purity, 3.05 mmol) in toluene (9 mL) and water (3 mL) was added palladium acetate (23 mg, 99% purity, 0.101 mmol) and tricyclohexyl phosphine (60 mg, 95% purity, 0.203 mmol) under nitrogen atmosphere. After stirred at 85° C. under nitrogen atmosphere for 16 hours, the reaction mixture was diluted with water (20 mL) and extracted with ethyl acetate (10 mL) for three times. The combined organic layers were washed with brine (10 mL), dried over $Na_2SO_{4(s)}$ and filtered. The filtrate was concentrated to give a residue, which was purified by silica gel column chromatography (petroleum ether:ethyl acetate=100:1 to 20:1) to give the title compound (90 mg, 90% purity, 35% yield) as white solids.

LC-MS (ESI): $R_T$=1.63 min, mass calcd. for $C_{10}H_{11}ClN_2O_2$ 226.1, m/z found 226.9 [M+H]$^+$. $^1$H NMR (400 MHz, CDCl$_3$) δ 8.62 (s, 1H), 5.33 (s, 1H), 5.07 (s, 1H), 4.43 (q, J=7.2 Hz, 2H), 2.11 (s, 3H), 1.39 (t, J=7.2 Hz, 3H).

Building Block 45

Ethyl 2-chloro-5-ethylpyrimidine-4-carboxylate

To a solution of ethyl 2-chloro-5-(prop-1-en-2-yl)pyrimidine-4-carboxylate BB45-1 (90 mg, 90% purity, 0.357 mmol) in ethanol (5 mL) was added platinum dioxide (20 mg, 99% purity, 0.087 mmol) under nitrogen atmosphere. After stirred at 20° C. under hydrogen atmosphere of balloon for 1 hour, the reaction mixture was filtered and the filtrate was concentrated to give the title compound (75 mg, 95% purity, 87% yield) as black solids. LC-MS (ESI): $R_T$=1.65 min, mass calcd. for $C_{10}H_{13}ClN_2O_2$ 228.1, m/z found 229.1 [M+H]$^+$.

Building Block 46

Ethyl 2-(2-chloropyrimidin-5-yl)-2-methylpropanoate (BB46)

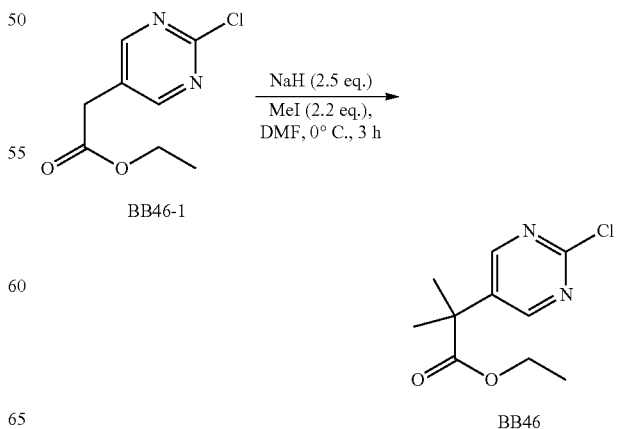

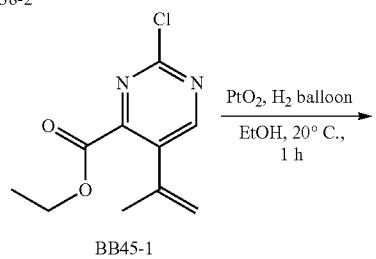

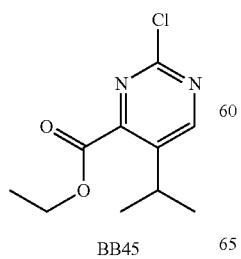

To a mixture of 60% wt. sodium hydride in mineral oil (50 mg, 1.25 mmol) in N,N-dimethylformamide (3 mL) was added slowly the solution of iodomethane (156 mg, 1.10 mmol) and ethyl 2-(2-chloropyrimidin-5-yl)acetate BB46-1 (100 mg, 0.498 mmol) in N,N-dimethylformamide (3 mL) under nitrogen atmosphere at 0° C. After stirring at 0° C. for 3 hours, the reaction mixture was quenched with water (10 mL), then extracted with ethyl acetate (20 mL) for three times. The combined organic layers were washed with water (5 mL), brine (5 mL), dried over $Na_2SO_{4(s)}$ and filtered. The filtrate was concentrated under reduced pressure to give a crude product, which was purified by C18 column (acetonitrile:water=40% to 80%) to give the title compound (65 mg, 90% purity from $^1$H NMR, 51% yield) as yellow oil. LC-MS (ESI): $R_T$=1.18 min, mass calcd. for $C_{10}H_{13}ClN_2O_2$ 228.1, m/z found 229.1 [M+H]$^+$. $^1$H NMR (400 MHz, CDCl$_3$) δ 8.63 (s, 2H), 4.16 (q, J=7.2 Hz, 2H), 1.64 (s, 6H), 1.23 (t, J=7.2 Hz, 3H).

Building Block 47

Methyl 2-chloro-4-(methoxymethyl)thiazole-5-carboxylate (BB47)

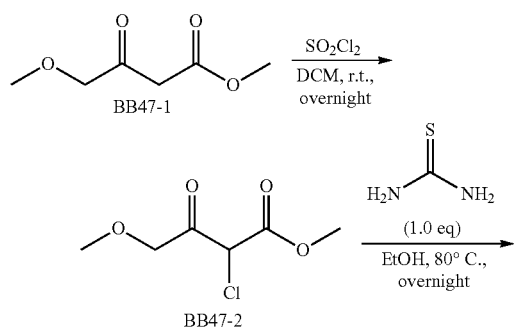

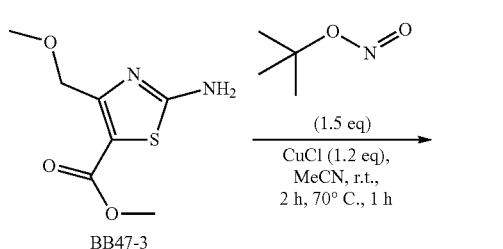

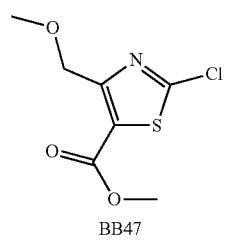

Intermediate BB47-2

Methyl 2-chloro-4-methoxy-3-oxobutanoate

To a solution of methyl 4-methoxy-3-oxobutanoate BB47-1 (2.0 g, 98% purity, 13.4 mmol) in dichloromethane (20 mL) was added sulfuryl chloride (1.2 mL). After stirred at room temperature under nitrogen atmosphere overnight, the mixture was concentrated under reduced pressure to give a residue, which was dissolved in ethyl acetate (100 mL). The solution was washed with water (50 mL) and brine (50 mL), dried over $Na_2SO_{4(s)}$, filtered and concentrated to give a residue, which was purified by silica gel column chromatography (petroleum ether:ethyl acetate=5:1) to give the title compound (1.6 g, 98.5% purity, 65% yield) as yellow oil. LC-MS (ESI): $R_T$=1.11 min, mass calcd. for $C_6H_9ClO_4$ 180.6, m/z found 181.1 [M+H]$^+$. $^1$H NMR (300 MHz, CDCl$_3$) δ 5.03 (s, 1H), 4.24 (s, 2H), 3.80 (s, 3H), 3.39 (s, 3H).

Intermediate BB47-3

Methyl 2-amino-4-(methoxymethyl)thiazole-5-carboxylate

The mixture of methyl 2-chloro-4-methoxy-3-oxobutanoate BB47-2 (1.6 g, 98.5% purity, 8.73 mmol) and thiourea (671 mg, 99% purity, 8.73 mmol) in ethanol (15 mL) was stirred at 80° C. under nitrogen atmosphere overnight. Then the mixture was cooled down to room temperature and concentrated under reduced pressure to give a residue, which was diluted with saturated aqueous sodium bicarbonate aqueous solution (20 mL). The resulting solids were collected by filtration and recrystallized from water (5 mL) and ethanol (5 mL) to give the title compound (1.18 g, 91.9% purity, 61.4% yield). LC-MS (ESI): $R_T$=0.35 min, mass calcd. for $C_7H_{10}N_2O_3S$, 202.2, m/z found 203.2 [M+H]$^+$. $^1$H NMR (300 MHz, CD$_3$OD) δ 4.64 (s, 2H), 3.78 (s, 3H), 3.38 (s, 3H).

Building Block 47

Methyl 2-chloro-4-(methoxymethyl)thiazole-5-carboxylate

To a suspension of tert-butyl nitrite (74 mg, 95% purity, 0.628 mmol), cuprous chloride (57 mg, 97% purity, 0.554 mmol) and in acetonitrile (1 mL) was added methyl 2-amino-4-(methoxymethyl)thiazole-5-carboxylate BB47-3 (100 mg, 91.9% purity, 0.454 mmol). After stirred at room temperature under nitrogen atmosphere for 2 hours and at 70° C. for 1 hour, the mixture was cooled to room temperature and filtered. The filtrate was poured into 6 N hydrochloride aqueous solution (10 mL) and extracted with ethyl acetate (20 mL). The organic layer was dried with $MgSO_{4(s)}$ and concentrated to give a residue, which was purified by silica gel column chromatography (petroleum ether:ethyl acetate=5:1) to give the title compound (78 mg, 99% purity, 77% yield) as yellow oil. LC-MS (ESI): $R_T$=1.54 min, mass calcd. for $C_7H_8ClNO_3S$, 221.7, m/z found 222.0 [M+H]$^+$. $^1$H NMR (300 MHz, CDCl$_3$) δ 4.85 (s, 2H), 3.90 (s, 3H), 3.49 (s, 3H).

Building Block 48 methyl 2-chloro-5-(trifluoromethyl)isonicotinate (BB48)

Building Block 49

6-chloro-4-(trifluoromethyl)nicotinic acid (BB49)

Building Block 50 tert-butyl 2-chloro-6-(trifluoromethyl)isonicotinate (BB50)

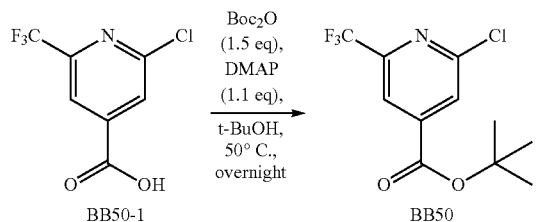

A mixture of 2-chloro-6-(trifluoromethyl)isonicotinic acid BB50-1 (300 mg, 1.26 mmol, 95% purity), di-tert-butyl dicarbonate (410 mg, 1.88 mmol) and N,N-dimethylpyridin-4-amine (170 mg, 1.39 mmol) in 2-methylpropan-2-ol (9 mL) was stirred at 50° C. overnight. The solvent was removed and the residue was purified by silica gel column chromatography (petroleum ether:ethyl acetate=100:1 to 30:1) to give title product (120 mg, 33% yield, 99% purity) as white solids. $^1$H NMR (400 MHz, CDCl$_3$) δ 8.08 (s, 1H), 8.01 (s, 1H), 1.62 (s, 9H).

Building Block 51 benzoyl Chloride (BB51)

Building Block 52

5-methylisoxazole-4-carbonyl Chloride (BB52)

Building Block 53

1H-pyrazole-4-carbonyl Chloride (BB53)

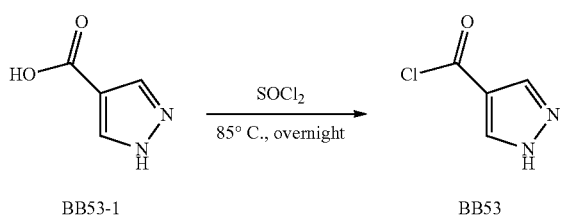 [SMILES: "BB53-1" ; O=C(O)c1cn[nH]c1 ; "SOCl2" ; "BB53" ; O=C(Cl)c1cn[nH]c1]

A mixture of 1H-pyrazole-4-carboxylic acid BB51-1 (641 mg, 5.72 mmol) in thionyl chloride (5 mL) was stirred at 85° C. under nitrogen atmosphere overnight. Then the mixture was concentrated to give the title compound (680 mg, 91% yield) as white solids which was directly used in next step.

Building Block 54

2-chloro-5-methylpyrimidine-4-carboxylic Acid (BB54)

Building Block 55

(trans)-3-(2-chloropyrimidin-5-yl)-3-hydroxycyclobutanecarboxylic Acid (BB55)

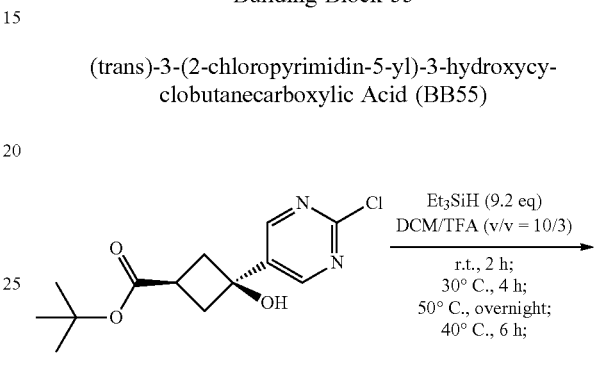

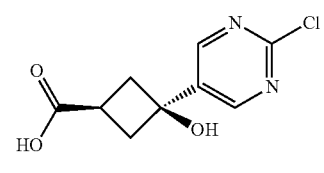

To a mixture of (trans)-tert-butyl 3-(2-chloropyrimidin-5-yl)-3-hydroxycyclobutanecarboxylate BB14 (150 mg, 0.530 mmol) in anhydrous dichloromethane (15 mL) was added trifluoroacetic acid (0.5 mL) and triethylsilane (565 mg, 4.86 mmol) at room temperature. After stirring at room temperature for 2 hours, 30° C. for 4 hours and 50° C. overnight under nitrogen atmosphere, trifluoroacetic acid (4 mL) was added. The obtained mixture was stirred at 40° C. for another 6 hours. Then it was cooled down to room temperature and concentrated to give a residue, which was dissolved in saturated sodium bicarbonate aqueous solution (0.5 mL). The aqueous solution was extracted with ethyl acetate (3 mL) for three times. The combined organic layers were concentrated to give the title compound (100 mg, 83% yield) as yellow solids. LC-MS (ESI): R$_T$=0.554 min, mass calcd. for C$_9$H$_9$ClN$_2$O$_3$ 228.0, m/z found 229.0 [M+H]$^+$.

Building Block 56 methyl 2-fluoro-5-methylisonicotinate (BB56)

Building Block 57

Ethyl 2-chloro-5-(dimethylamino)pyrimidine-4-carboxylate (BB57)

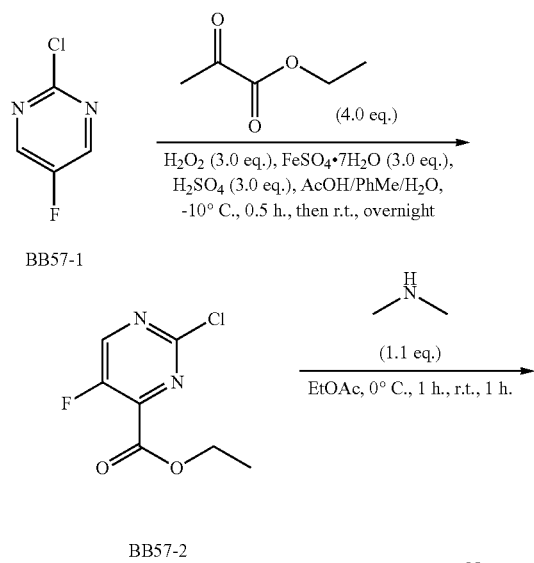

BB57-2

Intermediate BB57-2

Ethyl 2-chloro-5-fluoropyrimidine-4-carboxylate

To a round bottom flask was added ethyl 2-oxopropanoate (7.01 g, 60.4 mmol) and the mixture was cooled to −10° C. To the same flask, acetic acid (10 mL) was added while the internal temperature below −5° C. 30% wt. hydrogen peroxide aqueous solution (5.17 g, 45.6 mmol) was added dropwise maintaining the internal temperature below −5° C. To another round bottom flask with toluene (25 mL) and cooled to −10° C. was added 2-chloro-5-fluoropyrimidine BB57-1 (2 g, 15.1 mmol), concentrated sulfuric acid (2.5 mL, 46.0 mmol) and ferrous sulfate heptahydrate (15.12 g, 45.3 mmol) while the internal temperature below −5° C.

To this mixture, the peroxide solution was added over 0.5 hour under nitrogen atmosphere at −10° C. The mixture was stirred at −10° C. for 0.5 hour and warmed up to room temperature. After stirred at room temperature overnight, the mixture was quenched with water (25 mL) at 0° C., poured into saturated sodium bicarbonate solution (300 mL) and extracted with ethyl acetate (60 mL) for three times. The combined organic layers were washed with saturated sodium bicarbonate solution (50 mL) and brine (50 mL), dried over $Na_2SO_{4(s)}$ and filtered. The filtrate was concentrated and purified by silica gel column chromatography (petroleum ether:ethyl acetate=50:1 to 20:1) to give the title compound (997 mg, 90% purity from $^1H$ NMR, 29% yield) as yellow oil. LC-MS (ESI): $R_T$=1.41 min, mass calcd. for $C_7H_6ClFN_2O_2$ 204.0, m/z found 204.9 $[M+H]^+$. $^1H$ NMR (400 MHz, DMSO-$d_6$) δ 9.16 (d, J=2.4 Hz, 1H), 4.42 (q, J=6.8 Hz, 2H), 1.31 (t, J=7.2 Hz, 3H).

Building Block 57

Ethyl 2-chloro-5-(dimethylamino)pyrimidine-4-carboxylate

To a solution of ethyl 2-chloro-5-fluoropyrimidine-4-carboxylate BB57-2 (200 mg, 90% purity, 0.88 mmol) in ethyl acetate (1 mL) was added 33% wt. dimethylamine aqueous solution (0.2 mL, 0.996 mmol). The mixture was stirred at 0° C. for 1 hour and then warmed up to room temperature. After stirred at room temperature for 1 hour, the mixture was concentrated to give the residue, which was purified by Prep. TLC (petroleum ether:ethyl acetate=8:1) to afford the title compound (180 mg, 95% purity from $^1H$ NMR, 85% yield) as yellow oil. LC-MS (ESI): $R_T$=1.45 min, mass calcd. for $C_9H_{12}ClN_3O$, 2 229.1, m/z found 230.0 $[M+H]^+$. $^1H$ NMR (400 MHz, DMSO-$d_6$) δ 8.55 (s, 1H), 4.37 (q, J=7.2 Hz, 2H), 2.91 (s, 6H), 1.32 (t, J=7.2 Hz, 3H).

Building Block 58

Ethyl 5-(bis(2,4-dimethoxybenzyl)amino)-2-chloropyrimidine-4-carboxylate (BB58)

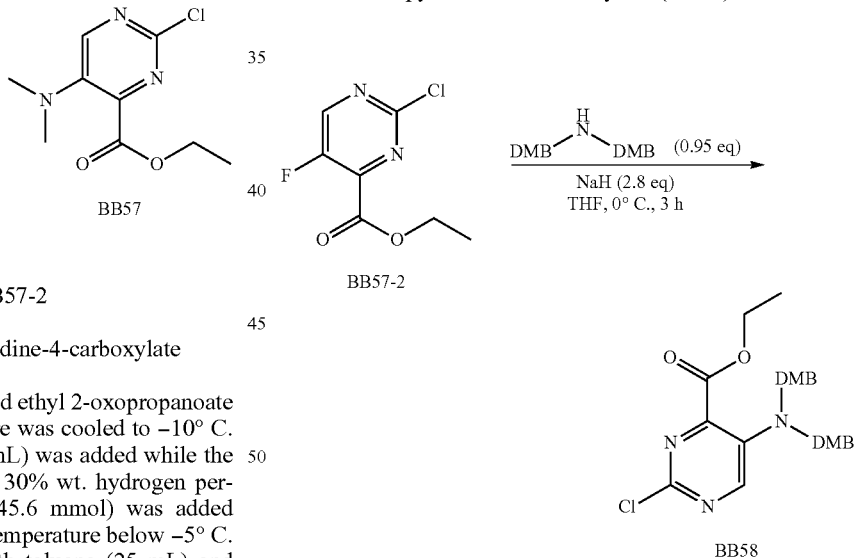

Sodium hydride (528 mg, 60% wt. in mineral oil, 13.2 mmol) was added into tetrahydrofuran (50 mL) at 0° C. and stirred for 3 minutes, then bis(2,4-dimethoxybenzyl)amine (1.47 g, 95% purity, 4.4 mmol) was added and stirring continued for 15 minutes, followed by addition of ethyl 2-chloro-5-fluoropyrimidine-4-carboxylate BB57-2 (1.0 g, 95% purity, 4.6 mmol) and the resulting mixture was stirred at 0° C. for 3 hours. The mixture was quenched with ice water (40 mL) at 0° C. and then it was extracted with ethyl acetate (50 mL) twice, the organic phase was combined and washed with water (50 mL) and brine (50 mL), dried over $Na_2SO_{4(s)}$ and filtered. The filtrate was concentrated and purified by silica gel column chromatography (petroleum ether:ethyl acetate=10:1) to afford the title compound (900 mg, 95% purity from $^1$H NMR, 37% yield) as yellow oil. LC-MS (ESI): $R_T$=1.971 min, mass calcd. for $C_{25}H_{28}ClN_3O_6$ 501.2, m/z found 502.2 [M+H]$^+$. $^1$H NMR (400 MHz, DMSO-$d_6$) δ 8.32 (s, 1H), 7.10 (d, J=8.4 Hz, 2H), 6.51 (d, J=2.0 Hz, 2H), 6.47 (dd, J=8.0 Hz, 2.0 Hz, 2H), 4.27 (q, J=7.2 Hz, 2H), 4.23 (s, 4H), 3.75-3.72 (m, 6H), 3.62 (s, 6H), 1.25 (t, J=7.2 Hz, 3H).

Building Block 59

Methyl 2-bromo-5-nitrosonicotinate (BB59)

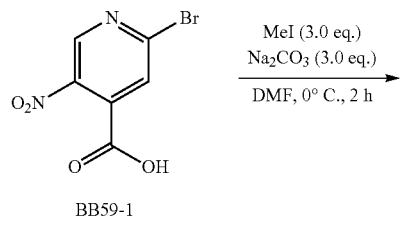

To the solution of 2-bromo-5-nitroisonicotinic acid BB59-1 (100 mg, 0.405 mmol) and sodium carbonate (130 mg, 1.23 mmol) in N,N-dimethylformamide (2 mL) was added iodomethane (173 mg, 1.22 mmol) at 0° C. After stirred at 0° C. for 2 hours, the mixture was poured into ethyl acetate (20 mL) and water (10 mL). Then the aqueous layer was extracted with ethyl acetate (20 mL) twice. The combined organic layers were washed with brine (120 mL), dried over Na$_2$SO$_{4(s)}$ and filtered. The filtrate was concentrated and purified by silica gel column chromatography (petroleum ether:ethyl acetate=10:1 to 5:1) give the tile compound (85 mg, 95% purity from $^1$H NMR, 76% yield) as white solids. $^1$H NMR (400 MHz, DMSO-$d_6$) δ 9.19 (s, 1H), 8.24 (s, 1H), 3.92 (s, 3H).

Building Block 60 ethyl 2-chloro-5-methoxypyrimidine-4-carboxylate (BB60)

Part VIII: Coupling of Dihydropyrimidines of General Formula XI

Compound XI-1-B: (Exemplified with Method E)

Methyl 4-(3,4-difluoro-2-methylphenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

To a solution of ethyl 2-(2-chloropyrimidin-5-yl)acetate BB1 (45 mg, 0.213 mmol) and methyl 4-(3,4-difluoro-2-methylphenyl)-6-(piperidin-4-yl)-2-(thiazol-2-yl)-1,4-dihy- dropyrimidine-5-carboxylate FA1 (100 mg, 93% purity, 0.220 mmol) in 1,4-dioxane (3 mL) was added triethylamine (112 mg, 1.11 mmol) at room temperature. After stirred at 100° C. under nitrogen atmosphere for 5 hours and cooled down to room temperature, the mixture was diluted with water (20 mL) and extracted with ethyl acetate (20 mL) twice. The combined organic layers were washed with brine (20 mL), dried over Na$_2$SO$_{4(s)}$ and filtered. The filtrate was concentrated under reduced pressure to give a residue, which was purified by C18 column (acetonitrile:water=75% to 85%) to give the title compound (78 mg, 56% yield) as yellow solids. LC-MS (ESI): $R_T$=1.98 min, mass calcd. for $C_{29}H_{30}F_2N_6O_4S$, 596.2, m/z found 597.0 [M+H]$^+$. $^1$H NMR (400 MHz, CDCl$_3$) δ 8.26 (d, J=2.4 Hz, 2H), 8.11 (s, 0.8H), 7.79-7.75 (m, 1H), 7.48 (d, J=3.2 Hz, 0.2H), 7.41 (d, J=3.2 Hz, 0.8H), 7.13-7.05 (m, 0.2H), 6.96-6.86 (m, 2H), 5.95 (s, 0.8H), 5.86 (d, J=2.0 Hz, 0.2H), 5.04-4.86 (m, 2H), 4.38-4.30 (m, 0.8H), 4.20-4.17 (m, 2H), 3.98-3.92 (m, 0.2H), 3.62 (s, 3H), 3.45 (s, 1.6H), 3.43 (s, 0.4H), 3.09-2.97 (m, 2H), 2.58 (d, J=2.4 Hz, 2.4H), 2.43 (d, J=2.0 Hz, 0.6H), 2.14-2.09 (m, 1H), 1.98-1.89 (m, 1H), 1.81-1.68 (m 2H), 1.26 (q, J=7.2 Hz, 3H).

Spectral Analyses of Dihydropyrimidine of General Formula XI

Compound XI-3-S

Ethyl 6-(1-(5-(2-ethoxy-2-oxoethyl)pyrimidin-2-yl) piperidin-4-yl)-4-(3-fluoro-2-methylphenyl)-2-(thi-azol-2-yl)-1,4-dihydropyrimidine-5-carboxylate (a Single Stereoisomer)

By utilizing the analogous procedure of Method E, the title compound was synthesized from compound BB1 and FA2.

LC-MS (ESI): $R_T$=2.00 min, mass calcd. for $C_{30}H_{33}FN_6O_4S$, 592.2, m/z found 593.0 [M+H]$^+$. $^1$H NMR (400 MHz, CDCl$_3$) δ 8.27-8.26 (m, 2H), 8.07 (s, 0.7H), 7.78-7.74 (m, 1H), 7.46 (d, J=3.2 Hz, 0.3H), 7.39 (d, J=3.2 Hz, 0.7H), 7.19-7.03 (m, 2.3H), 6.95-6.88 (m, 1H), 6.03 (s, 0.8H), 5.93 (d, J=2.0 Hz, 0.2H), 5.03-4.86 (m, 2H), 4.37-4.32 (m, 0.8H), 4.20-4.11 (m, 2.2H), 4.09-4.01 (m, 2H), 3.44 (s, 1.5H), 3.43 (s, 0.5H), 3.08-2.97 (m, 2H), 2.54 (s, 2.3H), 2.40 (s, 0.7H), 2.15-2.09 (m, 1H), 2.01-1.95 (m, 1H), 1.82-1.66 (m, 2H), 1.28 (t, J=7.2 Hz, 3H), 1.15-1.10 (m, 3H).

Compound XI-4-B

Methyl 2-(4-(5-(ethoxycarbonyl)-6-(4-fluoro-2-methylphenyl)-2-(thiazol-2-yl)-3,6-dihydropyrimi-din-4-yl)piperidin-1-yl)-5-methylpyrimidine-4-car-boxylate (a Single Stereoisomer)

By utilizing the analogous procedure of Method E, the title compound was synthesized from compound BB2 and FA3.

LC-MS (ESI): $R_T$=2.137 min, mass calcd. for $C_{29}H_{31}FN_6O_4S$, 578.2, m/z found 579.1 [M+H]$^+$. $^1$H NMR (400 MHz, DMSO-$d_6$) δ 9.50 (d, J=3.6 Hz, 0.8H), 9.09 (s, 0.2H), 8.45 (s, 0.2H), 8.43 (s, 0.8H), 8.01-7.88 (m, 2H), 7.29-7.25 (m, 0.8H), 7.17-7.14 (m, 0.2H), 7.06-6.96 (m, 2H), 5.81 (s, 0.2H), 5.69 (d, J=3.2 Hz, 0.8H), 4.88-4.73 (m, 2H), 4.00-3.98 (m, 2.1H), 3.93-3.88 (m, 3.9H), 2.95-2.85

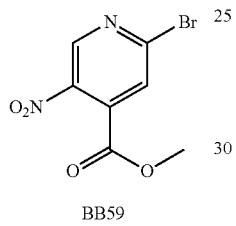

(m, 2H), 2.67-2.55 (m, 3H), 2.18 (s, 3H), 1.99-1.77 (m, 3H), 1.63-1.60 (m, 1H), 1.10-1.06 (m, 3H).

Compound XI-5-B

Methyl 2-(4-(6-(3-fluoro-2-methylphenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB2 and FA4.

$^1$H NMR (400 MHz, DMSO-d$_6$) δ 9.57 (d, J=3.6 Hz, 0.8H), 9.24 (s, 0.2H), 8.45 (s, 0.2H), 8.44 (s, 0.8H), 7.98 (d, J=3.2 Hz, 0.8H), 7.95 (d, J=3.2 Hz, 0.8H), 7.93 (d, J=3.2 Hz, 0.2H), 7.90 (d, J=2.8 Hz, 0.2H), 7.23-7.14 (m, 2H), 7.07-6.99 (m, 1H), 5.86 (s, 0.2H), 5.74 (d, J=3.2 Hz, 0.8H), 4.89-4.74 (m, 2H), 4.27-4.20 (m, 0.2H), 3.94-3.91 (m, 0.8H), 3.88 (s, 0.8H), 3.87 (s, 2.2H), 3.54 (s, 0.8H), 3.53 (s, 2.2H), 2.99-2.86 (m, 2H), 2.45 (d, J=1.2 Hz, 0.8H), 2.39 (d, J=1.6 Hz, 2.2H) 2.18 (s, 3H), 1.95-1.77 (m, 3H), 1.64-1.60 (m, 1H).

Compound XI-6-B

Methyl 6-(1-(5-(2-ethoxy-2-oxoethyl)pyrimidin-2-yl)piperidin-4-yl)-4-(3-fluoro-2-methylphenyl)-2-(thiazol-2-yl)-1,4-dihydropyrimidine-5-carboxylate (a Single Stereoisomer)

By utilizing the analogous procedure of Method E, the title compound was synthesized from compound BB1 and FA4.

LC-MS (ESI): R$_T$=1.65 min, mass calcd. for C$_{29}$H$_{31}$FN$_6$O$_4$S, 578.2, m/z found 578.9 [M+H]$^+$. $^1$H NMR (400 MHz, DMSO-d$_6$) δ 9.54 (d, J=3.6 Hz, 0.8H), 9.18 (s, 0.2H), 8.29-8.27 (m, 2H), 7.97-7.88 (m, 2H), 7.23-7.13 (m, 2H), 7.07-7.00 (m, 1H), 5.87 (s, 0.2H), 5.74 (d, J=3.2 Hz, 0.8H), 4.92-4.77 (m, 2H), 4.24-4.19 (m, 0.2H), 4.10 (q, J=7.2 Hz, 2H), 3.93-3.88 (m, 0.8H), 3.54 (s, 2H), 3.53 (s, 3H), 2.94-2.85 (m, 2H), 2.46 (s, 0.7H), 2.39 (s, 2.3H), 1.92-1.58 (m, 4H), 1.20 (t, J=7.2 Hz, 3H).

Compound XI-9-B

Methyl 4-(2-chloro-3-fluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA6.

$^1$H NMR (400 MHz, DMSO-d$_6$) δ 9.58 (d, J=3.2 Hz, 0.7H), 9.22 (s, 0.3H), 8.29 (s, 0.8H), 8.28 (s, 1.2H), 7.99-7.90 (m, 2H), 7.41-7.29 (m, 2H), 7.32-7.17 (m, 1H), 6.08 (s, 0.3H), 5.99 (d, J=3.6 Hz, 0.7H), 4.90-4.77 (m, 2H), 4.22-4.18 (m, 0.3H), 4.13-4.07 (m, 2H), 3.95-3.89 (m, 0.7H), 3.55 (s, 3H), 3.53 (s, 2H), 2.97-2.86 (m, 2H), 2.04-1.06 (m, 4H), 1.20 (t, J=7.2 Hz, 3H).

Compound XI-10-1

Methyl 2-(4-(6-(2-chloro-3-fluorophenyl)-5-(methoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA6.

$^1$H NMR (400 MHz, DMSO-d$_6$) δ 9.64 (d, J=4.0 Hz, 0.8H), 9.38 (s, 0.2H), 8.00-7.96 (m, 1.7H), 7.92 (d, J=2.8 Hz, 0.3H), 7.90 (s, 1H), 7.41-7.30 (m, 2H), 7.23-7.21 (m, 0.7H), 7.18-7.16 (m, 0.3H), 6.07 (s, 0.2H), 5.99 (d, J=3.6 Hz, 0.8H), 4.19-4.08 (m, 2.2H), 3.93-3.87 (m, 0.8H), 3.76 (s, 3H), 3.54 (s, 2.2H), 3.53 (s, 0.8H), 3.27-3.19 (m, 2H), 2.24-1.99 (m, 1H), 1.94-1.90 (m, 1H), 1.87-1.67 (m, 2H).

Compound XI-13-S

Methyl 4-(2-chloro-4-fluorophenyl)-6-(1-(4-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB9 and FA7.

$^1$H NMR (400 MHz, DMSO-d$_6$) δ 9.50 (d, J=3.6 Hz, 0.7H), 9.21 (s, 0.3H), 8.33-8.31 (m, 1H), 7.98 (d, J=3.2 Hz, 0.7H), 7.95-7.93 (m, 1H), 7.90 (d, J=3.2 Hz, 0.3H), 7.44-7.31 (m, 2H), 7.24-7.19 (m, 1H), 6.59-6.57 (m, 1H), 6.02 (s, 0.3H), 5.93 (d, J=4.0 Hz, 0.7H), 4.93-4.79 (m, 2H), 4.20-4.09 (m, 2.3H), 3.93-3.88 (m, 0.7H), 3.66 (s, 2H), 3.54 (s, 2H), 3.53 (s, 1H), 2.93-2.83 (m, 2H), 2.06-1.99 (m, 0.3H), 1.91-1.70 (m, 3H), 1.62-1.58 (m, 0.7H), 1.22-1.18 (m, 3H).

Compound XI-14-A

Ethyl 2-(4-(6-(2-chloro-4-fluorophenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB4 and FA7.

LC-MS (ESI): R$_T$=2.00 min, mass calcd. for C$_{28}$H$_{28}$ClFN$_6$O$_4$S, 598.2, m/z found 599.0 [M+H]$^+$. $^1$H NMR (400 MHz, CDCl$_3$) δ 8.28 (d, J=4.0 Hz, 1H), 8.13 (s, 0.5H), 7.81 (d, J=3.2 Hz, 0.5H), 7.77 (d, J=3.2 Hz, 0.5H), 7.47 (d, J=3.2 Hz, 0.5H), 7.42-7.41 (m, 1H), 7.32-7.29 (m, 1H), 7.15-7.12 (m, 1H), 6.97-6.89 (m, 1H), 6.20 (s, 0.5H), 6.07 (d, J=2.8 Hz, 0.5H), 5.03-4.87 (m, 2H), 4.43 (q, J=7.2 Hz, 2H), 4.33-4.27 (m, 0.5H), 4.07-4.01 (m, 0.5H), 3.63 (s, 1.6H), 3.61 (s, 1.4H), 3.06-2.95 (m, 2H), 2.28 (s, 1.5H), 2.26 (s, 1.5H), 2.17-2.13 (m, 0.8H), 2.01-1.92 (m, 1.6H), 1.80-1.68 (m, 1.6H), 1.42 (t, J=7.2 Hz, 3H).

Compound XI-15-S

Methyl 4-(2-chloro-4-fluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA7.

LC-MS (ESI): R$_T$=2.01 min, mass calcd. for C$_{28}$H$_{28}$ClFN$_6$O$_4$S, 598.2, m/z found 598.8 [M+H]$^+$. $^1$H NMR (400 MHz, CDCl$_3$) δ 8.27 (s, 1H), 8.26 (s, 1H), 8.13 (br s, 0.5H), 7.81 (d, J=3.2 Hz, 0.5H), 7.77 (br s, 0.5H), 7.47 (d, J=3.2 Hz, 0.5H), 7.42 (s, 1H), 7.32-7.29 (m, 1H), 7.15-7.12 (m, 1H), 6.97-6.89 (m, 1H), 6.21 (s, 0.5H), 6.07 (d, J=3.2 Hz, 0.5H), 5.03-4.85 (m, 2H), 4.35-4.28 (m, 0.5H), 4.20-4.03 (m, 2.5H), 3.63 (s, 1.5H), 3.61 (s, 1.5H), 3.45 (s, 1H), 3.43 (s, 1H), 3.08-2.96 (m, 2H), 2.20-2.09 (m, 1H), 2.01-1.94 (m, 1.5H), 1.81-1.67 (m, 1.5H), 1.28 (t, J=8.8 Hz, 3H).

Compound XI-16-B

Ethyl 2-(4-(6-(2-chloro-4-fluorophenyl)-5-(methoxycarbonyl)-2-(thiazol-2-yl)-3,6-dihydropyrimidin-4-yl)piperidin-1-yl)-4-methylpyrimidine-5-carboxylate (a Single Stereoisomer)

By utilizing the analogous procedure of Method E, the title compound was synthesized from compound BB8 and FA7.

LC-MS (ESI): $R_T$=4.252 min, mass calcd. for $C_{28}H_{28}ClFN_6O_4S$, 598.2, m/z found 598.9 [M+H]$^+$. $^1$H NMR (400 MHz, DMSO-d$_6$) δ 9.53 (d, J=3.6 Hz, 0.7H), 9.29 (s, 0.3H), 8.77 (s, 0.3H), 8.76 (s, 0.7H), 7.98 (d, J=2.8 Hz, 0.7H), 7.95-7.93 (m, 1H), 7.90 (d, J=3.2 Hz, 0.3H), 7.45-7.41 (m, 1H), 7.38-7.30 (m, 1H), 7.24-7.19 (m, 1H), 6.02 (s, 0.3H), 5.93 (d, J=3.6 Hz, 0.7H), 5.06-4.91 (m, 2H), 4.25 (q, J=7.2 Hz, 2.2H), 4.00-3.91 (m, 0.8H), 3.55 (s, 2H), 3.53 (s, 1H), 3.05-2.96 (m, 2H), 2.60 (s, 1H), 2.59 (s, 2H), 1.99-1.64 (m, 4H), 1.30 (t, J=7.2 Hz, 3H).

Compound XI-18-S

Ethyl 2-(4-(6-(2-chloro-4-fluorophenyl)-5-(methoxycarbonyl)-2-(thiazol-2-yl)-3,6-dihydropyrimidin-4-yl)piperidin-1-yl)oxazole-4-carboxylate (a Single Stereoisomer)

By utilizing the analogous procedure of Method E, the title compound was synthesized from compound BB6 and FA7.

LC-MS (ESI): $R_T$=3.051 min, mass calcd. for $C_{26}H_{25}ClFN_5O_5S$, 573.1, m/z found 573.9 [M+H]$^+$. $^1$H NMR (400 MHz, CDCl$_3$) δ 8.13 (s, 0.3H), 7.83-7.79 (m, 2H), 7.49 (d, J=3.2 Hz, 0.7H), 7.44 (s, 1H), 7.30-7.28 (m, 1H), 7.14 (d, J=8.0 Hz, 1H), 6.98-6.89 (m, 1H), 6.20 (s, 0.3H), 6.07 (s, 0.7H), 4.40-4.31 (m, 4H), 4.28-4.25 (m, 0.4H), 4.02-3.96 (m, 0.6H), 3.61 (s, 3H), 3.19-3.08 (m, 2H), 2.26-1.69 (m, 4H), 1.37 (t, J=6.8 Hz, 3H).

Compound XI-19-2

Methyl 2-(4-(6-(2-chloro-4-fluorophenyl)-5-(methoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA7.

LC-MS (ESI): $R_T$=1.63 min, mass calcd. for $C_{25}H_{23}ClFN_5O_4S_2$ 575.1, m/z found 575.8 [M+H]$^+$. $^1$H NMR (400 MHz, DMSO-d$_6$) δ 9.57 (d, J=3.6 Hz, 0.8H), 9.35 (s, 0.2H), 8.00-7.96 (m, 2H), 7.92-7.90 (m, 1H), 7.45-7.42 (m, 1H), 7.39-7.31 (m, 1H), 7.24-7.20 (m, 1H), 6.02 (s, 0.2H), 5.93 (d, J=3.6 Hz, 0.8H), 4.19-4.08 (m, 2.2H), 3.93-3.87 (m, 0.8H), 3.76 (s, 3H), 3.54 (s, 2.4H), 3.53 (s, 0.6H), 3.27-3.18 (m, 2H), 2.08-1.67 (m, 4H).

Compound XI-21-B

Ethyl 4-(2-chloro-4-fluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA8.

LC-MS (ESI): $R_T$=2.10 min, mass calcd. for $C_{29}H_{30}ClFN_6O_4S$, 612.2, m/z found 613.1 [M+H]$^+$. $^1$H NMR (400 MHz, CDCl$_3$) δ 8.52 (br s, 2H), 7.93 (br s, 1H), 7.69 (br s, 1H), 7.41-7.34 (m, 1H), 7.17-7.16 (m, 1H), 7.05-6.97 (m, 1H), 6.25 (br s, 1H), 5.23-5.09 (m, 2H), 4.38-4.29 (m, 1H), 4.22 (q, J=7.2 Hz, 2H), 4.14-4.05 (m, 2H), 3.57 (br s, 2H), 3.42-3.28 (m, 2H), 2.17-2.07 (m, 2H), 2.01-1.95 (m, 2H), 1.31 (t, J=7.2 Hz, 3H), 1.17-1.14 (m, 3H).

Compound XI-23-B

Ethyl 4-(2-chloro-3-fluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA9.

LC-MS (ESI): $R_T$=2.02 min, mass calcd. for $C_{29}H_{30}ClFN_6O_4S$, 612.2, m/z found 613.0 [M+H]$^+$. $^1$H NMR (400 MHz, CDCl$_3$) δ 8.52 (br s, 2H), 8.01 (br s, 1H), 7.87 (br s, 1H), 7.32-7.27 (m, 0.7H), 7.24-7.15 (m, 2.3H), 6.39 (br s, 1H), 5.25-5.13 (m, 2H), 4.46-4.36 (m, 1H), 4.21 (q, J=6.4 Hz, 2H), 4.11-4.07 (m, 2H), 3.59 (s, 2H), 3.37-3.24 (m, 2H), 2.47-2.25 (m, 2H), 2.19-2.09 (m, 1H), 1.99-1.96 (m, 1H), 1.29 (t, J=7.2 Hz, 3H), 1.16 (t, J=7.2 Hz, 3H).

Compound XI-24-B (cis)-Methyl 6-(1-(5-(3-(tert-butoxycarbonyl)-1-hydroxycyclobutyl)pyrimidin-2-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method E, the title compound was synthesized from compound BB14 and FA10.

LC-MS (ESI): $R_T$=1.73 min, mass calcd. for $C_{33}H_{35}ClF_2N_6O_5S$, 700.2, m/z found 701.0 [M+H]$^+$. $^1$H NMR (400 MHz, DMSO-d$_6$) δ 9.64 (d, J=3.6 Hz, 0.7H), 9.24 (s, 0.3H), 8.50 (s, 0.6H), 8.48 (s, 1.4H), 7.99-7.91 (m, 2H), 7.50-7.43 (m, 1H), 7.22-7.16 (m, 1H), 6.03 (s, 0.3H), 5.94 (d, J=3.2 Hz, 0.7H), 5.77 (s, 0.5H), 5.75 (s, 0.5H), 4.91-4.80 (m, 2H), 4.22-4.16 (m, 0.3H), 3.95-3.89 (m, 0.7H), 3.55 (s, 2H), 3.54 (s, 1H), 2.95-2.87 (m, 2H), 2.67-2.59 (m, 3H), 2.45-2.41 (m, 2H), 2.06-1.60 (m, 4H), 1.41 (s, 9H).

Compound XI-25-B

Ethyl 2-(4-(6-(2-chloro-3,4-difluorophenyl)-5-(methoxycarbonyl)-2-(thiazol-2-yl)-3,6-dihydropyrimidin-4-yl)piperidin-1-yl)oxazole-5-carboxylate (a Single Stereoisomer)

By utilizing the analogous procedure of Method E, the title compound was synthesized from compound BB10 and FA10.

LC-MS (ESI): $R_T$=1.86 min, mass calcd. for $C_{26}H_{24}ClF_2N_5O_5S$, 591.1, m/z found 591.9 [M+H]$^+$. $^1$H NMR (400 MHz, CDCl$_3$) δ 8.15 (s, 0.4H), 7.83-7.80 (m, 1H), 7.58 (s, 0.6H), 7.56 (s, 0.4H), 7.51 (d, J=3.2 Hz, 0.6H), 7.46 (d, J=3.2 Hz, 0.6H), 7.43 (s, 0.4H), 7.09-7.05 (m, 2H), 6.19 (s, 0.3H), 6.08 (d, J=2.4 Hz, 0.7H), 4.48-4.30 (m, 4.4H), 4.07-4.01 (m, 0.6H), 3.62 (s, 2H), 3.61 (s, 1H), 3.25-3.14 (m, 2H), 2.25-2.10 (m, 1H), 2.02-1.72 (m, 3H), 1.36 (t, J=6.4 Hz, 3H).

Compound XI-26-B

Ethyl 5-chloro-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylate (a Single Stereoisomer)

By utilizing the analogous procedure of Method E, the title compound was synthesized from compound BB13 and FA10.

LC-MS (ESI): $R_T$=2.237 min, mass calcd. for $C_{27}H_{24}Cl_2F_2N_6O_4S$, 636.1, m/z found 639.0 [M+H]$^+$.

Compound XI-28-6

Methyl 4-(2-chloro-3,4-difluorophenyl)-6-(1-(5-(2-ethoxy-2-oxoethyl)-4-methylpyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB12 and FA10.

LC-MS (ESI): $R_T$=1.79 min, mass calcd. for $C_{29}H_{29}ClF_2N_6O_4S$, 630.2, m/z found 630.8 [M+H]$^+$. $^1$H NMR (400 MHz, DMSO-d$_6$) δ 9.63 (d, J=4.0 Hz, 0.7H), 9.28 (s, 0.3H), 8.11-8.10 (m, 1H), 8.01-7.91 (m, 2H), 7.50-7.42 (m, 1H), 7.24-7.14 (m, 1H), 6.02 (s, 0.3H), 5.94 (d, J=3.6 Hz, 0.7H), 4.94-4.79 (m, 2H), 4.22-4.15 (m, 0.3H), 4.09 (q, J=6.8 Hz, 2H), 3.94-3.87 (m, 0.7H), 3.57 (s, 2H), 3.55 (s, 2.1H), 3.53 (s, 0.9H), 2.94-2.81 (m, 2H), 2.26 (s, 0.9H), 2.25 (s, 2.1H), 2.10-2.01 (m, 0.3H), 1.96-1.69 (m, 3H), 1.63-1.59 (m, 0.7H), 1.20 (t, J=6.8 Hz, 3H).

Compound XI-29-S

Methyl 4-(2-chloro-3,4-difluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA10.

$^1$H NMR (400 MHz, CDCl$_3$) δ 8.27-8.26 (m, 2H), 8.16 (s, 1H), 7.82-7.81 (m, 0.4H), 7.78-7.77 (m, 0.6H), 7.48-7.47 (m, 0.4H), 7.44-7.43 (m, 0.6H), 7.10-6.99 (m, 2H), 6.20 (s, 0.6H), 6.07-6.06 (m, 0.4H), 5.04-4.86 (m, 2H), 4.35-4.28 (m, 0.6H), 4.20-4.04 (m, 2.4H), 3.63 (s, 1.3H), 3.61 (s, 1.7H), 3.45 (s, 1.2H), 3.43 (s, 0.8H), 3.07-2.96 (m, 2H), 2.20-2.08 (m, 0.7H), 2.05-1.91 (m, 1.3H), 1.79-1.67 (m, 2H), 1.29-1.26 (m, 3H).

Compound XI-30-B

Methyl 4-(2-chloro-3,4-difluorophenyl)-6-(piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB3 and FA10.

$^1$H NMR (400 MHz, DMSO-d$_6$) δ 9.68 (d, J=3.2 Hz, 0.8H), 9.41 (s, 0.2H), 8.01-7.96 (m, 1.7H), 7.92 (d, J=3.2 Hz, 0.3H), 7.90 (s, 1H), 7.49-7.43 (m, 1H), 7.24-7.20 (m, 0.7H), 7.17-7.14 (m, 0.3H), 6.02 (s, 0.2H), 5.94 (d, J=3.6 Hz, 0.8H), 4.18-4.08 (m, 2.1H), 3.94-3.87 (m, 0.9H), 3.76 (s, 3H), 3.54 (s, 2.2H), 3.53 (s, 0.8H), 3.28-3.19 (m, 2H), 2.27-2.04 (m, 1H), 1.99-1.89 (m, 1H), 1.86-1.68 (m, 2H).

Compound XI-31-B 2-(4-(6-(2-chloro-3,4-difluorophenyl)-5-(methoxycarbonyl)-2-(thiazol-2-yl)-3,6-dihydropyrimidin-4-yl)piperidin-1-yl)-4-(trifluoromethyl)thiazole-5-carboxylate (a Single Stereoisomer)

By utilizing the analogous procedure of Method E, the title compound was synthesized from compound BB15 and FA10.

LC-MS (ESI): $R_T$=2.824 min, mass calcd. for $C_{27}H_{23}ClF_5N_5O_4S_2$ 675.1, m/z found 675.8 [M+H]$^+$. $^1$H NMR (400 MHz, DMSO-d$_6$) δ 9.67 (d, J=3.6 Hz, 0.7H), 9.42 (s, 0.3H), 8.01-7.92 (m, 2H), 7.49-7.42 (m, 1H), 7.24-7.14 (m, 1H), 6.03 (s, 0.3H), 5.95 (d, J=4.0 Hz, 0.7H), 4.25 (q, J=7.2 Hz, 2H), 4.20-4.02 (m, 2.3H), 3.94-3.86 (m, 0.7H), 3.54 (s, 2.1H), 3.53 (s, 0.9H), 3.29-3.21 (m, 2H), 2.29-1.83 (m, 3H), 1.76-1.69 (m, 1H), 1.26 (t, J=7.2 Hz, 3H).

Compound XI-32-B

Ethyl 2-(4-(6-(2-chloro-3,4-difluorophenyl)-5-(methoxycarbonyl)-2-(thiazol-2-yl)-3,6-dihydropyrimidin-4-yl)piperidin-1-yl)thiazole-4-carboxylate (a Single Stereoisomer)

By utilizing the analogous procedure of Method E, the title compound was synthesized from compound BB11 and FA10.

LC-MS (ESI): $R_T$=1.86 min, mass calcd. for $C_{26}H_{24}ClF_2N_5O_4S_2$ 607.1, m/z found 608.3 [M+H]$^+$. $^1$H NMR (400 MHz, DMSO-d$_6$) δ 9.64 (d, J=3.2 Hz, 0.7H), 9.30 (s, 0.3H), 8.00-7.96 (m, 1.7H), 7.92 (d, J=3.2 Hz, 0.3H), 7.70 (s, 1H), 7.49-7.42 (m, 1H), 7.24-7.15 (m, 1H), 6.03 (s, 0.3H), 5.94 (d, J=3.6 Hz, 0.7H), 4.24 (q, J=7.2 Hz, 2H), 4.16-3.98 (m, 2.3H), 3.90-3.83 (m, 0.7H), 3.54 (s, 2H), 3.53 (s, 1H), 3.20-3.06 (m, 2H), 2.10-1.65 (m, 4H), 1.28 (t, J=7.2 Hz, 3H).

Compound XI-33-B

Ethyl 2-(4-(6-(2-chloro-3,4-difluorophenyl)-5-(methoxycarbonyl)-2-(thiazol-2-yl)-3,6-dihydropyrimidin-4-yl)piperidin-1-yl)oxazole-4-carboxylate (a Single Stereoisomer)

By utilizing the analogous procedure of Method E, the title compound was synthesized from compound BB6 and FA10.

LC-MS (ESI): $R_T$=2.077 min, mass calcd. for $C_{26}H_{24}ClF_2N_5O_5S$, 591.1, m/z found 592.0 [M+H]$^+$.

Compound XI-34-10F ethyl 2-(4-(6-(2-chloro-3,4-difluorophenyl)-5-(ethoxycarbonyl)-2-(thiazol-2-yl)-3,6-dihydropyrimidin-4-yl)-2-methylpiperidin-1-yl)pyrimidine-5-carboxylate (a Mixture of 2 Stereoisomers)

Intermediate XI-34-10 ethyl 2-(4-(6-(2-chloro-3,4-difluorophenyl)-5-(ethoxycarbonyl)-2-(thiazol-2-yl)-3,6-dihydropyrimidin-4-yl)-2-methylpiperidin-1-yl)pyrimidine-5-carboxylate (a Mixture of 4 Stereoisomers)

By utilizing the analogous procedure of Method E, the title compound was synthesized from compound BB7 and FA11.

LC-MS (ESI): $R_T$=2.18 min, mass calcd. for $C_{29}H_{29}ClF_2N_6O_4S$, 630.2, m/z found 630.8 [M+H]$^+$. $^1$H NMR (300 MHz, DMSO-$d_6$) δ 9.65-9.61 (m, 0.8H), 9.28-9.07 (m, 0.2H), 8.81 (s, 2H), 7.97-7.95 (m, 2H), 7.51-7.41 (m, 1H), 7.26-7.15 (m, 1H), 6.05-5.92 (m, 1H), 5.37-5.18 (m, 1H), 4.91-4.76 (m, 1H), 4.27-4.25 (m, 3H), 4.03-3.98 (m, 2H), 3.19-3.07 (m, 1H), 1.95-1.62 (m, 4H), 1.28-1.24 (m, 6H), 1.10-1.06 (m, 3H).

A stereoisomeric mixture of XI-34-10 (550 mg, 0.87 mmol) was separated by Prep. HPLC (separation condition: Column: Chiralpak IA 20 mm*250 mm 5 μm Mobile phase: Hex-EtOH-DEA-40-60-0.3 Flow rate: 22 mL/min; Wavelength: 230 nm) to give compounds Group 1 XI-34-10A & XI-34-10B (240 mg, 43% yield, 100% de) as yellow solids and Group 2 XI-34-10F (140 mg, 25% yield, 98.8% de) as yellow solids. The Group 1 was separated by Prep. HPLC (separation condition: Column: Chiralpak IE 4.6 mm*250 mm 5um; Mobile Phase: Hex:EtOH:DEA=70:30:0.3 at 12 ml/min; Wavelength: 230 nm) to give the title compounds XI-34-10A (100 mg, 41% yield, 100% de) as yellow solids and XI-34-10B (100 mg, 41% yield, 99.8% de).

XI-34-10A: LC-MS (ESI): $R_T$=2.28 min, mass calcd. for $C_{29}H_{29}ClF_2N_6O_4S$, 630.2, m/z found 630.9 [M+H]$^+$. Chiral HPLC (Column: Chiralpak IE 4.6 mm*250 mm 5 μm; Mobile Phase: Hex-EtOH-DEA-70-30-0.2 at 1.0 mL/min; Wavelength: 230 nm, $R_T$=10.865 min). $^1$H NMR (400 MHz, CD$_3$OD) δ 8.82 (s, 0.8H), 8.81 (s, 1.2H), 7.86 (s, 0.4H), 7.85 (s, 0.4H), 7.70 (s, 0.6H), 7.69 (s, 0.4H), 7.27-7.21 (m, 2H), 6.18 (s, 0.4H), 6.11 (s, 0.6H), 5.44-5.33 (m, 1H), 5.01-4.90 (m, 1H), 4.68-4.60 (m, 0.4H), 4.36-4.30 (m, 2.6H), 4.10-4.04 (m, 2H), 3.25-3.13 (m, 1H), 2.21-1.83 (m 3.4H), 1.71-1.68 (m 0.6H), 1.38-1.35 (m 6H), 1.17-1.12 (m 3H).

XI-34-10B: LC-MS (ESI): $R_T$=2.31 min, mass calcd. for $C_{29}H_{29}ClF_2N_6O_4S$, 630.2, m/z found 630.9 [M+H]$^+$. Chiral HPLC (Column: Chiralpak IE 4.6 mm*250 mm 5 μm; Mobile Phase: Hex-EtOH-DEA-70-30-0.2 at 1.0 mL/min; Wavelength: 230 nm, $R_T$=14.122 min). $^1$H NMR (400 MHz, CD$_3$OD) δ 8.82 (s, 0.8H), 8.81 (s, 1.2H), 7.86-7.85 (m, 1H), 7.69-7.68 (m, 1H), 7.25-7.22 (m, 2H), 6.16 (s, 0.4H), 6.09 (s, 0.6H), 5.42-5.28 (m, 1H), 5.02-4.90 (m, 1H), 4.67-4.60 (m, 0.4H), 4.35-4.30 (m, 2.6H), 4.11-4.04 (m, 2H), 3.27-3.16 (m, 1H), 2.11-1.81 (m, 3.4H), 1.65-1.60 (m, 0.6H), 1.37-1.31 (m, 6H), 1.17-1.12 (m, 3H).

XI-34-10F: LC-MS (ESI): $R_T$=2.18 min, mass calcd. for $C_{29}H_{29}ClF_2N_6O_4S$, 630.2, m/z found 630.8 [M+H]$^+$. Chiral HPLC (Column: Chiralpak IA 4.6 mm*250 mm 5 μm; Mobile Phase: Hex-EtOH-DEA-40-60-0.2 at 1.0 mL/min; Wavelength: 230 nm, $R_T$=10.549 and 11.719 min). $^1$H NMR (400 MHz, CD$_3$OD) δ 8.81 (s, 2H), 7.85 (d, J=3.2 Hz, 1H), 7.69 (d, J=3.2 Hz, 1H), 7.25-7.21 (m, 2H), 6.12 (d, J=7.6 Hz, 1H), 5.41-5.31 (m, 1H), 5.00-4.91 (m, 1H), 4.60-4.45 (m, 1H), 4.33 (d, J=7.2 Hz, 2H), 4.10-4.05 (m, 2H), 3.25-3.14 (m, 1H), 2.20-1.72 (m, 4H), 1.38-1.32 (m, 6H), 1.16-1.13 (m, 3H).

Compound XI-35-5R and XI-35-5S

Ethyl 6-(1-(4-(tert-butoxycarbonyl)phenyl)piperidin-4-yl)-4-(2-chloro-3,4-difluorophenyl)-2-(thiazol-2-yl)-1,4-dihydropyrimidine-5-carboxylate (a Single Stereoisomer) and ethyl 6-(1-(4-(tert-butoxycarbonyl)phenyl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method B to give the racemic product (180 mg) as yellow solids, which was separated by chiral Prep. HPLC (separation condition: Column: Chiralpak IA 5 μm 20*250 mm; Mobile Phase: Hex:IPA:DEA=70:30:0.3 at 22 mL/min; Col. Temp: 30° C.; Wavelength: 214 nm) to afford the title compounds XI-35-5R (58 mg, 31% yield, 100% ee) and XI-35-5S (48 mg, 26% yield, 100% ee) as yellow solids.

XI-35-5R: Chiral analysis (Column:Chiralpak IG 5 μm 4.6*250 mm; Mobile Phase: Hex:EtOH:DEA=60:40:0.2 at 1.0 mL/min; Temp: 30° C.; Wavelength: 230 nm, $R_T$=10.261 min). $^1$H NMR (400 MHz, DMSO-$d_6$) δ 9.61 (d, J=3.6 Hz, 0.8H), 9.02 (s, 0.2H), 8.00-7.93 (m, 2H), 7.76-7.73 (m, 2H), 7.50-7.43 (m, 1H), 7.25-7.18 (m, 1H), 7.02-6.99 (m, 2H), 6.05 (s, 0.3H), 5.95 (d, J=3.2 Hz, 0.7H), 4.12-3.97 (m, 4H), 3.88-3.82 (m, 1H), 2.92-2.82 (m, 2H), 2.06-1.89 (m, 2H), 1.82-1.77 (m, 1H), 1.68-1.63 (m, 1H), 1.52 (s, 9H), 1.11-1.04 (m, 3H).

XI-35-5S: Chiral analysis (Column: Chiralpak IG 5 μm 4.6*250 mm; Mobile Phase: Hex:EtOH:DEA=60:40:0.2 at 1.0 mL/min; Temp: 30° C.; Wavelength: 230 nm, $R_T$=16.394 min). $^1$H NMR (400 MHz, DMSO-$d_6$) δ 9.61 (d, J=3.6 Hz, 0.7H), 9.02 (s, 0.3H), 8.00-7.93 (m, 2H), 7.76-7.73 (m, 2H), 7.50-7.44 (m, 1H), 7.25-7.18 (m, 1H), 7.02-6.99 (m, 2H), 6.05 (s, 0.3H), 5.95 (d, J=3.6 Hz, 0.7H), 4.12-3.97 (m, 4H), 3.88-3.81 (m, 1H), 2.94-2.82 (m, 2H), 2.06-1.88 (m, 2.2H), 1.82-1.79 (m, 1H), 1.66-1.63 (m, 0.8H), 1.52 (s, 9H), 1.11-1.04 (m, 3H).

Compound XI-36-S ethyl-6-(1-(5-(tert-butoxycarbonyl)-4-((4-methoxybenzyl)oxy)pyridin-2-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method E, the title compound was synthesized from compound BB32 and FA12.

LC-MS (ESI): $R_T$=2.11 min, mass calcd. for $C_{39}H_{40}ClF_2N_5O_6S$, 779.2, m/z found 779.8 [M+H]$^+$. $^1$H NMR (400 MHz, CDCl$_3$) δ 9.62 (d, J=3.6 Hz, 0.8H), 9.12 (d, J=4.0 Hz, 0.2H), 8.40 (s, 0.3H), 8.39 (s, 0.7H), 8.00-7.93 (m, 2H), 7.45-7.43 (m, 3H), 7.25-7.20 (m, 1H), 6.99-6.96 (m, 2H), 6.48 (s, 0.3H), 6.45 (s, 0.7H), 6.04 (s, 0.3H), 5.95 (d, J=3.2 Hz, 0.7H), 5.15 (s, 2H), 4.73-4.57 (m, 2H), 4.03-3.92 (m, 3H), 3.75 (s, 3H), 2.98-2.88 (m, 2H), 1.94-1.76 (m, 3.2H), 1.67-1.60 (m, 0.8H), 1.41 (s, 9H), 1.10 (t, J=7.2 Hz, 3H).

Compound XI-37-2

Ethyl 4-(2-chloro-3,4-difluorophenyl)-6-(1-(6-(methoxycarbonyl)pyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB20 and FA12.

LC-MS (ESI): $R_T$=3.676 min, mass calcd. for $C_{28}H_{26}ClF_2N_5O_4S$, 601.1, m/z found 601.9 [M+H]$^+$. $^1$H NMR (400 MHz, DMSO-d$_6$) δ 9.62 (d, J=3.6 Hz, 0.7H), 9.15 (s, 0.3H), 7.99-7.91 (m, 2H), 7.71-7.67 (m, 1H), 7.51-7.43 (m, 1H), 7.30-7.28 (m, 1H), 7.25-7.18 (m, 1H), 7.13 (d, J=8.8 Hz, 1H), 6.04 (s, 0.3H), 5.95 (d, J=3.6 Hz, 0.7H), 4.65-4.51 (m, 2H), 4.21-4.12 (m, 0.3H), 4.03-3.98 (m, 2H), 3.93-3.87 (m, 0.7H), 3.84 (s, 3H), 2.95-2.82 (m, 2H), 2.06-1.63 (m, 4H), 1.11-1.05 (m, 3H).

Compound XI-38-3 ethyl 6-(1-(4-(tert-butoxycarbonyl)-6-(trifluoromethyl)pyridin-2-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method E, the title compound was synthesized from compound BB50 and FA12.

$^1$H NMR (400 MHz, DMSO-d$_6$) δ 9.62 (br s, 0.7H), 9.24 (s, 0.3H), 7.99-7.90 (m, 2H), 7.50-7.44 (m, 2H), 7.25-7.17 (m, 2H), 6.04 (s, 0.3H), 5.95 (br s, 0.7H), 4.64-4.50 (m, 2H), 4.25-4.18 (m, 0.3H), 4.03-3.93 (m, 2.7H), 3.04-2.94 (m, 2H), 2.13-1.84 (m, 3H), 1.77-1.67 (m, 1H), 1.57 (s, 9H), 1.11-1.05 (m, 3H).

Compound XI-39-S

Ethyl 4-(2-chloro-3,4-difluorophenyl)-6-(1-(4-(methoxycarbonyl)-5-(trifluoromethyl)pyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB48 and FA12.

LC-MS (ESI): $R_T$=4.322 min, mass calcd. for $C_{29}H_{25}ClF_5N_5O_4S$, 669.1, m/z found 669.9 [M+H]$^+$. $^1$H NMR (400 MHz, DMSO-d$_6$) δ 9.62 (d, J=3.2 Hz, 0.6H), 9.32 (s, 0.4H), 8.50 (s, 1H), 7.99-7.90 (m, 2H), 7.50-7.43 (m, 1H), 7.24-7.15 (m, 2H), 6.04 (s, 0.3H), 5.95 (d, J=3.2 Hz, 0.7H), 4.71-4.58 (m, 2H), 4.26-4.20 (m, 0.3H), 4.03-3.95 (m, 2.7H), 3.87 (s, 3H), 3.07-2.98 (m, 2H), 2.12-1.66 (m, 4H), 1.11-1.04 (m, 3H).

Compound XI-40-B

Ethyl 4-(2-chloro-3,4-difluorophenyl)-6-(1-(3-fluoro-4-(methoxycarbonyl)pyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB34 and FA12.

1H NMR (300 MHz, CDCl$_3$) δ 8.28 (s, 0.5H), 8.18-8.12 (m, 1H), 7.85-7.78 (m, 1H), 7.52-7.48 (m, 1H), 7.46-7.43 (m, 0.5H), 7.38-7.30 (m, 1H), 7.16-7.01 (m, 2H), 6.22 (s, 0.5H), 6.10 (s, 0.5H), 4.26-4.08 (m, 2H), 4.00-3.95 (m, 3H), 3.33-3.18 (m, 3H), 3.12-2.90 (m, 1H), 2.39-2.17 (m, 2H), 2.04-1.80 (m, 3H), 1.18-1.13 (m, 3H).

Compound XI-41-B

Ethyl 4-(2-chloro-3,4-difluorophenyl)-6-(1-(4-(methoxycarbonyl)pyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB18 and FA12.

$^1$H NMR (400 MHz, DMSO-d$_6$) δ 9.62 (br s, 0.7H), 9.13 (s, 0.3H), 8.30 (d, J=5.2 Hz, 1H), 7.99-7.91 (m, 2H), 7.51-7.43 (m, 1H), 7.27-7.18 (m, 2H), 7.03 (d, J=4.8 Hz, 1H), 6.04 (s, 0.3H), 5.95 (s, 0.7H), 4.60-4.46 (m, 2H), 4.20-4.13 (m, 0.3H), 4.01-3.97 (m, 2H), 3.96-3.90 (m, 0.7H), 3.88 (s, 3H), 2.99-2.86 (m, 2H), 2.07-1.63 (m, 4H), 1.11-1.05 (m, 3H).

Compound XI-42-3B

Ethyl 6-(1-(6-(tert-butoxycarbonyl)-2-chloropyridin-3-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method E, the title compound was synthesized from compound BB44 and FA12.

LC-MS (ESI): $R_T$=7.814 min, mass calcd. for $C_{31}H_{31}Cl_2F_2N_5O_4S$, 677.1, m/z found 677.9 [M+H]$^+$. $^1$H NMR (400 MHz, DMSO-d$_6$) δ 9.64 (d, J=3.2 Hz, 0.8H), 9.07 (s, 0.2H), 8.02-8.00 (m, 1.7H), 7.97-7.94 (m, 1.3H), 7.69-7.65 (m, 1H), 7.51-7.45 (m, 1H), 7.26-7.22 (m, 1H), 6.06 (s, 0.2H), 5.96 (d, J=3.2 Hz, 0.8H), 4.02-3.96 (m, 2.2H), 3.85-3.79 (m, 0.8H), 3.64-3.56 (m, 2H), 2.86-2.78 (m, 2H), 2.22-1.83 (m, 3.3H), 1.70-1.67 (m, 0.7H), 1.55 (s, 9H), 1.11-1.05 (m, 3H).

Compound XI-43-1

Ethyl 4-(2-chloro-3,4-difluorophenyl)-6-(1-(5-(methoxycarbonyl)pyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB19 and FA12.

LC-MS (ESI): $R_T$=2.126 min, mass calcd. for $C_{28}H_{26}ClF_2N_5O_4S$, 601.1, m/z found 602.0 [M+H]$^+$.

Compound XI-45-B

Ethyl 6-(1-(5-(tert-butoxycarbonyl)-3-fluoropyridin-2-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method E, the title compound was synthesized from compound BB33 and FA12.

LC-MS (ESI): $R_T$=3.940 min, mass calcd. for $C_{31}H_{31}ClF_3N_5O_4S$, 661.2, m/z found 662.2 [M+H]$^+$. $^1$H NMR (400 MHz, DMSO-d$_6$) δ 9.60 (d, J=3.6 Hz, 0.7H), 9.13 (s, 0.3H), 8.50-8.49 (m, 1H), 7.99-7.91 (m, 2H), 7.77-7.72 (m, 1H), 7.50-7.43 (m, 1H), 7.24-7.17 (m, 1H), 6.04 (s, 0.3H), 5.95 (d, J=3.2 Hz, 0.7H), 4.55-4.39 (m, 2H), 4.22-4.16 (m, 0.2H), 4.03-3.91 (m, 2.8H), 3.10-3.01 (m, 2H), 2.16-1.76 (m, 3.5H), 1.68-1.64 (m, 0.5H), 1.53 (s, 9H), 1.11-1.04 (m, 3H).

Compound XI-46-S

Methyl 6-(4-(6-(2-chloro-3,4-difluorophenyl)-5-(ethoxycarbonyl)-2-(thiazol-2-yl)-3,6-dihydropyrimidin-4-yl)piperidin-1-yl)-4-methylpyridazine-3-carboxylate (a Single Stereoisomer)

By utilizing the analogous procedure of Method E, the title compound was synthesized from compound BB27 and FA12.
$^1$H NMR (300 MHz, CDCl$_3$) δ 8.11 (br s, 0.3H), 7.82-7.77 (m, 1H), 7.49-7.44 (m, 1H), 7.34 (br s, 0.7H), 7.10-7.04 (m, 2H), 6.71-6.67 (m, 1H), 6.21 (s, 0.5H), 6.09 (s, 0.5H), 4.80-4.67 (m, 2H), 4.47-4.33 (m, 0.5H), 4.18-4.06 (m, 2.5H), 3.98 (s, 1H), 3.97 (s, 2H), 3.21-3.12 (m, 2H), 2.55 (s, 3H), 2.13-2.09 (m, 1H), 2.04-1.98 (m, 1.5H), 1.83-1.73 (m, 1.5H), 1.14 (t, J=7.2 Hz, 3H).

Compound XI-47-3 ethyl 4-(2-chloro-3,4-difluorophenyl)-6-(1-(5-methoxy-6-(methoxycarbonyl)pyrazin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB41 and FA12.
LC-MS (ESI): $R_T$=4.167 min, mass calcd. for $C_{28}H_{27}ClF_2N_6O_5S$, 632.1, m/z found 632.9 [M+H]$^+$. $^1$H NMR (400 MHz, DMSO-d$_6$) δ 9.61 (d, J=3.6 Hz, 0.7H), 9.11 (s, 0.3H), 8.21 (s, 0.3H), 8.19 (s, 0.7H), 8.00-7.92 (m, 2H), 7.50-7.43 (m, 1H), 7.25-7.17 (m, 1H), 6.04 (s, 0.3H), 5.95 (d, J=3.2 Hz, 0.7H), 4.43-4.27 (m, 2H), 4.16-4.09 (m, 0.3H), 4.02-3.95 (m, 2H), 3.90-3.83 (m, 6.7H), 2.95-2.80 (m, 2H), 2.08-1.64 (m, 4H), 1.11-1.05 (m, 3H).

Compound XI-48-B

Ethyl 4-(2-chloro-3,4-difluorophenyl)-6-(1-(6-(methoxycarbonyl)-5-methylpyrazin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB30 and FA12.
LC-MS (ESI): $R_T$=1.858 min, mass calcd. for $C_{28}H_{27}ClF_2N_6O_4S$, 616.1, m/z found 617.0 [M+H]$^+$. $^1$H NMR (400 MHz, DMSO-d$_6$) δ 8.24 (s, 1H), 8.15 (s, 0.5H), 7.82 (d, J=3.2 Hz, 0.5H), 7.78 (d, J=3.2 Hz, 0.5H), 7.49 (d, J=3.2 Hz, 0.5H), 7.44 (d, J=3.2 Hz, 0.5H), 7.35 (s, 0.5H), 7.11-7.00 (m, 2H), 6.22 (s, 0.5H), 6.10 (d, J=2.4 Hz, 0.5H), 4.60-4.44 (m, 2H), 4.34-4.28 (m, 0.5H), 4.10-3.97 (m, 2.5H), 3.96 (s, 3H), 3.10-2.98 (m, 2H), 2.66 (s, 1.5H), 2.65 (s, 1.5H), 2.24-1.96 (m, 3H), 1.86-1.75 (m, 1H), 1.15 (t, J=7.2 Hz, 3H).

Compound XI-49-B

Ethyl 4-(2-chloro-3,4-difluorophenyl)-6-(1-(5-(methoxycarbonyl)-6-methylpyrazin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB29 and FA12.
LC-MS (ESI): $R_T$=2.127 min, mass calcd. for $C_{28}H_{27}ClF_2N_6O_4S$, 616.2, m/z found 617.1 [M+H]$^+$ 0.1H NMR (400 MHz, CDCl$_3$) δ 8.11 (s, 0.3H), 8.06 (s, 1H), 7.82-7.78 (m, 1H), 7.49-7.44 (m, 1H), 7.36 (s, 0.7H), 7.10-7.00 (m, 2H), 6.22 (s, 0.4H), 6.11 (d, J=2.8 Hz, 0.6H), 4.79-4.62 (m, 2H), 4.40-4.35 (m, 0.4H), 4.15-4.01 (m, 2.6H), 3.95-3.94 (m, 3H), 3.17-3.06 (m, 2H), 2.75 (s, 3H), 2.20-2.12 (m, 1H), 2.06-2.02 (m, 0.8H), 2.00-1.96 (m, 0.7H), 1.84-1.72 (m, 1.5H), 1.15 (t, J=7.2 Hz, 3H).

Compound XI-50-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)oxazole-5-carboxylate (a Single Stereoisomer)

By utilizing the analogous procedure of Method E, the title compound was synthesized from compound BB10 and FA12.
LC-MS (ESI): $R_T$=4.410 min, mass calcd. for $C_{27}H_{26}ClF_2N_5O_5S$, 605.1, m/z found 605.9 [M+H]$^+$. $^1$H NMR (400 MHz, CD$_3$OD) δ 7.89-7.87 (m, 1H), 7.73 (d, J=3.2 Hz, 1H), 7.61 (s, 1H), 7.26-7.22 (m, 2H), 6.16 (s, 0.3H), 6.10 (s, 0.7H), 4.36-4.26 (m, 4.2H), 4.09-4.02 (m, 2.8H), 3.26-3.19 (m, 2H), 2.18-1.92 (m, 3.3H), 1.75-1.72 (m, 0.7H), 1.34 (t, J=6.8 Hz, 3H), 1.16-1.11 (m, 3H).

Compound XI-52-S

Methyl 6-(4-(6-(2-chloro-3,4-difluorophenyl)-5-(ethoxycarbonyl)-2-(thiazol-2-yl)-3,6-dihydropyrimidin-4-yl)piperidin-1-yl)-2-methoxypyrimidine-4-carboxylate (a Single Stereoisomer)

By utilizing the analogous procedure of Method E, the title compound was synthesized from compound BB40 and FA12.
LC-MS (ESI): $R_T$=2.004 min, mass calcd. for $C_{28}H_{27}ClF_2N_6O_5S$, 632.1, m/z found 633.1 [M+H]$^+$. $^1$H NMR (400 MHz, CDCl$_3$) δ 8.12 (s, 0.4H), 7.86 (d, J=2.8 Hz, 0.6H), 7.83 (d, J=3.2 Hz, 0.4H), 7.53 (d, J=3.2 Hz, 0.6H), 7.48 (d, J=2.8 Hz, 0.4H), 7.39 (br s, 0.6H), 7.13-7.04 (m, 3H), 6.26 (s, 0.4H), 6.14 (d, J=2.4 Hz, 0.6H), 4.88-4.60 (m, 2H), 4.19-4.07 (m, 3H), 4.05 (s, 1.4H), 4.04 (s, 1.6H), 4.01 (s, 1.4H), 4.00 (s, 1.6H), 3.22-3.07 (m, 2H), 2.19-2.12 (m, 1H), 2.04-1.95 (m, 2H), 1.82-1.71 (m, 1H), 1.18 (t, J=7.2 Hz, 3H).

Compound XI-53-S

Methyl 6-(4-(6-(2-chloro-3,4-difluorophenyl)-5-(ethoxycarbonyl)-2-(thiazol-2-yl)-3,6-dihydropyrimidin-4-yl)piperidin-1-yl)-2-methylpyrimidine-4-carboxylate (a Single Stereoisomer)

By utilizing the analogous procedure of Method E, the title compound was synthesized from compound BB28 and FA12.

¹H NMR (400 MHz, DMSO-d₆) δ 9.62 (d, J=3.6 Hz, 0.7H), 9.31 (s, 0.3H), 7.99-7.90 (m, 2H), 7.50-7.42 (m, 1H), 7.24-7.15 (m, 2H), 6.03 (s, 0.3H), 5.94 (d, J=3.6 Hz, 0.7H), 4.73-4.56 (m, 2H), 4.27-4.20 (m, 0.3H), 4.04-3.94 (m, 2.7H), 3.86 (s, 3H), 3.03-2.93 (m, 2H), 2.44 (s, 3H), 2.11-2.01 (m, 0.3H), 1.99-1.65 (m, 3.7H), 1.11-1.04 (m, 3H).

Compound XI-54-S

Methyl 6-(4-(6-(2-chloro-3,4-difluorophenyl)-5-(ethoxycarbonyl)-2-(thiazol-2-yl)-3,6-dihydropyrimidin-4-yl)piperidin-1-yl)pyrimidine-4-carboxylate (a Single Stereoisomer)

By utilizing the analogous procedure of Method E, the title compound was synthesized from compound BB21 and FA12.

LC-MS (ESI): $R_T$=3.966 min, mass calcd. for $C_{27}H_{25}ClF_2N_6O_4S$, 602.1, m/z found 603.1 [M+H]⁺. ¹H NMR (400 MHz, DMSO-d₆) δ 9.61 (d, J=3.6 Hz, 0.7H), 9.27 (s, 0.3H), 8.61-8.60 (m, 1H), 7.98-7.90 (m, 2H), 7.50-7.37 (m, 2H), 7.24-7.15 (m, 1H), 6.04 (s, 0.3H), 5.95 (d, J=3.2 Hz, 0.7H), 4.61 (br s, 1.6H), 4.26-4.20 (m, 0.4H), 4.03-3.93 (m, 3H), 3.88 (s, 1H), 3.87 (s, 2H), 3.07-2.98 (m, 2H), 2.14-1.66 (m 4H), 1.11-1.04 (m 3H).

Compound XI-56-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5,6-dimethylpyrimidine-4-carboxylate (a Single Stereoisomer)

By utilizing the analogous procedure of Method E, the title compound was synthesized from compound BB37 and FA12.

LC-MS (ESI): $R_T$=2.18 min, mass calcd. for $C_{30}H_{31}ClF_2N_6O_4S$, 644.2, m/z found 644.9 [M+H]⁺. ¹H NMR (400 MHz, CDCl₃) δ 8.13 (s, 0.6H), 7.82-7.77 (m, 1H), 7.50-7.48 (m, 0.4H), 7.44-7.43 (m, 0.6H), 7.33 (s, 0.4H), 7.12-7.01 (m, 2H), 6.21 (s, 0.6H), 6.09 (d, J=2.4 Hz, 0.4H), 4.47-4.40 (m, 2H), 4.32-4.24 (m, 1H), 4.11-3.98 (m, 2H), 3.04-2.88 (m, 2H), 2.40 (s, 3H), 2.16 (s, 3H), 2.09-1.81 (m, 6H), 1.42 (t, J=6.8 Hz, 3H), 1.15 (t, J=7.2 Hz, 3H).

Compound XI-57-S methyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-6-methoxypyrimidine-4-carboxylate (a Single Stereoisomer)

By utilizing the analogous procedure of Method E, the title compound was synthesized from compound BB42 and FA12.

LC-MS (ESI): $R_T$=4.179 min, mass calcd. for $C_{28}H_{27}ClF_2N_6O_5S$, 632.1, m/z found 632.9 [M+H]⁺. ¹H NMR (400 MHz, DMSO-d₆) δ 9.60 (d, J=3.6 Hz, 0.7H), 9.23 (s, 0.3H), 7.99-7.90 (m, 2H), 7.50-7.43 (m, 1H), 7.25-7.17 (m, 1H), 6.53 (s, 0.3H), 6.52 (s, 0.7H), 6.04 (s, 0.3H), 5.95 (d, J=3.6 Hz, 0.7H), 4.94-4.83 (m, 2H), 4.25-4.18 (m, 0.3H), 4.03-3.93 (m, 2.7H), 3.92 (s, 3H), 3.85 (s, 3H), 3.00-2.90 (m, 2H), 2.09-1.65 (m, 4H), 1.12-1.05 (m, 3H).

Compound XI-58-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-6-methylpyrimidine-4-carboxylate (a Single Stereoisomer)

By utilizing the analogous procedure of Method E, the title compound was synthesized from compound BB31 and FA12.

LC-MS (ESI): $R_T$=4.338 min, mass calcd. for $C_{29}H_{29}ClF_2N_6O_4S$, 630.2, m/z found 630.9 [M+H]⁺. ¹H NMR (400 MHz, CDCl₃) δ 8.12 (s, 0.5H), 7.81 (d, J=2.8 Hz, 0.4H), 7.76 (d, J=2.8 Hz, 0.6H), 7.47 (d, J=3.2 Hz, 0.4H), 7.43 (d, J=2.8 Hz, 0.6H), 7.33 (d, J=2.4 Hz, 0.5H), 7.14-6.98 (m, 3H), 6.22 (s, 0.6H), 6.10 (d, J=2.8 Hz, 0.4H), 5.19-4.99 (m 2H), 4.44-4.36 (m 2H), 4.33-4.28 (m 0.6H), 4.13-4.00 (m, 2.4H), 3.09-2.95 (m, 2H), 2.43 (s, 1.2H), 2.42 (s, 1.8H), 2.25-1.90 (m, 2.5H), 1.81-1.66 (m, 1.5H), 1.42 (t, J=7.2 Hz, 3H), 1.17-1.13 (m, 3H).

Compound XI-59-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-isopropylpyrimidine-4-carboxylate (a Single Stereoisomer)

By utilizing the analogous procedure of Method E, the title compound was synthesized from compound BB45 and FA12.

LC-MS (ESI): $R_T$=2.569 min, mass calcd. for $C_{31}H_{33}ClF_2N_6O_4S$, 658.2, m/z found 658.9 [M+H]⁺. ¹H NMR (400 MHz, CDCl₃) δ 8.42 (d, J=1.2 Hz, 1H), 8.13 (s, 0.6H), 7.81 (d, J=3.2 Hz, 0.4H), 7.78 (d, J=3.6 Hz, 0.6H), 7.48 (d, J=2.8 Hz, 0.4H), 7.43 (d, J=2.8 Hz, 0.6H), 7.34 (d, J=2.4 Hz, 0.4H), 7.12-6.98 (m, 2H), 6.22 (s, 0.6H), 6.09 (d, J=2.4 Hz, 0.4H), 5.05-4.85 (m, 2H), 4.43 (q, J=7.2 Hz, 2H), 4.35-4.27 (m, 0.6H), 4.13-3.99 (m, 2.4H), 3.11-2.91 (m, 3H), 2.18-2.03 (m, 1H), 1.97-1.91 (m, 1H), 1.79-1.65 (m, 2H), 1.42 (t, J=7.2 Hz, 3H), 1.27-1.24 (m, 6H), 1.15 (t, J=7.2 Hz, 3H).

Compound XI-60-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-ethylpyrimidine-4-carboxylate (a Single Stereoisomer)

By utilizing the analogous procedure of Method E, the title compound was synthesized from compound BB38 and FA12.

LC-MS (ESI): $R_T$=3.851 min, mass calcd. for $C_{30}H_{31}ClF_2N_6O_4S$, 644.2, m/z found 644.9 [M+H]⁺. ¹H NMR (400 MHz, CDCl₃) δ 8.31 (d, J=2.8 Hz, 1H), 8.13 (s, 0.6H), 7.81 (d, J=2.8 Hz, 0.4H), 7.78 (d, J=3.2 Hz, 0.6H), 7.48 (d, J=3.2 Hz, 0.4H), 7.43 (d, J=2.8 Hz, 0.6H), 7.34 (d, J=2.4 Hz, 0.4H), 7.12-7.00 (m, 2H), 6.22 (s, 0.6H), 6.09 (d, J=2.8 Hz, 0.4H), 5.04-4.87 (m, 2H), 4.43 (q, J=7.2 Hz, 2H), 4.34-4.27 (m, 0.6H), 4.13-3.99 (m, 2.4H), 3.06-2.93 (m, 2H), 2.67-2.60 (m, 2H), 2.20-1.95 (m, 2.5H), 1.80-1.68 (m, 1.5H), 1.42 (t, J=7.2 Hz, 3H), 1.22-1.13 (m, 6H).

Compound XI-61-B

Ethyl 5-chloro-2-(4-(6-(2-chloro-3,4-difluorophenyl)-5-(ethoxycarbonyl)-2-(thiazol-2-yl)-3,6-dihydropyrimidin-4-yl)piperidin-1-yl)pyrimidine-4-carboxylate (a Single Stereoisomer)

By utilizing the analogous procedure of Method E, the title compound was synthesized from compound BB13 and FA12.

LC-MS (ESI): $R_T$=2.275 min, mass calcd. for $C_{28}H_{26}Cl_2F_2N_6O_4S$, 650.1, m/z found 651.0 [M+H]$^+$. $^1$H NMR (300 MHz, CDCl$_3$) δ 8.34 (d, J=4.8 Hz, 1H), 8.10 (s, 0.5H), 7.81-7.78 (m, 1H), 7.48 (d, J=2.8 Hz, 0.5H), 7.43 (d, J=3.2 Hz, 0.5H), 7.33 (s, 0.5H), 7.12-7.01 (m, 2H), 6.21 (s, 0.5H), 6.09 (d, J=2.7 Hz, 0.5H), 5.01-4.83 (m, 2H), 4.49-4.42 (m, 2H), 4.38-4.22 (m, 0.5H), 4.11-3.98 (m, 2.5H), 3.09-2.95 (m, 2H), 2.14-1.88 (m, 2.5H), 1.80-1.65 (m, 1.5H), 1.43 (t, J=7.2 Hz, 3H), 1.14 (t, J=7.2 Hz, 3H).

Compound XI-62-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-fluoropyrimidine-4-carboxylate (a Single Stereoisomer)

By utilizing the analogous procedure of Method E, the title compound was synthesized from compound BB35 and FA12.

LC-MS (ESI): $R_T$=2.08 min, mass calcd. for $C_{28}H_{26}ClF_3N_6O_4S$, 634.1, m/z found 634.8 [M+H]$^+$. $^1$H NMR (400 MHz, CDCl$_3$) δ 8.36 (s, 1H), 8.11 (s, 0.4H), 7.84-7.75 (m, 1H), 7.52-7.41 (m, 1H), 7.33 (s, 0.6H), 7.14-7.00 (m, 2H), 6.22 (s, 0.6H), 6.10 (s, 0.4H), 5.02-4.82 (m, 2H), 4.45 (q, J=7.2 Hz, 2H), 4.35-4.28 (m, 0.6H), 4.11-3.99 (m, 2.4H), 3.11-2.96 (m, 2H), 2.18-2.09 (m, 1H), 2.01-1.90 (m, 1.4H), 1.80-1.65 (m, 1.6H), 1.43 (t, J=7.2 Hz, 3H), 1.15 (t, J=6.8 Hz, 3H).

Compound XI-64-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-methyloxazole-5-carboxylate (a Single Stereoisomer)

By utilizing the analogous procedure of Method E, the title compound was synthesized from compound BB25 and FA12.

LC-MS (ESI): $R_T$=3.605 min, mass calcd. for $C_{28}H_{28}ClF_2N_5O_5S$, 619.2, m/z found 620.1 [M+H]$^+$. $^1$H NMR (400 MHz, DMSO-d$_6$) δ 9.63 (d, J=3.2 Hz, 0.7H), 9.29 (s, 0.3H), 8.00-7.91 (m, 2H), 7.50-7.42 (m, 1H), 7.24-7.16 (m, 1H) 6.04 (s, 0.3H), 5.95 (d, J=3.6 Hz, 0.7H), 4.26-4.11 (m, 4.3H), 4.02-3.95 (m, 2H), 3.90-3.82 (m, 0.7H), 3.16-3.06 (m, 2H), 2.30-2.29 (m, 3H), 2.23-1.80 (m, 3H), 1.72-1.64 (m, 1H), 1.29-1.23 (m, 3H), 1.10-1.04 (m, 3H).

Compound XI-66-N

Ethyl 4-(2-chloro-3,4-difluorophenyl)-6-(1-(5-(3-methoxy-3-oxopropyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB39 and FA12. LC-MS (ESI): $R_T$=3.407 min, mass calcd. for $C_{29}H_{29}ClF_2N_6O_4S$, 630.2, m/z found 631.2 [M+H]$^+$. $^1$H NMR (400 MHz, DMSO-d$_6$) δ 9.58 (d, J=3.6 Hz, 0.7H), 9.12 (s, 0.3H), 8.27 (d, J=4.8 Hz, 2H), 7.98-7.90 (m, 2H), 7.50-7.43 (m, 1H), 7.24-7.17 (m, 1H), 6.04 (s, 0.3H), 5.94 (d, J=3.6 Hz, 0.7H), 4.88-4.74 (m, 2H), 4.19-4.13 (m, 0.3H), 4.02-3.93 (m, 2H), 3.90-3.87 (m, 0.7H), 3.59 (s, 3H), 2.93-2.82 (m, 2H), 2.70-2.59 (m, 4H), 2.05-1.70 (m, 3.3H), 1.62-1.60 (m, 0.7H), 1.11-1.04 (m, 3H).

Compound XI-67-B

Ethyl 4-(2-chloro-3,4-difluorophenyl)-6-(1-(5-(1-ethoxy-2-methyl-1-oxopropan-2-yl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB46 and FA12.

LC-MS (ESI): $R_T$=1.90 min, mass calcd. for $C_{31}H_{33}ClF_2N_6O_4S$, 658.2, m/z found 659.1 [M+H]$^+$. $^1$H NMR (400 MHz, DMSO-d$_6$) δ 9.61 (d, J=3.2 Hz, 0.7H), 9.20 (s, 0.3H), 8.37 (s, 0.8H), 8.36 (m, 1.2H), 7.99-7.91 (m, 2H), 7.50-7.43 (m, 1H), 7.24-7.15 (m, 1H), 6.04 (s, 0.3H), 5.94 (d, J=3.2 Hz, 0.7H), 4.92-4.77 (m, 2H), 4.21-4.15 (m, 0.3H), 4.11-4.06 (m, 2H), 4.02-3.97 (m, 2H), 3.95-3.87 (m, 0.7H), 2.97-2.85 (m, 2H), 2.08-1.61 (m, 4H), 1.50 (s, 6H), 1.70-1.04 (m, 6H).

Compound XI-68-B

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-methyloxazole-4-carboxylate (a Single Stereoisomer)

By utilizing the analogous procedure of Method E, the title compound was synthesized from compound BB24 and FA12.

LC-MS (ESI): $R_T$=3.178 min, mass calcd. for $C_{28}H_{28}ClF_2N_5O_5S$, 619.2, m/z found 620.1 [M+H]$^+$. $^1$H NMR (400 MHz, DMSO-d$_6$) δ 9.62 (d, J=3.6 Hz, 0.8H), 9.16 (s, 0.2H), 8.00-7.92 (m, 2H), 7.50-7.43 (m, 1H), 7.24-7.16 (m, 1H), 6.04 (s, 0.3H), 5.94 (d, J=3.6 Hz, 0.7H), 4.26-4.20 (m, 2H), 4.08-3.95 (m, 4.3H), 3.84-3.78 (m, 0.7H), 3.07-2.94 (m, 2H), 2.48 (s, 3H), 2.13-1.61 (m, 4H), 1.27 (t, J=6.8 Hz, 3H), 1.10-1.04 (m 3H).

Compound XI-69-B

Ethyl-4-(2-chloro-3,4-difluorophenyl)-6-(1-(5-(2-ethoxy-2-oxoethyl)pyrimidin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB1 and FA12.

LC-MS (ESI): $R_T$=4.550 min, mass calcd. for $C_{29}H_{29}ClF_2N_6O_4S$, 630.2, m/z found 630.9 [M+H]$^+$. $^1$H NMR (400 MHz, DMSO-d$_6$) δ 9.59 (d, J=3.6 Hz, 0.7H), 9.16 (s, 0.3H), 8.28-8.27 (m, 2H), 7.98-7.90 (m, 2H), 7.50-7.42 (m, 1H), 7.24-7.16 (m, 1H), 6.04 (s, 0.3H), 5.94 (d, J=3.2 Hz, 0.7H), 4.91-4.76 (m, 2H), 4.20-4.14 (m, 0.3H), 4.10 (q, J=6.8 Hz, 2H), 4.00 (q, J=6.8 Hz, 2H), 3.95-3.88 (m, 0.7H), 3.54 (s, 2H), 2.93-2.84 (m, 2H), 2.04-1.71 (m, 3.3H), 1.63-1.60 (m, 0.7H), 1.20 (t, J=6.8 Hz, 3H), 1.11-1.04 (m, 3H).

Compound XI-70-N ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)oxazole-4-carboxylate (a Single Stereoisomer)

By utilizing the analogous procedure of Method E, the title compound was synthesized from compound BB6 and FA12.

LC-MS (ESI): $R_T$=4.433 min, mass calcd. for $C_{27}H_{26}ClF_2N_5O_5S$, 605.1, m/z found 606.1 [M+H]$^+$. Chiral analysis (Column: Chiralpak IA 5 μm 4.6*250 mm; Mobile Phase: Hex:EtOH=70:30 at 1.0 mL/min; Temp: 30° C.; Wavelength: 230 nm; $R_T$=8.799 min). $^1$H NMR (400 MHz, DMSO-d$_6$) δ 9.60 (s, 0.7H), 9.18 (s, 0.3H), 8.30 (d, J=5.2 Hz, 1H), 8.00-7.97 (m, 1.7H), 7.92 (d, J=3.2 Hz, 0.3H), 7.50-7.43 (m, 1H), 7.24-7.17 (m, 1H), 6.04 (s, 0.3H), 5.95 (s, 0.7H), 4.24 (q, J=7.2 Hz, 2H), 4.14-3.95 (m, 4.3H), 3.86-3.81 (m, 0.7H), 3.12-3.01 (m, 2H), 2.18-1.70 (m, 3H), 1.66-1.63 (m, 1H), 1.27 (t, J=7.2 Hz, 3H), 1.11-1.04 (m, 3H).

Compound XI-72-X and XI-72-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-methoxypyrimidine-5-carboxylate (a Single Stereoisomer) and ethyl 4-(4-(6-(2-chloro-3,4-difluorophenyl)-5-(ethoxycarbonyl)-2-(thiazol-2-yl)-3,6-dihydropyrimidin-4-yl)piperidin-1-yl)-2-methoxypyrimidine-5-carboxylate (a Single Stereoisomer)

By utilizing the analogous procedure of Method E, the title compound was synthesized from compound BB43 and FA12.

XI-72-X: $^1$H NMR (400 MHz, DMSO-d$_6$) δ 9.63-9.62 (m, 0.7H), 9.13 (s, 0.3H), 8.51-8.48 (m, 1H), 8.01-7.97 (m, 1.7H), 7.93-7.92 (m, 0.3H), 7.50-7.42 (m, 1H), 7.25-7.16 (m, 1H), 6.04 (s, 0.3H), 5.96-5.95 (s, 0.7H), 4.30-4.11 (m, 4H), 4.05-3.89 (m, 6H), 3.12-3.02 (m, 2H), 2.13-1.76 (m, 3.3H), 1.68-1.65 (m, 0.7H), 1.34-1.30 (m, 3H), 1.12-1.05 (m, 3H).

XI-72-S: $^1$H NMR (400 MHz, DMSO-d$_6$) δ 9.62-9.61 (m, 0.7H), 9.28 (s, 0.3H), 8.66-8.65 (m, 1H), 7.99-7.94 (m, 1.7H), 7.91-7.90 (m, 0.3H), 7.50-7.43 (m, 1H), 7.25-7.16 (m, 1H), 6.04 (s, 0.3H), 5.96-5.95 (m, 0.7H), 5.02-4.85 (m, 2H), 4.20 (q, J=7.2 Hz, 2.3H), 4.04-3.93 (m, 5.7H), 3.06-2.97 (m, 2H), 2.16-1.67 (m, 4H), 1.28-1.23 (m, 3H), 1.11-1.04 (m, 3H).

Compound XI-73-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-methylpyrimidine-5-carboxylate (a Single Stereoisomer)

By utilizing the analogous procedure of Method E, the title compound was synthesized from compound BB8 and FA12.

LC-MS (ESI): $R_T$=4.640 min, mass calcd. for $C_{29}H_{29}ClF_2N_6O_4S$, 630.2, m/z found 631.2 [M+H]$^+$. $^1$H NMR (400 MHz, DMSO-d$_6$) δ 9.61 (d, J=3.2 Hz, 0.7H), 9.26 (s, 0.3H), 8.77-8.76 (m, 1H), 7.99-7.90 (m, 2H), 7.50-7.42 (m, 1H), 7.24-7.16 (m, 1H), 6.04 (s, 0.3H), 5.95 (d, J=3.2 Hz, 0.7H), 5.04-4.91 (m, 2H), 4.28-4.22 (m, 2.3H), 4.03-3.92 (m, 2.7H), 3.04-2.96 (m, 2H), 2.60-(s, 1H), 2.59 (s, 2H), 2.10-1.66 (m, 4H), 1.30 (t, J=7.2 Hz, 3H), 1.11-1.04 (m, 3H).

Compound XI-75-S

Ethyl 5-(4-(6-(2-chloro-3,4-difluorophenyl)-5-(ethoxycarbonyl)-2-(thiazol-2-yl)-3,6-dihydropyrimidin-4-yl)piperidin-1-yl)-1,3,4-thiadiazole-2-carboxylate (a Single Stereoisomer)

By utilizing the analogous procedure of Method E, the title compound was synthesized from compound BB16 and FA12.

LC-MS (ESI): $R_T$=2.212 min, mass calcd. for $C_{26}H_{25}ClF_2N_6O_4S_2$ 622.1, m/z found 623.0 [M+H]$^+$. $^1$H NMR (400 MHz, DMSO-d$_6$ (one drop of D$_2$O)) δ 7.99-7.96 (m, 1.7H), 7.91-7.90 (m, 0.3H), 7.49-7.42 (m, 1H), 7.24-7.17 (m, 1H), 6.04 (s, 0.3H), 5.95 (s, 0.7H), 4.38-4.33 (m, 2H), 4.20-4.06 (m, 2H), 4.02-3.97 (m, 2H), 3.95-3.87 (m, 1H), 3.40-3.29 (m, 2H), 2.33-1.85 (m, 3H), 1.79-1.69 (m, 1H), 1.32 (t, J=6.8 Hz, 3H), 1.10-1.03 (m, 3H).

Compound XI-76-B

Ethyl 5-(4-(6-(2-chloro-3,4-difluorophenyl)-5-(ethoxycarbonyl)-2-(thiazol-2-yl)-3,6-dihydropyrimidin-4-yl)piperidin-1-yl)thiazole-2-carboxylate (a Single Stereoisomer)

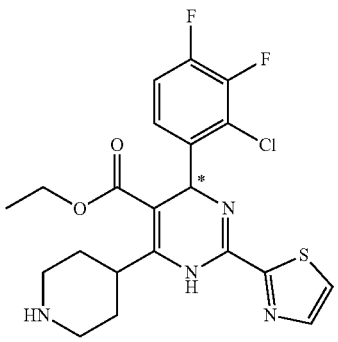

FA12

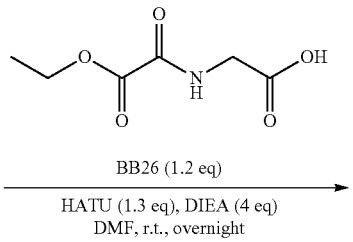

BB26 (1.2 eq)

HATU (1.3 eq), DIEA (4 eq)
DMF, r.t., overnight

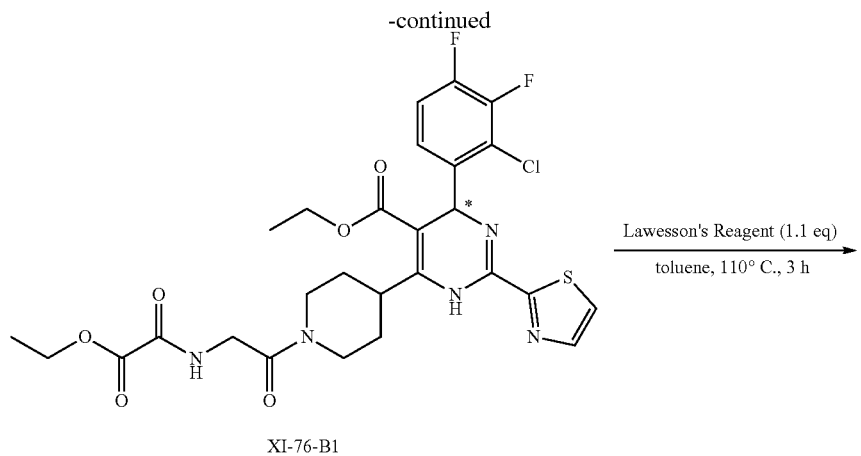

XI-76-B1

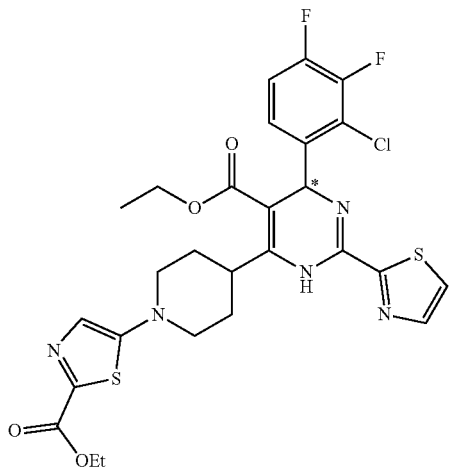

XI-76-B

Intermediate XI-76-B1

Ethyl 4-(2-chloro-3,4-difluorophenyl)-6-(1-(2-(2-ethoxy-2-oxoacetamido)acetyl)piperidin-4-yl)-2-(thiazol-2-yl)-1,4-dihydropyrimidine-5-carboxylate To a solution of 2-(2-ethoxy-2-oxoacetamido)acetic acid BB26 (122 mg, 70% purity, 0.488 mmol) and N,N-diisopropylethylamine (215 mg, 1.63 mmol) in N,N-dimethylformamide (4 mL) was added o-(7-azabenzotriazol-1-yl)-N,N,N',N'-tetramethyluronium hexafluorophosphate (205 mg, 0.528 mmol). The mixture was stirred at room temperature for 30 minutes, then (S*)-ethyl 4-(2-chloro-3,4-difluorophenyl)-6-(piperidin-4-yl)-2-(thiazol-2-yl)-1,4-dihydropyrimidine-5-carboxylate FA12 (200 mg, 95% purity, 0.407 mmol) was added. After stirred at room temperature overnight, the mixture was poured into water (30 mL) and extracted with ethyl acetate (30 mL) twice. The combined organic layers were washed with water (30 mL) and brine (30 mL), dried over $Na_2SO_{4(s)}$ and filtered.

The filtrate was concentrated to give a residue, which was purified by silica gel chromatography (petroleum ether:ethyl acetate=2:1 to 2:3) to give the title compound (130 mg, 90% purity, 46% yield) as yellow solids. LC-MS (ESI): $R_T$=1.45 min, mass calcd. for $C_{27}H_{28}ClF_2N_5O_6S$, 623.1, m/z found 624.0 [M+H]$^+$.

Compound XI-76-B

Ethyl 5-(4-(6-(2-chloro-3,4-difluorophenyl)-5-(ethoxycarbonyl)-2-(thiazol-2-yl)-3,6-dihydropyrimidin-4-yl)piperidin-1-yl)thiazole-2-carboxylate To a solution of ethyl 4-(2-chloro-3,4-difluorophenyl)-6-(1-(2-(2-ethoxy-2-oxoacetamido)acetyl)piperidin-4-yl)-2-(thiazol-2-yl)-1,4-dihydropyrimidine-5-carboxylate XI-76-B1 (130 mg, 90% purity, 0.187 mmol) in toluene (2 mL) was added 2,4-bis(4-methoxyphenyl)-1,3,2,4-dithiadiphosphetane 2,4-disulfide (Lawesson's reagent, 83 mg, 0.205 mmol) under nitrogen atmosphere at room temperature. After stirred at 110° C. for 3 hours and then cooled down to room temperature, the mixture was concentrated under reduced pressure to remove the volatile, then poured into brine (10 mL) and extracted with ethyl acetate (20 mL) for three times. The combined organic layers were dried over $Na_2SO_4$ (s) and filtered. The filtrate was concentrated under reduced pressure to give a crude product, which was purified by C18 column (acetonitrile:water=50% to 100%) to give the title compound (70 mg, 98% purity, 59% yield) as yellow solids. $^1$H NMR (400 MHz, DMSO-$d_6$) δ 9.64 (d, J=4.0 Hz, 0.7H), 9.18 (m, 0.3H), 8.00-7.92 (m, 2H), 7.50-7.44 (m, 1H), 7.33-7.32 (m, 1H), 7.25-7.17 (m, 1H), 6.04 (s, 0.3H), 5.95 (d, J=3.2 Hz, 0.7H), 4.29 (q, J=3.2 Hz, 0.7H), 4.02-3.95 (m, 2H), 3.87-3.72 (m, 3H), 3.19-3.04 (m, 2H), 2.33-1.75 (m, 3.3H), 1.69-1.65 (m, 0.7H), 1.29 (t, J=7.2 Hz, 3H), 1.10-1.04 (m, 3H).

Compound XI-77-S

Methyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-(methoxymethyl)thiazole-5-carboxylate (a Single Stereoisomer)

By utilizing the analogous procedure of Method E, the title compound was synthesized from compound BB47 and FA12.

LC-MS (ESI): $R_T$=4.022 min, mass calcd. for $C_{28}H_{28}ClF_2N_5O_5S_2$ 651.1, m/z found 652.1 [M+H]$^+$. $^1$H NMR (400 MHz, DMSO-d$_6$) δ 9.64 (d, J=3.6 Hz, 0.8H), 9.32 (s, 0.2H), 8.00-7.91 (m, 2H), 7.50-7.43 (m, 1H), 7.25-7.16 (m, 1H), 6.04 (s, 0.2H), 5.95 (d, J=3.2 Hz, 0.8H), 4.59 (s, 2H), 4.16-4.06 (m, 2H), 4.02-3.97 (m, 2H), 3.95-3.87 (m, 1H), 3.74 (s, 3H), 3.32 (s, 2.4H), 3.31 (s, 0.6H), 3.24-3.15 (m, 2H), 2.25-2.20 (m, 0.2H), 2.09-1.68 (m, 3.8H), 1.11-1.04 (m, 3H).

Compound XI-78-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA12.

LC-MS (ESI): $R_T$=3.944 min, mass calcd. for $C_{27}H_{26}ClF_2N_5O_4S_2$ 621.1, m/z found 622.1 [M+H]$^+$. $^1$H NMR (400 MHz, DMSO-d$_6$) δ 9.64 (d, J=3.2 Hz, 0.7H), 9.31 (s, 0.3H), 8.00-7.91 (m, 2H), 7.87 (s, 1H), 7.50-7.43 (m, 1H), 7.25-7.16 (m, 1H), 6.04 (s, 0.3H), 5.95 (d, J=3.2 Hz, 0.7H), 4.25-4.08 (m, 4.2H), 4.02-3.86 (m, 2.8H), 3.26-3.17 (m, 2H), 2.25-1.84 (m, 3H), 1.77-1.68 (m, 1H), 1.26 (t, J=7.2 Hz, 3H), 1.11-1.04 (m, 3H).

Compound XI-79-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-(trifluoromethyl)thiazole-5-carboxylate (a Single Stereoisomer)

By utilizing the analogous procedure of Method E, the title compound was synthesized from compound BB15 and FA12.

LC-MS (ESI): $R_T$=3.656 min, mass calcd. for $C_{28}H_{25}ClF_5N_5O_4S_2$ 689.1, m/z found 690.0 [M+H]$^+$. $^1$H NMR (400 MHz, DMSO-d$_6$) δ 9.65 (d, J=3.2 Hz, 0.7H), 9.35 (s, 0.3H), 8.00-7.92 (m, 2H), 7.50-7.43 (m, 1H), 7.25-7.12 (m, 1H) 6.04 (s, 0.3H), 5.95 (d, J=3.2 Hz, 0.7H), 4.28-4.02 (m, 4.3H), 4.00-3.87 (m, 2.7H), 3.27-3.20 (m, 2H), 2.27-1.85 (m, 3H), 1.76-1.70 (m, 1H), 1.26 (t, J=7.2 Hz, 3H), 1.11-1.03 (m, 3H).

Compound XI-80-S

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)thiazole-4-carboxylate (a Single Stereoisomer)

By utilizing the analogous procedure of Method E, the title compound was synthesized from compound BB11 and FA12.

LC-MS (ESI): $R_T$=1.84 min, mass calcd. for $C_{27}H_{26}ClF_2N_5O_4S_2$ 621.1, m/z found 622.3 [M+H]$^+$. $^1$H NMR (400 MHz, DMSO-d$_6$) δ 9.63 (d, J=4.0 Hz, 0.7H), 9.22 (s, 0.3H), 8.00-7.96 (m, 1.7H), 7.92 (d, J=3.2 Hz, 0.3H), 7.70 (s, 1H), 7.50-7.43 (m, 1H), 7.25-7.17 (m, 1H), 6.04 (s, 0.3H), 5.95 (d, J=3.2 Hz, 0.7H), 4.24 (q, J=7.2 Hz, 2H), 4.13-3.95 (m, 4.3H), 3.91-3.82 (m, 0.7H), 3.17-3.04 (m, 2H), 2.10-1.65 (m 4H), 1.28 (t, J=7.2 Hz, 3H), 1.01-1.04 (m 3H).

Compound XI-81-B

Ethyl 2-(4-(6-(4-bromo-2-chlorophenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB4 and FA13.

LC-MS (ESI): $R_T$=2.17 min, mass calcd. for $C_{28}H_{28}BrClN_6O_4S$ 658.1, m/z found 658.7 [M+H]$^+$. $^1$H NMR (400 MHz, CDCl$_3$) δ 8.29-8.28 (m, 1H), 8.14 (s, 0.5H), 7.81 (d, J=3.2 Hz, 0.5H), 7.77 (d, J=3.2 Hz, 0.5H), 7.56 (s, 1H), 7.47 (d, J=3.2 Hz, 0.5H), 7.43 (d, J=2.8 Hz, 1H), 7.38-7.32 (m, 1H), 7.21-7.18 (m, 1H), 6.19 (s, 0.5H), 6.05 (d, J=2.4 Hz, 0.5H), 5.00-4.87 (m, 2H), 4.43 (q, J=7.2 Hz, 2H), 4.33-4.27 (m, 0.5H), 4.07-4.02 (m, 0.5H), 3.63 (s, 1.5H), 3.61 (s, 1.5H), 3.06-2.98 (m, 2H), 2.28 (s, 1.5H), 2.27 (s, 1.5H), 2.19-2.05 (m, 1H), 1.98-1.89 (m, 1.4H), 1.78-1.67 (m, 1.6H), 1.43 (t, J=7.2 Hz, 3H).

Compound XI-82-B methyl 2-(4-(6-(2-bromo-3,4-difluorophenyl)-5-(methoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA14.

LC-MS (ESI): $R_T$=2.064 min, mass calcd. for $C_{25}H_{22}BrF_2N_5O_4S_2$ 637.0, m/z found 637.9 [M+H]$^+$. $^1$H NMR (400 MHz, DMSO-d$_6$) δ 9.67 (d, J=3.2 Hz, 0.7H), 9.40 (s, 0.3H), 8.00-7.95 (m, 2H), 7.90 (s, 1H), 7.53-7.46 (m, 1H), 7.25-7.21 (m, 0.7H), 7.16-7.13 (m, 0.3H), 6.01 (s, 0.3H), 5.94 (d, J=3.6 Hz, 0.7H), 4.18-4.08 (m, 2.5H), 3.93-3.87 (m, 0.5H), 3.76 (s, 3H), 3.54 (s, 2H), 3.53 (s, 1H), 3.28-3.18 (m, 2H), 2.07-1.97 (m, 1.5H), 1.92-1.84 (m, 1.5H), 1.77-1.64 (m, 1H).

Compound XI-83-B

Methyl 2-(4-(6-(2-bromo-3-fluorophenyl)-5-(methoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA15.

LC-MS (ESI): $R_T$=2.033 min, mass calcd. for $C_{25}H_{23}BrFN_5O_4S_2$ 619.0, m/z found 620.0 [M+H]$^+$. $^1$H NMR (400 MHz, CDCl$_3$) δ 8.14 (s, 0.2H), 7.92-7.91 (m, 1H), 7.83 (d, J=3.2 Hz, 0.8H), 7.79 (d, J=3.2 Hz, 0.2H), 7.53 (s, 0.8H), 7.50 (d, J=3.2 Hz, 0.8H), 7.45 (d, J=3.2 Hz, 0.2H), 7.25-7.20 (m, 1H), 7.13-7.01 (m 2H), 6.27 (s, 0.2H), 6.12 (d, J=2.8 Hz, 0.8H), 4.37-4.19 (m, 2H), 4.16-4.06 (m, 1H), 3.85 (s, 0.6H), 3.84 (s, 2.4H), 3.61 (s, 2.4H), 3.60 (s, 0.6H), 3.34-3.22 (m, 2H), 2.32-2.22 (m, 1H), 2.16-2.02 (m, 2H), 1.93-1.77 (m, 1H).

Compound XI-84-N

Methyl 2-(4-(6-(2-bromo-4-fluorophenyl)-5-(methoxycarbonyl)-2-(thiazol-2-yl)-3,6-dihydropyrimidin-4-yl)piperidin-1-yl)thiazole-5-carboxylate (a Single Stereoisomer)

By utilizing the analogous procedure of Method E, the title compound was synthesized from compound BB3 and FA16.

LC-MS (ESI): $R_T$=2.745 min, mass calcd. for $C_{25}H_{23}BrFN_5O_4S_2$ 619.0, m/z found 619.7 [M+H]$^+$. $^1$H NMR (400 MHz, CDCl$_3$) δ 8.12 (s, 1H), 7.91-7.90 (m, 1H), 7.83-7.79 (m, 1H), 7.50 (d, J=3.2 Hz, 1.7H), 7.44 (d, J=2.8 Hz, 0.3H), 7.34-7.32 (m, 1H), 7.03-6.93 (m, 1H), 6.18 (s, 0.2H), 6.05 (d, J=2.4 Hz, 0.8H), 4.35-4.15 (m, 2.2H), 4.10-4.04 (m, 0.8H), 3.85 (s, 0.5H), 3.84 (s, 2.5H), 3.62 (s, 2.5H), 3.61 (s, 0.5H), 3.33-3.21 (m, 2H), 2.31-2.21 (m, 0.8H), 2.15-1.97 (m, 2H), 1.91-1.76 (m, 1.2H).

Compound XI-85-M

Ethyl 2-(3-(6-(2-chloro-3,4-difluorophenyl)-5-(ethoxycarbonyl)-2-(thiazol-2-yl)-3,6-dihydropyrimidin-4-yl)pyrrolidin-1-yl)oxazole-4-carboxylate (a Single Stereoisomer)

Compound XI-85

Ethyl 2-(3-(6-(2-chloro-3,4-difluorophenyl)-5-(ethoxycarbonyl)-2-(thiazol-2-yl)-3,6-dihydropyrimidin-4-yl)pyrrolidin-1-yl)oxazole-4-carboxylate (a Mixture of 4 Stereoisomers)

By utilizing the analogous procedure of Method E, the title compound was synthesized from compound BB6 and FA17.

LC-MS (ESI): $R_T$=4.271 min, mass calcd. for $C_{26}H_{24}ClF_2N_5O_5S$, 591.1, m/z found 591.9 [M+H]$^+$. $^1$H NMR (400 MHz, CD$_3$OD) δ 8.08-8.01 (m, 1H), 7.87-7.86 (m, 1H), 7.71-7.69 (m, 1H), 7.28-7.23 (m, 2H), 6.17 (s, 0.2H), 6.11 (d, J=4.8 Hz, 0.8H), 4.62-4.59 (m, 1H), 4.34-4.28 (m, 2H), 4.09-4.00 (m, 2.4H), 3.88-3.62 (m, 3.6H), 2.45-2.39 (m, 1H), 2.33-2.28 (m, 1H), 1.36-1.28 (m, 3H), 1.14 (t, J=7.2 Hz, 3H).

A stereoisomeric mixture of ethyl-2-(3-(6-(2-chloro-3,4-difluorophenyl)-5-(ethoxycarbonyl)-2-(thiazol-2-yl)-3,6-dihydropyrimidin-4-yl)pyrrolidin-1-yl)oxazole-4-carboxylate XI-85 (800 mg, 90% purity, 1.20 mmol) was separated by chiral Prep. HPLC (Column: Chiralpak IF 5 μm 20*250 mm; Mobile Phase: Hex:EtOH:DEA=70:30:0.3 at 13 mL/min; Temp: 30° C.; Wavelength: 214 nm) to afford the title compounds XI-85-M (150 mg, 99.2% purity, 19% yield, 100% stereopure) and Group 1 (mixture of XI-85-N, XI-85-P and XI-85-Q, 600 mg) as yellow solids. Group 1 (600 mg, 0.960 mmol) was separated by chiral Prep. HPLC (Column: Chiralpak IG 5 μm 20*250 mm; Mobile Phase: Hex:EtOH:DEA=70:30:0.3 at 15 mL/min; Temp: 30° C.; Wavelength: 214 nm) to afford the title compounds XI-85-N (130 mg, 99.5% purity, 16% yield, 100% stereopure), XI-85-P (150 mg, 99.4% purity, 19% yield, 100% stereopure) and XI-85-Q (130 mg, 99.2% purity, 16% yield, 100% stereopure) as yellow solids.

XI-85-M: LC-MS (ESI): $R_T$=3.806 min, mass calcd. for $C_{26}H_{24}ClF_2N_5O_5S$, 591.1, m/z found 592.1 [M+H]$^+$. Chiral analysis (Column: Chiralpak IF 5 μm 4.6*250 mm; Mobile Phase: Hex:EtOH:DEA=70:30:0.2 at 1 mL/min; Temp: 30° C.; Wavelength: 230 nm, $R_T$=8.999 min). $^1$H NMR (400 MHz, DMSO-d$_6$) δ 9.73 (d, J=3.6 Hz, 0.9H), 9.42 (s, 0.1H), 8.33 (s, 0.1H), 8.28 (s, 0.9H), 8.00-7.93 (m, 2H), 7.50-7.43 (m, 1H), 7.27-7.23 (m, 1H), 6.05 (s, 0.1H), 5.96 (d, J=3.2 Hz, 0.9H), 4.47-4.43 (m, 1H), 4.23 (q, J=7.2 Hz, 2H), 3.99 (q, J=7.2 Hz, 2H), 3.84-3.67 (m, 3H), 3.56-3.53 (m, 1H), 2.23-2.18 (m, 2H), 1.26 (t, J=7.2 Hz, 3H), 1.09-1.02 (m, 3H).

XI-85-N: LC-MS (ESI): $R_T$=3.805 min, mass calcd. for $C_{26}H_{24}ClF_2N_5O_5S$, 591.1, m/z found 592.1 [M+H]$^+$. Chiral analysis (Column: Chiralpak IF 5 μm 4.6*250 mm; Mobile Phase: Hex:EtOH:DEA=70:30:0.2 at 1 mL/min; Temp: 30° C.; Wavelength: 230 nm, $R_T$=7.434 min). $^1$H NMR (400 MHz, DMSO-d$_6$) δ 9.72 (d, J=3.2 Hz, 0.8H), 9.41 (s, 0.2H), 8.33 (s, 0.2H), 8.27 (s, 0.8H), 8.00-7.94 (m, 2H), 7.45 (q, J=8.8 Hz, 1H), 7.27-7.23 (m, 1H), 6.05 (s, 0.1H), 5.96 (d, J=3.2 Hz, 0.9H), 4.47-4.43 (m, 1H), 4.21 (q, J=7.2 Hz, 2H), 3.98 (q, J=6.8 Hz, 2H), 3.84-3.66 (m, 3H), 3.54 (q, J=7.2 Hz, 1H), 2.22-2.17 (m, 2H), 1.26 (t, J=7.2 Hz, 3H), 1.09-1.02 (m, 3H).

XI-85-P: LC-MS (ESI): $R_T$=3.786 min, mass calcd. for $C_{26}H_{24}ClF_2N_5O_5S$, 591.1, m/z found 592.1 [M+H]$^+$. Chiral analysis (Column: Chiralpak IG 5 μm 4.6*250 mm; Mobile Phase: Hex:EtOH:DEA=70:30:0.2 at 1 mL/min; Temp: 30° C.; Wavelength: 230 nm, $R_T$=14.636 min). $^1$H NMR (400 MHz, DMSO-d$_6$) δ 9.72 (s, 0.8H), 9.44 (s, 0.2H), 8.34 (s, 0.2H), 8.27 (s, 0.8H), 8.00-7.94 (m 2H), 7.53-7.46 (m, 1H), 7.28-7.24 (m, 1H), 6.07 (s, 0.2H), 5.98 (s, 0.8H), 4.47-4.44 (m, 1H), 4.22 (q, J=6.8 Hz, 2H), 3.99 (q, J=7.6 Hz, 2H), 3.80-3.54 (m, 4H), 2.34-2.29 (m, 2H), 1.28 (t, J=6.8 Hz, 3H), 1.11-1.05 (m, 3H).

XI-85-Q: LC-MS (ESI): $R_T$=3.792 min, mass calcd. for $C_{26}H_{24}ClF_2N_5O_5S$, 591.1, m/z found 592.1 [M+H]$^+$. Chiral analysis (Column: Chiralpak IG 5 μm 4.6*250 mm; Mobile Phase: Hex:EtOH:DEA=70:30:0.2 at 1 mL/min; Temp: 30° C.; Wavelength: 230 nm, $R_T$=16.379 min). $^1$H NMR (400 MHz, DMSO-d$_6$) δ 9.72 (m, 0.8H), 9.44 (s, 0.2H), 8.33 (s, 0.2H), 8.26 (s, 0.8H), 7.99-7.93 (m, 2H), 7.52-7.45 (m, 1H), 7.27-7.22 (m, 1H), 6.06 (s, 0.1H), 5.97 (s, 0.9H), 4.48-4.44 (m, 1H), 4.21 (q, J=6.8 Hz, 2H), 3.97 (q, J=7.2 Hz, 2H), 3.78-3.53 (m, 4H), 2.33-2.27 (m, 2H), 1.26 (t, J=7.2 Hz, 3H), 1.09-1.02 (m, 3H).

Compound XI-86-N

Ethyl 2-(3-(6-(2-chloro-3,4-difluorophenyl)-5-(ethoxycarbonyl)-2-(thiazol-2-yl)-3,6-dihydropyrimidin-4-yl)azetidin-1-yl)oxazole-4-carboxylate (a Single Stereoisomer)

Intermediate XI-86-R

Ethyl-2-(3-(6-(2-chloro-3,4-difluorophenyl)-5-(ethoxycarbonyl)-2-(thiazol-2-yl)-3,6-dihydropyrimidin-4-yl)azetidin-1-yl)oxazole-4-carboxylate (a Mixture of 2 Stereoisomers)

By utilizing the analogous procedure of Method E, the title compound was synthesized from compound BB6 and FA18.

LC-MS (ESI): R$_T$=2.189 min, mass calcd. for C$_{25}$H$_{22}$ClF$_2$N$_5$O$_5$S, 577.1, m/z found 578.1 [M+H]$^+$. $^1$H NMR (400 MHz, DMSO-d$_6$) δ 9.82 (s, 0.9H), 9.48 (s, 0.1H), 8.37 (s, 0.1H), 8.32 (s, 0.9H), 8.02-8.00 (m, 1.8H), 9.48 (d, J=3.2 Hz, 0.2H), 7.48-7.42 (m, 1H), 7.31-7.28 (m, 1H), 6.05 (s, 0.1H), 5.97 (s, 0.9H), 4.93-4.88 (m, 0.1H), 4.71-4.64 (m, 0.9H), 4.37-4.34 (m, 3H), 4.30-4.21 (m, 3H), 3.99 (q, J=7.2 Hz, 2H), 1.26 (t, J=7.2H, 3H), 1.08 (t, J=7.2H, 3H).

A stereoisomeric mixture of ethyl 2-(3-(6-(2-chloro-3,4-difluorophenyl)-5-(ethoxycarbonyl)-2-(thiazol-2-yl)-3,6-dihydropyrimidin-4-yl)azetidin-1-yl)oxazole-4-carboxylate XI-86-R (300 mg, 96% purity, 0.498 mmol) was separated by chiral prep. HPLC (separation condition: Column: Chiralpak IE 5 μm 20*250 mm; Mobile Phase: Hex:EtOH=70:30 at 15 mL/min; Wavelength: 214 nm) to give the compounds XI-86-M (90 mg, 99.8% purity, 31% yield, 100% stereopure) and XI-86-N (80 mg, 99.5% purity, 28% yield, 98.6% stereopure).

XI-86-M: LC-MS (ESI): R$_T$=4.130 min, mass calcd. for C$_{25}$H$_{22}$ClF$_2$N$_5$O$_5$S, 577.1, m/z found 578.1 [M+H]$^+$. Chiral HPLC (Column: Chiralpak IE 5 μm 4.6*250 mm; Mobile Phase: Hex:EtOH=70:30 at 1.0 mL/min; Temp: 30° C.; Wavelength: 230 nm, R$_T$=16.261 min). $^1$H NMR (400 MHz, DMSO-d$_6$) δ 9.83 (s, 1H), 8.33 (s, 1H), 8.00-8.02 (m, 2H), 7.42-7.49 (m, 1H), 7.28-7.32 (m, 1H), 5.97 (s, 1H), 4.64-4.69 (m, 1H), 4.35-4.37 (m, 3H), 4.21-4.31 (m, 3H), 3.98 (q, J=7.2 Hz, 2H), 1.27 (t, J=7.2 Hz, 3H), 1.08 (t, J=6.8 Hz, 3H).

XI-86-N: LC-MS (ESI): R$_T$=4.135 min, mass calcd. for C$_{25}$H$_{22}$ClF$_2$N$_5$O$_5$S, 577.1, m/z found 578.1 [M+H]$^+$. Chiral HPLC (Column: Chiralpak IE 5 μm 4.6*250 mm; Mobile Phase: Hex:EtOH=70:30 at 1.0 mL/min; Temp: 30° C.; Wavelength: 230 nm, R$_T$=18.383 min). $^1$H NMR (400 MHz, DMSO-d$_6$) δ 9.82 (d, J=3.2 Hz, 0.9H), 9.49 (s, 0.1H), 8.38 (0.1H), 8.33 (s, 0.9H), 8.02-7.95 (m, 2H), 7.49-7.42 (m, 1H), 7.31-7.28 (m, 1H), 6.05 (s, 0.1H), 5.97 (d, J=3.2 Hz, 0.9H), 4.91 (s, 0.1H), 4.71-4.63 (m, 0.9H), 4.37-4.34 (m, 3H), 4.30-4.21 (m, 3H), 3.98 (q, J=7.2 Hz, 2H), 1.26 (t, J=7.2 Hz, 3H), 1.08 (t, J=7.2 Hz, 3H).

Compound XI-87-S

Methyl 4-(2-chloro-4-fluorophenyl)-6-(1-(4-(methoxycarbonyl)-5-methylpyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB56 and FA7.
LC-MS (ESI): R$_T$=2.028 min, mass calcd. for C$_{28}$H$_{27}$ClFN$_5$O$_4$S, 583.1, m/z found 584.1 [M+H]$^+$.

Compound XI-88-4

Ethyl 2-(4-(6-(2-chloro-3,4-difluorophenyl)-5-(methoxycarbonyl)-2-(thiazol-2-yl)-3,6-dihydropyrimidin-4-yl)piperidin-1-yl)-5-(dimethylamino)pyrimidine-4-carboxylate (a Single Stereoisomer)

By utilizing the analogous procedure of Method E, the title compound was synthesized from compound BB57 and FA10.
LC-MS (ESI): R$_T$=1.99 min, mass calcd. for C$_{29}$H$_{30}$ClF$_2$N$_7$O$_4$S, 645.2, m/z found 645.9 [M+H]$^+$. $^1$H NMR (400 MHz, DMSO-d$_6$) δ 9.62 (s, 0.7H), 9.32 (s, 0.3H), 8.51 (s, 0.3H), 8.49 (s, 0.7H), 7.99-7.91 (m, 2H), 7.49-7.45 (m, 1H), 7.23-7.14 (m, 1H), 6.02 (s, 0.3H), 5.94 (s, 0.7H), 4.78-4.66 (m, 2H), 4.34 (q, J=6.8 Hz, 2H), 4.22-4.16 (m, 0.3H), 3.92-3.87 (m, 0.7H), 3.54 (s, 3H), 2.96-2.82 (m, 2H), 2.65 (s, 6H), 2.08-1.60 (m, 4H), 1.30 (t, J=6.8 Hz, 3H).

Compound XI-89-2 ethyl 5-(bis(2,4-dimethoxybenzyl)amino)-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylate (a Single Stereoisomer)

By utilizing the analogous procedure of Method E, the title compound was synthesized from compound BB58 and FA10.
$^1$H NMR (400 MHz, CDCl$_3$) δ 8.16 (s, 0.6H), 8.04 (s, 0.6H), 8.03 (s, 0.4H), 7.81 (d, J=3.2 Hz, 0.4H), 7.78 (d, J=3.2 Hz, 0.6H), 7.49 (d, J=3.2 Hz, 0.4H), 7.43 (d, J=3.2 Hz, 0.6H), 7.40 (d, J=2.0 Hz, 0.4H), 7.31-7.28 (m, 2H), 7.11-6.98 (m, 2H), 6.43 (d, J=8.4 Hz, 2H), 6.39-6.38 (m, 2H), 6.19 (s, 0.6H), 6.06 (d, J=2.4 Hz, 0.4H), 4.95-4.73 (m, 2H), 4.37 (q, J=7.6 Hz, 2H), 4.32-4.22 (m, 0.6H), 4.11 (s, 2.4H), 4.10 (s, 1.6H), 4.05-3.96 (m, 0.4H), 3.78 (s, 6H), 3.71 (s, 6H), 3.62 (s, 1.8H), 3.60 (s, 1.2H), 2.99-2.87 (m, 2H), 2.18-2.03 (m, 0.5H), 2.01-1.97 (m, 0.5H), 1.96-1.86 (m, 1.5H), 1.78-1.64 (m, 1.5H), 1.35 (t, J=7.6 Hz, 3H).

Compound XI-90-3 methyl 4-(2-chloro-3,4-difluorophenyl)-6-(1-(4-(methoxycarbonyl)-5-nitropyridin-2-yl)piperidin-4-yl)-2-(thiazol-2-yl)-1,4-dihydropyrimidine-5-carboxylate (a Single Stereoisomer)

By utilizing the analogous procedure of Method E, the title compound was synthesized from compound BB59 and FA10.
LC-MS (ESI): R$_T$=1.81 min, mass calcd. for C$_{27}$H$_{23}$ClF$_2$N$_6$O$_6$S, 632.1, m/z found 633.1 [M+H]$^+$. $^1$H NMR (400 MHz, CDCl$_3$) δ 8.99 (s, 1H), 8.13 (s, 0.3H), 7.83-7.79 (m, 1H), 7.50 (d, J=3.2 Hz, 0.7H), 7.45 (s, 1H), 7.11-7.00 (m, 2H), 6.62-6.10 (m, 1H), 6.20 (s, 0.3H), 6.08 (d, J=2.0 Hz, 0.7H), 4.91-4.53 (m, 2H), 4.44-4.37 (m, 0.3H), 4.20-4.14 (m, 0.7H), 3.96 (s, 3H), 3.63 (s, 3H), 3.25-3.15 (m, 2H), 2.21-1.69 (m, 4H).

Compound XI-91-1

Ethyl 2-(4-(6-(3,4-difluoro-2-methylphenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB4 and FA10.
LC-MS (ESI): R$_T$=2.04 min, mass calcd. for C$_{29}$H$_{30}$ClF$_2$N$_6$O$_4$S, 596.2, m/z found 597.0 [M+H]$^+$. $^1$H NMR (400 MHz, CDCl$_3$) δ 8.28 (s, 1H), 8.10 (s, 0.8H), 7.78-7.75 (m, 1H), 7.47 (s, 0.2H), 7.40 (d, J=3.2 Hz, 0.8H), 7.10 (br s, 0.2H), 7.04 (br s, 0.2H), 6.96-6.86 (m, 1.8H), 5.95 (s, 0.8H), 5.86 (s, 0.2H), 5.04-4.88 (m. 2H), 4.42 (q, J=7.2 Hz, 2H), 4.32 (t, J=12.4 Hz, 1H), 3.61 (s, 3H), 3.07-2.98 (m, 2H), 2.57 (s, 2.5H), 2.43 (s, 0.5H), 2.28 (s, 3H), 2.11-2.08 (m, 1H), 1.97-1.94 (m, 1H), 1.82-1.68 (m, 2H), 1.42 (t, J=7.2 Hz, 3H).

Compound XI-92-1

Ethyl 2-(4-(6-(3,4-difluoro-2-methylphenyl)-5-(methoxycarbonyl)-2-(thiazol-2-yl)-3,6-dihydropyrimidin-4-yl)piperidin-1-yl)-5-methoxypyrimidine-4-carboxylate (a Single Stereoisomer)

By utilizing the analogous procedure of Method E, the title compound was synthesized from compound BB60 and FA1.

LC-MS (ESI): $R_T$=1.69 min, mass calcd. for $C_{29}H_{30}F_2N_6O_5S$, 612.2, m/z found 613.2 [M+H]$^+$. $^1$H NMR (400 MHz, CDCl$_3$) δ 8.26 (s, 1H), 8.11 (s, 0.8H), 7.79 (d, J=3.2 Hz, 0.2H), 7.76 (d, J=3.2 Hz, 0.8H), 7.48 (d, J=3.2 Hz, 0.2H), 7.41 (d, J=3.2 Hz, 0.8H), 7.12-7.08 (m, 0.2H), 7.03 (s, 0.2H), 6.96-6.86 (m, 1.8H), 5.94 (s, 0.8H), 5.86 (d, J=2.0 Hz, 0.2H), 4.95-4.77 (m, 2H), 4.44 (q, J=7.2 Hz, 2H), 4.34-4.26 (m, 1H), 3.87 (s, 2.4H), 3.86 (s, 0.6H), 3.61 (s, 3H), 3.07-2.91 (m, 2H), 2.57 (d, J=2.4 Hz, 2.4H), 2.43 (d, J=2.4 Hz, 0.6H), 2.12-2.05 (m, 1H), 1.97-1.88 (m, 1H), 1.82-1.65 (m, 2H), 1.42 (t, J=7.2 Hz, 3H).

Compound XI-93-3

Ethyl 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-ethoxypyrimidine-4-carboxylate (a Single Stereoisomer)

By utilizing the analogous procedure of Method E, the title compound was synthesized from compound BB60 and FA12.

LC-MS (ESI): $R_T$=1.86 min, mass calcd. For $C_{30}H_{31}ClF_2N_6O_5S$, 660.2, m/z found 661.2 [M+H]$^+$. $^1$H NMR (400 MHz, CDCl$_3$) δ 8.25 (s, 1H), 8.14 (s, 0.6H), 7.79 (s, 1H), 7.49-7.41 (m, 1H), 7.33 (br s, 0.4H), 7.12-7.00 (m, 2H), 6.22 (s, 0.6H), 6.09 (br s, 0.4H), 4.97-4.79 (m, 2H), 4.45 (q, J=6.8 Hz, 2H), 4.33-4.22 (m, 0.6H), 4.08-4.04 (m, 4.4H), 3.05-2.93 (m, 2H), 2.15-1.90 (m, 2.4H), 1.81-1.67 (m, 1.6H), 1.43-1.38 (m, 6H), 1.15 (t, J=7.2 Hz, 3H).

Compound XI-94-1

Ethyl 2-(4-(6-(2-bromo-3-fluorophenyl)-5-(ethoxycarbonyl)-2-(thiazol-2-yl)-3,6-dihydropyrimidin-4-yl)piperidin-1-yl)-5-(dimethylamino)pyrimidine-4-carboxylate (a Single Stereoisomer)

By utilizing the analogous procedure of Method E, the title compound was synthesized from compound BB57 and FA20.

LC-MS (ESI): $R_T$=2.06 min, mass calcd. for $C_{30}H_{33}BrFN_7O_4S$, 685.1, 687.1, m/z found 688.2 [M+H]$^+$. $^1$H NMR (400 MHz, CDCl$_3$) δ 8.33 (s, 0.5H), 8.32 (s, 0.5H), 8.11 (s, 0.5H), 7.80 (d, J=2.8 Hz, 0.5H), 7.77 (d, J=3.2 Hz, 0.5H), 7.46 (d, J=2.8 Hz, 0.5H), 7.42-7.40 (m, 1H), 7.25-7.18 (m, 1H), 7.16-7.14 (m, 1H), 7.07-6.99 (m, 1H), 6.28 (s, 0.5H), 6.13 (d, J=2.4 Hz, 0.5H), 4.97-4.81 (m, 2H), 4.44 (q, J=7.2 Hz, 2H), 4.35-4.26 (m, 0.5H), 4.09-3.98 (m, 2.5H), 3.04-2.90 (m, 2H), 2.74 (s, 3H), 2.73 (s, 3H), 2.24-2.06 (m, 1H), 2.02-1.94 (m, 1.5H), 1.81-1.68 (m, 1.5H), 1.41 (t, J=7.2 Hz, 3H), 1.12 (t, J=7.2 Hz, 3H).

Compound XI-95S

Ethyl 2-(4-(6-(2-bromo-3-fluorophenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB4 and FA15.

LC-MS (ESI): $R_T$=2.124 min, mass calcd. for $C_{28}H_{28}BrFN_6O_4S$, 642.1, 644.1, m/z found 645.0 [M+H]$^+$.

Compound XI-96-1

Ethyl 2-(4-(6-(2-bromo-4-fluorophenyl)-5-(methoxycarbonyl)-2-(thiazol-2-yl)-3,6-dihydropyrimidin-4-yl)piperidin-1-yl)-5-methylpyrimidine-4-carboxylate (a Single Stereoisomer)

By utilizing the analogous procedure of Method E, the title compound was synthesized from compound BB4 and FA16.

LC-MS (ESI): $R_T$=1.81 min, mass calcd. for $C_{28}H_{28}BrFN_6O_4S$, 642.1, m/z found 643.0, 645.0 [M+H]$^+$. $^1$H NMR (400 MHz, CDCl$_3$) δ 8.28 (d, J=3.6 Hz, 1H), 8.12 (s, 0.5H), 7.80 (d, J=3.2 Hz, 0.5H), 7.76 (d, J=3.2 Hz, 0.5H), 7.47-7.44 (m, 1H), 7.41 (d, J=3.2 Hz, 0.5H), 7.34-7.28 (m, 2H), 7.02-6.93 (m, 1H), 6.18 (s, 0.5H), 6.03 (d, J=2.4 Hz, 0.5H), 5.03-4.87 (m, 2H), 4.42 (q, J=7.2 Hz, 2H), 4.34-4.28 (m, 0.5H), 4.08-4.01 (m, 0.5H), 3.62 (s, 2H), 3.61 (s, 1H), 3.07-2.95 (m, 2H), 2.28 (s, 1.4H), 2.26 (s, 1.6H), 2.22-2.13 (m, 1H), 2.01-1.93 (m, 1.5H), 1.81-1.65 (m, 1.5H), 1.42 (t, J=7.2 Hz, 3H).

Compound XI-97-1 ethyl 2-(4-(6-(2-bromo-4-fluorophenyl)-5-(ethoxycarbonyl)-2-(thiazol-2-yl)-3,6-dihydropyrimidin-4-yl)piperidin-1-yl)-5-(dimethylamino)pyrimidine-4-carboxylate (a Single Stereoisomer)

By utilizing the analogous procedure of Method E, the title compound was synthesized from compound BB57 and FA21.

LC-MS (ESI): $R_T$=2.051 min, mass calcd. for $C_{30}H_{33}BrFN_7O_4S$, 685.1, m/z found 686.2 [M+H]$^+$. $^1$H NMR (400 MHz, DMSO-d$_6$) δ 9.40 (d, J=3.6 Hz, 0.6H), 9.14 (s, 0.4H), 8.50 (s, 0.4H), 8.49 (s, 0.6H), 7.98-7.89 (m, 2H), 7.57 (dd, J=8.4 Hz, 2.4 Hz, 1H), 7.39-7.32 (m, 1H), 7.29-7.22 (m, 1H), 6.01 (s, 0.3H), 5.92 (d, J=3.6 Hz, 0.7H), 4.81-4.64 (m, 2H), 4.40-4.34 (m, 2H), 4.22-4.13 (m, 0.4H), 4.06-3.95 (m, 2H), 3.93-3.84 (m, 0.6H), 2.88-2.82 (m, 2H), 2.65 (s, 6H), 1.99-1.61 (m, 4H), 1.34-1.30 (m, 3H), 1.12-1.07 (m, 3H).

Part IX: Hydrolysis of Dihydropyrimidines of General Formula VII and General Formula XI to the Final Products of General Formula I and General Formula II, Respectively Compound I-1-C: (Exemplified with Method C)

(trans)-2-(4-(6-(2-Chloro-3,4-difluorophenyl)-5-(methoxycarbonyl)-2-(thiazol-2-yl)-3,6-dihydropyrimidin-4-yl)cyclohexyl)oxazole-4-carboxylic Acid (a Single Stereoisomer)

To a solution of (trans)-methyl 2-(4-(6-(2-chloro-3,4-difluorophenyl)-5-(methoxycarbonyl)-2-(thiazol-2-yl)-3,6-dihydropyrimidin-4-yl)cyclohexyl)oxazole-4-carboxylate VII-1-X (120 mg, 0.198 mmol, 95% purity) in tetrahydrofuran (2 mL), methanol (2 mL) and water (1 mL) was added lithium hydroxide monohydrate (17.0 mg, 0.397 mmol) at 0° C. After stirred at 0° C. for 2 hours, the mixture was diluted with water (10 mL) and acidified to pH 5~6 with 1 M hydrochloride aqueous solution. The aqueous layer was extracted with ethyl acetate (10 mL) for three times. The combined organic layers were washed with brine (10 mL), dried over $Na_2SO_{4(s)}$ and filtered. The filtrate was concentrated to give a residue, which was purified by Prep. HPLC (Column:Waters X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 5-70% (% B)) to give the title compound (69.5 mg, 61% yield, 98.4% purity) as yellow solids. LC-MS (ESI): $R_T$=3.683 min, mass calcd. for $C_{25}H_{21}ClF_2N_4O_5S$ 562.1, m/z found 562.9 $[M+H]^+$. $^1H$ NMR (400 MHz, $CD_3OD$) δ 8.26 (s, 1H), 7.92 (d, J=2.8 Hz, 1H), 7.75 (d, J=3.2 Hz, 1H), 7.26-7.18 (m, 2H), 6.11 (s, 1H), 4.10-3.74 (m, 1H), 3.60 (s, 3H), 3.03-2.90 (m, 1H), 2.33-2.18 (m, 2H), 2.10-1.66 (m, 6H).

Similarly utilizing the above-mentioned analogous procedures of ester hydrolysis, the following acids could be prepared; these are indicated in Table 2 below, thereby related to the corresponding esters, which are listed with reference to their compound numbers ("Cpd. #").

TABLE 2

| Ester Cpd.# | Acid |
|---|---|
| VII-1-X | 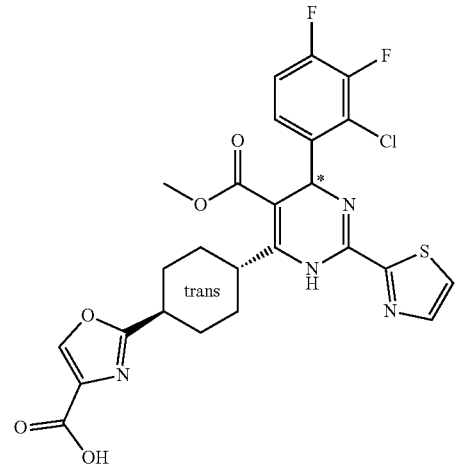<br>Compound I-1-C |
| VII-2-Y | 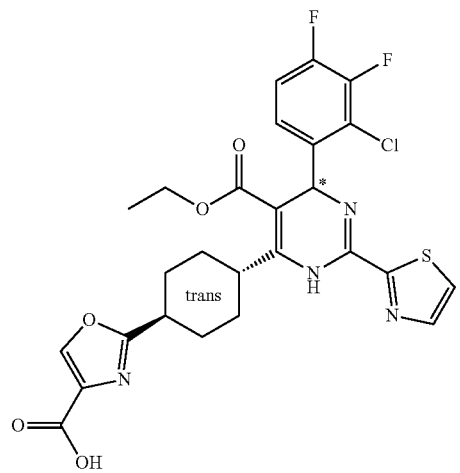<br>Compound I-2-D |

TABLE 2-continued
| Ester Cpd.# | Acid |
|---|---|
| VII-3-H | 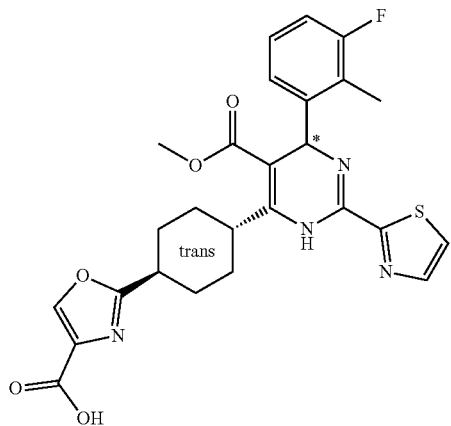<br>Compound I-3-D |
| VII-4-N | 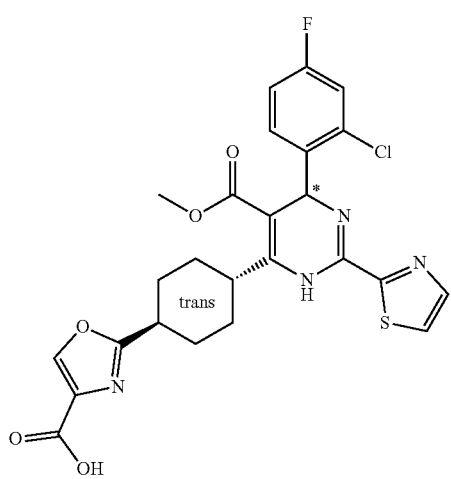<br>Compound I-4-B |
| VII-5-Q | 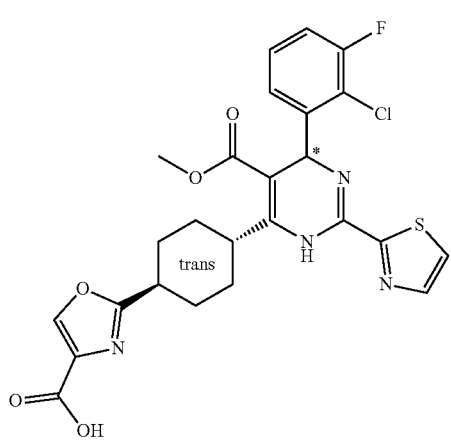<br>Compound I-5-B |

TABLE 2-continued
| Ester Cpd.# | Acid |
|---|---|
| VII-6-Q | 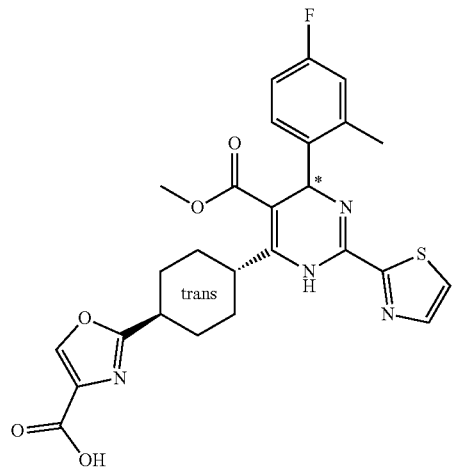<br>Compound I-6-B |
| VII-7-N | 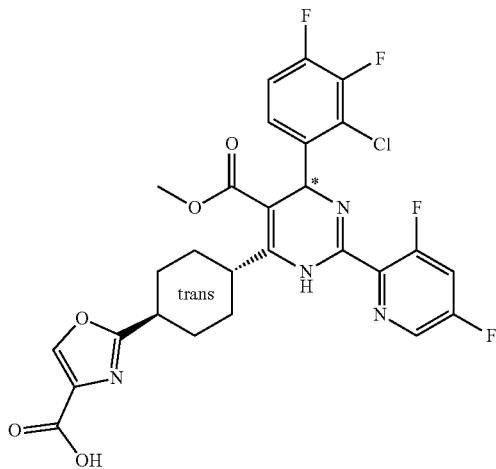<br>Compound I-7-B |
| VII-8-N | 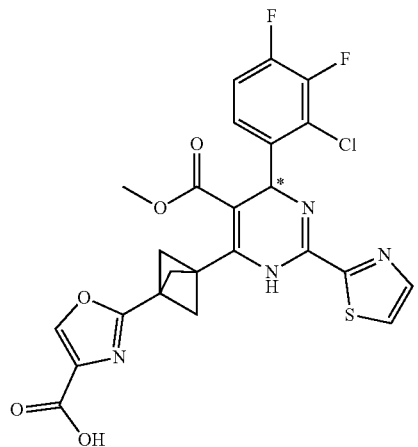<br>Compound I-8-B |

TABLE 2-continued
| Ester Cpd.# | Acid |
|---|---|
| VII-9-F | 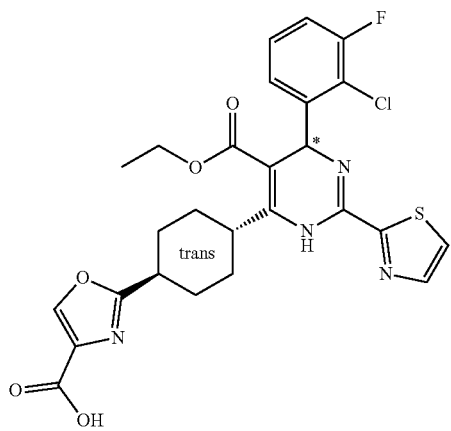<br>Compound I-9-B |
| VII-10-P | 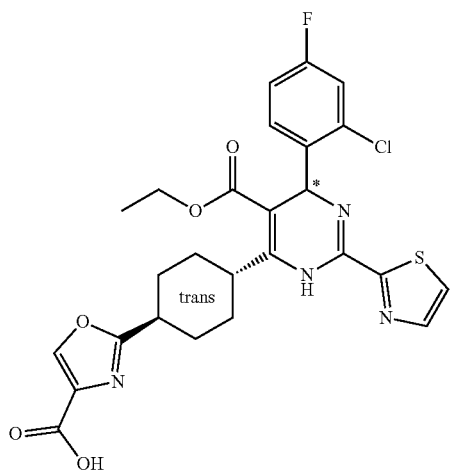<br>Compound I-10-C |
| VII-11-Q | 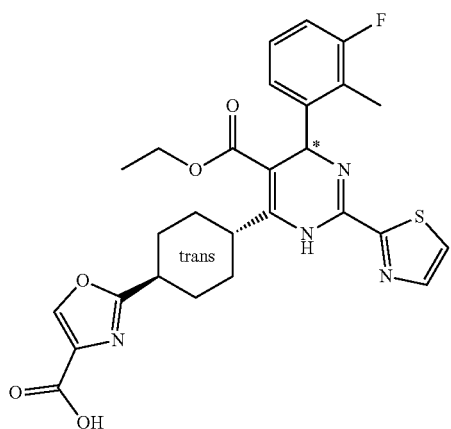<br>Compound I-11-B |

TABLE 2-continued
| Ester Cpd.# | Acid |
|---|---|
| VII-12-P | 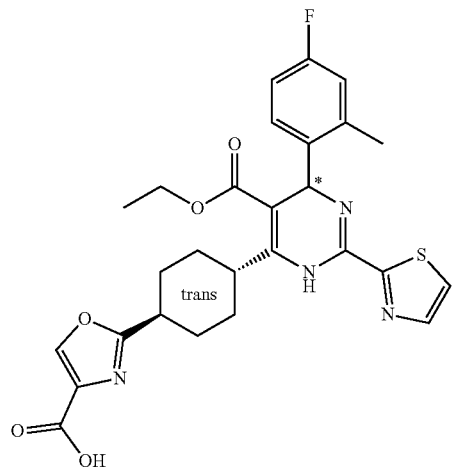<br>Compound I-12-C |
| VII-13-P and VII-13-Q | 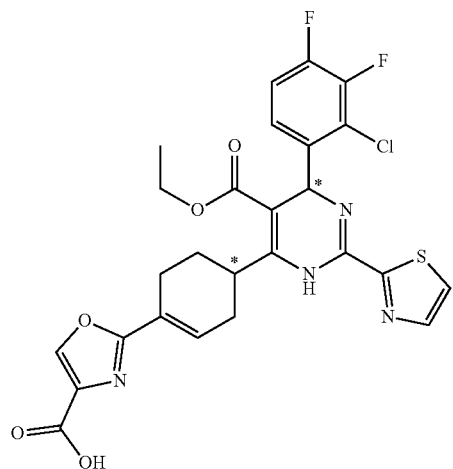<br>Compound I-13-C<br>Compound I-13-D |
| VII-14-N | 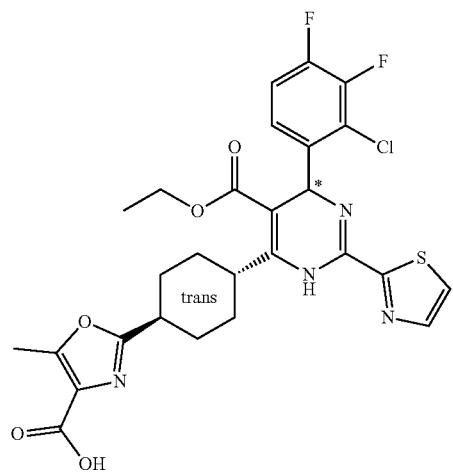<br>Compound I-14-B |

TABLE 2-continued
| Ester Cpd.# | Acid |
|---|---|
| VII-15-M | 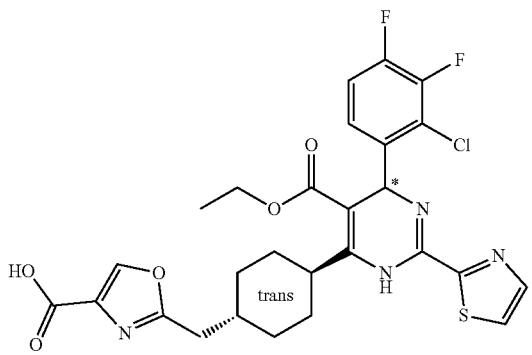<br>Compound I-15-A |
| VII-16-N | 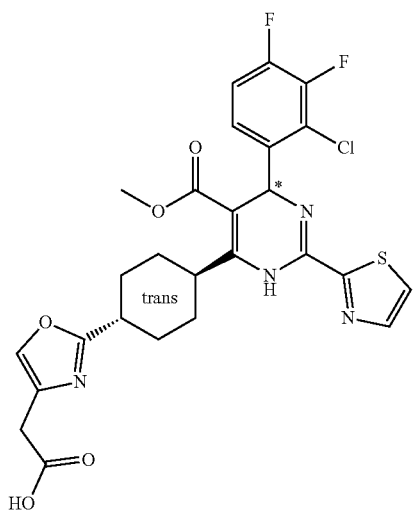<br>Compound I-16-B |
| VII-17-M | 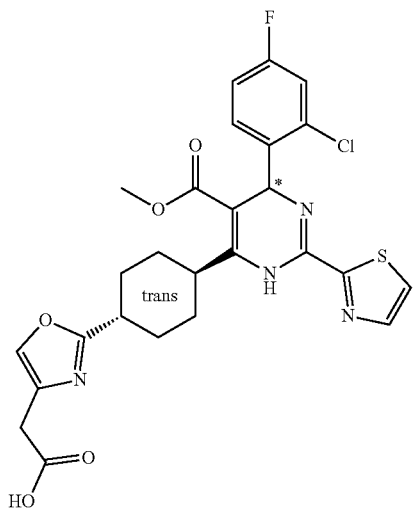<br>Compound I-17-A |

TABLE 2-continued
| Ester Cpd.# | Acid |
|---|---|
| VII-18-M | 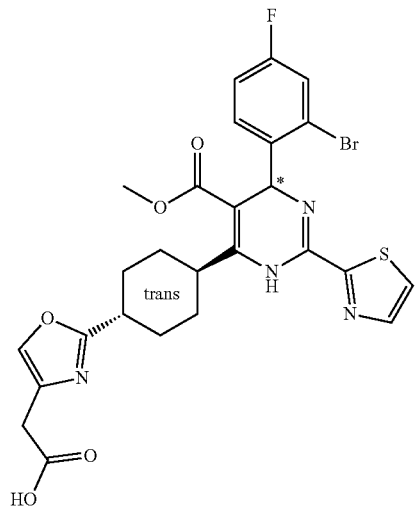
Compound I-18-A |
| VII-19-N | 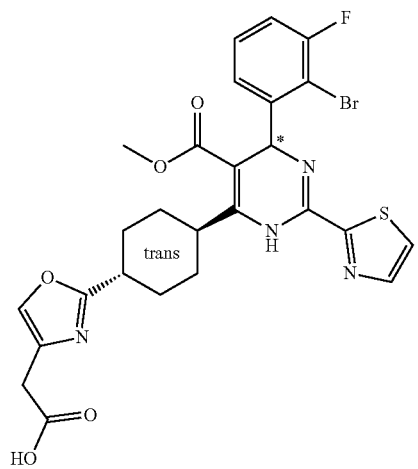
Compound I-19-B |
| VII-20-N | 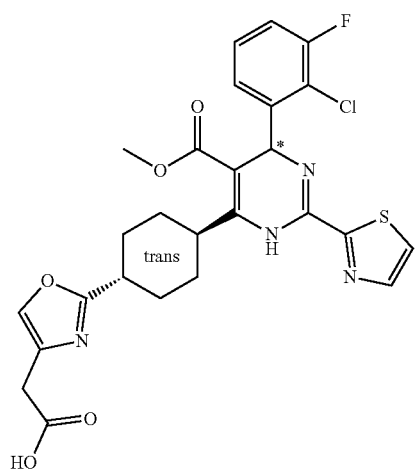
Compound I-20-B |

TABLE 2-continued
| Ester Cpd.# | Acid |
|---|---|
| VII-21-N | 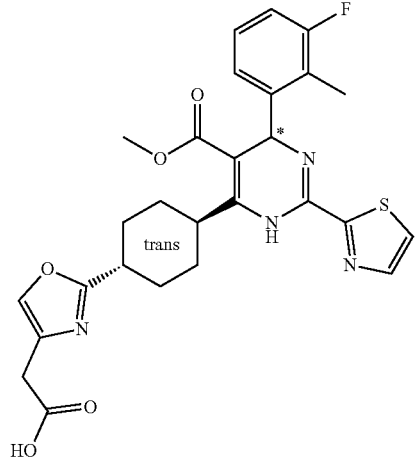<br>Compound I-21-B |
| VII-22-S | 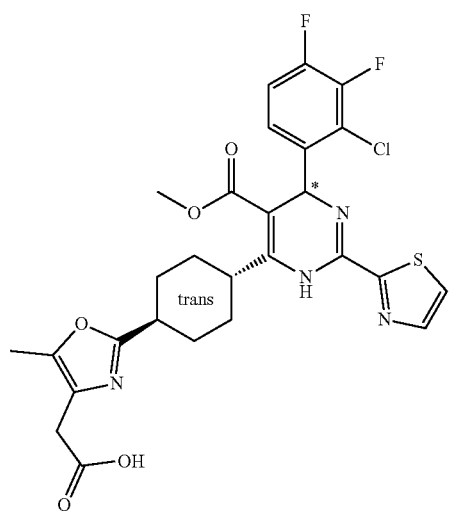<br>Compound I-22-B |
| VII-23-Y | 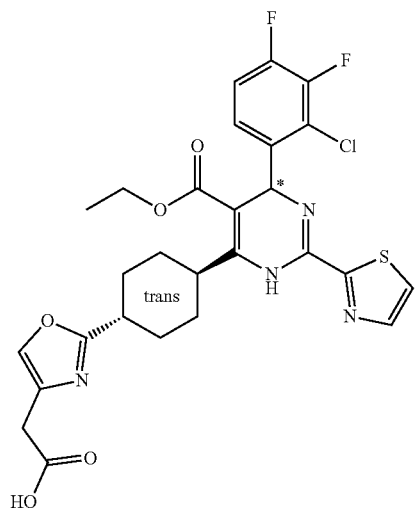<br>Compound I-23-B |

TABLE 2-continued
| Ester Cpd.# | Acid |
|---|---|
| VII-24-M | 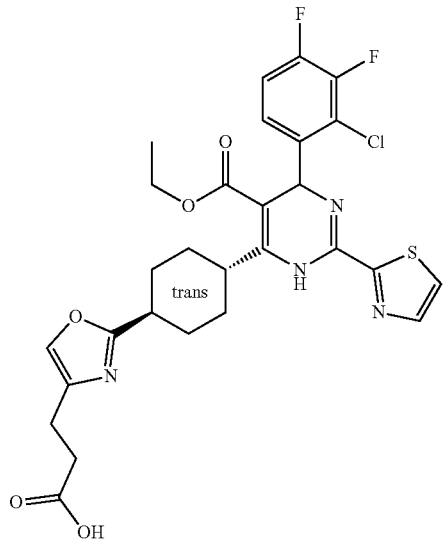<br>Compound I-24<br>Compound I-24-A |
| VII-25-N | 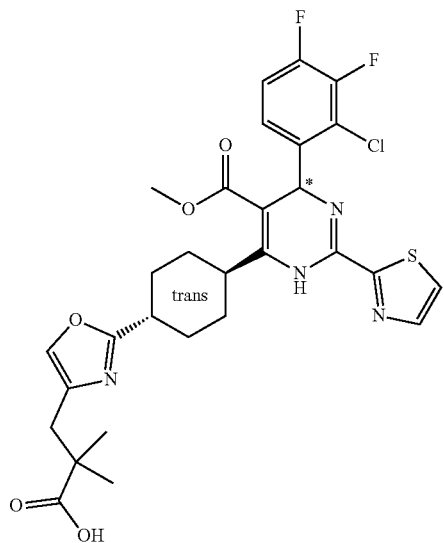<br>Compound I-25-B |

TABLE 2-continued
| Ester Cpd.# | Acid |
|---|---|
| VII-26-S | 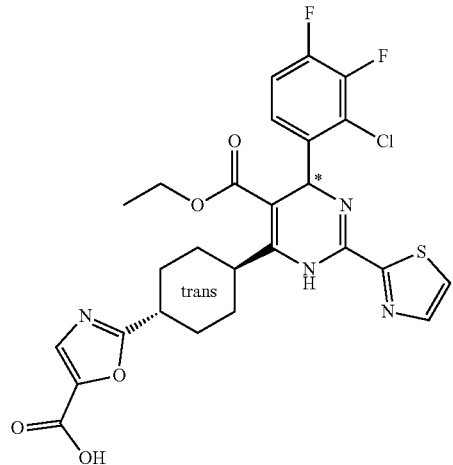<br>Compound I-26-B |
| VII-27-R | 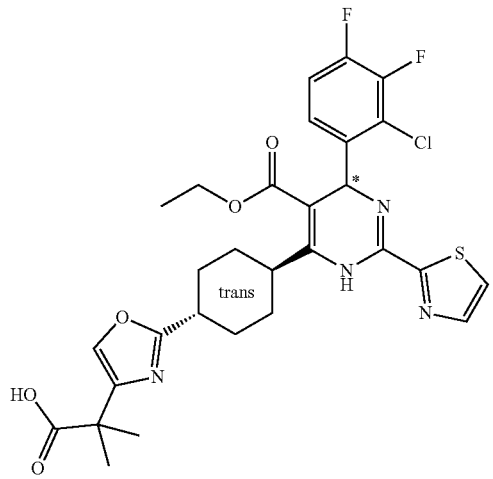<br>Compound I-27-B |
| VII-28-N | 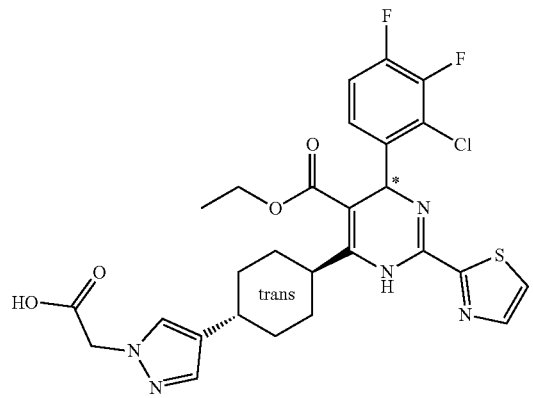<br>Compound I-28-B |

TABLE 2-continued
| Ester Cpd.# | Acid |
|---|---|
| VII-29-P | 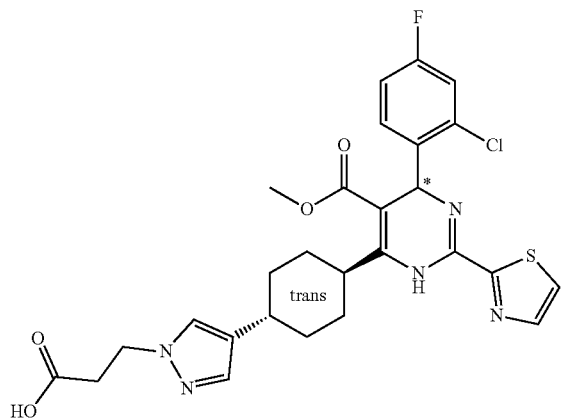<br>Compound I-29-C |
| VII-30-10 | 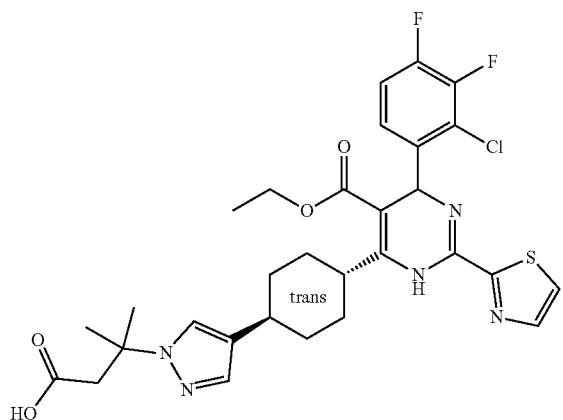<br>Compound I-30-D |
| VII-31 | 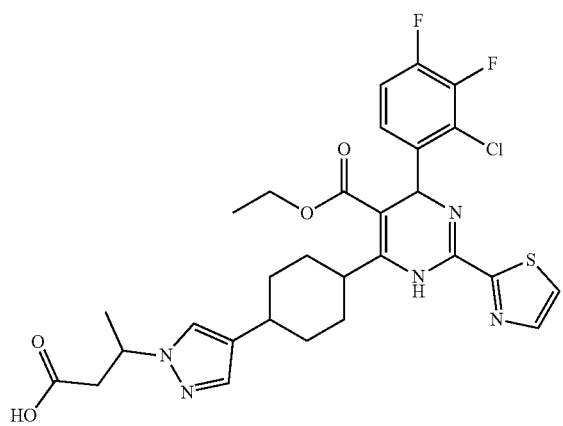<br>Compound I-31 |

TABLE 2-continued
| Ester Cpd.# | Acid |
|---|---|
| VII-32-N | 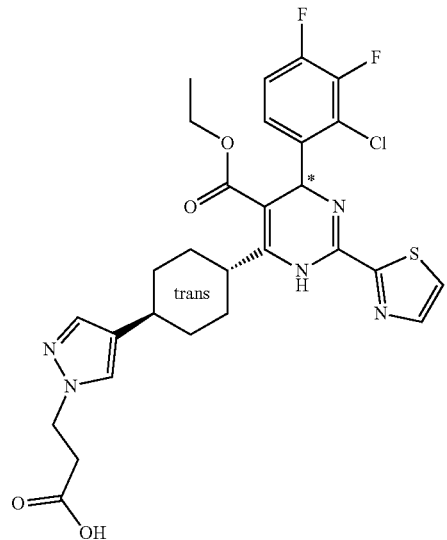
Compound I-32-B |
| VII-33-10 | 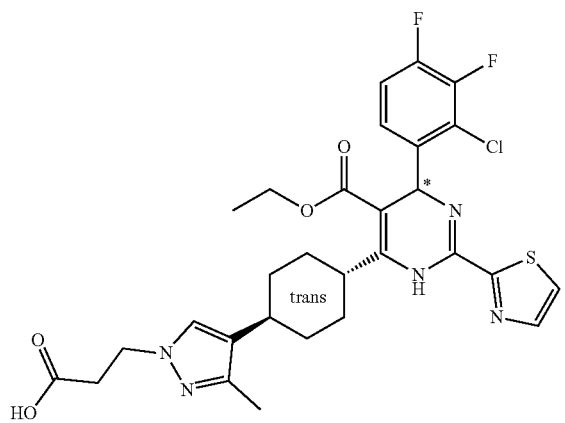
Compound I-33-C |
| VII-34 | 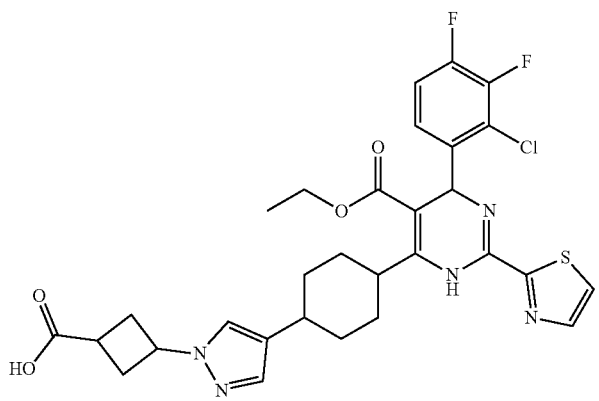
Compound I-34 |

TABLE 2-continued
| Ester Cpd.# | Acid |
|---|---|
| VII-35-P | 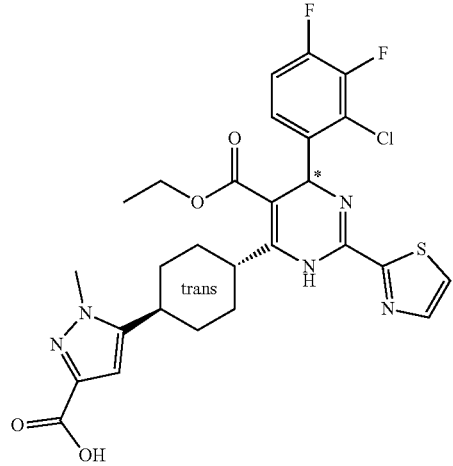<br>Compound I-35-C |
| VII-36-N | 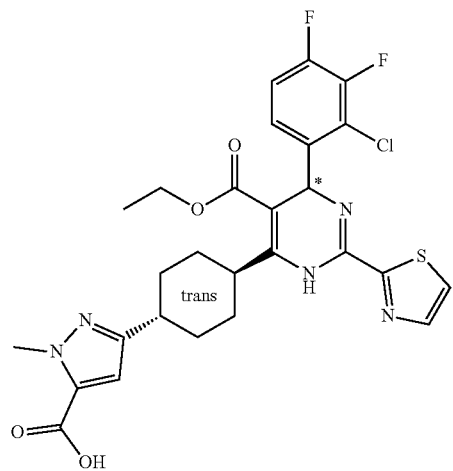<br>Compound I-36-B |
| VII-37-4C | 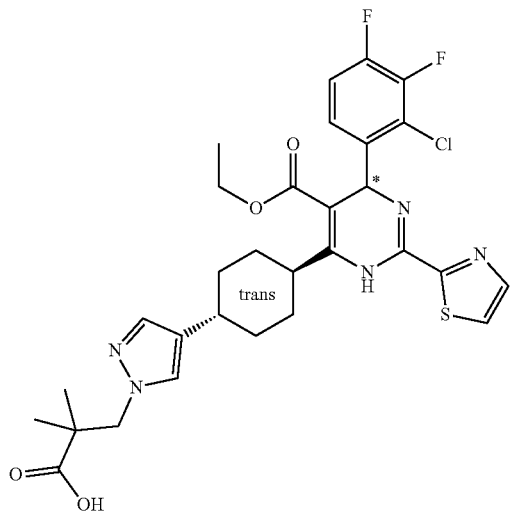<br>Compound I-37-C |

TABLE 2-continued
| Ester Cpd.# | Acid |
|---|---|
| VII-38-N | 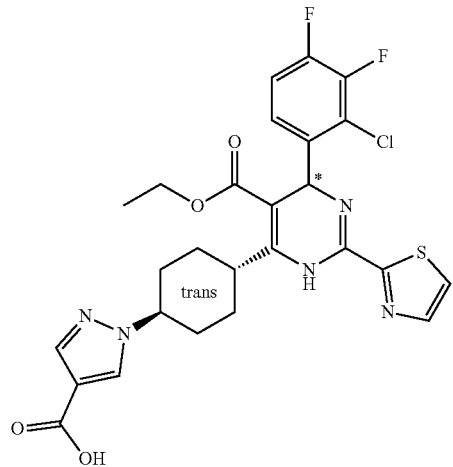
Compound I-38-B |
| VII-39-N and VII-39-P | 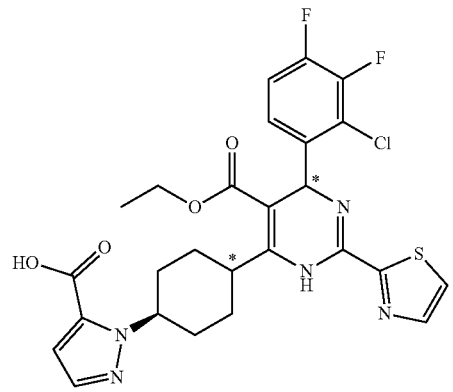
Compound I-39-B (cis-)
Compound I-39-C (trans-) |
| VII-40-M | 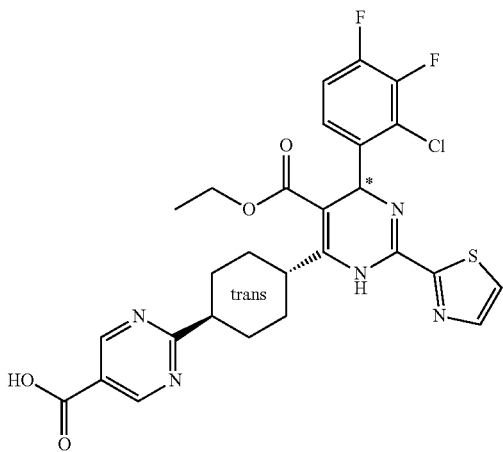
Compound I-40-A |

TABLE 2-continued
| Ester Cpd.# | Acid |
|---|---|
| VII-41-N | 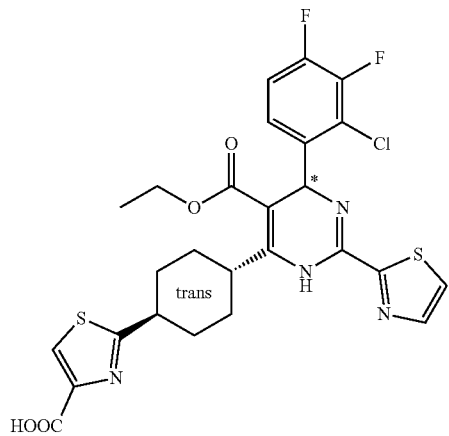<br>Compound I-41-B |
| VII-42-11 | 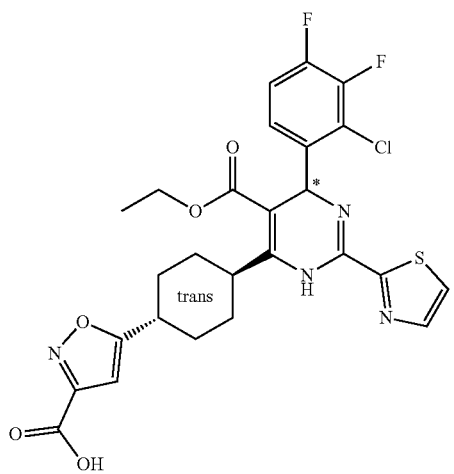<br>Compound I-42-B |
| VII-43-N | 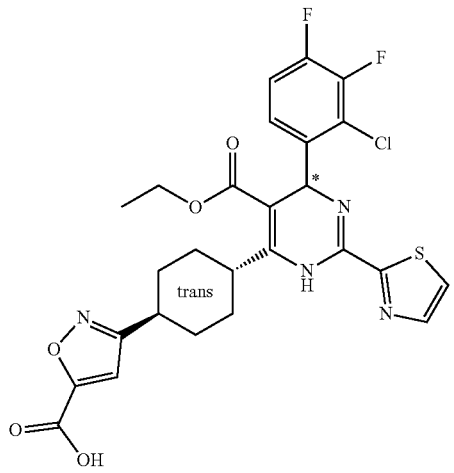<br>Compound I-43-B |

TABLE 2-continued
| Ester Cpd.# | Acid |
|---|---|
| VII-44-X | 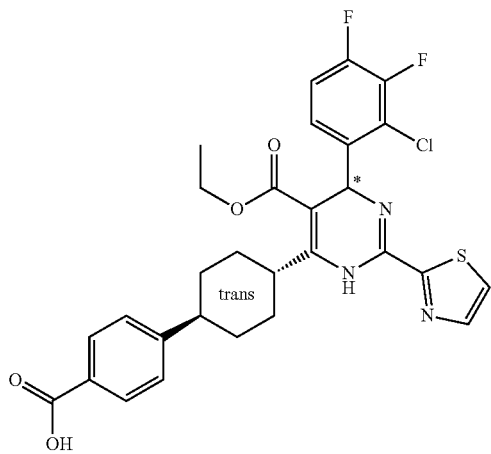
Compound I-44-A |
| VII-45-R | 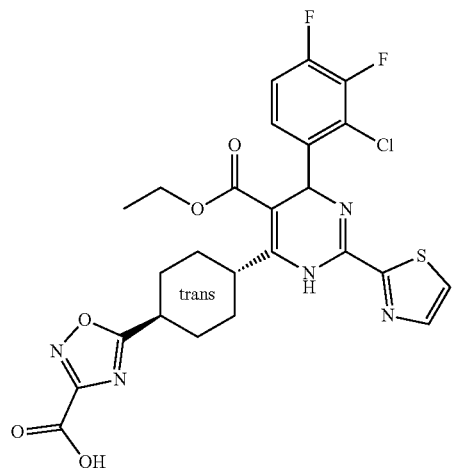
Compound I-45 |
| VII-46-P | 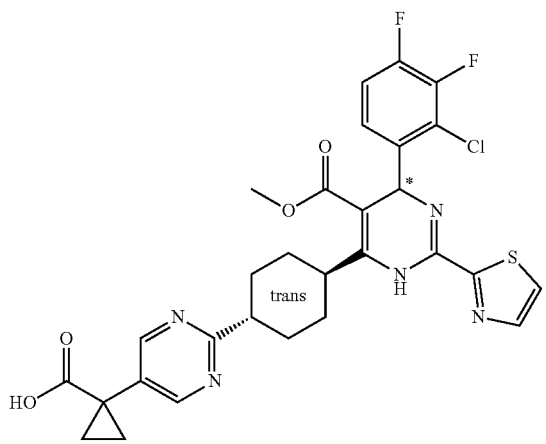
Compound I-46-C |

TABLE 2-continued
| Ester Cpd.# | Acid |
|---|---|
| VII-47-N | 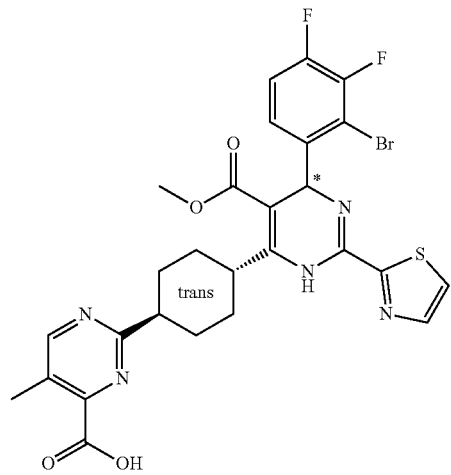<br>Compound I-47-D |
| VII-48-B | 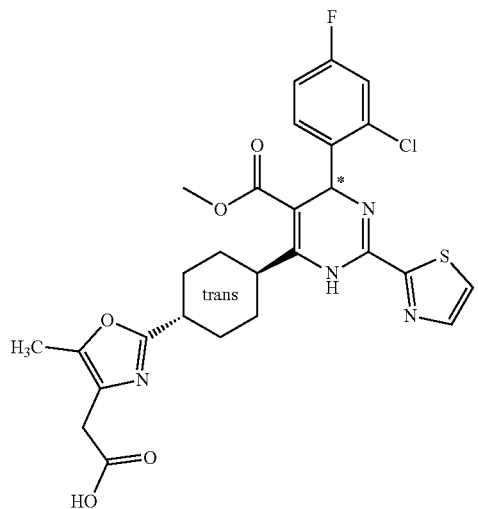<br>Compound I-48-B |
| VII-49-A | 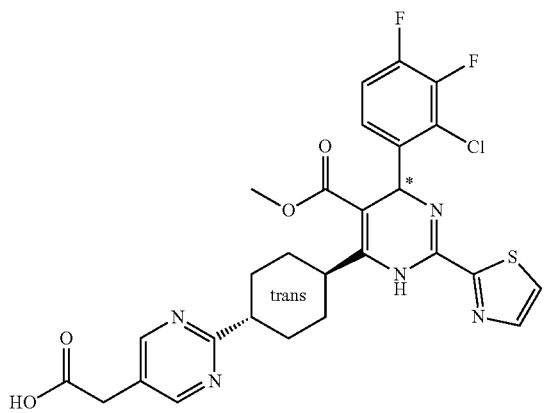<br>Compound I-49-A |

TABLE 2-continued
| Ester Cpd.# | Acid |
|---|---|
| VII-50-A | 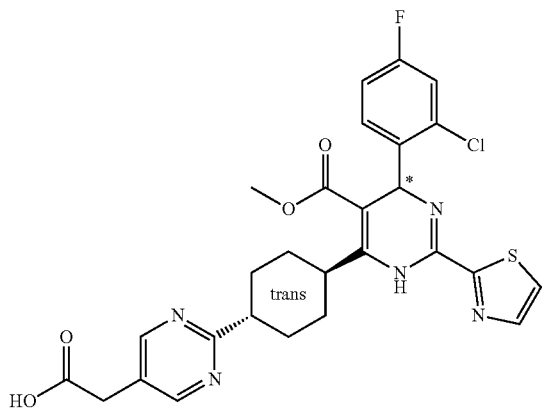
Compound I-50-A |
| XI-1-B | 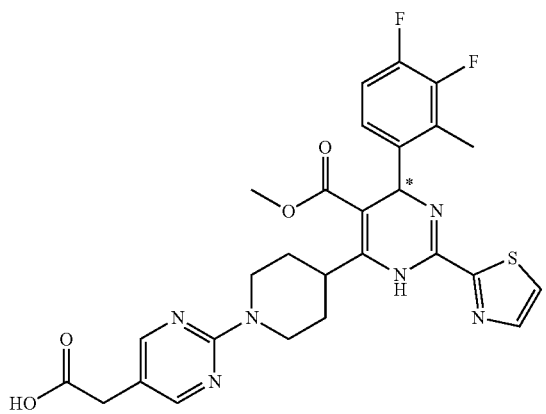
Compound II-1-B |
| FA2 and BB2 | 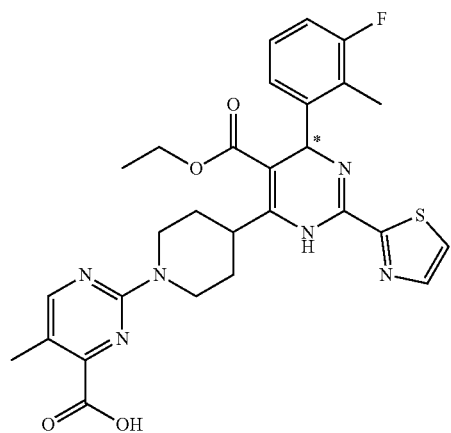
Compound II-2-B |

TABLE 2-continued
| Ester Cpd.# | Acid |
|---|---|
| XI-3-S | 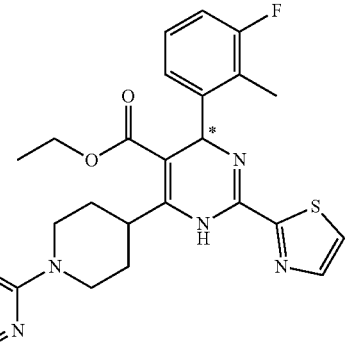<br>Compound II-3-B |
| XI-4-B | 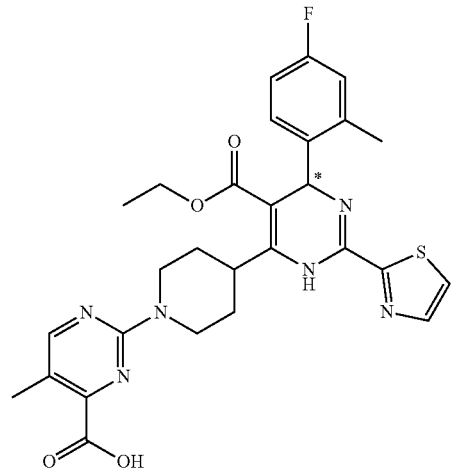<br>Compound II-4-B |
| XI-5-B | 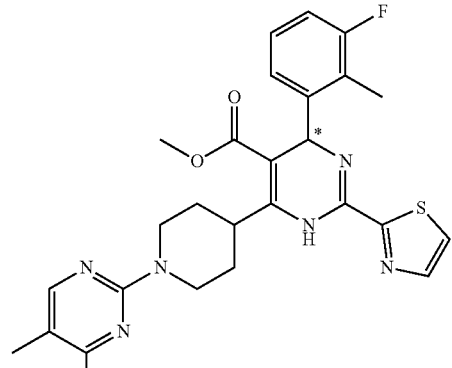<br>Compound II-5-B |

TABLE 2-continued
| Ester Cpd.# | Acid |
|---|---|
| XI-6-B | 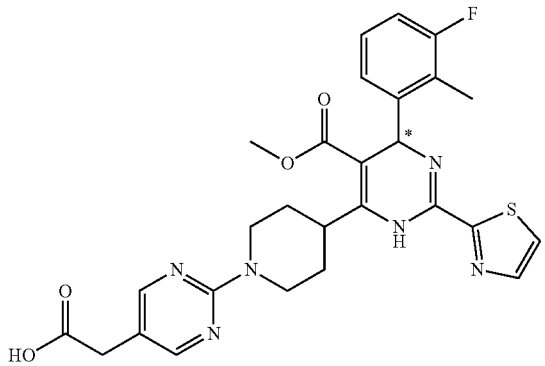
Compound II-6-B |
| FA5 and BB2 | 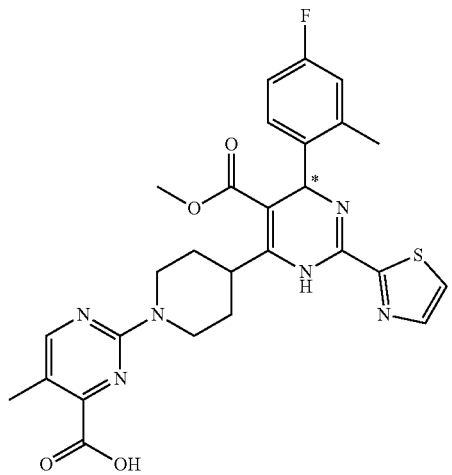
Compound II-7-B |
| FA6 and BB2-1 | 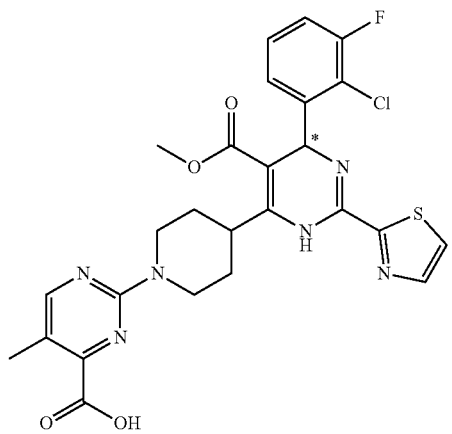
Compound II-8-B |

TABLE 2-continued
| Ester Cpd.# | Acid |
|---|---|
| XI-9-B | 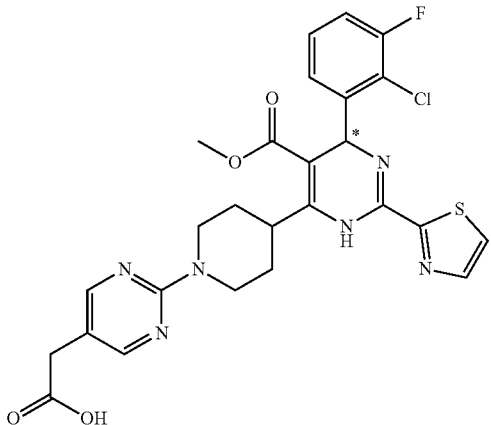<br>Compound II-9-B |
| XI-10-1 | 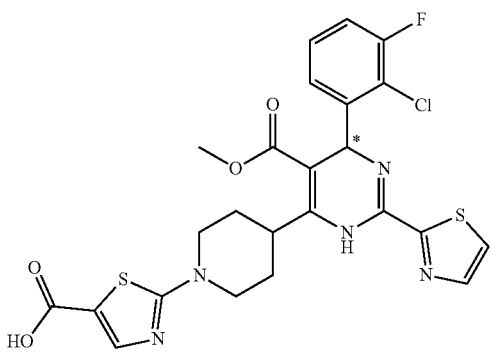<br>Compound II-10-B |
| FA7 and BB53 | 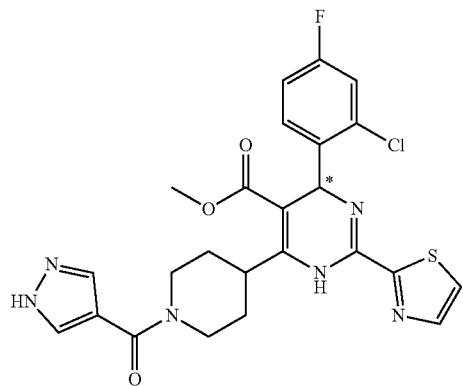<br>Compound II-11-X |

TABLE 2-continued
| Ester Cpd.# | Acid |
|---|---|
| FA7 and BB5 | 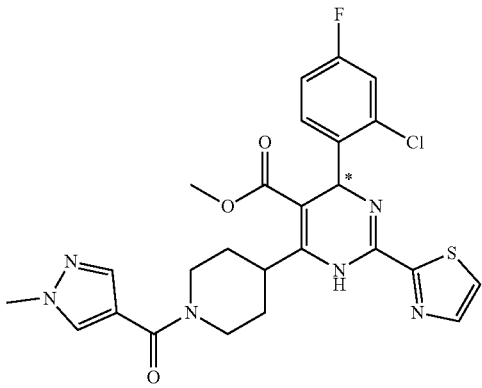<br>Compound II-12-B |
| XI-13-S | 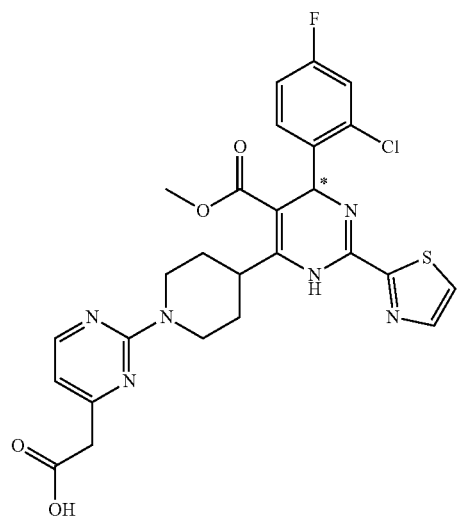<br>Compound II-13-A |
| XI-14-A | 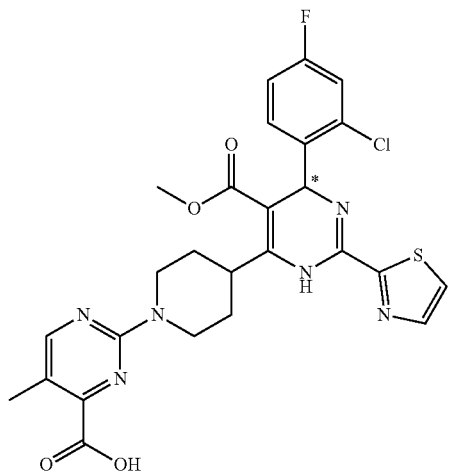<br>Compound II-14-A |

TABLE 2-continued
| Ester Cpd.# | Acid |
|---|---|
| XI-15-S | 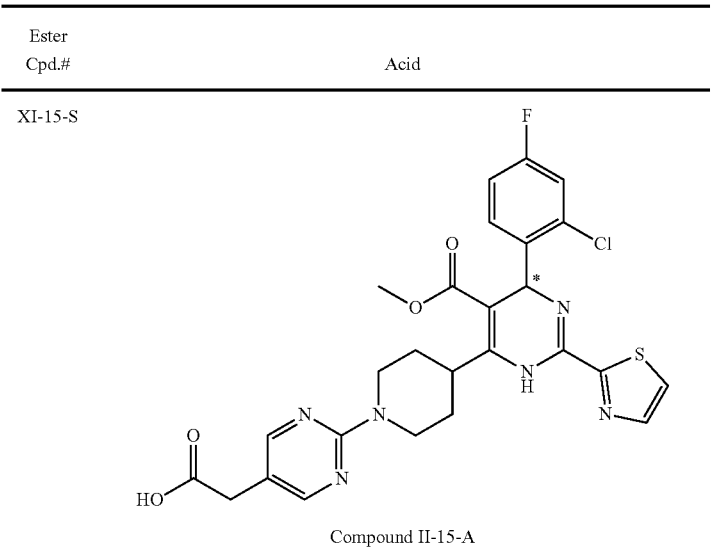<br>Compound II-15-A |
| XI-16-B | 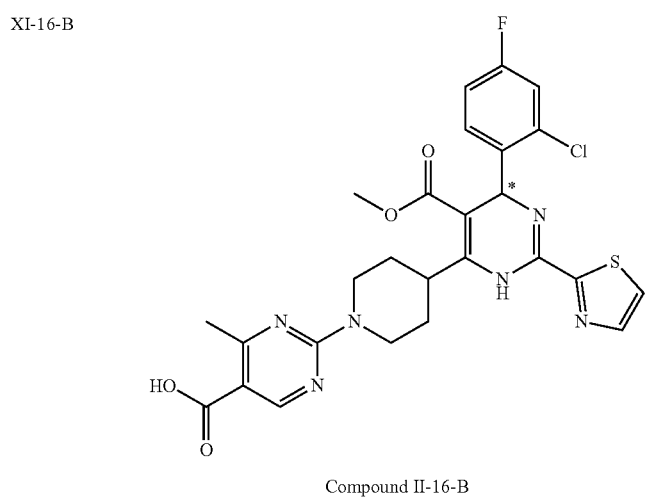<br>Compound II-16-B |
| FA7 and BB7 | 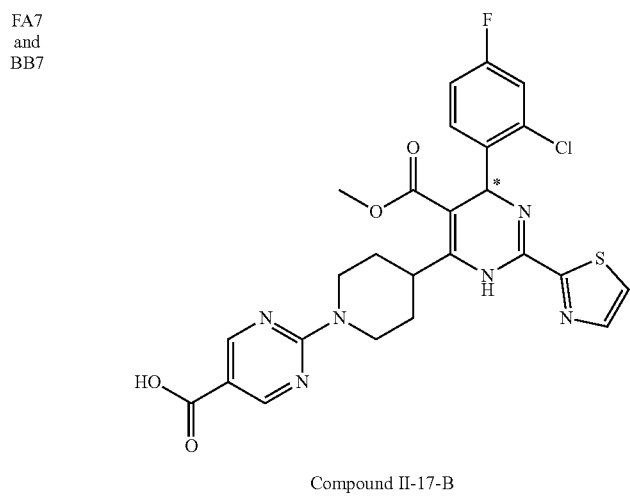<br>Compound II-17-B |

TABLE 2-continued
| Ester Cpd.# | Acid |
|---|---|
| XI-18-S | 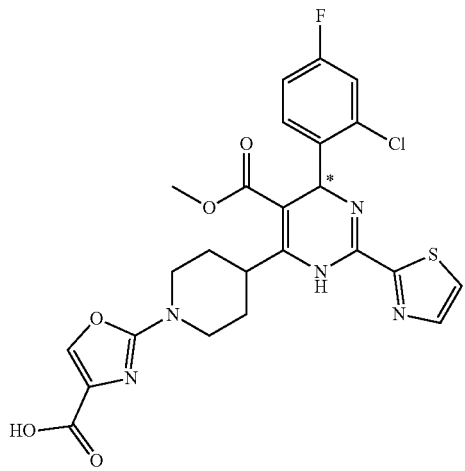<br>Compound II-18-B |
| XI-19-2 | 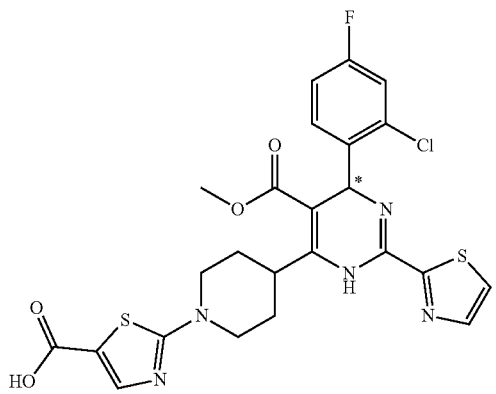<br>Compound II-19-A |
| FA8 and BB54 | 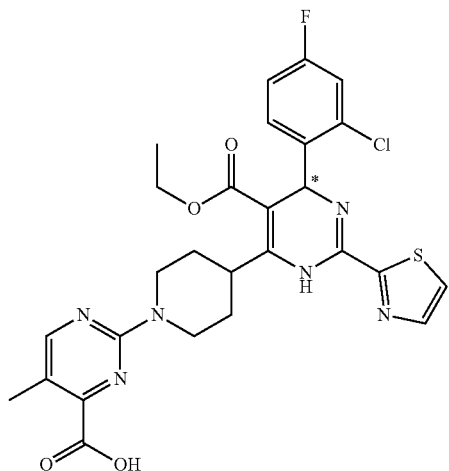<br>Compound II-20-B |

TABLE 2-continued
| Ester Cpd.# | Acid |
|---|---|
| XI-21-B | 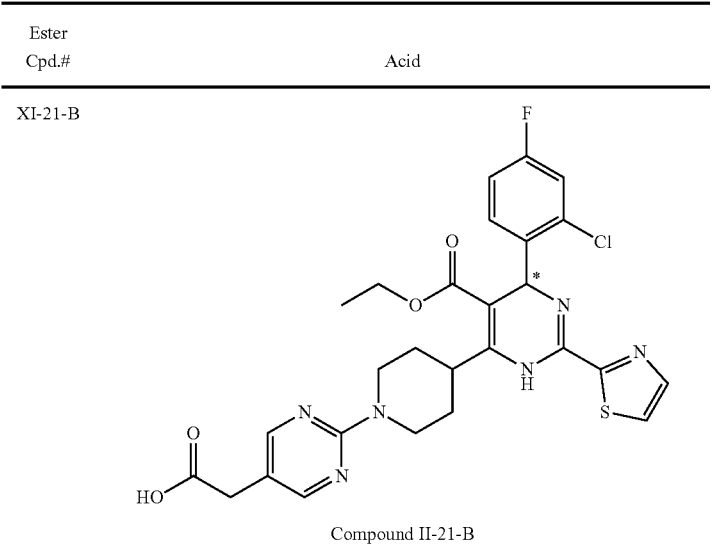
Compound II-21-B |
| FA9 and BB2-1 | 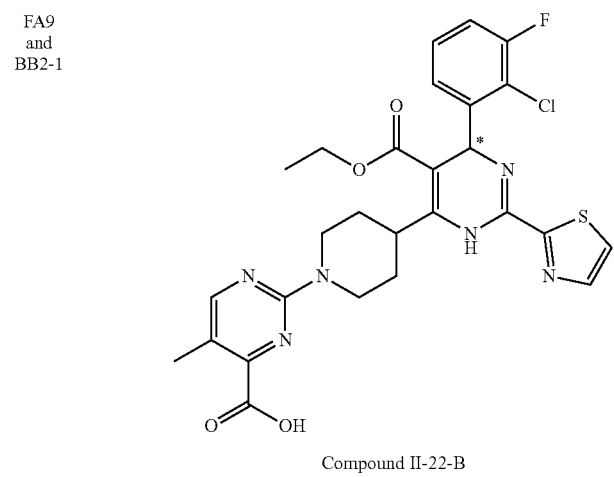
Compound II-22-B |
| XI-23-B | 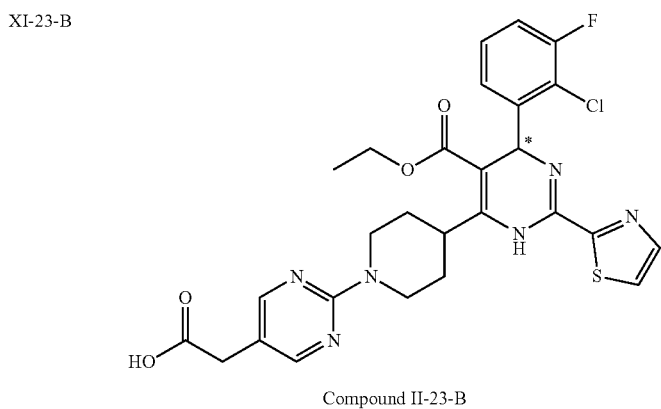
Compound II-23-B |

TABLE 2-continued
| Ester Cpd.# | Acid |
|---|---|
| XI-24-B | 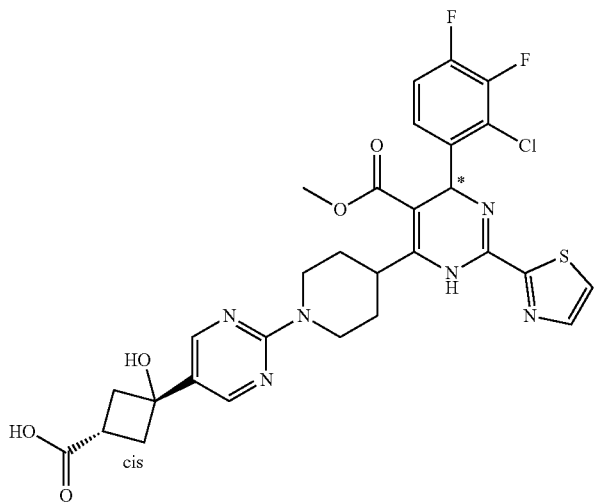<br>Compound II-24-B |
| XI-25-B | 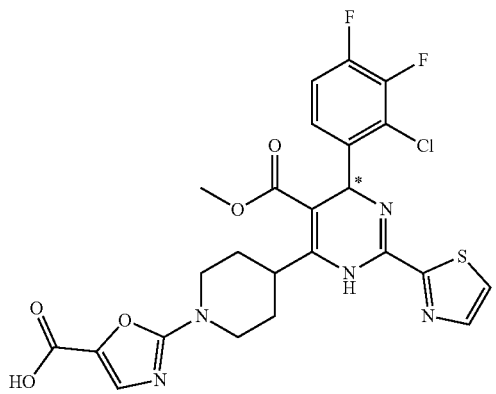<br>Compound II-25-B |
| XI-26-B | 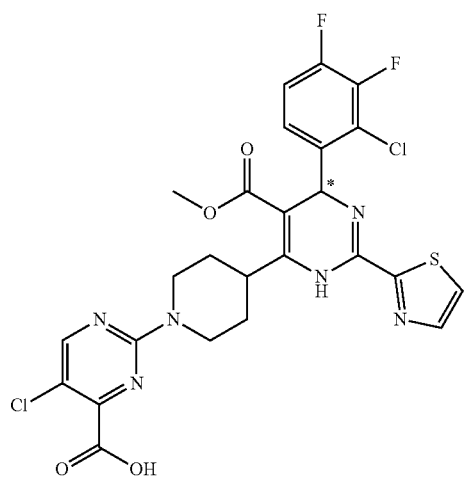<br>Compound II-26-B |

TABLE 2-continued
| Ester Cpd.# | Acid |
|---|---|
| FA10 and BB2-1 | 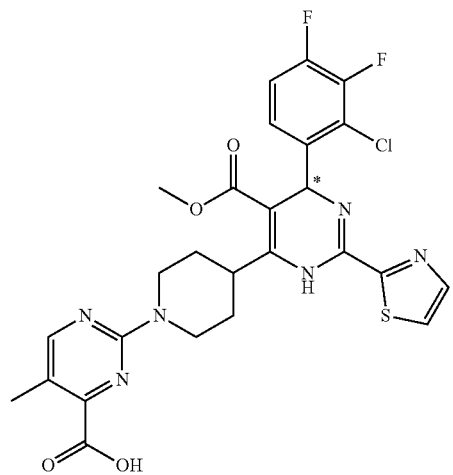<br>Compound II-27-B |
| XI-28-6 | 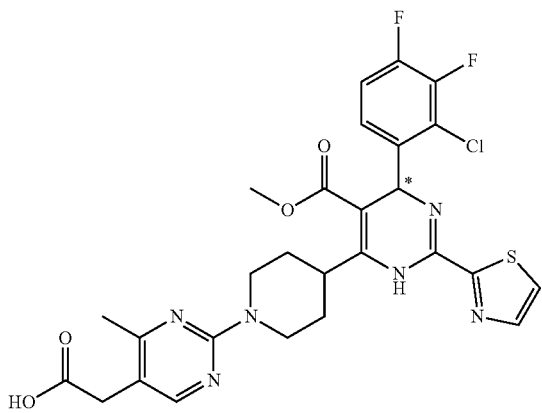<br>Compound II-28-B |
| XI-29-S | 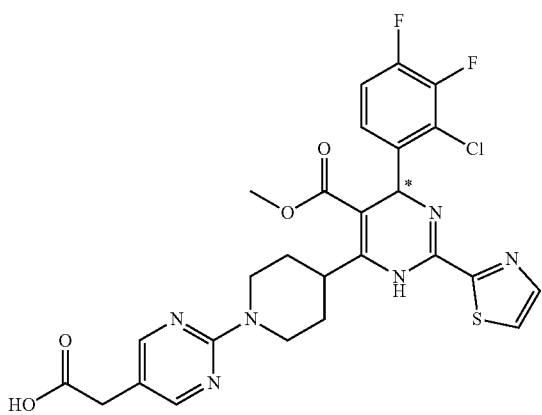<br>Compound II-29-B |

TABLE 2-continued
| Ester Cpd.# | Acid |
|---|---|
| XI-30-B | 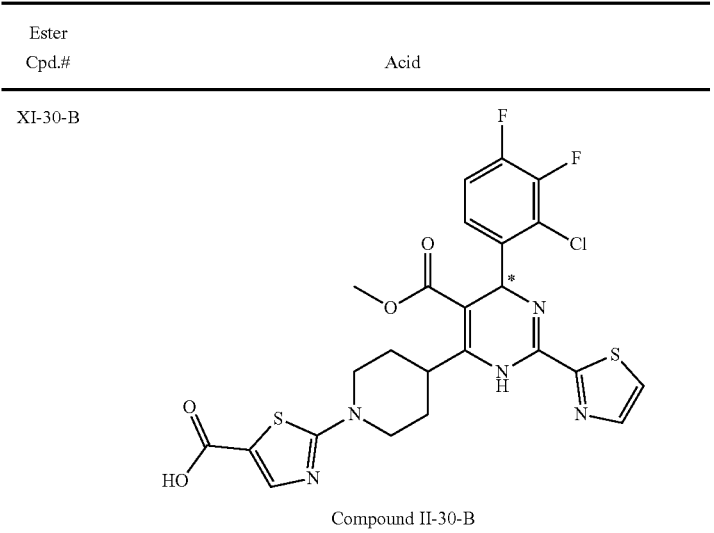
Compound II-30-B |
| XI-31-B | 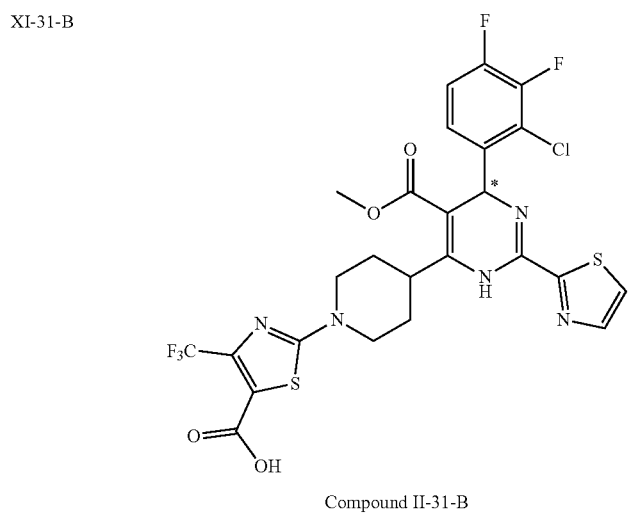
Compound II-31-B |
| XI-32-B | 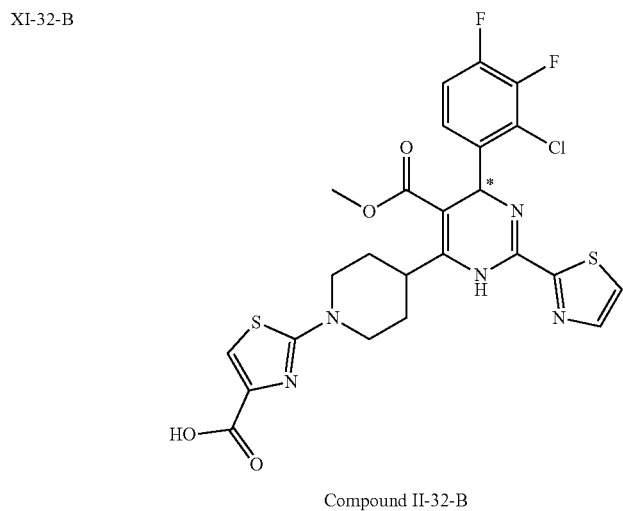
Compound II-32-B |

TABLE 2-continued
| Ester Cpd.# | Acid |
|---|---|
| XI-33-B | 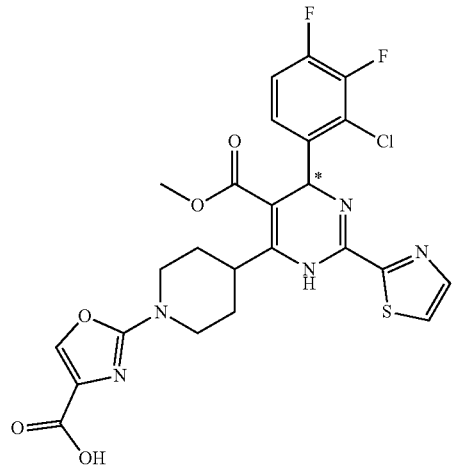<br>Compound II-33-B |
| XI-34-10F | 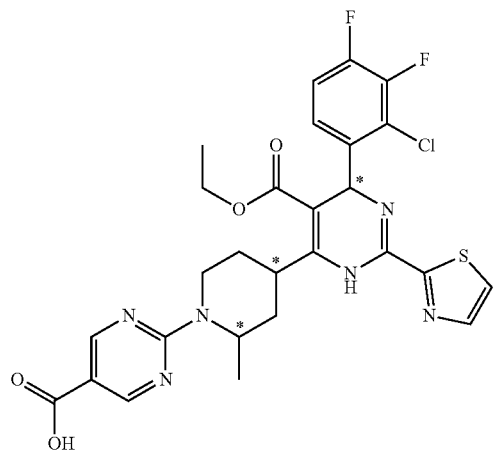<br>Compound II-34-F |
| XI-35-5R | 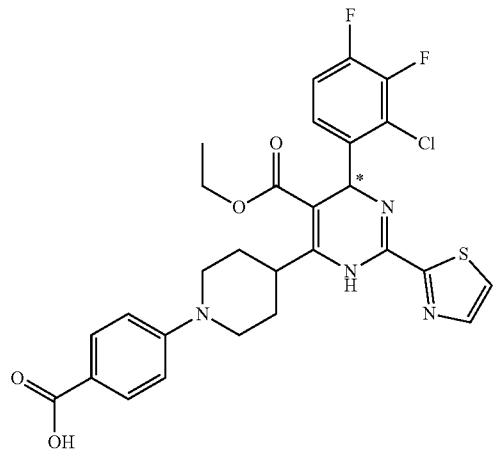<br>Compound II-35-A |

TABLE 2-continued
| Ester Cpd.# | Acid |
|---|---|
| XI-36-S | 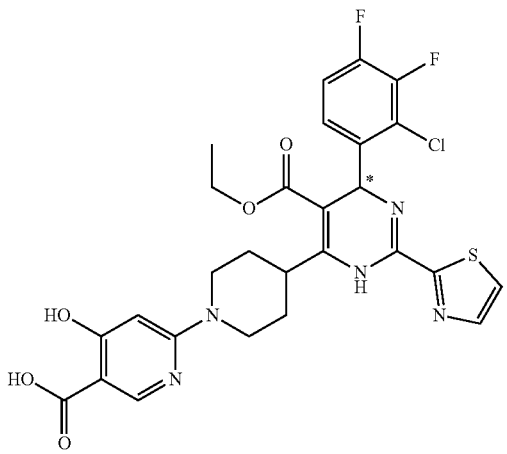
Compound II-36-B |
| XI-37-2 | 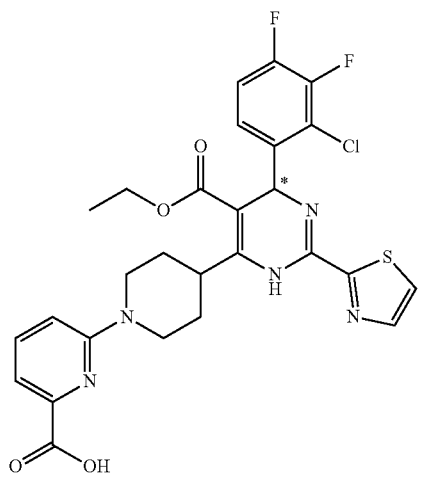
Compound II-37-B |
| XI-38-3 | 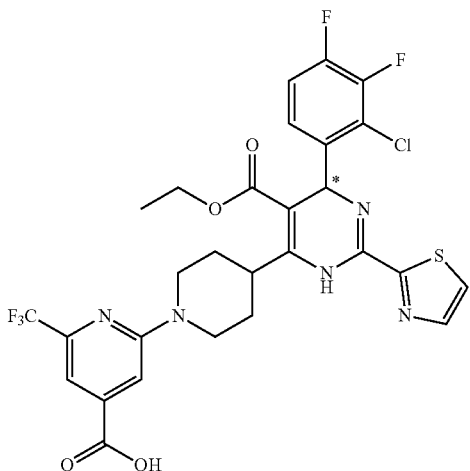
Compound II-38-B |

TABLE 2-continued
| Ester Cpd.# | Acid |
|---|---|
| XI-39-S | 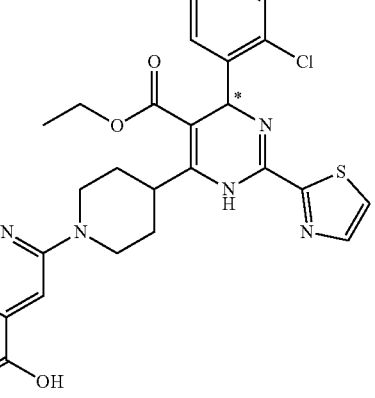<br>Compound II-39-B |
| XI-40-B | 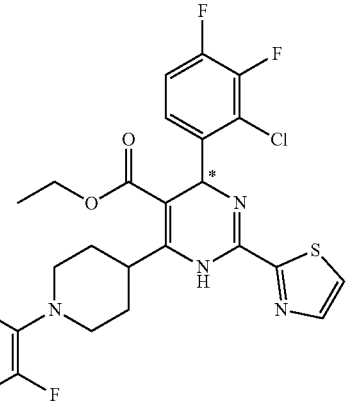<br>Compound II-40-B |
| XI-41-B | 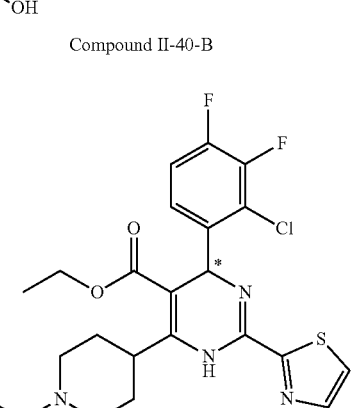<br>Compound II-41-B |

TABLE 2-continued
| Ester Cpd.# | Acid |
|---|---|
| XI-42-3B | 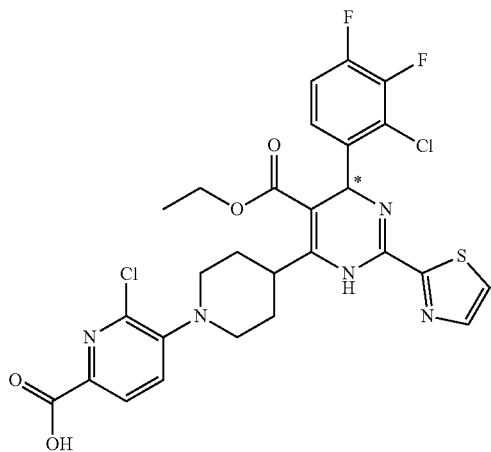<br>Compound II-42-B |
| XI-43-1 | 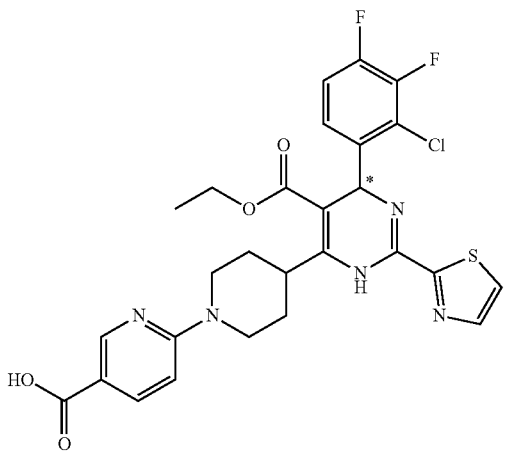<br>Compound II-43-B |
| FA12 and BB49 | 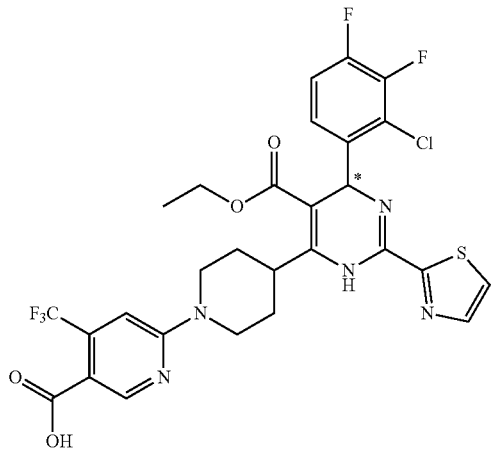<br>Compound II-44-B |

TABLE 2-continued
| Ester Cpd.# | Acid |
|---|---|
| XI-45-B | 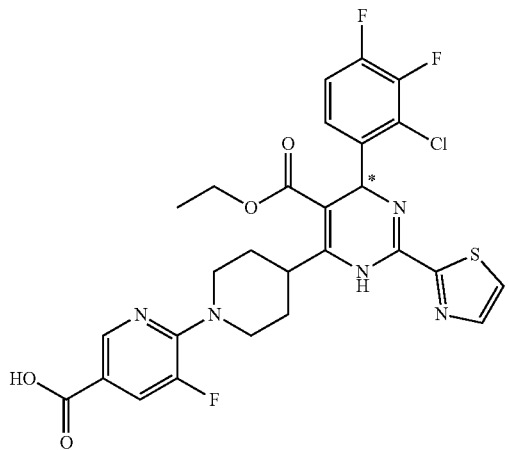<br>Compound II-45-B |
| XI-46-S | 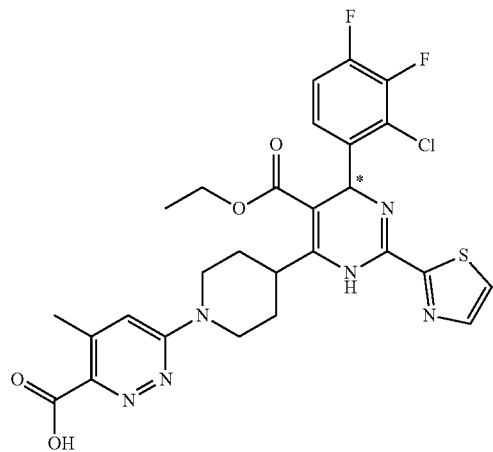<br>Compound II-46-B |
| XI-47-3 | 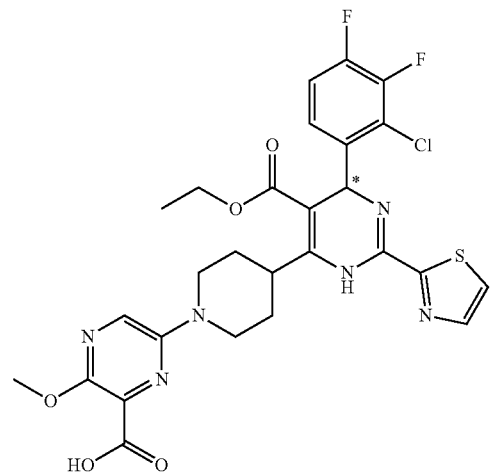<br>Compound II-47-B |

TABLE 2-continued
| Ester Cpd.# | Acid |
|---|---|
| XI-48-B | 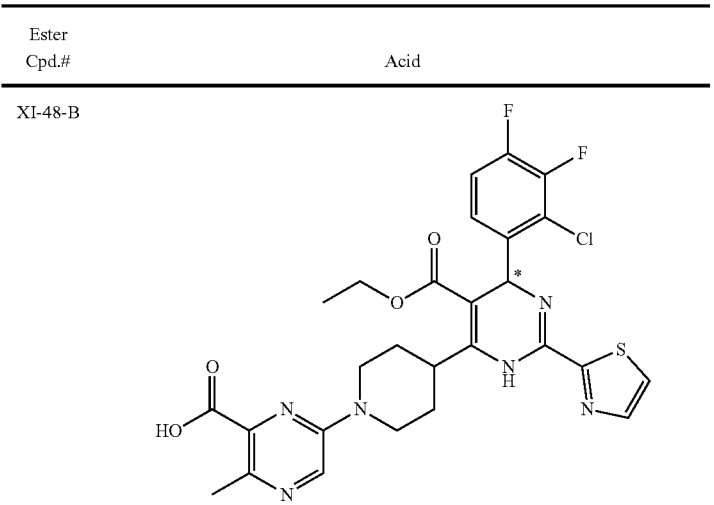<br>Compound II-48-B |
| XI-49-B | 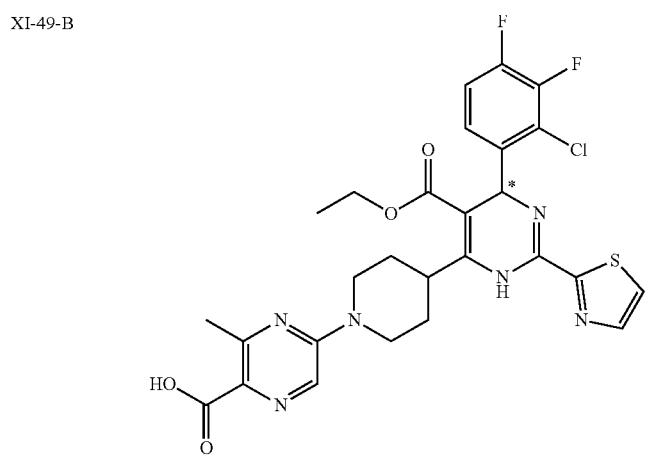<br>Compound II-49-B |
| XI-50-S | 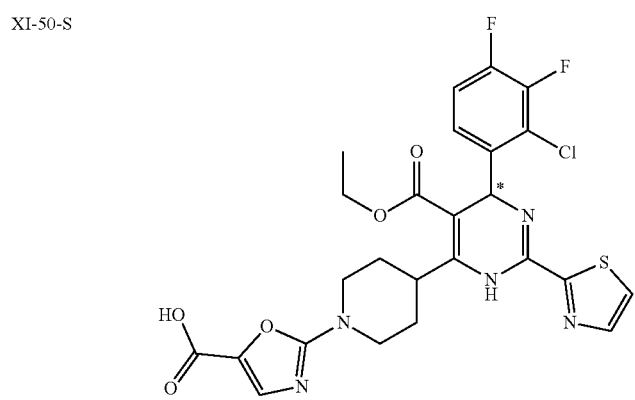<br>Compound II-50-B |

TABLE 2-continued
| Ester Cpd.# | Acid |
|---|---|
| FA12 and BB22 | 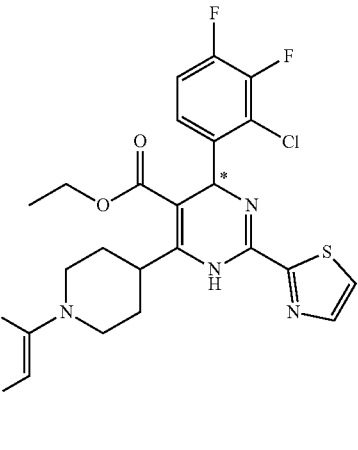<br>Compound II-51-B |
| XI-52-S | 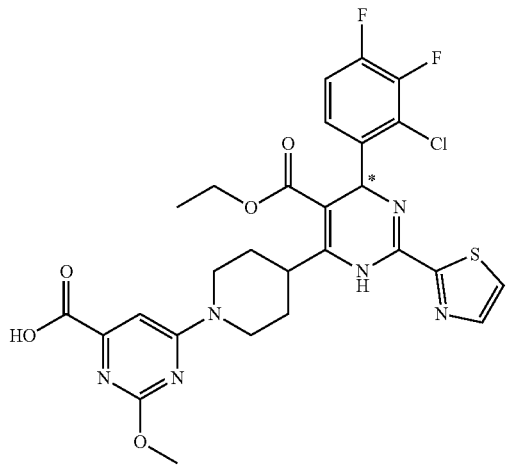<br>Compound II-52-B |
| XI-53-S | 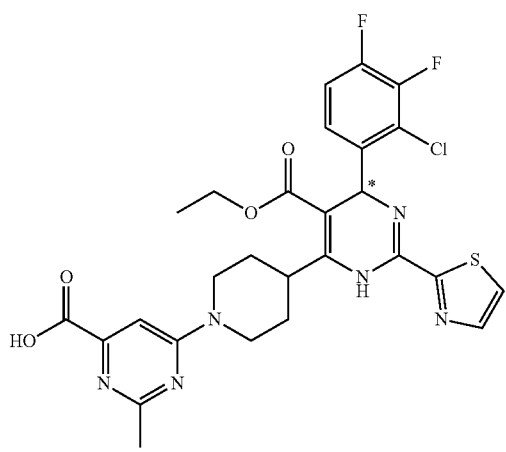<br>Compound II-53-B |

TABLE 2-continued
| Ester Cpd.# | Acid |
|---|---|
| XI-54-S | 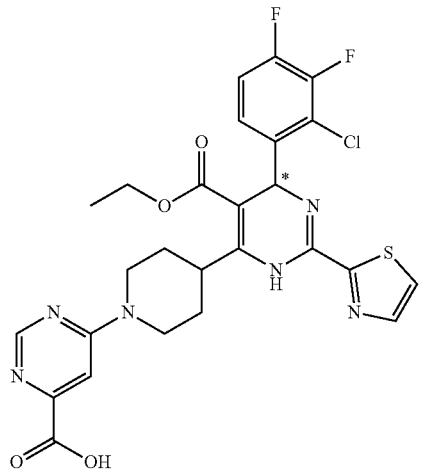<br>Compound II-54-B |
| FA12 and BB55 | 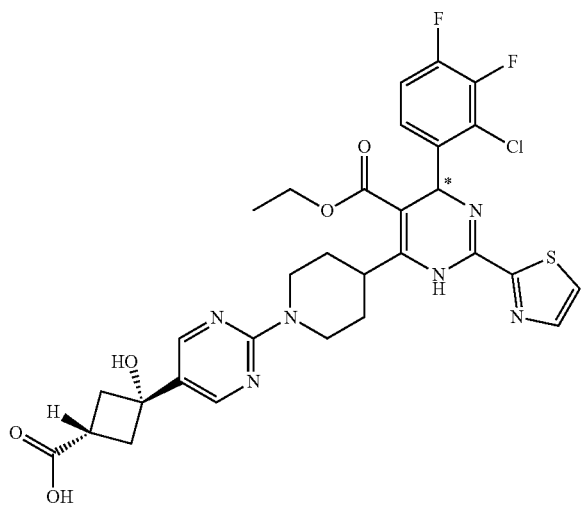<br>Compound II-55-B |
| XI-56-B | 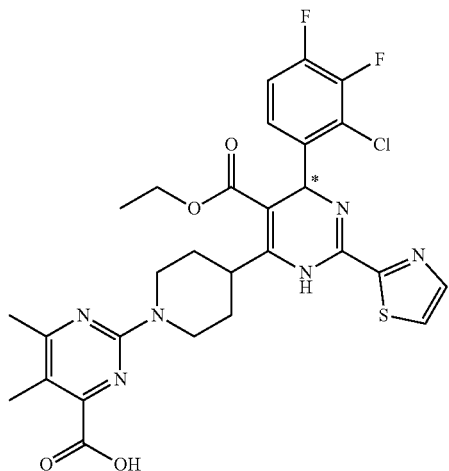<br>Compound II-56-B |

TABLE 2-continued
| Ester Cpd.# | Acid |
|---|---|
| XI-57-S | 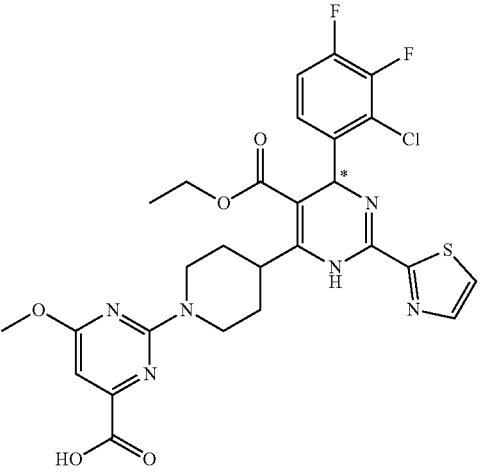<br>Compound II-57-B |
| XI-58-S | 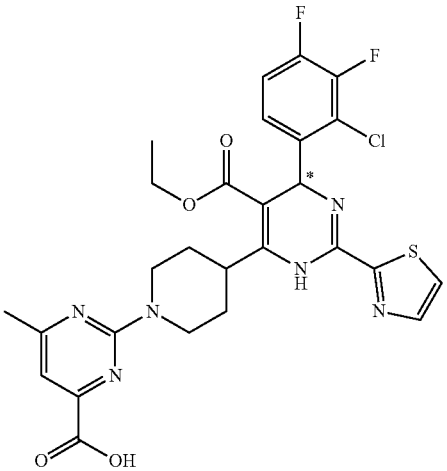<br>Compound II-58-B |
| XI-59-B | 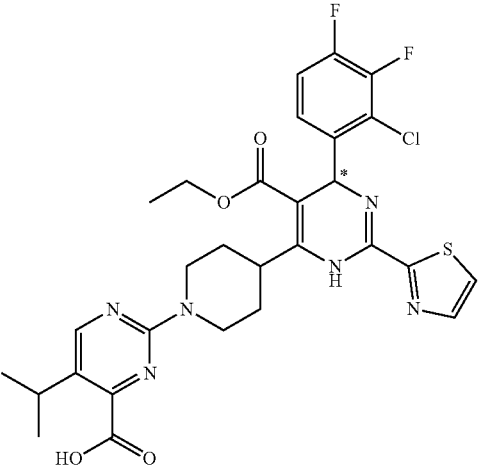<br>Compound II-59-B |

TABLE 2-continued

| Ester Cpd.# | Acid |
|---|---|
| XI-60-B | Compound II-60-B |
| XI-61-B | Compound II-61-B |
| XI-62-B | Compound II-62-B |

TABLE 2-continued
| Ester Cpd.# | Acid |
|---|---|
| FA12 and BB2-1 | 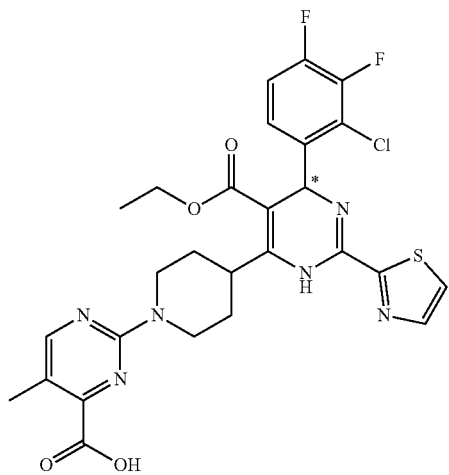
Compound II-63-B |
| XI-64-B | 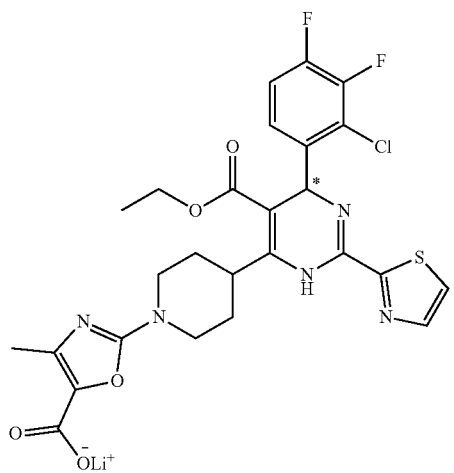
Compound II-64-B |
| FA12 and BB23 | 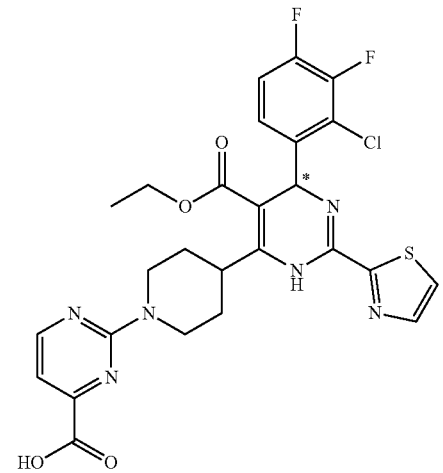
Compound II-65-B |

TABLE 2-continued
| Ester Cpd.# | Acid |
|---|---|
| XI-66-N | 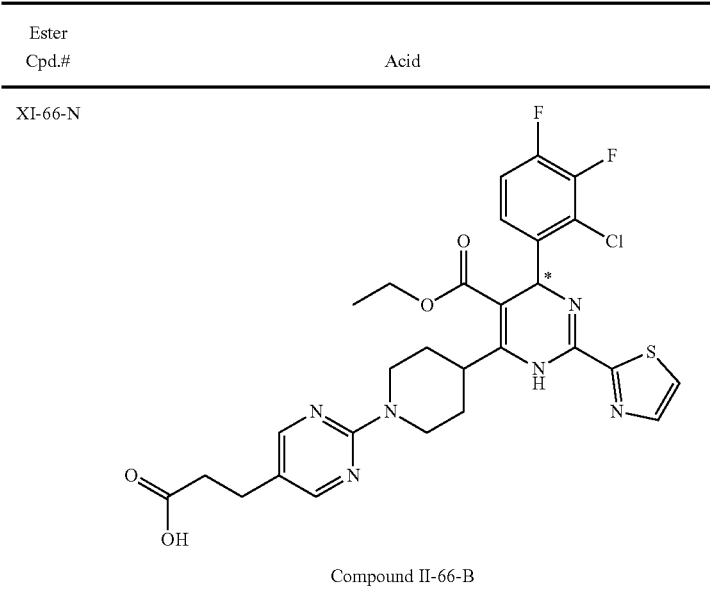<br>Compound II-66-B |
| XI-67-B | 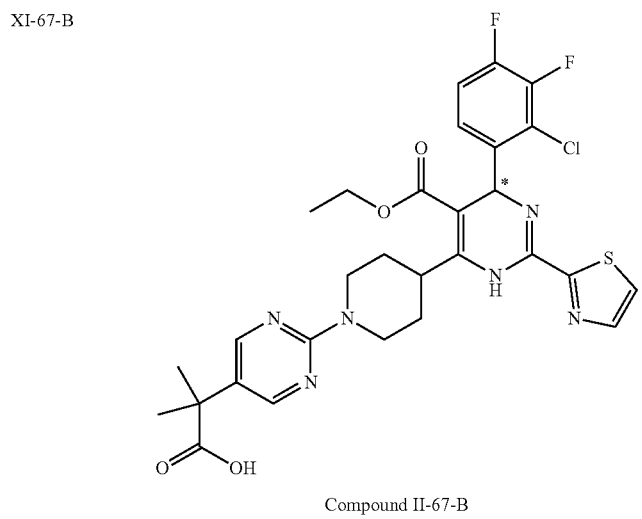<br>Compound II-67-B |
| XI-68-B | 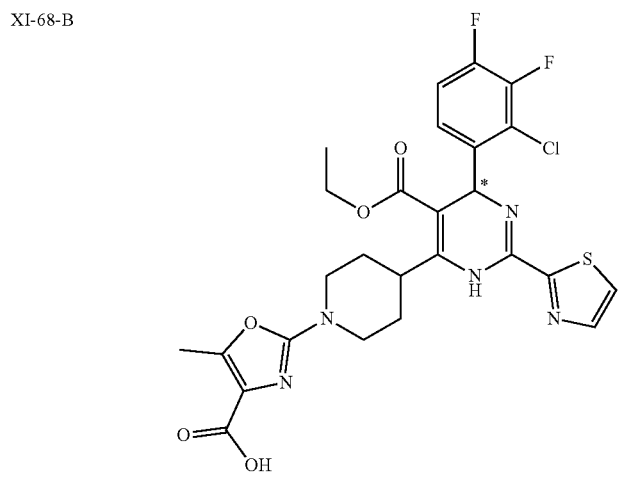<br>Compound II-68-B |

TABLE 2-continued
| Ester Cpd.# | Acid |
|---|---|
| XI-69-B | 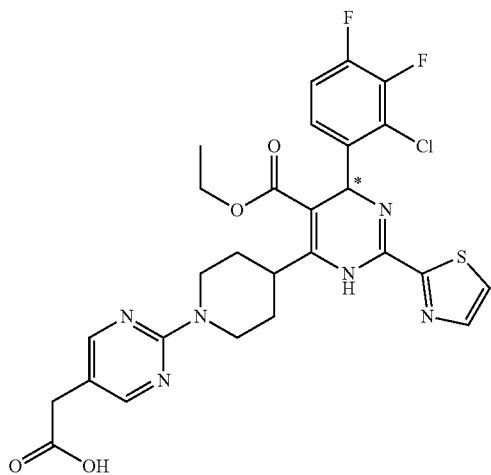
Compound II-69-B |
| XI-70-N | 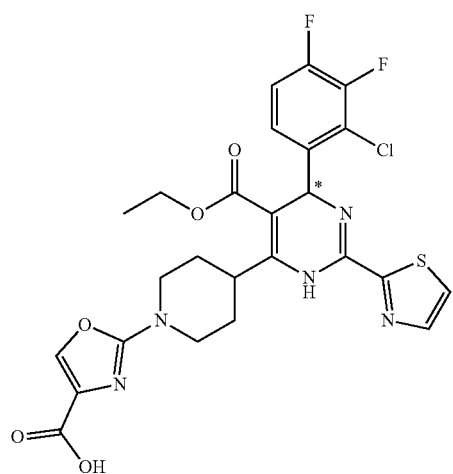
Compound II-70-B |
| FA12 and BB36 | 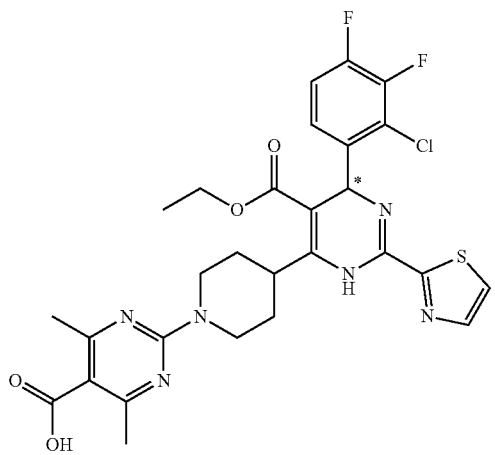
Compound II-71-B |

TABLE 2-continued
| Ester Cpd.# | Acid |
|---|---|
| XI-72-S | 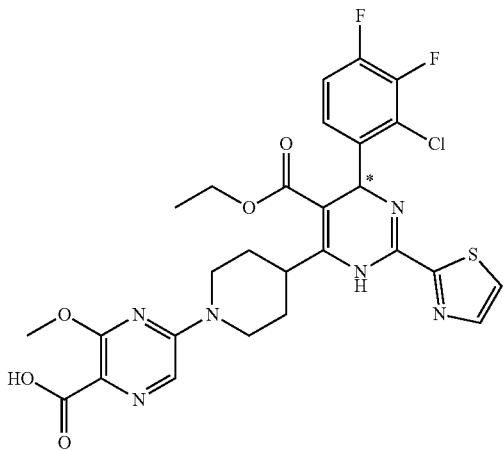<br>Compound II-72-B |
| XI-73-S | 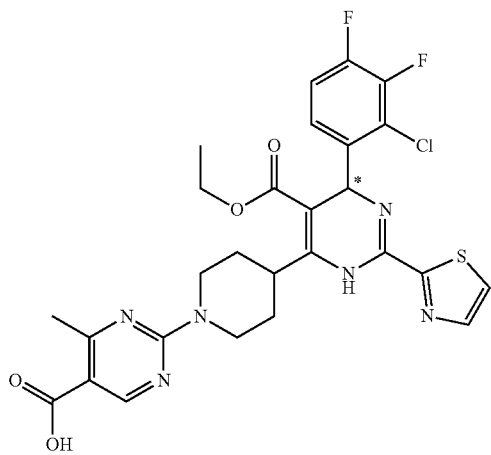<br>Compound II-73-B |
| FA12 and BB7 | 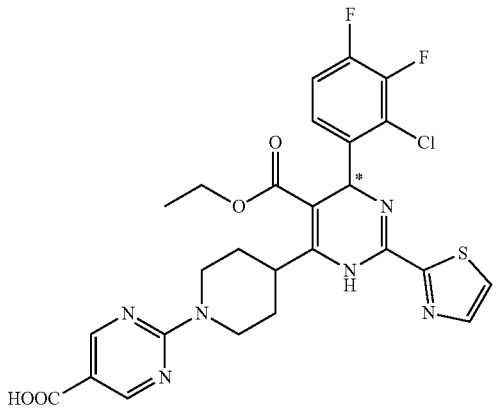<br>Compound II-74-B |

TABLE 2-continued
| Ester Cpd.# | Acid |
|---|---|
| XI-75-S | 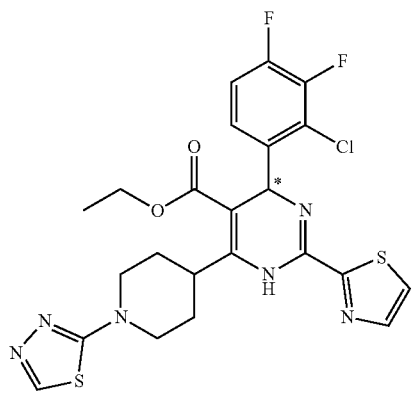<br>Compound II-75-X |
| XI-76-B | 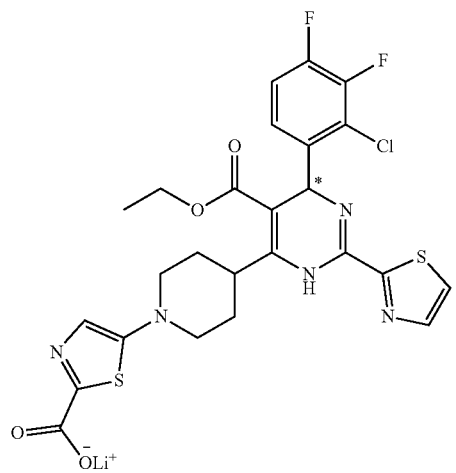<br>Compound II-76-B |
| XI-77-S | 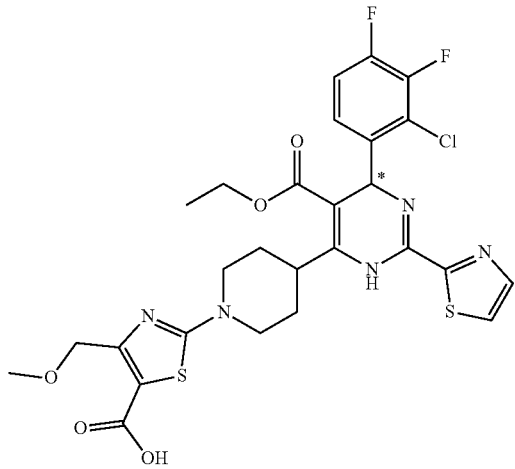<br>Compound II-77-B |

TABLE 2-continued
| Ester Cpd.# | Acid |
|---|---|
| XI-78-S | 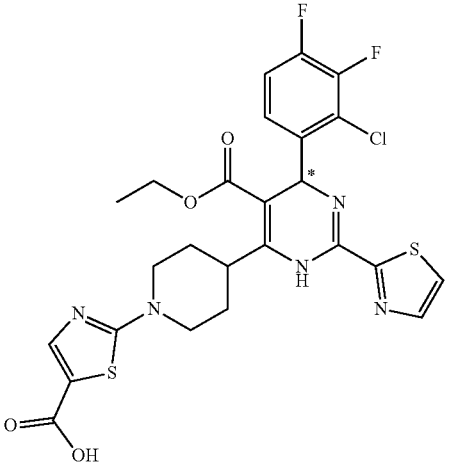
Compound II-78-B |
| XI-79-S | 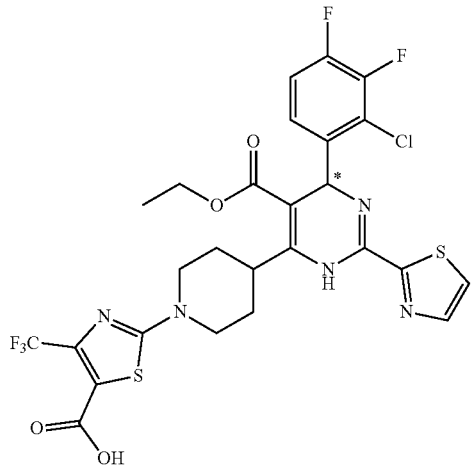
Compound II-79-B |
| XI-80-S | 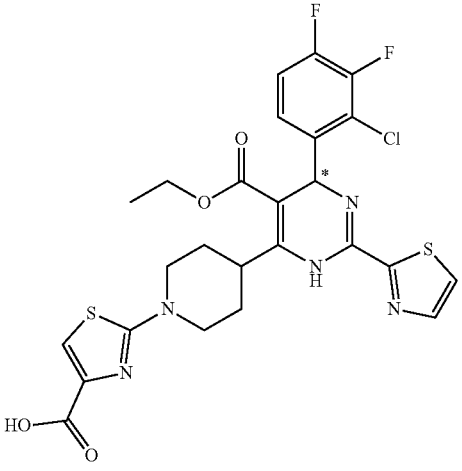
Compound II-80-B |

TABLE 2-continued
| Ester Cpd.# | Acid |
|---|---|
| XI-81-B | 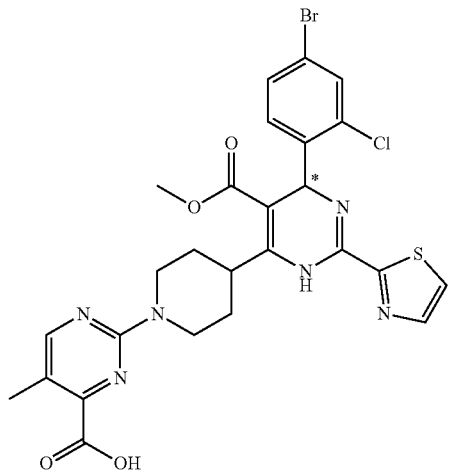<br>Compound II-81-B |
| XI-82-B | 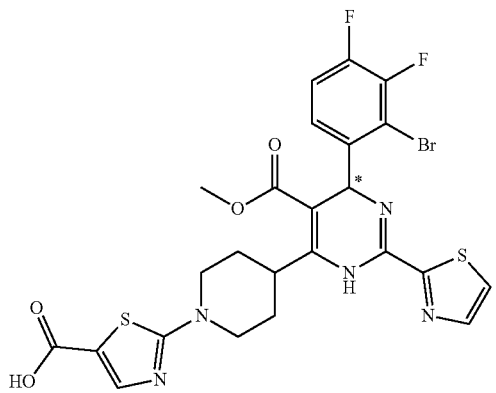<br>Compound II-82-B |
| XI-83-B | 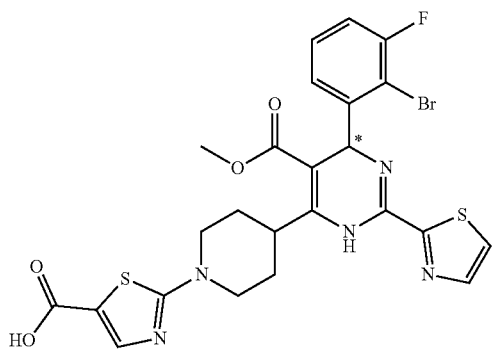<br>Compound II-83-B |

TABLE 2-continued
| Ester Cpd.# | Acid |
|---|---|
| XI-84-N | 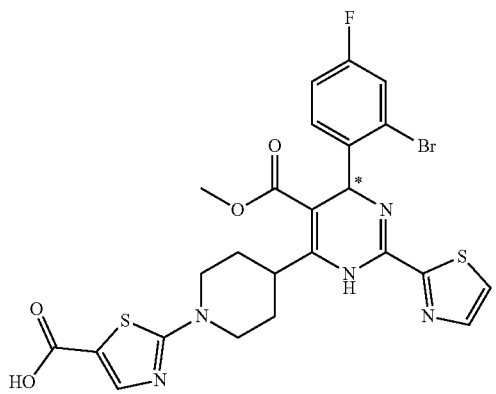
Compound II-84-B |
| XI-85-M | 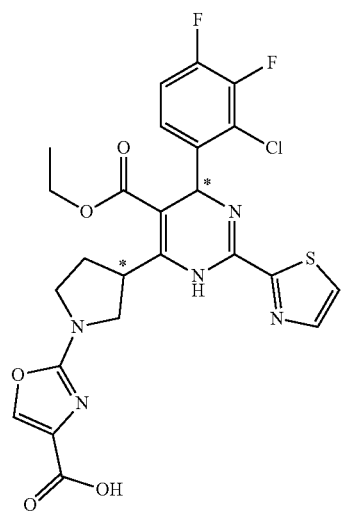
Compound II-85-A |
| XI-86-N | 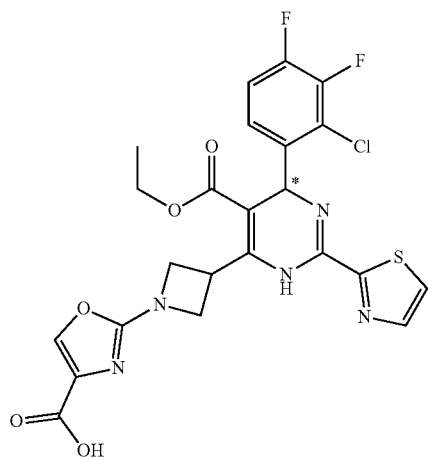
Compound II-86-B |

TABLE 2-continued
| Ester Cpd.# | Acid |
|---|---|
| FA19 and BB51 | 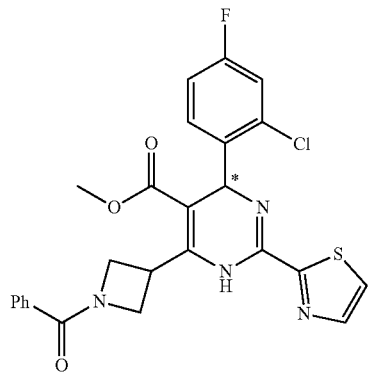<br>Compound II-87-B |
| FA19-1B and BB52 | 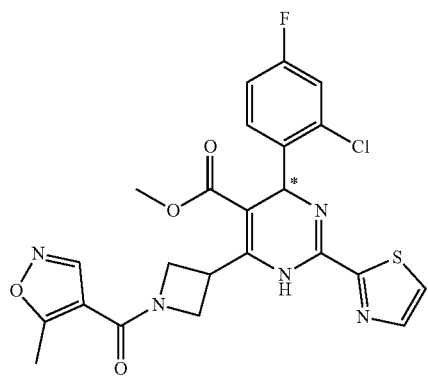<br>Compound II-88-B |
| XI-87-S | 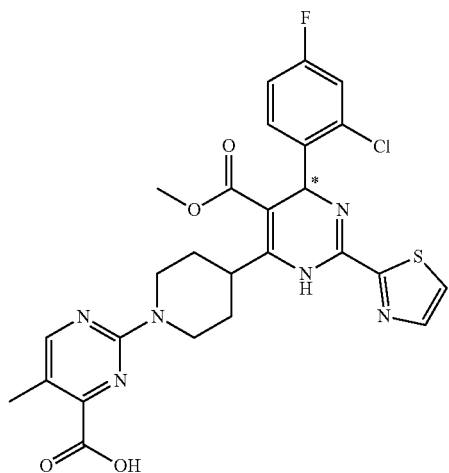<br>Compound II-89-B |

TABLE 2-continued
| Ester Cpd.# | Acid |
|---|---|
| VIII-20-6B | 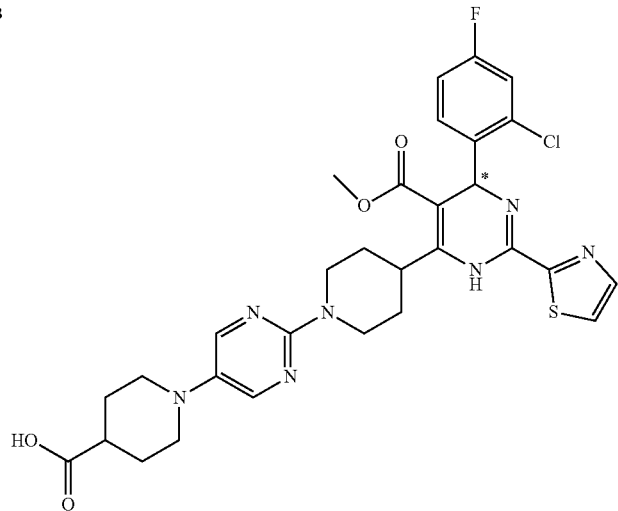<br>Compound II-90-B |
| XI-88-4 | 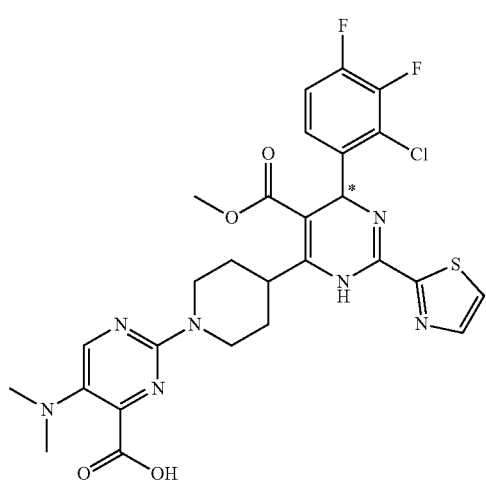<br>Compound II-91-B |
| XI-89-2 | 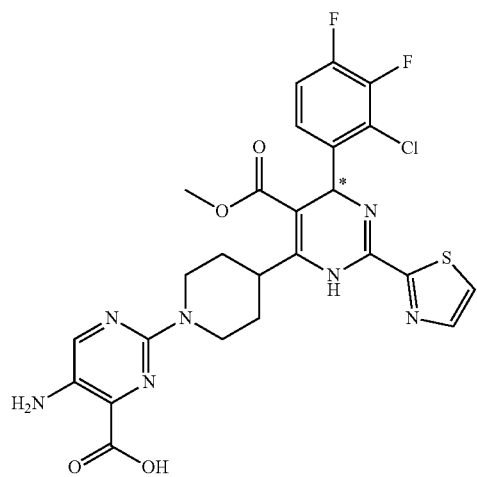<br>Compound II-92-B |

TABLE 2-continued
| Ester Cpd.# | Acid |
|---|---|
| XI-90-3 | 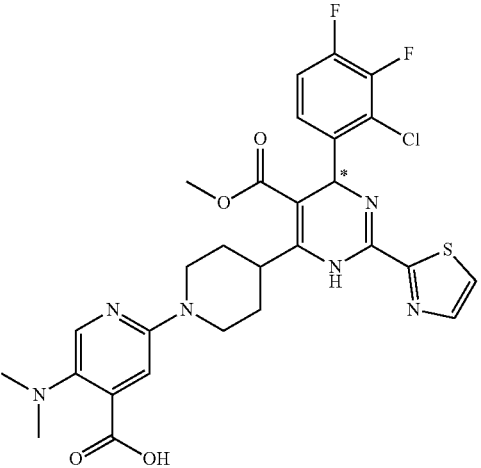<br>Compound II-93-B |
| XI-91-1 | 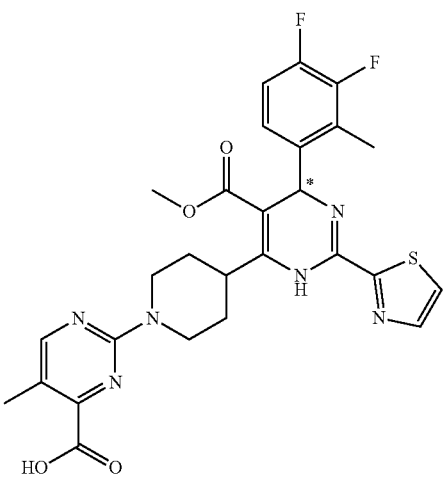<br>Compound II-94-B |
| XI-92-1 | 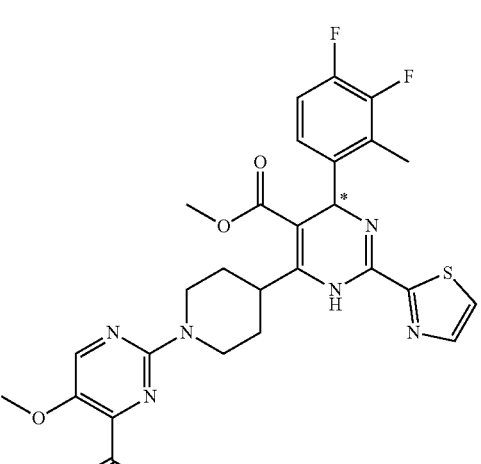<br>Compound II-95-B |

TABLE 2-continued
| Ester Cpd.# | Acid |
|---|---|
| XI-93-3 | 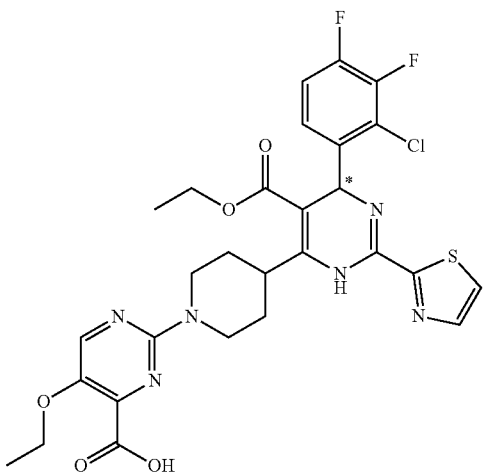<br>Compound II-96-B |
| XI-94-1 | 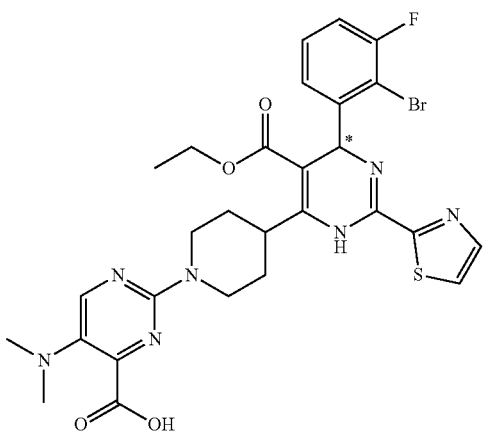<br>Compound II-97-B |
| XI-95S | 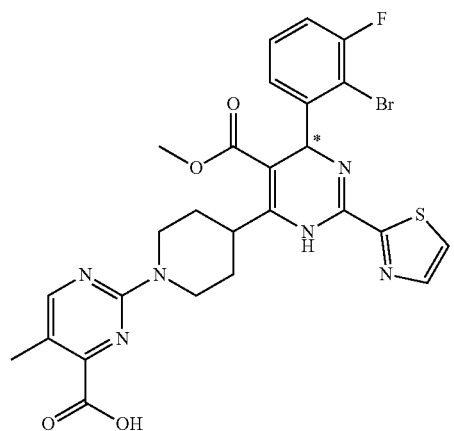<br>Compound II-98-B |

TABLE 2-continued
| Ester Cpd.# | Acid |
|---|---|
| XI-96-1 | 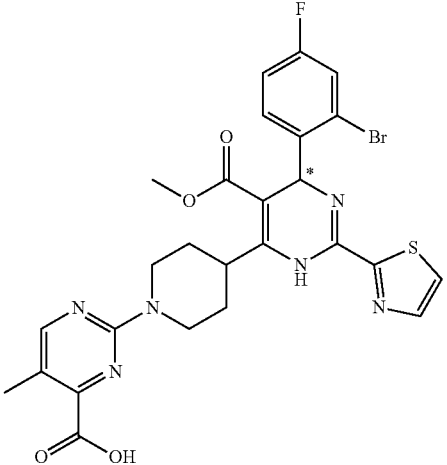<br>Compound II-99-B |
| XI-97-1 | 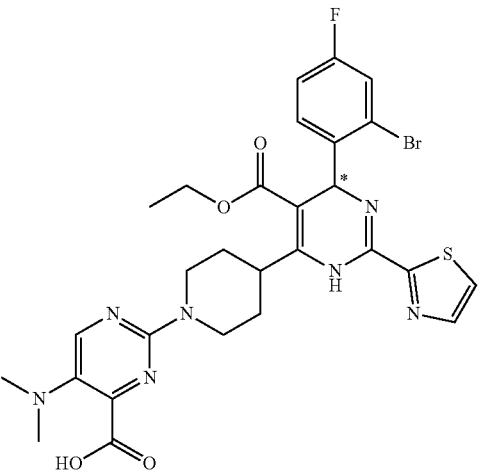<br>Compound II-100-B |
| VIII-23-B | 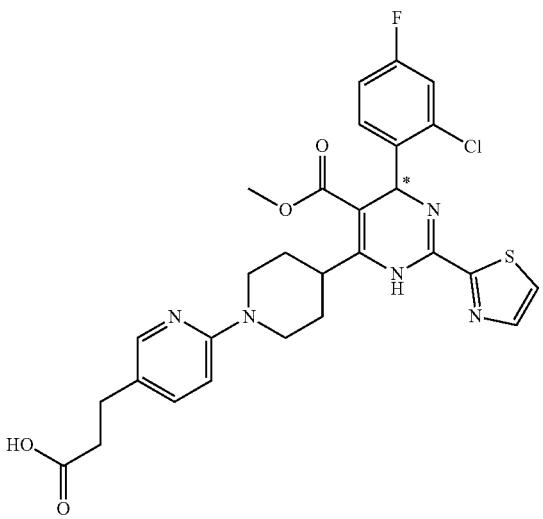<br>Compound II-101-B |

Spectral Analyses of the Final Products of General Formula I and General Formula II Compound

I-2-D (trans)-2-(4-(6-(2-Chloro-3,4-difluorophenyl)-5-(ethoxycarbonyl)-2-(thiazol-2-yl)-3,6-dihydropyrimidin-4-yl)cyclohexyl)oxazole-4-carboxylic Acid (a Single Stereoisomer)

Converted from compound VII-2-Y.
By utilizing the analogous procedure of Method C, the title compound was synthesized. LC-MS (ESI): $R_T$=3.558 min, mass calcd. for $C_{26}H_{23}ClF_2N_4O_5S$ 576.1, m/z found 577.1 [M+H]$^+$. Chiral analysis (Column: Chiralpak IE 5 μm 4.6*250 mm; Mobile Phase: Hex:EtOH:TFA=70:30:0.2 at 1.0 mL/min; Temp: 30° C.; Wavelength: 230 nm, $R_T$=11.206 min). $^1$H NMR (400 MHz, CD$_3$OD) δ 8.23 (s, 1H), 7.92 (d, J=2.8 Hz, 1H), 7.75 (d, J=3.2 Hz, 1H), 7.27-7.22 (m, 2H), 6.12 (s, 1H), 4.08-3.77 (m, 3H), 3.03-2.90 (m, 1H), 2.34-2.17 (m, 2H), 2.12-1.66 (m, 6H), 1.15 (t, J=7.2 Hz, 3H)

Compound I-3-D trans-2-(4-(6-(3-Fluoro-2-methylphenyl)-5-(methoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-3-H.
LC-MS (ESI): $R_T$=3.430 min, mass calcd. for $C_{26}H_{25}FN_4O_5S$, 524.2, m/z found 524.9 [M+H]$^+$. Chiral HPLC (Column: Chiralpak IA 5 μm 4.6*250 mm; Mobile Phase: Hex:IPA:TFA=80:20:0.2 at 1 mL/min; Temp: 30° C.; Wavelength: 254 nm, $R_T$=14.346 min). $^1$H NMR (400 MHz, CD$_3$OD) δ 8.33 (s, 1H), 7.93 (d, J=3.6 Hz, 1H), 7.76 (d, J=2.8 Hz, 1H), 7.17-7.13 (m, 2H), 6.98-6.93 (m, 1H), 5.96 (s, 1H), 4.06-3.89 (m, 1H), 3.63 (s, 3H), 3.05-2.98 (m, 1H), 2.50 (s, 3H), 2.33-2.27 (m, 2H), 2.15-1.75 (m, 6H).

Compound I-4-B (trans)-2-(4-(6-(2-Chloro-4-fluorophenyl)-5-(methoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-4-N.
LC-MS (ESI): $R_T$=4.127 min, mass calcd. for $C_{25}H_{22}ClFN_4O_5S$, 544.1, m/z found 544.9 [M+H]$^+$. $^1$H NMR (400 MHz, DMSO-d$_6$) δ 9.17-8.83 (m, 1H), 8.36 (s, 1H), 8.01-7.93 (m, 2H), 7.44-7.41 (m, 1H), 7.36-7.34 (m, 1H), 7.24-7.22 (m, 1H), 6.02 (s, 0.4H), 5.92 (s, 0.6H), 3.97-3.85 (m, 0.4H), 3.72-3.60 (m, 0.6H), 3.54 (s, 1.8H), 3.53 (s, 1.2H), 3.06-2.94 (m, 0.4H), 2.89-2.78 (m, 0.6H), 2.25-2.09 (m, 2H), 2.02-1.76 (m, 3H), 1.73-1.52 (m, 3H).

Compound I-5-B (trans)-2-(4-(6-(2-Chloro-3-fluorophenyl)-5-(methoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-5-Q.
LC-MS (ESI): $R_T$=3.127 min, mass calcd. for $C_{25}H_{22}ClFN_4O_5S$, 544.1 m/z found 545.1 [M+H]$^+$. $^1$H NMR (400 MHz, DMSO-d$_6$) δ 9.53 (d, J=3.2 Hz, 0.6H), 9.05 (s, 0.4H), 8.04-7.99 (m, 1.6H), 7.98-7.91 (m, 1.4H), 7.42-7.28 (m, 2H), 7.24-7.16 (m, 1H), 6.08 (s, 0.4H), 5.98 (d, J=3.2 Hz, 0.6H), 3.97-3.87 (m, 0.4H), 3.72-3.61 (m, 0.6H), 3.53 (s, 1.2H), 3.52 (s, 1.8H), 2.98-2.91 (m, 0.4H), 2.83-2.72 (m, 0.6H), 2.23-2.09 (m, 2H), 2.07-1.99 (0.4H), 1.98-1.85 (m, 2H), 1.84-1.74 (m, 1H), 1.71-1.65 (m, 0.6H), 1.64-1.46 (m, 2H).

Compound I-6-B (trans)-2-(4-(6-(4-Fluoro-2-methylphenyl)-5-(methoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-6-Q.
LC-MS (ESI): $R_T$=3.099 min, mass calcd. for $C_{26}H_{25}FN_4O_5S$, 524.15, m/z found 525.2 [M+H]$^+$. $^1$H NMR (400 MHz, DMSO-d$_6$) δ 9.51 (s, 0.7H), 8.97 (s, 0.3H), 8.03-7.90 (m, 3H), 7.32-7.24 (m, 0.7H), 7.19-7.12 (m, 0.3H), 7.08-6.92 (m, 2H), 5.81 (s, 0.3H), 5.71-5.64 (m, 0.7H), 3.98-3.88 (m, 0.3H), 3.69-3.59 (m, 0.7H), 3.53 (s, 3H), 2.99-2.89 (m, 0.3H), 2.83-2.71 (m, 0.7H), 2.59 (s, 1H), 2.50 (s, 2H), 2.24-2.08 (m, 2H), 2.06-1.75 (m, 3H), 1.71-1.46 (m, 3H).

Compound I-7-B (trans)-2-(4-(6-(2-chloro-3,4-difluorophenyl)-2-(3,5-difluoropyridin-2-yl)-5-(methoxycarbonyl)-3,6-dihydropyrimidin-4-yl)cyclohexyl)oxazole-4-carboxylic acid (a Single Stereoisomer)

By utilizing the analogous procedure of Method C, the title compound was synthesized from compound VII-7-N.
LC-MS (ESI): $R_T$=3.399 min, mass calcd. for $C_{27}H_{21}ClF_4N_4O_5$. HCl 629.4, m/z found 592.9 [M−HCl+H]$^+$. $^1$H NMR (400 MHz, DMSO-d$_6$) δ 12.94 (br s, 1H), 8.67 (s, 1H), 8.62 (s, 1H), 8.16-8.09 (m, 1H), 7.53-7.46 (m, 1H), 7.24-7.21 (m, 1H), 6.06 (s, 1H), 4.02-3.84 (m, 1H), 3.54 (s, 3H), 2.93-2.84 (m, 1H), 2.25-2.12 (m, 2H), 1.96-1.89 (m, 2H), 1.85-1.76 (m, 2H), 1.66-1.51 (m, 2H).

Compound I-8-B 2-(3-(6-(2-Chloro-3,4-difluorophenyl)-5-(methoxycarbonyl)-2-(thiazol-2-yl)-3,6-dihydropyrimidin-4-yl)bicyclo[1.1.1]pentan-1-yl)oxazole-4-carboxylic Acid (a Single Stereoisomer)

By utilizing the analogous procedure of Method C, the title compound was synthesized from compound VII-8-N.
LC-MS (ESI): $R_T$=3.618 min, mass calcd. for $C_{24}H_{17}ClF_2N_4O_5S$, 546.1, m/z found 546.8 [M+H]$^+$. Chiral HPLC (Column: Chiralpak IA 5 μm 4.6*250 mm; Mobile Phase: Hex:EtOH:TFA=80:20:0.2 at 1.0 mL/min; Temp: 30° C.; Wavelength: 230 nm, $R_T$=11.842 min). $^1$H NMR (400 MHz, CD$_3$OD) δ 8.31 (s, 1H), 7.92 (d, J=3.2 Hz, 1H), 7.76 (d, J=3.2 Hz, 1H), 7.27-7.19 (m, 2H), 6.10 (s, 1H), 3.62 (s, 3H), 2.72 (s, 6H).

Compound I-9-B (trans)-2-(4-(6-(2-chloro-3-fluorophenyl)-5-(ethoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-9-F.
LC-MS (ESI): $R_T$=2.974 min, mass calcd. for $C_{26}H_{24}ClFN_4O_5S$, 558.1, m/z found 559.1[M+H]$^+$. $^1$H NMR (400 MHz, DMSO-d$_6$) δ 9.50 (br s, 0.6H), 8.98 (s, 0.4H), 8.63 (s, 0.6H), 8.62 (s, 0.4H), 8.04-7.92 (m, 2H), 7.42-7.28 (m, 2H), 7.25-7.17 (m, 1H), 6.09 (s, 0.4H), 5.98 (s, 0.6H), 4.03-3.93 (m, 2H), 3.92-3.88 (m, 0.3H), 3.70-3.60 (m, 0.7H), 3.07-3.01 (m, 0.4H), 2.92-2.83 (m, 0.6H), 2.25-2.12 (m, 2H), 2.07-1.87 (m, 2.5H), 1.85-1.77 (m, 1H), 1.74-1.69 (m, 0.5H), 1.66-1.49 (m, 2H), 1.11-1.00 (m, 3H).

Compound I-10-C (trans)-2-(4-(6-(2-Chloro-4-fluorophenyl)-5-(ethoxycarbonyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-10-P.
LC-MS (ESI): $R_T$=3.590 min, mass calcd. for $C_{26}H_{24}ClFN_4O_5S$, 558.1, m/z found 558.9 [M+H]$^+$. Chiral analysis (Column: Chiralpak IE 5 μm 4.6*250 mm; Mobile Phase: Hex:EtOH:TFA=80:20:0.2 at 1.0 mL/min; Temp: 30° C.; Wavelength: 254 nm, $R_T$=19.068 min). $^1$H NMR (400 MHz, DMSO-d$_6$) δ 8.96 (br s, 1H), 8.33 (s, 1H), 8.01-8.00 (m, 1.5H), 7.95 (d, J=2.8 Hz, 0.5H), 7.44-7.41 (m, 1H), 7.38-7.35 (m, 1H), 7.25-7.20 (m, 1H), 6.03 (s, 0.4H), 5.93 (s, 0.6H), 4.02-3.96 (m, 2H), 3.91-3.87 (m, 0.3H), 3.70-3.61 (m, 0.7H), 3.01-2.95 (m, 0.4H), 2.86-2.79 (m, 0.6H), 2.20-2.13 (m, 2H), 2.05-1.71 (m, 4H), 1.64-1.48 (m, 2H), 1.11-1.04 (m, 3H).

Compound I-11-B (trans)-2-(4-(5-(Ethoxycarbonyl)-6-(3-fluoro-2-methylphenyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-11-Q.
LC-MS (ESI): $R_T$=3.668 min, mass calcd. for $C_{27}H_{27}FN_4O_5S$, 538.2, m/z found 538.9 [M+H]$^+$. Chiral analysis (Column: Chiralpak IC 5 μm 4.6*250 mm; Mobile phase: Hex:EtOH:TFA=80:20:0.2 at 1 mL/min; Temp: 30° C.; Wavelength: 254 nm; $R_T$=11.136 min). $^1$H NMR (400 MHz, CD$_3$OD) δ 8.30 (s, 1H), 7.90 (d, J=3.2 Hz, 1H), 7.73 (d, J=3.2 Hz, 1H), 7.17-7.08 (m, 2H), 6.97-6.89 (m, 1H), 5.93 (s, 1H), 4.05 (q, J=7.2 Hz, 2H), 4.01-3.81 (m, 1H), 3.04-2.92 (m, 1H), 2.47 (s, 3H), 2.34-2.21 (m, 2H), 2.14-2.03 (m, 1H), 2.01-1.85 (m, 3H), 1.84-1.68 (m, 2H), 1.14 (t, J=7.2 Hz, 3H).

Compound I-12-C (trans)-2-(4-(5-(Ethoxycarbonyl)-6-(4-fluoro-2-methylphenyl)-2-(thiazol-2-yl)-3,6-dihydropyrimidin-4-yl)cyclohexyl)oxazole-4-carboxylic Acid (a Single Stereoisomer)

By utilizing the analogous procedure of Method C, the title compound was synthesized from compound VII-12-P.
LC-MS (ESI): $R_T$=3.345 min, mass calcd. for $C_{27}H_{27}FN_4O_5S$, 538.2, m/z found 539.2 [M+H]$^+$. Chiral analysis (Column: Chiralpak OJ-H 5 μm 4.6*250 mm; Mobile Phase: Hex:EtOH:TFA=60:40:0.2 at 1.0 mL/min; Temp: 30° C.; Wavelength: 254 nm, $R_T$=6.430 min). $^1$H NMR (400 MHz, DMSO-d$_6$) δ 9.47 (br s, 0.7H), 8.90 (s, 0.3H), 8.36 (s, 1H), 7.99-7.98 (m, 1.7H), 7.93-7.92 (m, 0.3H), 7.29-7.25 (m, 0.7H), 7.18-7.15 (m, 0.3H), 7.07-6.97 (m, 2H), 5.82 (s, 0.3H), 5.68 (s, 0.7H), 4.01-3.84 (m, 2.3H), 3.68-3.60 (m, 0.7H), 3.02-2.96 (m, 0.3H), 2.86-2.80 (m, 0.7H), 2.56 (s, 0.7H), 2.52 (m, 2.3H), 2.20-2.13 (m, 2H), 2.02-1.80 (m, 3H), 1.71-1.48 (m, 3H), 1.10-1.06 (m, 3H).

Compound I-13-C 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylic Acid (a Single Stereoisomer)

By utilizing the analogous procedure of Method C, the title compound was synthesized from compound VII-13-P.
LC-MS (ESI): $R_T$=3.177 min, mass calcd. for $C_{26}H_{21}ClF_2N_4O_5S$, 574.1, m/z found 575.0 [M+H]$^+$. Chiral HPLC (Column: Chiralpak IA 5 μm 4.6*250 mm; Mobile Phase: Hex:EtOH:TFA=70:30:0.2 at 1.0 mL/min; Temp: 30° C.; Wavelength: 254 nm, $R_T$=10.796 min). $^1$H NMR (400 MHz, DMSO-d$_6$) δ 8.42 (s, 1H), 8.01-7.93 (m, 2H), 7.51-7.45 (m, 1H), 7.26-7.20 (m, 1H), 6.86-6.82 (m, 1H), 6.07 (s, 0.3H), 5.97 (s, 0.7H), 4.12 (br s, 0.3H), 4.01-3.90 (m, 2.7H), 2.78-2.65 (m, 2H), 2.44-2.33 (m, 2H), 2.07-1.82 (m, 2H), 1.08-1.01 (m, 3H).

Compound I-13-D 2-(4-(6-(2-chloro-3,4-difluorophenyl)-5-(ethoxycarbonyl)-2-(thiazol-2-yl)-3,6-dihydropyrimidin-4-yl)cyclohex-1-en-1-yl)oxazole-4-carboxylic Acid (a Single Stereoisomer)

By utilizing the analogous procedure of Method C, the title compound was synthesized from compound VII-13-Q.
LC-MS (ESI): $R_T$=3.176 min, mass calcd. for $C_{26}H_{21}ClF_2N_4O_5S$, 574.1, m/z found 575.0 [M+H]$^+$. Chiral HPLC (Column: Chiralpak IA 5 μm 4.6*250 mm; Mobile Phase: Hex:EtOH:TFA=70:30:0.2 at 1.0 mL/min; Temp: 30° C.; Wavelength: 254 nm, $R_T$=14.955 min). $^1$H NMR (400 MHz, DMSO-d$_6$) δ 8.43 (s, 1H), 8.01-7.94 (m, 2H), 7.53-7.47 (m, 1H), 7.29-7.25 (m, 1H), 6.83-6.81 (m, 1H), 6.05 (s, 0.2H), 5.96 (s, 0.8H), 4.13 (br s, 0.3H), 4.00-3.89 (m, 2.7H), 2.75-2.57 (m, 2H), 2.49-2.23 (m, 2H), 2.07-1.99 (m, 2H), 1.08-1.01 (m, 3H).

Compound I-14-B (trans)-2-(4-(6-(2-Chloro-3,4-difluorophenyl)-5-(ethoxycarbonyl)-2-(thiazol-2-yl)-3,6-dihydropyrimidin-4-yl)cyclohexyl)-5-methyloxazole-4-carboxylic Acid (a Single Stereoisomer)

By utilizing the analogous procedure of Method C, the title compound was synthesized from compound VII-14-N.
LC-MS (ESI): $R_T$=3.572 min, mass calcd. for $C_{27}H_{25}ClF_2N_4O_5S$, 590.1, m/z found 591.1 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 254 nm, $R_T$=10.076 min). $^1$H NMR (400

MHz, DMSO-d$_6$) δ 8.01-8.00 (m, 1.6H), 7.95 (d, J=2.8 Hz, 0.4H), 7.50-7.43 (m, 1H), 7.22-7.18 (m, 1H), 6.04 (s, 0.4H), 5.93 (s, 0.6H), 4.02-3.87 (m, 2.4H), 3.68-3.62 (m, 0.6H), 2.98-2.91 (m, 0.4H), 2.81-2.75 (m, 0.6H), 2.53 (s, 3H), 2.19-1.55 (m, 8H), 1.11-1.04 (m, 3H).

Compound I-15-A (trans)-2-((4-(6-(2-chloro-3,4-difluorophenyl)-5-(ethoxycarbonyl)-2-(thiazol-2-yl)-3,6-dihydropyrimidin-4-yl)cyclohexyl)methyl)oxazole-4-carboxylic Acid (a Single Stereoisomer)

By utilizing the analogous procedure of Method C, the title compound was synthesized from compound VII-15-M. LC-MS (ESI): R$_T$=3.367 min, mass calcd. for C$_{27}$H$_{25}$ClF$_2$N$_4$O$_5$S, 590.1, m/z found 591.0 [M+H]$^+$. Chiral analysis (Chiralpak IA 5 μm 4.6*250 mm; Mobile Phase: Hex:IPA:TFA=80:20:0.2 at 1 mL/min; Temp: 30° C.; Wavelength: 254 nm, R$_T$=10.887 min). $^1$H NMR (400 MHz, DMSO-d$_6$) δ 8.93 (s, 1H), 8.34 (br s, 1H), 7.99-7.97 (m, 1.5H), 7.94-7.93 (m, 0.5H), 7.49-7.42 (m, 1H), 7.21-7.15 (m, 1H), 6.02 (s, 0.5H), 5.91 (s, 0.5H), 4.00-3.93 (m, 2H), 3.86-3.79 (m, 0.5H), 3.62-3.56 (m, 0.5H), 2.69-2.67 (m, 2H), 1.99-1.56 (m, 7H), 1.21-1.04 (m, 5H).

Compound I-16-B (trans)-2-(2-(4-(6-(2-Chloro-3,4-difluorophenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-16-N. LC-MS (ESI): R$_T$=3.406 min, mass calcd. for C$_{26}$H$_{23}$ClF$_2$N$_4$O$_5$S, 576.1, m/z found 577.2 [M+H]$^+$. Chiral analysis (Column: Chiralpak IE 5 μm 4.6*250 mm; Mobile Phase: Hex:EtOH:TFA=50:50:0.2 at 1.0 mL/min; Temp: 30° C.; Wavelength: 254 nm, R$_T$=7.928 min). $^1$H NMR (400 MHz, DMSO-d$_6$) δ 8.01-7.95 (m, 2H), 7.77 (s, 1H), 7.49-7.43 (m, 1H), 7.22-7.14 (m, 1H), 6.02 (s, 0.4H), 5.93 (s, 0.6H), 3.94-3.87 (m, 0.5H), 3.69-3.61 (m, 0.5H), 3.53 (s, 3H), 3.38 (s, 2H), 2.99-2.92 (m, 0.5H), 2.82-2.74 (m, 0.5H), 2.18-2.10 (m, 2H), 2.04-1.67 (m, 4H), 1.61-1.48 (m, 2H).

Compound I-17-A (trans)-2-(2-(4-(6-(2-Chloro-4-fluorophenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-17-M. LC-MS (ESI): R$_T$=3.287 min, mass calcd. for C$_{26}$H$_{24}$ClFN$_4$O$_5$S, 558.1, m/z found 558.9 [M+H]$^+$. Chiral analysis (Column: Chiralpak IE 5 μm 4.6*250 mm; Mobile Phase: Hex:EtOH:TFA=60:40:0.2 at 1.0 mL/min; Temp: 30° C.; Wavelength: 254 nm, R$_T$=9.850 min). $^1$H NMR (400 MHz, DMSO-d$_6$) δ 9.47 (br s, 0.6H), 9.01 (s, 0.4H), 8.00 (s, 1.6H), 7.94 (d, J=3.2 Hz, 0.4H), 7.81 (d, J=4.0 Hz, 1H), 7.45-7.41 (m, 1H), 7.38-7.33 (m, 1H), 7.25-7.20 (m, 1H), 6.02 (s, 0.4H), 5.92 (s, 0.6H), 3.92-3.87 (m, 0.3H), 3.67-3.61 (m, 0.7H), 3.54 (s, 2.5H), 3.52 (s, 0.5H), 3.45 (s, 2H), 3.00-2.93 (m, 0.4H), 2.82-2.76 (m, 0.6H), 2.17-2.10 (m, 2H), 2.01-1.76 (m, 3.4H), 1.69-1.51 (m, 2.6H).

Compound I-18-A (trans)-2-(2-(4-(6-(2-Bromo-4-fluorophenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-18-M. LC-MS (ESI): R$_T$=3.438 min, mass calcd. for C$_{26}$H$_{24}$BrFN$_4$O$_5$S, 602.1, m/z found 602.8 [M+H]$^+$. $^1$H NMR (400 MHz, CD$_3$OD) δ 8.31-8.29 (m, 2H), 7.78 (s, 1H), 7.61-7.55 (m, 2H), 7.30-7.26 (m, 1H), 6.35 (s, 1H), 4.00-3.89 (m, 1H), 3.70 (s, 3H), 3.61 (s, 2H), 3.05-2.93 (m, 1H), 2.33-2.29 (m, 2H), 2.18-1.92 (m, 4H), 1.85-1.66 (m, 2H).

Compound I-19-B (trans)-2-(2-(4-6-(2-Bromo-3-fluorophenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-19-N. LC-MS (ESI): R$_T$=3.310 min, mass calcd. for C$_{26}$H$_{24}$BrFN$_4$O$_5$S, 602.1, m/z found 605.1 [M+H]$^+$. Chiral analysis (Column: Chiralpak IE 5 μm 4.6*250 mm; Mobile Phase: Hex:EtOH:TFA=60:40:0.2 at 1 mL/min; Temp: 30° C.; Wavelength: 254 nm, R$_T$=9.644 min). $^1$H NMR (400 MHz, DMSO-d$_6$) δ 9.49 (s, 0.5H), 9.02 (s, 0.5H), 8.00 (d, J=2.8 Hz, 1.5H), 7.94 (d, J=3.2 Hz, 0.5H), 7.81 (d, J=4.0 Hz, 1H), 7.44-7.39 (m, 1H), 7.31-7.15 (m, 2H), 6.06 (s, 0.5H), 5.96 (s, 0.5H), 3.96-3.88 (m, 0.5H), 3.70-3.63 (m, 0.5H), 3.53 (s, 1.5H), 3.52 (s, 1.5H), 3.44 (s, 2H), 3.01-2.93 (m, 0.5H), 2.84-2.78 (m, 0.5H), 2.17-2.10 (m, 2H), 2.01-1.95 (m, 0.5H), 1.88-1.82 (m, 2H), 1.78-1.76 (m, 1H), 1.71-1.67 (m, 0.5H), 1.61-1.51 (m, 2H).

Compound I-20-B (trans)-2-(2-(4-(6-(2-Chloro-3-fluorophenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-20-N. LC-MS (ESI): R$_T$=3.104 min, mass calcd. for C$_{26}$H$_{24}$ClFN$_4$O$_5$S, 558.1, m/z found 559.2 [M+H]$^+$. $^1$H NMR (400 MHz, CD$_3$OD) δ 7.96 (d, J=2.4 Hz, 1H), 7.82 (br s, 1H), 7.72 (s, 1H), 7.34-7.28 (m, 1H), 7.25-7.23 (m, 1H), 7.19-7.15 (m, 1H), 6.19 (s, 1H), 4.01-3.88 (m, 1H), 3.60 (s, 3H), 3.58 (s, 2H), 2.98-2.89 (m, 1H), 2.31-2.19 (m, 2H), 2.11-1.85 (m, 4H), 1.83-1.69 (m, 2H).

Compound I-21-B (trans)-2-(2-(4-(6-(3-Fluoro-2-methylphenyl)-5-(methoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-21-N.

LC-MS (ESI): $R_T$=3.336 min, mass calcd. for $C_{27}H_{27}FN_4O_5S$, 538.6, m/z found 539.9 [M+H]$^+$. $^1$H NMR (400 MHz, CD$_3$OD) δ 7.93 (d, J=3.6 Hz, 1H), 7.76 (d, J=2.8 Hz, 1H), 7.73 (s, 1H), 7.21-7.12 (m, 2H), 6.98-6.91 (m, 1H), 5.96 (s, 1H), 4.10-3.84 (m, 1H), 3.62 (s, 3H), 3.58 (s, 2H), 3.02-2.90 (m, 1H), 2.50 (s, 3H), 2.38-2.19 (m, 2H), 2.15-2.05 (m, 1H), 2.03-1.70 (m, 5H).

Compound I-22-B (trans)-2-(2-(4-(6-(2-Chloro-3,4-difluorophenyl)-5-(methoxycarbonyl)-2-(thiazol-2-yl)-3,6-dihydropyrimidin-4-yl)cyclohexyl)-5-methyloxazol-4-yl)acetic Acid (a Single Stereoisomer)

By utilizing the analogous procedure of Method C, the title compound was synthesized from compound VII-22-S.
LC-MS (ESI): $R_T$=3.540 min, mass calcd. for $C_{27}H_{25}ClF_2N_4O_5S$, 590.1, m/z found 591.2 [M+H]$^+$. Chiral analysis (Colum: Chiralpak IA 5 μm 4.6 mm*250 mm; Mobile Phase: Hex:EtOH:TFA=80:20:0.2 at 1.0 mL/min; Temp: 30° C.; Wavelength: 254 nm, $R_T$=9.844 min). $^1$H NMR (400 MHz, DMSO-d$_6$) δ 9.07 (br s, 1H), 8.01 (s, 1.6H), 7.95 (d, J=3.2 Hz, 0.4H), 7.50-7.44 (m, 1H), 7.22-7.15 (m, 1H), 6.02 (s, 0.4H), 5.92 (s, 0.6H), 3.93-3.87 (m, 0.5H), 3.66-3.60 (m, 0.5H), 3.54 (s, 1.6H), 3.53 (s, 1.4H), 3.36 (s, 2H), 2.91-2.86 (m, 0.5H), 2.75-2.69 (m, 0.5H), 2.22 (s, 3H), 2.15-1.49 (m, 8H).

Compound I-23-B (trans)-2-(2-(4-(6-(2-Chloro-3,4-difluorophenyl)-5-(ethoxycarbonyl)-2-(thiazol-2-yl)-3,6-dihydropyrimidin-4-yl)cyclohexyl)oxazol-4-yl)acetic Acid (a Single Stereoisomer)

By utilizing the analogous procedure of Method C, the title compound was synthesized from compound VII-23-Y.
LC-MS (ESI): $R_T$=3.341 min, mass calcd. for $C_{27}H_{25}ClF_2N_4O_5S$, 590.1, m/z found 591.1 [M+H]$^+$. Chiral analysis (Column: Chiralpak IE 5 μm 4.6*250 mm; Mobile Phase: Hex:EtOH:TFA=50:50:0.2 at 1.0 mL/min; Temp: 30° C.; Wavelength: 230 nm, $R_T$=8.867 min). $^1$H NMR (400 MHz, DMSO-d$_6$) δ 9.59-9.51 (m, 0.6H), 8.99 (br s, 0.4H), 8.01-8.00 (m, 1.6H), 7.95 (d, J=3.6 Hz, 0.4H), 7.82 (d, J=4.4 Hz, 1H), 7.50-7.43 (m, 1H), 7.22-7.17 (m, 1H), 6.03 (s, 0.4H), 5.93 (m, 0.6H), 4.01-3.95 (m, 2H), 3.93-3.87 (m, 0.4H), 3.67-3.61 (m, 0.6H), 3.47 (s, 2H), 3.00-2.92 (m, 0.4H), 2.82-2.75 (m, 0.6H), 2.19-2.10 (m, 2H), 2.04-1.67 (m, 4H), 1.61-1.47 (m, 2H), 1.10-1.04 (m, 3H).

Compound I-24

(trans)-3-(2-(4-(6-(2-Chloro-3,4-difluorophenyl)-5-(ethoxycarbonyl)-2-(thiazol-2-yl)-3,6-dihydropyrimidin-4-yl)cyclohexyl)oxazol-4-yl)propanoic acid (a mixture of 2 Stereoisomers)

By utilizing the analogous procedure of Method C, the title compound was synthesized from compound VII-24-R.
LC-MS (ESI): $R_T$=3.880 min, mass calcd. for $C_{28}H_{27}ClF_2N_4O_5S$, 604.1, m/z found mass 605.2 [M+H]$^+$. $^1$H NMR (400 MHz, CD$_3$OD) δ 7.91 (s, 1H), 7.75 (s, 1H), 7.55 (s, 1H), 7.22 (d, J=5.2 Hz, 2H), 6.15 (s, 0.4H) 6.08 (s, 0.6H), 4.06-4.02 (m, 2H), 3.80 (s, 1H), 3.05-3.02 (m, 1H), 2.95-2.79 (m, 2H), 2.63-2.61 (m, 2H), 2.24-2.00 (m, 4H), 2.00-1.75 (m, 4H), 1.14 (t, J=6.8 Hz, 3H).

Compound I-24-A (trans)-3-(2-(4-(6-(2-Chloro-3,4-difluorophenyl)-5-(ethoxycarbonyl)-2-(thiazol-2-yl)-3,6-dihydropyrimidin-4-yl)cyclohexyl)oxazol-4-yl)propanoic Acid (a Single Stereoisomer)

By utilizing the analogous procedure of Method C, the title compound was synthesized from compound VII-24-M.
LC-MS (ESI): $R_T$=3.663 min, mass calcd. for $C_{28}H_{27}ClF_2N_4O_5S$, 604.1, m/z found mass 605.1 [M+H]$^+$. Chiral analysis (Column: Chiralpak IG 5 μm 4.6*250 mm; Mobile Phase: Hex:EtOH:TFA=80:20:0.2 at 1.0 mL/min; Temp: 30° C.; Wavelength: 254 nm, $R_T$=11.811 min). $^1$H NMR (400 MHz, CD$_3$OD) δ 7.91 (s, 1H), 7.75 (d, J=2.8 Hz, 1H), 7.55 (s, 1H), 7.24-7.22 (m, 2H), 6.14 (s, 0.6H), 6.09 (s, 0.4H), 4.05 (q, J=7.2 Hz, 2H), 4.02-3.98 (m, 0.6H), 3.84-3.75 (m, 0.4H), 2.98-2.87 (m, 1H), 2.80 (t, J=7.6 Hz, 2H), 2.61 (t, J=7.6 Hz, 2H), 2.28-2.15 (m, 2H), 2.08-1.97 (m, 2H), 1.89-1.79 (m, 2H), 1.76-1.67 (m, 2H), 1.14 (t, J=7.2 Hz, 3H).

Compound I-25-B (trans)-3-(2-(4-(6-(2-Chloro-3,4-difluorophenyl)-5-(methoxycarbonyl)-2-(thiazol-2-yl)-3,6-dihydropyrimidin-4-yl)cyclohexyl)oxazol-4-yl)-2,2-dimethyl-propanoic acid (a Single Stereoisomer)

By utilizing the analogous procedure of Method C, the title compound was synthesized from compound VII-25-N.
LC-MS (ESI): $R_T$=3.045 min, mass calcd. for $C_{29}H_{29}ClF_2N_4O_5S$, 618.2, m/z found 619.0 [M+H]$^+$. $^1$H NMR (400 MHz, CD$_3$OD) δ 7.92 (br s, 1H), 7.76-7.75 (m, 1H), 7.52 (s, 1H), 7.27-7.17 (m, 2H), 6.16-6.04 (m, 1H), 4.12-3.97 (m, 0.5H), 3.88-3.72 (m, 0.5H), 3.60 (s, 3H), 3.00-2.82 (m, 1H), 2.76 (s, 2H), 2.29-1.98 (m, 4H), 1.95-1.60 (m, 4H), 1.21 (s, 6H).

Compound I-26-B (trans)-2-(4-(6-(2-chloro-3,4-difluorophenyl)-5-(ethoxycarbonyl)-2-(thiazol-2-yl)-3,6-dihydropyrimidin-4-yl)cyclohexyl)oxazole-5-carboxylic Acid (a Single Stereoisomer)

By utilizing the analogous procedure of Method C, the title compound was synthesized from compound VII-26-8.
LC-MS (ESI): $R_T$=3.782 min, mass calcd. for $C_{26}H_{23}ClF_2N_4O_5S$, 576.1, m/z found 576.9 [M+H]$^+$. $^1$H NMR (400 MHz, CD$_3$OD) δ 7.92 (d, J=3.2 Hz, 1H), 7.76 (d, J=2.8 Hz, 1H), 7.57 (s, 1H), 7.27-7.22 (m, 2H), 6.12 (s, 1H), 4.05 (q, J=7.2 Hz, 2H), 3.95-3.93 (m, 1H), 3.05-2.97 (m, 1H), 2.33-2.26 (m, 2H), 2.09-2.01 (m, 1H), 1.97-1.71 (m, 5H), 1.14 (t, J=7.2 Hz, 3H).

Compound I-27-B (trans)-2-(2-(4-(6-(2-chloro-3,4-difluorophenyl)-5-(ethoxycarbonyl)-2-(thiazol-2-yl)-3,6-dihydropyrimidin-4-yl)cyclohexyl)oxazol-4-yl)-2-methylpropanoic Acid (a Single Stereoisomer)

Intermediate I-27-R (trans)-2-(2-(4-(6-(2-Chloro-3,4-difluorophenyl)-5-(ethoxycarbonyl)-2-(thiazol-2-yl)-3,6-dihydropyrimidin-4-yl)cyclohexyl)oxazol-4-yl)-2-methylpropanoic Acid (a Mixture of 2 Stereoisomers)

By utilizing the analogous procedure of Method C, the title compound was synthesized from compound VII-27-R.

LC-MS (ESI): $R_T$=3.929 min, mass calcd. for $C_{29}H_{29}ClF_2N_4O_5S$, 618.2, m/z found 619.2 [M+H]$^+$. $^1$H NMR (400 MHz, DMSO-d$_6$) δ 12.21 (br s, 1H), 9.57 (s, 0.5H), 8.98 (s, 0.5H), 8.02-8.00 (m, 1.5H), 7.96-7.45 (m, 0.5H), 7.83-7.82 (m, 1H), 7.51-7.44 (m, 1H), 7.22-7.17 (m, 1H), 6.04 (s, 0.4H), 5.93 (s, 0.6H), 4.01-3.94 (m, 2H), 3.90-3.87 (m, 0.4H), 3.68-3.61 (m, 0.6H), 2.98-2.92 (m, 0.4H), 2.82-2.76 (m, 0.6H), 2.17-2.09 (m, 2H), 2.03-1.66 (m, 4H), 1.60-1.50 (m, 2H), 1.41 (s, 6H), 1.10-1.03 (m, 3H).

A stereoisomeric mixture of (trans)-2-(2-(4-(6-(2-chloro-3,4-difluorophenyl)-5-(ethoxycarbonyl)-2-(thiazol-2-yl)-3,6-dihydropyrimidin-4-yl)cyclohexyl)oxazol-4-yl)-2-methylpropanoic acid I-27-R (190 mg, 0.292 mmol) was separated by chiral Prep. HPLC (separation condition: Column: Chiralpak IA 5 μm 20*250 mm; Mobile Phase: Hex:EtOH:TFA=85:15:0.2 at 10 ml/min; Temp 30° C.; Wavelength: 254 nm) to afford the title compounds I-27-A (40 mg, 95.4% purity, 21% yield) and I-27-B (35 mg, 97.9% purity, 19% yield) as yellow solids.

I-27-A: LC-MS (ESI): $R_T$=4.290 min, mass calcd. for $C_{29}H_{29}ClF_2N_4O_5S$, 618.2, m/z found 619.0 [M+H]$^+$. Chiral HPLC (Column: Chiralpak IA 5 μm 4.6*250 mm; Mobile Phase: Hex:EtOH:TFA=85:15:0.2 at 1.0 mL/min; Temp: 30° C.; Wavelength: 254 nm, $R_T$=7.612 min). $^1$H NMR (400 MHz, DMSO-d$_6$) δ 8.99 (s, 1H), 8.01 (s, 1.3H), 7.96-7.95 (m, 0.7H), 7.76 (s, 1H), 7.51-7.44 (m, 1H), 7.22-7.18 (m, 1H), 6.03 (s, 0.4H), 5.93 (s, 0.6H), 3.99-3.86 (m, 2.4H), 3.68-3.61 (m, 0.6H), 3.00-2.90 (m, 0.5H), 2.85-2.76 (m, 0.5H), 2.18-2.11 (m, 2H), 2.06-1.66 (m, 4H), 1.61-1.49 (m, 2H), 1.38 (s, 6H), 1.10-1.03 (m, 3H).

I-27-B: LC-MS (ESI): $R_T$=4.304 min, mass calcd. for $C_{29}H_{29}ClF_2N_4O_5S$, 618.2, m/z found 619.0 [M+H]$^+$. Chiral HPLC (Column: Chiralpak IA 5 μm 4.6*250 mm; Mobile Phase: Hex:EtOH:TFA=85:15:0.2 at 1.0 mL/min; Temp: 30° C.; Wavelength: 254 nm, $R_T$=8.661 min). $^1$H NMR (400 MHz, DMSO-d$_6$) δ 8.99 (s, 1H), 8.00 (s, 1.4H), 7.96-7.95 (m, 0.6H), 7.80 (s, 1H), 7.51-7.44 (m, 1H), 7.23-7.17 (m, 1H), 6.03 (s, 0.4H), 5.93 (s, 0.6H), 4.01-3.86 (m, 2.4H), 3.68-3.62 (m, 0.6H), 2.97-2.92 (m, 0.5H), 2.84-2.74 (m, 0.5H), 2.17-2.08 (m, 2H), 2.02-1.66 (m, 4H), 1.60-1.50 (m, 2H), 1.40 (s, 6H), 1.10-1.03 (m, 3H).

Compound I-28-B (trans)-2-(4-(4-(6-(2-chloro-3,4-difluorophenyl)-5-(ethoxycarbonyl)-2-(thiazol-2-yl)-3,6-dihydropyrimidin-4-yl)cyclohexyl)-1H-pyrazol-1-yl)acetic Acid (a Single Stereoisomer)

By utilizing the analogous procedure of Method C, the title compound was synthesized from compound VII-28-N.

LC-MS (ESI): $R_T$=3.381 min, mass calcd. for $C_{27}H_{26}ClF_2N_5O_4S$, 589.1, m/z found 590.2 [M+H]$^+$. Chiral HPLC (Column: Chiralpak IE (5 μm 4.6*250 mm); Mobile Phase: Hex:EtOH:TFA=80:20:0.2 at 1.0 mL/min; Temp: 30° C.; Wavelength: 254 nm, $R_T$=18.729 min). $^1$H NMR (400 MHz, DMSO-d$_6$) δ 8.95 (br s, 1H), 8.02-7.99 (m, 1.6H), 7.96 (d, J=2.8 Hz, 0.4H), 7.51-7.44 (m, 2H), 7.26 (s, 1H), 7.23-7.17 (m, 1H), 6.03 (s, 0.4H), 5.92 (s, 0.6H), 4.58 (s, 2H), 4.00-3.95 (m, 2H), 3.94-3.87 (m 0.3H), 3.69-3.63 (m 0.7H), 2.65-2.58 (m 0.6H), 2.50-2.45 (m, 0.4H), 2.05-1.79 (m, 5.4H), 1.66-1.63 (m, 0.6H), 1.43-1.34 (m, 2H), 1.10-1.05 (m, 3H).

Compound I-29-C (trans)-3-(4-(4-(6-(2-Chloro-4-fluorophenyl)-5-(methoxycarbonyl)-2-(thiazol-2-yl)-3,6-dihydropyrimidin-4-yl)cyclohexyl)-1H-pyrazol-1-yl)propanoic Acid (a Single Stereoisomer)

By utilizing the analogous procedure of Method C, the title compound was synthesized from compound VII-29-P.

LC-MS (ESI): $R_T$=3.400 min, mass calcd. for $C_{27}H_{27}ClFN_5O_4S$, 571.2, m/z found 572.2 [M+H]$^+$. Chiral analysis (Column: Chiralpak IC 5 μm 4.6*250 mm; Mobile Phase: Hex:EtOH:TFA=80:20:0.2 at 1 mL/min; Temp.: 30° C.; Wavelength: 254 nm, $R_T$=10.246 min). $^1$H NMR (400 MHz, CD$_3$OD) δ 7.92 (d, J=2.8 Hz, 1H), 7.75 (d, J=3.2 Hz, 1H), 7.49 (s, 1H), 7.42-7.38 (m, 2H), 7.24-7.22 (m, 1H), 7.07-7.02 (m, 1H), 6.11 (s, 1H), 4.36 (t, J=6.4 Hz, 2H), 3.93 (br s, 1H), 3.59 (s, 3H), 2.84 (t, J=6.4 Hz, 2H), 2.67-2.57 (m, 1H), 2.15-1.74 (m, 6H), 1.59-1.45 (m, 2H).

Compound I-30-D (trans)-3-(6-(2-Chloro-3,4-difluorophenyl)-5-(ethoxycarbonyl)-2-(thiazol-2-yl)-3,6-dihydropyrimidin-4-yl)cyclohexyl)-1H-pyrazol-1-yl)-3-methylbutanoic Acid (a Single Stereoisomer)

By utilizing the analogous procedure of Method C, the title compound was synthesized from compound VII-30-10.

LC-MS (ESI): $R_T$=3.905 min, mass calcd. for $C_{30}H_{32}ClF_2N_5O_4S$, 631.2, m/z found 632.0 [M+H]$^+$. Chiral analysis (Column: Chiralpak IE 5 μm 4.6*250 mm; Mobile Phase: Hex:EtOH:TFA=70:30:0.2 at 1 mL/min; Wavelength: 254 nm, $R_T$=9.296 min). $^1$H NMR (400 MHz, CD$_3$OD) δ 7.86-7.78 (m, 1H), 7.66 (d, J=3.2 Hz, 1H), 7.51 (s, 1H), 7.30 (s, 1H), 7.17-7.08 (m, 2H), 6.05 (s, 0.7H), 5.98 (s, 0.3H), 4.00-3.87 (m, 2.7H), 3.75-3.63 (m, 0.3H), 2.77 (s, 2H), 2.62-2.43 (m, 1H), 2.11-1.64 (m, 6H), 1.60 (s, 6H), 1.53-1.34 (m, 2H), 1.04 (t, J=7.2 Hz, 3H).

Compound I-31

3-(4-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazol-1-yl)butanoic Acid (a Mixture of 8 Stereoisomers)

By utilizing the analogous procedure of Method C, the title compound was synthesized from compound VII-31.

LC-MS (ESI): $R_T$=4.309 and 4.456 min, mass calcd. for $C_{29}H_{30}ClF_2N_5O_4S$, 617.2, m/z found 618.0 [M+H]$^+$. $^1$H NMR (400 MHz, CD$_3$OD) δ 7.93-7.92 (m, 0.5H), 7.87 (d, J=3.2 Hz, 0.5H), 7.75 (d, J=3.2 Hz, 0.5H), 7.72 (d, J=2.8 Hz, 0.5H), 7.68 (s, 0.5H), 7.57-7.49 (m, 1H), 7.39 (s, 0.5H), 7.24-7.19 (m, 2H), 6.14-6.05 (m, 1H), 4.85-4.74 (m, 1H), 4.07-4.01 (m, 2.7H), 3.93-3.79 (m, 0.3H), 3.13-3.06 (m, 0.5H), 2.98-2.87 (m, 1H), 2.83-2.72 (m, 1H), 2.66-2.57 (m, 0.5H), 2.21-1.69 (m, 7H), 1.58-1.56 (m, 2H), 1.50 (d, J=6.8 Hz, 2H), 1.16-1.12 (m, 3H).

Compound I-32-B 3-(4-((trans)-4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazol-1-yl)propanoic Acid (a Single Stereoisomer)

By utilizing the analogous procedure of Method C, the title compound was synthesized from compound VII-32-N. LC-MS (ESI): $R_T$=3.261 min, mass calcd. for $C_{28}H_{28}ClF_2N_5O_4S$, 603.2, m/z found 603.9 [M+H]$^+$. Chiral analysis (Column: Chiralpak IE 5 μm 4.6*250 mm; Mobile Phase: Hex:EtOH:TFA=80:20:0.2 at 1.0 mL/min, Temp: 30° C.; Wavelength: 230 nm, $R_T$=19.003 min). $^1$H NMR (400 MHz, CD$_3$OD) δ 7.92 (d, J=2.8 Hz, 1H), 7.75 (d, J=3.2 Hz, 1H), 7.49 (s, 1H), 7.39 (s, 1H), 7.26-7.22 (m, 2H), 6.13 (s, 1H), 4.36 (t, J=7.2 Hz, 2H), 4.04 (q, J=7.2 Hz, 3H), 2.82 (t, J=6.8 Hz, 2H), 2.68-2.56 (m, 1H), 2.13-1.70 (m, 6H), 1.60-1.46 (m, 2H), 1.13 (t, J=7.2 Hz, 3H).

Compound I-33-C (trans)-3-(4-(4-(6-(2-Chloro-3,4-difluorophenyl)-5-(ethoxycarbonyl)-2-(thiazol-2-yl)-3,6-dihydropyrimidin-4-yl)cyclohexyl)-3-methyl-1H-pyrazol-1-yl)propanoic Acid (a Single Stereoisomer)

By utilizing the analogous procedure of Method C, the title compound was synthesized from compound VII-33-10. LC-MS (ESI): $R_T$=3.668 min, mass calcd. for $C_{29}H_{30}ClF_2N_5O_4S$, 617.2, m/z found 618.2 [M+H]$^+$. Chiral analysis (Column: Chiralpak IA 5 μm 4.6*250 mm; Mobile Phase: Hex:IPA:TFA=80:20:0.2 at 1 mL/min, Temp: 30° C.; Wavelength: 254 nm, $R_T$=8.339 min). $^1$H NMR (400 MHz, CD$_3$OD) δ 7.92 (s, 1H), 7.75 (d, J=3.2 Hz, 1H), 7.37 (s, 1H), 7.26-7.22 (m, 2H), 6.13 (s, 1H), 4.28 (t, J=6.8 Hz, 2H), 4.07-4.02 (m, 2.5H), 3.97-3.73 (m, 0.5H), 2.79 (t, J=6.4 Hz, 2H), 2.62-2.45 (m, 1H), 2.22 (s, 3H), 2.03-1.73 (m, 6H), 1.59-1.41 (m, 2H), 1.14 (t, J=6.8 Hz, 3H).

Compound I-34

3-(4-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazol-1-yl)cyclobutanecarboxylic acid (a Mixture of 4 Stereoisomers)

To a solution of ethyl 6-(4-(1-(3-(tert-butoxycarbonyl)cyclobutyl)-1H-pyrazol-4-yl)cyclohexyl)-4-(2-chloro-3,4-difluorophenyl)-2-(thiazol-2-yl)-1,4-dihydropyrimidine-5-carboxylate VII-34 (50 mg, 95% purity, 0.069 mmol) in dichloromethane (1 mL) was added trifluoroacetic acid (1 mL) at room temperature. After stirred at room temperature for 12 hours under nitrogen atmosphere, the reaction mixture was concentrated under reduced pressure to give a residue, which was purified by C18 column (acetonitrile:water (0.1% hydrochloric acid)=5% to 95%) to give the title compound (41 mg, 99.8% purity, 94% yield) as yellow solids. LC-MS (ESI): $R_T$=3.602 min, mass calcd. for $C_{30}H_{30}CF_2N_5O_4S$, 629.2, m/z found 630.2 [M+H]$^+$. $^1$H NMR (400 MHz, CD$_3$OD) δ 8.30-8.27 (m, 0.1H), 8.21-8.18 (m, 0.9H), 8.11-8.10 (m, 1H), 7.76 (s, 0.6H), 7.64 (s, 0.4H), 7.60 (s, 0.3H), 7.57 (s, 0.3H), 7.50 (s, 0.2H), 7.47 (s, 0.2H), 7.38-7.27 (m, 2H), 6.29 (s, 0.4H), 6.24 (s, 0.6H), 5.11-5.02 (m, 0.5H), 4.80-4.73 (m, 0.5H), 4.14-4.08 (m, 2H), 3.99-3.89 (m, 1H), 3.20-3.10 (m, 1H), 3.04-2.97 (m, 0.5H), 2.88-2.83 (m, 0.5H), 2.78-2.66 (m, 4H), 2.27-2.15 (m, 2H), 2.01-1.85 (m, 4H), 1.80-1.77 (m, 0.5H), 1.71-1.68 (m, 0.5H), 1.61-1.45 (m, 1H), 1.17 (t, J=7.2 Hz, 3H).

Compound I-35-C (trans)-5-(4-(6-(2-chloro-3,4-difluorophenyl)-5-(ethoxycarbonyl)-2-(thiazol-2-yl)-3,6-dihydropyrimidin-4-yl)cyclohexyl)-1-methyl-1H-pyrazole-3-carboxylic Acid (a Single Stereoisomer)

By utilizing the analogous procedure of Method C, the title compound was synthesized from compound VII-35-P. LC-MS (ESI): $R_T$=2.531 min, mass calcd. for $C_{27}H_{26}ClF_2N_5O_4S$, 589.1, m/z found 589.9 [M+H]$^+$. Chiral HPLC (Column: Chiralpak IE 5 μm 4.6*250 mm; Mobile Phase: Hex:EtOH:TFA=70:30:0.2 at 1.0 mL/min; Temp: 30° C.; Wavelength: 254 nm, $R_T$=11.982 min). $^1$H NMR (400 MHz, DMSO-d$_6$) 8.02-7.97 (m, 2H), 7.51-7.44 (m, 1H), 7.23-7.19 (m, 1H), 6.43 (s, 1H), 6.04 (s, 0.4H), 5.94 (s, 0.6H), 4.01-3.97 (m, 2H), 3.85 (s, 3H), 3.72-3.67 (s, 1H), 2.94-2.88 (m, 0.5H), 2.78-2.68 (m, 0.5H), 2.05-1.85 (m, 5H), 1.82-1.79 (m, 0.4H), 1.71-1.68 (m, 0.6H), 1.47-1.41 (m, 2H), 1.11-1.04 (m, 3H).

Compound I-36-B (trans)-3-(4-(6-(2-Chloro-3,4-difluorophenyl)-5-(ethoxycarbonyl)-2-(thiazol-2-yl)-3,6-dihydropyrimidin-4-yl)cyclohexyl)-1-methyl-1H-pyrazole-5-carboxylic Acid (a Single Stereoisomer)

By utilizing the analogous procedure for Compound I-34, the title compound was synthesized from compound VII-36-N. LC-MS (ESI): $R_T$=3.373 min, mass calcd. for $C_{27}H_{26}ClF_2N_5O_4S$, 589.1, m/z found mass 590.0 [M+H]$^+$. Chiral analysis (Column: Chiralpak IA 5 μm 4.6*250 mm; Mobile Phase: Hex:IPA:TFA=80:20:0.2 at 1.0 mL/min; Temp: 30° C.; Wavelength: 254 nm, $R_T$=12.684 min). $^1$H NMR (400 MHz, DMSO-d$_6$) δ 9.54 (br s, 0.6H), 8.96 (s, 0.4H), 8.02-7.99 (m, 1.5H), 7.96-7.95 (m, 0.5H), 7.51-7.44 (m, 1H), 7.23-7.18 (m, 1H), 6.57 (s, 1H), 6.04 (s, 0.4H), 5.93 (s, 0.6H), 4.01 (s, 3H), 4.00-3.92 (m, 2H), 3.90-3.87 (m, 0.4H), 3.69-3.63 (m, 0.6H), 2.75-2.67 (m, 0.6H), 2.62-2.58 (m, 0.4H), 2.08-1.99 (m, 2H), 1.96-1.85 (m, 2H), 1.82-1.65 (m, 2H), 1.53-1.40 (m, 2H), 1.10-1.04 (m, 3H).

Compound I-37-C (trans)-3-(4-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazol-1-yl)-2,2-dimethylpropanoic Acid (a Single Stereoisomer)

By utilizing the analogous procedure for compound I-34, the title compound was synthesized from compound VII-37-4C. LC-MS (ESI): $R_T$=3.883 min, mass calcd. for $C_{30}H_{32}ClF_2N_5O_4S$, 631.2, m/z found 632.3 [M+H]$^+$. Chiral analysis (Column: Chiralpak IE 5 μm 4.6*250 mm; Mobile Phase: Hex:EtOH:TFA=85:15:0.2 at 1.0 mL/min; Temp: 30°

C.; Wavelength: 254 nm, $R_T$=15.769 min). $^1$H NMR (400 MHz, CD$_3$OD) δ 7.96-7.89 (m, 1H), 7.76 (d, J=3.2 Hz, 1H), 7.45 (s, 1H), 7.37 (s, 1H), 7.27-7.20 (m, 2H), 6.15 (s, 0.7H), 6.08 (s, 0.3H), 4.27 (s, 2H), 4.07-3.98 (m, 2.7H), 3.86-3.72 (m, 0.3H), 2.71-2.54 (m, 1H), 2.20-1.68 (m, 6H), 1.62-1.42 (m, 2H), 1.17-1.12 (m, 9H).

Compound I-38-B (trans)-1-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazole-4-carboxylic Acid (a Single Stereoisomer)

By utilizing the analogous procedure of Method C, the title compound was synthesized from compound VII-38-N.
LC-MS (ESI): $R_T$=4.469 min, mass calcd. for C$_{26}$H$_{24}$ClF$_2$N$_5$O$_4$S, 575.1, m/z found 575.9 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 254 nm, $R_T$=10.027 min). $^1$H NMR (400 MHz, CD$_3$OD) δ 8.20 (s, 1H), 7.96-7.88 (m, 2H), 7.76 (d, J=2.8 Hz, 1H), 7.24-7.22 (m, 2H), 6.15-6.10 (m, 1H), 4.41-4.27 (m, 1H), 4.12-4.03 (m, 2.5H), 3.89-3.81 (m, 0.5H), 2.29-1.85 (m, 8H), 1.15 (t, J=7.2 Hz, 3H).

Compounds I-39-B (cis)-1-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazole-5-carboxylic Acid (a Single Stereoisomer)

By utilizing the analogous procedure of Method C, the title compound was synthesized from compound VII-39-N.
LC-MS (ESI): $R_T$=3.547 min, mass calcd. for C$_{26}$H$_{24}$ClF$_2$N$_5$O$_4$S, 575.1, m/z found 576.1 [M+H]$^+$. Chiral analysis (Column: Chiralpak IE 5 μm 4.6*250 mm; Mobile Phase: Hex:EtOH:TFA=90:10:0.2 at 1.0 mL/min; Temp: 30° C.; Wavelength: 254 nm, $R_T$=9.103 min). $^1$H NMR (400 MHz, DMSO-d$_6$+D$_2$O) δ 8.08 (d, J=3.2 Hz, 0.6H), 7.99 (d, J=3.2 Hz, 0.4H), 7.97 (d, J=3.2 Hz, 0.4H), 7.96 (d, J=2.8 Hz, 0.6H), 7.58 (d, J=1.6 Hz, 0.6H), 7.50-7.41 (m, 1.4H), 7.25-7.19 (m, 1H), 6.74 (d, J=2.0 Hz, 0.4H), 6.70 (d, J=1.6 Hz, 0.6H), 6.05 (s, 0.6H), 5.95 (s, 0.4H), 5.79-5.73 (m, 0.6H), 5.43-5.36 (m, 0.4H), 4.15-4.03 (m, 0.6H), 3.98 (q, J=7.2 Hz, 2H), 3.81-3.73 (m, 0.4H), 2.37-2.26 (m, 1H), 2.24-2.15 (m, 1H), 2.10-2.01 (m, 1H), 1.99-1.75 (m, 2.6H), 1.72-1.62 (m, 1H), 1.56-1.47 (m, 0.4H), 1.10-1.05 (m, 3H).

Compound I-39-C (trans)-1-(4-(6-(2-Chloro-3,4-difluorophenyl)-5-(ethoxycarbonyl)-2-(thiazol-2-yl)-3,6-dihydropyrimidin-4-yl)cyclohexyl)-1H-pyrazole-5-carboxylic Acid (a Single Stereoisomer)

By utilizing the analogous procedure of Method C, the title compound was synthesized from compound VII-39-P.
LC-MS (ESI): $R_T$=3.091 min, mass calcd. for C$_{26}$H$_{24}$ClF$_2$N$_5$O$_4$S, 575.1, m/z found 575.9 [M+H]$^+$. Chiral analysis (Column: Chiralpak IF 5 μm 4.6*250 mm; Mobile Phase: Hex:EtOH:TFA=95:5:0.2 at 1.0 mL/min; Temp: 30° C.; Wavelength: 254 nm, $R_T$=16.725 min). $^1$H NMR (400 MHz, DMSO-d$_6$+D$_2$O) δ 8.03-7.99 (m, 1H), 7.97 (d, J=3.6 Hz, 0.6H), 7.92 (d, J=2.8 Hz, 0.4H), 7.50-7.42 (m, 2H), 7.25-7.18 (m, 1H), 6.66 (d, J=1.6 Hz, 1H), 6.04 (s, 0.4H), 5.95 (s, 0.6H), 5.51-5.42 (m, 0.4H), 5.40-5.32 (m, 0.6H), 4.04-3.90 (m, 2.4H), 3.74-3.69 (m, 0.6H), 2.12-1.79 (m, 7.4H), 1.76-1.68 (m, 0.6H), 1.13-1.03 (m, 3H).

Compound I-40-A (trans)-2-(4-(6-(2-Chloro-3,4-difluorophenyl)-5-(ethoxycarbonyl)-2-(thiazol-2-yl)-3,6-dihydropyrimidin-4-yl)cyclohexyl)pyrimidine-5-carboxylic Acid (a Single Stereoisomer)

By utilizing the analogous procedure of Method C, the title compound was synthesized from compound VII-40-M.
LC-MS (ESI): $R_T$=3.422 min, mass calcd. for C$_{27}$H$_{24}$ClF$_2$N$_5$O$_4$S, 587.1, m/z found 587.9 [M+H]$^+$. $^1$H NMR (400 MHz, DMSO-d$_6$) δ 9.55 (br s, 0.4H), 9.09 (s, 2H), 9.03 (s, 0.6H), 8.02-7.95 (m, 2H), 7.51-7.44 (m, 1H), 7.24-7.18 (m, 1H), 6.04 (s, 0.5H), 5.94 (s, 0.5H), 4.02-3.95 (m, 2.4H), 3.75-3.68 (m, 0.6H), 3.11-3.05 (m, 0.5H), 2.95-2.88 (m, 0.5H), 2.16-2.13 (m, 2.4H), 1.96-1.83 (m, 3H), 1.74-1.67 (m, 2.6H), 1.11-1.04 (m, 3H).

Compound I-41-B (trans)-2-(4-(6-(2-Chloro-3,4-difluorophenyl)-5-(ethoxycarbonyl)-2-(thiazol-2-yl)-3,6-dihydropyrimidin-4-yl)cyclohexyl)thiazole-4-carboxylic Acid (a Single Stereoisomer)

By utilizing the analogous procedure of Method C, the title compound was synthesized from compound VII-41-N.
LC-MS (ESI): $R_T$=3.684 min, mass calcd. for C$_{26}$H$_{23}$ClF$_2$N$_4$O$_4$S$_2$ 592.1, m/z found 593.0 [M+H]$^+$. Chiral analysis (Column: Chiralpak IE 5 μm 4.6*250 mm; Mobile Phase: Hex:EtOH:TFA=70:30:0.2 at 1 mL/min; Temp: 30° C.; Wavelength: 230 nm; $R_T$=9.361 min). $^1$H NMR (400 MHz, CD$_3$OD) δ 8.12 (s, 1H), 7.92 (d, J=3.2 Hz, 1H), 7.75 (d, J=3.6 Hz, 1H), 7.27-7.20 (m, 2H), 6.13 (s, 1H), 4.05 (q, J=7.2 Hz, 2H), 4.03-3.93 (m, 1H), 3.23-3.15 (m, 1H), 2.36-2.30 (m, 2H), 2.15-1.87 (m, 4H), 1.80-1.72 (m, 2H), 1.15 (t, J=7.2 Hz, 3H).

Compound I-42-B (trans)-5-(4-(6-(2-Chloro-3,4-difluorophenyl)-5-(ethoxycarbonyl)-2-(thiazol-2-yl)-3,6-dihydropyrimidin-4-yl)cyclohexyl)isoxazole-3-carboxylic Acid (a Single Stereoisomer)

By utilizing the analogous procedure of Method C, the title compound was synthesized from compound VII-42-11.
LC-MS (ESI): $R_T$=3.704 min, mass calcd. for C$_{26}$H$_{23}$ClF$_2$N$_4$O$_5$S, 576.1, m/z found 577.1 [M+H]$^+$. $^1$H NMR (400 MHz, CDCl$_3$) δ 7.84 (d, J=2.8 Hz, 1H), 7.48 (d, J=2.4 Hz, 1H), 7.09-7.01 (m, 2H), 6.46 (s, 1H), 6.16 (s, 1H), 4.07-4.02 (m, 3H), 2.99-2.93 (m, 1H), 2.30-2.25 (m, 2H), 2.15-2.10 (m, 1H), 2.01-1.94 (m, 1H), 1.88-1.81 (m, 1H), 1.72-1.65 (m, 3H), 1.13 (t, J=6.8 Hz, 3H).

Compound I-43-B (trans)-4-(6-(2-Chloro-3,4-difluorophenyl)-5-(ethoxycarbonyl)-2-(thiazol-2-yl)-3,6-dihydropyrimidin-4-yl)cyclohexyl)isoxazole-5-carboxylic Acid (a Single Stereoisomer)

By utilizing the analogous procedure of Method C, the title compound was synthesized from compound VII-43-N.

LC-MS (ESI): $R_T$=3.246 min, mass calcd. for $C_{26}H_{23}ClF_2N_4O_5S$, 576.1, m/z found 576.9 [M+H]$^+$. Chiral analysis (Column: Chiralpak IA 5 μm 4.6*250 mm; Mobile Phase: Hex:IPA:TFA=80:20:0.2 at 1.0 mL/min; Temp: 30° C.; Wavelength: 230 nm, $R_T$=10.178 min). $^1$H NMR (400 MHz, CD$_3$OD) δ 7.92 (d, J=3.2 Hz, 1H), 7.75 (d, J=3.2 Hz, 1H), 7.25-7.22 (m, 2H), 6.81 (s, 1H), 6.13 (s, 1H), 4.05 (q, J=7.2 Hz, 2H), 4.01-3.92 (m, 1H), 2.94-2.87 (m, 1H), 2.21-2.05 (m, 3H), 2.01-1.82 (m, 3H), 1.75-1.61 (m, 2H), 1.14 (t, J=7.2 Hz, 3H).

Compound I-44-A (trans)-4-(4-(6-(2-Chloro-3,4-difluorophenyl)-5-(ethoxycarbonyl)-2-(thiazol-2-yl)-3,6-dihydropyrimidin-4-yl)cyclohexyl)benzoic Acid (a Single Stereoisomer)

Intermediate I-44-E (trans)-4-(4-(6-(2-Chloro-3,4-difluorophenyl)-5-(ethoxycarbonyl)-2-(thiazol-2-yl)-3,6-dihydropyrimidin-4-yl)cyclohexyl)benzoic Acid (a Mixture of 2 Stereoisomers)

By utilizing the analogous procedure of Method C, the title compound was synthesized from compound VII-44-X as yellow solids. LC-MS (ESI): $R_T$=3.922 min, mass calcd. for $C_{29}H_{26}ClF_2N_3O_4S$, 585.1, m/z found 586.0 [M+H]$^+$. $^1$H NMR (400 MHz, DMSO-d$_6$) δ 8.99 (br s, 1H), 8.02-8.01 (m, 1.6H), 7.96 (d, J=3.2 Hz, 0.4H), 7.89-7.86 (m, 2H), 7.51-7.44 (m, 1H), 7.40-7.36 (m, 2H), 7.24-7.19 (m, 1H), 6.05 (s, 0.4H), 5.94 (s, 0.6H), 4.02-3.96 (m, 2.5H), 3.75-3.69 (m, 0.5H), 2.83-2.76 (m, 0.4H), 2.69-2.63 (m, 0.6H), 2.04-1.81 (m, 5.5H), 1.73-1.70 (m, 0.5H), 1.62-1.51 (m, 2H), 1.11-1.05 (m, 3H).

A stereoisomeric mixture of (trans)-4-(4-(6-(2-chloro-3,4-difluorophenyl)-5-(ethoxycarbonyl)-2-(thiazol-2-yl)-3,6-dihydropyrimidin-4-yl)cyclohexyl)benzoic acid I-44-E (95 mg, 95% purity, 0.154 mmol) was separated by chiral Prep. HPLC (separation condition: Column: Chiralpak IA 5 μm 20*250 mm; Mobile Phase: Hex:EtOH:TFA=80:20:0.3 at 15 mL/min; Temp: 30° C.; Wavelength: 254 nm) and further purified by C18 column (acetonitrile:water=75% to 25%) to give the title compounds I-44-A (19 mg, 20% yield, 98.7% purity, 100% stereopure) and I-44-B (19.0 mg, 21% yield, 97.7% purity, 95.2% stereopure) as yellow solids.

I-44-A: LC-MS (ESI): $R_T$=3.948 min, mass calcd. for $C_{29}H_{26}ClF_2N_3O_4S$, 585.1, m/z found 586.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 254 nm, $R_T$=9.681 min). $^1$H NMR (400 MHz, DMSO-d$_6$) δ 12.81 (br s, 1H), 9.58 (br s, 0.6H), 9.00 (s, 0.4H), 8.03-8.01 (m, 1.6H), 7.97-7.96 (m, 0.4H), 7.90-7.87 (m, 2H), 7.51-7.39 (m, 3H), 7.24-7.19 (m, 1H), 6.05 (s, 0.4H), 5.94 (d, J=2.0 Hz, 0.6H), 4.03-3.93 (m, 2.4H), 3.76-3.69 (m, 0.6H), 2.85-2.78 (m, 0.4H), 2.71-2.65 (m, 0.6H), 2.08-1.85 (m, 5.5H), 1.73-1.70 (m, 0.5H), 1.64-1.50 (m, 2H), 1.11-1.05 (m, 3H).

I-44-B: LC-MS (ESI): $R_T$=3.942 min, mass calcd. for $C_{29}H_{26}ClF_2N_3O_4S$, 585.1, m/z found 586.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 254 nm, $R_T$=11.272 min). $^1$H NMR (400 MHz, DMSO-d$_6$) δ 12.77 (br s, 1H), 9.57 (br s, 0.6H), 9.00 (s, 0.4H), 8.03-8.01 (m, 1.6H), 7.97-7.96 (m, 0.4H), 7.91-7.87 (m, 2H), 7.51-7.40 (m, 3H), 7.24-7.19 (m, 1H), 6.05 (s, 0.4H), 5.94 (d, J=2.8 Hz, 0.6H), 4.02-3.93 (m, 2.4H), 3.76-3.68 (m, 0.6H), 2.84-2.78 (m, 0.4H), 2.71-2.65 (m, 0.6H), 2.07-1.81 (m, 5.5H), 1.75-1.69 (m, 0.5H), 1.63-1.51 (m, 2H), 1.11-1.05 (m, 3H).

Compound I-45

(trans)-5-(-4-(6-(2-Chloro-3,4-difluorophenyl)-5-(ethoxycarbonyl)-2-(thiazol-2-yl)-3,6-dihydropyrimidin-4-yl)cyclohexyl)-1,2,4-oxadiazole-3-carboxylic Acid (a Mixture of 2 Stereoisomers)

By utilizing the analogous procedure of Method C, the title compound was synthesized from compound VII-45-R.

LC-MS (ESI): $R_T$=3.070 min, mass calcd. for $C_{25}H_{22}ClF_2N_5O_5S$, 577.1, m/z found 577.9 [M+H]$^+$. $^1$H NMR (400 MHz, CD$_3$OD) δ 7.91 (dd, J=4.0, 3.2 Hz, 1H), 7.75 (t, J=2.8 Hz, 1H), 7.26-7.18 (m, 2H), 6.12 (s, 0.5H), 6.11 (s, 0.5H), 4.08-4.02 (m, 2H), 3.97-3.91 (m, 0.5H), 3.89-3.84 (m, 0.5H), 3.18-3.12 (m, 0.5H), 2.47-2.41 (m, 0.5H), 2.36-2.30 (m, 1H), 2.08-1.93 (m, 3H), 1.91-1.74 (m, 3H), 1.68-1.56 (m, 1H), 1.16-1.12 (m, 3H).

Compound I-46-C 1-(2-((trans)-4-(6-(2-chloro-3,4-difluorophenyl)-5-(methoxycarbonyl)-2-(thiazol-2-yl)-3,6-dihydropyrimidin-4-yl)cyclohexyl)pyrimidin-5-yl)cyclopropanecarboxylic Acid (a Single Stereoisomer)

By utilizing the analogous procedure of Method C, the title compound was synthesized from compound VII-46-P.

LC-MS (ESI): $R_T$=3.557 min, mass calcd. for $C_{29}H_{26}ClF_2N_5O_4S$, 613.1, m/z found 614.2 [M+H]$^+$. Chiral analysis (Column: Chiralpak IA 5 μm 4.6*250 mm; Mobile Phase: Hex:EtOH:TFA=50:50:0.2 at 1 mL/min; Temp: 30° C.; Wavelength: 280 nm, Rt=6.186 min).

$^1$H NMR (400 MHz, CD$_3$OD) δ 8.74 (s, 2H), 7.95 (s, 1H), 7.78 (d, J=2.8 Hz, 1H), 7.26 (d, J 10=4.8 Hz, 2H), 6.16 (s, 1H), 4.14-4.07 (m, 0.7H), 3.89-3.85 (m, 0.3H), 3.63 (s, 3H), 3.07-3.00 (m, 1H), 2.20-2.15 (m, 3H), 2.06-2.01 (m, 1H), 1.95-1.88 (m, 4H), 1.68 (dd, J=7.2 Hz, 4.0 Hz, 2H), 1.32 (dd, J=7.2 Hz, 4.0 Hz, 2H).

Compound I-47-D 2-((Trans)-4-(6-(2-bromo-3,4-difluorophenyl)-5-(methoxycarbonyl)-2-(thiazol-2-yl)-3,6-dihydropyrimidin-4-yl)cyclohexyl)-5-methylpyrimidine-4-carboxylic Acid (a Single Stereoisomer)

By utilizing the analogous procedure of Method C, the title compound was synthesized from compound VII-47-N.

LC-MS (ESI): $R_T$=2.830 min, mass calcd. for $C_{27}H_{24}BrF_2N_5O_4S$, 631.1, m/z found 632.1 [M+H]$^+$. $^1$H NMR (400 MHz, CD$_3$OD) δ 8.77 (s, 0.1H), 8.66 (s, 0.9H), 7.91 (d, J=3.2 Hz, 0.9H), 7.87 (d, J=3.2 Hz, 0.1H), 7.74 (d, J=3.2 Hz, 0.9H), 7.70 (d, J=3.2 Hz, 0.1H), 7.31-7.16 (m, 2H), 6.11 (s, 0.9H), 6.09 (s, 0.1H), 4.09-3.91 (m, 1H), 3.60

(s, 3H), 3.08-2.93 (m, 1H), 2.48 (s, 0.3H), 2.43 (s, 2.7H), 2.20-2.05 (m, 3H), 1.99-1.78 (m, 5H).

Compound I-48-B (trans)-2-(2-(4-(6-(2-Chloro-4-fluorophenyl)-5-(methoxycarbonyl)-2-(thiazol-2-yl)-3,6-dihydropyrimidin-4-yl)cyclohexyl)-5-methyloxazol-4-yl)acetic Acid (a Single Stereoisomer)

By utilizing the analogous procedure of Method C, the title compound was synthesized from compound VII-48-B as yellow solids.

LC-MS (ESI): $R_T$=3.986 min, mass calcd. for $C_{27}H_{26}ClFN_4O_5S$, 572.1, m/z found 573.1 $[M+H]^+$. Chiral analysis (analytical condition: Column: Chiralpak IA 5 μm 4.6*250 mm; Mobile Phase: Hex:EtOH:TFA=80:20:0.2 at 1 mL/min; Temp.: 30° C.; Wavelength: 254 nm, $R_T$=8.870 min). $^1$H NMR (400 MHz, CD$_3$OD) δ 7.94 (br s, 1H), 7.78-7.77 (m, 1H), 7.43-7.40 (m, 1H), 7.26-7.24 (m, 1H), 7.09-7.05 (m, 1H), 6.16 (s, 0.6H), 6.09 (s, 0.4H), 4.10-3.98 (m, 0.5H), 3.87-3.75 (m, 0.5H), 3.62 (s, 3H), 3.43 (s, 2H), 2.93-2.85 (m, 1H), 2.29-2.13 (m, 5H), 2.02-1.69 (m, 6H).

Compound I-49-A 2-(2-((trans)-4-(6-(2-chloro-3,4-difluorophenyl)-5-(methoxycarbonyl)-2-(thiazol-2-yl)-3,6-dihydropyrimidin-4-yl)cyclohexyl)pyrimidin-5-yl)acetic Acid (a Single Stereoisomer)

By utilizing the analogous procedure of Method C, the title compound was synthesized from compound VII-49-A as yellow solids.

LC-MS (ESI): $R_T$=3.485 min, mass calcd. for $C_{27}H_{24}ClF_2N_5O_4S$, 587.1, m/z found 588.2 $[M+H]^+$. $^1$H NMR (400 MHz, DMSO-d$_6$) δ 9.05 (br s, 1H), 8.62 (s, 1H), 8.61 (s, 1H), 8.02-8.00 (m, 1.5H), 7.95-7.94 (m, 0.5H), 7.47-7.41 (m, 1H), 7.25-7.14 (m, 1H), 6.03 (s, 0.5H), 5.94 (s, 0.5H), 3.98-3.91 (m, 0.5H), 3.73-3.68 (m, 0.5H), 3.57 (s, 2H), 3.54 (s, 1.5H), 3.53 (s, 1.5H), 3.03-2.98 (m, 0.5H), 2.88-2.82 (m, 0.5H), 2.10-1.69 (m, 8H).

Compound I-50-A 2-(2-((trans)-4-(6-(2-chloro-4-fluorophenyl)-5-(methoxycarbonyl)-2-(thiazol-2-yl)-3,6-dihydropyrimidin-4-yl)cyclohexyl)pyrimidin-5-yl)acetic Acid (a Single Stereoisomer)

By utilizing the analogous procedure of Method C, the title compound was synthesized from compound VII-50-A as yellow solids.

LC-MS (ESI): $R_T$=3.361 min, mass calcd. for $C_{27}H_{25}ClFN_5O_4S$, 569.1, m/z found 570.2 $[M+H]^+$. Chiral analysis (Column: Chiralpak IA 5 μm 4.6*250 mm; Mobile Phase: Hex:EtOH:TFA=70:30:0.2 at 1 mL/min; Temp: 30° C.; Wavelength: 254 nm, $R_T$=8.867 min). $^1$H NMR (400 MHz, DMSO-d$_6$) δ 9.41 (br s, 0.5H), 9.00 (br s, 0.5H), 8.64 (s, 1H), 8.63 (s, 1H), 8.01-8.00 (m, 1.5H), 7.94-7.93 (m, 0.5H), 7.43-7.32 (m, 2H), 7.24-7.20 (m, 1H), 6.03 (s, 0.4H), 5.92 (s, 0.6H), 3.98-3.88 (m, 0.5H), 3.73-3.70 (m, 0.5H), 3.63 (s, 2H), 3.54 (s, 1.5H), 3.53 (s, 1.5H), 3.05-2.99 (m, 0.5H), 2.86-2.79 (m, 0.5H), 2.14-1.64 (m, 8H).

Compound II-1-B 2-(2-(4-(6-(3,4-Difluoro-2-methylphenyl)-5-(methoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-1-B as yellow solids.

LC-MS (ESI): $R_T$=3.839 min, mass calcd. for $C_{27}H_{26}F_2N_6O_4S$, 568.2, m/z found 569.0 $[M+H]^+$. $^1$H NMR (400 MHz, DMSO-d$_6$) δ 12.42 (br s, 1H), 9.58 (s, 0.8H), 9.24 (s, 0.2H), 8.27 (s, 0.4H), 8.26 (s, 1.6H), 7.98 (d, J=3.2 Hz, 0.8H), 7.94-7.93 (m, 1H), 7.89 (d, J=3.2 Hz, 0.2H), 7.27-7.17 (m, 1H), 7.13-7.09 (m, 0.8H), 6.98-6.95 (m, 0.2H), 5.82 (s, 0.2H), 5.70 (s, 0.8H), 4.91-4.76 (m, 2H), 4.24-4.17 (m, 0.2H), 3.94-3.87 (m, 0.8H), 3.54 (s, 3H), 3.45 (s, 2H), 2.97-2.84 (m, 2H), 2.44 (d, J=1.6 Hz, 3H), 2.07-1.59 (m, 4H).

Compound II-2-B 2-(4-(5-(Ethoxycarbonyl)-6-(3-fluoro-2-methylphenyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method E, the title compound was synthesized from compound BB2 and FA2.

LC-MS (ESI): $R_T$=2.905 min, mass calcd. for $C_{28}H_{29}FN_6O_4S$, 564.2, m/z found 565.2 $[M+H]^+$. $^1$H NMR (400 MHz, DMSO-d$_6$) δ 9.53 (d, J=2.8 Hz, 0.8H), 9.10 (s, 0.2H), 8.30-8.29 (m, 1H), 7.97-7.88 (m, 2H), 7.23-7.14 (m, 2H), 7.07-7.01 (m, 1H), 5.87 (s, 0.2H), 5.74 (d, J=2.8 Hz, 0.8H), 4.90-4.76 (m, 2H), 4.22-4.15 (m, 0.2H), 3.99 (q, J=7.2 Hz, 2H), 3.92-3.87 (m, 0.8H), 2.92-2.82 (m, 2H), 2.45 (s, 0.6H), 2.40 (s, 2.4H), 2.13 (s, 3H), 2.01-1.59 (m, 4H), 1.08 (t, J=7.2 Hz, 3H).

Compound II-3-B 2-(2-(4-(5-(ethoxycarbonyl)-6-(3-fluoro-2-methylphenyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-3-S as yellow solids.

LC-MS (ESI): $R_T$=3.142 min, mass calcd. for $C_{28}H_{29}FN_6O_4S$, 564.2, m/z found 565.1 $[M+H]^+$. $^1$H NMR (400 MHz, DMSO-d$_6$) δ 9.52 (br s, 0.7H), 9.12 (s, 0.3H), 8.28-8.26 (m, 2H), 7.97-7.88 (m, 2H), 7.23-7.13 (m, 2H), 7.07-7.01 (m, 1H), 5.87 (s, 0.2H), 5.75 (s, 0.8H), 4.91-4.77 (m, 2H), 4.21-4.16 (m, 0.2H), 3.99 (q, J=7.2 Hz, 2H), 3.93-3.87 (m, 0.8H), 3.42 (s, 2H), 2.93-2.84 (m, 2H), 2.45 (s, 0.7H), 2.40 (s, 2.3H), 2.09-1.59 (m, 4H), 1.10-1.05 (m, 3H).

Compound II-4-B 2-(4-(5-(Ethoxycarbonyl)-6-(4-fluoro-2-methylphenyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the title compound was synthesized from compound XI-4-B as yellow solids.

LC-MS (ESI): $R_T$=3.299 min, mass calcd. for $C_{28}H_{29}FN_6O_4S$, 564.2, m/z found 565.1 [M+H]$^+$. 1H NMR (400 MHz, DMSO-$d_6$) δ 13.33 (s, 1H), 9.53 (s, 0.8H), 9.10 (s, 0.2H), 8.39 (s, 0.2H), 8.38 (s, 0.8H), 7.97-7.93 (m, 1.7H), 7.92-7.88 (m, 0.3H), 7.29-7.25 (m, 0.8H), 7.17-7.14 (m, 0.2H), 7.07-6.99 (m, 2H), 5.82 (s, 0.2H), 5.69 (d, J=2.8 Hz, 0.8H), 4.91-4.76 (m, 2H), 4.21-4.15 (m, 0.2H), 4.00-3.98 (m, 2H), 3.93-3.87 (m, 0.8H), 2.94-2.84 (m, 2H), 2.55-2.52 (m, 3H), 2.18 (s, 3H), 1.96-1.78 (m, 3H), 1.71-1.59 (m, 1H), 1.10-1.07 (m, 3H).

Compound II-5-B 6-(4-(6-(3-Fluoro-2-methylphenyl)-5-(methoxycarbonyl)-2-(thiazol-2-yl)-3,6-dihydropyrimidin-4-yl)piperidin-1-yl)-3-methylpicolinic Acid (a Single Stereoisomer)

By utilizing the analogous procedure of Method C, the title compound was synthesized from compound XI-5-B as yellow solids.

LC-MS (ESI): $R_T$=4.362 min, mass calcd. for $C_{27}H_{27}FN_6O_4S$, 550.2, m/z found mass 551.0 [M+H]$^+$. $^1$H NMR (400 MHz, DMSO-$d_6$) δ 9.54 (d, J=3.6 Hz, 0.8H), 9.18 (s, 0.2H), 8.37 (s, 0.2H), 8.36 (s, 0.8H), 7.97-7.88 (m, 2H), 7.21-7.14 (m, 2H), 7.07-7.00 (m, 1H), 5.87 (s, 0.2H), 5.75 (d, J=3.2 Hz, 0.8H), 4.90-4.76 (m, 2H), 4.25-4.19 (m, 0.2H), 3.94-3.88 (m, 0.8H), 3.54 (s, 3H), 2.94-2.85 (m, 2H), 2.46 (s, 0.8H), 2.39 (s, 2.2H), 2.17 (s, 3H), 2.04-1.78 (m, 3H), 1.71-1.59 (m, 1H).

Compound II-6-B 2-(2-(4-(6-(3-Fluoro-2-methylphenyl)-5-(methoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-6-B as yellow solids.

LC-MS (ESI): $R_T$=4.064 min, mass calcd. for $C_{27}H_{27}FN_6O_4S$, 550.2, m/z found 551.0 [M+H]$^+$. $^1$H NMR (400 MHz, DMSO-$d_6$) δ 9.56 (br s, 0.8H), 9.22 (s, 0.2H), 8.27-8.26 (m, 2H), 7.97-7.88 (m, 2H), 7.23-7.13 (m, 1.8H), 7.07-7.00 (m, 1.2H), 5.87 (s, 0.2H), 5.74 (s, 0.8H), 4.92-4.77 (m, 2H), 4.25-4.19 (m, 0.2H), 3.94-3.88 (m, 0.8H), 3.54 (s, 3H), 3.44 (s, 2H), 2.94-2.85 (m, 2H), 2.45 (s, 0.6H), 2.39 (s, 2.4H), 2.07-1.59 (m, 4H).

Compound II-7-B 2-(4-(6-(4-fluoro-2-methylphenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method E, the title compound was synthesized from compound BB2 and FA5.

LC-MS (ESI): $R_T$=2.973 min, mass calcd. for $C_{27}H_{27}FN_6O_4S$, 550.2, m/z found 551.1 [M+H]$^+$. $^1$H NMR (400 MHz, DMSO-$d_6$) δ 9.52 (d, J=3.2 Hz, 0.8H), 9.06 (s, 0.2H), 8.15-8.10 (m, 1H), 7.98-7.86 (m, 2H), 7.30-7.26 (m, 0.8H), 7.18-7.13 (m, 0.2H), 7.06-6.94 (m, 2H), 5.81 (s, 0.2H), 5.69 (d, J=3.2 Hz, 0.8H), 4.90-4.72 (m, 2H), 4.20-4.13 (m, 0.2H), 3.91-3.81 (m, 0.8H), 3.54 (s, 3H), 2.89-2.76 (m, 2H), 2.04 (s, 3H), 1.94-1.71 (m, 3H), 1.60-1.53 (m, 1H).

Compound II-8-B 2-(4-(6-(2-Chloro-3-fluorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method E, the title compound was synthesized from compound BB2-1 and FA6.

LC-MS (ESI): $R_T$=2.920 min, mass calcd. for $C_{26}H_{24}ClFN_6O_4S$, 570.1, m/z found 571.0 [M+H]$^+$. $^1$H NMR (400 MHz, DMSO-$d_6$) δ 9.57 (s, 0.7H), 9.20 (s, 0.3H), 8.33 (s, 0.3H), 8.32 (s, 0.7H), 7.98-7.94 (m, 1.7H), 7.90 (d, J=3.2 Hz, 0.3H), 7.41-7.29 (m, 2H), 7.23-7.15 (m, 1H), 6.05 (s, 0.3H), 5.95 (s, 0.7H), 4.88-4.76 (m, 2H), 4.22-4.16 (m, 0.3H), 3.94-3.88 (m, 0.7H), 3.54 (s, 2.1H), 3.53 (s, 0.9H), 2.93-2.83 (m, 2H), 2.14 (s, 3H), 2.03-1.59 (m, 4H).

Compound II-9-B 2-(2-(4-(6-(2-Chloro-3-fluorophenyl)-5-(methoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-9-B as yellow solids.

LC-MS (ESI): $R_T$=3.242 min, mass calcd. for $C_{26}H_{24}ClFN_6O_4S$, 570.1, m/z found mass 571.2 [M+H]$^+$. $^1$H NMR (400 MHz, DMSO-$d_6$) δ 9.57 (s br, 0.7H), 9.23 (s, 0.3H) 8.27 (s, 0.6H), 8.26 (s, 1.4H), 7.98-7.90 (m, 2H), 7.41-7.29 (m, 2H), 7.23-7.16 (m, 1H), 6.08 (s, 0.3H), 5.98 (s, 0.7H), 4.91-4.76 (m, 2H), 4.22-4.16 (m, 0.3H), 3.95-3.88 (m, 0.7H), 3.54 (s, 2.1H), 3.53 (s, 0.9H), 3.43 (s, 2H), 2.96-2.85 (m, 2H), 2.05-1.60 (m, 4H).

Compound II-10-B 2-(4-(6-(2-Chloro-3-fluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-10-1 as yellow solids.

LC-MS (ESI): $R_T$=3.167 min, mass calcd. For $C_{24}H_{21}ClFN_5O_4S_2$ 561.1, m/z found mass 562.1 [M+H]$^+$. $^1$H NMR (400 MHz, DMSO-$d_6$) δ 9.61 (br s, 0.5H), 9.38 (s, 0.5H), 8.00-7.96 (m, 1.7H), 7.92-7.91 (d, J=3.2 Hz, 0.3H), 7.71 (s, 1H), 7.41-7.32 (m, 2H), 7.23-7.21 (m, 0.7H), 7.18-7.16 (m, 0.3H), 6.07 (s, 0.2H), 5.99 (s, 0.8H), 4.20-4.05 (m, 2.3H), 3.93-3.85 (m, 0.7H), 3.54 (s, 2.2H), 3.53 (s, 0.8H), 3.22-3.13 (m, 2H), 2.28-1.90 (m, 2H), 1.85-1.69 (m, 2H).

467

Compound II-11-X

Methyl 6-(1-(1H-pyrazole-4-carbonyl)piperidin-4-yl)-4-(2-chloro-4-fluorophenyl)-2-(thiazol-2-yl)-1,4-dihydropyrimidine-5-carboxylate (a Single Stereoisomer)

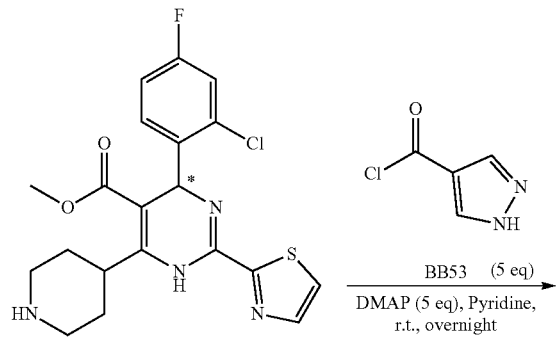

FA7

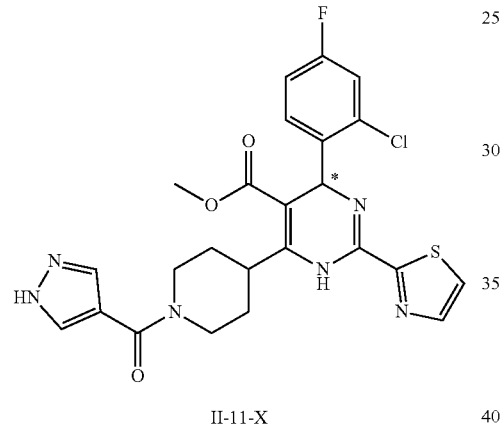

II-11-X

To a solution of 1H-pyrazole-4-carbonyl chloride BB53 (225 mg, 1.73 mmol) in acetonitrile (15 mL) was added N,N-dimethylpyridin-4-amine (210 mg, 1.73 mmol), methyl 4-(2-chloro-4-fluorophenyl)-6-(piperidin-4-yl)-2-(thiazol-2-yl)-1,4-dihydropyrimidine-5-carboxylate FA7 (150 mg, 0.345 mmol) and pyridine (0.54 mL). After stirred at room temperature under nitrogen atmosphere overnight, the mixture was diluted with ethyl acetate (20 mL) and washed with water (15 mL). The aqueous layer was extracted with ethyl acetate (10 mL) for three times. The combined organic layers were washed with brine (10 mL), dried over $Na_2SO_{4(s)}$ and filtered. The filtrate was concentrated under reduced pressure to give the crude product, which was further purified by C18 column (acetonitrile: water=45% to 95%) to give the title compound (76 mg, 98.6% purity, 42% yield) as yellow solids. LC-MS (ESI): $R_T$=7.739 min, mass calcd. for $C_{24}H_{22}CFN_6O_3S$, 528.1, m/z found 529.2 [M+H]$^+$. $^1$H NMR (400 MHz, CDCl$_3$) δ 8.18 (s, 0.3H), 7.88-7.87 (m, 2H), 7.83-7.81 (m, 1H), 7.51 (d, J=2.8 Hz, 0.7H), 7.48 (d, J=2.0 Hz, 0.7H), 7.45 (d, J=3.2 Hz, 0.3H), 7.30-7.28 (m, 1H), 7.18-7.12 (m, 1H), 7.01-6.91 (m, 1H), 6.20 (s, 0.3H), 6.08 (d, J=2.4 Hz, 0.7H), 5.01-4.65 (m, 1H), 4.48-4.33 (m 0.4H), 4.19-4.03 (m 0.6H), 3.62 (s, 3H), 3.45-2.81 (m, 2H), 2.23-1.96 (m, 4H), 1.87-1.55 (m, 2H).

468

Compound II-12-B

Methyl 4-(2-chloro-4-fluorophenyl)-6-(1-(1-methyl-1H-pyrazole-4-carbonyl)piperidin-4-yl)-2-(thiazol-2-yl)-1,4-dihydropyrimidine-5-carboxylate (a Single Stereoisomer)

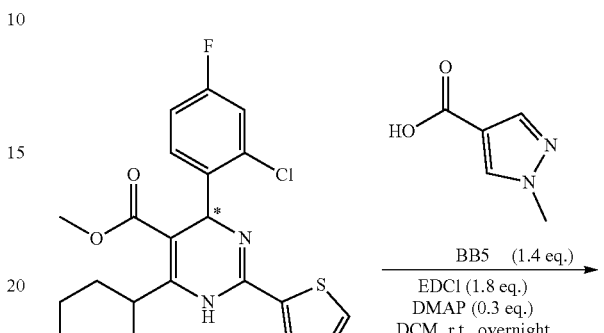

FA7

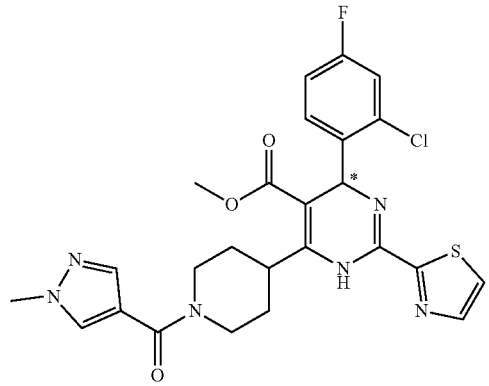

II-12-B

To a solution of methyl 4-(2-chloro-4-fluorophenyl)-6-(piperidin-4-yl)-2-(thiazol-2-yl)-1,4-dihydropyrimidine-5-carboxylate FA7 (50 mg, 0.115 mmol) in dichloromethane (10 mL) was added 1-methyl-1H-pyrazole-4-carboxylic acid BB5 (20 mg, 0.159 mmol), 1-ethyl-3-(3-dimethyllaminopropyl)carbodiimide hydrochloride (40 mg, 0.209 mmol) and 4-dimethylaminopyridine (4 mg, 0.033 mmol) at room temperature. After stirred at room temperature overnight, the resulting mixture was diluted with water (15 mL) and extracted with ethyl acetate (20 mL) for three times. The combined organic layers were washed with water (20 mL) for three times, dried over $Na_2SO_{4(s)}$ and concentrated. The residue was purified by C18 column (acetonitrile:water=70% to 80%) to give the desired compound (50 mg, 80% yield) as yellow solids. LC-MS (ESI): $R_T$=2.788 min, mass calcd. for $C_{25}H_{24}ClFN_6O_3S$, 542.1, m/z found 542.9 [M+H]$^+$ 0.1H NMR (400 MHz, CDCl$_3$) δ 8.14 (s, 0.3H), 7.83-7.81 (m, 1H), 7.75-7.73 (m, 1H), 7.67-7.66 (m, 1H), 7.51-7.50 (m, 0.7H), 7.45 (s, 1H), 7.30-7.28 (m, 1H), 7.15-7.12 (m, 1H), 6.97-6.87 (m, 1H), 6.20 (s, 0.3H), 6.07 (s, 0.7H), 5.00-4.36 (m, 2H), 4.33-4.27 (m, 0.3H), 4.13-4.05 (m, 0.7H), 3.94 (s, 3H), 3.61-3.60 (m, 3H), 3.50-2.75 (m, 2H), 2.21-1.88 (m, 3H), 1.81-1.70 (m, 1H).

Compound II-13-A 2-(2-(4-(6-(2-chloro-4-fluorophenyl)-5-(methoxycarbonyl)-2-(thiazol-2-yl)-3,6-dihydropyrimidin-4-yl)piperidin-1-yl)pyrimidin-4-yl)acetate (a Single Stereoisomer)

By utilizing the analogous procedure of Method C, the title compound was synthesized from compound XI-13-S as yellow solids.

LC-MS (ESI): $R_T$=3.269 min, mass calcd. for $C_{26}H_{24}ClFN_6O_4S$, 570.1, m/z found 571.2 [M+H]$^+$. $^1$H NMR (400 MHz, DMSO-$d_6$) δ 9.50 (br s, 0.7H), 9.15 (br s, 0.3H), 8.14 (d, J=5.2 Hz, 1H), 7.95-7.92 (m, 2H), 7.43-7.35 (m, 2H), 7.24-7.19 (m, 1H), 6.53-6.52 (m, 1H), 6.01 (br s, 0.3H), 5.93 (s, 0.7H), 4.97-4.83 (m, 2H), 4.19-4.11 (m, 0.3H), 3.93-3.86 (m, 0.7H), 3.54 (s, 3H), 3.18 (s, 2H), 2.87-2.77 (m, 2H), 1.97-1.76 (m, 3.2H), 1.62-1.58 (m, 0.8H).

Compound II-14-A 2-(4-(6-(2-Chloro-4-fluorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the title compound was synthesized from compound XI-14-A as yellow solids.

LC-MS (ESI): $R_T$=1.39 min, mass calcd. for $C_{26}H_{24}ClFN_6O_4S$, 570.1, m/z found 571.0 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 230 nm, $R_T$=8.514 min). $^1$H NMR (400 MHz, DMSO-$d_6$) δ 13.42 (br s, 1H), 9.47 (d, J=3.6 Hz, 0.7H), 9.15 (s, 0.3H), 8.40 (s, 0.3H), 8.39 (s, 0.7H), 7.98-7.89 (m, 2H), 7.43-7.32 (m, 2H), 7.24-7.17 (m, 1H), 6.02 (s, 0.3H), 5.93 (d, J=3.6 Hz, 0.7H), 4.88-4.76 (m, 2H), 4.21-4.15 (m, 0.3H), 3.94-3.88 (m, 0.7H), 3.55 (s, 2H), 3.53 (s, 1H), 2.95-2.86 (m, 2H), 2.19 (s, 3H), 1.93-1.60 (m, 4H).

Compound II-15-A 2-(2-(4-(6-(2-Chloro-4-fluorophenyl)-5-(methoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-15-S as yellow solids.

LC-MS (ESI): $R_T$=2.712 min, mass calcd. for $C_{26}H_{24}ClFN_6O_4S$, 570.1, m/z found 571.0 [M+H]$^+$. $^1$H NMR (400 MHz, DMSO-$d_6$ added one drop of $D_2O$) δ 8.26 (s, 0.6H), 8.25 (s, 1.4H), 7.97-7.94 (m, 1H), 7.89-7.85 (m, 1H), 7.43-7.33 (m, 2H), 7.23-7.17 (m, 1H), 6.01 (s, 0.3H), 5.94 (s, 0.7H), 4.88-4.74 (m, 2H), 4.19-4.11 (m, 0.3H), 3.94-3.87 (m, 0.7H), 3.55 (s, 2.1H), 3.53 (s, 0.9H), 3.43 (s, 2H), 2.95-2.86 (m, 2H), 2.01-1.59 (m, 4H).

Compound II-16-B 2-(4-(6-(2-Chloro-4-fluorophenyl)-5-(methoxycarbonyl)-2-(thiazol-2-yl)-3,6-dihydropyrimidin-4-yl)piperidin-1-yl)-4-methylpyrimidine-5-carboxylic Acid (a Single Stereoisomer)

By utilizing the analogous procedure of Method C, the title compound was synthesized from compound XI-16-B as yellow solids.

LC-MS (ESI): $R_T$=3.874 min, mass calcd. for $C_{26}H_{24}ClFN_6O_4S$, 570.1, m/z found 570.9 [M+H]$^+$. $^1$H NMR (400 MHz, $CD_3OD$) δ 8.79 (s, 1H), 7.87 (d, J=2.8 Hz, 1H), 7.70 (d, J=2.8 Hz, 1H), 7.42-7.38 (m, 1H), 7.25-7.22 (m, 1H), 7.09-7.02 (m, 1H), 6.15 (s, 0.4H), 6.08 (s, 0.6H), 5.19-5.00 (m, 2H), 4.38-4.28 (m, 0.3H), 4.12-4.03 (m, 0.7H), 3.61 (s, 3H), 3.12-2.98 (m, 2H), 2.65 (s, 3H), 2.10-1.68 (m, 4H).

Compound II-17-B 2-(4-(6-(2-chloro-4-fluorophenyl)-5-(methoxycarbonyl)-2-(thiazol-2-yl)-3,6-dihydropyrimidin-4-yl)piperidin-1-yl)pyrimidine-5-carboxylic Acid (a Single Stereoisomer)

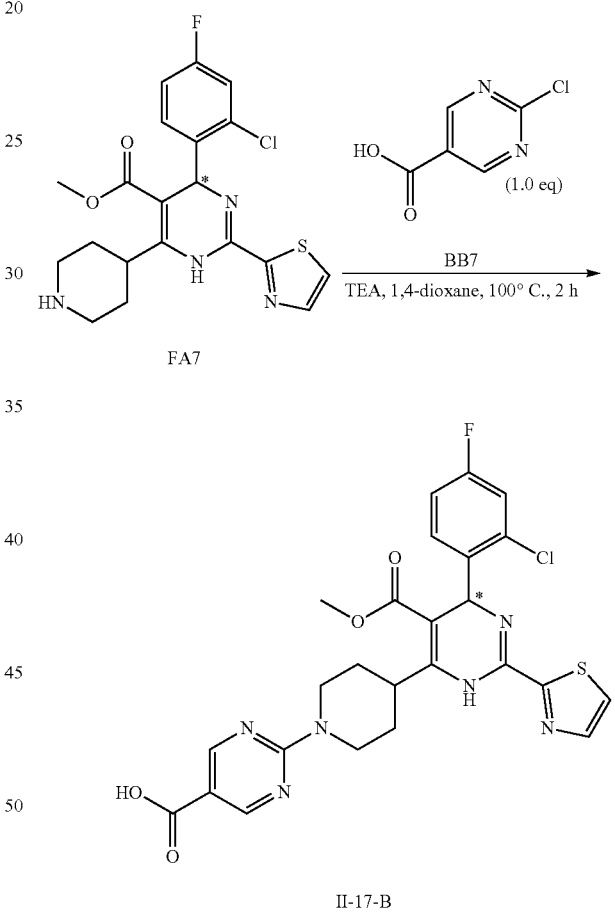

By utilizing the analogous procedure of Method E, the title compound was synthesized from compound BB7 and FA7.

LC-MS (ESI): $R_T$=3.263 min, mass calcd. for $C_{25}H_{22}ClFN_6O_4S$, 556.1, m/z found 557.2 [M+H]$^+$. $^1$H NMR (400 MHz, DMSO-$d_6$) δ 12.75 (br s, 1H), 9.50 (s, 0.7H), 9.26 (s, 0.3H), 8.80-8.79 (m, 2H), 7.98-7.89 (m, 2H), 7.43-7.31 (m, 2H), 7.24-7.20 (m, 1H), 6.02 (s, 0.3H), 5.94 (s, 0.7H), 5.02-4.89 (m, 2H), 4.26-4.20 (m, 0.3H), 3.99-3.93 (m, 0.7H), 3.55 (s, 2H), 3.54 (s, 1H), 3.09-3.00 (m, 2H), 2.14-1.66 (m, 4H).

Compound II-18-B 2-(4-(6-(2-Chloro-4-fluorophenyl)-5-(methoxycarbonyl)-2-(thiazol-2-yl)-3,6-dihydropyrimidin-4-yl)piperidin-1-yl)oxazole-4-carboxylic Acid (a Single Stereoisomer)

By utilizing the analogous procedure of Method C, the title compound was synthesized from compound XI-18-S as yellow solids.

LC-MS (ESI): $R_T$=3.226 min, mass calcd. for $C_{24}H_{21}ClFN_5O_5S$, 545.1, m/z found 546.1 [M+H]$^+$. $^1$H NMR (400 MHz, CD$_3$OD) δ 7.89 (s, 2H), 7.72 (d, J=3.2 Hz, 1H), 7.42-7.38 (m, 1H), 7.23 (dd, J=8.8, 2.4 Hz, 1H), 7.07-7.03 (m, 1H), 6.09 (s, 1H), 4.28-4.18 (m, 2.4H), 4.02-3.94 (m, 0.6H), 3.64 (s, 0.5H), 3.60 (s, 2.5H), 3.17-3.06 (m, 2H), 2.19-2.02 (m, 2H), 1.92-1.70 (m, 2H).

Compound II-19-A 2-(4-(6-(2-Chloro-4-fluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-19-2 as yellow solids.

LC-MS (ESI): $R_T$=2.059 min, mass calcd. for $C_{24}H_{21}ClFN_5O_4S_2$ 561.1, m/z found 562.2 [M+H]$^+$. $^1$H NMR (400 MHz, DMSO-d$_6$) δ 8.00-7.97 (m, 1.6H), 7.92-7.91 (m, 0.4H), 7.50 (s, 1H), 7.44-7.32 (m, 2H), 7.24-7.19 (m, 1H), 6.02 (s, 0.2H), 5.93 (s, 0.8H), 4.12-4.01 (m, 2.2H), 3.89-3.84 (m, 0.8H), 3.54 (s, 2.1H), 3.53 (s, 0.9H), 3.15-3.06 (m, 2H), 2.08-1.63 (m, 4H).

Compound II-20-B 2-(4-(6-(2-Chloro-4-fluorophenyl)-5-(ethoxycarbonyl)-2-(thiazol-2-yl)-3,6-dihydropyrimidin-4-yl)piperidin-1-yl)-5-methylpyrimidine-4-carboxylic Acid (a Single Stereoisomer)

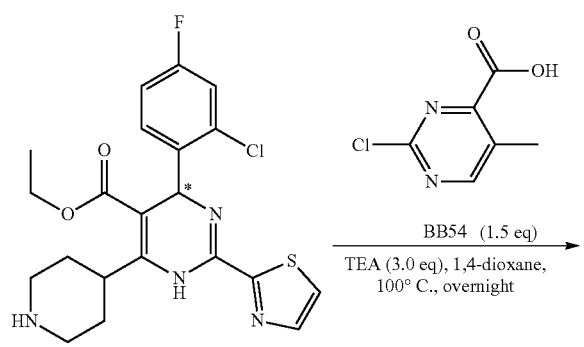

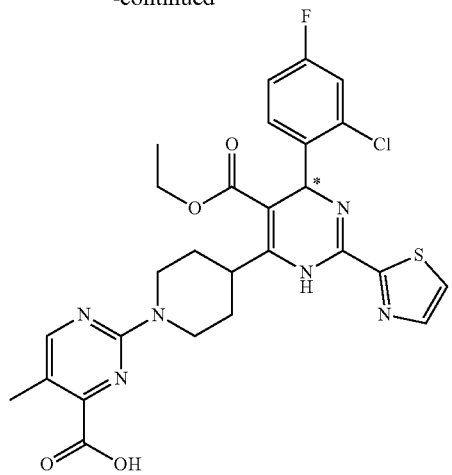

II-20-B

By utilizing the analogous procedure of Method E, the title compound was synthesized from compound BB54 and FA8.

LC-MS (ESI): $R_T$=3.999 min, mass calcd. for $C_{27}H_{26}ClFN_6O_4S$, 584.1, m/z found 584.9 [M+H]$^+$. $^1$H NMR (400 MHz, DMSO-d$_6$) δ 9.51 (d, J=3.2 Hz, 0.7H), 9.13 (s, 0.3H), 8.35-8.33 (m, 1H), 7.98-7.90 (m, 2H), 7.45-7.33 (m, 2H), 7.25-7.20 (m, 1H), 6.03 (s, 0.3H), 5.94 (d, J=3.6 Hz, 0.7H), 4.89-4.76 (m, 2H), 4.20-4.14 (m, 0.3H), 4.00 (q, J=7.2 Hz, 2H), 3.94-3.88 (m, 0.7H), 2.92-2.83 (m, 2H), 2.15 (s, 3H), 2.02-1.60 (m, 4H), 1.11-1.05 (m, 3H).

Compound II-21-B 2-(2-(4-(6-(2-Chloro-4-fluorophenyl)-5-(ethoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-21-B as yellow solids.

LC-MS (ESI): $R_T$=3.311 min, mass calcd. for $C_{27}H_{26}ClFN_6O_4S$, 584.1, m/z found 585.1 [M+H]$^+$. $^1$H NMR (400 MHz, DMSO-d$_6$) δ 9.49 (s, 0.7), 9.13 (s, 0.3H), 8.27-8.25 (m, 2H), 7.97-7.93 (m, 2H), 7.44-7.33 (m, 2H), 7.26-7.18 (m, 1H), 6.03 (s, 0.3H), 5.94 (s, 0.7H), 4.92-4.74 (m, 2H), 4.22-4.13 (m, 0.4H), 4.02-3.86 (m, 2.6H), 3.42 (s, 2H), 2.97-2.80 (m, 2H), 2.07-1.56 (m, 4H), 1.11-1.05 (m, 3H).

Compound II-22-B 2-(4-(6-(2-Chloro-3-fluorophenyl)-5-(ethoxycarbonyl)-2-(thiazol-2-yl)-3,6-dihydropyrimidin-4-yl)piperidin-1-yl)-5-methylpyrimidine-4-carboxylic Acid (a Single Stereoisomer)

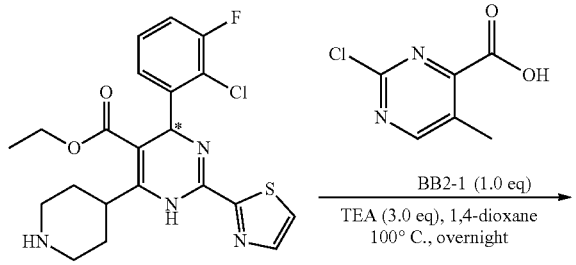

FA9

BB2-1 (1.0 eq)
TEA (3.0 eq), 1,4-dioxane
100° C., overnight

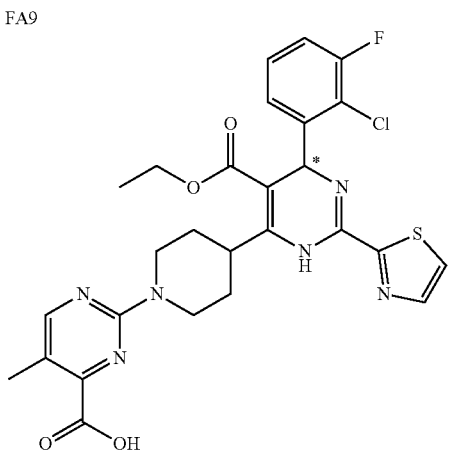

II-22-B

By utilizing the analogous procedure of Method E, the title compound was synthesized from compound BB2-1 and FA9.

LC-MS (ESI): $R_T$=3.279 min, mass calcd. for $C_{27}H_{26}ClFN_6O_4S$, 584.1, m/z found 585.0 [M+H]$^+$. $^1$H NMR (400 MHz, DMSO-d$_6$) δ 9.54 (s, 0.7H), 9.10 (s, 0.3H), 8.26 (s, 1H), 7.98-7.90 (m, 2H), 7.39-7.31 (m, 2H), 7.23-7.18 (m, 1H), 6.09 (s, 0.3H), 5.99 (s, 0.7H), 4.88-4.76 (m, 2H), 4.02-3.87 (m, 3H), 2.90-2.81 (m, 2H), 2.12 (s, 3H), 1.91-1.72 (m, 3H), 1.63-1.59 (m, 1H), 1.10-1.03 (m, 3H).

Compound II-23-B 2-(2-(4-(6-(2-Chloro-3-fluorophenyl)-5-(ethoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-23-B as yellow solids.

LC-MS (ESI): $R_T$=3.312 min, mass calcd. for $C_{27}H_{26}ClFN_6O_4S$, 584.1, m/z found 585.1 [M+H]$^+$. $^1$H NMR (400 MHz, CD$_3$OD) δ 8.18 (s, 2H), 7.77 (d, J=2.8 Hz, 1H), 7.60 (d, J=3.2 Hz, 1H), 7.24-7.13 (m, 2H), 7.08-7.03 (m, 1H), 6.07 (br s, 1H), 4.98-4.82 (m, 1H), 4.75-4.66 (m, 1H), 4.26-3.93 (m, 3H), 3.38 (s, 2H), 2.96-2.85 (m, 2H), 2.05-1.55 (m, 4H), 1.04 (t, J=7.2 Hz, 3H).

Compound II-24-B (cis)-3-(2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidin-5-yl)-3-hydroxycyclobutanecarboxylic Acid (a Single Stereoisomer)

By utilizing the analogous procedure of Method E, the title compound was synthesized from compound XI-24-B as yellow solids.

LC-MS (ESI): $R_T$=2.322 min, mass calcd. for $C_{29}H_{27}ClF_2N_6O_5S$, 644.1, m/z found 644.9 [M+H]$^+$. $^1$H NMR (400 MHz, DMSO-d$_6$) δ 8.50-8.49 (m, 1.9H), 8.40-8.39 (m, 0.1H), 7.99-7.91 (m, 2H), 7.50-7.43 (m, 1H), 7.22-7.16 (m, 1H), 6.03 (s, 0.3H), 5.94 (s, 0.7H), 4.94-4.80 (m, 2H), 4.23-4.16 (m, 0.3H), 3.95-3.89 (m, 0.7H), 3.55 (s, 2.1H), 3.54 (s, 0.9H), 2.95-2.87 (m, 2H), 2.67-2.60 (m, 3H), 2.45-2.39 (m, 2H), 2.07-1.60 (m, 4H).

Compound II-25-B 2-(4-(6-(2-Chloro-3,4-difluorophenyl)-5-(methoxycarbonyl)-2-(thiazol-2-yl)-3,6-dihydropyrimidin-4-yl)piperidin-1-yl)oxazole-5-carboxylic Acid (a Single Stereoisomer)

By utilizing the analogous procedure of Method C, the title compound was synthesized from compound XI-25-B as yellow solids.

LC-MS (ESI): $R_T$=3.769 min, mass calcd. for $C_{24}H_{20}ClF_2N_5O_5S$, 563.1, m/z found 564.2 [M+H]$^+$. $^1$H NMR (400 MHz, DMSO-d$_6$) δ 9.34 (br s, 1H), 8.00-7.97 (m, 1.7H), 7.92-7.91 (m, 0.3H), 7.49-7.43 (m, 2H), 7.24-7.14 (m, 1H), 6.02 (s, 0.3H), 5.94 (s, 0.7H), 4.20-4.10 (m, 2.2H), 3.88-3.83 (m, 0.8H), 3.54 (s, 3H), 3.13-3.04 (m, 2H), 2.20-2.12 (m, 0.2H), 2.01-1.81 (m, 2.8H), 1.72-1.63 (m, 1H).

Compound II-26-B

5-Chloro-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylic Acid (a Single Stereoisomer)

By utilizing the analogous procedure of Method C, the title compound was synthesized from compound XI-26-B as yellow solids.

LC-MS (ESI): $R_T$=3.347 min, mass calcd. for $C_{25}H_2Cl_2F_2N_6O_4S$, 608.1, m/z found 609.1 [M+H]$^+$. $^1$H NMR (400 MHz, DMSO-d$_6$+one drop of D$_2$O) δ 8.42 (s, 1H), 7.97-7.88 (m, 2H), 7.47-7.40 (m, 1H), 7.23-7.12 (m, 1H), 6.00 (s, 0.4H), 5.93 (s, 0.6H), 4.83-4.67 (m, 2H), 4.23-4.13 (m, 0.3H), 3.96-3.85 (m, 0.7H), 3.53 (s, 3H), 3.00-2.87 (m, 2H), 2.05-1.60 (m, 4H).

Compound II-27-B 2-(4-(6-(2-Chloro-3,4-difluorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method E, the title compound was synthesized from compound FA10 and BB2-1 as yellow solids.

LC-MS (ESI): $R_T$=3.064 min, mass calcd. for $C_{26}H_{23}ClF_2N_6O_4S$, 588.1, m/z found 588.9 [M+H]$^+$. $^1$H NMR (400 MHz, DMSO-$d_6$) δ 13.39 (brs, 1H), 9.59 (s, 0.7H), 9.22 (s, 0.3H), 8.40 (s, 0.3H), 8.39 (s, 0.7H), 7.97 (d, J=3.2 Hz, 0.7H), 7.94 (d, J=5.2 Hz, 1H), 7.90 (d, J=3.2 Hz, 0.3H), 7.49-7.41 (m, 1H), 7.23-7.14 (m, 1H), 6.02 (s, 0.3H), 5.94 (d, J=3.6 Hz, 0.7H), 4.90-4.74 (m, 2H), 4.24-4.14 (m, 0.3H), 3.96-3.86 (m, 0.7H), 3.55 (s, 2H), 3.54 (s, 1H), 2.99-2.84 (m, 2H), 2.19 (s, 3H), 2.07-1.58 (m, 4H).

Compound II-28-B 2-(2-(4-(6-(2-Chloro-3,4-difluorophenyl)-5-(methoxycarbonyl)-2-(thiazol-2-yl)-3,6-dihydropyrimidin-4-yl)piperidin-1-yl)-4-methylpyrimidin-5-yl)acetic Acid (a Single Stereoisomer)

By utilizing the analogous procedure of Method C, the title compound was synthesized from compound XI-28-6 as yellow solids.

LC-MS (ESI): $R_T$=3.414 min, mass calcd. for $C_{27}H_{25}ClF_2N_6O_4S$, 602.1, m/z found 603.2 [M+H]$^+$. $^1$H NMR (400 MHz, DMSO-$d_6$) δ 8.08-8.06 (m, 1H), 7.99-7.90 (m, 2H), 7.50-7.42 (m, 1H), 7.24-7.14 (m, 1H), 6.02 (s, 0.3H), 5.94 (s, 0.7H), 4.94-4.79 (m, 2H), 4.22-4.16 (m, 0.3H), 3.94-3.86 (m, 0.7H), 3.55 (s, 2.1H), 3.54 (s, 0.9H), 3.43 (s, 2H), 2.93-2.80 (m, 2H), 2.26 (s, 0.9H), 2.25 (s, 2.1H), 2.09-1.59 (m 4H).

Compound II-29-B 2-(2-(4-(6-(2-Chloro-3,4-difluorophenyl)-5-(methoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-29-S as yellow solids.

LC-MS (ESI): $R_T$=3.349 min, mass calcd. for $C_{26}H_{23}ClF_2N_6O_4S$, 588.1, m/z found 589.0 [M+H]$^+$. $^1$H NMR (400 MHz, DMSO-$d_6$) δ 7.91 (d, J=3.2 Hz, 1H), 7.75 (d, J=3.6 Hz, 1H), 7.37 (s, 1H), 7.32-7.24 (m, 2H), 6.19 (s, 0.3H), 6.13 (s, 0.7H), 4.88-4.84 (m, 2H), 4.50-4.45 (m, 0.3H), 4.24-4.16 (m, 0.7H), 4.13-4.06 (m, 2H), 3.31-3.27 (m, 2H), 2.64 (s, 3H), 2.18-1.97 (m, 3.3H), 1.90-1.87 (m, 0.7H), 1.20-1.15 (m, 3H).

Compound II-30-B 2-(4-(6-(2-Chloro-3,4-difluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-30-B as yellow solids.

LC-MS (ESI): $R_T$=3.253 min, mass calcd. for $C_{24}H_{20}ClF_2N_5O_4S_2$ 579.1, m/z found mass 580.1 [M+H]$^+$. $^1$H NMR (400 MHz, DMSO-$d_6$) δ 12.62 (br s, 1H), 9.67 (d, J=3.2 Hz, 0.8H), 9.41 (s, 0.2H), 8.01-7.96 (m, 1.7H), 7.92 (d, J=3.2 Hz, 0.3H), 7.80 (s, 1H), 7.49-7.43 (m, 1H), 7.24-7.14 (m, 1H), 6.03 (s, 0.2H), 5.94 (d, J=3.6 Hz, 0.8H), 4.20-4.04 (m, 2.3H), 3.93-3.86 (m, 0.7H), 3.55 (s, 2.2H), 3.53 (s, 0.8H), 3.25-3.15 (m, 2H), 2.25-1.90 (m, 2H), 1.89-1.66 (m, 2H).

Compound II-31-B 2-(4-(6-(2-Chloro-3,4-difluorophenyl)-5-(methoxycarbonyl)-2-(thiazol-2-yl)-3,6-dihydropyrimidin-4-yl)piperidin-1-yl)-4-(trifluoromethyl)thiazole-5-carboxylic Acid (a Single Stereoisomer)

By utilizing the analogous procedure of Method C, the title compound was synthesized from compound XI-31-B as yellow solids.

LC-MS (ESI): $R_T$=3.317 min, mass calcd. for $C_{25}H_{19}ClF_5N_5O_4S_2$ 647.1, m/z found 648.0 [M+H]$^+$. $^1$H NMR (400 MHz, DMSO-$d_6$) δ 9.67 (s, 0.7H), 9.44 (s, 0.3H), 8.01-7.92 (m, 2H), 7.50-7.43 (m, 1H), 7.25-7.14 (m, 2H), 6.03 (s, 0.3H), 5.94 (s, 0.7H), 4.21-3.98 (m, 2.3H), 3.92-3.85 (m, 0.7H), 3.55 (s, 2.1H), 3.53 (s, 0.9H), 3.24-3.13 (m, 2H), 2.30-1.82 (m 3H), 1.75-1.67 (m, 1H).

Compound II-32-B 2-(4-(6-(2-Chloro-3,4-difluorophenyl)-5-(methoxycarbonyl)-2-(thiazol-2-yl)-3,6-dihydropyrimidin-4-yl)piperidin-1-yl)thiazole-4-carboxylic Acid (a Single Stereoisomer)

By utilizing the analogous procedure of Method C, the title compound was synthesized from compound XI-32-B as yellow solids.

LC-MS (ESI): $R_T$=3.348 min, mass calcd. for $C_{24}H_{20}ClF_2N_5O_4S_2$ 579.1, m/z found 580.0 [M+H]$^+$. $^1$H NMR (400 MHz, CD$_3$OD) δ 7.91-7.85 (m, 1H), 7.72 (d, J=3.2 Hz, 1H), 7.49 (s, 1H), 7.25-7.18 (m, 2H), 6.16 (s, 0.3H), 6.08 (s, 0.7H), 4.29-4.10 (m, 2.4H), 4.03-3.92 (m, 0.6H), 3.60 (s, 3H), 3.21-3.14 (m, 2H), 2.26-1.91 (m, 3.3H), 1.78-1.70 (m, 0.7H).

Compound II-33-B 2-(4-(6-(2-Chloro-3,4-difluorophenyl)-5-(methoxycarbonyl)-2-(thiazol-2-yl)-3,6-dihydropyrimidin-4-yl)piperidin-1-yl)oxazole-4-carboxylic Acid (a Single Stereoisomer)

By utilizing the analogous procedure of Method C, the title compound was synthesized from compound XI-33-B as yellow solids.

LC-MS (ESI): $R_T$=3.836 min, mass calcd. for $C_{24}H_{20}ClF_2N_5O_5S$, 563.1, m/z found 563.9 [M+H]$^+$. $^1$H NMR (400 MHz, DMSO-$d_6$) δ 9.30 (s, 0.3H), 8.18 (s, 0.7H), 8.00-7.99 (m, 1.6H), 7.95-7.93 (m, 0.4H), 7.51-7.42 (m, 1H), 7.27-7.16 (m, 1H), 6.03 (s, 0.3H), 5.94 (s, 0.7H), 4.16-3.99 (m, 2H), 3.91-3.78 (m, 1H), 3.54 (s, 2H), 3.53 (s, 1H), 3.12-2.96 (m, 2H), 2.14-1.61 (m, 4H).

Compound II-34-F 2-(4-(6-(2-chloro-3,4-difluorophenyl)-5-(ethoxycarbonyl)-2-(thiazol-2-yl)-3,6-dihydropyrimidin-4-yl)-2-methylpiperidin-1-yl)pyrimidine-5-carboxylic acid (a Mixture of 2 Stereoisomers)

By utilizing the analogous procedure of Method D, the title compound was synthesized from compound XI-34-10F as yellow solids.

LC-MS (ESI): $R_T$=3.337 min, mass calcd. for $C_{27}H_{25}ClF_2N_6O_4S$, 602.1, m/z found 602.9 [M+H]$^+$, $^1$H NMR (400 MHz, DMSO-$d_6$) δ 8.79 (s, 0.4H), 8.78 (s, 1.6H), 7.99-7.92 (m, 2H), 7.52-7.44 (m, 1H), 7.26-7.15 (m, 1H), 6.06 (s, 0.1H), 6.03 (s, 0.1H), 5.97 (s, 0.4H), 5.94 (s, 0.4H), 5.36-5.21 (m, 1H), 4.90-4.77 (m, 1H), 4.53-4.46 (m, 0.3H), 4.26-4.21 (m, 0.7H), 4.05-4.00 (m, 2H), 3.13-3.06 (m, 1H), 2.12-1.66 (m, 4H), 1.27-1.24 (m, 3H), 1.12-1.07 (m, 3H).

Compound II-35-A 4-(4-(6-(2-Chloro-3,4-difluorophenyl)-5-(ethoxycarbonyl)-2-(thiazol-2-yl)-3,6-dihydropyrimidin-4-yl)piperidin-1-yl)benzoic Acid (a Single Stereoisomer)

By utilizing the analogous procedure of Method D, the title compound was synthesized from compound XI-35-5R as yellow solids.

LC-MS (ESI): $R_T$=3.148 min, mass calcd. for $C_{28}H_{25}ClF_2N_4O_4S$, 586.1, m/z found 587.1 [M+H]$^+$. Chiral analysis (Column: Chiralpak ID 5 μm 4.6*250 mm; Mobile Phase: Hex:EtOH:TFA=75:25:0.2 at 1.0 mL/min; Temp: 30° C.; Wavelength: 230 nm, $R_T$=8.375 min). $^1$H NMR (400 MHz, DMSO-$d_6$) δ 7.99-7.96 (m, 1.7H), 7.93-7.92 (d, J=2.8 Hz, 0.3H), 7.78 (d, J=8.8 Hz, 2H), 7.50-7.44 (m, 1H), 7.24-7.19 (m, 1H), 7.01 (d, J=8.8 Hz, 2H), 6.05 (s, 0.3H), 5.95 (s, 0.7H), 4.13-3.97 (m, 4.2H), 3.89-3.80 (m, 0.8H), 2.95-2.82 (m, 2H), 2.10-1.88 (m, 2.3H), 1.82-1.79 (m, 1H), 1.66-1.62 (m, 0.7H), 1.11-1.04 (m, 3H).

Compound II-36-B 6-(4-(6-(2-chloro-3,4-difluorophenyl)-5-(ethoxycarbonyl)-2-(thiazol-2-yl)-3,6-dihydropyrimidin-4-yl)piperidin-1-yl)-4-hydroxynicotinic Acid (a Single Stereoisomer)

By utilizing the analogous procedure of Method D, the title compound was synthesized from compound XI-36-S as yellow solids.

LC-MS (ESI): $R_T$=3.231 min, mass calcd. for $C_{27}H_{24}ClF_2N_5O_5S$, 603.1 m/z found 603.9 [M+H]$^+$. $^1$H NMR (400 MHz, DMSO-$d_6$) δ 9.64 (d, J=3.2 Hz, 0.7H), 9.20 (s, 0.3H), 8.20-8.19 (m, 1H), 8.00-7.97 (m, 1.7H), 7.92 (d, J=3.2 Hz, 0.3H), 7.50-7.43 (m, 1H), 7.26-7.20 (m, 1H), 7.19-7.00 (m, 0.7H), 6.09 (s, 0.3H), 6.07 (s, 0.7H), 6.04 (s, 0.3H), 5.94 (d, J=2.8 Hz, 0.7H), 4.30-4.14 (m, 2.3H), 4.02-3.95 (m, 2H), 3.91-3.85 (m, 0.7H), 3.02-2.94 (m, 2H), 2.11-1.74 (m, 3H), 1.69-1.63 (m, 1H), 1.10-1.06 (m, 3H).

Compound II-37-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)picolinic Acid (a Single Stereoisomer)

By utilizing the analogous procedure of Method C, the title compound was synthesized from compound XI-37-2 as yellow solids.

LC-MS (ESI): $R_T$=3.474 min, mass calcd. for $C_{27}H_{24}ClF_2N_5O_5S$, 587.1, m/z found 587.9 [M+H]$^+$. $^1$H NMR (400 MHz, DMSO-$d_6$) δ 7.99-7.91 (m, 2H), 7.68-7.64 (m, 1H), 7.51-7.44 (m, 1H), 7.28-7.18 (m, 2H), 7.10-7.06 (m, 1H), 6.05 (s, 0.3H), 5.95 (s, 0.7H), 4.68-4.53 (m, 2H), 4.19-4.12 (m, 0.2H), 4.03-3.96 (m, 2H), 3.92-3.87 (m 0.8H), 2.94-2.80 (m 2H), 2.06-1.87 (m 4H), 1.12-1.05 (m 3H).

Compound II-38-B 2-(4-(6-(2-chloro-3,4-difluorophenyl)-5-(ethoxycarbonyl)-2-(thiazol-2-yl)-3,6-dihydropyrimidin-4-yl)piperidin-1-yl)-6-(trifluoromethyl)isonicotinic Acid (a Single Stereoisomer)

By utilizing the analogous procedure of Method D, the title compound was synthesized from compound XI-38-3 as yellow solids.

LC-MS (ESI): $R_T$=2.938 min, mass calcd. for $C_{28}H_{23}ClF_5N_5O_4S$, 655.1, m/z found 656.0 [M+H]$^+$. $^1$H NMR (400 MHz, DMSO-$d_6$) δ 9.61 (br s, 0.6H), 9.25 (s, 0.4H), 7.99-7.90 (m, 2H), 7.51-7.43 (m, 2H), 7.30 (s, 0.6H), 7.29 (s, 0.4H), 7.25-7.17 (m, 1H), 6.04 (s, 0.3H), 5.95 (s, 0.7H), 4.60-4.49 (m, 2H), 4.25-4.17 (m, 0.4H), 4.03-3.92 (m, 2.6H), 3.05-2.89 (m, 2H), 2.13-1.82 (m, 3H), 1.76-1.66 (m, 1H), 1.11-1.05 (m, 3H).

Compound II-39-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5-(trifluoromethyl)isonicotinic Acid (a Single Stereoisomer)

By utilizing the analogous procedure of Method C, the title compound was synthesized from compound XI-39-S as yellow solids.

LC-MS (ESI): $R_T$=2.728 min, mass calcd. for $C_{28}H_{23}ClF_5N_5O_4S$, 655.1, m/z found 656.1 [M+H]$^+$. $^1$H NMR (400 MHz, DMSO-$d_6$+$D_2O$) δ 8.41 (s, 1H), 7.98-7.88 (m, 2H), 7.48-7.42 (m, 1H), 7.24-7.18 (m, 1H), 7.01-7.00 (m, 1H), 6.04 (s, 0.3H), 5.96 (s, 0.7H), 4.68-4.55 (m, 2H), 4.23-4.17 (m, 0.3H), 4.03-3.91 (m, 2.7H), 3.04-2.95 (m, 2H), 2.04-1.64 (m, 4H), 1.11-1.05 (m, 3H).

Compound II-40-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-3-fluoroisonicotinic Acid (a Single Stereoisomer)

By utilizing the analogous procedure of Method C, the title compound was synthesized from compound XI-40-B as yellow solids.

LC-MS (ESI): $R_T$=4.321 min, mass calcd. for $C_{27}H_{23}ClF_3N_5O_4S$, 605.1, m/z found 605.9 [M+H]$^+$. $^1$H NMR (400 MHz, CD$_3$OD) δ 8.05 (d, J=4.8 Hz, 1H), 7.91 (d, J=3.2 Hz, 1H), 7.75 (d, J=3.2 Hz, 1H), 7.26-7.24 (m, 2H), 7.18-7.16 (m, 1H), 6.13 (s, 1H), 4.21-4.14 (m, 3H), 4.07 (q, J=7.2 Hz, 2H), 3.08-2.98 (m, 2H), 2.23-2.06 (m, 2H), 1.98-1.95 (m, 1H), 1.83-1.79 (m, 1H), 1.15 (t, J=7.2 Hz, 3H).

Compound II-41-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)isonicotinic Acid (a Single Stereoisomer)

By utilizing the analogous procedure of Method C, the title compound was synthesized from compound XI-41-B as yellow solids.

LC-MS (ESI): $R_T$=3.589 min, mass calcd. for $C_{27}H_{24}ClF_2N_5O_4S$, 587.1, m/z found mass 587.9 [M+H]$^+$. $^1$H NMR (400 MHz, DMSO-$d_6$) δ 9.59 (br s, 0.7H), 9.11 (s, 0.3H), 8.24 (d, J=5.2 Hz, 1H), 7.99-7.91 (m, 2H), 7.51-7.44 (m, 1H), 7.26-7.21 (m, 2H), 7.02 (d, J=4.8 Hz, 1H), 6.04 (s, 0.3H), 5.95 (s, 0.7H), 4.58-4.44 (m, 2H), 4.18-4.12 (m, 0.3H), 4.03-3.96 (m, 2H), 3.93-3.87 (m, 0.7H), 2.96-2.83 (m, 2H), 2.04-1.62 (m, 4H), 1.11-1.05 (m, 3H).

Compound II-42-B

6-Chloro-5-(4-(6-(2-chloro-3,4-difluorophenyl)-5-(ethoxycarbonyl)-2-(thiazol-2-yl)-3,6-dihydropyrimidin-4-yl)piperidin-1-yl)picolinic Acid (a Single Stereoisomer)

By utilizing the analogous procedure of Method D, the title compound was synthesized from compound XI-42-3B as yellow solids.

$^1$H NMR (400 MHz, DMSO-$d_6$) δ 8.02-8.00 (m, 1.7H), 7.96-7.93 (m, 1.3H), 7.64-7.61 (m, 1H), 7.51-7.45 (m, 1H), 7.25-7.21 (m, 1H), 6.06 (s, 0.3H), 5.95 (s, 0.7H), 4.02-3.96 (m, 2.2H), 3.84-3.78 (m, 0.8H), 3.61-3.53 (m, 2H), 2.84-2.76 (m, 2H), 2.23-1.82 (m, 3.3H), 1.69-1.66 (m, 0.7H), 1.11-1.05 (m, 3H).

Compound II-43-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)nicotinic Acid (a Single Stereoisomer)

By utilizing the analogous procedure of Method C, the title compound was synthesized from compound XI-43-1 as yellow solids.

LC-MS (ESI): $R_T$=3.394 min, mass calcd. for $C_{27}H_{24}ClF_2N_5O_4S$, 587.1, m/z found 587.9 [M+H]$^+$. $^1$H NMR (400 MHz, DMSO-$d_6$) δ 9.60 (br s, 0.7H), 9.19 (br s, 0.3H), 8.65 (s, 1H), 8.00-7.90 (m, 3H), 7.54-7.44 (m, 1H), 7.27-7.15 (m, 1H), 6.90-6.88 (m, 1H), 6.04 (s, 0.3H), 5.94 (s, 0.7H), 4.72-4.53 (m, 2H), 4.24-4.14 (m, 0.2H), 4.05-3.92 (m, 2.8H), 3.03-2.89 (m, 2H), 2.01-1.62 (m, 4H), 1.13-1.02 (m, 3H).

Compound II-44-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)-4-(trifluoromethyl)nicotinic Acid (a Single Stereoisomer)

By utilizing the analogous procedure of Method D, the title compound was synthesized from compounds FA12 and BB49 as yellow solids.

LC-MS (ESI): $R_T$=3.719 min, mass calcd. for $C_{28}H_{23}ClF_5N_5O_4S$, 655.1, m/z found 656.1 [M+H]$^+$. $^1$H NMR (400 MHz, DMSO-$d_6$) δ 9.24 (br s, 1H), 8.70 (s, 0.4H), 8.69 (s, 0.6H), 7.98-7.90 (m, 2H), 7.50-7.42 (m, 1H), 7.24-7.12 (m, 2H) 6.04 (s, 0.3H), 5.95 (s, 0.7H), 4.77-4.58 (m, 2H), 4.27-4.18 (m, 0.3H), 4.03-3.95 (m, 2.7H), 3.07-2.98 (m, 2H), 2.16-1.82 (m, 3H), 1.76-1.64 (m, 1H), 1.11-1.04 (m, 3H).

Compound II-45-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)-5-fluoronicotinic Acid (a Single Stereoisomer)

By utilizing the analogous procedure of Method D, the title compound was synthesized from compound XI-45-B as yellow solids.

LC-MS (ESI): $R_T$=3.468 min, mass calcd. for $C_{27}H_{23}ClF_3N_5O_4S$, 605.1, m/z found 606.1 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 230 nm; $R_T$=5.833 min). $^1$H NMR (400 MHz, DMSO-$d_6$) δ 9.17 (s, 1H), 8.52 (s, 1H), 7.99-7.91 (m, 2H), 7.78 (dd, J=14.4, 1.6 Hz, 1H), 7.50-7.43 (m, 1H), 7.24-7.17 (m, 1H), 6.04 (s, 0.3H), 5.95 (s, 0.7H), 4.55-4.39 (m, 2H), 4.21-4.16 (m, 0.3H), 4.03-3.90 (m, 2.7H), 3.10-3.01 (m, 2H), 2.18-1.75 (m, 3.5H), 1.67-1.64 (m, 0.5H), 1.11-1.05 (m, 3H).

Compound II-46-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)-4-methylpyridazine-3-carboxylic Acid (a Single Stereoisomer)

By utilizing the analogous procedure of Method C, the title compound was synthesized from compound XI-46-S as yellow solids.

LC-MS (ESI): $R_T$=3.397 min, mass calcd. for $C_{27}H_{25}ClF_2N_6O_4S$, 602.1, m/z found 603.2 [M+H]$^+$. $^1$H NMR (400 MHz, CD$_3$OD) δ 7.88 (d, J=2.8 Hz, 1H), 7.72 (d, J=2.8 Hz, 1H), 7.31 (s, 1H), 7.27-7.21 (m, 2H), 6.12 (br s, 1H), 4.72-4.64 (m, 2H), 4.41-4.31 (m, 0.3H), 4.18-4.13 (m, 0.7H), 4.07 (q, J=7.2 Hz, 2H), 3.22-3.13 (m, 2H), 2.58 (s, 3H), 2.18-1.79 (m, 4H), 1.15 (t, J=7.2 Hz, 3H).

Compound II-47-B 6-(4-(6-(2-chloro-3,4-difluorophenyl)-5-(ethoxycarbonyl)-2-(thiazol-2-yl)-3,6-dihydropyrimidin-4-yl)piperidin-1-yl)-3-methoxypyrazine-2-carboxylic Acid (a Single Stereoisomer)

By utilizing the analogous procedure of Method C, the title compound was synthesized from compound XI-47-3 as yellow solids.

LC-MS (ESI): $R_T$=3.677 min, mass calcd. for $C_{27}H_{25}ClF_2N_6O_5S$, 618.1, m/z found 619.0 [M+H]$^+$. $^1$H NMR (400 MHz, DMSO-$d_6$) δ 9.62 (s, 0.7H), 9.10 (s, 0.3H), 8.05-7.92 (m, 3H), 7.51-7.44 (m, 1H), 7.25-7.18 (m, 1H), 6.04 (s, 0.3H), 5.95 (s, 0.7H), 4.41-4.24 (m, 2H), 4.14-3.95 (m, 2.4H), 3.87-3.81 (m, 3.6H), 2.91-2.76 (m, 2H), 2.08-1.63 (m, 4H), 1.11-1.05 (m, 3H).

Compound II-48-B 6-(4-(6-(2-chloro-3,4-difluorophenyl)-5-(ethoxycarbonyl)-2-(thiazol-2-yl)-3,6-dihydropyrimidin-4-yl)piperidin-1-yl)-3-methylpyrazine-2-carboxylic Acid (a Single Stereoisomer)

By utilizing the analogous procedure of Method C, the title compound was synthesized from compound XI-48-B as yellow solids.

LC-MS (ESI): $R_T$=3.071 min, mass calcd. for $C_{27}H_{25}ClF_2N_6O_4S$, 602.1, m/z found 603.2 [M+H]$^+$. $^1$H NMR (400 MHz, DMSO-d$_6$) δ 9.61 (s, 0.7H), 9.18 (s, 0.3H), 8.39 (s, 0.3H), 8.37 (s, 0.7H), 7.99-7.91 (m, 2H), 7.51-7.44 (m, 1H), 7.24-7.17 (m, 1H), 6.04 (s, 0.3H), 5.95 (s, 0.7H), 4.60-4.45 (m, 2H), 4.20-4.14 (m, 0.3H), 4.03-3.96 (m, 2H), 3.92-3.86 (m, 0.7H), 2.93-2.84 (m, 2H), 2.48 (s, 3H), 2.09-1.63 (m, 4H), 1.11-1.05 (m, 3H).

Compound II-49-B 5-(4-(6-(2-Chloro-3,4-difluorophenyl)-5-(ethoxycarbonyl)-2-(thiazol-2-yl)-3,6-dihydropyrimidin-4-yl)piperidin-1-yl)-3-methylpyrazine-2-carboxylic Acid (a Single Stereoisomer)

By utilizing the analogous procedure of Method C, the title compound was synthesized from compound XI-49-B as yellow solids.

LC-MS (ESI): $R_T$=4.115 min, mass calcd. for $C_{27}H_{25}ClF_2N_6O_4S$, 602.1, m/z found 602.9 [M+H]$^+$. $^1$H NMR (400 MHz, CD$_3$OD) δ 7.94 (br s, 1H), 7.77 (d, J=3.2 Hz, 1H), 7.61 (d, J=3.2 Hz, 1H), 7.12-7.11 (m, 2H), 6.03-5.95 (m, 1H), 4.70-4.50 (m, 2H), 4.29-4.18 (m, 0.4H), 4.00-3.93 (m, 2.6H), 3.02-2.95 (m, 2H), 2.63 (s, 3H), 2.00-1.75 (m, 3.4H), 1.70-1.64 (m, 0.6H), 1.04 (t, J=7.2 Hz, 3H).

Compound II-50-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)oxazole-5-carboxylic Acid (a Single Stereoisomer)

By utilizing the analogous procedure of Method C, the title compound was synthesized as yellow solids. LC-MS (ESI): $R_T$=3.054 min, mass calcd. for $C_{25}H_{22}ClF_2N_5O_5S$, 577.1, m/z found 577.9 [M+H]$^+$. $^1$H NMR (400 MHz, DMSO-d$_6$) δ 9.62 (br s, 0.7H), 9.27 (s, 0.3H), 8.00-7.91 (m, 2H), 7.58-7.54 (m, 1H), 7.50-7.43 (m, 1H), 7.25-7.18 (m, 1H), 6.04 (s, 0.3H), 5.95 (s, 0.7H), 4.22-4.12 (m, 2.3H), 4.02-3.95 (m, 2H), 3.89-3.83 (m, 0.7H), 3.16-3.06 (m, 2H), 2.22-1.64 (m, 4H), 1.11-1.04 (m, 3H).

Compound II-51-B 5-(4-(6-(2-Chloro-3,4-difluorophenyl)-5-(ethoxycarbonyl)-2-(thiazol-2-yl)-3,6-dihydropyrimidin-4-yl)piperidin-1-yl)pyrazine-2-carboxylic Acid (a Single Stereoisomer)

By utilizing the analogous procedure of Method E, the title compound was synthesized from compound BB22 and FA12.

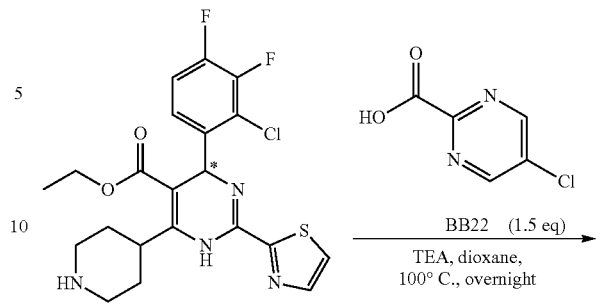

FA12

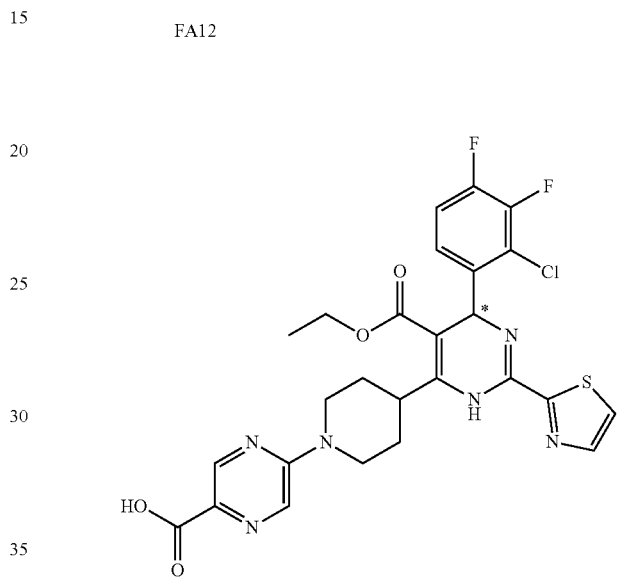

II-51-B

LC-MS (ESI): $R_T$=3.325 min, mass calcd. for $C_{26}H_{23}ClF_2N_6O_4S$, 588.1, m/z found 588.9 [M+H]$^+$ 0.1H NMR (400 MHz, DMSO-d$_6$) δ 9.61 (d, J=3.6 Hz, 0.7H), 9.25 (s, 0.3H), 8.67 (s, 1H), 8.43 (s, 0.4H), 8.41 (s, 0.6H), 7.98-7.90 (m, 2H), 7.50-7.42 (m, 1H), 7.24-7.16 (m, 1H), 6.04 (s, 0.4H), 5.95 (s, 0.6H), 4.76-4.60 (m, 2H), 4.27-4.20 (m, 0.3H), 4.03-3.93 (m, 2.7H), 3.11-3.00 (m, 2H), 2.07-1.68 (m, 4H), 1.11-1.04 (m, 3H).

Compound II-52-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)-2-methoxypyrimidine-4-carboxylic Acid (a Single Stereoisomer)

By utilizing the analogous procedure of Method C, the title compound was synthesized as yellow solids. LC-MS (ESI): $R_T$=3.417 min, mass calcd. for $C_{27}H_{25}ClF_2N_6O_5S$, 618.1, m/z found 618.9 [M+H]$^+$. $^1$H NMR (400 MHz, DMSO-d$_6$) δ 9.26 (br s, 1H), 7.98-7.91 (m, 2H), 7.50-7.43 (m, 1H), 7.19-7.16 (m, 1H), 6.96-6.94 (m, 1H), 6.04 (s, 0.3H), 5.95 (s, 0.7H), 4.70-4.43 (m, 2H), 4.25-4.17 (m, 0.5H), 4.03-3.91 (m, 2.5H), 3.84 (s, 3H), 3.03-2.94 (m, 2H), 2.13-1.73 (m, 3H), 1.64-1.60 (m, 1H), 1.11-1.04 (m, 3H).

Compound II-53-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)-2-methylpyrimidine-4-carboxylic Acid (a Single Stereoisomer)

By utilizing the analogous procedure of Method C, the title compound was synthesized as yellow solids. LC-MS (ESI): $R_T$=3.647 min, mass calcd. for $C_{27}H_{25}ClF_2N_6O_4S$, 602.1, m/z found 603.1 [M+H]$^+$. $^1$H NMR (400 MHz, CD$_3$OD) δ 7.91 (d, J=3.2 Hz, 1H), 7.75 (d, J=3.6 Hz, 1H), 7.37 (s, 1H), 7.32-7.24 (m, 2H), 6.19 (s, 0.3H), 6.13 (s, 0.7H), 4.88-4.84 (m, 2H), 4.50-4.45 (m, 0.3H), 4.24-4.16 (m, 0.7H), 4.13-4.06 (m, 2H), 3.31-3.27 (m, 2H), 2.64 (s, 3H), 2.18-1.97 (m, 3.3H), 1.90-1.87 (m, 0.7H), 1.20-1.15 (m, 3H).

Compound II-54-B 6-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidine-4-carboxylic Acid (a Single Stereoisomer)

By utilizing the analogous procedure of Method C, the title compound was synthesized as yellow solids. LC-MS (ESI): $R_T$=3.373 min, mass calcd. for $C_{26}H_{23}ClF_2N_6O_4S$, 588.1, m/z found 588.9 [M+H]$^+$. $^1$H NMR (400 MHz, DMSO-d$_6$) δ 9.27 (s, 1H), 8.57 (d, J=3.2 Hz, 1H), 7.98-7.90 (m, 2H), 7.50-7.43 (m, 1H), 7.31-7.29 (m, 1H), 7.24-7.16 (m, 1H), 6.04 (s, 0.3H), 5.95 (s, 0.7H), 4.61 (br s, 1.6H), 4.27-4.20 (m, 0.4H), 4.03-3.93 (m, 3H), 3.08-3.00 (m, 2H), 2.12-1.67 (m, 4H), 1.11-1.04 (m, 3H).

Compound II-55-B (trans)-3-(2-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidin-5-yl)-3-hydroxycyclobutanecarboxylic Acid (a Single Stereoisomer)

By utilizing the analogous procedure of Method E, the title compound was synthesized from compound BB55 and FA12.

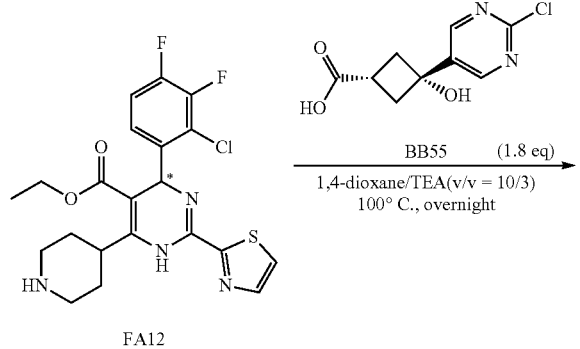

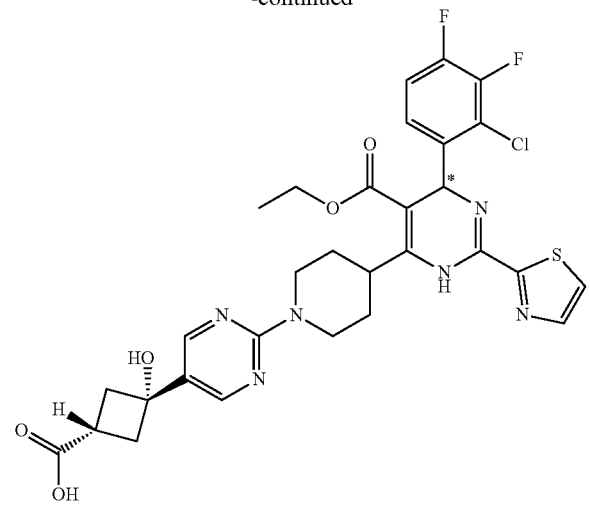

II-55-B

LC-MS (ESI): $R_T$=3.604 min, mass calcd. for $C_{30}H_{29}ClF_2N_6O_5S$, 658.2, m/z found 659.0 [M+H]$^+$. $^1$H NMR (400 MHz, DMSO-d$_6$) δ 8.50 (s, 0.6H), 8.49 (s, 1.4H), 7.99-7.95 (m, 1.7H), 7.91 (s, 0.3H), 7.50-7.43 (m, 1H), 7.24-7.17 (m, 1H), 6.04 (s, 0.3H), 5.94 (s, 0.7H), 4.94-4.80 (m, 2H), 4.22-4.14 (m, 0.3H), 3.98 (q, J=7.2 Hz, 2H), 3.95-3.89 (m, 0.7H), 2.95-2.86 (m, 2H), 2.68-2.62 (m, 4H), 2.45-2.43 (m, 1H), 1.93-1.61 (m, 4H), 1.11-1.04 (m, 3H).

Compound II-56-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5,6-dimethylpyrimidine-4-carboxylic Acid (a Single Stereoisomer)

By utilizing the analogous procedure of Method C, the title compound was synthesized from compound XI-56-B.

LC-MS (ESI): $R_T$=3.331 min, mass calcd. for $C_{28}H_{27}ClF_2N_6O_4S$, 616.2, m/z found 617.1 [M+H]$^+$. $^1$H NMR (400 MHz, CD$_3$OD) δ 7.90 (d, J=3.2 Hz, 1H), 7.74 (d, J=3.2 Hz, 1H), 7.31-7.23 (m, 2H), 6.15 (s, 1H), 5.05-4.95 (m, 2H), 4.24-4.13 (m, 1H), 4.09 (q, J=7.2 Hz, 2H), 3.04-2.92 (m, 2H), 2.44 (s, 3H), 2.26 (s, 3H), 2.05-1.75 (m, 4H), 1.18 (t, J=7.2 Hz, 3H).

Compound II-57-B 2-(4-(6-(2-chloro-3,4-difluorophenyl)-5-(ethoxycarbonyl)-2-(thiazol-2-yl)-3,6-dihydropyrimidin-4-yl)piperidin-1-yl)-6-methoxypyrimidine-4-carboxylic Acid (a Single Stereoisomer)

By utilizing the analogous procedure of Method C, the title compound was synthesized from compound XI-57-S as yellow solids.

LC-MS (ESI): $R_T$=3.541 min, mass calcd. for $C_{27}H_{25}ClF_2N_6O_5S$, 618.1, m/z found 619.0 [M+H]$^+$. $^1$H NMR (400 MHz, DMSO-d$_6$) δ 9.21 (br s, 1H), 7.99-7.90 (m, 2H), 7.50-7.43 (m, 1H), 7.24-7.17 (m, 1H), 6.41 (s, 0.4H), 6.40 (s, 0.6H), 6.04 (s, 0.4H), 5.95 (s, 0.6H), 4.98-4.86 (m, 2H), 4.23-4.16 (m, 0.4H), 4.03-3.91 (m, 2.6H), 3.88 (s, 3H), 2.96-2.86 (m, 2H), 2.07-1.63 (m, 4H), 1.12-1.05 (m, 3H).

Compound II-58-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-6-methylpyrimidine-4-carboxylic Acid (a Single Stereoisomer)

By utilizing the analogous procedure of Method C, the title compound was synthesized from compound XI-58-S as yellow solids.

LC-MS (ESI): $R_T$=3.508 min, mass calcd. for $C_{27}H_{25}ClF_2N_6O_4S$, 602.1, m/z found 603.1 $[M+H]^+$. $^1H$ NMR (400 MHz, $CD_3OD$) δ 7.89-7.87 (m, 1H), 7.72-7.71 (m, 1H), 7.26-7.24 (m, 2H), 7.04 (s, 1H), 6.14 (s, 1H), 5.14-5.07 (m, 2H), 4.32-4.21 (m, 1H), 4.14-4.06 (m, 2H), 3.05-2.94 (m, 2H), 2.43 (s, 3H), 2.07-1.71 (m, 4H), 1.18-1.15 (m, 3H).

Compound II-59-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5-isopropylpyrimidine-4-carboxylic Acid (a Single Stereoisomer)

By utilizing the analogous procedure of Method C, the title compound was synthesized from compound XI-59-B as yellow solids.

LC-MS (ESI): $R_T$=3.327 min, mass calcd. for $C_{29}H_{29}ClF_2N_6O_4S$, 630.2, m/z found 631.1 $[M+H]^+$. $^1H$ NMR (400 MHz, $CD_3OD$) δ 8.44 (s, 1H), 7.87 (d, J=3.6 Hz, 1H), 7.71 (d, J=2.8 Hz, 1H), 7.27-7.22 (m, 2H), 6.12 (s, 1H), 4.99-4.93 (m, 2H), 4.21-4.13 (m, 1H), 4.07 (q, J=7.2 Hz, 2H), 3.26-3.19 (m, 1H), 3.04-2.94 (m, 2H), 2.00-1.76 (m, 4H), 1.27 (d, J=7.2 Hz, 6H), 1.15 (t, J=7.2 Hz, 3H).

Compound II-60-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5-ethylpyrimidine-4-carboxylic Acid (a Single Stereoisomer)

By utilizing the analogous procedure of Method C, the title compound was synthesized from compound XI-60-B as yellow solids.

LC-MS (ESI): $R_T$=2.832 min, mass calcd. for $C_{28}H_{27}ClF_2N_6O_4S$, 616.2, m/z found 616.9 $[M+H]^+$. $^1H$ NMR (400 MHz, $CD_3OD$) δ 8.33 (s, 1H), 7.87 (d, J=3.2 Hz, 1H), 7.71 (d, J=3.2 Hz, 1H), 7.27-7.22 (m, 2H), 6.12 (s, 1H), 4.98-4.94 (m, 2H), 4.22-4.13 (m, 1H), 4.06 (q, J=7.2 Hz, 2H), 3.04-2.95 (m, 2H), 2.70 (q, J=7.2 Hz, 2H), 2.04-1.73 (m 4H), 1.20 (d, J=7.6 Hz, 3H), 1.15 (t, J=7.2 Hz, 3H).

Compound II-61-B

5-Chloro-2-(4-(6-(2-chloro-3,4-difluorophenyl)-5-(ethoxycarbonyl)-2-(thiazol-2-yl)-3,6-dihydropyrimidin-4-yl)piperidin-1-yl)pyrimidine-4-carboxylic Acid (a Single Stereoisomer)

By utilizing the analogous procedure of Method C, the title compound was synthesized from compound XI-61-B as yellow solids.

LC-MS (ESI): $R_T$=3.564 min, mass calcd. for $C_{26}H_{22}Cl_2F_2N_6O_4S$, 622.1, m/z found 623.1 $[M+H]^+$. $^1H$ NMR (400 MHz, DMSO-$d_6$+one drop of $D_2O$) δ 8.44 (s, 1H), 7.95-7.87 (m, 2H), 7.47-7.40 (m, 1H), 7.22-7.14 (m, 1H), 6.01 (s, 0.4H), 5.93 (s, 0.6H), 4.82-4.66 (m, 2H), 4.21-4.10 (m, 0.4H), 4.00-3.88 (m, 2.6H), 2.98-2.88 (m, 2H), 2.05-1.59 (m, 4H), 1.08-1.05 (m, 3H).

Compound II-62-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5-fluoropyrimidine-4-carboxylic Acid (a Single Stereoisomer)

By utilizing the analogous procedure of Method C, the title compound was synthesized from compound XI-62-B as yellow solids.

LC-MS (ESI): $R_T$=3.973 min, mass calcd. for $C_{26}H_{22}ClF_3N_6O_4S$, 606.1, m/z found 606.9 $[M+H]^+$. $^1H$ NMR (400 MHz, DMSO-$d_6$) δ 9.60 (s, 0.7H), 9.16 (s, 0.3H), 8.40 (s, 1H), 8.02-7.93 (m, 1.7H), 7.91 (d, J=3.6 Hz, 0.3H), 7.52-7.42 (m, 1H), 7.25-7.20 (m, 1H), 6.04 (s, 0.3H), 5.94 (s, 0.7H), 4.84-4.66 (m, 2H), 4.21-4.11 (m, 0.3H), 4.04-3.95 (m, 2H), 3.94-3.85 (m, 0.7H), 2.97-2.82 (m, 2H), 2.06-1.68 (m, 3.3H), 1.65-1.57 (m, 0.7H), 1.13-1.03 (m, 3H).

Compound II-63-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method E, the title compound was synthesized from compound BB2-1 and FA12.

LC-MS (ESI): $R_T$=2.909 min, mass calcd. for $C_{27}H_{25}ClF_2N_6O_4S$, 602.1, m/z found 603.2 $[M+H]^+$. $^1H$ NMR (400 MHz, DMSO-$d_6$) δ 9.59 (s, 0.6H), 9.15 (s, 0.4H), 8.35 (d, J=4.0 Hz, 1H), 7.98-7.90 (m, 2H), 7.50-7.43 (m, 1H), 7.24-7.16 (m, 1H), 6.04 (s, 0.3H), 5.95 (s, 0.7H), 4.88-4.76 (m, 2H), 4.21-4.15 (m, 0.2H), 4.02-3.88 (m, 2.8H), 2.95-2.84 (m, 2H), 2.16 (s, 3H), 2.02-1.61 (m, 4H), 1.11-1.04 (m, 3H).

Compound II-64-B

Lithium 2-(4-(6-(2-chloro-3,4-difluorophenyl)-5-(ethoxycarbonyl)-2-(thiazol-2-yl)-3,6-dihydropyrimidin-4-yl)piperidin-1-yl)-4-methyloxazole-5-carboxylate (a Single Stereoisomer)

By utilizing the analogous procedure of Method C, the title compound was synthesized from compound XI-64-B as a lithium salt form of yellow solids.

LC-MS (ESI): $R_T$=3.019 min, mass calcd. for $C_{26}H_{23}ClF_2N_5O_5SLi$ 597.1, m/z found 592.0 $[(M-Li^+)+2H]^+$. $^1H$ NMR (400 MHz, DMSO-$d_6$) δ 9.61 (s, 0.7H), 9.20 (s, 0.3H), 7.99-7.91 (m, 2H), 7.50-7.44 (m, 1H), 7.24-7.17 (m, 1H), 6.03 (s, 0.3H), 5.94 (s, 0.7H), 4.14-3.95 (m, 4.3H), 3.85-3.77 (m, 0.7H), 3.00-2.87 (m, 2H), 2.19 (s, 3H), 2.12-1.58 (m, 4H), 1.11-1.04 (m, 3H).

Compound II-65-B 2-(4-(6-(2-chloro-3,4-difluorophenyl)-5-(ethoxycarbonyl)-2-(thiazol-2-yl)-3,6-dihydropyrimidin-4-yl)piperidin-1-yl)pyrimidine-4-carboxylic Acid (a Single Stereoisomer)

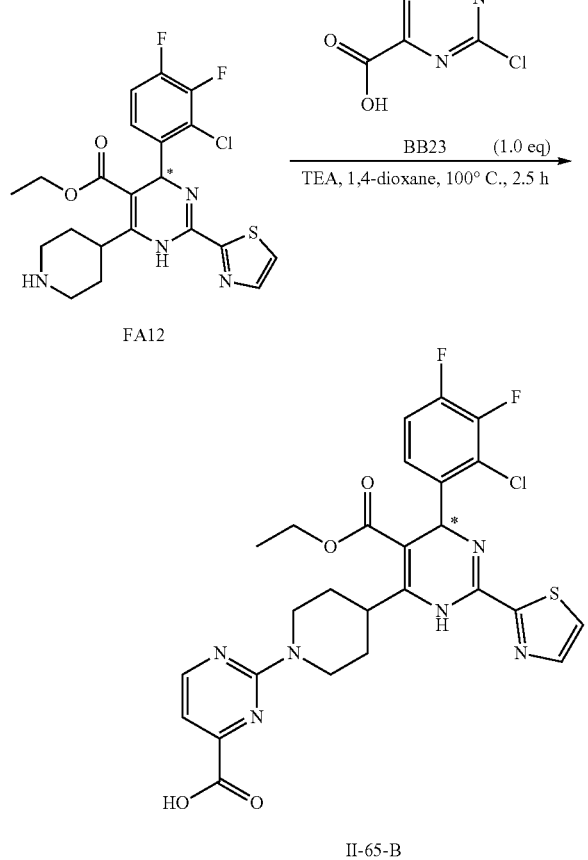

By utilizing the analogous procedure of Method E, the title compound was synthesized from compound BB23 and FA12.

LC-MS (ESI): $R_T$=3.255 min, mass calcd. for $C_{26}H_{23}ClF_2N_6O_4S$, 588.1, m/z found 588.9 [M+H]$^+$. $^1$H NMR (400 MHz, CD$_3$OD) δ 8.54-8.48 (m, 1H), 7.87 (s, 1H), 7.70 (s, 1H), 7.28-7.19 (m, 2H), 7.14-7.07 (m, 1H), 6.13 (s, 1H), 5.14-4.98 (m, 2.7H), 4.12-4.03 (m, 2.3H), 3.09-2.95 (m, 2H), 2.09-1.70 (m, 4H), 1.16 (t, J=2.8 Hz, 3H).

Compound II-66-B 3-(2-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidin-5-yl)propanoic Acid (a Single Stereoisomer)

By utilizing the analogous procedure of Method C, the title compound was synthesized from compound XI-66-N as yellow solids.

LC-MS (ESI): $R_T$=3.832 min, mass calcd. for $C_{28}H_{27}ClF_2N_6O_4S$, 616.2, m/z found 617.1 [M+H]$^+$. $^1$H NMR (400 MHz, CD$_3$OD) δ 8.26 (s, 2H), 7.87 (d, J=3.2 Hz, 1H), 7.71 (d, J=3.2 Hz, 1H), 7.25-7.22 (m, 2H), 6.15-6.10 (m, 1H), 4.97-4.90 (m, 1H), 4.83-4.76 (m, 1H), 4.29 (s, 0.5H), 4.09-4.04 (m, 2.5H), 3.03-2.93 (m, 2H), 2.76 (t, J=7.6 Hz, 2H), 2.58-2.53 (m, 2H), 2.11-1.68 (m, 4H), 1.15 (t, J=7.2 Hz, 3H).

Compound II-67-B 2-(2-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidin-5-yl)-2-methylpropanoic Acid (a Single Stereoisomer)

By utilizing the analogous procedure of Method C, the title compound was synthesized from compound XI-67-B as yellow solids.

LC-MS (ESI): $R_T$=2.854 min, mass calcd. for $C_{29}H_{29}ClF_2N_6O_4S$, 630.2, m/z found 631.1 [M+H]$^+$. $^1$H NMR (400 MHz, DMSO-d$_6$) δ 9.61 (br s, 0.7H), 9.23 (s, 0.3H), 8.38 (s, 0.6H), 8.37 (s, 1.4H), 7.99-7.90 (m, 2H), 7.50-7.43 (m, 1H), 7.24-7.16 (m, 1H), 6.03 (s, 0.3H), 5.94 (s, 0.7H), 4.92-4.77 (m, 2H), 4.22-4.14 (m, 0.3H), 4.02-3.87 (m, 2.7H), 2.96-2.84 (m, 2H), 2.09-1.61 (m, 4H), 1.47 (s, 6H), 1.11-1.04 (m, 3H).

Compound II-68-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)5-methyloxazole-4-carboxylic Acid (a Single Stereoisomer)

By utilizing the analogous procedure of Method C, the title compound was synthesized from compound XI-68-B as yellow solids.

LC-MS (ESI): $R_T$=3.571 min, mass calcd. for $C_{26}H_{24}ClF_2N_5O_5S$, 591.1, m/z found 592.0 [M+H]$^+$. $^1$H NMR (400 MHz, DMSO-d$_6$) δ 8.00-7.92 (m, 2H), 7.50-7.43 (m, 1H), 7.24-7.19 (m, 1H), 6.04 (s, 0.3H), 5.94 (s, 0.7H), 4.07-3.96 (m, 4.2H), 3.84-3.78 (m, 0.8H), 3.01-2.93 (m, 2H), 2.46 (s, 3H), 2.06-1.60 (m, 4H), 1.10-1.04 (m, 3H).

Compound II-69-B 2-(2-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidin-5-yl)acetic Acid (a Single Stereoisomer)

By utilizing the analogous procedure of Method C, the title compound was synthesized from compound XI-69-B as yellow solids.

LC-MS (ESI): $R_T$=3.467 min, mass calcd. for $C_{27}H_{25}ClF_2N_6O_4S$, 602.1, m/z found 603.2 [M+H]$^+$. $^1$H NMR (400 MHz, CD$_3$OD) δ 8.28 (s, 2H), 7.87 (d, J=3.2 Hz, 1H), 7.71 (d, J=3.2 Hz, 1H), 7.25-7.23 (m, 2H), 6.12 (s, 1H), 5.06-4.89 (m, 2H), 4.34-4.23 (m, 0.5H), 4.10-3.99 (m, 2.5H), 3.47 (s, 2H), 3.05-2.95 (m, 2H), 2.12-1.38 (m, 4H), 1.15 (t, J=6.8 Hz, 3H).

Compound II-70-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)oxazole-4-carboxylic Acid (a Single Stereoisomer)

By utilizing the analogous procedure of Method C, the title compound was synthesized from compound XI-70-N as yellow solids.

LC-MS (ESI): R$_T$=3.374 min, mass calcd. for C$_{25}$H$_{22}$ClF$_2$N$_5$O$_5$S, 577.1, m/z found 578.1 [M+H]$^+$. $^1$H NMR (400 MHz, CD$_3$OD) δ 7.88 (s, 2H), 7.73 (d, J=3.2 Hz, 1H), 7.25-7.22 (m, 2H), 6.15-6.11 (m, 1H), 4.29-4.17 (m, 2.5H), 4.05 (q, J=7.2 Hz, 2H), 3.93 (br s, 0.5H), 3.16-3.06 (m, 2H), 2.19-1.68 (m, 4H), 1.14 (t, J=7.2 Hz, 3H).

Compound II-71-B 2-(4-(6-(2-chloro-3,4-difluorophenyl)-5-(ethoxycarbonyl)-2-(thiazol-2-yl)-3,6-dihydropyrimidin-4-yl)piperidin-1-yl)-4,6-dimethylpyrimidine-5-carboxylic Acid (a Single Stereoisomer)

By utilizing the analogous procedure of Method E, the title compound was synthesized from compound BB36 and FA12.

LC-MS (ESI): R$_T$=3.317 min, mass calcd. for C$_{28}$H$_{27}$ClF$_2$N$_6$O$_4$S, 616.2, m/z found 617.0 [M+H]$^+$. $^1$H NMR (400 MHz, DMSO-d$_6$) δ 9.61 (d, J=2.0 Hz, 0.7H), 9.28 (s, 0.3H), 7.99-7.90 (m, 2H), 7.51-7.42 (m, 1H), 7.25-7.15 (m, 1H), 6.03 (s, 0.3H), 5.94 (d, J=2.0 Hz, 0.7H), 5.03-4.86 (m, 2H), 4.27-4.16 (m, 0.3H), 4.04-3.89 (m, 2.7H), 2.98-2.85 (m, 2H), 2.40 (d, J=3.2 Hz, 6H), 2.10-1.60 (m, 4H), 1.11-1.04 (m, 3H).

Compound II-72-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-4-methoxypyrimidine-5-carboxylic Acid (a Single Stereoisomer)

By utilizing the analogous procedure of Method C, the title compound was synthesized from compound XI-72-S as yellow solids.

LC-MS (ESI): R$_T$=3.583 min, mass calcd. for C$_{27}$H$_{25}$ClF$_2$N$_6$O$_5$S, 618.1, m/z found 619.0 [M+H]$^+$. $^1$H NMR (400 MHz, DMSO-d$_6$) δ 9.31 (br s, 1H), 8.64-8.63 (m, 1H), 7.99-7.95 (m, 1.7H), 7.92-7.91 (m, 0.3H), 7.50-7.44 (m, 1H), 7.24-7.16 (m, 1H), 6.04 (s, 0.3H), 5.95 (s, 0.7H), 4.98-4.88 (m, 2H), 4.26-4.20 (m, 0.4H), 4.03-3.94 (m, 2.6H), 3.92 (s, 3H), 3.04-2.96 (m, 2H), 2.14-1.65 (m, 4H), 1.11-1.04 (m, 3H).

Compound II-73-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-4-methylpyrimidine-5-carboxylic Acid (a Single Stereoisomer)

By utilizing the analogous procedure of Method C, the title compound was synthesized from compound XI-73-S as yellow solids.

LC-MS (ESI): R$_T$=3.539 min, mass calcd. for C$_{27}$H$_{25}$ClF$_2$N$_6$O$_4$S, 602.1, m/z found 602.9 [M+H]$^+$. $^1$H NMR (400 MHz, CD$_3$OD) δ 8.81 (s, 1H), 7.87 (d, J=3.2 Hz, 1H), 7.71 (d, J=2.8 Hz, 1H), 7.24 (d, J=6.4 Hz, 2H), 6.16 (s, 0.4H), 6.11 (s, 0.6H), 5.16-5.02 (m, 2H), 4.40-4.30 (m, 0.4H), 4.10-4.05 (m, 2.6H), 3.09-3.00 (m, 2H), 2.65 (s, 3H), 2.10-1.70 (m, 4H), 1.16 (t, J=7.2 Hz, 3H).

Compound II-74-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)pyrimidine-5-carboxylic Acid (a Single Stereoisomer)

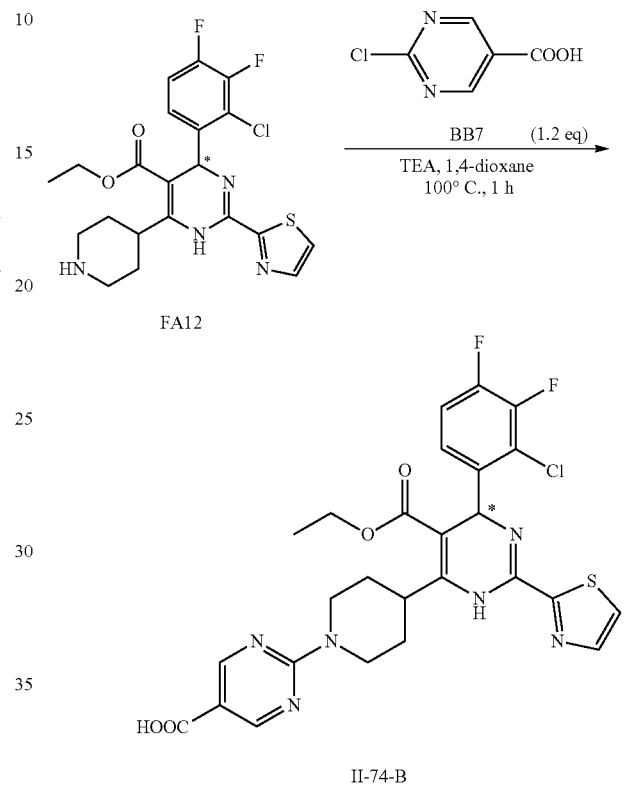

By utilizing the analogous procedure of Method E, the title compound was synthesized from compound BB7 and FA12.

LC-MS (ESI): R$_T$=3.448 min, mass calcd. for C$_{26}$H$_{23}$ClF$_2$N$_6$O$_4$S, 588.1, m/z found 589.1 [M+H]$^+$. Chiral HPLC (Column: Chiralpak IF 5 μm 4.6*250 mm; Mobile Phase: Hex:EtOH:TFA=50:50:0.2 at 1.0 mL/min Temp: 30° C.; Wavelength: 230 nm, R$_T$=12.275 min). $^1$H NMR (400 MHz, DMSO-d$_6$) δ 12.68 (br s, 1H), 9.61 (s, 0.7H), 9.26 (s, 0.3H), 8.80 (s, 0.6H), 8.79 (s, 1.4H), 7.98-7.90 (m, 2H), 7.50-7.43 (m, 1H), 7.24-7.16 (m, 1H), 6.04 (s, 0.3H), 5.95 (s, 0.7H), 5.02-4.89 (m, 2H), 4.27-4.20 (m, 0.3H), 4.03-4.00 (m, 2.7H), 3.09-2.99 (m, 2H), 2.13-1.66 (m, 4H), 1.11-1.04 (m, 3H).

Compound II-75-X

Ethyl 6-(1-(1,3,4-thiadiazol-2-yl)piperidin-4-yl)-4-(2-chloro-3,4-difluorophenyl)-2-(thiazol-2-yl)-1,4-dihydropyrimidine-5-carboxylate (a Single Stereoisomer)

By utilizing the analogous procedure of Method C, the title compound was synthesized from compound XI-75-S as yellow solids.

LC-MS (ESI): R$_T$=3.387 min, mass calcd. for C$_{23}$H$_{21}$ClF$_2$N$_6$O$_2$S$_2$ 550.1, m/z found 550.8 [M+H]$^+$. $^1$H NMR (400 MHz, DMSO-d$_6$) δ 9.66 (d, J=3.6 Hz, 0.7H), 9.26 (s, 0.3H), 8.82 (s, 1H), 8.01-7.92 (m, 2H), 7.51-7.44 (m, 1H), 7.25-7.17 (m, 1H), 6.04 (s, 0.3H), 5.95 (d, J=3.6 Hz, 0.7H), 4.16-3.91 (m, 4.3H), 3.88-3.84 (m, 0.7H), 3.30-3.17 (m, 2H), 2.28-1.65 (m, 4H), 1.11-1.04 (m, 3H).

Compound II-76-B 5-(4-(6-(2-Chloro-3,4-difluorophenyl)-5-(ethoxycarbonyl)-2-(thiazol-2-yl)-3,6-dihydropyrimidin-4-yl)piperidin-1-yl)thiazole-2-carboxylate lithium salt (a Single Stereoisomer)

By utilizing the analogous procedure of Method C, the title compound was synthesized from compound XI-76-B as lithium salt form of yellow solids.

LC-MS (ESI): R$_T$=3.003 min, mass calcd. for C$_{25}$H$_{21}$ClF$_2$N$_5$O$_4$S$_2$Li 599.1, m/z found 591.9 [M-Li]$^-$. $^1$H NMR (400 MHz, DMSO-d$_6$) δ 9.61 (d, J=3.2 Hz, 0.7H), 9.04 (s, 0.3H), 8.00-7.99 (m, 1.7H), 7.94-7.93 (m, 0.3H), 7.50-7.43 (m, 1H), 7.25-7.18 (m, 1H), 6.89 (s, 1H), 6.04 (s, 0.3H), 5.94 (d, J=3.2 Hz, 0.7H), 4.02-3.95 (m, 2.3H), 3.80-3.72 (m, 0.7H), 3.63-3.54 (m, 2H), 2.93-2.79 (m, 2H), 2.20-1.97 (m, 2H), 1.90-1.86 (m, 0.3H), 1.80-1.77 (m, 1H), 1.64-1.61 (m, 0.7H), 1.10-1.04 (m, 3H).

Compound II-77-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-4-(methoxymethyl)thiazole-5-carboxylic Acid (a Single Stereoisomer)

By utilizing the analogous procedure of Method C, the title compound was synthesized from compound XI-77-S as yellow solids.

LC-MS (ESI): R$_T$=3.479 min, mass calcd. for C$_{27}$H$_{26}$ClF$_2$N$_5$O$_5$S$_2$ 637.1, m/z found 638.0 [M+H]$^+$. $^1$H NMR (400 MHz, DMSO-d$_6$) δ 12.7 (br s, 1H), 9.64 (d, J=2.0 Hz, 0.8H), 9.33 (s, 0.2H), 8.00-7.91 (m, 2H), 7.50-7.44 (m, 1H), 7.25-7.17 (m, 1H), 6.04 (s, 0.2H), 5.95 (d, J=2.4 Hz, 0.8H), 4.59 (s, 2H), 4.18-4.06 (m, 2H), 4.02-3.95 (m, 2H), 3.92-3.86 (m, 1H), 3.31-3.30 (m, 3H), 3.21-3.12 (m, 2H), 2.24-2.20 (m, 0.2H), 2.06-1.67 (m, 3.8H), 1.11-1.04 (m, 3H).

Compound II-78-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-78-S as yellow solids.

LC-MS (ESI): R$_T$=4.263 min, mass calcd. for C$_{25}$H$_{22}$ClF$_2$N$_5$O$_4$S$_2$ 593.1, m/z found 594.1 [M+H]$^+$. $^1$H NMR (400 MHz, DMSO-d$_6$) δ 9.30 (br s, 1H), 8.00-7.96 (m, 1.7H), 7.92 (d, J=3.2 Hz, 0.3H), 7.70 (s, 1H), 7.47 (dd, J=17.6, 9.6 Hz, 1H), 7.25-7.16 (m, 1H), 6.04 (s, 0.3H), 5.95 (s, 0.7H), 4.18-4.05 (m, 2.3H), 4.02-3.96 (m, 2H), 3.92-3.85 (m, 0.7H), 3.21-3.12 (m, 2H), 2.26-1.66 (m, 4H), 1.11-1.04 (m, 3H).

Compound II-79-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)-4-(trifluoromethyl)thiazole-5-carboxylic Acid (a Single Stereoisomer)

By utilizing the analogous procedure of Method C, the title compound was synthesized from compound XI-79-S as yellow solids.

LC-MS (ESI): R$_T$=2.845 min, mass calcd. for C$_{26}$H$_{21}$ClF$_5$N$_5$O$_4$S$_2$ 661.1, m/z found 662.0 [M+H]$^+$. $^1$H NMR (400 MHz, DMSO-d$_6$) δ 9.65 (s, 0.7H), 9.36 (s, 0.3H), 8.00-7.92 (m, 2H), 7.50-7.44 (m, 1H), 7.25-7.16 (m, 1H), 6.04 (s, 0.3H), 5.95 (s, 0.7H), 4.19-3.92 (m, 4.3H), 3.88-3.83 (m, 0.7H), 3.19-3.11 (m, 2H), 2.25-1.82 (m, 3H), 1.75-1.66 (m, 1H), 1.10-1.04 (m, 3H).

Compound II-80-B 2-(4-(6-(2-Chloro-3,4-difluorophenyl)-5-(ethoxycarbonyl)-2-(thiazol-2-yl)-3,6-dihydropyrimidin-4-yl)piperidin-1-yl)thiazole-4-carboxylic Acid (a Single Stereoisomer)

By utilizing the analogous procedure of Method C, the title compound was synthesized from compound XI-80-S as yellow solids.

LC-MS (ESI): R$_T$=3.473 min, mass calcd. for C$_{25}$H$_{22}$ClF$_2$N$_5$O$_4$S$_2$ 593.1, m/z found 594.0 [M+H]$^+$. $^1$H NMR (400 MHz, DMSO-d$_6$) δ 8.00-7.97 (m, 1.7H), 7.92 (d, J=3.2 Hz, 0.3H), 7.58-7.54 (m, 1H), 7.51-7.44 (m, 1H), 7.25-7.17 (m, 1H), 6.04 (s, 0.3H), 5.95 (s, 0.7H), 4.12-3.95 (m, 4.2H), 3.91-3.82 (m, 0.8H), 3.14-3.04 (m, 2H), 2.15-1.65 (m, 4H), 1.11-1.04 (m, 3H).

Compound II-81-B 2-(4-(6-(4-bromo-2-chlorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the title compound was synthesized from compound XI-81-B as yellow solids.

LC-MS (ESI): R$_T$=3.308 min, mass calcd. for C$_{26}$H$_{24}$BrClN$_6$O$_4$S, 630.1, m/z found 631.1 [M+H]$^+$. $^1$H NMR (400 MHz, DMSO-d$_6$) δ 9.50 (s, 0.7H), 9.06 (s, 0.3H), 8.00-7.91 (m, 3H), 7.72-7.71 (m, 1H), 7.57-7.55 (m, 1H), 7.29-7.24 (m, 1H), 6.01 (s, 0.3H), 5.92 (s, 0.7H), 4.84-4.73 (m, 2H), 4.16-4.09 (m, 0.3H), 3.89-3.83 (m, 0.7H), 3.54 (s, 3H), 2.83-2.74 (m, 2H), 1.98 (s, 3H), 1.93-1.68 (m, 3.4H), 1.57-1.55 (m, 0.6H).

Compound II-82-B 2-(4-(6-(2-Bromo-3,4-difluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-82-B as yellow solids.

LC-MS (ESI): R$_T$=3.333 min, mass calcd. for C$_{24}$H$_{20}$BrF$_2$N$_5$O$_4$S$_2$ 623.0, m/z found 623.9 [M+H]$^+$. H NMR (400 MHz, DMSO-d$_6$) δ 9.68 (s, 0.7H), 9.41 (s, 0.3H), 8.00-7.96 (m, 1.7H), 7.92 (d, J=3.2 Hz, 0.3H), 7.77 (s, 1H), 7.53-7.46 (m, 1H), 7.25-7.21 (m, 0.7H), 7.16-7.13 (m, 0.3H), 6.01 (s, 0.3H), 5.94 (s, 0.7H), 4.17-4.06 (m, 2.3H), 3.92-3.87 (m, 0.7H), 3.54 (s, 2H), 3.53 (s, 1H), 3.24-3.18 (m, 2H), 2.29-2.22 (m, 0.3H), 2.08-197 (m, 1H), 1.93-1.82 (m, 1.7H), 1.76-1.67 (m, 1H).

Compound II-83-B 2-(4-(6-(2-Bromo-3-fluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-83-B as yellow solids.
LC-MS (ESI): R$_T$=4.273 min, mass calcd. for C$_{24}$H$_{21}$BrFN$_5$O$_4$S$_2$ 605.0, m/z found 605.8 [M+H]$^+$. $^1$H NMR (400 MHz, DMSO-d$_6$) δ 8.00-7.96 (m, 1.6H), 7.92-7.89 (m, 0.4H), 7.64 (s, 1H), 7.45-7.39 (m, 1H), 7.32-7.28 (m, 1H), 7.25-7.14 (m, 1H), 6.06 (s, 0.3H), 5.98 (s, 0.7H), 4.17-4.04 (m, 2H), 3.92-3.86 (m, 1H), 3.54 (s, 2H), 3.52 (s, 1H), 3.23-3.11 (m, 2H), 2.28-2.09 (m, 1H), 2.05-1.97 (m, 1H), 1.95-1.85 (m, 1H), 1.82-1.65 (m, 1H).

Compound II-84-B 2-(4-(6-(2-Bromo-4-fluorophenyl)-5-(methoxycarbonyl)-2-(thiazol-2-yl)-3,6-dihydropyrimidin-4-yl)piperidin-1-yl)thiazole-5-carboxylic Acid (a Single Stereoisomer)

By utilizing the analogous procedure of Method C, the title compound was synthesized from compound XI-84-N as yellow solids.
LC-MS (ESI): R$_T$=2.958 min, mass calcd. for C$_{24}$H$_{21}$BrFN$_5$O$_4$S$_2$ 605.0, m/z found 606.0 [M+H]$^+$. Chiral analysis (Column: Chiralpak ID 5 μm 4.6*250 mm; Mobile Phase: Hex:EtOH:TFA=70:30:0.2 at 1.0 mL/min; Temp: 30° C.; Wavelength: 214 nm, R$_T$=11.972 min). $^1$H NMR (400 MHz, DMSO-d$_6$) δ 12.58 (br s, 1H), 9.55 (d, J=3.6 Hz, 0.7H), 9.34 (s, 0.3H), 8.00-7.96 (m, 1.8H), 7.92-7.91 (m, 0.2H), 7.78 (s, 1H), 7.59-7.56 (m, 1H), 7.38-7.24 (m, 2H), 5.99 (s, 0.2H), 5.91 (d, J=3.2 Hz, 0.8H), 4.17-4.07 (m, 2.3H), 3.92-3.86 (m, 0.7H), 3.55 (s, 2.5H), 3.53 (s, 0.5H), 3.24-3.16 (m, 2H), 2.04-1.75 (m, 3H), 1.69-1.65 (m, 1H).

Compound II-85-A 2-(3-(6-(2-chloro-3,4-difluorophenyl)-5-(ethoxycarbonyl)-2-(thiazol-2-yl)-3,6-dihydropyrimidin-4-yl)pyrrolidin-1-yl)oxazole-4-carboxylic Acid (a Single Stereoisomer)

By utilizing the analogous procedure of Method C, the title compound was synthesized from compound XI-85-M as yellow solids.
LC-MS (ESI): R$_T$=3.139 min, mass calcd. for C$_{24}$H$_{20}$ClF$_2$N$_5$O$_5$S, 563.1, m/z found 563.8 [M+H]$^+$. Chiral analysis (Column: Chiralpak IF 5 μm 4.6*250 mm; Mobile Phase: Hex:EtOH:TFA=80:20:0.2 at 1 mL/min; Col. Temp: 30° C.; Wavelength: 254 nm, R$_T$=9.215 min). $^1$H NMR (400 MHz, DMSO-d$_6$) δ 7.98-7.94 (m, 3H), 7.53-7.48 (m, 1H), 7.25-7.22 (m, 1H), 5.96 (s, 1H), 4.76-4.69 (m, 0.1H), 4.46-4.43 (m, 0.9H), 3.99 (q, J=6.8 Hz, 2H), 3.81-3.67 (m, 3H), 3.55-3.49 (m, 1H), 2.23-2.16 (m, 2H), 1.07 (t, J=6.8 Hz, 3H).

Compound II-86-B 2-(3-(6-(2-Chloro-3,4-difluorophenyl)-5-(ethoxycarbonyl)-2-(thiazol-2-yl)-3,6-dihydropyrimidin-4-yl)azetidin-1-yl)oxazole-4-carboxylic Acid (a Single Stereoisomer)

By utilizing the analogous procedure of Method C, the title compound was synthesized from compound XI-86-N as yellow solids.
LC-MS (ESI): R$_T$=3.019 min, mass calcd. for C$_{23}$H$_{18}$ClF$_2$N$_5$O$_5$S, 549.1, m/z found 549.8 [M+H]$^+$. Chiral HPLC (Column: Chiralpak OD-H 5 μm 4.6*250 mm; Mobile Phase: Hex:IPA:TFA=70:30:0.2 at 1.0 mL/min; Temp: 30° C.; Wavelength: 230 nm, R$_T$=10.127 min). $^1$H NMR (400 MHz, DMSO-d$_6$) δ 8.04-8.00 (m, 3H), 7.49-7.43 (m, 1H), 7.31-7.27 (m, 1H), 5.97 (s, 1H), 4.65 (br s, 1H), 4.34-4.22 (m, 4H), 3.98 (q, J=7.2 Hz, 2H), 1.08 (t, J=7.2 Hz, 3H).

Compound II-87-A

Methyl 6-(1-benzoylazetidin-3-yl)-4-(2-chloro-4-fluorophenyl)-2-(thiazol-2-yl)-1,4-dihydropyrimidine-5-carboxylate (a Single Stereoisomer)

Intermediate II-87-X

Methyl 6-(1-benzoylazetidin-3-yl)-4-(2-chloro-4-fluorophenyl)-2-(thiazol-2-yl)-1,4-dihydropyrimidine-5-carboxylate (a Mixture of 2 Stereoisomers)

To a solution of methyl 6-(azetidin-3-yl)-4-(2-chloro-4-fluorophenyl)-2-(thiazol-2-yl)-1,4-dihydropyrimidine-5-carboxylate FA19 (150 mg, 0.37 mmol) in dichloromethane (10 mL) was added triethylamine (57 mg, 0.56 mmol) and benzoyl chloride BB51 (52 mg, 0.37 mmol) at 0° C. under nitrogen atmosphere.
After stirred at room temperature overnight, the mixture was concentrated under reduced pressure to give a residue, which was purified by Prep. HPLC (Column: Gilson X-bridge C18 (5 μm 19*150 mm), Mobile Phase A: water (0.1% ammonium bicarbonate), Mobile Phase B: acetonitrile, UV: 214 nm, Flow rate: 20 mL/min, Gradient: 40-70% (% B)) to give the title compound (156 mg, 62% yield) as yellow solids. LC-MS (ESI): R$_T$=3.383 min, mass calcd. for C$_{25}$H$_{20}$ClFN$_4$O$_3$S, 510.1, m/z found 510.9 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=12.587 min and 14.340 min). $^1$HNMR (400 MHz, DMSO-d$_6$) δ 9.69 (d, J=3.2 Hz, 1H), 8.02-8.01 (m, 2H), 7.68 (t, J=7.2 Hz, 2H), 7.52-7.39 (m, 5H), 7.25-7.14 (m, 1H), 6.02 (s, 0.1H), 5.95 (d, J=2.8 Hz, 0.9H), 4.62-4.42 (m, 3H), 4.39-4.19 (m, 2H), 3.53 (s, 3H).
A stereoisomeric mixture of II-87-X (156 mg, 0.310 mmol) was separated by chiral Prep. HPLC (Column: Chiralpak IE 5 μm 20*250 mm; Mobile Phase: Hex:EtOH=60:40 at 13 mL/min; Temp: 30° C.; Wavelength: 214 nm) to afford the compounds II-87-A (38 mg, 24% yield, 100% stereopure) and II-87-B (41 mg, 26% yield, 99.1% stereopure) as yellow solids.
II-87-A: LC-MS (ESI): R$_T$=3.379 min, mass calcd. for C$_{25}$H$_2$OClFN$_4$O$_3$S, 510.1, m/z found 510.9 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, $R_T$=12.433 min). $^1$H NMR (400 MHz, DMSO-$d_6$) δ 9.69 (s, 1H), 8.03-8.01 (m, 2H), 7.68 (t, J=7.2 Hz, 2H), 7.54-7.45 (m, 3H), 7.43-7.39 (m, 2H), 7.25-7.13 (m, 1H), 6.02 (s, 0.1H), 5.94 (t, J=2.8 Hz, 0.9H), 4.62-4.42 (m, 3H), 4.39-4.19 (m, 2H), 3.53 (s, 3H).

II-87-B: LC-MS (ESI): $R_T$=3.379 min, mass calcd. for $C_{25}H_2OClFN_4O_3S$, 510.1, m/z found 510.9 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, $R_T$=14.174 min). $^1$H NMR (400 MHz, DMSO-$d_6$) δ 9.69 (s, 1H), 8.03-8.01 (m, 2H), 7.69 (t, J=6.8 Hz, 2H), 7.54-7.39 (m, 5H), 7.25-7.14 (m, 1H), 6.02 (s, 0.1H), 5.94 (t, J=2.8 Hz, 0.9H), 4.63-4.49 (m, 3H), 4.44-4.19 (m, 2H), 3.53 (s, 3H).

Compound II-88-B methyl 4-(2-chloro-4-fluorophenyl)-6-(1-(5-methyl-isoxazole-4-carbonyl)azetidin-3-yl)-2-(thiazol-2-yl)-1,4-dihydropyrimidine-5-carboxylate (a Single Stereoisomer)

By utilizing the analogous procedure of Method E, the title compound was synthesized from compound BB52 and FA19-1B.

LC-MS (ESI): $R_T$=1.959 min, mass calcd. for $C_{23}H_{19}ClFN_5O_4S$, 515.1, m/z found 515.9 [M+H]$^+$. Chiral analysis (Column: Chiralpak IA 5 μm 4.6*250 mm; Mobile Phase: Hex:EtOH=60:40 at 1.0 mL/min; Temp: 30° C.; Wavelength: 230 nm, $R_T$=8.135 min). $^1$H NMR (400 MHz, DMSO-$d_6$) 9.71 (d, J=2.8 Hz, 1H), 8.84 (d, J=10.8 Hz, 1H), 8.01 (s, 2H), 7.45-7.41 (m, 2H), 7.24-7.16 (m, 1H), 5.95 (s, 1H), 4.67-4.48 (m, 3H), 4.36-4.13 (m, 2H), 3.54 (s, 3H), 2.65 (s, 3H).

Compound II-89-B 2-(4-(6-(2-Chloro-4-fluorophenyl)-5-(methoxycarbonyl)-2-(thiazol-2-yl)-3,6-dihydropyrimidin-4-yl)piperidin-1-yl)-5-methylisonicotinic Acid (a Single Stereoisomer)

By utilizing the analogous procedure of Method C, the title compound was synthesized from compound XI-87-S as yellow solids.

LC-MS (ESI): $R_T$=2.895 min, mass calcd. for $C_{27}H_{25}ClFN_5O_4S$, 569.1, m/z found 569.9 [M+H]$^+$. 1H NMR (400 MHz, $CD_3OD$) δ 7.91 (s, 1H), 7.88 (d, J=3.2 Hz, 1H), 7.72 (d, J=3.2 Hz, 1H), 7.42-7.39 (m, 1H), 7.24-7.21 (m, 2H), 7.07-7.03 (m, 1H), 6.11 (s, 1H), 4.38-4.31 (m, 2H), 4.11 (br s, 1H), 3.61 (s, 3H), 3.15-3.06 (m, 2H), 2.35 (s, 3H), 2.13-1.98 (m, 3H), 1.86-1.76 (m, 1H).

Compound II-90-B 1-(2-(4-(6-(2-chloro-4-fluorophenyl)-5-(methoxycarbonyl)-2-(thiazol-2-yl)-3,6-dihydropyrimidin-4-yl)piperidin-1-yl)pyrimidin-5-yl)piperidine-4-carboxylic acid (a Single Stereoisomer)

By utilizing the analogous procedure of Method C, the title compound was synthesized from compound VIII-20-6B as yellow solids.

LC-MS (ESI): $R_T$=3.663 min, mass calcd. for $C_{30}H_{31}ClFN_7O_4S$, 639.2, m/z found 639.9 [M+H]$^+$. 1H NMR (400 MHz, DMSO-$d_6$) δ 9.45 (s, 0.7H), 9.04 (s, 0.3H), 8.21 (s, 0.6H), 8.20 (s, 1.4H), 7.98-7.90 (m, 2H), 7.44-7.40 (m, 1H), 7.38-7.32 (m, 1H), 7.24-7.17 (m, 1H), 6.02 (s, 0.3H), 5.93 (s, 0.7H), 4.80-4.65 (m, 2H), 4.15-4.09 (m, 0.3H), 3.90-3.82 (m, 0.7H), 3.54 (s, 2H), 3.53 (s, 1H), 3.40-3.36 (m, 2H), 2.88-2.79 (m, 2H), 2.69-2.64 (m, 2H), 2.37-2.30 (m, 1H), 1.97-1.56 (m, 8H).

Compound II-91-B 2-(4-(6-(2-chloro-3,4-difluorophenyl)-5-(methoxycarbonyl)-2-(thiazol-2-yl)-3,6-dihydropyrimidin-4-yl)piperidin-1-yl)-5-(dimethylamino)pyrimidine-4-carboxylic Acid (a Single Stereoisomer)

By utilizing the analogous procedure of Method C, the title compound was synthesized from compound XI-88-4 as yellow solids.

LC-MS (ESI): $R_T$=3.720 min, mass calcd. for $C_{27}H_{26}ClF_2N_7O_4S$, 617.1, m/z found 618.1 [M+H]$^+$. 1H NMR (400 MHz, DMSO-$d_6$) δ 9.59 (br s, 0.7H), 9.21 (s, 0.3H), 8.54 (s, 0.7H), 8.53 (s, 0.3H), 7.99-7.90 (m, 2H), 7.49-7.42 (m, 1H), 7.24-7.15 (m, 1H), 6.03 (s, 0.3H), 5.94 (s, 0.7H), 4.85-4.73 (m, 2H), 4.21-4.14 (m, 0.3H), 3.94-3.87 (m, 0.7H), 3.55 (s, 2.1H), 3.54 (s, 0.9H), 2.96-2.85 (m, 2H), 2.73 (s, 4.2H), 2.72 (s, 1.8H), 2.07-1.61 (m, 4H).

Compound II-92-B 5-amino-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylic Acid (a Single Stereoisomer)

Intermediate XI-89-3

5-(bis(2,4-dimethoxybenzyl)amino)-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylic Acid (a Single Stereoisomer)

By utilizing the analogous procedure of Method C, the compound XI-89-3 was synthesized from compound XI-89-2 as yellow solids. 1H NMR (400 MHz, $CDCl_3$) δ 8.55 (s, 0.5H), 8.51 (s, 0.5H), 8.13 (s, 0.5H), 7.82 (d, J=2.8 Hz, 0.5H), 7.79 (d, J=2.8 Hz, 0.5H), 7.49 (d, J=2.8 Hz, 0.5H), 7.45-7.43 (m, 1H), 7.08-7.06 (m, 2H), 7.01-6.98 (m, 2H), 6.39-6.37 (m, 4H), 6.19 (s, 0.5H), 6.07 (d, J=2.8 Hz, 0.5H), 5.08-4.94 (m, 2H), 4.38-4.23 (m, 0.5H), 4.16 (s, 4H), 4.05-3.92 (m, 0.5H), 3.78 (s, 6H), 3.73 (s, 3H), 3.72 (s, 3H), 3.63 (s, 1.3H), 3.61 (s, 1.7H), 3.08-2.97 (m, 2H), 2.15-2.01 (m, 2H), 1.75-1.69 (m, 2H).

Compound II-92-B 5-amino-2-(4-(6-(2-chloro-3,4-difluorophenyl)-5-(methoxycarbonyl)-2-(thiazol-2-yl)-3,6-dihydropyrimidin-4-yl)piperidin-1-yl)pyrimidine-4-carboxylic Acid (a Single Stereoisomer)

To a solution of 5-(bis(2,4-dimethoxybenzyl)amino)-2-(4-(6-(2-chloro-3,4-difluorophenyl)-5-(methoxycarbonyl)-2-(thiazol-2-yl)-3,6-dihydropyrimidin-4-yl)piperidin-1-yl) pyrimidine-4-carboxylic acid XI-89-3 (70 mg, 90% purity, 0.071 mmol) in dichloromethane (1 mL) was added trifluoroacetic acid (1 mL) at room temperature. After the mixture was stirred at room temperature for 2 hours, water (20 mL) was added. The resulting mixture was extracted with ethyl acetate (20 mL) twice. The combined organic layers were washed with saturated sodium bicarbonate solution until pH ~6, and then washed with brine (20 mL), dried over $Na_2SO_{4(s)}$ and filtered. The filtrate was concentrated and purified by C18 (acetonitrile:water=40% to 80%) to afford the title compound (13 mg, 97.4% purity, 30% yield) as yellow solids. LC-MS (ESI): $R_T$=3.377 min, mass calcd. for $C_{25}H_{22}ClF_2N_7O_4S$, 589.1, m/z found 590.1 [M+H]$^+$. 1H NMR (400 MHz, DMSO-d$_6$) δ 9.57 (s, 0.6H), 9.06 (s, 0.4H), 8.32 (s, 0.4H), 8.31 (s, 0.6H), 7.99-7.95 (m, 2H), 7.49-7.42 (m, 1H), 7.24-7.15 (m, 1H), 6.03 (s, 0.4H), 5.94 (s, 0.6H), 4.78-4.64 (m, 2H), 4.15-4.08 (m, 0.3H), 3.87-3.82 (m, 0.7H), 3.54 (s, 1.8H), 3.53 (s, 1.2H), 2.87-2.73 (m, 2H), 1.99-1.57 (m, 4H).

Compound II-93-B 2-(4-(6-(2-chloro-3,4-difluorophenyl)-5-(methoxycarbonyl)-2-(thiazol-2-yl)-3,6-dihydropyrimidin-4-yl)piperidin-1-yl)-5-(dimethylamino)isonicotinic Acid (a Single Stereoisomer)

Intermediate XI-90-4 methyl 6-(1-(5-amino-4-(methoxycarbonyl)pyridin-2-yl)piperidin-4-yl)-4-(2-chloro-3,4-difluorophenyl)-2-(thiazol-2-yl)-1,4-dihydropyrimidine-5-carboxylate (a Single Stereoisomer)

To a solution of methyl 4-(2-chloro-3,4-difluorophenyl)-6-(1-(4-(methoxycarbonyl)-5-nitropyridin-2-yl)piperidin-4-yl)-2-(thiazol-2-yl)-1,4-dihydropyrimidine-5-carboxylate XI-90-3 (120 mg, 95% purity, 0.18 mmol) in ethanol (5 mL) and water (2 mL) was added ammonium chloride (25 mg, 0.467 mmol) and iron powder (52 mg, 0.931 mmol). After stirred at 80° C. for 1 hour, the mixture was cooled down to room temperature, poured into water (20 mL) and extracted with ethyl acetate (30 mL) twice. The combined organic layers were concentrated and purified by silica gel column chromatography (petroleum ether:ethyl acetate=3:1 to 1:1) to give the title compound (100 mg, 90% purity from $^1$H NMR, 83% yield) as brown solids. LC-MS (ESI): $R_T$=1.73 min, mass calcd. for $C_{27}H_{25}ClF_2N_6O_4S$, 602.1, m/z found 603.1 [M+H]$^+$. $^1$H NMR (400 MHz, CDCl$_3$) δ 8.24 (br s, 0.7H), 7.98 (s, 0.3H), 7.97 (s, 0.7H), 7.82-7.80 (m, 0.3H), 7.79-7.76 (m, 0.7H), 7.49-7.46 (m, 0.3H), 7.44-7.42 (m, 0.7H), 7.40-7.39 (m, 0.3H), 7.15-6.99 (m, 3H), 6.20 (s, 0.7H), 6.07 (d, J=2.8 Hz, 0.3H), 5.14-5.04 (m, 2H), 4.43-4.34 (m, 0.3H), 4.23-4.10 (m, 2.7H), 3.92 (s, 3H), 3.63 (s, 0.9H), 3.61 (s, 2.1H), 2.91-2.79 (m, 2H), 2.37-1.73 (m, 4H).

Intermediate XI-90-5 methyl 4-(2-chloro-3,4-difluorophenyl)-6-(1-(5-(dimethylamino)-4-(methoxycarbonyl)pyridin-2-yl)piperidin-4-yl)-2-(thiazol-2-yl)-1,4-dihydropyrimidine-5-carboxylate (a Single Stereoisomer)

To a solution of methyl 6-(1-(5-amino-4-(methoxycarbonyl)pyridin-2-yl) piperidin-4-yl)-4-(2-chloro-3,4-difluorophenyl)-2-(thiazol-2-yl)-1,4-dihydropyrimidine-5-carboxylate XI-90-4 (100 mg, 90% purity, 0.149 mmol) in methanol (4 mL) was added 37% formaldehyde aqueous solution (30 mg, 0.37 mmol) and acetic acid (40 mg, 0.666 mmol) at 0° C. After stirred at room temperature for 10 minutes, sodium cyanotrihydroborate (20 mg, 0.318 mmol) was added. After stirred at room temperature for 2 hours, the mixture was quenched with ammonium chloride aqueous solution (5 mL) and extracted with ethyl acetate (30 mL) twice. The combined organic layers were concentrated and purified by C18 column (acetonitrile:water=70% to 80%) to give the title compound (55 mg, 95% purity from $^1$H NMR, 55% yield) as yellow solids. LC-MS (ESI): $R_T$=1.83 min, mass calcd. for $C_{29}H_{29}ClF_2N_6O_4S$, 630.2, m/z found 631.2 [M+H]$^+$. $^1$H NMR (400 MHz, CDCl$_3$) δ 8.20 (s, 0.6H), 8.09 (s, 0.4H), 8.08 (s, 0.6H), 7.82 (d, J=2.8 Hz, 0.4H), 7.78 (d, J=3.2 Hz, 0.6H), 7.48 (d, J=3.2 Hz, 0.4H), 7.44 (d, J=2.8 Hz, 0.6H), 7.40 (d, J=2.4 Hz, 0.4H), 7.12-7.00 (m, 2H), 6.92-6.91 (m, 1H), 6.20 (s, 0.6H), 6.07 (d, J=2.8 Hz, 0.4H), 4.42-4.20 (m, 2.6H), 4.02-3.98 (m, 0.4H), 3.94 (s, 3H), 3.63 (s, 1.3H), 3.61 (s, 1.7H), 3.00-2.88 (m, 2H), 2.79 (s, 3.3H), 2.78 (s, 2.7H), 2.30-2.19 (m, 0.4H), 2.11-1.72 (m, 3.6H).

Compound II-93-B 2-(4-(6-(2-chloro-3,4-difluorophenyl)-5-(methoxycarbonyl)-2-(thiazol-2-yl)-3,6-dihydropyrimidin-4-yl)piperidin-1-yl)-5-(dimethylamino)isonicotinic Acid (a Single Stereoisomer)

By utilizing the analogous procedure of Method C, the compound II-93-B was synthesized from compound XI-90-5 as yellow solids.
LC-MS (ESI): $R_T$=4.043 min, mass calcd. for $C_{28}H_{27}ClF_2N_6O_4S$, 616.1, m/z found 617.2 [M+H]$^+$. $^1$H NMR (400 MHz, DMSO-d$_6$) δ 9.63 (d, J=2.8 Hz, 0.7H), 9.19 (s, 0.3H), 8.61 (s, 1H), 8.00-7.91 (m, 2H), 7.50-7.43 (m, 1H), 7.23-7.15 (m, 2H), 6.03 (s, 0.3H), 5.94 (d, J=2.0 Hz, 0.7H), 4.56-4.43 (m, 2H), 4.20-4.12 (m, 0.3H), 3.93-3.86 (m, 0.7H), 3.55 (s, 2.1H), 3.54 (s, 0.9H), 3.00-2.83 (m, 8H), 2.27-1.63 (m, 4H).

Compound II-94-B 2-(4-(6-(3,4-Difluoro-2-methylphenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the compound II-94-B was synthesized from compound XI-91-1 as yellow solids.
LC-MS (ESI): $R_T$=3.971 min, mass calcd. for $C_{27}H_{26}ClF_2N_6O_4S$, 568.2, m/z found 568.9 [M+H]$^+$. 1H NMR (400 MHz, DMSO-d$_6$) δ 9.53 (s, 0.8H), 9.04 (s, 0.2H), 8.01 (s, 1H), 7.97-7.93 (m, 1.8H), 7.88 (d, J=3.2 Hz, 0.2H), 7.27-7.17 (m, 1H), 7.13-7.10 (m, 0.8H), 7.00-6.96 (m, 0.2H), 5.83 (s, 0.2H), 5.70 (d, J=3.2 Hz, 0.8H), 4.87-4.73 (m, 2H), 4.19-4.12 (m, 0.2H), 3.89-3.83 (m, 0.8H), 3.55 (s, 0.8H), 3.54 (s, 2.2H), 2.88-2.74 (m, 2H), 2.44 (s, 3H), 1.97 (s, 3H), 1.94-1.71 (m, 3.2H), 1.57-1.54 (m, 0.8H).

Compound II-95-B 2-(4-(6-(3,4-Difluoro-2-methylphenyl)-5-(methoxycarbonyl)-2-(thiazol-2-yl)-3,6-dihydropyrimidin-4-yl)piperidin-1-yl)-5-methoxypyrimidine-4-carboxylic Acid (a Single Stereoisomer)

By utilizing the analogous procedure of Method C, the compound 11-95-B was synthesized from compound XI-92-1 as yellow solids.

LC-MS (ESI): $R_T$=4.210 min, mass calcd. for $C_{27}H_{26}F_2N_6O_5S$, 584.2, m/z found 585.2 [M+H]$^+$. 1H NMR (400 MHz, CD$_3$OD) δ 8.26 (s, 1H), 7.87 (d, J=3.2 Hz, 1H), 7.71 (d, J=3.2 Hz, 1H), 7.12-7.09 (m, 1H), 7.06-6.99 (m, 1H), 5.88 (s, 1H), 4.88-4.80 (m, 2H), 4.18-4.07 (m, 1H), 3.86 (s, 3H), 3.62 (s, 3H), 3.02-2.91 (m, 2H), 2.51 (d, J=2.4 Hz, 3H), 2.01-1.85 (m, 3H), 1.77-1.73 (m, 1H).

Compound II-96-B 2-(4-(6-(2-chloro-3,4-difluorophenyl)-5-(ethoxycarbonyl)-2-(thiazol-2-yl)-3,6-dihydropyrimidin-4-yl)piperidin-1-yl)-5-ethoxypyrimidine-4-carboxylic Acid (a Single Stereoisomer)

By utilizing the analogous procedure of Method C, the compound 11-96-B was synthesized from compound XI-93-3 as yellow solids.

LC-MS (ESI): $R_T$=3.626 min, mass calcd. For $C_{28}H_{27}ClF_2N_6O_5S$, 632.1, m/z found 632.9 [M+H]$^+$. 1H NMR (400 MHz, CD$_3$OD) δ 7.43 (s, 1H), 7.78 (d, J=2.8 Hz, 1H), 7.62 (d, J=3.2 Hz, 1H), 7.20-7.10 (m, 2H), 6.03 (s, 1H), 4.73-4.63 (m, 2H), 4.01-3.94 (m, 5H), 2.94-2.78 (m, 2H), 1.95-1.61 (m, 4H), 1.27 (t, J=6.8 Hz, 3H), 1.05 (t, J=7.2 Hz, 3H).

Compound II-97-B 2-(4-(6-(2-Bromo-3-fluorophenyl)-5-(ethoxycarbonyl)-2-(thiazol-2-yl)-3,6-dihydropyrimidin-4-yl)piperidin-1-yl)-5-(dimethylamino)pyrimidine-4-carboxylic Acid (a Single Stereoisomer)

By utilizing the analogous procedure of Method C, the compound 11-97-B was synthesized from compound XI-94-1 as yellow solids.

LC-MS (ESI): $R_T$=3.670 min, mass calcd. for $C_{28}H_{29}BrFN_7O_4S$, 657.1, m/z found 658.2 [M+H]$^+$. 1H NMR (400 MHz, CD$_3$OD) δ 8.85 (s, 1H), 7.88 (d, J=2.8 Hz, 1H), 7.72 (d, J=3.2 Hz, 1H), 7.39-7.33 (m, 1H), 7.25-7.24 (m, 1H), 7.16-7.12 (m, 1H), 6.19 (s, 1H), 5.18-5.07 (m, 2H), 4.33 (br s, 1H), 4.08 (q, J=7.2 Hz, 2H), 3.34-3.32 (m, 6H), 3.12-2.96 (m, 2H), 2.09-1.70 (m, 4H), 1.15 (t, J=7.2 Hz, 3H).

Compound II-98-B 2-(4-(6-(2-Bromo-3-fluorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the compound 11-98-B was synthesized from compound XI-95S as yellow solids.

LC-MS (ESI): $R_T$=4.078 min, mass calcd. for $C_{26}H_{24}BrFN_6O_4S$, 614.1, m/z found 614.8 [M+H]$^+$. 1H NMR (400 MHz, DMSO-d$_6$) δ 9.49 (s, 0.6H), 9.07 (s, 0.4H), 8.12 (s, 1H), 8.00-7.85 (m, 2H), 7.47-7.35 (m, 1H), 7.28-7.13 (m, 2H), 6.06 (s, 0.3H), 5.98 (s, 0.7H), 4.91-4.68 (m, 2H), 4.20-4.12 (m, 0.3H), 3.94-3.82 (m, 0.7H), 3.54 (s, 2.1H), 3.52 (s, 0.9H), 2.94-2.68 (m, 2H), 1.99 (s, 3H), 1.91-1.71 (m, 3.5H), 1.62-1.54 (m, 0.5H).

Compound II-99-B 2-(4-(6-(2-Bromo-4-fluorophenyl)-5-(methoxycarbonyl)-2-(thiazol-2-yl)-3,6-dihydropyrimidin-4-yl)piperidin-1-yl)-5-methylpyrimidine-4-carboxylic Acid (a Single Stereoisomer)

By utilizing the analogous procedure of Method C, the compound 11-99-B was synthesized from compound XI-96-1 as yellow solids.

LC-MS (ESI): $R_T$=3.439 min, mass calcd. for $C_{26}H_{24}BrFN_6O_4S$, 614.1, m/z found 614.9 [M+H]$^+$. 1H NMR (400 MHz, CD$_3$OD) δ 8.16 (s, 1H), 7.86 (d, J=3.2 Hz, 1H), 7.70 (t, J=2.8 Hz, 1H), 7.42-7.38 (m, 2H), 7.10 (td, J=8.4 Hz, 2.8 Hz, 1H), 6.08 (s, 1H), 5.02-4.95 (m, 2H), 4.23-4.02 (m, 1H), 3.61 (s, 3H), 3.01-2.91 (m, 2H), 2.19 (s, 3H), 1.93-1.79 (m, 3H), 1.75-1.65 (m, 1H).

Compound II-100-B 2-(4-(6-(2-bromo-4-fluorophenyl)-5-(ethoxycarbonyl)-2-(thiazol-2-yl)-3,6-dihydropyrimidin-4-yl)piperidin-1-yl)-5-(dimethylamino)pyrimidine-4-carboxylic Acid (a Single Stereoisomer)

By utilizing the analogous procedure of Method C, the compound 11-100-B was synthesized from compound XI-97-1 as yellow solids.

LC-MS (ESI): $R_T$=3.638 min, mass calcd. for $C_{28}H_{29}BrFN_7O_4S$, 657.1, m/z found 657.9 [M+H]$^+$. 1H NMR (400 MHz, CDCl$_3$) δ 8.63 (s, 0.4H), 8.61 (s, 0.6H), 8.07 (s, 0.4H), 7.81 (d, J=2.8 Hz, 0.6H), 7.76 (d, J=3.2 Hz, 0.4H), 7.47 (d, J=3.2 Hz, 0.6H), 7.43 (d, J=3.2 Hz, 0.4H), 7.40 (s, 0.6H), 7.33-7.28 (m, 2H), 7.04-6.95 (m, 1H), 6.20 (s, 0.4H), 6.07 (d, J=2.4 Hz, 0.6H), 5.15-4.99 (m, 2H), 4.39-4.33 (m, 0.3H), 4.11-4.01 (m, 2.7H), 3.14-3.02 (m, 2H), 2.88 (s, 2H), 2.86 (s, 4H), 2.19-2.09 (m, 1H), 2.05-1.94 (m 2H), 1.80-1.75 (m, 1H), 1.16-1.11 (m 3H).

Compound II-101-B 3-(6-(4-(6-(2-Chloro-4-fluorophenyl)-5-(methoxycarbonyl)-2-(thiazol-2-yl)-3,6-dihydropyrimidin-4-yl)piperidin-1-yl)pyridin-3-yl)propanoic Acid (a Single Stereoisomer)

By utilizing the analogous procedure of Method D, the compound 11-101-B was synthesized from compound VIII-23-B as yellow solids.

LC-MS (ESI): $R_T$=3.252 min, mass calcd. for $C_{28}H_{27}ClFN_5O_4S$, 583.1, m/z found 583.9 [M+H]$^+$. 1H NMR (400 MHz, CD$_3$OD) δ 7.96 (s, 1H), 7.87 (d, J=3.2 Hz, 1H), 7.72 (d, J=3.2 Hz, 1H), 7.56-7.54 (m, 1H), 7.42-7.38 (m, 1H), 7.25-7.22 (m, 1H), 7.07-7.03 (m, 1H), 6.92-6.90 (m, 1H), 6.10 (br s, 1H), 4.43-3.96 (m, 3H), 3.60 (s, 3H), 3.03-2.93 (m, 2H), 2.82 (t, J=7.2 Hz, 2H), 2.57 (t, J=7.6 Hz, 2H), 2.18-1.68 (m, 4H).

Example 2: Anti-Viral Assay in HepG2.2.15 Cells

1. Materials and Equipments
   1.1. Cell Line
   HepG2.2.15 (the HepG2.2.15 cell line can be produced by transfection of the HepG2 cell line as described in Sells, Chen, and Acs 1987 (Proc. Natl. Acad. Sci. USA 84:1005-1009), and the HepG2 cell line is available from ATCC® under number HB-8065™).

Reagents
DMEM/F12 (INVITROGEN-11330032)
FBS (GIBCO-10099-141)
Dimethyl sulfoxide(DMSO) (SIGMA-D2650)
Penicillin-streptomycin solution (HYCLONE-SV30010)
NEAA (INVITROGEN-1114050)
L-Glutamine (INVITROGEN-25030081)
Geneticin Selective Antibiotic (G418, 500 mg/ml) (INVITROGEN-10131027)
Trypsinase digestion solution (INVITROGEN-25300062)
CCK8 (BIOLOTE-35004)
QIAamp 96 DNA Blood Kit (12) (QIAGEN-51162)
FastStart Universal Probe Mast Mix (ROCHE-04914058001)
1.2. Consumables
96-well cell culture plate (COSTAR-3599)
Micro Amp Optical 96-well reaction plate (APPLIED BIOSYSTEMS-4306737)
Micro Amp Optical 384-well reaction plate (APPLIED BIOSYSTEMS)
1.3. Equipment
Plate reader (MOLECULAR DEVICES, SPECTRA-MAX M2e)
Centrifuge (BECKMAN, ALLEGRA-X15R)
Real Time PCR system (APPLIED BIOSYSTEMS, QUANTSTUDIO 6)
Real Time PCR system (APPLIED BIOSYSTEMS, 7900HT)
2. Methods
2.1. HBV Inhibitory Activity and Cytotoxicity Determination Seed the cell HepG2.2.15 cells into 96-well plate in 2% FBS culture medium at the density of 40,000 cells/well and 5,000 cells/well for HBV inhibitory activity and cytotoxicity determination, respectively. After seeding, incubate the cell plates at 37° C., 5% CO2 overnight. The next day, medium containing compounds is added to the cell to treat the cells for 6 days with medium refreshed once in the middle of the treatment. 8 dose points with 3 folds dilution of each compound were adopted and the highest concentration of the compounds is 10 uM and 100 uM for HBV inhibitory activity and cytotoxicity determination, respectively.

After 6 days of compounds treatment, add 20 μl CCK-8 reagents to each well of cytotoxicity assay plates, incubate the plate at 37° C., 5% $CO_2$ for 2.5 h and measure the absorbance at 450 nm wavelength, at the same time read the absorbance at 630 nm wavelength as reference.

The HBV DAN change in the cell culture medium induced by the compounds is measured by q-PCR method. Briefly, the HBV DNA in the culture medium is extracted using QIAamp 96 DNA Blood Kit according to the manual and then quantified by q-PCR using the primers and probe in the table below.

TABLE 3

| Primers or Probe | Sequence | SEQ ID NO: |
|---|---|---|
| HBV-Fw | GTGTCTGCGGCGTTTTATCA | 1 |
| HBV-Rev | GACAAACGGGCAACATACCTT | 2 |
| HBV-Probe With Fam reporter and BHQ1 quencher | CCTCTKCATCCTGCTGCTATGCCTCATC | 3 |

2.2. DATA Analysis $EC_{50}$ and $CC_{50}$ values are calculated by the GRAPHPAD PRISM software. If the CV % of DMSO controls is below 15% and the reference compounds shows expected activity or cytotoxicity, the data of this batch of experiment is considered qualified.

2.3. Results

See Table 4.

TABLE 4

| Compound No. | $EC_{50}$ (μM) | $CC_{50}$ (μM) |
|---|---|---|
| I-1-C | 0.0075 | 13.57 |
| I-2-D | 0.006 | 9.37 |
| I-2-Y | 0.016 | >100 |
| I-3-D | 0.14 | 14.24 |
| I-4-B | 0.011 | 16.37 |
| I-5-B | 0.06 | 19.26 |
| I-6-B | 0.072 | 17.41 |
| I-7-B | 0.024 | 14.28 |
| I-8-B | 0.051 | 26.57 |
| I-9-B | 0.025 | 12.3 |
| I-10-C | 0.022 | 7.64 |
| I-11-B | 0.037 | 12.09 |
| I-12-C | 0.036 | 11.13 |
| I-13-C | 0.0065 | 5.61 |
| I-13-D | 0.0032 | 6.09 |
| I-14-B | 0.0047 | 3.72 |
| I-15-A | 0.066 | 6.27 |
| I-16-B | 0.0048 | 12.4 |
| I-17-A | 0.014 | 25.74 |
| I-18-A | 0.007 | 15.27 |
| I-19-B | 0.036 | 15.19 |
| I-20-B | 0.03 | 7.21 |
| I-21-B | 0.057 | 8.04 |
| I-22-B | 0.015 | 7.68 |
| I-23-B | 0.013 | 5.48 |
| I-24 | 0.012 | 7.55 |
| I-24-A | <0.0046 | 6.79 |
| I-25-B | 0.0061 | 7.9 |
| I-26-B | 0.055 | 15.54 |
| I-27-B | 0.018 | 5.17 |
| I-28-B | 0.033 | 5.28 |
| I-29-C | 0.01 | 11.23 |
| I-30-D | 0.026 | 1.16 |
| I-31 | 0.059 | 3.78 |
| I-32-B | <0.0046 | 5.81 |
| I-33-C | 0.0072 | 2.97 |
| I-34 | 0.055 | 2.79 |
| I-35-C | 0.063 | 7.16 |
| I-36-B | 0.0062 | 5.94 |
| I-37-C | 0.0083 | 2.22 |
| I-38-B | <0.0046 | 11.26 |
| I-39-B | 0.082 | 7.59 |
| I-39-C | 0.11 | 7.75 |
| I-40-A | <0.0046 | 4.43 |
| I-41-B | 0.017 | 1.02 |
| I-42-B | 0.083 | 10.83 |
| I-43-B | 0.029 | 13.7 |
| I-44-A | 0.0085 | 1.81 |
| I-45 | 0.071 | 16.83 |
| I-46-C | 0.015 | 16.09 |
| I-47-D | 0.0059 | 19.28 |
| I-48-B | 0.022 | 23.04 |
| I-49-A | 0.011 | 24.69 |
| I-50-A | 0.011 | 16.43 |
| II-1-B | <0.0046 | 4.97 |
| II-2-B | 0.0084 | 12.36 |
| II-3-B | <0.0046 | 4.22 |
| II-4-B | 0.019 | 16.28 |
| II-5-B | 0.049 | 25.76 |

TABLE 4-continued

| Compound No. | EC$_{50}$ (µM) | CC$_{50}$ (µM) |
|---|---|---|
| II-6-B | 0.0057 | 5.42 |
| II-7-B | 0.041 | 28.38 |
| II-8-B | 0.0081 | 18.96 |
| II-9-B | <0.0046 | 4.9 |
| II-10-B | 0.0092 | 17.15 |
| II-11-X | 0.058 | 16.19 |
| II-12-B | 0.066 | 25.5 |
| II-13-A | 0.19 | 24.43 |
| II-14-A | 0.0081 | 32.06 |
| II-15-A | 0.0055 | 14.02 |
| II-16-B | 0.0069 | 7.48 |
| II-17-B | 0.014 | >100 |
| II-18-B | 0.089 | 70 |
| II-19-A | 0.0064 | 19.31 |
| II-20-B | 0.015 | 16.82 |
| II-21-B | 0.0062 | 7.11 |
| II-22-B | 0.015 | 11.16 |
| II-23-B | <0.0046 | 3.88 |
| II-24-B | <0.0046 | 11.02 |
| II-25-B | 0.054 | 18.13 |
| II-26-B | 0.045 | 11.14 |
| II-27-B | 0.0055 | 20.22 |
| II-28-B | <0.0046 | 5.33 |
| II-29-B | <0.0046 | 9.46 |
| II-30-B | 0.0072 | 16.01 |
| II-31-B | 0.025 | 2.61 |
| II-32-B | 0.046 | 11.11 |
| II-33-B | 0.045 | 18.64 |
| II-34-F | <0.0046 | 7.96 |
| II-35-A | 0.02 | 3.96 |
| II-36-B | 0.052 | 8.65 |
| II-37-B | 0.061 | 6.41 |
| II-38-B | 0.081 | 3.88 |
| II-39-B | 0.014 | 5.38 |
| II-40-B | 0.0091 | 8.37 |
| II-41-B | 0.0052 | 10.19 |
| II-42-B | 0.056 | 2.57 |
| II-43-B | 0.016 | 11.36 |
| II-44-B | 0.0076 | 4.77 |
| II-45-B | 0.0087 | 4.43 |
| II-46-B | 0.1 | 3.67 |
| II-47-B | 0.025 | 11.09 |
| II-48-B | 0.079 | 12.91 |
| II-49-B | 0.05 | 0.11 |
| II-50-B | 0.026 | 18.99 |
| II-51-B | <0.0046 | 0.67 |
| II-52-B | 0.051 | 3.7 |
| II-53-B | 0.098 | 9.05 |
| II-54-B | 0.019 | 10.28 |
| II-55-B | <0.0046 | 7.96 |
| II-56-B | 0.022 | 5.54 |
| II-57-B | 0.1 | 4.88 |
| II-58-B | 0.037 | 4.8 |
| II-59-B | 0.013 | 8.65 |
| II-60-B | 0.0059 | 8.92 |
| II-61-B | 0.0091 | 6.68 |
| II-62-B | 0.016 | 6.69 |
| II-63-B | 0.021 | 8.28 |
| II-64-B | 0.075 | 6.84 |
| II-65-B | 0.0046 | 6.64 |
| II-66-B | 0.0072 | 10.87 |
| II-67-B | 0.012 | 2.02 |
| II-68-B | 0.016 | 8.32 |
| II-69-B | 0.0031 | 4.08 |
| II-70-B | 0.01 | 11.83 |
| II-71-B | 0.02 | 6.33 |
| II-72-B | 0.062 | 5.59 |
| II-73-B | 0.025 | 5.92 |
| II-74-B | 0.0066 | 9.31 |
| II-75-X | 0.03 | 9.81 |
| II-76-B | 0.09 | 6.68 |
| II-77-B | 0.029 | 9.74 |
| II-78-B | <0.0046 | 12.14 |
| II-79-B | 0.013 | 1.14 |
| II-80-B | 0.045 | 10.23 |
| II-81-B | 0.054 | 12.44 |
| II-82-B | 0.0091 | 9.48 |
| II-83-B | 0.016 | 2.84 |
| II-84-B | 0.0064 | 14.93 |
| II-85-A | 0.72 | 4.49 |
| II-86-B | 2.87 | 9.4 |
| II-87-A | 4.02 | 9.86 |
| II-88-B | 2.05 | 9.96 |
| II-89-B | 0.009 | 20.31 |
| II-90-B | 0.0054 | 18.97 |
| II-91-B | 0.012 | 26.09 |
| II-92-B | 0.007 | 18.31 |
| II-93-B | 0.0066 | 28.86 |
| II-94-B | 0.0061 | 26.77 |
| II-95-B | 0.0086 | 25.75 |
| II-96-B | 0.0051 | 16.34 |
| II-97-B | 0.014 | 27.58 |
| II-98-B | 0.02 | 21.42 |
| II-99-B | 0.0073 | 20.66 |
| II-100-B | 0.022 | 24.49 |
| II-101-B | <0.0046 | 16.56 |
| VII-23-Y | 0.023 | 8.18 |
| XI-13-S | 0.15 | >100 |
| XI-85-M | 0.77 | 11.63 |

The invention claimed is:

1. A compound of formula (I):

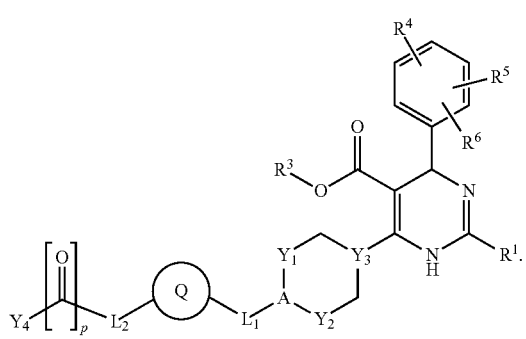

or a pharmaceutically acceptable salt, stereoisomer, or tautomer thereof, wherein:

$L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;

$L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^{15}$;

$Y_4$ is $R^{14}$, OH, or $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

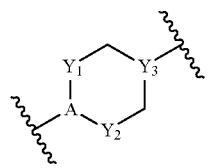

is selected from the group consisting of:

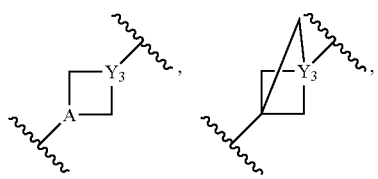

-continued

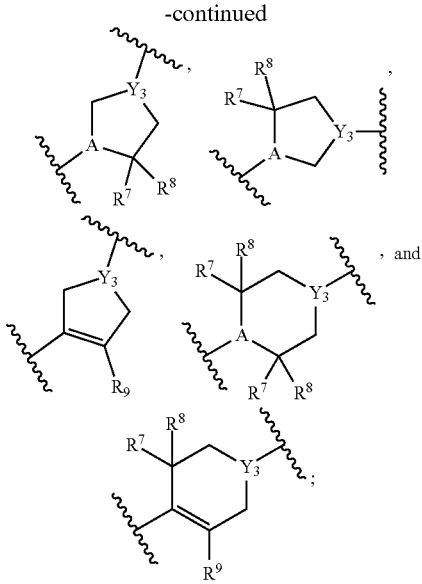

wherein:
each $R^7$ is independently H, $C_1$-$C_4$ alkyl, or $C_1$-$C_4$ haloalkyl;
each $R^8$ is independently H or $C_1$-$C_4$ alkyl;
$R^9$ is H or $C_1$-$C_4$ alkyl;
A is CH or N; and
$Y_3$ is CH or C;
$R^1$ is thiazolyl or pyridyl, wherein the thiazolyl and pyridyl are each optionally substituted with one or more independently selected halogen substituents;
$R^3$ is $C_1$-$C_3$ alkyl;
$R^4$ is H, halogen, or $C_1$-$C_3$ alkyl;
$R^5$ is H, halogen, or $C_1$-$C_3$ alkyl;
$R^6$ is H, halogen, or $C_1$-$C_3$ alkyl;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^{12}$ is independently H or $C_1$-$C_4$ alkyl;
each $R^{13}$ is independently H or $C_1$-$C_4$ alkyl;
$R^{14}$ is $C_1$-$C_4$ alkyl;
each $R^{15}$ is independently H or $C_1$-$C_4$ alkyl; and
p is 0 or 1.

2. The compound of claim 1, or a pharmaceutically acceptable salt, stereoisomer, or tautomer thereof, wherein $Y_4$ is OH, $OCH_3$, or $OCH_2CH_3$.

3. The compound of claim 1, or a pharmaceutically acceptable salt, stereoisomer, or tautomer thereof, wherein $L_2$ is —$CH_2$—, —$CH_2CH_2$—, —$CH_2C(CH_3)_2$—, or cyclobutylene.

4. The compound of claim 1, or a pharmaceutically acceptable salt, stereoisomer, or tautomer thereof, wherein

Q is pyrazolyl, imidazolyl, oxazolyl, isoxazolyl, thiazolyl, oxadiazolyl, thiadiazolyl, phenyl, pyridyl, pyridazinyl, pyrimidinyl, or pyrazinyl.

5. The compound of claim 1, or a pharmaceutically acceptable salt, stereoisomer, or tautomer thereof, wherein:

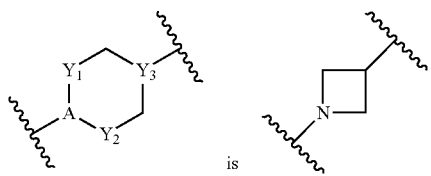

6. The compound of claim 1, or a pharmaceutically acceptable salt, stereoisomer, or tautomer thereof, wherein:

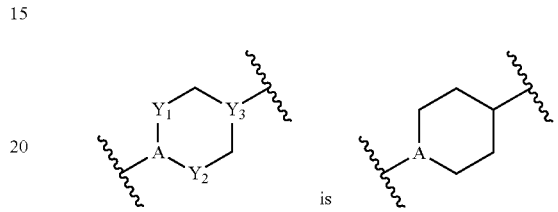

7. The compound of claim 1, or a pharmaceutically acceptable salt, stereoisomer, or tautomer thereof, wherein:

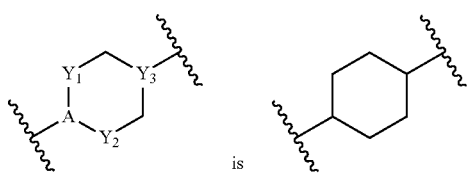

8. The compound of claim 1, or a pharmaceutically acceptable salt, stereoisomer, or tautomer thereof, wherein:

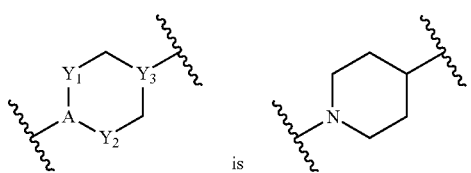

9. The compound of claim 1, or a pharmaceutically acceptable salt, stereoisomer, or tautomer thereof, wherein:

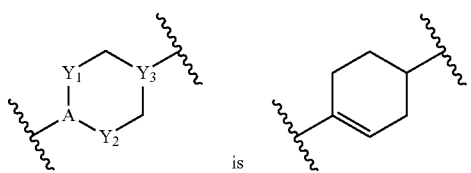

10. The compound of claim 1, or a pharmaceutically acceptable salt, stereoisomer, or tautomer thereof, wherein $R^3$ is $CH_3$ or $CH_2CH_3$.

11. The compound of claim 1, or a pharmaceutically acceptable salt, stereoisomer, or tautomer thereof, wherein:
$R^4$ is F, Cl, Br, or $CH_3$;
$R^5$ is F, Cl, Br, or $CH_3$; and
$R^6$ is F, Cl, Br, or $CH_3$.

12. The compound of claim 1, or a pharmaceutically acceptable salt, stereoisomer, or tautomer thereof, wherein the compound, or pharmaceutically acceptable salt, stereoisomer, or tautomer thereof, is selected from the group consisting of:
Compound I-1-C
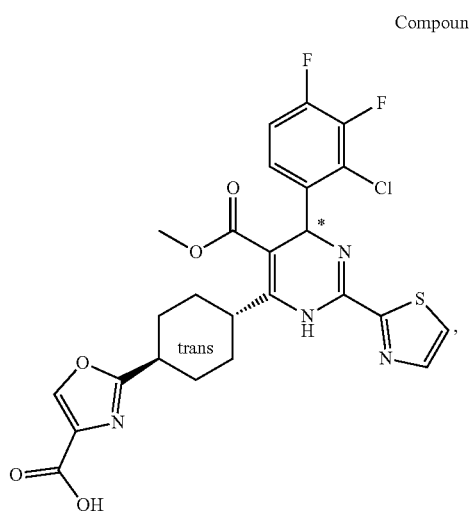
Compound I-2-D
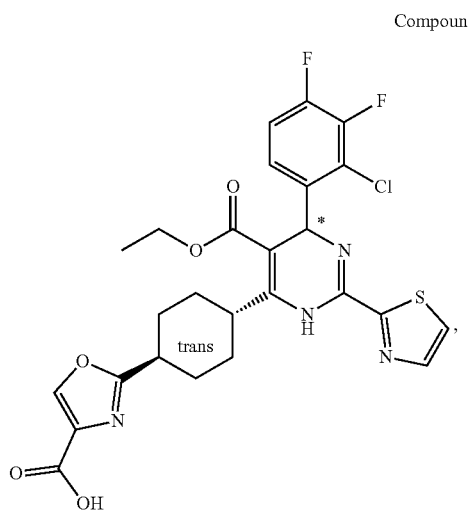
Compound I-4-B
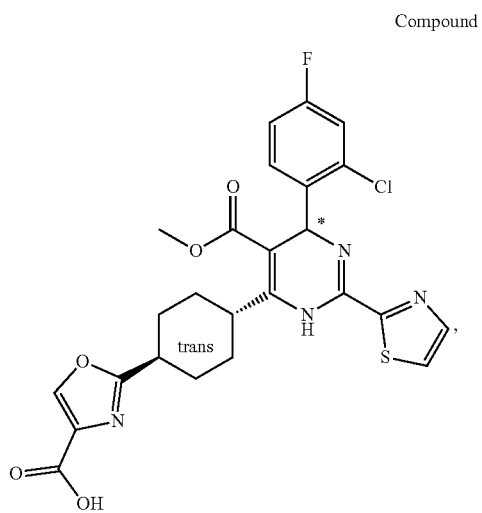
-continued
Compound I-6-B
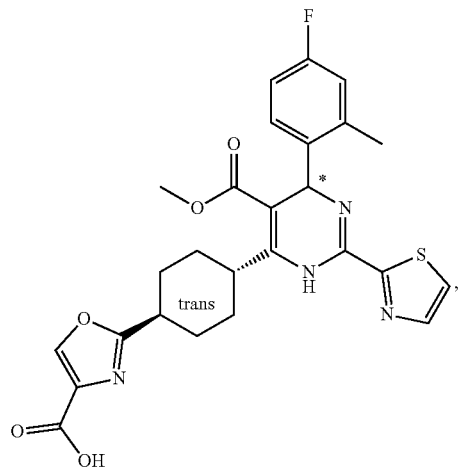
Compound I-9-B
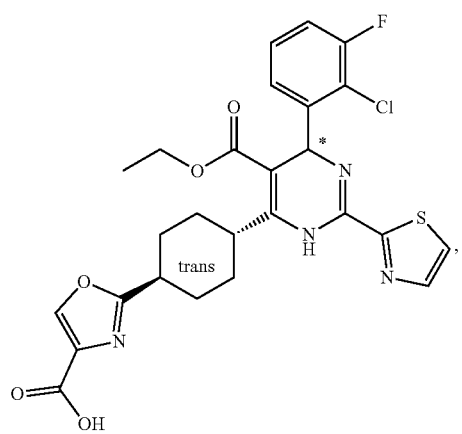
Compound I-13-C Compound I-13-D
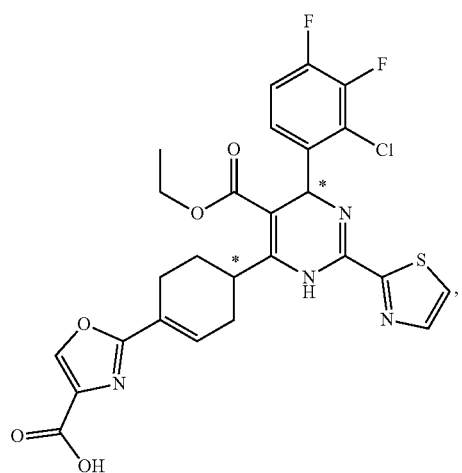

Compound I-14-B
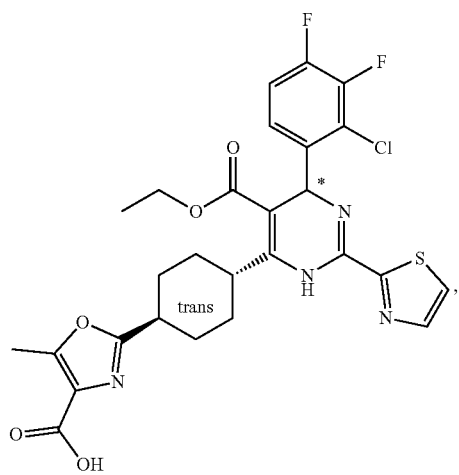
Compound I-16-B
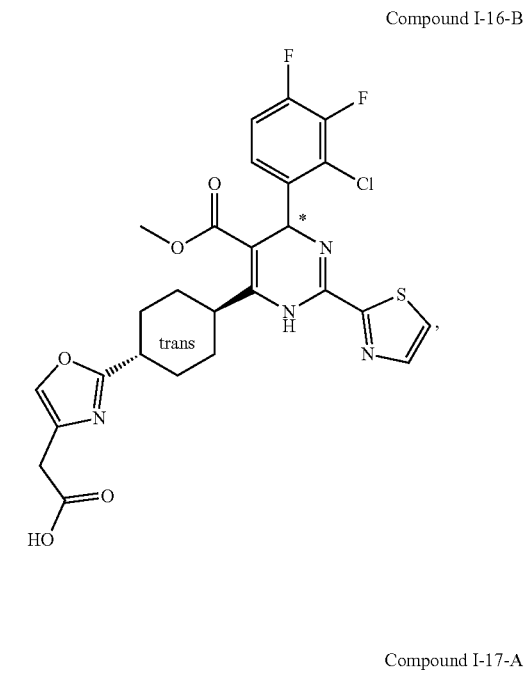
Compound I-17-A
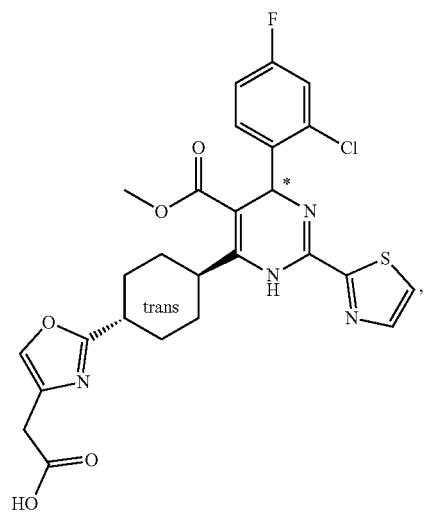
Compound I-18-A
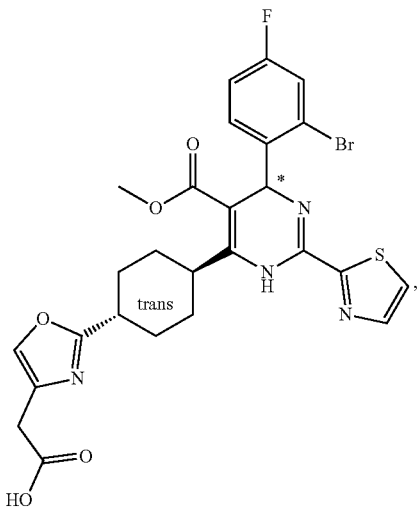
Compound I-19-B
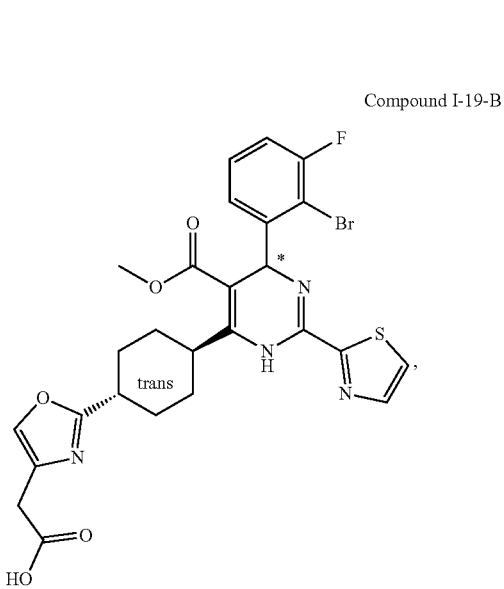
Compound I-20-B
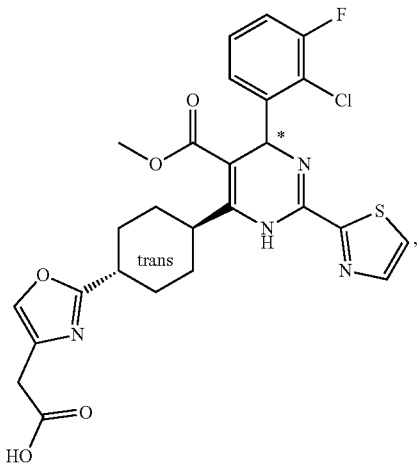

Compound I-23-B
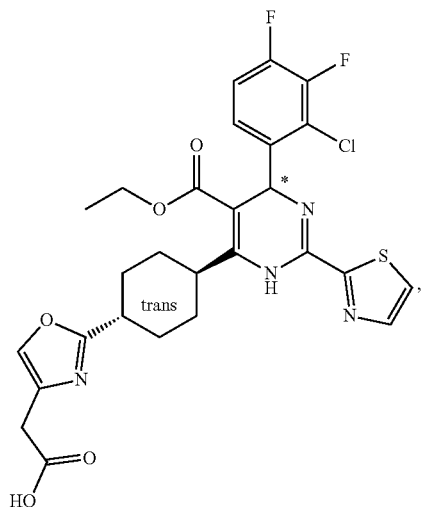
Compound I-24 Compound I-24-A
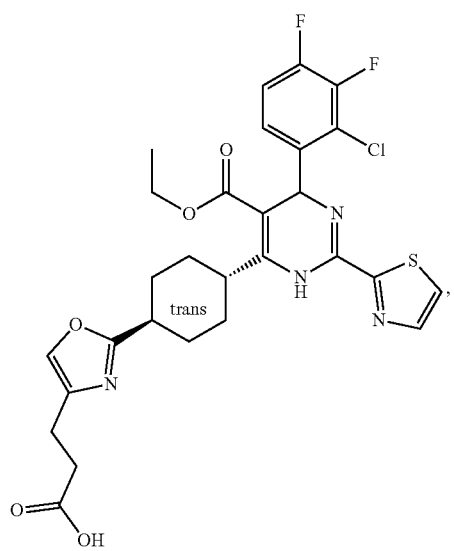
Compound I-25-B
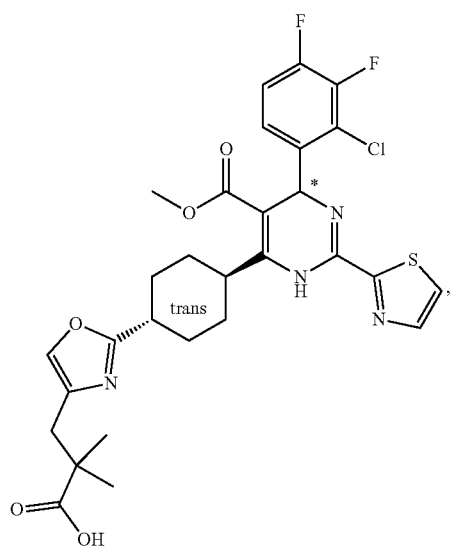
Compound I-28-B
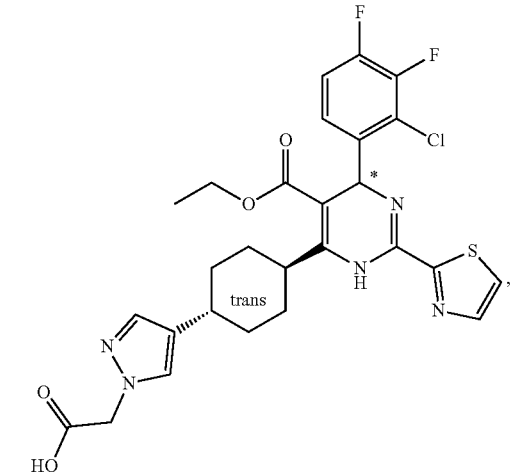
Compound I-32-B
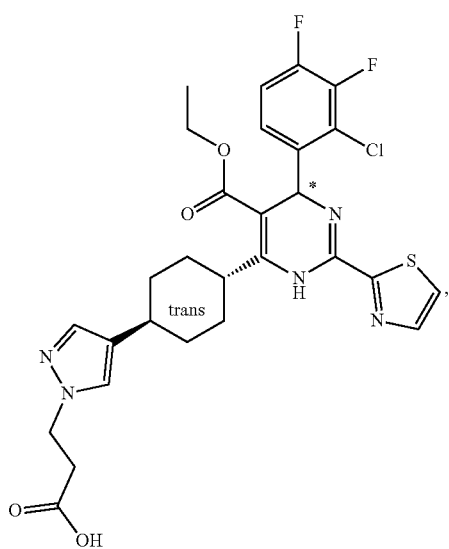
Compound I-33-C
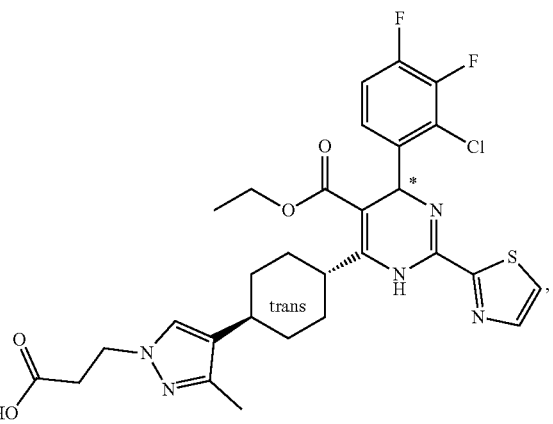

-continued
Compound I-38-B
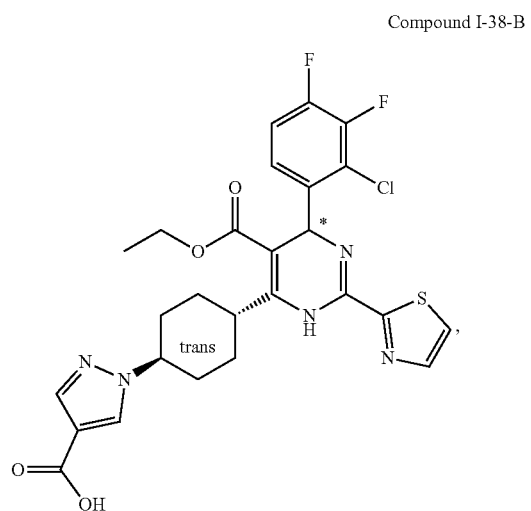
Compound II-1-B
Compound II-2-B
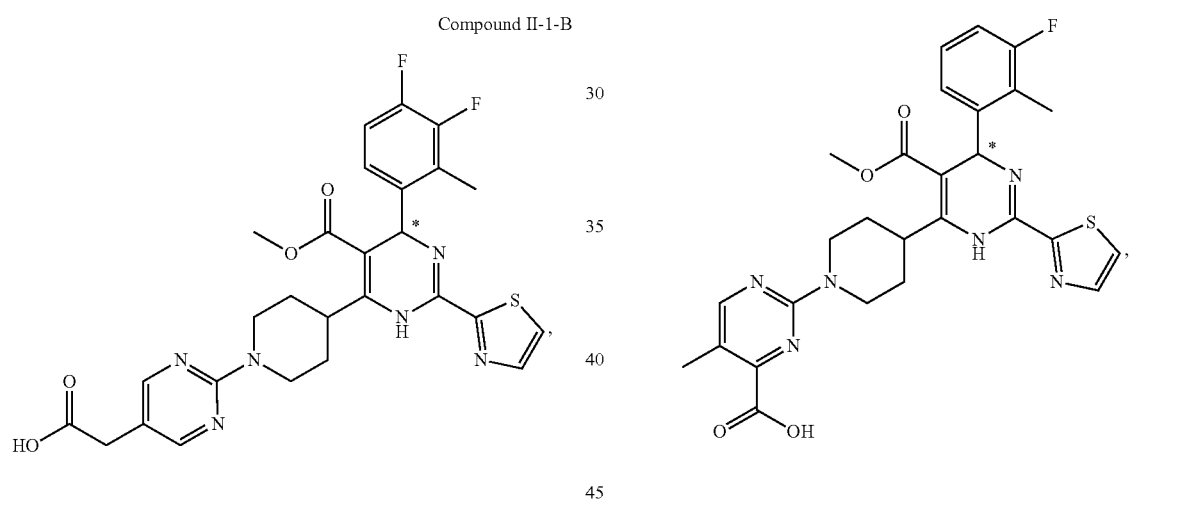
-continued
Compound II-3-B
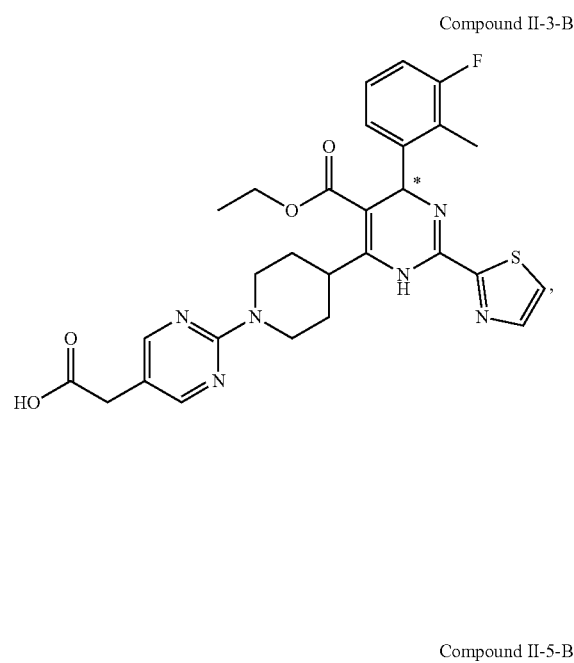
Compound II-5-B
Compound II-6-B -continued
Compound II-8-B
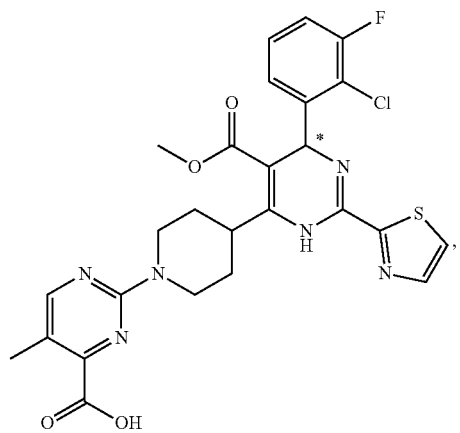
Compound II-9-B
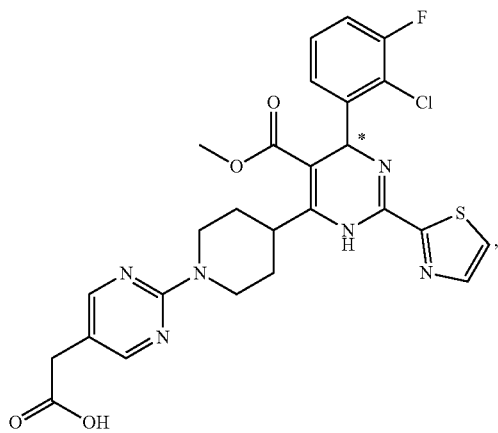
Compound II-10-B
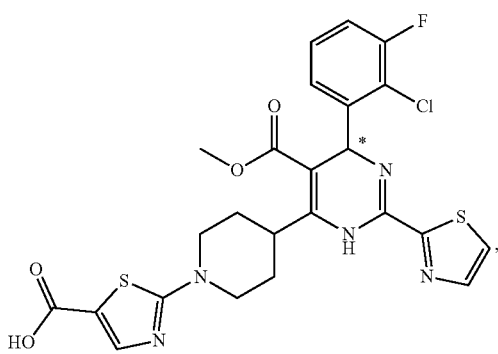
Compound II-14-A
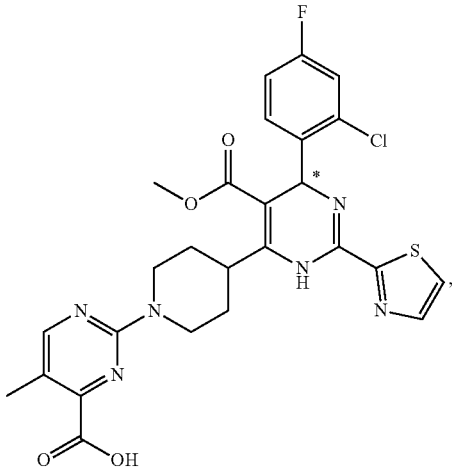
Compound II-15-A
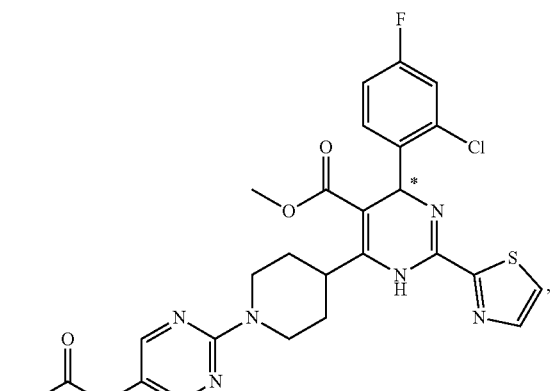
Compound II-16-A
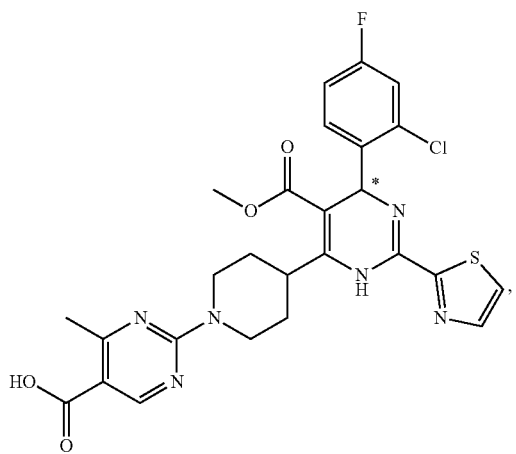

Compound II-18-B
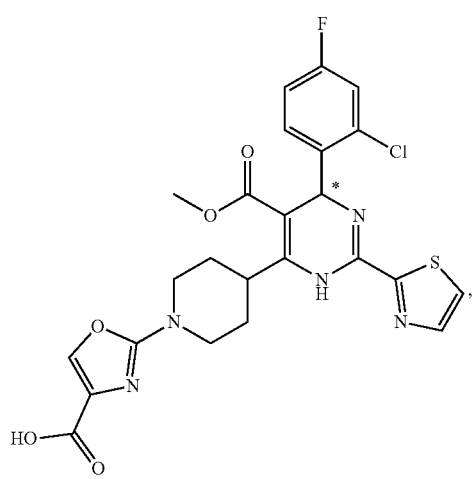
Compound II-19-B
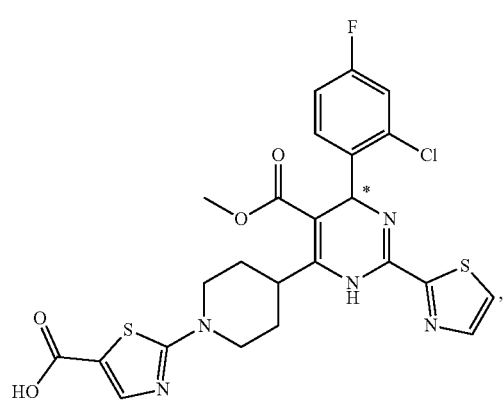
Compound II-20-B
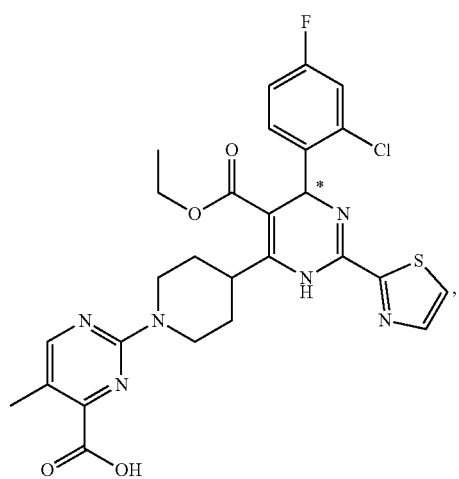
Compound II-22-B
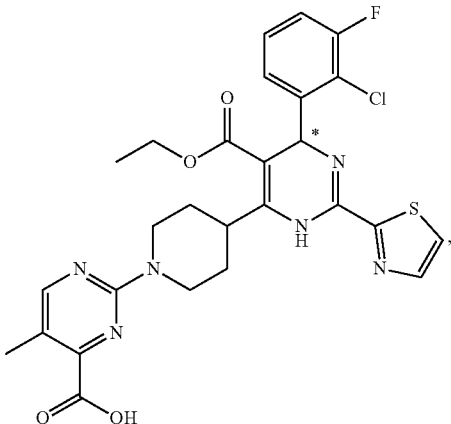
Compound II-24-B
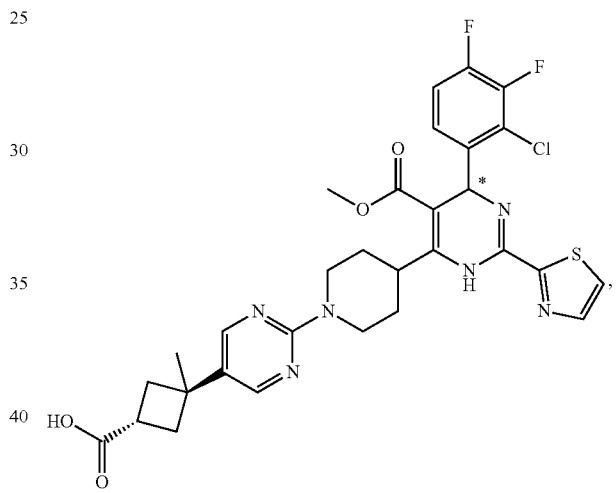
Compound II-27-B
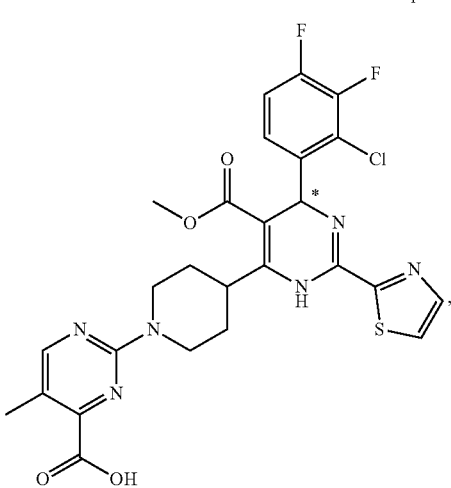

521
-continued
Compound II-28-B
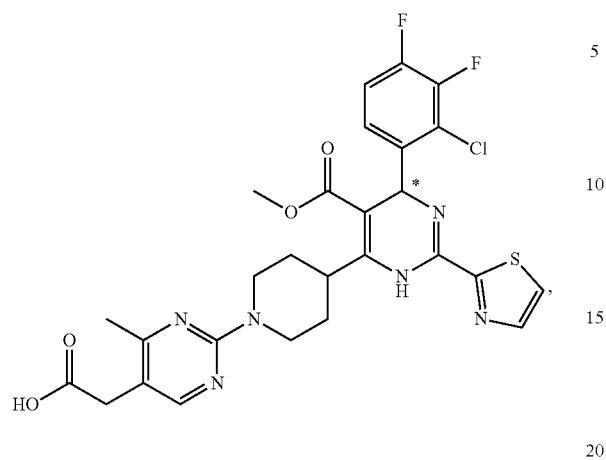
Compound II-29-B
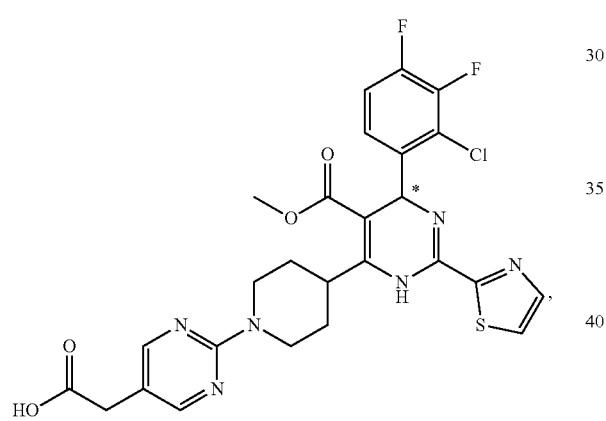
Compound II-30-B
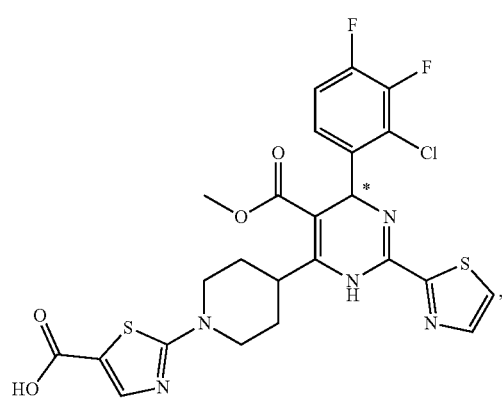
522
-continued
Compound II-41-B
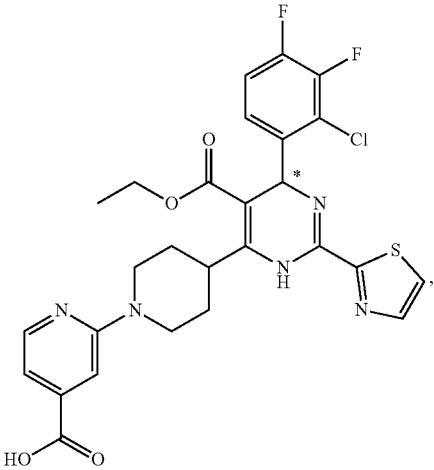
Compound II-50-B
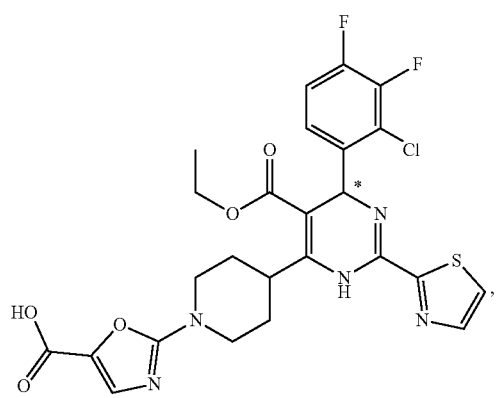
Compound II-55-B
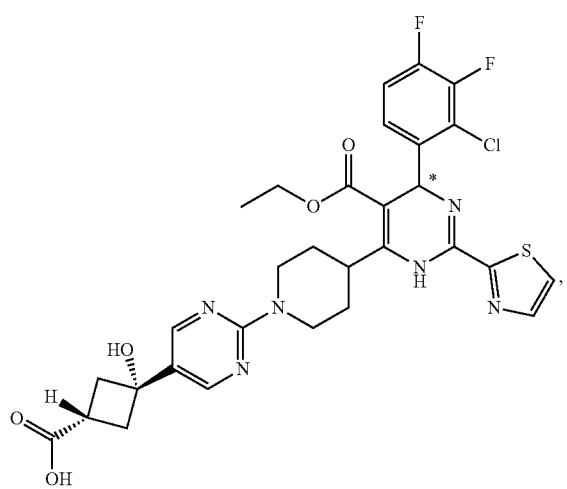

Compound II-58-B
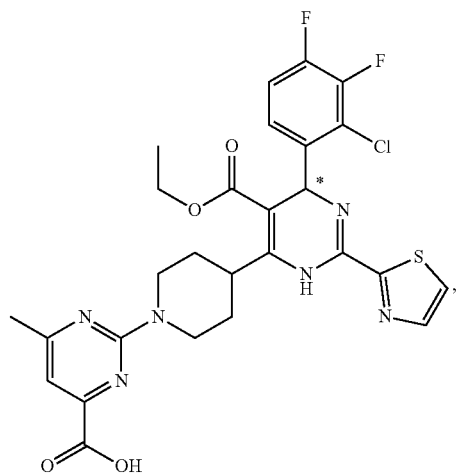
Compound II-59-B
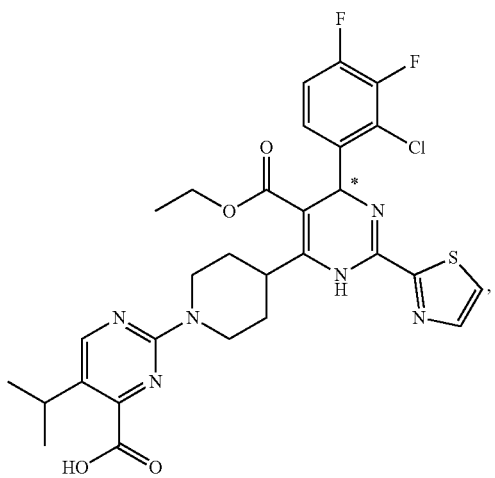
Compound II-60-B
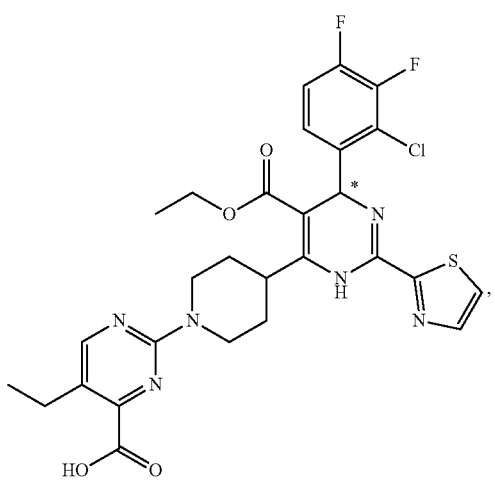
Compound II-61-B
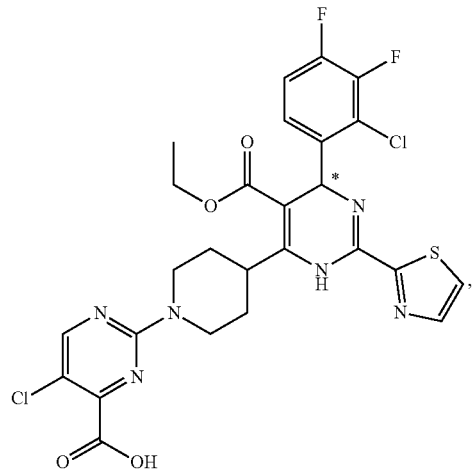
Compound II-63-B
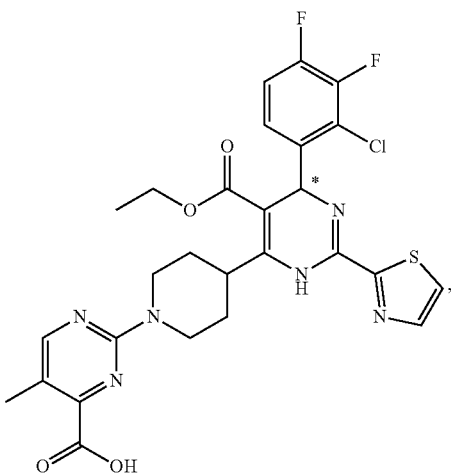
Compound II-65-B
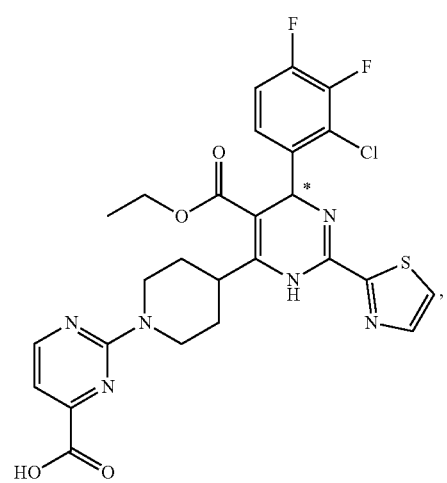

-continued
Compound II-66-B
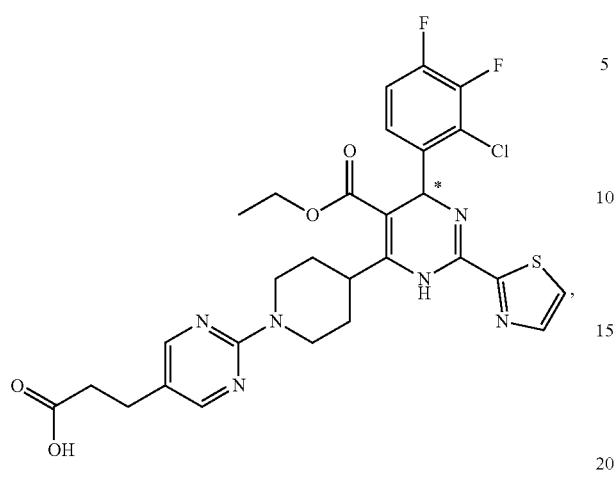
Compound II-67-B
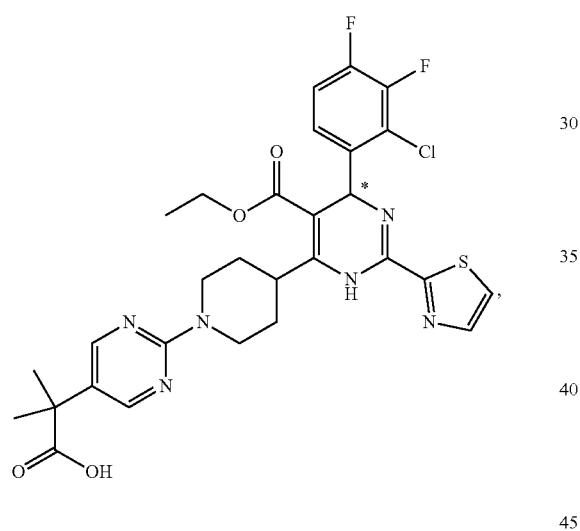
Compound II-68-B
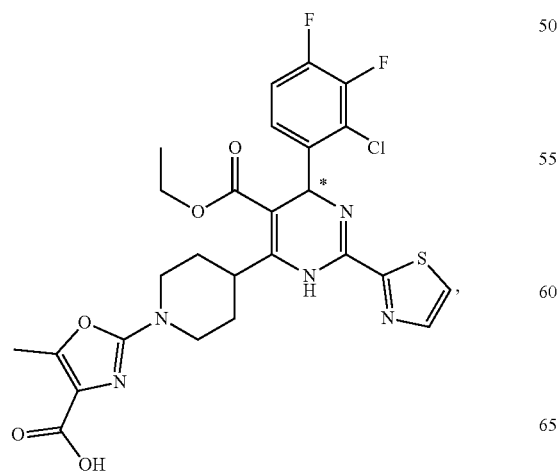
-continued
Compound II-69-B
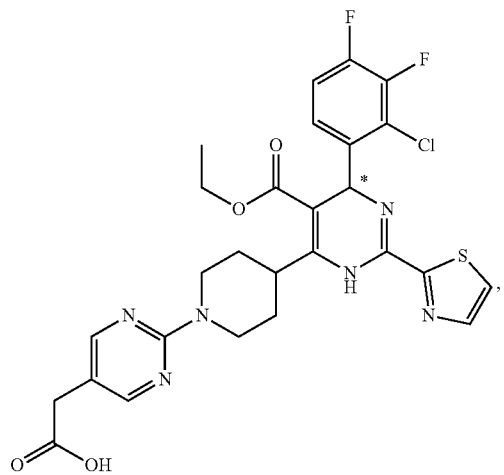
Compound II-70-B
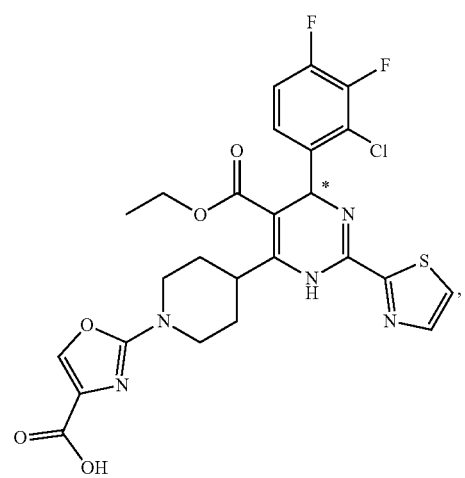
Compound II-74-B
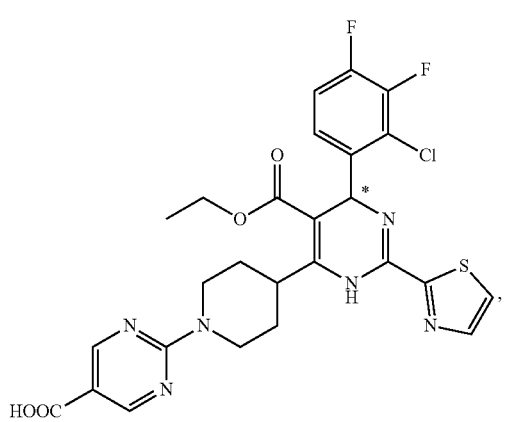

Compound II-78-B

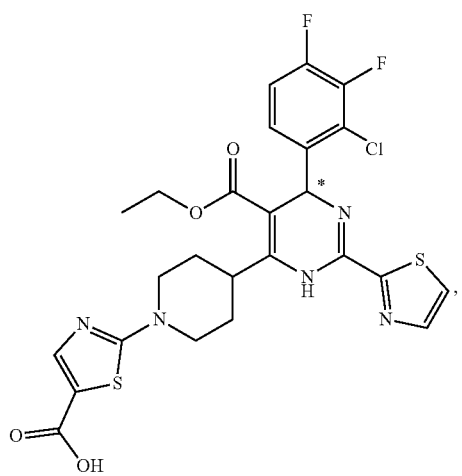

Compound II-80-B

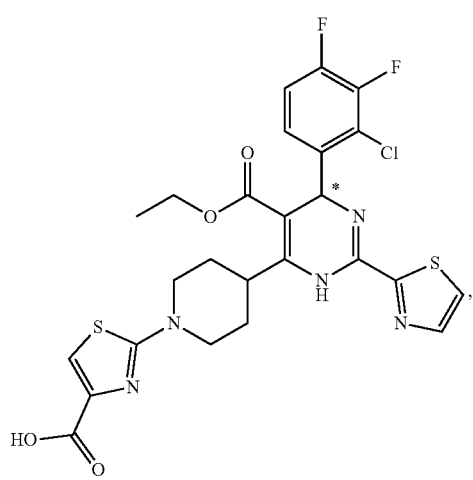

Compound II-80-B

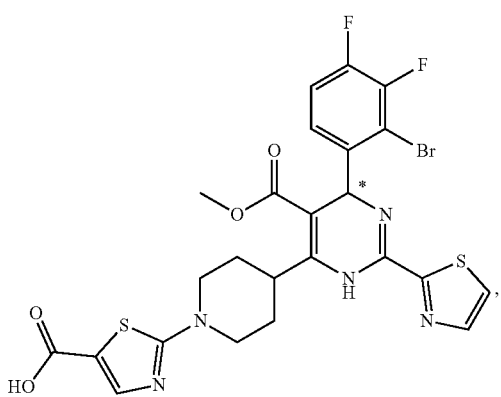

Compound II-84-B

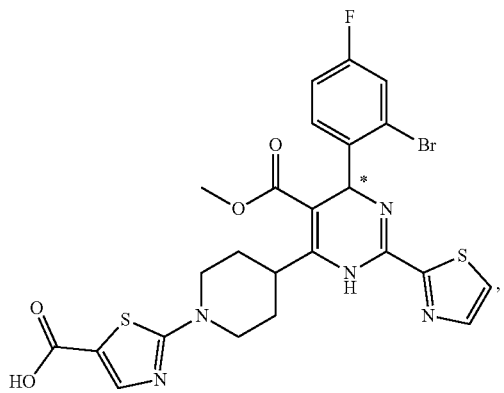

Compound II-86-B

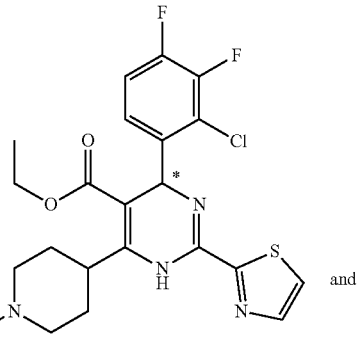

and

Compound II-17-B

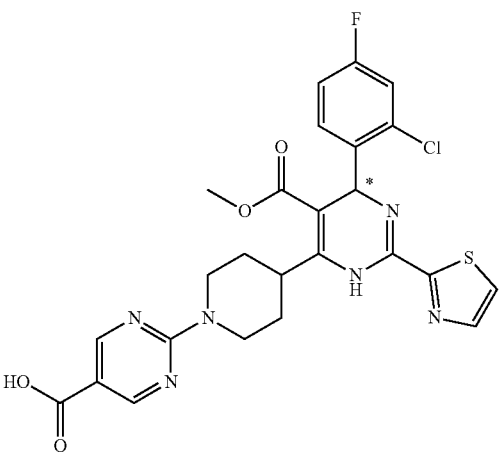

13. A pharmaceutical composition comprising at least one pharmaceutically acceptable carrier and the compound of claim 1, or a pharmaceutically acceptable salt, stereoisomer, or tautomer thereof.

14. A method for treating a hepatitis B virus infection or a hepatitis B virus-induced disease in a mammal in need thereof, wherein the method comprises administering to the mammal a therapeutically effective amount of the compound of claim 1, or a pharmaceutically acceptable salt, stereoisomer, or tautomer thereof.

15. A method for treating a hepatitis B virus infection or a hepatitis B virus-induced disease in a mammal in need thereof, wherein the method comprises administering to the mammal a therapeutically effective amount of the pharmaceutical composition of claim 13.

16. A process for producing a compound of formula (I) as defined in claim 1:

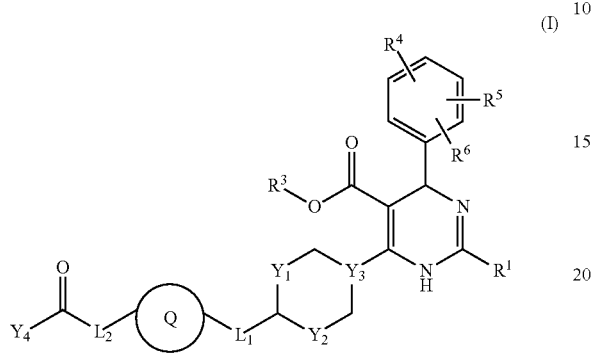

(I)

wherein:
- $L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
- $L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^5$;
- $Y_4$ is OH;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

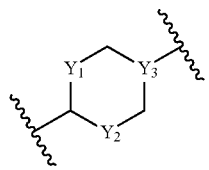

is selected from the group consisting of:

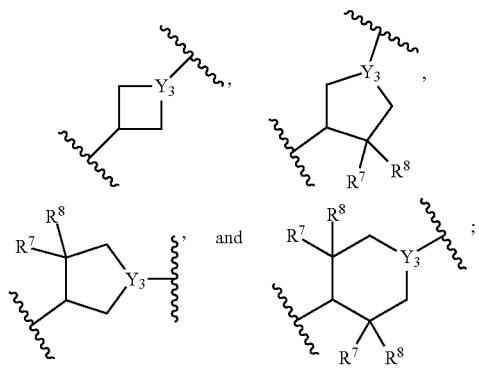

wherein:
- each $R^7$ is independently H, $C_1$-$C_4$ alkyl, or $C_1$-$C_4$ haloalkyl;
- each $R^8$ is independently H or $C_1$-$C_4$ alkyl; and
- $Y_3$ is CH;
- $R^1$ is thiazolyl or pyridyl, wherein the thiazolyl and pyridyl are each optionally substituted with one or more independently selected halogen substituents;
- $R^3$ is $C_1$-$C_3$ alkyl;
- $R^4$ is H, halogen, or $C_1$-$C_3$ alkyl;
- $R^5$ is H, halogen, or $C_1$-$C_3$ alkyl;
- $R^6$ is H, halogen, or $C_1$-$C_3$ alkyl;
- each $R^{10}$ is independently H or $C_1$-$C_4$ alkyl;
- each $R^{11}$ is independently H or $C_1$-$C_4$ alkyl; or
- $R^{10}$ and $R^{11}$, together with the nitrogen atom to which they are attached, form a ring, wherein the ring comprises 4, 5, or 6 carbon atoms;
- each $R^{12}$ is independently H or $C_1$-$C_4$ alkyl;
- each $R^{13}$ is independently H or $C_1$-$C_4$ alkyl;
- $R^{14}$ is $C_1$-$C_4$ alkyl; and
- each $R^{15}$ is independently H or $C_1$-$C_4$ alkyl;

wherein the process comprises the following steps:
1) reacting a compound of formula III-1:

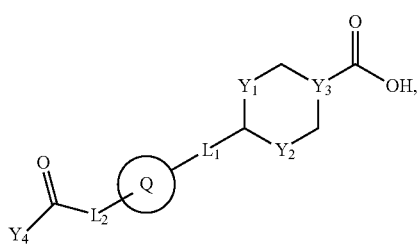

III-1 wherein:
- $L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
- $L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^{15}$;
$Y_4$ is $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

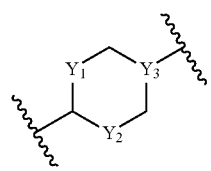

is selected from the group consisting of:

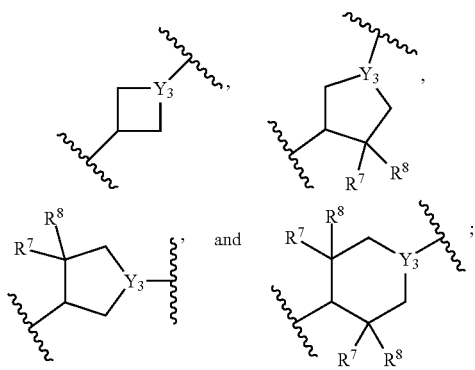

wherein:
each $R^7$ is independently H, $C_1$-$C_4$ alkyl, or $C_1$-$C_4$ haloalkyl;
each $R^8$ is independently H or $C_1$-$C_4$ alkyl; and
$Y_3$ is CH;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^{12}$ is independently H or $C_1$-$C_4$ alkyl;
each $R^{13}$ is independently H or $C_1$-$C_4$ alkyl;
$R^{14}$ is $C_1$-$C_4$ alkyl; and
each $R^{15}$ is independently H or $C_1$-$C_4$ alkyl;
with a compound of the following formula:

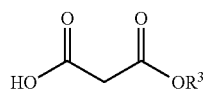

wherein:
$R^3$ is $C_1$-$C_3$ alkyl;
to provide a compound of formula IV-1:

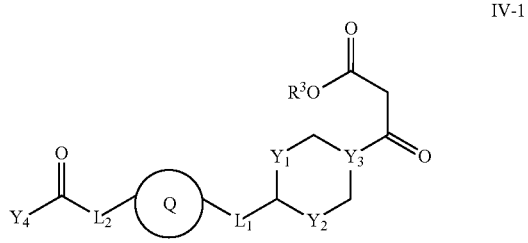

IV-1 wherein:
$L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
$L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^5$;
$Y_4$ is $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

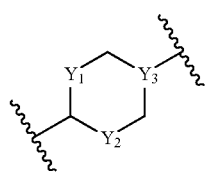

is selected from the group consisting of:

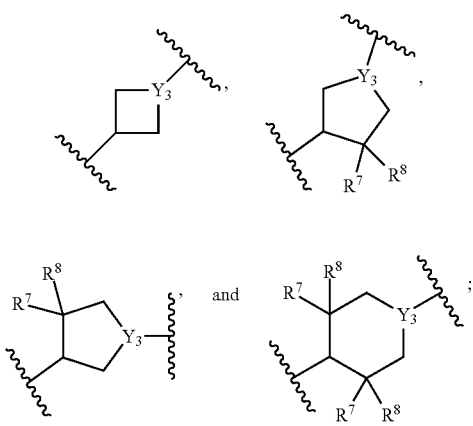

wherein:
  each $R^7$ is independently H, $C_1$-$C_4$ alkyl, or $C_1$-$C_4$ haloalkyl;
  each $R^8$ is independently H or $C_1$-$C_4$ alkyl; and
  $Y_3$ is CH;
$R^3$ is $C_1$-$C_3$ alkyl;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^{12}$ is independently H or $C_1$-$C_4$ alkyl;
each $R^{13}$ is independently H or $C_1$-$C_4$ alkyl;
$R^{14}$ is $C_1$-$C_4$ alkyl; and
each $R^{15}$ is independently H or $C_1$-$C_4$ alkyl;

2) reacting the compound of formula IV-1 above with a compound of formula VI:

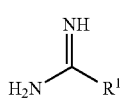

VI or a pharmaceutically acceptable salt thereof, wherein:
  $R^1$ is thiazolyl or pyridyl, wherein the thiazolyl and pyridyl are each optionally substituted with one or more independently selected halogen substituents;
in the presence of a base and a compound of formula V:

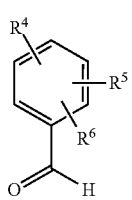

V wherein:
  $R^4$ is H, halogen, or $C_1$-$C_3$ alkyl;
  $R^5$ is H, halogen, or $C_1$-$C_3$ alkyl; and
  $R^6$ is H, halogen, or $C_1$-$C_3$ alkyl;
to provide a compound of formula VII:

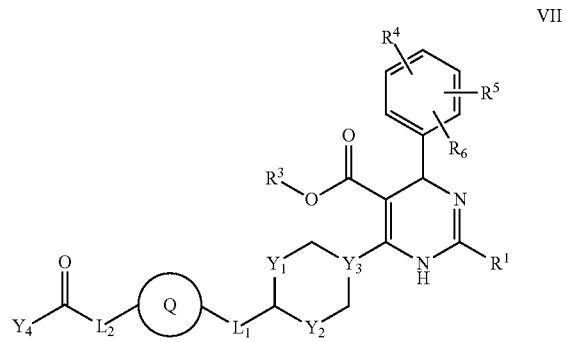

VII wherein:
  $L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
  $L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^{15}$;
  $Y_4$ is $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

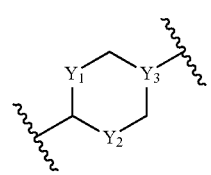

is selected from the group consisting of:

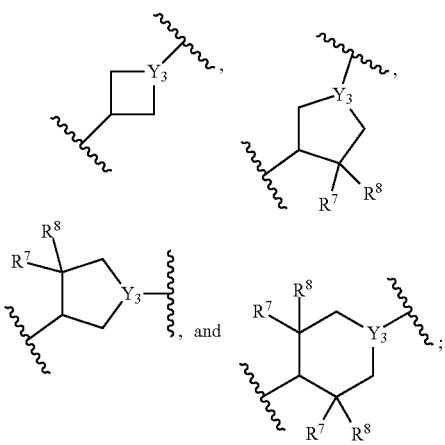

wherein:
each $R^7$ is independently H, $C_1$-$C_4$ alkyl, or $C_1$-$C_4$ haloalkyl;
each $R^8$ is independently H or $C_1$-$C_4$ alkyl; and
$Y_3$ is CH;
$R^1$ is thiazolyl or pyridyl, wherein the thiazolyl and pyridyl are each optionally substituted with one or more independently selected halogen substituents;
$R^3$ is $C_1$-$C_3$ alkyl;
$R^4$ is H, halogen, or $C_1$-$C_3$ alkyl;
$R^5$ is H, halogen, or $C_1$-$C_3$ alkyl;
$R^6$ is H, halogen, or $C_1$-$C_3$ alkyl;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^{12}$ is independently H or $C_1$-$C_4$ alkyl;
each $R^{13}$ is independently H or $C_1$-$C_4$ alkyl;
$R^{14}$ is $C_1$-$C_4$ alkyl; and
each $R^{15}$ is independently H or $C_1$-$C_4$ alkyl; and
3) hydrolyzing the compound of formula VII above in the presence of a base, followed by the addition of aqueous acid, to provide the compound of formula (I) above.

17. A process for producing a compound of formula (I) as defined in claim 1:

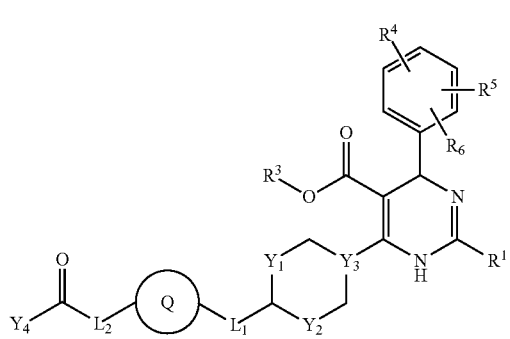

wherein:
$L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
$L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and OR;
$Y_4$ is OH;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

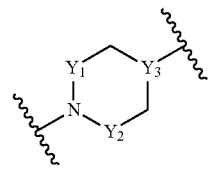

is selected from the group consisting of:

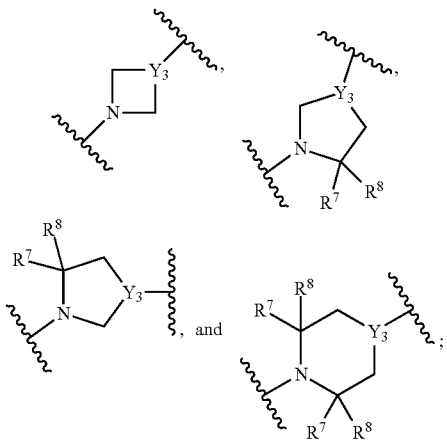

wherein:
each $R^7$ is independently H, $C_1$-$C_4$ alkyl, or $C_1$-$C_4$ haloalkyl;
each $R^7$ is independently H or $C_1$-$C_4$ alkyl; and
$Y_3$ is CH;
$R^1$ is thiazolyl or pyridyl, wherein the thiazolyl and pyridyl are each optionally substituted with one or more independently selected halogen substituents;

$R^3$ is $C_1$-$C_3$ alkyl;
$R^4$ is H, halogen, or $C_1$-$C_3$ alkyl;
$R^5$ is H, halogen, or $C_1$-$C_3$ alkyl;
$R^6$ is H, halogen, or $C_1$-$C_3$ alkyl;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^1$ is independently H or $C_1$-$C_4$ alkyl;
each $R^{13}$ is independently H or $C_1$-$C_4$ alkyl;
$R^{14}$ is $C_1$-$C_4$ alkyl; and
each $R^{15}$ is independently H or $C_1$-$C_4$ alkyl;
wherein the process comprises the following steps:
1) reacting a compound of formula III-2:

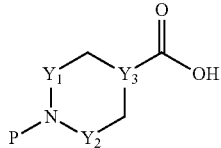

wherein:
P is a protecting group; and

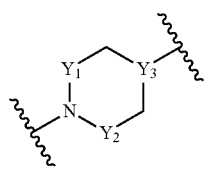

is selected from the group consisting of:

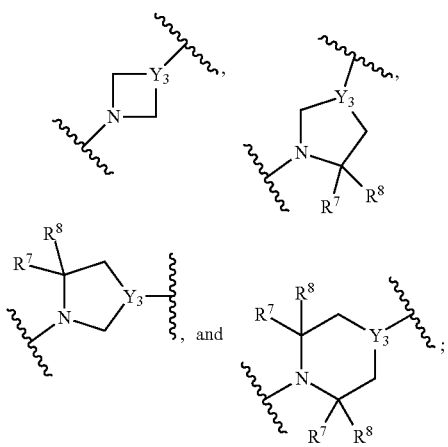

wherein:
each $R^7$ is independently H, $C_1$-$C_4$ alkyl, or $C_1$-$C_4$ haloalkyl;
each $R^8$ is independently H or $C_1$-$C_4$ alkyl; and
$Y_3$ is CH;

with N,N-carbonyldiimidazole and a compound of the following formula:

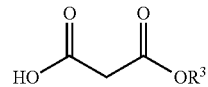

wherein:
$R^3$ is $C_1$-$C_3$ alkyl;
to provide a compound of formula IV-2:

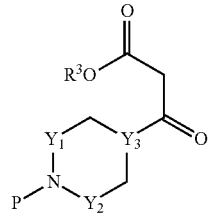

wherein:
P is a protecting group;

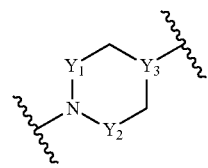

is selected from the group consisting of:

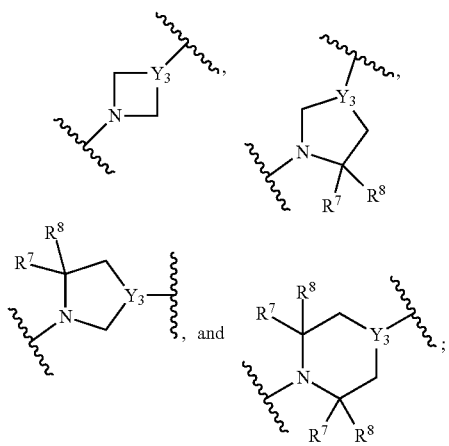

wherein:
each $R^7$ is independently H, $C_1$-$C_4$ alkyl, or $C_1$-$C_4$ haloalkyl;
each $R^8$ is independently H or $C_1$-$C_4$ alkyl; and
$Y_3$ is CH; and
$R^3$ is $C_1$-$C_3$ alkyl;

2) reacting the compound of formula IV-2 above with a compound of formula VI:

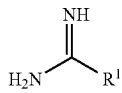

VI or a pharmaceutically acceptable salt thereof,
wherein:
R¹ is thiazolyl or pyridyl, wherein the thiazolyl and pyridyl are each optionally substituted with one or more independently selected halogen substituents;
in the presence of a base and a compound of formula V:

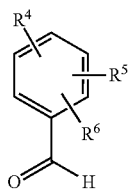

V wherein:
R⁴ is H, halogen, or $C_1$-$C_3$ alkyl;
R⁵ is H, halogen, or $C_1$-$C_3$ alkyl; and
R⁶ is H, halogen, or $C_1$-$C_3$ alkyl;
to provide a compound of formula VIII:

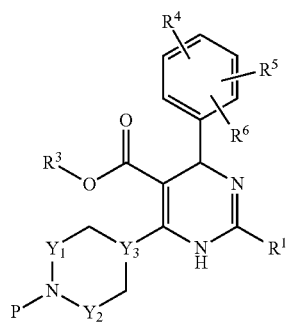

VIII wherein:
P is a protecting group;

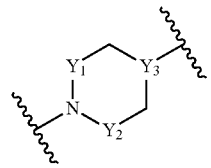

is selected from the group consisting of:

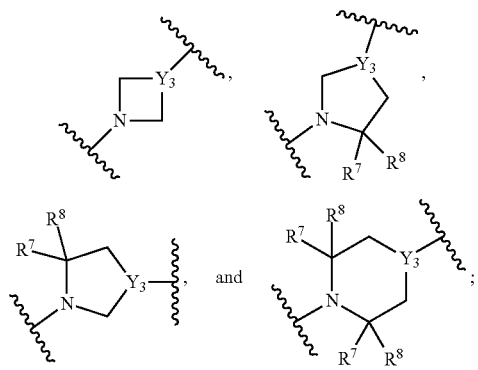

wherein:
each $R^7$ is independently H, $C_1$-$C_4$ alkyl, or $C_1$-$C_4$ haloalkyl;
each $R^8$ is independently H or $C_1$-$C_4$ alkyl; and
$Y_3$ is CH;
R¹ is thiazolyl or pyridyl, wherein the thiazolyl and pyridyl are each optionally substituted with one or more independently selected halogen substituents;
R³ is $C_1$-$C_3$ alkyl;
R⁴ is H, halogen, or $C_1$-$C_3$ alkyl;
R⁵ is H, halogen, or $C_1$-$C_3$ alkyl; and
R⁶ is H, halogen, or $C_1$-$C_3$ alkyl;
3) deprotecting the compound of formula VIII above, to provide a compound of formula IX:

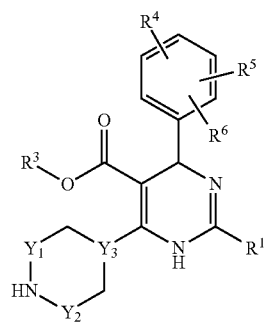

IX wherein:

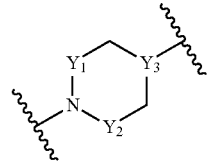

is selected from the group consisting of:

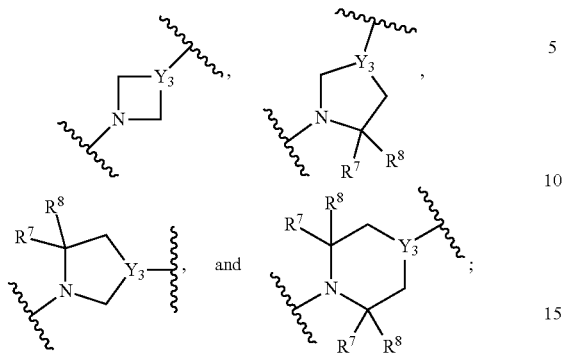

wherein:
  each $R^7$ is independently H, $C_1$-$C_4$ alkyl, or $C_1$-$C_4$ haloalkyl;
  each $R^8$ is independently H or $C_1$-$C_4$ alkyl; and
  $Y_3$ is CH;
$R^1$ is thiazolyl or pyridyl, wherein the thiazolyl and pyridyl are each optionally substituted with one or more independently selected halogen substituents;
$R^3$ is $C_1$-$C_3$ alkyl;
$R^4$ is H, halogen, or $C_1$-$C_3$ alkyl;
$R^5$ is H, halogen, or $C_1$-$C_3$ alkyl; and
$R^6$ is H, halogen, or $C_1$-$C_3$ alkyl;
4) reacting the compound of formula IX above with a compound of formula X:

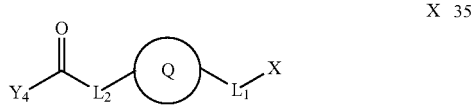

wherein:
  $L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
  $L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^5$;
  $Y_4$ is $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$; and X is halogen or OH;
to provide a compound of formula XI:

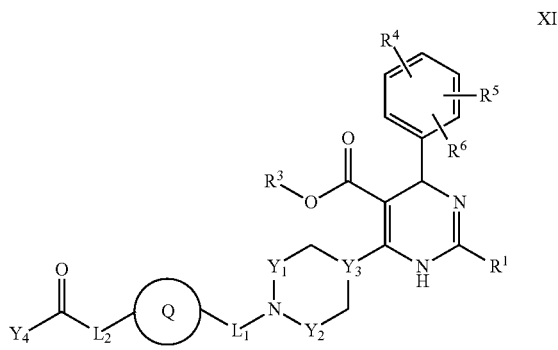

wherein:
  $L_1$ is a bond or $C_1$-$C_4$ alkylene, wherein the $C_1$-$C_4$ alkylene is optionally substituted with one or more substituents independently selected from the group consisting of oxo, halogen, $C_1$-$C_4$ alkyl, $C_1$-$C_4$ haloalkyl, and $OR^7$;
  $L_2$ is a bond, $C_1$-$C_4$ alkylene, or a 3- to 7-membered saturated ring, wherein the 3- to 7-membered saturated ring optionally comprises one or more nitrogen heteroatoms, and further wherein the $C_1$-$C_4$ alkylene and 3- to 7-membered saturated ring are each optionally substituted with one or more substituents independently selected from the group consisting of halogen, $C_1$-$C_4$ alkyl, $C_1$-$C_4$ haloalkyl, and $OR^{15}$;
  $Y_4$ is $OR^{14}$;

is a 5- or 6-membered aromatic ring, wherein the 5- or 6-membered aromatic ring optionally comprises 1, 2, or 3 heteroatoms independently selected from the group consisting of nitrogen, oxygen, and sulfur, and further wherein the 5- or 6-membered aromatic ring is optionally substituted with one or more substituents independently selected from the group consisting of halogen, $C_1$-$C_4$ alkyl, $C_1$-$C_4$ haloalkyl, $C_1$-$C_4$ alkyl-$OR^{12}$, $NR^{10}R^{11}$, and $OR^{13}$;

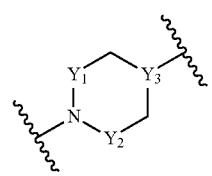

is selected from the group consisting of:

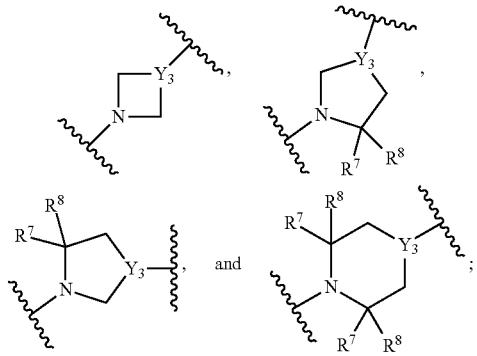

wherein:

each $R^7$ is independently H, $C_1$-$C_4$ alkyl, or $C_1$-$C_4$ haloalkyl;

each $R^8$ is independently H or $C_1$-$C_4$ alkyl; and
$Y_3$ is CH;
$R^1$ is thiazolyl or pyridyl, wherein the thiazolyl and pyridyl are each optionally substituted with one or more independently selected halogen substituents;
$R^3$ is $C_1$-$C_3$ alkyl;
$R^4$ is H, halogen, or $C_1$-$C_3$ alkyl;
$R^5$ is H, halogen, or $C_1$-$C_3$ alkyl;
$R^6$ is H, halogen, or $C_1$-$C_3$ alkyl;
each $R^{10}$ is independently H or $C_1$-$C_4$ alkyl;
each $R^{11}$ is independently H or $C_1$-$C_4$ alkyl; or
$R^{10}$ and $R^{11}$, together with the nitrogen atom to which they are attached, form a ring, wherein the ring comprises 4, 5, or 6 carbon atoms;
each $R^{12}$ is independently H or $C_1$-$C_4$ alkyl;
each $R^{13}$ is independently H or $C_1$-$C_4$ alkyl;
$R^{14}$ is $C_1$-$C_4$ alkyl; and
each $R^{15}$ is independently H or $C_1$-$C_4$ alkyl; and
5) hydrolyzing the compound of formula XI above in the presence of a base, followed by the addition of aqueous acid, to provide the compound of formula (I) above.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="primer"
      /mol_type="unassigned DNA"

<400> SEQUENCE: 1
gtgtctgcgg cgttttatca                                           20

<210> SEQ ID NO 2
<211> LENGTH: 21

```
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="primer"
      /mol_type="unassigned DNA"

<400> SEQUENCE: 2
gacaaacggg caacatacct t                                        21

<210> SEQ ID NO 3
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /organism="Artificial Sequence"
      /note="probe"
      /mol_type="unassigned DNA"

<400> SEQUENCE: 3
cctctkcatc ctgctgctat gcctcatc                                 28
```